US012528847B2

(12) United States Patent
Coukos et al.

(10) Patent No.: US 12,528,847 B2
(45) Date of Patent: Jan. 20, 2026

(54) HETERODIMERIC INACTIVATABLE CHIMERIC ANTIGEN RECEPTORS

(71) Applicants: Ludwig Institute for Cancer Research Ltd, Zurich (CH); École Polytechnique Fédérale de Lausanne, Lausanne (CH)

(72) Inventors: George Coukos, Épalinges (CH); Melita Irving, Épalinges (CH); Bruno Correia, Lausanne (CH); Pablo Gainza-Cirauqui, Lausanne (CH); Greta Maria Paola Giordano Attianese, Lausanne (CH)

(73) Assignees: Ludwig Institute for Cancer Research Ltd, () (CH); École Polytechnique Fédérale de Lausanne, Lausanne (CH)

( * ) Notice: Subject to any disclaimer, the term of this patent is extended or adjusted under 35 U.S.C. 154(b) by 1117 days.

(21) Appl. No.: 17/046,760

(22) PCT Filed: Apr. 12, 2019

(86) PCT No.: PCT/EP2019/059576

§ 371 (c)(1),
(2) Date: Oct. 9, 2020

(87) PCT Pub. No.: WO2019/197676

PCT Pub. Date: Oct. 17, 2019

(65) Prior Publication Data

US 2021/0113615 A1 Apr. 22, 2021

Related U.S. Application Data

(60) Provisional application No. 62/832,767, filed on Apr. 11, 2019, provisional application No. 62/657,534, filed on Apr. 13, 2018.

(51) Int. Cl.

| | |
|---|---|
| ***A61K 40/31*** | (2025.01) |
| ***A61K 40/11*** | (2025.01) |
| ***A61K 40/42*** | (2025.01) |
| ***C07K 14/47*** | (2006.01) |
| ***C07K 14/725*** | (2006.01) |
| *A61K 31/404* | (2006.01) |

(52) U.S. Cl.

CPC .......... *C07K 14/4748* (2013.01); *A61K 40/11* (2025.01); *A61K 40/31* (2025.01); *A61K 40/4211* (2025.01); *A61K 40/4276* (2025.01); *C07K 14/7051* (2013.01); *A61K 31/404* (2013.01); *A61K 2239/23* (2023.05); *A61K 2239/24* (2023.05); *A61K 2239/25* (2023.05); *A61K 2239/31* (2023.05); *A61K 2239/38* (2023.05); *A61K 2239/48* (2023.05); *A61K 2239/58* (2023.05); *C07K 2319/74* (2013.01)

(58) Field of Classification Search

CPC A61K 40/31; A61K 40/4211; A61K 40/4276; C07K 14/4748

USPC ........................................... 424/133.1, 134.1

See application file for complete search history.

(56) References Cited

U.S. PATENT DOCUMENTS

| | | | |
|---|---|---|---|
| 9,587,020 B2 | 3/2017 | Wu et al. | |
| 9,821,012 B2 | 11/2017 | Wu et al. | |
| 11,466,070 B2 * | 10/2022 | Pulé ................ | C07K 14/70514 |
| 2017/0292118 A1 | 10/2017 | Duchateau et al. | |
| 2017/0306303 A1 | 10/2017 | Taunton et al. | |

FOREIGN PATENT DOCUMENTS

| | | | |
|---|---|---|---|
| JP | 2006516383 | A * | 7/2006 |
| JP | 2006516383 | A5 * | 12/2006 |
| WO | 2014/127261 | A1 | 8/2014 |
| WO | 2015090229 | | 6/2015 |
| WO | 2016030691 | | 3/2016 |
| WO | 2016030691 | A1 † | 3/2016 |
| WO | 2017137758 | | 8/2017 |
| WO | 2017137758 | A1 † | 8/2017 |
| WO | 2017216562 | | 12/2017 |

OTHER PUBLICATIONS

Giordano-Attianese, G. Nat. Biotechnol. 2020, 38, 426-432.*
Caulier et al (Int J Mol Sci. May 2021; 22(9): 4320; Published online Apr. 21, 2021).*
Giordano Atteniese Nat Biotechnol Apr. 2020;38(4):426-432. doi: 10.1038/s41587-019-0403-9. Epub Feb. 2020.*
Chao DT, Korsmeyer SJ (1998). "BCL-2 family: regulators of cell death". Annu. Rev. Immunol. 16: 395-419.*
Delbridge et al (Cell Death and Differentiation (2015) 22, 1071-1080).*
C-Y. Wu et al., "Remote control of therapeutic T cells through a small molecule-gated chimeric receptor", Science, vol. 350, No. 6258, Sep. 24, 2015, pp. 4077-1-4077-10.
M. Cartellieri et al., "Switching CAR T cells on and off: a novel modular platform for retargeting of T cells to AML plasts", Blood Cancer Journal, vol. 6, No. 8, Aug. 1, 2016, pp. e458.
Alexandre Juillerat et al., "Design of chimeric antigen receptors with integrated controllable transient functions", Scientific Reports, vol. 6, 11 Janaury 2016, p. 18950.
S. P. Santoro et al., "T Cells Bearing a Chimeric Antigen Receptor against Prostate-Specific Membrane Antigen Mediate Vascular Disruption and Result in Tumor Regression", Cancer Immunology research, vol. 3, No. 1, Jan. 1, 2015, pp. 68-84.
International Search Report and Written Opinion of the International Searching Authority in International Application No. PCT/EP2019/059576 dated Aug. 5, 2019.

(Continued)

*Primary Examiner* — Lynn A Bristol

(74) *Attorney, Agent, or Firm* — Troutman Pepper Locke LLP

(57) ABSTRACT

The invention relates to heterodimeric inactivatable chimeric antigen receptors (CARs) and their use for treatment.

25 Claims, 133 Drawing Sheets
(12 of 133 Drawing Sheet(s) Filed in Color)
Specification includes a Sequence Listing.

(56) References Cited

OTHER PUBLICATIONS

Bouillet P et al., "BH3-only proteins—evolutionarily conserved proapoptotic Bcl-2 family members essential for initiating programmed cell death," Journal of Cell Science, 115: 1567-1574 (2002).

Soderquist R.S. et al., "BCL2 inhibitors as anticancer drugs: a plethora of misleading BH3 mimetics," Mol Cancer Ther., 15(9): 2011-2017 (2016).

Lampson B.L. et al., "The Development and Current Use of BCL-2 Inhibitors for the Treatment of Chronic Lymphocytic Leukemia," Curr Hematol Malig Rep., 12(1): 11-19 (2017).

Gray-Gaillard E.F. et al., "OFF-switch CAR T cell for safety-enhanced cancer immunotherapy" [abstract] In: Proceedings of the American Association for Cancer Research Annual Meeting 2018; Apr. 14-18, 2018; Chicago, IL. Philadelphia (PA): AACR; Cancer Res 2018;78(13 Suppl):Abstract nr 2570.

Gray-Gaillard E.F. et al., "OFF-switch CAR T cell for safety-enhanced cancer immunotherapy," Poster presented at American Association for Cancer Research Annual Meeting 2018; Apr. 14-18, 2018; Chicago, IL.

Wang Z. et al., "New development in CAR-T cell therapy," Journal of Hematology & Oncology, 10:53 (2017).

Wu C-Y. et al., "Remote control of therapeutic T cells through a small molecule-gated chimeric receptor," Science, 350 (6258): aab4077 (2015).

Juillerat A. et al., "Design of chimeric antigen receptors with integrated controllable transient functions," Scientific Reports, 6(11): 18950 (2016).

Lanitis E. et al., "Chimeric antigen receptor T Cells with dissociated signaling domains exhibit focused antitumor activity with reduced potential for toxicity in vivo," Cancer Immunol Res, 1(1): 43-53 (2013).

Lim, W.A. & June, C.H. "The Principles of Engineering Immune Cells to Treat Cancer," Cell, 168: 724-740 (2017).

Gargett, T. & Brown, M.P. "The inducible caspase-9 suicide gene system as a "safety switch" to limit on-target, off-tumor toxicities of chimeric antigen receptor T cells," Front Pharmacol, 5, 235 (2014).

Jones B.S. et al., "Improving the safety of cell therapy products by suicide gene transfer," Front Pharmacol, 5, 254 (2014).

Fedorov V.D. et al., "PD-1- and CTLA-4-based inhibitory chimeric antigen receptors (iCARs) divert off-target immunotherapy responses," Sci Transl Med, 5, 215ra172 (2013).

Lee E.F. et al., "High-resolution structural characterization of a helical alpha/beta-peptide foldamer bound to the anti-apoptotic protein Bcl-XL," Angew Chem Int Ed Engl, 48(24): 4318-4322 (2009).

Leverson, J.D. et al., "Exploiting selective BCL-2 family inhibitors to dissect cell survival dependencies and define improved strategies for cancer therapy," Sci Transl Med, 7, 279ra240 (2015).

Third Party Observations dated Sep. 15, 2021 in conection with EPO Application No. 19720071.0.

* cited by examiner
† cited by third party

Figure 2A
Figure 2B
Figure 2C
Molecular composition of the heterodimerizing domains
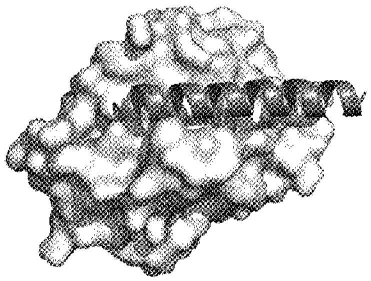
Bcl-xL:BimBH3
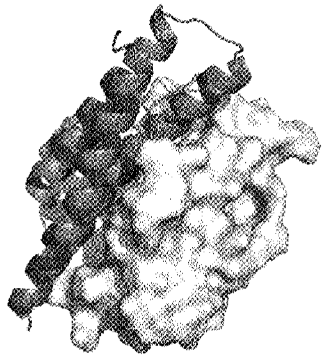
Bcl-xL:1LE4A
$K_D$ = 400 pM
Protein B:Protein A
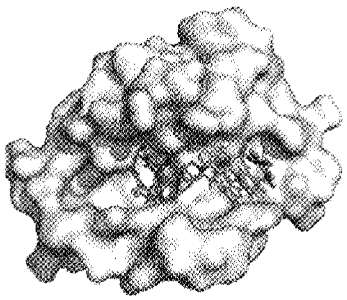
Bcl-xL:Navitoclax (1nM)
$K_D$ = 10 pM
Protein B:Navitoclax

Figure 4A. Amino Acid Sequence of OFF-CAR: CHAIN A

CD8A LEADER - scFv ANTI-PSMA (linker underlined) - AS - CD8a HINGE - CD28 TRANSMEMBRANE - HUMAN CD28 – HM - Serine-Glycine Linker - 1LE4A – PROTEIN A – T2A MALPVTALLLPLALLLHAARPVQLQQSGPELVKPGTSVRISCKTSGYTFT
EYTIHWVKQSHGKSLEWIGNINPNNGGTTYNQKFEDKATLTVDKSSS
TAYMELRSLTSEDSAVYYCAAGWNFDYWGQGTTVTVSSGGGGSGGG
GSGGGGSDIVMTQSHKFMSTSVGDRVSIICKASQDVGTAVDWYQQK
PGQSPKLLIYWASTRHTGVPDRFTGSGSGTDFTLTITNVQSEDLADYFC
QQYNSYPLTFGAGTMLDLKRASTTTPAPRPPTPAPTIASQPLSLRPEACR
PAAGGAVHTRGLDFACDFWVLVVVGGVLACYSLLVTVAFIIFWVRSKR
SRLLHSDYMNMTPRRPGPTRKHYQPYAPPRDFAAYRSHMGGGGSG
GGGSGGGGSQRWELALGRFLEYLSWVSTLSEQVQEELLSSQVTQELR
ALMDETMKELKAYKSELEEQLTPVAEETRARLSKELQAAQARLGADM
EDVRGRLVQYRGEVQAMLGQSTEELRVRLASHLIALQLRLIGDAFDLQ
KRLAVYQAGAAERKRRSGSGRSGSGEGRGSLLTCGDVEENPGP

Figure 4B. Nucleic Acid Sequence of OFF-CAR: CHAIN A

CD8a leader CD28 transmembrane
scFv anti-PSMA Human CD28
Restriction enzyme cut site Serine-Glycine Linker
CD8a hinge 1LE4A -- Protein A T2A atggccttaccagtgaccgccttgctcctgccgctggccttgctgctccacgccgccaggccggtgcagctgcagcagtcaggacctgaactggtga
agcctgggacttcagtgaggatatcctgcaagacttctggatacacattcactgaatataccatacactgggtgaagcagagccatggaaagagcc
ttgagtggattggaaacatcaatcctaacaatggtggtaccacctacaatcagaagttcgaggacaaggccacattgactgtagacaagtcctcca
gtacagcctacatggagctccgcagcctaacatctgaggattctgcagtctattattgtgcagctggttggaactttgactactggggccaagggac
cacggtcaccgtctcctcaggtggaggtggatcaggtggaggtggatctggtggaggtggatctgacattgtgatgacccagtctcacaaattcatg
tccacatcagtaggagacagggtcagcatcatctgtaaggccagtcaagatgtgggtactgctgtagactggtatcaacagaaaccaggacaatct
cctaaactactgatttattgggcatccactcggcacactggagtccctgatcgcttcacaggcagtggatctgggacagacttcactctcaccattac
taatgttcagtctgaagacttggcagattatttctgtcagcaatataacagctatcccctcacgttcggtgctgggaccatgctggacctgaaacggg
ctagcACAACAACCCCTGCCCCCAGACCTCCTACCCCAGCCCCTACAATTGCCAGCCAGCCTCTGAGCCTGAGGCC
CGAGGCTTGTAGACCTGCTGCTGGCGGAGCCGTGCACACCAGAGGACTGGATTTCGCCTGCGACTTCTGGGTG
CTGGTGGTCGTGGGCGGAGTGCTGGCCTGTTACAGCCTGCTCGTGACCGTGGCCTTCATCATCTTTTGGGTGCG
GAGCAAGAGAAGCAGACTGCTGCACAGCGACTACATGAACATGACCCCCAGACGGCCTGGCCCCACCAGAAAG
CACTACCAGCCTTACGCCCCTCCCAGAGACTTCGCCGCCTACAGATCTcatatgGGAGGCGGAGGATCTGGCGGAG
GTGGAAGTGGCGGAGGCGGATCTCAAAGATGGGAACTCGCCCTGGGCAGATTCCTGGAATACCTGAGCTGGGT
GTCCACACTGAGCGAACAGGTGCAAGAGGAACTGCTGAGCAGCCAAGTGACCCAAGAGCTGAGAGCCCTGAT
GGACGAGACAATGAAGGAACTGAAGGCCTACAAGAGCGAGCTGGAAGAACAGCTGACCCCTGTGGCCGAGGA
AACCAGAGCCAGACTGAGCAAAGAACTGCAGGCCGCTCAGGCCAGACTGGGAGCCGATATGGAAGATGTTCG
GGGCAGACTGGTGCAGTACAGAGGCGAAGTTCAGGCCATGCTGGGCCAGTCTACCGAGGAACTGAGAGTGCG
GCTGGCCTCTCATCTGATTGCCCTGCAGCTGAGACTGATCGGCGACGCATTCGACCTGCAGAAAAGACTGGCCG
TGTACCAGGCTGGCGCTGCTGAACGGAAGCGGCGCAGCGGCAGCGGGCGCAGCGGCAGCGGCgagggcagagg
aagtcttctaacatgcggtgacgtggaggagaatcccggccct

Figure 5A. Amino Acid Sequence of OFF-CAR: CHAIN B

CD8a leader CD28 transmembrane
CD3-zeta Human CD28
Restriction enzyme cut site Serine-Glycine Linker
CD8a hinge DAP10 cMyc BCL-XL GSMALPVTALLLPLALLLHAARPEQKLISEEDLQTTPGERSSLPAFYPGTSGSCSG
CGSLSLPTTTPAPRPPTPAPTIASQPLSLRPEACRPAAGGAVHTRGLDFACDPRF
WVLVVVGGVLACYSLLVTVAFIIFWVRSKRSRLLHSDYMNMTPRRPGPTRKHY
QPYAPPRDFAAYRSPGGGGGSGGGGSGGGGSMSQSNRELVVDFLSYKLSQKG
YSWSQFSDVEENRTEAPEGTESEAVKQALREAGDEFELRYRRAFSDLTSQLHITP
GTAYQSFEQVVNELFRDGVNWGRIVAFFSFGGALCVESVDKEMQVLVSRIAA
WMATYLNDHLEPWIQENGGWDTFVELYGNNAAAESRKGQEREDGGGGSGG
GGSGGGGSMHRVKFSRSADAPAYQQGQNQLYNELNLGRREEYDVLDKRRGR
DPEMGGKPRRKNPQEGLYNELQKDKMAEAYSEIGMKGERRRGKGHDGLYQG
LSTATKDTYDALHMQALPPR*

Figure 5B. Nucleic Acid Sequence of OFF-CAR: CHAIN B

CD8a leader CD28 transmembrane
CD3-zeta Human CD28
Restriction enzyme cut site Serine-Glycine Linker
CD8a hinge DAP10 cMyc BCL-XL ggatccatggccttaccagtgaccgccttgctcctgccgctggccttgctgctccacgccgccaggccggaacagaaactcatc
agtgaggaagatttgcagacgactccaggagagagatcatcactccctgcctttaccctggcacttcaggctcttgttccggat
gtgggtccctctctctgccgACAACAACCCCTGCCCCCAGACCTCCTACCCCAGCCCCTACAATTGCCAG
CCAGCCTCTGAGCCTGAGGCCCGAGGCTTGTAGACCTGCTGCTGGCGGAGCCGTGCACACCAG
AGGACTGGATTTCGCCTGCGACcctaggTTCTGGGTGCTGGTGGTCGTGGGCGGAGTGCTGGCCT
GTTACAGCCTGCTCGTGACCGTGGCCTTCATCATCTTTTGGGTGCGGAGCAAGAGAAGCAGACT
GCTGCACAGCGACTACATGAACATGACCCCCAGACGGCCTGGCCCCACCAGAAAGCACTACCAG
CCTTACGCCCCTCCCAGAGACTTCGCCGCCTACAGATCTcccgggGGAGGCGGAGGATCTGGCGG
AGGTGGAAGTGGCGGAGGCGGATCTATGAGCCAGAGCAACAGAGAACTGGTGGTGGACTTCCT
GAGCTACAAGCTGAGCCAGAAGGGCTACAGCTGGTCCCAGTTCAGCGACGTGGAAGAGAACA
GAACAGAGGCCCCTGAGGGCACAGAGTCTGAGGCTGTGAAACAGGCCCTGAGAGAAGCCGGC
GACGAGTTCGAGCTGAGATACAGAAGGGCCTTCAGCGACCTGACCAGCCAGCTGCACATCACAC
CTGGCACAGCCTACCAGAGCTTCGAGCAGGTCGTGAACGAGCTGTTCAGAGATGGCGTGAACT
GGGGCAGAATCGTGGCCTTCTTCAGCTTTGGCGGAGCCCTGTGTGTGGAAAGCGTGGACAAAG
AAATGCAGGTCCTGGTGTCCAGAATCGCCGCCTGGATGGCCACCTACCTGAACGATCATCTGGAA
CCCTGGATtCAAGAGAACGGCGGCTGGGACACCTTCGTGGAACTGTACGGAAACAACGCCGCT
GCCGAGAGCAGAAAGGGCCAAGAACGAGAAGATGGCGGCGGTGGTTCTGGTGGCGGCGGTA
GTGGTGGCGGTGGATCAatgcatagagtgaagttcagcaggagcgcagacgcccccgcgtaccagcagggccagaa
ccagctctataacgagctcaatctaggacgaagagaggagtacgatgttttggacaagagacgtggccgggaccctgagatg
gggggaaagccgagaaggaagaaccctcaggaaggcctgtacaatgaactgcagaaagataagatggcggaggcctaca
gtgagattgggatgaaaggcgagcgccggaggggcaaggggcacgatggcctttaccagggtctcagtacagccaccaagg
acacctacgacgcccttcacatgcaggccctgccccctcgctaa DAP10 OFF-CAR Expression in Jurkat and Primary T cells Both CAR1 and CAR2 are labeled with antibodies conjugated to APC, so their presence is denoted as the population on the right hand side of the gate (more positive APC population).

UTD = untransduced, control. HD_=healthy donor ## (these are primary human T cells)

DAP10 OFF-CAR Expression in Primary T cells

Both CAR1 and CAR2 are labeled with antibodies in APC, so their presence is denoted as the population on the right hand side of the gate (more positive APC population).

UTD = untransduced, control. HD_=healthy donor ## (these are primary human T cells)

Figure 7
Amnis® Imaging Reveals Co-Localization of the OFF-CAR Chains
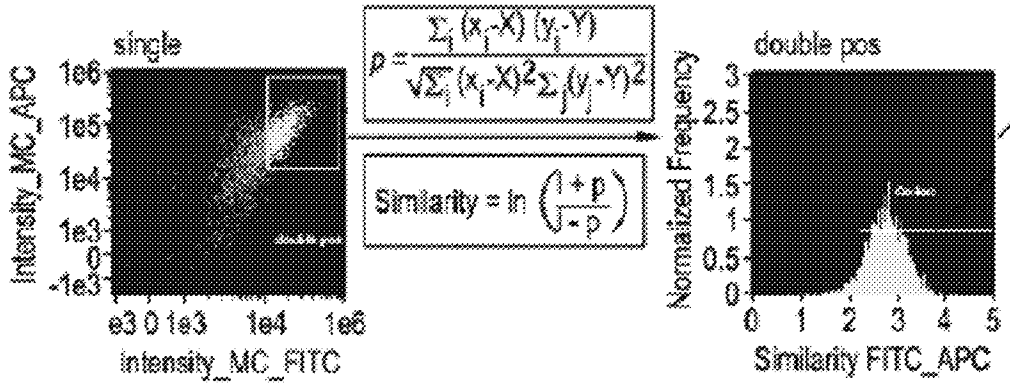
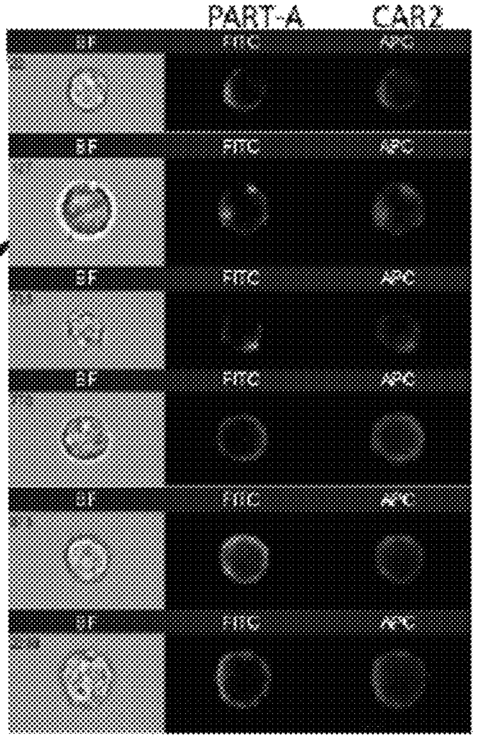
Intensity_MC_FITC, Intensity_MC_APC
| Population | Count | %Gated |
|---|---|---|
| single | 6073 | 100 |
| double pos & single | 3083 | 50.8 |
Similarity FITC_APC
| Population | Count | %Gated |
|---|---|---|
| double pos & single | 3083 | 100 |
| Co-loc & double pos & single | 2816 | 91.3 |
xi and yi are the per-pixel intensity values of the two images.
X and Y are the corresponding mean intensity values Expression, Stability and Co-Localization of OFF-CAR Chains
CHAIN 1
CHAIN 2
SSC
Q1 0.22
Q2 0.79
Q3 77.1
Q4 21.9
Q1 1.19
Q2 1.62
Q3 47.6
Q4 49.6
CHAIN Expression CAR Component Stability
% Expression
CHAIN 1
CHAIN 2

BF
CHAIN1
CHAIN2
1&2

Activation of Jurkat Cells
% Activation
UTD
OFF-CAR
Pz-1

Expression and Functionality of OFF-CAR in Primary Human T Cells
CHAIN A
CHAIN B
SSC
250K
200K
150K
100K
50K
0
Q1 0
Q2 0
Q3 42.9
Q4 57.1
Q3 17.0
Q4 83.0
$-10^3$ 0 $10^3$ $10^4$ $10^5$
CHAIN Expression 10 Day Expansion
Fold Expansion
100
80
60
40
20
0
UTD
OFF-CAR h-IL-2 Production
h-IL-2 [ng/mL]
25
20
15
10
5
0
UTD
OFF-CAR
Pz-1 h-IFN-γ Production
h-IFN-γ [ng/mL]
30
20
10
0
UTD
OFF-CAR
Pz-1

Figure 10A

OFF-CAR *versus* Second Generation CAR T cell Cytotoxicity Measured by IncuCyte® (Dye Shading = dead tumor cells)

The dye/area is a cytotoxicity dye that labels cells (the tumor cells) being killed (by the T cells) DAP10 is the split architecture CAR. The Pz1 is the single component second generation equivalent that is the control CAR to compare DAP10 to in terms of functionality, as the drug should not affect Pz1 functionality.

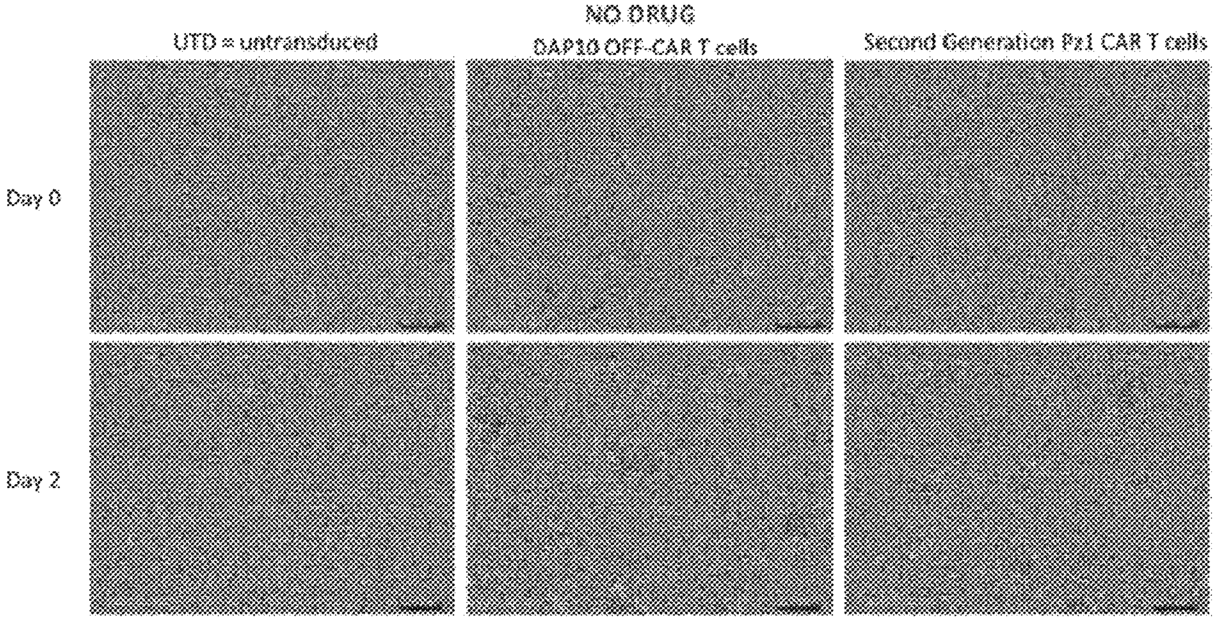

Figure 10B

OFF-CAR *versus* Second Generation CAR T cell Cytotoxicity Measured by IncuCyte® (Dye Shading = dead tumor cells)

The dye/area is a cytotoxicity dye that labels cells (the tumor cells) being killed (by the T cells) DAP10 is the split architecture CAR. The Pz1 is the single component second generation equivalent that is the control CAR to compare DAP10 to in terms of functionality, as the drug should not affect Pz1 functionality.

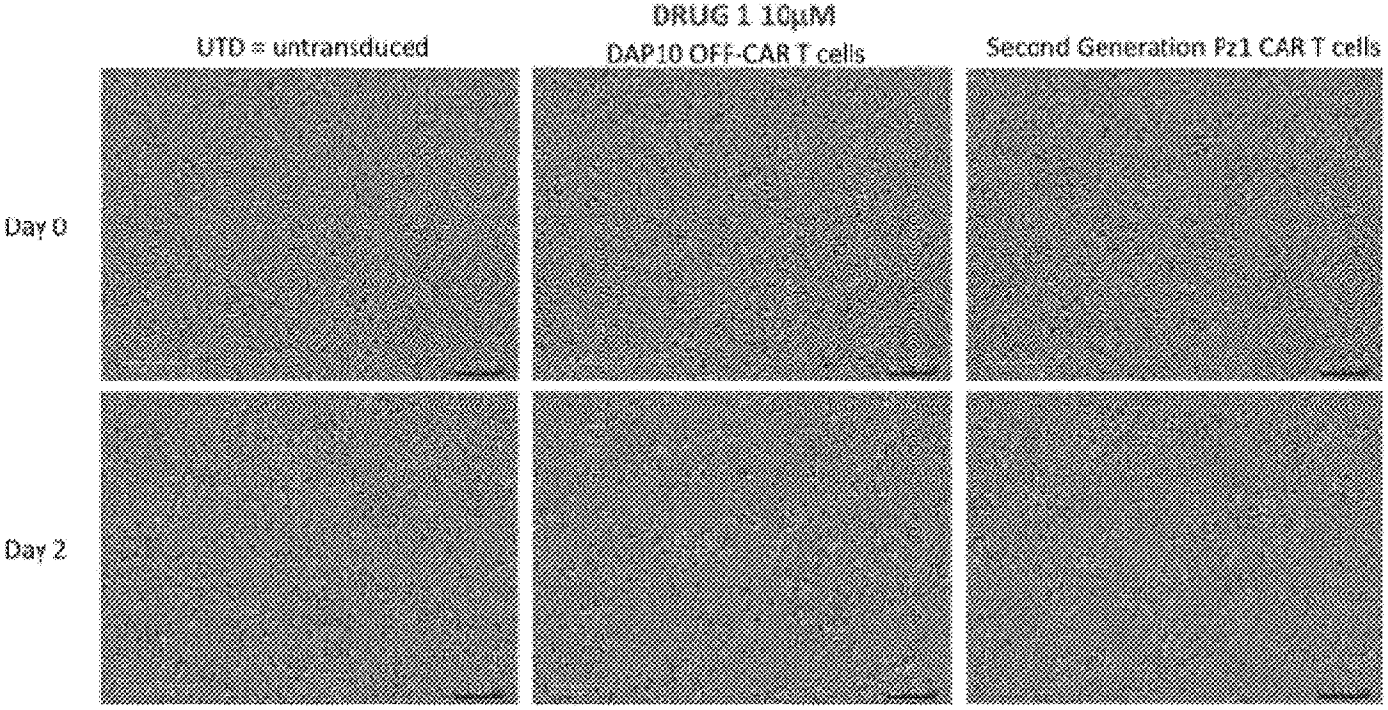

Drug 1 = A-1331852
Drug 2 = A-1155463

Figure 10C

DAP10 OFF-CAR *versus* Second Generation CAR T cell Cytotoxicity Measured by IncuCyte® (Dye Shading = dead tumor cells)

The dye/area is a cytotoxicity dye that labels cells (the tumor cells) being killed (by the T cells) DAP10 is the split architecture CAR. The Pz1 is the single component second generation equivalent that is the control CAR to compare DAP10 to in terms of functionality, as the drug should not affect Pz1 functionality.

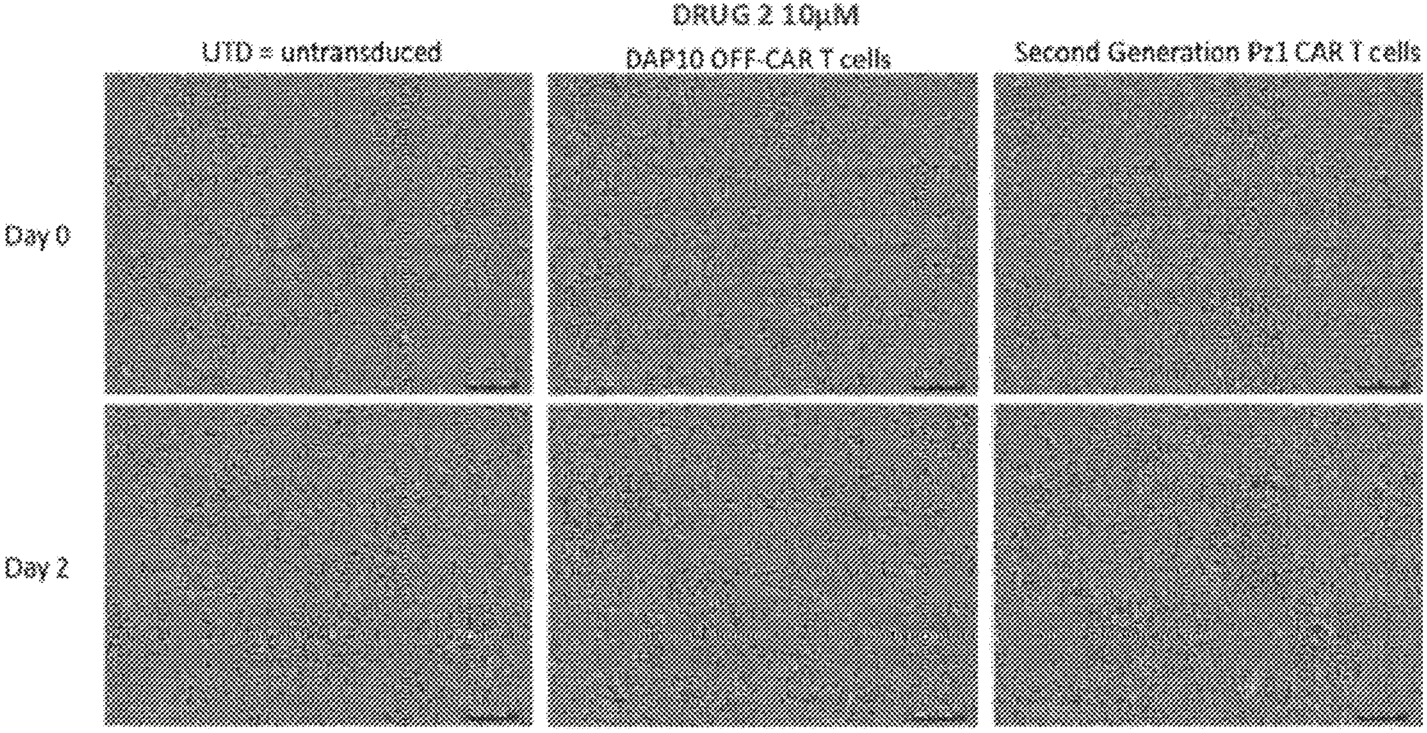

Drug 1 = A-1331852
Drug 2 = A-1155463

Figure 11

Tumor Cell Killing by OFF-CAR T Cells is Stopped by Competitive Binding Drugs 1 & 2

This is the plot of the dyed total area/mm^2 (represented on the past couple of slides), used as a measure of cytotoxicity/ killing capacity of the T cells. Both drugs eliminate the killing capacity of DAP10 in both of these donors.
A titration of drugs was performed, and 10μM displayed the best splitting of the two components as shown here.

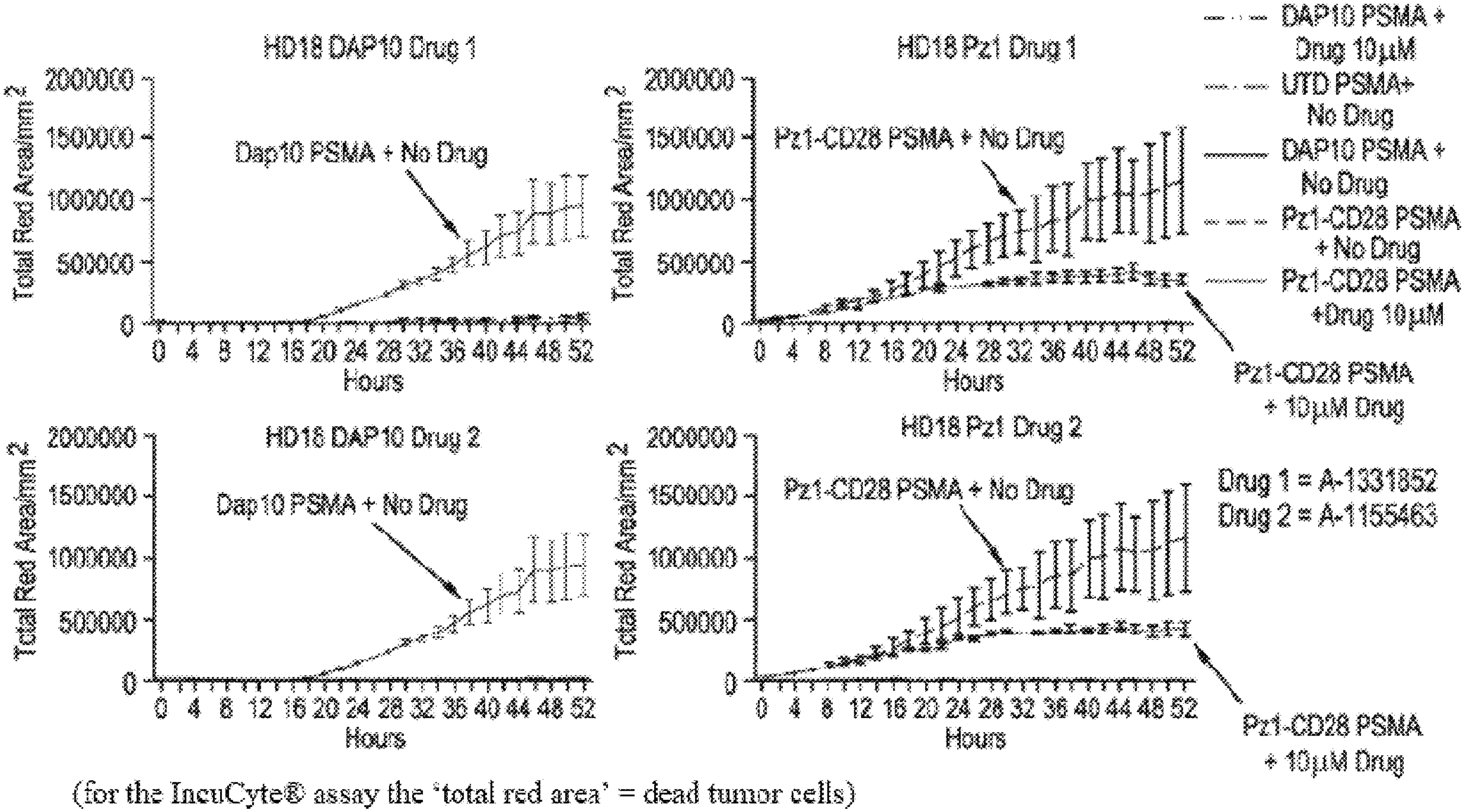

(for the IncuCyte® assay the 'total red area' = dead tumor cells)

Figure 12. Lower Affinity 1LE4A (Protein A) Sequences forChain A will also be Assessed

- Original sequence

- GQRWELALGRFLEYLSWVSTLSEQVQEELLSSQVTQELRALMDETMKELKAYKSELEEQLTPVAEETRARLSKELQAAQ
ARLGADMEDVRGRLVQYRGEVQAMLGQSTEELRVRLASHLIALQLRLIGDAFDLQKRLAVYQAGA

- 'Medium' affinity binder: LEU→ALA

- Full sequence:
GQRWELALGRFLEYLSWVSTLSEQVQEELLSSQVTQELRALMDETMKELKAYKSELEEQLTPVAEETRARLSKELQAAQ
ARLGADMEDVRGRLVQYRGEVQAMLGQSTEELRVRLASHLIALQARLIGDAFDLQKRLAVYQAGA

- 'Weakest' affinity binder: ASP → ALA:

- Full sequence:
GQRWELALGRFLEYLSWVSTLSEQVQEELLSSQVTQELRALMDETMKELKAYKSELEEQLTPVAEETRARLSKELQAAQ
ARLGADMEDVRGRLVQYRGEVQAMLGQSTEELRVRLASHLIALQLRLIGAAFDLQKRLAVYQAGA pELNS OFF-CAR Map pELNS(SpeI)_pELNS(SpeI)_PZ1-PARTA-T2A-DAP10-CAR2-CD28zeta(1)
10,913 bp pELNS OFF-CAR

| Design id | LD1 | LD2 | LD3 |
|---|---|---|---|
| Scaffold PDB id | 1LVF | 3GM2 | 1LE4 |
| Scaffold protein name | Syntaxin 6 | FAT Domain | Apolipoprotein E4 |
| Organism of scaffold | Rat | Human | Human |
| Rosetta ddG | -13 | -11 | -14 |
| globularity | 0.81 | 0.86 | 0.86 |
| vdw Dots to scaffold | 1056 | 1238 | 926 |
| SASA of seed | 4794 | 4795 | 4304 |
| # Manual reversions to WT | 3 | 4 | 0 |
| Total # mutations on scaffold | 13 | 12 | 11 |

Figure 15B

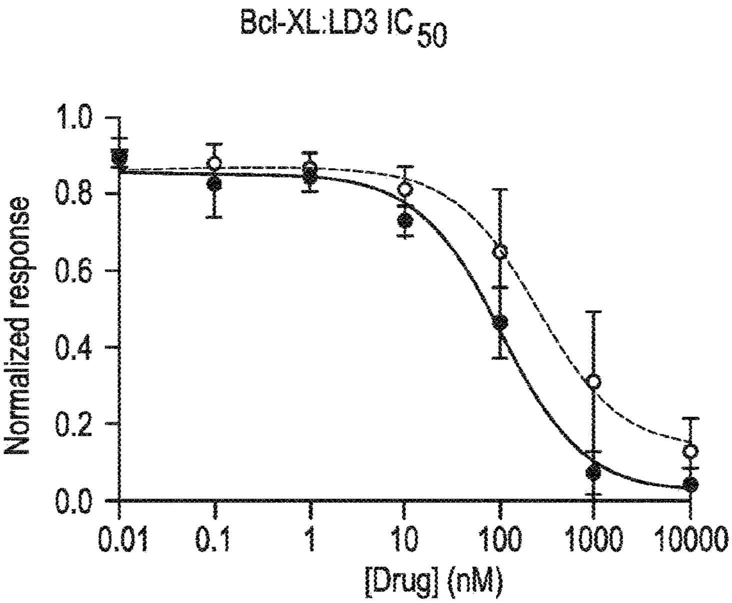
Drug-1
(A-1331852)
$IC_{50}$: 242 nM
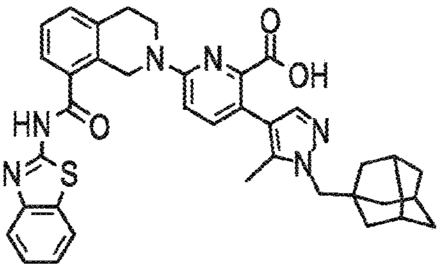
Drug-2
(A-1155463)
$IC_{50}$: 101 nM
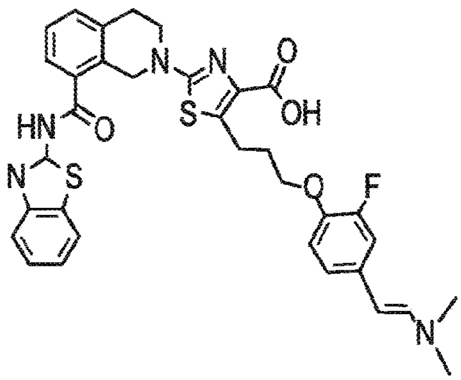
Figure 16D

| Data Collection | | Refinement | |
|---|---|---|---|
| X-ray source[a] | 11C, PAL | Resolution (Å) | 50.0-2.5 |
| Space group | $P6_5$ | No. of reflections | 24082 |
| Unit cell dimensions | | $R_{work}$ / $R_{free}$ (%) | 23.18 / 26.87 |
| a, b, c (Å) | 129.72, 129.72, 80.29 | R.m.s deviations | |
| α, β, γ (°) | 90, 90, 120 | bond lengths (Å) / angles (º) | 0.006 / 0.965 |
| Wavelength (Å) | 1.0000 | Average B-values ($Å^2$) | 61.9 |
| Resolution (Å) | 50.0-2.5 | Ramachandran plot (%) | |
| $R_{sym}$ (%)[b] | 8.2 (23.7) | Most favored/Favored | 89.4 / 10.2 |
| $I/\sigma(I)$ | 21.4 (2.2) | Generously allowed | 0.4 |
| Completeness (>1σ) | 90.0 (67.5) | | |
| Redundancy | 9.7 (2.8) | | |

[a]Beamline 11C at Pohang Accelerator Laboratory

[b]The numbers in parentheses are the statistics from the highest resolution shell.

Figure 18C

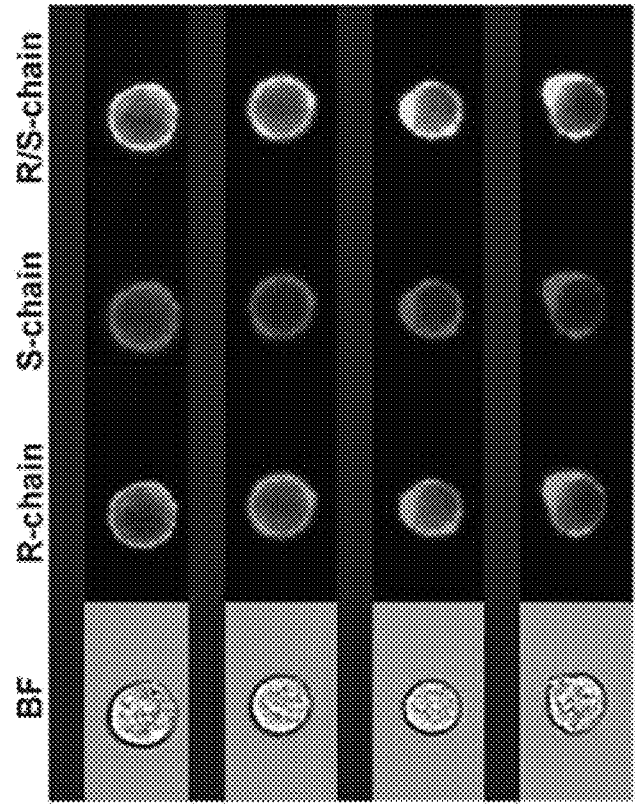
Figure 19B
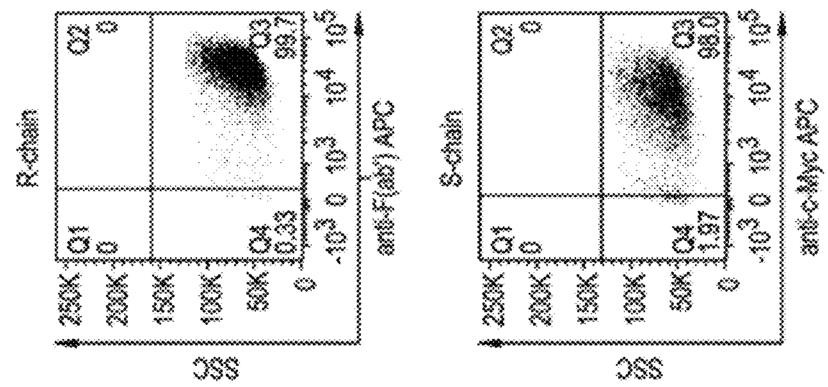

CD8 Leader: MALPVTALLLPLALLLHAARP (SEQ ID NO: 25)
PZ1 scfv:
VQLQQSGPELVKPGTSVRISCKTSGYTFTEYTIHWVKQSHGKSLEWIGNINPNNGGTTYNQKFEDKATLTVDKSSSTAYMELRSLT
SEDSAVYYCAAGWNFDYWGQGTTVTVSSGGGGSGGGGSGGGGSDIVMTQSHKFMSTSVGDRVSIICKASQDVGTAVDWYQ
QKPGQSPKLLIYWASTRHTGVPDRFTGSGSGTDFTLTITNVQSEDLADYFCQQYNSYPLTFGAGTMLDLKR (SEQ ID NO: 6)
Restriction Enzyme: AS
CD8 Hinge: TTTPAPRPPTPAPTIASQPLSLRPEACRPAAGGAVHTRGLDFACD (SEQ ID NO: 9)
CD28 transmembrane domain: FWVLVVVGGVLACYSLLVTVAFIIFWV (SEQ ID NO: 10)
CD28 intracellular domain: RSKRSRLLHSDYMNMTPRRPGPTRKHYQPYAPPRDFAAYRS (SEQ ID NO: 11)
Restriction Enzyme: HM
Ser/Gly linker: GGGGSGGGGSGGGGS (SEQ ID NO: 26)
Des3 :
QRWELALGRFLEYLSWVSTLSEQVQEELLSSQVTQELRALMDETMKELKAYKSELEEQLTPVAEETRARLSKELQAAQARLGADM
EDVRGRLVQYRGEVQAMLGQSTEELRVRLASHLIALQLRLIGDAFDLQKRLAVYQAGAAE (SEQ ID NO: 1)
T2A Peptide: RKRRSGSGRSGSGEGRGSLLTCGDVEENPGP (SEQ ID NO: 27)
Restriction Enzyme: GS
CD8 Leader: MALPVTALLLPLALLLHAARP (SEQ ID NO: 25)
cMyc-Tag: EQKLISEEDL (SEQ ID NO: 28)

Figure 32A

DAP10 ECTO-DOMAIN: QTTPGERSSLPAFYPGTSGSCSGCGSLSLP (SEQ ID NO: 8)
CD8 Hinge: TTTPAPRPPTPAPTIASQPLSLRPEACRPAAGGAVHTRGLDFACD (SEQ ID NO: 9)
Restriction Enzyme: PR
CD28 transmembrane domain: FWVLVVVGGVLACYSLLVTVAFIIFWV (SEQ ID NO: 10)
CD28 intracellular domain: RSKRSRLLHSDYMNMTPRRPGPTRKHYQPYAPPRDFAAYRS (SEQ ID NO: 11)
Restriction Enzyme: PG
Ser/Gly linker: GGGGSGGGGSGGGGS (SEQ ID NO: 26)
BCLXL WT_
MSQSNRELVVDFLSYKLSQKGYSWSQFSDVEENRTEAPEGTESEAVKQALREAGDEFELRYRRAFSDLTSQLHITPGTAYQSFE
QVVNELFRDGVNWGRIVAFFSFGGALCVESVDKEMQVLVSRIAAWMATYLNDHLEPWIQENGGWDTFVELYGNNAAAES
RKGQERED (SEQ ID NO: 5)
Ser/Gly linker: GGGGSGGGGSGGGGS (SEQ ID NO: 26)
Restriction Enzyme: MH
CD3 zeta
RVKFSRSADAPAYQQGQNQLYNELNLGRREEYDVLDKRRGRDPEMGGKPRRKNPQEGLYNELQKDKMAEAYSEIGMKGER
RRGKGHDGLYQGLSTATKDTYDALHMQALPPR (SEQ ID NO: 29)

Figure 32B

BCLXL mut (binding Venetoclax) E96D
MSQSNRELVVDFLSYKLSQKGYSWSQFSDVEENRTEAPEGTESEAVKQALREAGDDFELRYRRAFSDLTSQLHITPGTAYQSFEQVVNE
LFRDGVNWGRIVAFFSFGGALCVESVDKEMQVLVSRIAAWMATYLNDHLEPWIQENGGWDTFVELYGNNAAAESRKGQERED
(SEQ ID NO: 30)

DES3a high affinity variant: GLU124ALA
QRWELALGRFLAYLSWVSTLSEQVQEELLSSQVTQELRALMDETMKELKAYKSELEEQLTPVAEETRARLSKELQAAQARLGADMEDVRG
RLVQYRGEVQAMLGQSTEELRVRLASHLIALQLRLIGDAFDLQKRLAVYQAGAAE (SEQ ID NO: 31)

DES3a medium affinity variant: LEU235ALA
QRWELALGRFLEYLSWVSTLSEQVQEELLSSQVTQELRALMDETMKELKAYKSELEEQLTPVAEETRARLSKELQAAQARLGADMEDVRG
RLVQYRGEVQAMLGQSTEELRVRLASHLIALQARLIGDAFDLQKRLAVYQAGAAE (SEQ ID NO: 32)

DES3a low affinity variant: ASP204ALA
QRWELALGRFLEYLSWVSTLSEQVQEELLSSQVTQELRALMDETMKELKAYKSELEEQLTPVAEETRARLSKELQAAQARLGADMEDVRG
RLVQYRGEVQAMLGQSTEELRVRLASHLIALQLRLIGAAFDLQKRLAVYQAGAAE (SEQ ID NO: 33)

BCL-2
MAHAGRTGYDNREIVMKYIHYKLSQRGYEWDAGDVGAAPPGAAPAPGIFSSQPGHTPHPAASRDPVARTSPLQTPAAPGAAAGPA
LSPVPPVVHLTLRQAGDDFSRRYRRDFAEMSSQLHLTPFTARGRFATVVEELFRDGVNWGRIVAFFEFGGVMCVESVNREMSPLVDNI
ALWMTEYLNRHLHTWIQDNGGWDAFVELYGPSMR (SEQ ID NO: 34)

Figure 32C

Original anti-PSMA STOP CAR

MALPVTALLLPLALLLHAARPVQLQQSGPELVKPGTSVRISCKTSGYTFTEYTIHWVKQSHGKSLEWIGNINPNNGGTTYNQKFEDKATLTVDK
SSSTAYMELRSLTSEDSAVYYCAAGWNFDYWGQGTTVTVSSGGGGSGGGGSGGGGSDIVMTQSHKFMSTSVGDRVSIICKASQDVGTAVD
WYQQKPGQSPKLLIYWASTRHTGVPDRFTGSGSGTDFTLTITNVQSEDLADYFCQQYNSYPLTFGAGTMLDLKRASTTTPAPRPPTPAPTIASQ
PLSLRPEACRPAAGGAVHTRGLDFACDFWVLVVVGGVLACYSLLVTVAFIIFWVRSKRSRLLHSDYMNMTPRRPGPTRKHYQPYAPPRDFAAY
RSHMGGGGSGGGGSGGGGS*QRWELALGRFLEYLSWVSTLSEQVQEELLSSQVTQELRALMDETMKELKAYKSELEEQLTPVAEETRARLSKE*
*LQAAQARLGADMEDVRGRLVQYRGEVQAMLGQSTEELRVRLASHLIALQLRLIGDAFDLQKRLAVYQAGAAE*RKRRSGSGRSGSGEGRGSLL
TCGDVEENPGPGSMALPVTALLLPLALLLHAARPEQKLISEEDLQTTPGERSSLPAFYPGTSGSCSGCGSLSLPTTTPAPRPPTPAPTIASQPLSL
RPEACRPAAGGAVHTRGLDFACDPRFWVLVVVGGVLACYSLLVTVAFIIFWVRSKRSRLLHSDYMNMTPRRPGPTRKHYQPYAPPRDFAAYR
SPGGGGGSGGGGSGGGGSMSQSNRELVVDFLSYKLSQKGYSWSQFSDVEENRTEAPEGTESEAVKQALREAGDEFELRYRRAFSDLTSQLHI
TPGTAYQSFEQVVNELFRDGVNWGRIVAFFSFGGALCVESVDKEMQVLVSRIAAWMATYLNDHLEPWIQENGGWDTFVELYGNNAAAESR
KGQEREDGGGGSGGGGSGGGGSMHRVKFSRSADAPAYQQGQNQLYNELNLGRREEYDVLDKRRGRDPEMGGKPRRKNPQEGLYNELQK
DKMAEAYSEIGMKGERRRGKGHDGLYQGLSTATKDTYDALHMQALPPR
(SEQ ID NO: 35)

Figure 33A anti-PSMA STOP CAR : DES3 WT + BCL-XL Mut (binds venetoclax)

MALPVTALLLPLALLLHAARPVQLQQSGPELVKPGTSVRISCKTSGYTFTEYTIHWVKQSHGKSLEWIGNINPNNGGTTYNQKFEDKATLTV
DKSSSTAYMELRSLTSEDSAVYYCAAGWNFDYWGQGTTVTVSSGGGGSGGGGSGGGGSDIVMTQSHKFMSTSVGDRVSIICKASQDVGT
AVDWYQQKPGQSPKLLIYWASTRHTGVPDRFTGSGSGTDFTLTITNVQSEDLADYFCQQYNSYPLTFGAGTMLDLKRASTTTPAPRPPTPA
PTIASQPLSLRPEACRPAAGGAVHTRGLDFACDFWVLVVVGGVLACYSLLVTVAFIIFWVRSKRSRLLHSDYMNMTPRRPGPTRKHYQPYAP
PRDFAAYRSHMGGGGSGGGGSGGGGS*QRWELALGRFLEYLSWVSTLSEQVQEELLSSQVTQELRALMDETMKELKAYKSELEEQLTPVAE*
*ETRARLSKELQAAQARLGADMEDVRGRLVQYRGEVQAMLGQSTEELRVRLASHLIALQLRLIGDAFDLQKRLAVYQAGAAE*RKRRSGSGRS
GSGEGRGSLLTCGDVEENPGPGSMALPVTALLLPLALLLHAARPEQKLISEEDLQTTPGERSSLPAFYPGTSGSCSGCGSLSLPTTTPAPRPP
TPAPTIASQPLSLRPEACRPAAGGAVHTRGLDFACDPRFWVLVVVGGVLACYSLLVTVAFIIFWVRSKRSRLLHSDYMNMTPRRPGPTRKH
YQPYAPPRDFAAYRSPGGGGGSGGGGSGGGGSMSQSNRELVVDFLSYKLSQKGYSWSQFSDVEENRTEAPEGTESEAVKQALREAGDDF
ELRYRRAFSDLTSQLHITPGTAYQSFEQVVNELFRDGVNWGRIVAFFSFGGALCVESVDKEMQVLVSRIAAWMATYLNDHLEPWIQENGG
WDTFVELYGNNAAAESRKGQEREDGGGGSGGGGSGGGGSMHRVKFSRSADAPAYQQGQNQLYNELNLGRREEYDVLDKRRGRDPEM
GGKPRRKNPQEGLYNELQKDKMAEAYSEIGMKGERRRGKGHDGLYQGLSTATKDTYDALHMQALPPR
(SEQ ID NO: 36)

Figure 33B anti-PSMA STOP CAR : DES3 WT + BCL-2 (binds venetoclax)

MALPVTALLLPLALLLHAARPVQLQQSGPELVKPGTSVRISCKTSGYTFTEYTIHWVKQSHGKSLEWIGNINPNNGGTTYNQKFEDKATLTVD
KSSSTAYMELRSLTSEDSAVYYCAAGWNFDYWGQGTTVTVSSGGGGSGGGGSGGGGSDIVMTQSHKFMSTSVGDRVSIICKASQDVGTAV
DWYQQKPGQSPKLLIYWASTRHTGVPDRFTGSGSGTDFTLTITNVQSEDLADYFCQQYNSYPLTFGAGTMLDLKRASTTTPAPRPPTPAPTIA
SQPLSLRPEACRPAAGGAVHTRGLDFACDFWVLVVVGGVLACYSLLVTVAFIIFWVRSKRSRLLHSDYMNMTPRRPGPTRKHYQPYAPPRDF
AAYRSHMGGGGSGGGGSGGGGS*QRWELALGRFLEYLSWVSTLSEQVQEELLSSQVTQELRALMDETMKELKAYKSELEEQLTPVAEETRA*
*RLSKELQAAQARLGADMEDVRGRLVQYRGEVQAMLGQSTEELRVRLASHLIALQLRLIGDAFDLQKRLAVYQAGAAE*RKRRSGSGRSGSGE
GRGSLLTCGDVEENPGPGSMALPVTALLLPLALLLHAARPEQKLISEEDLQTTPGERSSLPAFYPGTSGSCSGCGSLSLPTTTPAPRPPTPAPTI
ASQPLSLRPEACRPAAGGAVHTRGLDFACDPRFWVLVVVGGVLACYSLLVTVAFIIFWVRSKRSRLLHSDYMNMTPRRPGPTRKHYQPYAP
PRDFAAYRSPGGGGGSGGGGSGGGGSMAHAGRTGYDNREIVMKYIHYKLSQRGYEWDAGDVGAAPPGAAPAPGIFSSQPGHTPHPAAS
RDPVARTSPLQTPAAPGAAAGPALSPVPPVVHLTLRQAGDDFSRRYRRDFAEMSSQLHLTPFTARGRFATVVEELFRDGVNWGRIVAFFEFG
GVMCVESVNREMSPLVDNIALWMTEYLNRHLHTWIQDNGGWDAFVELYGPSMRGGGGSGGGGSGGGGSMHRVKFSRSADAPAYQQ
GQNQLYNELNLGRREEYDVLDKRRGRDPEMGGKPRRKNPQEGLYNELQKDKMAEAYSEIGMKGERRRGKGHDGLYQGLSTATKDTYDAL
HMQALPPR
(SEQ ID NO: 37)

Figure 33C anti-PSMA STOP CAR : DES3 a + BCL-XL Mut (binds venetoclax)

MALPVTALLLPLALLLHAARPVQLQQSGPELVKPGTSVRISCKTSGYTFTEYTIHWVKQSHGKSLEWIGNINPNNGGTTYNQKFEDKATLTVDK
SSSTAYMELRSLTSEDSAVYYCAAGWNFDYWGQGTTVTVSSGGGGSGGGGSGGGGSDIVMTQSHKFMSTSVGDRVSIICKASQDVGTAVD
WYQQKPGQSPKLLIYWASTRHTGVPDRFTGSGSGTDFTLTITNVQSEDLADYFCQQYNSYPLTFGAGTMLDLKRASTTTPAPRPPTPAPTIASQ
PLSLRPEACRPAAGGAVHTRGLDFACDFWVLVVVGGVLACYSLLVTVAFIIFWVRSKRSRLLHSDYMNMTPRRPGPTRKHYQPYAPPRDFAAY
RSHMGGGGSGGGGSGGGGSQ*QRWELALGRFLAYLSWVSTLSEQVQEELLSSQVTQELRALMDETMKELKAYKSELEEQLTPVAEETRARLS*
*KELQAAQARLGADMEDVRGRLVQYRGEVQAMLGQSTEELRVRLASHLIALQLRLIGDAFDLQKRLAVYQAGAAE*RKRRSGSGRSGSGEGRG
SLLTCGDVEENPGPGSMALPVTALLLPLALLLHAARPEQKLISEEDLQTTPGERSSLPAFYPGTSGSCSGCGSLSLPTTTPAPRPPTPAPTIASQPL
SLRPEACRPAAGGAVHTRGLDFACDPRFWVLVVVGGVLACYSLLVTVAFIIFWVRSKRSRLLHSDYMNMTPRRPGPTRKHYQPYAPPRDFAA
YRSPGGGGGSGGGGSGGGGSMSQSNRELVVDFLSYKLSQKGYSWSQFSDVEENRTEAPEGTESEAVKQALREAGDDFELRYRRAFSDLTSQ
LHITPGTAYQSFEQVVNELFRDGVNWGRIVAFFSFGGALCVESVDKEMQVLVSRIAAWMATYLNDHLEPWIQENGGWDTFVELYGNNAAA
ESRKGQEREDGGGGSGGGGSGGGGSMHRVKFSRSADAPAYQQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR
(SEQ ID NO: 38)

Figure 33D anti-PSMA STOP CAR : DES3 b + BCL-XL Mut (binds venetoclax)

MALPVTALLLPLALLLHAARPVQLQQSGPELVKPGTSVRISCKTSGYTFTEYTIHWVKQSHGKSLEWIGNINPNNGGTTYNQKFEDKATLTVD
KSSSTAYMELRSLTSEDSAVYYCAAGWNFDYWGQGTTVTVSSGGGGSGGGGSGGGGSDIVMTQSHKFMSTSVGDRVSIICKASQDVGTA
VDWYQQKPGQSPKLLIYWASTRHTGVPDRFTGSGSGTDFTLTITNVQSEDLADYFCQQYNSYPLTFGAGTMLDLKRASTTTPAPRPPTPAPTI
ASQPLSLRPEACRPAAGGAVHTRGLDFACDFWVLVVVGGVLACYSLLVTVAFIIFWVRSKRSRLLHSDYMNMTPRRPGPTRKHYQPYAPPR
DFAAYRSHMGGGGSGGGGSGGGGSQ*QRWELALGRFLEYLSWVSTLSEQVQEELLSSQVTQELRALMDETMKELKAYKSELEEQLTPVAEE*
*TRARLSKELQAAQARLGADMEDVRGRLVQYRGEVQAMLGQSTEELRVRLASHLIALQARLIGDAFDLQKRLAVYQAGAAE*RKRRSGSGRSG
SGEGRGSLLTCGDVEENPGPGSMALPVTALLLPLALLLHAARPEQKLISEEDLQTTPGERSSLPAFYPGTSGSCSGCGSLSLPTTTPAPRPPTP
APTIASQPLSLRPEACRPAAGGAVHTRGLDFACDPRFWVLVVVGGVLACYSLLVTVAFIIFWVRSKRSRLLHSDYMNMTPRRPGPTRKHYQ
PYAPPRDFAAYRSPGGGGGSGGGGSGGGGSMSQSNRELVVDFLSYKLSQKGYSWSQFSDVEENRTEAPEGTESEAVKQALREAGDDFELR
YRRAFSDLTSQLHITPGTAYQSFEQVVNELFRDGVNWGRIVAFFSFGGALCVESVDKEMQVLVSRIAAWMATYLNDHLEPWIQENGGWDT
FVELYGNNAAAESRKGQEREDGGGGSGGGGSGGGGSMHRVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATKDTYDALHMQALPPR
(SEQ ID NO: 39)

Figure 33E anti-PSMA STOP CAR : DES3 c + BCL-XL Mut (binds venetoclax)

MALPVTALLLPLALLLHAARPVQLQQSGPELVKPGTSVRISCKTSGYTFTEYTIHWVKQSHGKSLEWIGNINPNNGGTTYNQKFE
DKATLTVDKSSSTAYMELRSLTSEDSAVYYCAAGWNFDYWGQGTTVTVSSGGGGSGGGGSGGGGSDIVMTQSHKFMSTSVG
DRVSIICKASQDVGTAVDWYQQKPGQSPKLLIYWASTRHTGVPDRFTGSGSGTDFTLTITNVQSEDLADYFCQQYNSYPLTFGAG
TMLDLKRASTTTPAPRPPTPAPTIASQPLSLRPEACRPAAGGAVHTRGLDFACDFWVLVVVGGVLACYSLLVTVAFIIFWVRSKRS
RLLHSDYMNMTPRRPGPTRKHYQPYAPPRDFAAYRSHMGGGGSGGGGSGGGGSQ*QRWELALGRFLEYLSWVSTLSEQVQE*
*ELLSSQVTQELRALMDETMKELKAYKSELEEQLTPVAEETRARLSKELQAAQARLGADMEDVRGRLVQYRGEVQAMLGQSTEEL*
*RVRLASHLIALQLRLIGAAFDLQKRLAVYQAGAAE*RKRRSGSGRSGSGEGRGSLLTCGDVEENPGPGSMALPVTALLLPLALLLH
AARPEQKLISEEDLQTTPGERSSLPAFYPGTSGSCSGCGSLSLPTTTPAPRPPTPAPTIASQPLSLRPEACRPAAGGAVHTRGLDFA
CDPRFWVLVVVGGVLACYSLLVTVAFIIFWVRSKRSRLLHSDYMNMTPRRPGPTRKHYQPYAPPRDFAAYRSPGGGGGSGGG
GSGGGGSMSQSNRELVVDFLSYKLSQKGYSWSQFSDVEENRTEAPEGTESEAVKQALREAGDDFELRYRRAFSDLTSQLHITPG
TAYQSFEQVVNELFRDGVNWGRIVAFFSFGGALCVESVDKEMQVLVSRIAAWMATYLNDHLEPWIQENGGWDTFVELYGNN
AAAESRKGQEREDGGGGSGGGGSGGGGSMHRVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATKDTYDALHMQALPPR
(SEQ ID NO: 40)

Figure 33F anti-PSMA STOP CAR : DES3 a + BCL2 (binds venetoclax)

MALPVTALLLPLALLLHAARPVQLQQSGPELVKPGTSVRISCKTSGYTFTEYTIHWVKQSHGKSLEWIGNINPNNGGTTYNQKFED
KATLTVDKSSSTAYMELRSLTSEDSAVYYCAAGWNFDYWGQGTTVTVSSGGGGSGGGGSGGGGSDIVMTQSHKFMSTSVGDRV
SIICKASQDVGTAVDWYQQKPGQSPKLLIYWASTRHTGVPDRFTGSGSGTDFTLTITNVQSEDLADYFCQQYNSYPLTFGAGTMLD
LKRASTTTPAPRPPTPAPTIASQPLSLRPEACRPAAGGAVHTRGLDFACDFWVLVVVGGVLACYSLLVTVAFIIFWVRSKRSRLLHSD
YMNMTPRRPGPTRKHYQPYAPPRDFAAYRSHMGGGGSGGGGSGGGGS*QQRWELALGRFLAYLSWVSTLSEQVQEELLSSQVT*
*QELRALMDETMKELKAYKSELEEQLTPVAEETRARLSKELQAAQARLGADMEDVRGRLVQYRGEVQAMLGQSTEELRVRLASHLI*
*ALQLRLIGDAFDLQKRLAVYQAGAAE*RKRRSGSGRSGSGEGRGSLLTCGDVEENPGPGSMALPVTALLLPLALLLHAARPEQKLISE
EDLQTTPGERSSLPAFYPGTSGSCSGCGSLSLPTTTPAPRPPTPAPTIASQPLSLRPEACRPAAGGAVHTRGLDFACDPRFWVLVVV
GGVLACYSLLVTVAFIIFWVRSKRSRLLHSDYMNMTPRRPGPTRKHYQPYAPPRDFAAYRSPGGGGGSGGGGSGGGGSMAHA
GRTGYDNREIVMKYIHYKLSQRGYEWDAGDVGAAPPGAAPAPGIFSSQPGHTPHPAASRDPVARTSPLQTPAAPGAAAGPALSP
VPPVVHLTLRQAGDDFSRRYRRDFAEMSSQLHLTPFTARGRFATVVEELFRDGVNWGRIVAFFEFGGVMCVESVNREMSPLVDNI
ALWMTEYLNRHLHTWIQDNGGWDAFVELYGPSMRGGGGSGGGGSGGGGSMHRVKFSRSADAPAYQQGQNQLYNELNLGR
REEYDVLDKRRGRDPEMGGKPRRKNPQEGLYNELQKDKMAEAYSEIGMKGERRRGKGHDGLYQGLSTATKDTYDALHMQALPP
R
(SEQ ID NO: 41)

Figure 33G anti-PSMA STOP CAR : DES3 b + BCL2 (binds venetoclax)

MALPVTALLLPLALLLHAARPVQLQQSGPELVKPGTSVRISCKTSGYTFTEYTIHWVKQSHGKSLEWIGNINPNNGGTTYNQKF
EDKATLTVDKSSSTAYMELRSLTSEDSAVYYCAAGWNFDYWGQGTTVTVSSGGGGSGGGGSGGGGSDIVMTQSHKFMSTSV
GDRVSIICKASQDVGTAVDWYQQKPGQSPKLLIYWASTRHTGVPDRFTGSGSGTDFTLTITNVQSEDLADYFCQQYNSYPLTFG
AGTMLDLKRASTTTPAPRPPTPAPTIASQPLSLRPEACRPAAGGAVHTRGLDFACDFWVLVVVGGVLACYSLLVTVAFIIFWVRS
KRSRLLHSDYMNMTPRRPGPTRKHYQPYAPPRDFAAYRSHMGGGGSGGGGSGGGGS*QQRWELALGRFLEYLSWVSTLSE*
*QVQEELLSSQVTQELRALMDETMKELKAYKSELEEQLTPVAEETRARLSKELQAAQARLGADMEDVRGRLVQYRGEVQAMLG*
*QSTEELRVRLASHLIALQARLIGDAFDLQKRLAVYQAGAAE*RKRRSGSGRSGSGEGRGSLLTCGDVEENPGPGSMALPVTALLL
PLALLLHAARPEQKLISEEDLQTTPGERSSLPAFYPGTSGSCSGCGSLSLPTTTPAPRPPTPAPTIASQPLSLRPEACRPAAGGAV
HTRGLDFACDPRFWVLVVVGGVLACYSLLVTVAFIIFWVRSKRSRLLHSDYMNMTPRRPGPTRKHYQPYAPPRDFAAYRSPG
GGGGSGGGGSGGGGSMAHAGRTGYDNREIVMKYIHYKLSQRGYEWDAGDVGAAPPGAAPAPGIFSSQPGHTPHPAASRD
PVARTSPLQTPAAPGAAAGPALSPVPPVVHLTLRQAGDDFSRRYRRDFAEMSSQLHLTPFTARGRFATVVEELFRDGVNWGRI
VAFFEFGGVMCVESVNREMSPLVDNIALWMTEYLNRHLHTWIQDNGGWDAFVELYGPSMRGGGGSGGGGSGGGGSMH
RVKFSRSADAPAYQQGQNQLYNELNLGRREEYDVLDKRRGRDPEMGGKPRRKNPQEGLYNELQKDKMAEAYSEIGMKGERR
RGKGHDGLYQGLSTATKDTYDALHMQALPPR
(SEQ ID NO: 42)

Figure 33H anti-PSMA STOP CAR : DES3 c + BCL2 (binds venetoclax)

MALPVTALLLPLALLLHAARPVQLQQSGPELVKPGTSVRISCKTSGYTFTEYTIHWVKQSHGKSLEWIGNINPNNGGTTYNQKFEDK
ATLTVDKSSSTAYMELRSLTSEDSAVYYCAAGWNFDYWGQGTTVTVSSGGGGSGGGGSGGGGSDIVMTQSHKFMSTSVGDRVSII
CKASQDVGTAVDWYQQKPGQSPKLLIYWASTRHTGVPDRFTGSGSGTDFTLTITNVQSEDLADYFCQQYNSYPLTFGAGTMLDLK
RASTTTPAPRPPTPAPTIASQPLSLRPEACRPAAGGAVHTRGLDFACDFWVLVVVGGVLACYSLLVTVAFIIFWVRSKRSRLLHSDYM
NMTPRRPGPTRKHYQPYAPPRDFAAYRSHMGGGGSGGGGSGGGGS*QQRWELALGRFLEYLSWVSTLSEQVQEELLSSQVTQEL*
*RALMDETMKELKAYKSELEEQLTPVAEETRARLSKELQAAQARLGADMEDVRGRLVQYRGEVQAMLGQSTEELRVRLASHLIALQL*
*RLIGAAFDLQKRLAVYQAGAAE*RKRRSGSGRSGSGEGRGSLLTCGDVEENPGPGSMALPVTALLLPLALLLHAARPEQKLISEEDLQ
TTPGERSSLPAFYPGTSGSCSGCGSLSLPTTTPAPRPPTPAPTIASQPLSLRPEACRPAAGGAVHTRGLDFACDPRFWVLVVVGGVL
ACYSLLVTVAFIIFWVRSKRSRLLHSDYMNMTPRRPGPTRKHYQPYAPPRDFAAYRSPGGGGGSGGGGSGGGGSMAHAGRTGY
DNREIVMKYIHYKLSQRGYEWDAGDVGAAPPGAAPAPGIFSSQPGHTPHPAASRDPVARTSPLQTPAAPGAAAGPALSPVPPVVH
LTLRQAGDDFSRRYRRDFAEMSSQLHLTPFTARGRFATVVEELFRDGVNWGRIVAFFEFGGVMCVESVNREMSPLVDNIALWMTE
YLNRHLHTWIQDNGGWDAFVELYGPSMRGGGGSGGGGSGGGGSMHRVKFSRSADAPAYQQGQNQLYNELNLGRREEYDVLD
KRRGRDPEMGGKPRRKNPQEGLYNELQKDKMAEAYSEIGMKGERRRGKGHDGLYQGLSTATKDTYDALHMQALPPR
(SEQ ID NO: 43)

Figure 33I

List of the single components:

VH murine 14F7
QVQLQQSGASMKMSCRASGYSFTSYWIHWLKQRPDQGLEWIGYIDPATAYTESNQKFKDKAILTADRSSNTAFMYLNSLTSEDSAVYYCARESPRLRRGIYYYAMDY
WGQGTSVTVSSAPQAKSSGSGSESKVD (SEQ ID NO: 44)

Ser/Gly linker: GGGGSGGGGSGGGGS (SEQ ID NO: 26)

VL murine 3FMmut
DIQMTQTPSSLSASLGDRVTISCRASQDISNYLNWYQQKPDGTVKLLIYYTSRLHSGVPSRFSGSGSGTDYSLTISNLEQEDIATYFCQQGNTLPPTFGAGTKLELK
(SEQ ID NO: 45)

7AH human VL 14F7
GSESKVDQSVVTQPPSASGGPGQSLTISCTGTSSDVGGYNHVSWYQQHPGKAPKLMIYDVSKRPSGVPHRFSGSKSGNTASLTVSGLQAEDEAVYYCSSYAGSNNL
VFGGGTKVTVL (SEQ ID NO: 46)

7BH human VL 14F7
GSESKVDDIQMTQTPSSLSASVGDRVTITCRASQSISSFLNWYQQKPGKAPKLLIYAASNLQSGVPSRFSGRGSGTDFTLTISSLQPEDFAAYYCQQGYTTPLTFGQGT
KLE (SEQ ID NO: 47)

8BH human VL 14F7
GSESKVDSSELTQDPAVSVALGQTVRITCQGDSLRSYYASWYQQKPGQAPVLVIYGKNNRPSGIPDRFSGSSSGNTASLTITGAQAEDEADYYCNSRDSSGNHVVFG
GGTKLTVL (SEQ ID NO: 48)

Figure 34A

List of the possible scFv:

CD19scfv

GSDIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEITGSTSG
SGKPGSGEGSTKGEVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHY
YYGGSYAMDYWGQGTSVTVSS (SEQ ID NO: 49)

anti-14F7-VHVH

QVQLQQSGASMKMSCRASGYSFTSYWIHWLKQRPDQGLEWIGYIDPATAYTESNQKFKDKAILTADRSSNTAFMYLNSLTSEDSAVYYCARESPRLRRGIYYYAMDYWGQGT
SVTVSSAPQAKSSGSGSESKVDQVQLQQSGASMKMSCRASGYSFTSYWIHWLKQRPDQGLEWIGYIDPATAYTESNQKFKDKAILTADRSSNTAFMYLNSLTSEDSAVYYCAR
ESPRLRRGIYYYAMDYWGQGTSVTVSSAPQAKSSGSGSESKVD (SEQ ID NO: 50)

anti-14F7-VHVH with linker

QVQLQQSGASMKMSCRASGYSFTSYWIHWLKQRPDQGLEWIGYIDPATAYTESNQKFKDKAILTADRSSNTAFMYLNSLTSEDSAVYYCARESPRLRRGIYYYAMDYWGQGT
SVTVSSAPQAKSSGSGSESKVDGGGGSGGGGSGGGGSQVQLQQSGASMKMSCRASGYSFTSYWIHWLKQRPDQGLEWIGYIDPATAYTESNQKFKDKAILTADRSSNTAF
MYLNSLTSEDSAVYYCARESPRLRRGIYYYAMDYWGQGTSVTVSSAPQAKSSGSGSESKVD (SEQ ID NO: 51)

anti-14F7-VH-7AH

QVQLQQSGASMKMSCRASGYSFTSYWIHWLKQRPDQGLEWIGYIDPATAYTESNQKFKDKAILTADRSSNTAFMYLNSLTSEDSAVYYCARESPRLRRGIYYYAMDYWGQGT
SVTVSSAPQAKSSGSGSESKVDGSESKVDQSVVTQPPSASGGPGQSLTISCTGTSSDVGGYNHVSWYQQHPGKAPKLMIYDVSKRPSGVPHRFSGSKSGNTASLTVSGLQAE
DEAVYYCSSYAGSNNLVFGGGTKVTVL (SEQ ID NO: 52)

anti-14F7-VH-linker-7AH

QVQLQQSGASMKMSCRASGYSFTSYWIHWLKQRPDQGLEWIGYIDPATAYTESNQKFKDKAILTADRSSNTAFMYLNSLTSEDSAVYYCARESPRLRRGIYYYAMDYWGQGT
SVTVSSAPQAKSSGSGSESKVDGGGGSGGGGSGGGGSGSESKVDQSVVTQPPSASGGPGQSLTISCTGTSSDVGGYNHVSWYQQHPGKAPKLMIYDVSKRPSGVPHRFSG
SKSGNTASLTVSGLQAEDEAVYYCSSYAGSNNLVFGGGTKVTVL (SEQ ID NO: 53)

Figure 34B anti-14F7-VH-7BH
QVQLQQSGASMKMSCRASGYSFTSYWIHWLKQRPDQGLEWIGYIDPATAYTESNQKFKDKAILTADRSSNTAFMYLNSLTSEDSAVYYCARESPRLRR
GIYYYAMDYWGQGTSVTVSSAPQAKSSGSGSESKVDGSESKVDDIQMTQTPSSLSASVGDRVTITCRASQSISSFLNWYQQKPGKAPKLLIYAASNLQ
SGVPSRFSGRGSGTDFTLTISSLQPEDFAAYYCQQGYTTPLTFGQGTKLE (SEQ ID NO: 54)

anti-14F7-VH-linker-7BH
QVQLQQSGASMKMSCRASGYSFTSYWIHWLKQRPDQGLEWIGYIDPATAYTESNQKFKDKAILTADRSSNTAFMYLNSLTSEDSAVYYCARESPRLRR
GIYYYAMDYWGQGTSVTVSSAPQAKSSGSGSESKVDGGGGSGGGGSGGGGSGSESKVDDIQMTQTPSSLSASVGDRVTITCRASQSISSFLNWYQ
QKPGKAPKLLIYAASNLQSGVPSRFSGRGSGTDFTLTISSLQPEDFAAYYCQQGYTTPLTFGQGTKLE (SEQ ID NO: 55)

anti-14F7-VH-8BH
QVQLQQSGASMKMSCRASGYSFTSYWIHWLKQRPDQGLEWIGYIDPATAYTESNQKFKDKAILTADRSSNTAFMYLNSLTSEDSAVYYCARESPRLRR
GIYYYAMDYWGQGTSVTVSSAPQAKSSGSGSESKVDGSESKVDSSELTQDPAVSVALGQTVRITCQGDSLRSYYASWYQQKPGQAPVLVIYGKNNRP
SGIPDRFSGSSSGNTASLTITGAQAEDEADYYCNSRDSSGNHVVFGGGTKLTVL (SEQ ID NO: 56)

anti-14F7-VH-linker-8BH
QVQLQQSGASMKMSCRASGYSFTSYWIHWLKQRPDQGLEWIGYIDPATAYTESNQKFKDKAILTADRSSNTAFMYLNSLTSEDSAVYYCARESPRLRR
GIYYYAMDYWGQGTSVTVSSAPQAKSSGSGSESKVDGGGGSGGGGSGGGGSGSESKVDSSELTQDPAVSVALGQTVRITCQGDSLRSYYASWYQQK
PGQAPVLVIYGKNNRPSGIPDRFSGSSSGNTASLTITGAQAEDEADYYCNSRDSSGNHVVFGGGTKLTVL (SEQ ID NO: 57)

Figure 34C

2aM murine VL 14F7
GSESKVDDIVMFQSPASLAVSLGQRATISCRASQSVSSSSYSYMHWYQQKPGQPPKLLIKYASNLESGVPARFSGSGSGTDFTLNIHPVEEEDAATYY
CQHSRDVPLTFGAGTKLEIK (SEQ ID NO: 58)
3fM murine VL 14F7
GSESKVDDIQMTQTPSSLSASLGDRVTISCRASQDISNYLNWYQQKPDGTVKLLIVYTSRLHSGVPSRFSGSGSGTDYSLTISNLEQEDIATYFCQQG
NTLPPTFGAGTKLELK (SEQ ID NO: 59)

Murine VH-2aM murine VL (14F7)
QVQLQQSGASMKMSCRASGYSFTSYWIHWLKQRPDQGLEWIGYIDPATAYTESNQKFKDKAILTADRSSNTAFMYLNSLTSEDSAVYYCARESPRL
RRGIYYYAMDYWGQGTSVTVSSAPQAKSSGSGSESKVDGSESKVDDIVMFQSPASLAVSLGQRATISCRASQSVSSSSYSYMHWYQQKPGQPPKL
LIKYASNLESGVPARFSGSGSGTDFTLNIHPVEEEDAATYYCQHSRDVPLTFGAGTKLEIK (SEQ ID NO: 60)

Murine VH-Linker-2aM murine VL (14F7)
QVQLQQSGASMKMSCRASGYSFTSYWIHWLKQRPDQGLEWIGYIDPATAYTESNQKFKDKAILTADRSSNTAFMYLNSLTSEDSAVYYCARESPRLR
RGIYYYAMDYWGQGTSVTVSSAPQAKSSGSGSESKVDGGGGSGGGGSGGGGSGSESKVDDIVMFQSPASLAVSLGQRATISCRASQSVSSSSYSY
MHWYQQKPGQPPKLLIKYASNLESGVPARFSGSGSGTDFTLNIHPVEEEDAATYYCQHSRDVPLTFGAGTKLEIK (SEQ ID NO: 61)

Murine VH-3fM murine VL (14F7)
QVQLQQSGASMKMSCRASGYSFTSYWIHWLKQRPDQGLEWIGYIDPATAYTESNQKFKDKAILTADRSSNTAFMYLNSLTSEDSAVYYCARESPR
LRRGIYYYAMDYWGQGTSVTVSSAPQAKSSGSGSESKVDGSESKVDDIQMTQTPSSLSASLGDRVTISCRASQDISNYLNWYQQKPDGTVKLLIV
YTSRLHSGVPSRFSGSGSGTDYSLTISNLEQEDIATYFCQQGNTLPPTFGAGTKLELK (SEQ ID NO: 62)

Murine VH-Linker-3fM murine VL (14F7)
QVQLQQSGASMKMSCRASGYSFTSYWIHWLKQRPDQGLEWIGYIDPATAYTESNQKFKDKAILTADRSSNTAFMYLNSLTSEDSAVYYCARESPRL
RRGIYYYAMDYWGQGTSVTVSSAPQAKSSGSGSESKVDGGGGSGGGGSGGGGSGSESKVDDIQMTQTPSSLSASLGDRVTISCRASQDISNYLN
WYQQKPDGTVKLLIVYTSRLHSGVPSRFSGSGSGTDYSLTISNLEQEDIATYFCQQGNTLPPTFGAGTKLELK (SEQ ID NO: 63)

Figure 34D

Anti-NGcGM3 14F7-derived CARs:

Functional 14F7 derived scFv variants

Properties of $V_L$ regions forming binding sites to *N*-glycolyl GM3

| $V_L$ region | Origin | Isotype | 14F7 $V_L$ identity (%) | Kabat's subgroup |
|---|---|---|---|---|
| 14F7 Mab | Murine | Kappa | -- | V |
| scFv 2Am | Murine | Kappa | 59.46 | III |
| scFv 3Fm | Murine | Kappa | 59.81 | V |
| scFv 7Bhk | Human | Kappa | 60.74 | I |
| scFv 7Ahl | Human | Lambda | 35.45 | I |
| scFv 8Bhl | Human | Lambda | 37.04 | III |

(Rojas et al, J of Immunological Methods, 2004)

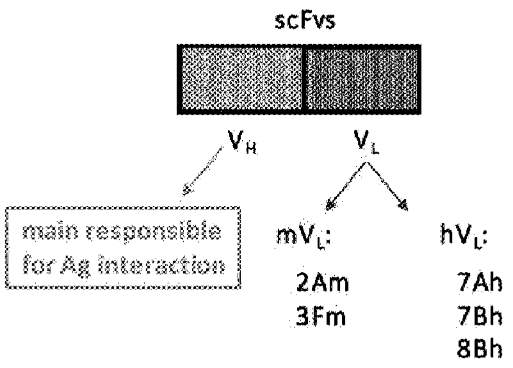

VH is murine
2Am and 3Fm are murine
7Ah, 7bH and 8Bh are human

Figure 34E

STOP-CAR original version (DES3 high affinity+WT BCL-XL)

Actagaaatggccttaccagtgaccgccttgctcctgccgctggccttgctgctccacgccgccaggccggtgcagctgcagcagtcaggacctgaactggtgaagcctgggacttcagtgaggatatcctgcaagacttctggatacacattcactgaatata
ccatacactgggtgaagcagagccatggaaagagccttgagtggattggaaacatcaatcctaacaatggtggtaccacctacaatcagaagttcgaggacaaggccacattgactgtagacaagtcctccagtacagcctacatggagctccgcagcctaa
catctgaggattctgcagtctattattgtgcagctggttggaactttgactactggggccaagggaccacggtcaccgtctcctcaggtggaggtggatcaggtggaggtggatctggtggaggtggatctgacattgtgatgacccagtctcacaaattcatgtc
cacatcagtaggagacagggtcagcatcatctgtaaggccagtcaagatgtgggtactgctgtagactggtatcaacagaaaccaggacaatctcctaaactactgatttattgggcatccactcggcacactggagtccctgatcgcttcacaggcagtggat
ctgggacagacttcactctcaccattactaatgttcagtctgaagacttggcagattatttctgtcagcaatataacagctatccctcacgttcggtgctgggaccatgctggacctgaaacgggctagcACAACAACCCCTGCCCCCAGACCTCCT
ACCCCAGCCCCTACAATTGCCAGCCAGCCTCTGAGCCTGAGGCCCGAGGCTTGTAGACCTGCTGCTGGCGGAGCCGTGCACACCAGAGGACTGGATTTCGCCTGCGACTTCTGGGTGCTGGTGG
TCGTGGGCGGAGTGCTGGCCTGTTACAGCCTGCTCGTGACCGTGGCCTTCATCATCTTTTGGGTGCGGAGCAAGAGAAGCAGACTGCTGCACAGCGACTACATGAACATGACCCCCAGACGGCCT
GGCCCCACCAGAAAGCACTACCAGCCTTACGCCCCTCCCAGAGACTTCGCCGCCTACAGATCTcatatgGGAGGCGGAGGATCTGGCGGAGGTGGAAGTGGCGGAGGCGGATCTCAAAGATGGGA
ACTCGCCCTGGGCAGATTCCTGGAATACCTGAGCTGGGTGTCCACACTGAGCGAACAGGTGCAAGAGGAACTGCTGAGCAGCCAAGTGACCCAAGAGCTGAGAGCCCTGATGGACGAGACAA
TGAAGGAACTGAAGGCCTACAAGAGCGAGCTGGAAGAACAGCTGACCCCTGTGGCCGAGGAAACCAGAGCCAGACTGAGCAAAGAACTGCAGGCCGCTCAGGCCAGACTGGGAGCCGATAT
GGAAGATGTTCGGGGCAGACTGGTGCAGTACAGAGGCGAAGTTCAGGCCATGCTGGGCCAGTCTACCGAGGAACTGAGAGTGCGGCTGGCCTCTCATCTGATTGCCCTGCAGCTGAGACTGAT
CGGCGACGCATTCGACCTGCAGAAAAGACTGGCCGTGTACCAGGCTGGCGCTGCTGAACGGAAGCGGCGCAGCGGCAGCGGGCGCAGCGGCAGCGGCgagggcagaggaagtcttctaacatgcggtga
cgtggaggagaatcccggccctggatccatggccttaccagtgaccgccttgctcctgccgctggccttgctgctccacgccgccaggccggaacagaaactcatcagtgaggaagatttgcagacgactccaggagagagatcatcactccctgcctttac
cctggcacttcaggctcttgttccggatgtgggtccctctctctgccgACAACAACCCCTGCCCCCAGACCTCCTACCCCAGCCCCTACAATTGCCAGCCAGCCTCTGAGCCTGAGGCCCGAGGCTTGTAGACCTGCTG
CTGGCGGAGCCGTGCACACCAGAGGACTGGATTTCGCCTGCGAcctaggTTCTGGGTGCTGGTGGTCGTGGGCGGAGTGCTGGCCTGTTACAGCCTGCTCGTGACCGTGGCCTTCATCATCTTTTGG
GTGCGGAGCAAGAGAAGCAGACTGCTGCACAGCGACTACATGAACATGACCCCCAGACGGCCTGGCCCCACCAGAAAGCACTACCAGCCTTACGCCCCTCCCAGAGACTTCGCCGCCTACAGATC
TcccgggGGAGGCGGAGGATCTGGCGGAGGTGGAAGTGGCGGAGGCGGATCTATGAGCCAGAGCAACAGAGAACTGGTGGTGGACTTCCTGAGCTACAAGCTGAGCCAGAAGGGCTACAGCT
GGTCCCAGTTCAGCGACGTGGAAGAGAACAGAACAGAGGCCCCTGAGGGCACAGAGTCTGAGGCTGTGAAACAGGCCCTGAGAGAAGCCGGCGACGAGTTCGAGCTGAGATACAGAAGGG
CCTTCAGCGACCTGACCAGCCAGCTGCACATCACACCTGGCACAGCCTACCAGAGCTTCGAGCAGGTCGTGAACGAGCTGTTCAGAGATGGCGTGAACTGGGGCAGAATCGTGGCCTTCTTCAG
CTTTGGCGGAGCCCTGTGTGTGGAAAGCGTGGACAAAGAAATGCAGGTCCTGGTGTCCAGAATCGCCGCCTGGATGGCCACCTACCTGAACGATCATCTGGAACCCTGGATtCAAGAGAACGGC
GGCTGGGACACCTTCGTGGAACTGTACGGAAACAACGCCGCTGCCGAGAGCAGAAAGGGCCAAGAACGAGAAGATGGAGGCGGAGGATCTGGCGGAGGTGGAAGTGGCGGAGGCGGATCT
atgcatagagtgaagttcagcaggagcgcagacgcccccgcgtaccagcagggccagaaccagctctataacgagctcaatctaggacgaagagaggagtacgatgttttggacaagagacgtggccgggaccctgagatggggggaaagccgagaa
ggaagaaccctcaggaaggcctgtacaatgaactgcagaaagataagatggcggaggcctacagtgagattgggatgaaaggcgagcgccggaggggcaaggggcacgatggcctttaccagggtctcagtacagccaccaaggacacctacgacg
cccttcacatgcaggccctgccccctcgctaa
(SEQ ID NO: 64)

leader-Pz1 scFv-CD8 hinge region-CD28 transmembrane domain-CD28 extracellular domain-Ser/Gly linker-Des3 high affinity-Furin+Gslinker-T2A peptide-leader-cMyc-tag-DAP10 ectodomain-CD8 hinge region-CD28 transmembrane domain-CD28 extracellular domain-Bcl-XL wildtype-Ser/Gly linker-CD3zeta domain

Figure 35A

STOP-CAR original version (DES3 high affinity+ WT BCL-XL)

MALPVTALLLPLALLLHAARPVQLQQSGPELVKPGTSVRISCKTSGYTFTEYTIHWVKQSHGKSLEWIGNINPNNGGTTYNQKFEDKAT
LTVDKSSSTAYMELRSLTSEDSAVYYCAAGWNFDYWGQGTTVTVSSGGGGSGGGGSGGGGSDIVMTQSHKFMSTSVGDRVSIICKA
SQDVGTAVDWYQQKPGQSPKLLIYWASTRHTGVPDRFTGSGSGTDFTLTITNVQSEDLADYFCQQYNSYPLTFGAGTMLDLKRASTT
TPAPRPPTPAPTIASQPLSLRPEACRPAAGGAVHTRGLDFACDFWVLVVVGGVLACYSLLVTVAFIIFWVRSKRSRLLHSDYMNMTPR
RPGPTRKHYQPYAPPRDFAAYRSHMGGGGSGGGGSGGGGSQRWELALGRFLEYLSWVSTLSEQVQEELLSSQVTQELRALMDET
MKELKAYKSELEEQLTPVAEETRARLSKELQAAQARLGADMEDVRGRLVQYRGEVQAMLGQSTEELRVRLASHLIALQLRLIGDAF
DLQKRLAVYQAGAAERKRRSGSGRSGSGEGRGSLLTCGDVEENPGPGSMALPVTALLLPLALLLHAARPEQKLISEEDLQTTPGERSSL
PAFYPGTSGSCSGCGSLSLPTTTPAPRPPTPAPTIASQPLSLRPEACRPAAGGAVHTRGLDFACDPRFWVLVVVGGVLACYSLLVTVAFII
FWVRSKRSRLLHSDYMNMTPRRPGPTRKHYQPYAPPRDFAAYRSPGGGGSGGGGSGGGGSMSQSNRELVVDFLSYKLSQKGYS
WSQFSDVEENRTEAPEGTESEAVKQALREAGDEFELRYRRAFSDLTSQLHITPGTAYQSFEQVVNELFRDGVNWGRIVAFFSFGGAL
CVESVDKEMQVLVSRIAAWMATYLNDHLEPWIQENGGWDTFVELYGNNAAAESRKGQERGGGGSGGGGSGGGGSMHRVKFS
RSADAPAYQQGQNQLYNELNLGRREEYDVLDKRRGRDPEMGGKPRRKNPQEGLYNELQKDKMAEAYSEIGMKGERRRGKGHDGLY
QGLSTATKDTYDALHMQALPPR
(SEQ ID NO: 65)

leader-Pz1 scFv-CD8 hinge region-CD28 transmembrane domain-CD28 extracellular domain-Ser/Gly linker-Des3 high affinity-Furin+Gslinker-T2A peptide-leader-cMyc-tag-DAP10 ectodomain-CD8 hinge region-CD28 transmembrane domain-CD28 extracellular domain-Ser/Gly linker-Bcl-XL wildtype-Ser/Gly linker-CD3zeta domain

Figure 35B

STOP-CAR BCL-XL sentitive to venetoclax (DES3 high affinity+ Mutated BCL-XL which can bind Venetoclax)

Actagaaatggccttaccagtgaccgccttgctcctgccgctggccttgctgctccacgccgccaggccggtgcagctgcagcagtcaggacctgaactggtgaagcctgggacttcagtgaggatatcctgcaagacttctggatacacattcactgaatata
ccatacactgggtgaagcagagccatggaaagagccttgagtggattggaaacatcaatcctaacaatggtggtaccacctacaatcagaagttcgaggacaaggccacattgactgtagacaagtcctccagtacagcctacatggagctccgcagccta
acatctgaggattctgcagtctattattgtgcagctggttggaactttgactactggggccaagggaccacggtcaccgtctcctcaggtggaggtggatcaggtggaggtggatctggtggaggtggatctgacattgtgatgacccagtctcacaaattcatgt
ccacatcagtaggagacagggtcagcatcatctgtaaggccagtcaagatgtgggtactgctgtagactggtatcaacagaaaccaggacaatctcctaaactactgatttattgggcatccactcggcacactggagtccctgatcgcttcacaggcagtgg
atctgggacagacttcactctcaccattactaatgttcagtctgaagacttggcagattatttctgtcagcaatataacagctatcccctcacgttcggtgctgggaccatgctggacctgaaacgggctagcACAACAACCCCTGCCCCCAGACCTC
CTACCCCAGCCCCTACAATTGCCAGCCAGCCTCTGAGCCTGAGGCCCGAGGCTTGTAGACCTGCTGCTGGCGGAGCCGTGCACACCAGAGGACTGGATTTCGCCTGCGACTTCTGGGTGCTGGT
GGTCGTGGGCGGAGTGCTGGCCTGTTACAGCCTGCTCGTGACCGTGGCCTTCATCATCTTTTGGGTGCGGAGCAAGAGAAGCAGACTGCTGCACAGCGACTACATGAACATGACCCCCAGACGGC
CTGGCCCCACCAGAAAGCACTACCAGCCTTACGCCCCTCCCAGAGACTTCGCCGCCTACAGATCTcatatgGGAGGCGGAGGATCTGGCGGAGGTGGAAGTGGCGGAGGCGGATCTCAAAGATGG
GAACTCGCCCTGGGCAGATTCCTGGAATACCTGAGCTGGGTGTCCACACTGAGCGAACAGGTGCAAGAGGAACTGCTGAGCAGCCAAGTGACCCAAGAGCTGAGAGCCCTGATGGACGAGAC
AATGAAGGAACTGAAGGCCTACAAGAGCGAGCTGGAAGAACAGCTGACCCCTGTGGCCGAGGAAACCAGAGCCAGACTGAGCAAAGAACTGCAGGCCGCTCAGGCCAGACTGGGAGCCGA
TATGGAAGATGTTCGGGGCAGACTGGTGCAGTACAGAGGCGAAGTTCAGGCCATGCTGGGCCAGTCTACCGAGGAACTGAGAGTGCGGCTGGCCCTCTCATCTGATTGCCCTGCAGCTGAGACT
GATCGGCGACGCATTCGACCTGCAGAAAAGACTGGCCGTGTACCAGGCTGGCGCTGCTGAACGGAAGCGGCGCAGCGGCAGCGGGCGCAGCGGCAGCGGCgagggcagaggaagtcttctaacatgcg
gtgacgtggaggagaatcccggccctggatccatggccttaccagtgaccgccttgctcctgccgctggccttgctgctccacgccgccaggccggaacagaaactcatcagtgaggaagatttgcagacgactccaggagagagatcatcactccctgcctt
ttaccctggcacttcaggctcttgttccggatgtgggtccctctctgccgACAACAACCCCTGCCCCCAGACCTCCTACCCCAGCCCCTACAATTGCCAGCCAGCCTCTGAGCCTGAGGCCCGAGGCTTGTAGACCTG
CTGCTGGCGGAGCCGTGCACACCAGAGGACTGGATTTCGCCTGCGAcctaggTTCTGGGTGCTGGTGGTCGTGGGCGGAGTGCTGGCCTGTTACAGCCTGCTCGTGACCGTGGCCTTCATCATCTTT
TGGGTGCGGAGCAAGAGAAGCAGACTGCTGCACAGCGACTACATGAACATGACCCCCAGACGGCCTGGCCCCACCAGAAAGCACTACCAGCCTTACGCCCCTCCCAGAGACTTCGCCGCCTACAG
ATCTcccgggGGAGGCGGAGGATCTGGCGGAGGTGGAAGTGGCGGAGGCGGATCTATGAGCCAGAGCAACAGAGAACTGGTGGTGGACTTCCTGAGCTACAAGCTGAGCCAGAAGGGCTACA
GCTGGTCCCAGTTCAGCGACGTGGAAGAGAACAGAACAGAGGCCCCTGAGGGCACAGAGTCTGAGGCTGTGAAACAGGCCCTGAGAGAAGCCGGCGACGACTTCGAGCTGAGATACAGAA
GGGCCTTCAGCGACCTGACCAGCCAGCTGCACATCACACCTGGCACAGCCTACCAGAGCTTCGAGCAGGTCGTGAACGAGCTGTTCAGAGATGGCGTGAACTGGGGCAGAATCGTGGCCTTCT
TCAGCTTTGGCGGAGCCCTGTGTGTGGAAAGCGTGGACAAAGAAATGCAGGTCCTGGTGTCCAGAATCGCCGCCTGGATGGCCACCTACCTGAACGATCATCTGGAACCCTGGATtCAAGAGAA
CGGCGGCTGGGACACCTTCGTGGAACTGTACGGAAACAACGCCGCTGCCGAGAGCAGAAAGGGCCAAGAACGAGAAGATGAAGATGGAGGCGGAGGATCTGGCGGAGGTGGAAGTGGCGG
AGGCGGATCTatgcatagagtgaagttcagcaggagcgcagacgcccccgcgtaccagcagggccagaaccagctctataacgagctcaatctaggacgaagagaggagtacgatgttttggacaagagacgtggccgggaccctgagatggggg
gaaagccgagaaggaagaaccctcaggaaggcctgtacaatgaactgcagaaagataagatggcggaggcctacagtgagattgggatgaaaggcgagcgccggaggggcaaggggcacgatggcctttaccagggtctcagtacagccaccaag
gacacctacgacgcccttcacatgcaggccctgccccctcgctaa
(SEQ ID NO: 66)

leader-Pz1 scFv-CD8 hinge region-CD28 transmembrane domain-CD28 extracellular domain-Ser/Gly linker-Des3 high affinity-Furin+Gslinker-T2A peptide-leader-cMyc-tag-DAP10 ectodomain-CD8 hinge region-CD28 transmembrane domain-CD28 extracellular domain-Ser/Gly linker-Bcl-XL mutated-Ser/Gly linker-CD3zeta domain

Figure 35C

STOP-CAR BCL-XL sentitive to venetoclax (DES3 high affinity+ Mutated BCL-XL which can bind Venetoclax)

MALPVTALLLPLALLLHAARPVQLQQSGPELVKPGTSVRISCKTSGYTFTEYTIHWVKQSHGKSLEWIGNINPNNGGTTYNQKFEDKAT
LTVDKSSSTAYMELRSLTSEDSAVYYCAAGWNFDYWGQGTTVTVSSGGGGSGGGGSGGGGSDIVMTQSHKFMSTSVGDRVSIICKA
SQDVGTAVDWYQQKPGQSPKLLIYWASTRHTGVPDRFTGSGSGTDFTLTITNVQSEDLADYFCQQYNSYPLTFGAGTMLDLKRASTT
TPAPRPPTPAPTIASQPLSLRPEACRPAAGGAVHTRGLDFACDFWVLVVVGGVLACYSLLVTVAFIIFWVRSKRSRLLHSDYMNMTPR
RPGPTRKHYQPYAPPRDFAAYRSHMGGGGSGGGGSGGGGSQRWELALGRFLEYLSWVSTLSEQVQEELLSSQVTQELRALMDET
MKELKAYKSELEEQLTPVAEETRARLSKELQAAQARLGADMEDVRGRLVQYRGEVQAMLGQSTEELRVRLASHLIALQLRLIGDAF
DLQKRLAVYQAGAAERKRRSGSGRSGSGEGRGSLLTCGDVEENPGPGSMALPVTALLLPLALLLHAARPEQKLISEEDLQTTPGERSSL
PAFYPGTSGSCSGCGSLSLPTTTPAPRPPTPAPTIASQPLSLRPEACRPAAGGAVHTRGLDFACDPRFWVLVVVGGVLACYSLLVTVAFII
FWVRSKRSRLLHSDYMNMTPRRPGPTRKHYQPYAPPRDFAAYRSPGGGGGSGGGGSGGGGSMSQSNRELVVDFLSYKLSQKGYS
WSQFSDVEENRTEAPEGTESEAVKQALREAGDDFELRYRRAFSDLTSQLHITPGTAYQSFEQVVNELFRDGVNWGRIVAFFSFGGA
LCVESVDKEMQVLVSRIAAWMATYLNDHLEPWIQENGGWDTFVELYGNNAAAESRKGQEREDGGGGSGGGGSGGGGSMHRV
KFSRSADAPAYQQGQNQLYNELNLGRREEYDVLDKRRGRDPEMGGKPRRKNPQEGLYNELQKDKMAEAYSEIGMKGERRRGKG
HDGLYQGLSTATKDTYDALHMQALPPR
(SEQ ID NO: 67)

leader-Pz1 scFv-CD8 hinge region-CD28 transmembrane domain-CD28 extracellular domain-Ser/Gly linker-Des3 high affinity-Furin+Gslinker-T2A peptide-leader-cMyc-tag-DAP10 ectodomain-CD8 hinge region-CD28 transmembrane domain-CD28 extracellular domain-Ser/Gly linker-Bcl-XL mutated-Ser/Gly linker-CD3zeta domain

Figure 35D

STOP-CAR Ventoclax high affinity (DES3 high affinity+WT BCL2)

Actagaaatggccttaccagtgaccgccttgctcctgccgctggccttgctgctccacgccgccaggccggtgcagctgcagcagtcaggacctgaactggtgaagcctgggacttcagtgaggatatcctgcaagacttctggatacacattcactgaatata
ccatacactgggtgaagcagagccatggaaagagccttgagtggattggaaacatcaatcctaacaatggtggtaccacctacaatcagaagttcgaggacaaggccacattgactgtagacaagtcctccagtacagcctacatggagctccgcagccta
acatctgaggattctgcagtctattattgtgcagctggttggaactttgactactggggccaagggaccacggtcaccgtctcctcaggtggaggtggatcaggtggaggtggatctggtggaggtggatctgacattgtgatgacccagtctcacaaattcatgt
ccacatcagtaggagacagggtcagcatcatctgtaaggccagtcaagatgtgggtactgctgtagactggtatcaacagaaaccaggacaatctcctaaactactgatttattgggcatccactcggcacactggagtccctgatcgcttcacaggcagtgg
atctgggacagacttcactctcaccattactaatgttcagtctgaagacttggcagattatttctgtcagcaatataacagctatcccctcacgttcggtgctgggaccatgctggacctgaaacgggctagcACAACAACCCCTGCCCCCAGACCTC
CTACCCCAGCCCCTACAATTGCCAGCCAGCCTCTGAGCCTGAGGCCCGAGGCTTGTAGACCTGCTGCTGGCGGAGCCGTGCACACCAGAGGACTGGATTTCGCCTGCGACTTCTGGGTGCTGGT
GGTCGTGGGCGGAGTGCTGGCCTGTTACAGCCTGCTCGTGACCGTGGCCTTCATCATCTTTTGGGTGCGGAGCAAGAGAAGCAGACTGCTGCACAGCGACTACATGAACATGACCCCCAGACGGC
CTGGCCCCACCAGAAAGCACTACCAGCCTTACGCCCCTCCCAGAGACTTCGCCGCCTACAGATCTcatatgGGAGGCGGAGGATCTGGCGGAGGTGGAAGTGGCGGAGGCGGATCTCAAAGATGG
GAACTCGCCCTGGGCAGATTCCTGGAATACCTGAGCTGGGTGTCCACACTGAGCGAACAGGTGCAAGAGGAACTGCTGAGCAGCCAAGTGACCCAAGAGCTGAGAGCCCTGATGGACGAGAC
AATGAAGGAACTGAAGGCCTACAAGAGCGAGCTGGAAGAACAGCTGACCCCTGTGGCCGAGGAAACCAGAGCCAGACTGAGCAAAGAACTGCAGGCCGCTCAGGCCAGACTGGGAGCCGA
TATGGAAGATGTTCGGGGCAGACTGGTGCAGTACAGAGGCGAAGTTCAGGCCATGCTGGGCCAGTCTACCGAGGAACTGAGAGTGCGGCTGGCCTCTCATCTGATTGCCCTGCAGCTGAGACT
GATCGGCGACGCATTCGACCTGCAGAAAAGACTGGCCGTGTACCAGGCTGGCGCTGCTGAACGGAAGCGGCGCAGCGGCAGCGGGCGCAGCGGCAGCGGCgagggcagaggaagtcttctaacatgcg
gtgacgtggaggagaatcccggccctggatccatggccttaccagtgaccgccttgctcctgccgctggccttgctgctccacgccgccaggccggaacagaaactcatcagtgaggaagatttgcagacgactccaggagagagatcatcactccctgcctt
ttaccctggcacttcaggctcttgttccggatgtgggtccctctctctgccgACAACAACCCCTGCCCCCAGACCTCCTACCCCAGCCCCTACAATTGCCAGCCAGCCTCTGAGCCTGAGGCCCGAGGCTTGTAGACCTG
CTGCTGGCGGAGCCGTGCACACCAGAGGACTGGATTTCGCCTGCGAcctaggTTCTGGGTGCTGGTGGTCGTGGGCGGAGTGCTGGCCTGTTACAGCCTGCTCGTGACCGTGGCCTTCATCATCTTT
TGGGTGCGGAGCAAGAGAAGCAGACTGCTGCACAGCGACTACATGAACATGACCCCCAGACGGCCTGGCCCCACCAGAAAGCACTACCAGCCTTACGCCCCTCCCAGAGACTTCGCCGCCTACAG
ATCTcccgggGGAGGCGGAGGATCTGGCGGAGGTGGAAGTGGCGGAGGCGGATCTATGGCCCACGCCGGCAGGACCGGCTACGACAACAGGGAGATCGTGATGAAGTACATCCACTACAAGCT
GAGCCAGAGGGGCTACGAGTGGGACGCCGGCGACGTGGGCGCCGCCCCCCCCGGCGCCGCCCCCGCCCCCGGCATCTTCAGCAGCCAGCCCGGCCACACCCCCCACCCCGCCGCCAGCAGGG
ACCCCGTGGCCAGGACCAGCCCCCTGCAGACCCCCGCCGCCCCCGGCGCCGCCGCCGGCCCCGCCCTGAGCCCCGTGCCCCCCGTGGTGCACCTGACCCTGAGGCAGGCCGGCGACGACTTCA
GCAGGAGGTACAGGAGGGACTTCGCCGAGATGAGCAGCCAGCTGCACCTGACCCCCTTCACCGCCAGGGGCAGGTTCGCCACCGTGGTGGAGGAGCTGTTCAGGGACGGCGTGAACTGGGG
CAGGATCGTGGCCTTCTTCGAGTTCGGCGGCGTGATGTGCGTGGAGAGCGTGAACAGGGAGATGAGCCCCCTGGTGGACAACATCGCCCTGTGGATGACCGAGTACCTGAACAGGCACCTGCA
CACCTGGATCCAGGACAACGGCGGCTGGGACGCCTTCGTGGAGCTGTACGGCCCCAGCATGAGGGGAAGATGGAGGCGGAGGATCTGGCGGAGGTGGAAGTGGCGGAGGCGGATCTatgcatag
agtgaagttcagcaggagcgcagacgcccccgcgtaccagcagggccagaaccagctctataacgagctcaatctaggacgaagagaggagtacgatgttttggacaagagacgtggccgggaccctgagatggggggaaagccgagaaggaagaa
ccctcaggaaggcctgtacaatgaactgcagaaagataagatggcggaggcctacagtgagattgggatgaaaggcgagcgccggaggggcaaggggcacgatggcctttaccagggtctcagtacagccaccaaggacacctacgacgcccttcac
atgcaggccctgccccctcgctaa (SEQ ID NO: 68)

leader-Pz1 scFv-CD8 hinge region-CD28 transmembrane domain-CD28 extracellular domain-Ser/Gly linker-Des3 high affinity-Furin+Gslinker-T2A peptide-leader-cMyc-tag-DAP10 ectodomain-CD8 hinge region-CD28 transmembrane domain-CD28 extracellular domain-Ser/Gly linker-Bcl2 wild type-Ser/Gly linker-CD3zeta domain

Figure 35E

STOP-CAR Ventoclax high affinity (DES3 high affinity+WT BCL2)

MALPVTALLLPLALLLHAARPVQLQQSGPELVKPGTSVRISCKTSGYTFTEYTIHWVKQSHGKSLEWIGNINPNNGGTTYNQKFEDKAT
LTVDKSSSTAYMELRSLTSEDSAVYYCAAGWNFDYWGQGTTVTVSSGGGGSGGGGSGGGGSDIVMTQSHKFMSTSVGDRVSIICKA
SQDVGTAVDWYQQKPGQSPKLLIYWASTRHTGVPDRFTGSGSGTDFTLTITNVQSEDLADYFCQQYNSYPLTFGAGTMLDLKRASTT
TPAPRPPTPAPTIASQPLSLRPEACRPAAGGAVHTRGLDFACDFWVLVVVGGVLACYSLLVTVAFIIFWVRSKRSRLLHSDYMNMTPR
RPGPTRKHYQPYAPPRDFAAYRSHMGGGGSGGGGSGGGGSQRWELALGRFLEYLSWVSTLSEQVQEELLSSQVTQELRALMDET
MKELKAYKSELEEQLTPVAEETRARLSKELQAAQARLGADMEDVRGRLVQYRGEVQAMLGQSTEELRVRLASHLIALQLRLIGDAF
DLQKRLAVYQAGAAERKRRSGSGRSGSGEGRGSLLTCGDVEENPGPGSMALPVTALLLPLALLLHAARPEQKLISEEDLQTTPGERSSL
PAFYPGTSGSCSGCGSLSLPTTTPAPRPPTPAPTIASQPLSLRPEACRPAAGGAVHTRGLDFACDPRFWVLVVVGGVLACYSLLVTVAFII
FWVRSKRSRLLHSDYMNMTPRRPGPTRKHYQPYAPPRDFAAYRSPGGGGGSGGGGSGGGGSMAHAGRTGYDNREIVMKYIHYK
LSQRGYEWDAGDVGAAPPGAAPAPGIFSSQPGHTPHPAASRDPVARTSPLQTPAAPGAAAGPALSPVPPVVHLTLRQAGDDFSR
RYRRDFAEMSSQLHLTPFTARGRFATVVEELFRDGVNWGRIVAFFEFGGVMCVESVNREMSPLVDNIALWMTEYLNRHLHTWIQ
DNGGWDAFVELYGPSMRGGGGSGGGGSGGGGSMHRVKFSRSADAPAYQQGQNQLYNELNLGRREEYDVLDKRRGRDPEMG
GKPRRKNPQEGLYNELQKDKMAEAYSEIGMKGERRRGKGHDGLYQGLSTATKDTYDALHMQALPPR

(SEQ ID NO: 69)

leader-Pz1 scFv-CD8 hinge region-CD28 transmembrane domain-CD28 extracellular domain-Ser/Gly linker-Des3 high affinity-Furin+Gslinker-T2A peptide-leader-cMyc-tag-DAP10 ectodomain-CD8 hinge region-CD28 transmembrane domain-CD28 extracellular domain-Ser/Gly linker-Bcl2 wild type-Ser/Gly linker-CD3zeta domain

Figure 35F

STOP-CAR (DES3 medium affinity+WT BCL-XL)

Actagaaatggccttaccagtgaccgccttgctcctgccgctggccttgctgctccacgccgccaggccggtgcagctgcagcagtcaggacctgaactggtgaagcctgggacttcagtgaggatatcctgcaagacttctggatacacattcactgaatata
ccatacactgggtgaagcagagccatggaaagagccttgagtggattggaaacatcaatcctaacaatggtggtaccacctacaatcagaagttcgaggacaaggccacattgactgtagacaagtcctccagtacagcctacatggagctccgcagccta
acatctgaggattctgcagtctattattgtgcagctggttggaactttgactactggggccaagggaccacggtcaccgtctcctcaggtggaggtggatcaggtggaggtggatctggtggaggtggatctgacattgtgatgacccagtctcacaaattcatgt
ccacatcagtaggagacagggtcagcatcatctgtaaggccagtcaagatgtgggtactgctgtagactggtatcaacagaaaccaggacaatctcctaaactactgatttattgggcatccactcggcacactggagtccctgatcgcttcacaggcagtgg
atctgggacagacttcactctcaccattactaatgttcagtctgaagacttggcagattatttctgtcagcaatataacagctatcccctcacgttcggtgctgggaccatgctggacctgaaacgggctagcACAACAACCCCTGCCCCCAGACCTC
CTACCCCAGCCCCTACAATTGCCAGCCAGCCTCTGAGCCTGAGGCCCGAGGCTTGTAGACCTGCTGCTGGCGGAGCCGTGCACACCAGAGGACTGGATTTCGCCTGCGACTTCTGGGTGCTGGT
GGTCGTGGGCGGAGTGCTGGCCTGTTACAGCCTGCTCGTGACCGTGGCCTTCATCATCTTTTGGGTGCGGAGCAAGAGAAGCAGACTGCTGCACAGCGACTACATGAACATGACCCCCAGACGGC
CTGGCCCCACCAGAAAGCACTACCAGCCTTACGCCCCTCCCAGAGACTTCGCCGCCTACAGATCTcatatgGGAGGCGGAGGATCTGGCGGAGGTGGAAGTGGCGGAGGCGGATCTCCAAAGATG
GGAACTCGCCCTGGGCAGATTCCTGGAATACCTGAGCTGGGTGTCCACACTGAGCGAACAGGTGCAAGAGGAACTGCTGAGCAGCCAAGTGACCCAAGAGCTGAGAGCCCTGATGGACGAGA
CAATGAAGGAACTGAAGGCCTACAAGAGCGAGCTGGAAGAACAGCTGACCCCTGTGGCCGAGGAAACCAGAGCCAGACTGAGCAAAGAACTGCAGGCCGCTCAGGCCAGACTGGGAGCCG
ATATGGAAGATGTTCGGGGCAGACTGGTGCAGTACAGAGGCGAAGTTCAGGCCATGCTGGGCCAGTCTACCGAGGAACTGAGAGTGCGGCTGGCCTCTCATCTGATTGCCCTGCAGGCAAGAC
TGATCGGCGACGCATTCGACCTGCAGAAAAGACTGGCCGTGTACCAGGCTGGCGCTGCTGAACGGAAGCGGCGCAGCGGCAGCGGGCGCAGCGGCAGCGGCgagggcagaggaagtcttctaacatgc
ggtgacgtggaggagaatcccggccctggatccatggccttaccagtgaccgccttgctcctgccgctggccttgctgctccacgccgccaggccgggaacagaaactcatcagtgaggaagatttgcagacgactccaggagagagatcatcactccctgcc
ttttaccctggcacttcaggctcttgttccggatgtgggtccctctctctgccgACAACAACCCCTGCCCCCAGACCTCCTACCCCAGCCCCTACAATTGCCAGCCAGCCTCTGAGCCTGAGGCCCGAGGCTTGTAGACCT
GCTGCTGGCGGAGCCGTGCACACCAGAGGACTGGATTTCGCCTGCGAcctaggTTCTGGGTGCTGGTGGTCGTGGGCGGAGTGCTGGCCTGTTACAGCCTGCTCGTGACCGTGGCCTTCATCATCTT
TTGGGTGCGGAGCAAGAGAAGCAGACTGCTGCACAGCGACTACATGAACATGACCCCCAGACGGCCTGGCCCCACCAGAAAGCACTACCAGCCTTACGCCCCTCCCAGAGACTTCGCCGCCTACA
GATCTcccgggGGAGGCGGAGGATCTGGCGGAGGTGGAAGTGGCGGAGGCGGATCTATGAGCCAGAGCAACAGAGAACTGGTGGTGGACTTCCTGAGCTACAAGCTGAGCCAGAAGGGCTAC
AGCTGGTCCCAGTTCAGCGACGTGGAAGAGAACAGAACAGAGGCCCCTGAGGGCACAGAGTCTGAGGCTGTGAAACAGGCCCTGAGAGAAGCCGGCGACGAGTTCGAGCTGAGATACAGA
AGGGCCTTCAGCGACCTGACCAGCCAGCTGCACATCACACCTGGCACAGCCTACCAGAGCTTCGAGCAGGTCGTGAACGAGCTGTTCAGAGATGGCGTGAACTGGGGCAGAATCGTGGCCTTC
TTCAGCTTTGGCGGAGCCCTGTGTGTGGAAAGCGTGGACAAAGAAATGCAGGTCCTGGTGTCCAGAATCGCCGCCTGGATGGCCACCTACCTGAACGATCATCTGGAACCCTGGATtCAAGAGA
ACGGCGGCTGGGACACCTTCGTGGAACTGTACGGAAACAACGCCGCTGCCGAGAGCAGAAAGGGCCAAGAACGAGAAGATGGAGGCGGAGGATCTGGCGGAGGTGGAAGTGGCGGAGGC
GGATCTatgcatagagtgaagttcagcaggagcgcagacgcccccgcgtaccagcagggccagaaccagctctataacgagctcaatctaggacgaagagaggagtacgatgttttggacaagagacgtggccgggaccctgagatggggggaaa
gccgagaaggaagaaccctcaggaaggcctgtacaatgaactgcagaaagataagatggcggaggcctacagtgagattgggatgaaaggcgagcgccggaggggcaaggggcacgatggcctttaccagggtctcagtacagccaccaaggaca
cctacgacgcccttcacatgcaggccctgccccctcgctaa (SEQ ID NO: 70)

leader-Pz1 scFv-CD8 hinge region-CD28 transmembrane domain-CD28 extracellular domain-Ser/Gly linker-Des3 medium affinity-Furin+Gslinker-T2A peptide-leader-cMyc-tag-DAP10 ectodomain-CD8 hinge region-CD28 transmembrane domain-CD28 extracellular domain-Ser/Gly linker-Bcl-XL wild type-Ser/Gly linker-CD3zeta domain

Figure 35G

STOP-CAR (DES3 medium affinity+WT BCL-XL)

MALPVTALLLPLALLLHAARPVQLQQSGPELVKPGTSVRISCKTSGYTFTEYTIHWVKQSHGKSLEWIGNINPNNGGTTYNQKFEDKAT
LTVDKSSSTAYMELRSLTSEDSAVYYCAAGWNFDYWGQGTTVTVSSGGGGSGGGGSGGGGSDIVMTQSHKFMSTSVGDRVSIICKA
SQDVGTAVDWYQQKPGQSPKLLIYWASTRHTGVPDRFTGSGSGTDFTLTITNVQSEDLADYFCQQYNSYPLTFGAGTMLDLKRASTT
TPAPRPPTPAPTIASQPLSLRPEACRPAAGGAVHTRGLDFACDFWVLVVVGGVLACYSLLVTVAFIIFWVRSKRSRLLHSDYMNMTPR
RPGPTRKHYQPYAPPRDFAAYRSHMGGGGSGGGGSGGGGSQRWELALGRFLEYLSWVSTLSEQVQEELLSSQVTQELRALMDET
MKELKAYKSELEEQLTPVAEETRARLSKELQAAQARLGADMEDVRGRLVQYRGEVQAMLGQSTEELRVRLASHLIALQARLIGDAF
DLQKRLAVYQAGAAERKRRSGSGRSGSGEGRGSLLTCGDVEENPGPGSMALPVTALLLPLALLLHAARPEQKLISEEDLQTTPGERSSL
PAFYPGTSGSCSGCGSLSLPTTTPAPRPPTPAPTIASQPLSLRPEACRPAAGGAVHTRGLDFACDPRFWVLVVVGGVLACYSLLVTVAFII
FWVRSKRSRLLHSDYMNMTPRRPGPTRKHYQPYAPPRDFAAYRSPGGGGGSGGGGSGGGGSMSQSNRELVVDFLSYKLSQKGYS
WSQFSDVEENRTEAPEGTESEAVKQALREAGDEFELRYRRAFSDLTSQLHITPGTAYQSFEQVVNELFRDGVNWGRIVAFFSFGGAL
CVESVDKEMQVLVSRIAAWMATYLNDHLEPWIQENGGWDTFVELYGNNAAAESRKGQERGGGGSGGGGSGGGGSMHRVKFS
RSADAPAYQQGQNQLYNELNLGRREEYDVLDKRRGRDPEMGGKPRRKNPQEGLYNELQKDKMAEAYSEIGMKGERRRGKGHD
GLYQGLSTATKDTYDALHMQALPPR

(SEQ ID NO: 71)

leader-Pz1 scFv-CD8 hinge region-CD28 transmembrane domain-CD28 extracellular domain-Ser/Gly linker-Des3 medium affinity-Furin+Gslinker-T2A peptide-leader-cMyc-tag-DAP10 ectodomain-CD8 hinge region-CD28 transmembrane domain-CD28 extracellular domain-Ser/Gly linker-Bcl-XL wild type-Ser/Gly linker-CD3zeta domain

Figure 35H

STOP-CAR (DES3 weakest affinity+WT BCL-XL)

Actagaaatggccttaccagtgaccgccttgctcctgccgctggccttgctgctccacgccgccaggccggtgcagctgcagcagtcaggacctgaactggtgaagcctgggacttcagtgaggatatcctgcaagacttctggatacacattcactgaatata
ccatacactgggtgaagcagagccatggaaagagccttgagtggattggaaacatcaatcctaacaatggtggtaccacctacaatcagaagttcgaggacaaggccacattgactgtagacaagtcctccagtacagcctacatggagctccgcagccta
acatctgaggattctgcagtctattattgtgcagctggttggaactttgactactggggccaagggaccacggtcaccgtctcctcaggtggaggtggatcaggtggaggtggatctggtggaggtggatctgacattgtgatgacccagtctcacaaattcatgt
ccacatcagtaggagacagggtcagcatcatctgtaaggccagtcaagatgtgggtactgctgtagactggtatcaacagaaaccaggacaatctcctaaactactgatttattgggcatccactcggcacactggagtccctgatcgcttcacaggcagtgg
atctgggacagacttcactctcaccattactaatgttcagtctgaagacttggcagattatttctgtcagcaatataacagctatcccctcacgttcggtgctgggaccatgctggacctgaaacgggctagcACAACAACCCCTGCCCCCAGACCTCC
TACCCCAGCCCCTACAATTGCCAGCCAGCCTCTGAGCCTGAGGCCCGAGGCTTGTAGACCTGCTGCTGGCGGAGCCGTGCACACCAGAGGACTGGATTTCGCCTGCGACTTCTGGGTGCTGGTGG
TCGTGGGCGGAGTGCTGGCCTGTTACAGCCTGCTCGTGACCGTGGCCTTCATCATCTTTTGGGTGCGGAGCAAGAGAAGCAGACTGCTGCACAGCGACTACATGAACATGACCCCCAGACGGCCT
GGCCCCACCAGAAAGCACTACCAGCCTTACGCCCCTCCCAGAGACTTCGCCGCCTACAGATCTcatatgGGAGGCGGAGGATCTGGCGGAGGTGGAAGTGGCGGAGGCGGATCTCAAAGATGGGA
ACTCGCCCTGGGCAGATTCCTGGAATACCTGAGCTGGGTGTCCACACTGAGCGAACAGGTGCAAGAGGAACTGCTGAGCAGCCAAGTGACCCAAGAGCTGAGAGCCCTGATGGACGAGACAA
TGAAGGAACTGAAGGCCTACAAGAGCGAGCTGGAAGAACAGCTGACCCCTGTGGCCGAGGAAACCAGAGCCAGACTGAGCAAAGAACTGCAGGCCGCTCAGGCCAGACTGGGAGCCGATAT
GGAAGATGTTCGGGGCAGACTGGTGCAGTACAGAGGCGAAGTTCAGGCCATGCTGGGCCAGTCTACCGAGGAACTGAGAGTGCGGCTGGCCTCTCATCTGATTGCCCTGCAGCTGAGACTGAT
CGGCGCAGCATTCGACCTGCAGAAAAGACTGGCCGTGTACCAGGCTGGCGCTCTGAACGGAAGCGGCGCAGCGGCAGCGGGCGCAGCGGCAGCGGCgagggcagaggaagtcttctaacatgcggtgac
gtggaggagaatcccggccctggatccatggccttaccagtgaccgccttgctcctgccgctggccttgctgctccacgccgccaggccggaacagaaactcatcagtgaggaagatttgcagacgactccaggagagagatcatcactccctgcctttacc
ctggcacttcaggctcttgttccggatgtgggtccctctctctgccgACAACAACCCCTGCCCCCAGACCTCCTACCCCAGCCCCTACAATTGCCAGCCAGCCTCTGAGCCTGAGGCCCGAGGCTTGTAGACCTGCTGC
TGGCGGAGCCGTGCACACCAGAGGACTGGATTTCGCCTGCGAcctaggTTCTGGGTGCTGGTGGTCGTGGGCGGAGTGCTGGCCTGTTACAGCCTGCTCGTGACCGTGGCCTTCATCATCTTTTGG
GTGCGGAGCAAGAGAAGCAGACTGCTGCACAGCGACTACATGAACATGACCCCCAGACGGCCTGGCCCCACCAGAAAGCACTACCAGCCTTACGCCCCTCCCAGAGACTTCGCCGCCTACAGATC
TcccgggGGAGGCGGAGGATCTGGCGGAGGTGGAAGTGGCGGAGGCGGATCTATGAGCCAGAGCAACAGAGAACTGGTGGTGGACTTCCTGAGCTACAAGCTGAGCCAGAAGGGCTACAGCT
GGTCCCAGTTCAGCGACGTGGAAGAGAACAGAACAGAGGCCCCTGAGGGCACAGAGTCTGAGGCTGTGAAACAGGCCCTGAGAGAAGCCGGCGACGAGTTCGAGCTGAGATACAGAAGGG
CCTTCAGCGACCTGACCAGCCAGCTGCACATCACACCTGGCACAGCCTACCAGAGCTTCGAGCAGGTCGTGAACGAGCTGTTCAGAGATGGCGTGAACTGGGGCAGAATCGTGGCCTTCTTCAG
CTTTGGCGGAGCCCTGTGTGTGGAAAGCGTGGACAAAGAAATGCAGGTCCTGGTGTCCAGAATCGCCGCCTGGATGGCCACCTACCTGAACGATCATCTGGAACCCTGGATtCAAGAGAACGG
CGGCTGGGACACCTTCGTGGAACTGTACGGAAACAACGCCGCTGCCGAGAGCAGAAAGGGCCAAGAACGAGAAGATGGAGGCGGAGGATCTGGCGGAGGTGGAAGTGGCGGAGGCGGATC
Tatgcatagagtgaagttcagcaggagcgcagacgcccccgcgtaccagcagggccagaaccagctctataacgagctcaatctaggacgaagagaggagtacgatgttttggacaagagacgtggccgggaccctgagatgggggggaaagccgaga
aggaagaaccctcaggaaggcctgtacaatgaactgcagaaagataagatggcggaggcctacagtgagattgggatgaaaggcgagcgccggaggggcaaggggcacgatggcctttaccagggtctcagtacagccaccaaggacacctacgac
gcccttcacatgcaggccctgccccctcgctaa (SEQ ID NO: 72)

leader-Pz1 scFv-CD8 hinge region-CD28 transmembrane domain-CD28 extracellular domain-Ser/Gly linker-Des3 weakest affinity-Furin+Gslinker-T2A peptide-leader-cMyc-tag-DAP10 ectodomain-CD8 hinge region-CD28 transmembrane domain-CD28 extracellular domain-Ser/Gly linker-Bcl-XL wild type-Ser/Gly linker-CD3zeta domain

Figure 35I

STOP-CAR (DES3 weakest affinity+WT BCL-XL)

MALPVTALLLPLALLLHAARPVQLQQSGPELVKPGTSVRISCKTSGYTFTEYTIHWVKQSHGKSLEWIGNINPNNGGTTYNQKFEDKAT
LTVDKSSSTAYMELRSLTSEDSAVYYCAAGWNFDYWGQGTTVTVSSGGGGSGGGGSGGGGSDIVMTQSHKFMSTSVGDRVSIICKA
SQDVGTAVDWYQQKPGQSPKLLIYWASTRHTGVPDRFTGSGSGTDFTLTITNVQSEDLADYFCQQYNSYPLTFGAGTMLDLKRASTT
TPAPRPPTPAPTIASQPLSLRPEACRPAAGGAVHTRGLDFACDFWVLVVVGGVLACYSLLVTVAFIIFWVRSKRSRLLHSDYMNMTPRR
PGPTRKHYQPYAPPRDFAAYRSHMGGGGSGGGGSGGGGSQRWELALGRFLEYLSWVSTLSEQVQEELLSSQVTQELRALMDETM
KELKAYKSELEEQLTPVAEETRARLSKELQAAQARLGADMEDVRGRLVQYRGEVQAMLGQSTEELRVRLASHLIALQLRLIGAAFDL
QKRLAVYQAGAAERKRRSGSGRSGSGEGRGSLLTCGDVEENPGPGSMALPVTALLLPLALLLHAARPEQKLISEEDLQTTPGERSSLP
AFYPGTSGSCSGCGSLSLPTTTPAPRPPTPAPTIASQPLSLRPEACRPAAGGAVHTRGLDFACDPRFWVLVVVGGVLACYSLLVTVAFIIF
WVRSKRSRLLHSDYMNMTPRRPGPTRKHYQPYAPPRDFAAYRSPGGGGGSGGGGSGGGGSMSQSNRELVVDFLSYKLSQKGYSW
SQFSDVEENRTEAPEGTESEAVKQALREAGDEFELRYRRAFSDLTSQLHITPGTAYQSFEQVVNELFRDGVNWGRIVAFFSFGGALC
VESVDKEMQVLVSRIAAWMATYLNDHLEPWIQENGGWDTFVELYGNNAAAESRKGQERGGGGSGGGGSGGGGSMHRVKFSR
SADAPAYQQGQNQLYNELNLGRREEYDVLDKRRGRDPEMGGKPRRKNPQEGLYNELQKDKMAEAYSEIGMKGERRRGKGHDG
LYQGLSTATKDTYDALHMQALPPR

(SEQ ID NO: 73)

leader-Pz1 scFv-CD8 hinge region-CD28 transmembrane domain-CD28 extracellular domain-Ser/Gly linker-Des3 weakest affinity-Furin+Gslinker-T2A peptide-leader-cMyc-tag-DAP10 ectodomain-CD8 hinge region-CD28 transmembrane domain-CD28 extracellular domain-Ser/Gly linker-Bcl-XL wild type-Ser/Gly linker-CD3zeta domain

Figure 35J

SEQUENCE LISTING

```
<160> NUMBER OF SEQ ID NOS: 179

<210> SEQ ID NO 1
<211> LENGTH: 145
<212> TYPE: PRT
<213> ORGANISM: Artificial sequence
<220> FEATURE:
<223> OTHER INFORMATION: Homo sapiens

<400> SEQUENCE: 1

Gln Arg Trp Glu Leu Ala Leu Gly Arg Phe Leu Glu Tyr Leu Ser Trp
1               5                   10                  15

Val Ser Thr Leu Ser Glu Gln Val Gln Glu Glu Leu Leu Ser Ser Gln
```

```
            20                  25                  30

Val Thr Gln Glu Leu Arg Ala Leu Met Asp Glu Thr Met Lys Glu Leu
        35                  40                  45

Lys Ala Tyr Lys Ser Glu Leu Glu Glu Gln Leu Thr Pro Val Ala Glu
    50                  55                  60

Glu Thr Arg Ala Arg Leu Ser Lys Glu Leu Gln Ala Ala Gln Ala Arg
65                  70                  75                  80

Leu Gly Ala Asp Met Glu Asp Val Arg Gly Arg Leu Val Gln Tyr Arg
                85                  90                  95

Gly Glu Val Gln Ala Met Leu Gly Gln Ser Thr Glu Glu Leu Arg Val
            100                 105                 110

Arg Leu Ala Ser His Leu Ile Ala Leu Gln Leu Arg Leu Ile Gly Asp
        115                 120                 125

Ala Phe Asp Leu Gln Lys Arg Leu Ala Val Tyr Gln Ala Gly Ala Ala
    130                 135                 140

Glu
145


<210> SEQ ID NO 2
<211> LENGTH: 143
<212> TYPE: PRT
<213> ORGANISM: Artificial sequence
<220> FEATURE:
<223> OTHER INFORMATION: Homo sapiens

<400> SEQUENCE: 2

Gln Arg Trp Glu Leu Ala Leu Gly Arg Phe Leu Glu Tyr Leu Ser Trp
1               5                   10                  15

Val Ser Thr Leu Ser Glu Gln Val Gln Glu Glu Leu Leu Ser Ser Gln
            20                  25                  30

Val Thr Gln Glu Leu Arg Ala Leu Met Asp Glu Thr Met Lys Glu Leu
        35                  40                  45

Lys Ala Tyr Lys Ser Glu Leu Glu Glu Gln Leu Thr Pro Val Ala Glu
    50                  55                  60

Glu Thr Arg Ala Arg Leu Ser Lys Glu Leu Gln Ala Ala Gln Ala Arg
65                  70                  75                  80

Leu Gly Ala Asp Met Glu Asp Val Arg Gly Arg Leu Val Gln Tyr Arg
                85                  90                  95

Gly Glu Val Gln Ala Met Leu Gly Gln Ser Thr Glu Glu Leu Arg Val
            100                 105                 110

Arg Leu Ala Ser His Leu Ile Ala Leu Gln Leu Arg Leu Ile Gly Asp
        115                 120                 125

Ala Phe Asp Leu Gln Lys Arg Leu Ala Val Tyr Gln Ala Gly Ala
    130                 135                 140


<210> SEQ ID NO 3
<211> LENGTH: 143
<212> TYPE: PRT
<213> ORGANISM: Artificial sequence
<220> FEATURE:
<223> OTHER INFORMATION: Homo sapiens

<400> SEQUENCE: 3

Gln Arg Trp Glu Leu Ala Leu Gly Arg Phe Leu Glu Tyr Leu Ser Trp
1               5                   10                  15

Val Ser Thr Leu Ser Glu Gln Val Gln Glu Glu Leu Leu Ser Ser Gln
            20                  25                  30
```

-continued

```
Val Thr Gln Glu Leu Arg Ala Leu Met Asp Glu Thr Met Lys Glu Leu
        35                  40                  45

Lys Ala Tyr Lys Ser Glu Leu Glu Glu Gln Leu Thr Pro Val Ala Glu
    50                  55                  60

Glu Thr Arg Ala Arg Leu Ser Lys Glu Leu Gln Ala Ala Gln Ala Arg
65                  70                  75                  80

Leu Gly Ala Asp Met Glu Asp Val Arg Gly Arg Leu Val Gln Tyr Arg
                85                  90                  95

Gly Glu Val Gln Ala Met Leu Gly Gln Ser Thr Glu Glu Leu Arg Val
            100                 105                 110

Arg Leu Ala Ser His Leu Ile Ala Leu Gln Ala Arg Leu Ile Gly Asp
        115                 120                 125

Ala Phe Asp Leu Gln Lys Arg Leu Ala Val Tyr Gln Ala Gly Ala
    130                 135                 140


<210> SEQ ID NO 4
<211> LENGTH: 143
<212> TYPE: PRT
<213> ORGANISM: Artificial sequence
<220> FEATURE:
<223> OTHER INFORMATION: Homo sapiens

<400> SEQUENCE: 4

Gln Arg Trp Glu Leu Ala Leu Gly Arg Phe Leu Glu Tyr Leu Ser Trp
1               5                   10                  15

Val Ser Thr Leu Ser Glu Gln Val Gln Glu Glu Leu Leu Ser Ser Gln
            20                  25                  30

Val Thr Gln Glu Leu Arg Ala Leu Met Asp Glu Thr Met Lys Glu Leu
        35                  40                  45

Lys Ala Tyr Lys Ser Glu Leu Glu Glu Gln Leu Thr Pro Val Ala Glu
    50                  55                  60

Glu Thr Arg Ala Arg Leu Ser Lys Glu Leu Gln Ala Ala Gln Ala Arg
65                  70                  75                  80

Leu Gly Ala Asp Met Glu Asp Val Arg Gly Arg Leu Val Gln Tyr Arg
                85                  90                  95

Gly Glu Val Gln Ala Met Leu Gly Gln Ser Thr Glu Glu Leu Arg Val
            100                 105                 110

Arg Leu Ala Ser His Leu Ile Ala Leu Gln Leu Arg Leu Ile Gly Ala
        115                 120                 125

Ala Phe Asp Leu Gln Lys Arg Leu Ala Val Tyr Gln Ala Gly Ala
    130                 135                 140


<210> SEQ ID NO 5
<211> LENGTH: 171
<212> TYPE: PRT
<213> ORGANISM: Artificial sequence
<220> FEATURE:
<223> OTHER INFORMATION: Homos sapiens

<400> SEQUENCE: 5

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Ala Val Lys Gln
        35                  40                  45

Ala Leu Arg Glu Ala Gly Asp Glu Phe Glu Leu Arg Tyr Arg Arg Ala
    50                  55                  60
```

```
Phe Ser Asp Leu Thr Ser Gln Leu His Ile Thr Pro Gly Thr Ala Tyr
65                  70                  75                  80

Gln Ser Phe Glu Gln Val Val Asn Glu Leu Phe Arg Asp Gly Val Asn
                85                  90                  95

Trp Gly Arg Ile Val Ala Phe Phe Ser Phe Gly Gly Ala Leu Cys Val
            100                 105                 110

Glu Ser Val Asp Lys Glu Met Gln Val Leu Val Ser Arg Ile Ala Ala
        115                 120                 125

Trp Met Ala Thr Tyr Leu Asn Asp His Leu Glu Pro Trp Ile Gln Glu
    130                 135                 140

Asn Gly Gly Trp Asp Thr Phe Val Glu Leu Tyr Gly Asn Asn Ala Ala
145                 150                 155                 160

Ala Glu Ser Arg Lys Gly Gln Glu Arg Glu Asp
                165                 170


<210> SEQ ID NO 6
<211> LENGTH: 237
<212> TYPE: PRT
<213> ORGANISM: Artificial sequence
<220> FEATURE:
<223> OTHER INFORMATION: Homo sapiens

<400> SEQUENCE: 6

Val Gln Leu Gln Gln Ser Gly Pro Glu Leu Val Lys Pro Gly Thr Ser
1               5                   10                  15

Val Arg Ile Ser Cys Lys Thr Ser Gly Tyr Thr Phe Thr Glu Tyr Thr
            20                  25                  30

Ile His Trp Val Lys Gln Ser His Gly Lys Ser Leu Glu Trp Ile Gly
        35                  40                  45

Asn Ile Asn Pro Asn Asn Gly Gly Thr Thr Tyr Asn Gln Lys Phe Glu
    50                  55                  60

Asp Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Ala Gly Trp Asn Phe Asp Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Asp Ile Val Met Thr Gln Ser His Lys Phe Met Ser Thr Ser Val
    130                 135                 140

Gly Asp Arg Val Ser Ile Ile Cys Lys Ala Ser Gln Asp Val Gly Thr
145                 150                 155                 160

Ala Val Asp Trp Tyr Gln Gln Lys Pro Gly Gln Ser Pro Lys Leu Leu
                165                 170                 175

Ile Tyr Trp Ala Ser Thr Arg His Thr Gly Val Pro Asp Arg Phe Thr
            180                 185                 190

Gly Ser Gly Ser Gly Thr Asp Phe Thr Leu Thr Ile Thr Asn Val Gln
        195                 200                 205

Ser Glu Asp Leu Ala Asp Tyr Phe Cys Gln Gln Tyr Asn Ser Tyr Pro
    210                 215                 220

Leu Thr Phe Gly Ala Gly Thr Met Leu Asp Leu Lys Arg
225                 230                 235


<210> SEQ ID NO 7
```

<211> LENGTH: 112
<212> TYPE: PRT
<213> ORGANISM: Artificial sequence
<220> FEATURE:
<223> OTHER INFORMATION: Homo sapiens

<400> SEQUENCE: 7

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 8
<211> LENGTH: 30
<212> TYPE: PRT
<213> ORGANISM: Artificial sequence
<220> FEATURE:
<223> OTHER INFORMATION: Homo sapiens

<400> SEQUENCE: 8

Gln Thr Thr Pro Gly Glu Arg Ser Ser Leu Pro Ala Phe Tyr Pro Gly
1               5                   10                  15

Thr Ser Gly Ser Cys Ser Gly Cys Gly Ser Leu Ser Leu Pro
            20                  25                  30

<210> SEQ ID NO 9
<211> LENGTH: 45
<212> TYPE: PRT
<213> ORGANISM: Artificial sequence
<220> FEATURE:
<223> OTHER INFORMATION: Homo sapiens

<400> SEQUENCE: 9

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 10
<211> LENGTH: 27
<212> TYPE: PRT
<213> ORGANISM: Artificial sequence
<220> FEATURE:
<223> OTHER INFORMATION: Homo sapiens

<400> SEQUENCE: 10

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 11
<211> LENGTH: 41
<212> TYPE: PRT
<213> ORGANISM: Artificial sequence
<220> FEATURE:
<223> OTHER INFORMATION: Homo sapiens

<400> SEQUENCE: 11

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 12
<211> LENGTH: 566
<212> TYPE: PRT
<213> ORGANISM: Artificial sequence
<220> FEATURE:
<223> OTHER INFORMATION: Homo sapiens

<400> SEQUENCE: 12

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
```

```
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro
                565
```

<210> SEQ ID NO 13
<211> LENGTH: 495
<212> TYPE: PRT
<213> ORGANISM: Artificial sequence
<220> FEATURE:
<223> OTHER INFORMATION: Homo sapiens

<400> SEQUENCE: 13

```
Gly Ser Met Ala Leu Pro Val Thr Ala Leu Leu Leu Pro Leu Ala Leu
1               5                   10                  15

Leu Leu His Ala Ala Arg Pro Glu Gln Lys Leu Ile Ser Glu Glu Asp
            20                  25                  30

Leu Gln Thr Thr Pro Gly Glu Arg Ser Ser Leu Pro Ala Phe Tyr Pro
        35                  40                  45

Gly Thr Ser Gly Ser Cys Ser Gly Cys Gly Ser Leu Ser Leu Pro Thr
```

```
    50                  55                  60

Thr Thr Pro Ala Pro Arg Pro Pro Thr Pro Ala Pro Thr Ile Ala Ser
65                  70                  75                  80

Gln Pro Leu Ser Leu Arg Pro Glu Ala Cys Arg Pro Ala Ala Gly Gly
                85                  90                  95

Ala Val His Thr Arg Gly Leu Asp Phe Ala Cys Asp Pro Arg Phe Trp
            100                 105                 110

Val Leu Val Val Val Gly Gly Val Leu Ala Cys Tyr Ser Leu Leu Val
        115                 120                 125

Thr Val Ala Phe Ile Ile Phe Trp Val Arg Ser Lys Arg Ser Arg Leu
    130                 135                 140

Leu His Ser Asp Tyr Met Asn Met Thr Pro Arg Arg Pro Gly Pro Thr
145                 150                 155                 160

Arg Lys His Tyr Gln Pro Tyr Ala Pro Pro Arg Asp Phe Ala Ala Tyr
                165                 170                 175

Arg Ser Pro Gly Gly Gly Gly Gly Ser Gly Gly Gly Gly Ser Gly Gly
            180                 185                 190

Gly Gly Ser Met Ser Gln Ser Asn Arg Glu Leu Val Val Asp Phe Leu
        195                 200                 205

Ser Tyr Lys Leu Ser Gln Lys Gly Tyr Ser Trp Ser Gln Phe Ser Asp
    210                 215                 220

Val Glu Glu Asn Arg Thr Glu Ala Pro Glu Gly Thr Glu Ser Glu Ala
225                 230                 235                 240

Val Lys Gln Ala Leu Arg Glu Ala Gly Asp Glu Phe Glu Leu Arg Tyr
                245                 250                 255

Arg Arg Ala Phe Ser Asp Leu Thr Ser Gln Leu His Ile Thr Pro Gly
            260                 265                 270

Thr Ala Tyr Gln Ser Phe Glu Gln Val Val Asn Glu Leu Phe Arg Asp
        275                 280                 285

Gly Val Asn Trp Gly Arg Ile Val Ala Phe Phe Ser Phe Gly Gly Ala
    290                 295                 300

Leu Cys Val Glu Ser Val Asp Lys Glu Met Gln Val Leu Val Ser Arg
305                 310                 315                 320

Ile Ala Ala Trp Met Ala Thr Tyr Leu Asn Asp His Leu Glu Pro Trp
                325                 330                 335

Ile Gln Glu Asn Gly Gly Trp Asp Thr Phe Val Glu Leu Tyr Gly Asn
            340                 345                 350

Asn Ala Ala Ala Glu Ser Arg Lys Gly Gln Glu Arg Glu Asp Gly Gly
        355                 360                 365

Gly Gly Ser Gly Gly Gly Gly Ser Gly Gly Gly Gly Ser Met His Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480
```

```
Lys Asp Thr Tyr Asp Ala Leu His Met Gln Ala Leu Pro Pro Arg
                485                 490                 495
```

<210> SEQ ID NO 14
<211> LENGTH: 1698
<212> TYPE: DNA
<213> ORGANISM: Artificial sequence
<220> FEATURE:
<223> OTHER INFORMATION: Homo sapiens

<400> SEQUENCE: 14

```
atggccttac cagtgaccgc cttgctcctg ccgctggcct tgctgctcca cgccgccagg     60
ccggtgcagc tgcagcagtc aggacctgaa ctggtgaagc ctgggacttc agtgaggata    120
tcctgcaaga cttctggata cacattcact gaatatacca tacactgggt gaagcagagc    180
catggaaaga gccttgagtg gattggaaac atcaatccta acaatggtgg taccacctac    240
aatcagaagt tcgaggacaa ggccacattg actgtagaca agtcctccag tacagcctac    300
atggagctcc gcagcctaac atctgaggat tctgcagtct attattgtgc agctggttgg    360
aactttgact actggggcca agggaccacg gtcaccgtct cctcaggtgg aggtggatca    420
ggtggaggtg gatctggtgg aggtggatct gacattgtga tgacccagtc tcacaaattc    480
atgtccacat cagtaggaga cagggtcagc atcatctgta aggccagtca agatgtgggt    540
actgctgtag actggtatca acagaaacca ggacaatctc ctaaactact gatttattgg    600
gcatccactc ggcacactgg agtccctgat cgcttcacag gcagtggatc tgggacagac    660
ttcactctca ccattactaa tgttcagtct gaagacttgg cagattattt ctgtcagcaa    720
tataacagct atcccctcac gttcggtgct gggaccatgc tggacctgaa acgggctagc    780
acaacaaccc ctgcccccag acctcctacc ccagccccta caattgccag ccagcctctg    840
agcctgaggc ccgaggcttg tagacctgct gctggcggag ccgtgcacac cagaggactg    900
gatttcgcct gcgacttctg ggtgctggtg gtcgtgggcg gagtgctggc ctgttacagc    960
ctgctcgtga ccgtggcctt catcatcttt tgggtgcgga gcaagagaag cagactgctg   1020
cacagcgact acatgaacat gacccccaga cggcctggcc ccaccagaaa gcactaccag   1080
ccttacgccc ctcccagaga cttcgccgcc tacagatctc atatgggagg cggaggatct   1140
ggcggaggtg gaagtggcgg aggcggatct caaagatggg aactcgccct gggcagattc   1200
ctggaatacc tgagctgggt gtccacactg agcgaacagg tgcaagagga actgctgagc   1260
agccaagtga cccaagagct gagagccctg atggacgaga caatgaagga actgaaggcc   1320
tacaagagcg agctggaaga acagctgacc cctgtggccg aggaaaccag agccagactg   1380
agcaaagaac tgcaggccgc tcaggccaga ctgggagccg atatggaaga tgttcggggc   1440
agactggtgc agtacagagg cgaagttcag gccatgctgg gccagtctac cgaggaactg   1500
agagtgcggc tggcctctca tctgattgcc ctgcagctga gactgatcgg cgacgcattc   1560
gacctgcaga aaagactggc cgtgtaccag gctggcgctg ctgaacggaa gcggcgcagc   1620
ggcagcgggc gcagcggcag cggcgagggc agaggaagtc ttctaacatg cggtgacgtg   1680
gaggagaatc ccggccct                                                1698
```

<210> SEQ ID NO 15
<211> LENGTH: 1488
<212> TYPE: DNA
<213> ORGANISM: Artificial sequence
<220> FEATURE:
<223> OTHER INFORMATION: Homo sapiens

<400> SEQUENCE: 15
ggatccatgg ccttaccagt gaccgccttg ctcctgccgc tggccttgct gctccacgcc 60
gccaggccgg aacagaaact catcagtgag gaagatttgc agacgactcc aggagagaga 120
tcatcactcc ctgcctttta ccctggcact tcaggctctt gttccggatg tgggtccctc 180
tctctgccga caacaacccc tgcccccaga cctcctaccc cagcccctac aattgccagc 240
cagcctctga gcctgaggcc cgaggcttgt agacctgctg ctggcggagc cgtgcacacc 300
agaggactgg atttcgcctg cgaccctagg ttctgggtgc tggtggtcgt gggcggagtg 360
ctggcctgtt acagcctgct cgtgaccgtg gccttcatca tcttttgggt gcggagcaag 420
agaagcagac tgctgcacag cgactacatg aacatgaccc ccagacggcc tggccccacc 480
agaaagcact accagcctta cgcccctccc agagacttcg ccgcctacag atctcccggg 540
ggaggcggag gatctggcgg aggtggaagt ggcggaggcg gatctatgag ccagagcaac 600
agagaactgg tggtggactt cctgagctac aagctgagcc agaagggcta cagctggtcc 660
cagttcagcg acgtggaaga gaacagaaca gaggcccctg agggcacaga gtctgaggct 720
gtgaaacagg ccctgagaga agccggcgac gagttcgagc tgagatacag aagggccttc 780
agcgacctga ccagccagct gcacatcaca cctggcacag cctaccagag cttcgagcag 840
gtcgtgaacg agctgttcag agatggcgtg aactggggca gaatcgtggc cttcttcagc 900
tttggcggag ccctgtgtgt ggaaagcgtg gacaaagaaa tgcaggtcct ggtgtccaga 960
atcgccgcct ggatggccac ctacctgaac gatcatctgg aaccctggat tcaagagaac 1020
ggcggctggg acaccttcgt ggaactgtac ggaaacaacg ccgctgccga gagcagaaag 1080
ggccaagaac gagaagatgg cggcggtggt tctggtggcg gcggtagtgg tggcggtgga 1140
tcaatgcata gagtgaagtt cagcaggagc gcagacgccc ccgcgtacca gcagggccag 1200
aaccagctct ataacgagct caatctagga cgaagagagg agtacgatgt tttggacaag 1260
agacgtggcc gggaccctga gatgggggga aagccgagaa ggaagaaccc tcaggaaggc 1320
ctgtacaatg aactgcagaa agataagatg gcggaggcct acagtgagat tgggatgaaa 1380
ggcgagcgcc ggaggggcaa ggggcacgat ggcctttacc agggtctcag tacagccacc 1440
aaggacacct acgacgccct tcacatgcag gccctgcccc ctcgctaa 1488

<210> SEQ ID NO 16
<211> LENGTH: 566
<212> TYPE: PRT
<213> ORGANISM: Artificial sequence
<220> FEATURE:
<223> OTHER INFORMATION: Homo sapiens

<400> SEQUENCE: 16

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
```

-continued

```
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510
```

```
Leu Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro
                565


<210> SEQ ID NO 17
<211> LENGTH: 566
<212> TYPE: PRT
<213> ORGANISM: Artificial sequence
<220> FEATURE:
<223> OTHER INFORMATION: Homo sapiens

<400> SEQUENCE: 17

Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300
```

```
Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro
                565
```

<210> SEQ ID NO 18
<211> LENGTH: 10913
<212> TYPE: DNA
<213> ORGANISM: Artificial sequence
<220> FEATURE:
<223> OTHER INFORMATION: Homo sapiens

<400> SEQUENCE: 18

```
gagtgggtta catcgaactg gatctcaaca gcggtaagat ccttgagagt tttcgccccg     60

aagaacgttt tccaatgatg agcactttta aagttctgct atgtggcgcg gtattatccc    120

gtattgacgc cgggcaagag caactcggtc gccgcataca ctattctcag aatgacttgg    180

ttgagtactc accagtcaca gaaaagcatc ttacggatgg catgacagta agagaattat    240

gcagtgctgc cataaccatg agtgataaca ctgcggccaa cttacttctg acaacgatcg    300

gaggaccgaa ggagctaacc gcttttttgc acaacatggg ggatcatgta actcgccttg    360

atcgttggga accggagctg aatgaagcca taccaaacga cgagcgtgac accacgatgc    420

ctgtagcaat ggcaacaacg ttgcgcaaac tattaactgg cgaactactt actctagctt    480

cccggcaaca attaatagac tggatggagg cggataaagt tgcaggacca cttctgcgct    540
```

-continued

```
cggcccttcc ggctggctgg tttattgctg ataaatctgg agccggtgag cgtgggtctc    600

gcggtatcat tgcagcactg gggccagatg gtaagccctc ccgtatcgta gttatctaca    660

cgacggggag tcaggcaact atggatgaac gaaatagaca gatcgctgag ataggtgcct    720

cactgattaa gcattggtaa ctgtcagacc aagtttactc atatatactt tagattgatt    780

taaaacttca tttttaattt aaaaggatct aggtgaagat cctttttgat aatctcatga    840

ccaaaatccc ttaacgtgag ttttcgttcc actgagcgtc agaccccgta gaaaagatca    900

aaggatcttc ttgagatcct ttttttctgc gcgtaatctg ctgcttgcaa acaaaaaaac    960

caccgctacc agcggtggtt tgtttgccgg atcaagagct accaactctt tttccgaagg   1020

taactggctt cagcagagcg cagataccaa atactgtcct tctagtgtag ccgtagttag   1080

gccaccactt caagaactct gtagcaccgc ctacatacct cgctctgcta atcctgttac   1140

cagtggctgc tgccagtggc gataagtcgt gtcttaccgg gttggactca agacgatagt   1200

taccggataa ggcgcagcgg tcgggctgaa cggggggttc gtgcacacag cccagcttgg   1260

agcgaacgac ctacaccgaa ctgagatacc tacagcgtga gctatgagaa agcgccacgc   1320

ttcccgaagg gagaaaggcg gacaggtatc cggtaagcgg cagggtcgga acaggagagc   1380

gcacgaggga gcttccaggg ggaaacgcct ggtatcttta tagtcctgtc gggtttcgcc   1440

acctctgact tgagcgtcga tttttgtgat gctcgtcagg ggggcggagc ctatggaaaa   1500

acgccagcaa cgcggccttt ttacggttcc tggccttttg ctggcctttt gctcacatgt   1560

tctttcctgc gttatcccct gattctgtgg ataaccgtat taccgccttt gagtgagctg   1620

ataccgctcg ccgcagccga acgaccgagc gcagcgagtc agtgagcgag gaagcggaag   1680

agcgcccaat acgcaaaccg cctctccccg cgcgttggcc gattcattaa tgcagctggc   1740

acgacaggtt tcccgactgg aaagcgggca gtgagcgcaa cgcaattaat gtgagttagc   1800

tcactcatta ggcaccccag gctttacact ttatgcttcc ggctcgtatg ttgtgtggaa   1860

ttgtgagcgg ataacaattt cacacaggaa acagctatga ccatgattac gccaagcgcg   1920

caattaaccc tcactaaagg gaacaaaagc tggagctgca agcttaatgt agtcttatgc   1980

aatactcttg tagtcttgca acatggtaac gatgagttag caacatgcct tacaaggaga   2040

gaaaaagcac cgtgcatgcc gattggtgga agtaaggtgg tacgatcgtg ccttattagg   2100

aaggcaacag acgggtctga catggattgg acgaaccact gaattgccgc attgcagaga   2160

tattgtattt aagtgcctag ctcgatacaa taaacgggtc tctctggtta gaccagatct   2220

gagcctggga gctctctggc taactaggga acccactgct taagcctcaa taaagcttgc   2280

cttgagtgct tcaagtagtg tgtgcccgtc tgttgtgtga ctctggtaac tagagatccc   2340

tcagaccctt ttagtcagtg tggaaaatct ctagcagtgg cgcccgaaca gggacctgaa   2400

agcgaaaggg aaaccagagc tctctcgacg caggactcgg cttgctgaag cgcgcacggc   2460

aagaggcgag gggcggcgac tggtgagtac gccaaaaatt ttgactagcg gaggctagaa   2520

ggagagagat gggtgcgaga gcgtcagtat taagcggggg agaattagat cgcgatggga   2580

aaaaattcgg ttaaggccag ggggaaagaa aaaatataaa ttaaaacata tagtatgggc   2640

aagcagggag ctagaacgat tcgcagttaa tcctggcctg ttagaaacat cagaaggctg   2700

tagacaaata ctgggacagc tacaaccatc ccttcagaca ggatcagaag aacttagatc   2760

attatataat acagtagcaa ccctctattg tgtgcatcaa aggatagaga taaaagacac   2820

caaggaagct ttagacaaga tagaggaaga gcaaaacaaa agtaagacca ccgcacagca   2880
```

-continued

```
agcggccgct gatcttcaga cctggaggag gagatatgag ggacaattgg agaagtgaat   2940
tatataaata taaagtagta aaaattgaac cattaggagt agcacccacc aaggcaaaga   3000
gaagagtggt gcagagagaa aaaagagcag tgggaatagg agctttgttc cttgggttct   3060
tgggagcagc aggaagcact atgggcgcag cctcaatgac gctgacggta caggccagac   3120
aattattgtc tggtatagtg cagcagcaga acaatttgct gagggctatt gaggcgcaac   3180
agcatctgtt gcaactcaca gtctggggca tcaagcagct ccaggcaaga atcctggctg   3240
tggaaagata cctaaaggat caacagctcc tggggatttg gggttgctct ggaaaactca   3300
tttgcaccac tgctgtgcct tggaatgcta gttggagtaa taaatctctg gaacagattg   3360
gaatcacacg acctggatgg agtgggacag agaaattaac aattacacaa gcttaataca   3420
ctccttaatt gaagaatcgc aaaaccagca agaaaagaat gaacaagaat tattggaatt   3480
agataaatgg gcaagtttgt ggaattggtt taacataaca aattggctgt ggtatataaa   3540
attattcata atgatagtag gaggcttggt aggtttaaga atagtttttg ctgtactttc   3600
tatagtgaat agagttaggc agggatattc accattatcg tttcagaccc acctcccaac   3660
cccgagggga cccgacaggc ccgaaggaat agaagaagaa ggtggagaga gagacagaga   3720
cagatccatt cgattagtga acggatctcg acggtatcga ttagactgta gcccaggaat   3780
atggcagcta gattgtacac atttagaagg aaaagttatc ttggtagcag ttcatgtagc   3840
cagtggatat atagaagcag aagtaattcc agcagagaca gggcaagaaa cagcatactt   3900
cctcttaaaa ttagcaggaa gatggccagt aaaaacagta catacagaca atggcagcaa   3960
tttcaccagt actacagtta aggccgcctg ttggtgggcg gggatcaagc aggaatttgg   4020
cattccctac aatccccaaa gtcaaggagt aatagaatct atgaataaag aattaaagaa   4080
aattatagga caggtaagag atcaggctga acatcttaag acagcagtac aaatggcagt   4140
attcatccac aattttaaaa gaaaaggggg gattgggggg tacagtgcag gggaaagaat   4200
agtagacata atagcaacag acatacaaac taaagaatta caaaaacaaa ttacaaaaat   4260
tcaaaatttt cgggtttatt acagggacag cagagatcca gtttggctgc atacgcgtcg   4320
tgaggctccg gtgcccgtca gtgggcagag cgcacatcgc ccacagtccc cgagaagttg   4380
gggggagggg tcggcaattg aaccggtgcc tagagaaggt ggcgcggggt aaactgggaa   4440
agtgatgtcg tgtactggct ccgccttttt cccgagggtg ggggagaacc gtatataagt   4500
gcagtagtcg ccgtgaacgt tctttttcgc aacgggtttg ccgccagaac acaggtaagt   4560
gccgtgtgtg gttcccgcgg gcctggcctc tttacgggtt atggcccttg cgtgccttga   4620
attacttcca cctggctgca gtacgtgatt cttgatcccg agcttcgggt tggaagtggg   4680
tgggagagtt cgaggccttg cgcttaagga gccccttcgc ctcgtgcttg agttgaggcc   4740
tggcctgggc gctggggccg ccgcgtgcga atctggtggc accttcgcgc ctgtctcgct   4800
gctttcgata agtctctagc catttaaaat ttttgatgac ctgctgcgac gctttttttc   4860
tggcaagata gtcttgtaaa tgcgggccaa gatctgcaca ctggtatttc ggtttttggg   4920
gccgcgggcg gcgacggggc ccgtgcgtcc cagcgcacat gttcggcgag gcggggcctg   4980
cgagcgcggc caccgagaat cggacggggg tagtctcaag ctggccggcc tgctctggtg   5040
cctggcctcg cgccgccgtg tatcgccccg ccctgggcgg caaggctggc ccggtcggca   5100
ccagttgcgt gagcggaaag atggccgctt cccggccctg ctgcagggag ctcaaaatgg   5160
aggacgcggc gctcgggaga gcgggcgggt gagtcaccca cacaaaggaa aagggccttt   5220
ccgtcctcag ccgtcgcttc atgtgactcc acggagtacc gggcgccgtc caggcacctc   5280
```

gattagttct cgagcttttg gagtacgtcg tctttaggtt ggggggaggg gttttatgcg 5340
atggagtttc cccacactga gtgggtggag actgaagtta ggccagcttg gcacttgatg 5400
taattctcct tggaatttgc cctttttgag tttggatctt ggttcattct caagcctcag 5460
acagtggttc aaagtttttt tcttccattt caggtgtcgt gagctagacg actagtcgtc 5520
tagctctaga atggccttac cagtgaccgc cttgctcctg ccgctggcct tgctgctcca 5580
cgccgccagg ccggtgcagc tgcagcagtc aggacctgaa ctggtgaagc ctgggacttc 5640
agtgaggata tcctgcaaga cttctggata cacattcact gaatatacca tacactgggt 5700
gaagcagagc catggaaaga gccttgagtg gattggaaac atcaatccta acaatggtgg 5760
taccacctac aatcagaagt tcgaggacaa ggccacattg actgtagaca agtcctccag 5820
tacagcctac atggagctcc gcagcctaac atctgaggat tctgcagtct attattgtgc 5880
agctggttgg aactttgact actggggcca agggaccacg gtcaccgtct cctcaggtgg 5940
aggtggatca ggtggaggtg gatctggtgg aggtggatct gacattgtga tgacccagtc 6000
tcacaaattc atgtccacat cagtaggaga cagggtcagc atcatctgta aggccagtca 6060
agatgtgggt actgctgtag actggtatca acagaaacca ggacaatctc ctaaactact 6120
gatttattgg gcatccactc ggcacactgg agtccctgat cgcttcacag gcagtggatc 6180
tgggacagac ttcactctca ccattactaa tgttcagtct gaagacttgg cagattattt 6240
ctgtcagcaa tataacagct atcccctcac gttcggtgct gggaccatgc tggacctgaa 6300
acgggctagc acaacaaccc ctgcccccag acctcctacc ccagccccta caattgccag 6360
ccagcctctg agcctgaggc ccgaggcttg tagacctgct gctggcggag ccgtgcacac 6420
cagaggactg gatttcgcct gcgacttctg ggtgctggtg gtcgtgggcg gagtgctggc 6480
ctgttacagc ctgctcgtga ccgtggcctt catcatcttt tgggtgcgga gcaagagaag 6540
cagactgctg cacagcgact acatgaacat gacccccaga cggcctggcc ccaccagaaa 6600
gcactaccag ccttacgccc ctcccagaga cttcgccgcc tacagatctc atatgggagg 6660
cggaggatct ggcggaggtg gaagtggcgg aggcggatct caaagatggg aactcgccct 6720
gggcagattc ctggaatacc tgagctgggt gtccacactg agcgaacagg tgcaagagga 6780
actgctgagc agccaagtga cccaagagct gagagccctg atggacgaga caatgaagga 6840
actgaaggcc tacaagagcg agctggaaga acagctgacc cctgtggccg aggaaaccag 6900
agccagactg agcaaagaac tgcaggccgc tcaggccaga ctgggagccg atatggaaga 6960
tgttcggggc agactggtgc agtacagagg cgaagttcag gccatgctgg gccagtctac 7020
cgaggaactg agagtgcggc tggcctctca tctgattgcc ctgcagctga gactgatcgg 7080
cgacgcattc gacctgcaga aaagactggc cgtgtaccag gctggcgctg ctgaacggaa 7140
gcggcgcagc ggcagcgggc gcagcggcag cggcgagggc agaggaagtc ttctaacatg 7200
cggtgacgtg gaggagaatc ccggccctgg atccatggcc ttaccagtga ccgccttgct 7260
cctgccgctg gccttgctgc tccacgccgc caggccggaa cagaaactca tcagtgagga 7320
agatttgcag acgactccag gagagagatc atcactccct gccttttacc ctggcacttc 7380
aggctcttgt tccggatgtg ggtccctctc tctgccgaca acaaccccctg cccccagacc 7440
tcctacccca gcccctacaa ttgccagcca gcctctgagc ctgaggcccg aggcttgtag 7500
acctgctgct ggcggagccg tgcacaccag aggactggat ttcgcctgcg accctaggtt 7560
ctgggtgctg gtggtcgtgg gcggagtgct ggcctgttac agcctgctcg tgaccgtggc 7620

-continued

```
cttcatcatc ttttgggtgc ggagcaagag aagcagactg ctgcacagcg actacatgaa   7680
catgaccccc agacggcctg gccccaccag aaagcactac cagccttacg cccctcccag   7740
agacttcgcc gcctacagat ctcccggggg aggcggagga tctggcggag gtggaagtgg   7800
cggaggcgga tctatgagcc agagcaacag agaactggtg gtggacttcc tgagctacaa   7860
gctgagccag aagggctaca gctggtccca gttcagcgac gtggaagaga acagaacaga   7920
ggcccctgag ggcacagagt ctgaggctgt gaaacaggcc ctgagagaag ccggcgacga   7980
gttcgagctg agatacagaa gggccttcag cgacctgacc agccagctgc acatcacacc   8040
tggcacagcc taccagagct tcgagcaggt cgtgaacgag ctgttcagag atggcgtgaa   8100
ctggggcaga atcgtggcct tcttcagctt tggcggagcc ctgtgtgtgg aaagcgtgga   8160
caaagaaatg caggtcctgg tgtccagaat cgccgcctgg atggccacct acctgaacga   8220
tcatctggaa ccctggattc aagagaacgg cggctgggac accttcgtgg aactgtacgg   8280
aaacaacgcc gctgccgaga gcagaaaggg ccaagaacga gaagatggcg gcggtggttc   8340
tggtggcggc ggtagtggtg gcggtggatc aatgcataga gtgaagttca gcaggagcgc   8400
agacgccccc gcgtaccagc agggccagaa ccagctctat aacgagctca atctaggacg   8460
aagagaggag tacgatgttt tggacaagag acgtggccgg gaccctgaga tgggggggaaa   8520
gccgagaagg aagaaccctc aggaaggcct gtacaatgaa ctgcagaaag ataagatggc   8580
ggaggcctac agtgagattg ggatgaaagg cgagcgccgg aggggcaagg ggcacgatgg   8640
cctttaccag ggtctcagta cagccaccaa ggacacctac gacgcccttc acatgcaggc   8700
cctgccccct cgctaagtcg acaatcaacc tctggattac aaaatttgtg aaagattgac   8760
tggtattctt aactatgttg ctccttttac gctatgtgga tacgctgctt taatgccttt   8820
gtatcatgct attgcttccc gtatggcttt cattttctcc tccttgtata aatcctggtt   8880
gctgtctctt tatgaggagt tgtggcccgt tgtcaggcaa cgtggcgtgg tgtgcactgt   8940
gtttgctgac gcaaccccca ctggttgggg cattgccacc acctgtcagc tcctttccgg   9000
gactttcgct ttccccctcc ctattgccac ggcggaactc atcgccgcct gccttgcccg   9060
ctgctggaca ggggctcggc tgttgggcac tgacaattcc gtggtgttgt cggggaagct   9120
gacgtccttt ccatggctgc tcgcctgtgt tgccacctgg attctgcgcg ggacgtcctt   9180
ctgctacgtc ccttcggccc tcaatccagc ggaccttcct tcccgcggcc tgctgccggc   9240
tctgcggcct cttccgcgtc ttcgccttcg ccctcagacg agtcggatct ccctttgggc   9300
cgcctccccg cctggaattc gagctcggta cctttaagac caatgactta caaggcagct   9360
gtagatctta gccacttttt aaaagaaaag gggggactgg aagggctaat tcactcccaa   9420
cgaagacaag atctgctttt tgcttgtact gggtctctct ggttagacca gatctgagcc   9480
tgggagctct ctggctaact agggaaccca ctgcttaagc ctcaataaag cttgccttga   9540
gtgcttcaag tagtgtgtgc ccgtctgttg tgtgactctg gtaactagag atccctcaga   9600
cccttttagt cagtgtggaa aatctctagc agtagtagtt catgtcatct tattattcag   9660
tatttataac ttgcaaagaa atgaatatca gagagtgaga ggaacttgtt tattgcagct   9720
tataatggtt acaaataaag caatagcatc acaaatttca caaataaagc atttttttca   9780
ctgcattcta gttgtggttt gtccaaactc atcaatgtat cttatcatgt ctggctctag   9840
ctatcccgcc cctaactccg cccagttccg cccattctcc gccccatggc tgactaattt   9900
tttttattta tgcagaggcc gaggccgcct cggcctctga gctattccag aagtagtgag   9960
gaggcttttt tggaggccta gctaggcttt tgcgtcgaga cgtacccaat tcgccctata  10020
```

```
gtgagtcgta ttacgcgcgc tcactggccg tcgttttaca acgtcgtgac tgggaaaacc  10080

ctggcgttac ccaacttaat cgccttgcag cacatccccc tttcgccagc tggcgtaata  10140

gcgaagaggc ccgcaccgat cgcccttccc aacagttgcg cagcctgaat ggcgaatggc  10200

gcgacgcgcc ctgtagcggc gcattaagcg cggcgggtgt ggtggttacg cgcagcgtga  10260

ccgctacact tgccagcgcc ctagcgcccg ctcctttcgc tttcttccct tcctttctcg  10320

ccacgttcgc cggctttccc cgtcaagctc taaatcgggg gctcccttta gggttccgat  10380

ttagtgcttt acggcacctc gaccccaaaa aacttgatta gggtgatggt tcacgtagtg  10440

ggccatcgcc ctgatagacg gtttttcgcc ctttgacgtt ggagtccacg ttctttaata  10500

gtggactctt gttccaaact ggaacaacac tcaaccctat ctcggtctat tcttttgatt  10560

tataagggat tttgccgatt tcggcctatt ggttaaaaaa tgagctgatt taacaaaaat  10620

ttaacgcgaa ttttaacaaa atattaacgt ttacaatttc ccaggtggca cttttcgggg  10680

aaatgtgcgc ggaaccccta tttgtttatt tttctaaata cattcaaata tgtatccgct  10740

catgagacaa taaccctgat aaatgcttca ataatattga aaaaggaaga gtatgagtat  10800

tcaacatttc cgtgtcgccc ttattccctt ttttgcggca ttttgccttc ctgtttttgc  10860

tcacccagaa acgctggtga aagtaaaaga tgctgaagat cagttgggtg cac         10913
```

<210> SEQ ID NO 19
<211> LENGTH: 143
<212> TYPE: PRT
<213> ORGANISM: Artificial sequence
<220> FEATURE:
<223> OTHER INFORMATION: Homo sapiens

<400> SEQUENCE: 19

```
Gln Arg Trp Glu Leu Ala Leu Gly Arg Phe Leu Ala Tyr Leu Ser Trp
1               5                   10                  15

Val Ser Thr Leu Ser Glu Gln Val Gln Glu Glu Leu Leu Ser Ser Gln
            20                  25                  30

Val Thr Gln Glu Leu Arg Ala Leu Met Asp Glu Thr Met Lys Glu Leu
        35                  40                  45

Lys Ala Tyr Lys Ser Glu Leu Glu Glu Gln Leu Thr Pro Val Ala Glu
    50                  55                  60

Glu Thr Arg Ala Arg Leu Ser Lys Glu Leu Gln Ala Ala Gln Ala Arg
65                  70                  75                  80

Leu Gly Ala Asp Met Glu Asp Val Arg Gly Arg Leu Val Gln Tyr Arg
                85                  90                  95

Gly Glu Val Gln Ala Met Leu Gly Gln Ser Thr Glu Glu Leu Arg Val
            100                 105                 110

Arg Leu Ala Ser His Leu Ile Ala Leu Gln Leu Arg Leu Ile Gly Asp
        115                 120                 125

Ala Phe Asp Leu Gln Lys Arg Leu Ala Val Tyr Gln Ala Gly Ala
    130                 135                 140
```

<210> SEQ ID NO 20
<211> LENGTH: 1487
<212> TYPE: DNA
<213> ORGANISM: Artificial sequence
<220> FEATURE:
<223> OTHER INFORMATION: Homo sapiens

<400> SEQUENCE: 20

```
ggatccatgg ccttaccagt gaccgccttg ctcctgccgc tggccttgct gctccacgcc     60
```

```
gccaggccgg aacagaaact catcagtgag gaagatttgc agacgactcc aggagagaga    120
tcatcactcc ctgcctttta ccctggcact tcaggctctt gttccggatg tgggtccctc    180
tctctgccga caacaacccc tgcccccaga cctcctaccc cagcccctac aattgccagc    240
cagcctctga gcctgaggcc cgaggcttgt agacctgctg ctggcggagc cgtgcacacc    300
agaggactgg atttcgcctg cgacctaggt tctgggtgct ggtggtcgtg ggcggagtgc    360
tggcctgtta cagcctgctc gtgaccgtgg ccttcatcat cttttgggtg cggagcaaga    420
gaagcagact gctgcacagc gactacatga acatgacccc cagacggcct ggccccacca    480
gaaagcacta ccagccttac gcccctccca gagacttcgc cgcctacaga tctcccgggg    540
gaggcggagg atctggcgga ggtggaagtg gcggaggcgg atctatgagc cagagcaaca    600
gagaactggt ggtggacttc ctgagctaca agctgagcca gaagggctac agctggtccc    660
agttcagcga cgtggaagag aacagaacag aggcccctga gggcacagag tctgaggctg    720
tgaaacaggc cctgagagaa gccggcgacg agttcgagct gagatacaga agggccttca    780
gcgacctgac cagccagctg cacatcacac ctggcacagc ctaccagagc ttcgagcagg    840
tcgtgaacga gctgttcaga gatggcgtga actggggcag aatcgtggcc ttcttcagct    900
ttggcggagc cctgtgtgtg gaaagcgtgg acaaagaaat gcaggtcctg gtgtccagaa    960
tcgccgcctg gatggccacc tacctgaacg atcatctgga accctggatt caagagaacg   1020
gcggctggga caccttcgtg gaactgtacg gaaacaacgc cgctgccgag agcagaaagg   1080
gccaagaacg agaagatgga ggcggaggat ctggcggagg tggaagtggc ggaggcggat   1140
ctatgcatag agtgaagttc agcaggagcg cagacgcccc cgcgtaccag cagggccaga   1200
accagctcta taacgagctc aatctaggac gaagagagga gtacgatgtt ttggacaaga   1260
gacgtggccg ggaccctgag atgggggaa agccgagaag gaagaaccct caggaaggcc   1320
tgtacaatga actgcagaaa gataagatgg cggaggccta cagtgagatt gggatgaaag   1380
gcgagcgccg gaggggcaag gggcacgatg gcctttacca gggtctcagt acagccacca   1440
aggacaccta cgacgccctt cacatgcagg ccctgccccc tcgctaa                1487
```

<210> SEQ ID NO 21
<211> LENGTH: 1487
<212> TYPE: DNA
<213> ORGANISM: Artificial sequence
<220> FEATURE:
<223> OTHER INFORMATION: Homo sapiens

<400> SEQUENCE: 21

```
ggatccatgg ccttaccagt gaccgccttg ctcctgccgc tggccttgct gctccacgcc     60
gccaggccgg aacagaaact catcagtgag gaagatttgc agacgactcc aggagagaga    120
tcatcactcc ctgcctttta ccctggcact tcaggctctt gttccggatg tgggtccctc    180
tctctgccga caacaacccc tgcccccaga cctcctaccc cagcccctac aattgccagc    240
cagcctctga gcctgaggcc cgaggcttgt agacctgctg ctggcggagc cgtgcacacc    300
agaggactgg atttcgcctg cgacctaggt tctgggtgct ggtggtcgtg ggcggagtgc    360
tggcctgtta cagcctgctc gtgaccgtgg ccttcatcat cttttgggtg cggagcaaga    420
gaagcagact gctgcacagc gactacatga acatgacccc cagacggcct ggccccacca    480
gaaagcacta ccagccttac gcccctccca gagacttcgc cgcctacaga tctcccgggg    540
gaggcggagg atctggcgga ggtggaagtg gcggaggcgg atctatgagc cagagcaaca    600
```

-continued

```
gagaactggt ggtggacttc ctgagctaca agctgagcca gaagggctac agctggtccc     660

agttcagcga cgtggaagag aacagaacag aggcccctga gggcacagag tctgaggctg     720

tgaaacaggc cctgagagaa gccggcgacg agttcgagct gagatacaga agggccttca     780

gcgacctgac cagccagctg cacatcacac ctggcacagc ctaccagagc ttcgagcagg     840

tcgtgaacga gctgttcaga gatggcgtga actggggcag aatcgtggcc ttcttcagct     900

ttggcggagc cctgtgtgtg gaaagcgtgg acaaagaaat gcaggtcctg gtgtccagaa     960

tcgccgcctg gatggccacc tacctgaacg atcatctgga accctggatt caagagaacg    1020

gcggctggga caccttcgtg gaactgtacg gaaacaacgc cgctgccgag agcagaaagg    1080

gccaagaacg agaagatgga ggcggaggat ctggcggagg tggaagtggc ggaggcggat    1140

ctatgcatag agtgaagttc agcaggagcg cagacgcccc cgcgtaccag cagggccaga    1200

accagctcta taacgagctc aatctaggac gaagagagga gtacgatgtt ttggacaaga    1260

gacgtggccg ggaccctgag atggggggaa agccgagaag gaagaaccct caggaaggcc    1320

tgtacaatga actgcagaaa gataagatgg cggaggccta cagtgagatt gggatgaaag    1380

gcgagcgccg gaggggcaag gggcacgatg gcctttacca gggtctcagt acagccacca    1440

aggacaccta cgacgccctt cacatgcagg ccctgccccc tcgctaa                  1487
```

<210> SEQ ID NO 22
<211> LENGTH: 169
<212> TYPE: PRT
<213> ORGANISM: Artificial sequence
<220> FEATURE:
<223> OTHER INFORMATION: Homo sapiens

<400> SEQUENCE: 22

```
Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Ala Val Lys Gln
        35                  40                  45

Ala Leu Arg Glu Ala Gly Asp Glu Phe Glu Leu Arg Tyr Arg Arg Ala
    50                  55                  60

Phe Ser Asp Leu Thr Ser Gln Leu His Ile Thr Pro Gly Thr Ala Tyr
65                  70                  75                  80

Gln Ser Phe Glu Gln Val Val Asn Glu Leu Phe Arg Asp Gly Val Asn
                85                  90                  95

Trp Gly Arg Ile Val Ala Phe Phe Ser Phe Gly Gly Ala Leu Cys Val
            100                 105                 110

Glu Ser Val Asp Lys Glu Met Gln Val Leu Val Ser Arg Ile Ala Ala
        115                 120                 125

Trp Met Ala Thr Tyr Leu Asn Asp His Leu Glu Pro Trp Ile Gln Glu
    130                 135                 140

Asn Gly Gly Trp Asp Thr Phe Val Glu Leu Tyr Gly Asn Asn Ala Ala
145                 150                 155                 160

Ala Glu Ser Arg Lys Gly Gln Glu Arg
                165
```

<210> SEQ ID NO 23
<211> LENGTH: 169
<212> TYPE: PRT
<213> ORGANISM: Artificial sequence
<220> FEATURE:

<223> OTHER INFORMATION: Homo sapiens

<400> SEQUENCE: 23

Met Ser Gln Ser Asn Arg Glu Leu Val Val Asp Phe Leu Ser Tyr Lys
1 5 10 15

Leu Ser Gln Lys Gly Tyr Ser Trp Ser Gln Phe Ser Asp Val Glu Glu
20 25 30

Asn Arg Thr Glu Ala Pro Glu Gly Thr Glu Ser Glu Ala Val Lys Gln
35 40 45

Ala Leu Arg Glu Ala Gly Asp Asp Phe Glu Leu Arg Tyr Arg Arg Ala
50 55 60

Phe Ser Asp Leu Thr Ser Gln Leu His Ile Thr Pro Gly Thr Ala Tyr
65 70 75 80

Gln Ser Phe Glu Gln Val Val Asn Glu Leu Phe Arg Asp Gly Val Asn
85 90 95

Trp Gly Arg Ile Val Ala Phe Phe Ser Phe Gly Gly Ala Leu Cys Val
100 105 110

Glu Ser Val Asp Lys Glu Met Gln Val Leu Val Ser Arg Ile Ala Ala
115 120 125

Trp Met Ala Thr Tyr Leu Asn Asp His Leu Glu Pro Trp Ile Gln Glu
130 135 140

Asn Gly Gly Trp Asp Thr Phe Val Glu Leu Tyr Gly Asn Asn Ala Ala
145 150 155 160

Ala Glu Ser Arg Lys Gly Gln Glu Arg
165

<210> SEQ ID NO 24
<211> LENGTH: 207
<212> TYPE: PRT
<213> ORGANISM: Artificial sequence
<220> FEATURE:
<223> OTHER INFORMATION: Homo sapiens

<400> SEQUENCE: 24

Met Ala His Ala Gly Arg Thr Gly Tyr Asp Asn Arg Glu Ile Val Met
1 5 10 15

Lys Tyr Ile His Tyr Lys Leu Ser Gln Arg Gly Tyr Glu Trp Asp Ala
20 25 30

Gly Asp Val Gly Ala Ala Pro Pro Gly Ala Ala Pro Ala Pro Gly Ile
35 40 45

Phe Ser Ser Gln Pro Gly His Thr Pro His Pro Ala Ala Ser Arg Asp
50 55 60

Pro Val Ala Arg Thr Ser Pro Leu Gln Thr Pro Ala Ala Pro Gly Ala
65 70 75 80

Ala Ala Gly Pro Ala Leu Ser Pro Val Pro Pro Val Val His Leu Thr
85 90 95

Leu Arg Gln Ala Gly Asp Asp Phe Ser Arg Arg Tyr Arg Arg Asp Phe
100 105 110

Ala Glu Met Ser Ser Gln Leu His Leu Thr Pro Phe Thr Ala Arg Gly
115 120 125

Arg Phe Ala Thr Val Val Glu Glu Leu Phe Arg Asp Gly Val Asn Trp
130 135 140

Gly Arg Ile Val Ala Phe Phe Glu Phe Gly Gly Val Met Cys Val Glu
145 150 155 160

Ser Val Asn Arg Glu Met Ser Pro Leu Val Asp Asn Ile Ala Leu Trp
165 170 175

```
Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg
        195                 200                 205


<210> SEQ ID NO 25
<211> LENGTH: 21
<212> TYPE: PRT
<213> ORGANISM: Artificial sequence
<220> FEATURE:
<223> OTHER INFORMATION: Homo sapiens

<400> SEQUENCE: 25

Met Ala Leu Pro Val Thr Ala Leu Leu Leu Pro Leu Ala Leu Leu Leu
1               5                   10                  15

His Ala Ala Arg Pro
            20


<210> SEQ ID NO 26
<211> LENGTH: 15
<212> TYPE: PRT
<213> ORGANISM: Artificial sequence
<220> FEATURE:
<223> OTHER INFORMATION: Synthetic peptide: serine/glycine linker

<400> SEQUENCE: 26

Gly Gly Gly Gly Ser Gly Gly Gly Gly Ser Gly Gly Gly Gly Ser
1               5                   10                  15


<210> SEQ ID NO 27
<211> LENGTH: 31
<212> TYPE: PRT
<213> ORGANISM: Artificial sequence
<220> FEATURE:
<223> OTHER INFORMATION: Homo sapiens

<400> SEQUENCE: 27

Arg Lys Arg Arg Ser Gly Ser Gly Arg Ser Gly Ser Gly Glu Gly Arg
1               5                   10                  15

Gly Ser Leu Leu Thr Cys Gly Asp Val Glu Glu Asn Pro Gly Pro
            20                  25                  30


<210> SEQ ID NO 28
<211> LENGTH: 10
<212> TYPE: PRT
<213> ORGANISM: Artificial sequence
<220> FEATURE:
<223> OTHER INFORMATION: c-myc tag

<400> SEQUENCE: 28

Glu Gln Lys Leu Ile Ser Glu Glu Asp Leu
1               5                   10


<210> SEQ ID NO 29
<211> LENGTH: 112
<212> TYPE: PRT
<213> ORGANISM: Artificial sequence
<220> FEATURE:
<223> OTHER INFORMATION: Homo sapiens

<400> SEQUENCE: 29

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
```

```
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 30
<211> LENGTH: 171
<212> TYPE: PRT
<213> ORGANISM: Artificial sequence
<220> FEATURE:
<223> OTHER INFORMATION: Homo sapiens

<400> SEQUENCE: 30

```
Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Ala Val Lys Gln
        35                  40                  45

Ala Leu Arg Glu Ala Gly Asp Asp Phe Glu Leu Arg Tyr Arg Arg Ala
    50                  55                  60

Phe Ser Asp Leu Thr Ser Gln Leu His Ile Thr Pro Gly Thr Ala Tyr
65                  70                  75                  80

Gln Ser Phe Glu Gln Val Val Asn Glu Leu Phe Arg Asp Gly Val Asn
                85                  90                  95

Trp Gly Arg Ile Val Ala Phe Phe Ser Phe Gly Gly Ala Leu Cys Val
            100                 105                 110

Glu Ser Val Asp Lys Glu Met Gln Val Leu Val Ser Arg Ile Ala Ala
        115                 120                 125

Trp Met Ala Thr Tyr Leu Asn Asp His Leu Glu Pro Trp Ile Gln Glu
    130                 135                 140

Asn Gly Gly Trp Asp Thr Phe Val Glu Leu Tyr Gly Asn Asn Ala Ala
145                 150                 155                 160

Ala Glu Ser Arg Lys Gly Gln Glu Arg Glu Asp
                165                 170
```

<210> SEQ ID NO 31
<211> LENGTH: 145
<212> TYPE: PRT
<213> ORGANISM: Artificial sequence
<220> FEATURE:
<223> OTHER INFORMATION: Homo sapiens

<400> SEQUENCE: 31

```
Gln Arg Trp Glu Leu Ala Leu Gly Arg Phe Leu Ala Tyr Leu Ser Trp
1               5                   10                  15

Val Ser Thr Leu Ser Glu Gln Val Gln Glu Glu Leu Leu Ser Ser Gln
            20                  25                  30

Val Thr Gln Glu Leu Arg Ala Leu Met Asp Glu Thr Met Lys Glu Leu
        35                  40                  45
```

-continued

```
Lys Ala Tyr Lys Ser Glu Leu Glu Glu Gln Leu Thr Pro Val Ala Glu
    50                  55                  60

Glu Thr Arg Ala Arg Leu Ser Lys Glu Leu Gln Ala Ala Gln Ala Arg
65                  70                  75                  80

Leu Gly Ala Asp Met Glu Asp Val Arg Gly Arg Leu Val Gln Tyr Arg
                85                  90                  95

Gly Glu Val Gln Ala Met Leu Gly Gln Ser Thr Glu Glu Leu Arg Val
            100                 105                 110

Arg Leu Ala Ser His Leu Ile Ala Leu Gln Leu Arg Leu Ile Gly Asp
        115                 120                 125

Ala Phe Asp Leu Gln Lys Arg Leu Ala Val Tyr Gln Ala Gly Ala Ala
    130                 135                 140

Glu
145


<210> SEQ ID NO 32
<211> LENGTH: 145
<212> TYPE: PRT
<213> ORGANISM: Artificial sequence
<220> FEATURE:
<223> OTHER INFORMATION: Homo sapiens

<400> SEQUENCE: 32

Gln Arg Trp Glu Leu Ala Leu Gly Arg Phe Leu Glu Tyr Leu Ser Trp
1               5                   10                  15

Val Ser Thr Leu Ser Glu Gln Val Gln Glu Glu Leu Leu Ser Ser Gln
            20                  25                  30

Val Thr Gln Glu Leu Arg Ala Leu Met Asp Glu Thr Met Lys Glu Leu
        35                  40                  45

Lys Ala Tyr Lys Ser Glu Leu Glu Glu Gln Leu Thr Pro Val Ala Glu
    50                  55                  60

Glu Thr Arg Ala Arg Leu Ser Lys Glu Leu Gln Ala Ala Gln Ala Arg
65                  70                  75                  80

Leu Gly Ala Asp Met Glu Asp Val Arg Gly Arg Leu Val Gln Tyr Arg
                85                  90                  95

Gly Glu Val Gln Ala Met Leu Gly Gln Ser Thr Glu Glu Leu Arg Val
            100                 105                 110

Arg Leu Ala Ser His Leu Ile Ala Leu Gln Ala Arg Leu Ile Gly Asp
        115                 120                 125

Ala Phe Asp Leu Gln Lys Arg Leu Ala Val Tyr Gln Ala Gly Ala Ala
    130                 135                 140

Glu
145


<210> SEQ ID NO 33
<211> LENGTH: 145
<212> TYPE: PRT
<213> ORGANISM: Artificial sequence
<220> FEATURE:
<223> OTHER INFORMATION: Homo sapiens

<400> SEQUENCE: 33

Gln Arg Trp Glu Leu Ala Leu Gly Arg Phe Leu Glu Tyr Leu Ser Trp
1               5                   10                  15

Val Ser Thr Leu Ser Glu Gln Val Gln Glu Glu Leu Leu Ser Ser Gln
            20                  25                  30

Val Thr Gln Glu Leu Arg Ala Leu Met Asp Glu Thr Met Lys Glu Leu
        35                  40                  45
```

```
Lys Ala Tyr Lys Ser Glu Leu Glu Glu Gln Leu Thr Pro Val Ala Glu
    50                  55                  60

Glu Thr Arg Ala Arg Leu Ser Lys Glu Leu Gln Ala Ala Gln Ala Arg
65                  70                  75                  80

Leu Gly Ala Asp Met Glu Asp Val Arg Gly Arg Leu Val Gln Tyr Arg
                85                  90                  95

Gly Glu Val Gln Ala Met Leu Gly Gln Ser Thr Glu Glu Leu Arg Val
            100                 105                 110

Arg Leu Ala Ser His Leu Ile Ala Leu Gln Leu Arg Leu Ile Gly Ala
        115                 120                 125

Ala Phe Asp Leu Gln Lys Arg Leu Ala Val Tyr Gln Ala Gly Ala Ala
    130                 135                 140

Glu
145


<210> SEQ ID NO 34
<211> LENGTH: 207
<212> TYPE: PRT
<213> ORGANISM: Artificial sequence
<220> FEATURE:
<223> OTHER INFORMATION: Homo sapiens

<400> SEQUENCE: 34

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg
        195                 200                 205


<210> SEQ ID NO 35
<211> LENGTH: 1061
<212> TYPE: PRT
<213> ORGANISM: Artificial sequence
<220> FEATURE:
<223> OTHER INFORMATION: Homo sapiens
```

<400> SEQUENCE: 35

Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

```
Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro Gly Ser Met Ala Leu Pro Val Thr Ala Leu
                565                 570                 575

Leu Leu Pro Leu Ala Leu Leu Leu His Ala Ala Arg Pro Glu Gln Lys
            580                 585                 590

Leu Ile Ser Glu Glu Asp Leu Gln Thr Thr Pro Gly Glu Arg Ser Ser
        595                 600                 605

Leu Pro Ala Phe Tyr Pro Gly Thr Ser Gly Ser Cys Ser Gly Cys Gly
    610                 615                 620

Ser Leu Ser Leu Pro Thr Thr Thr Pro Ala Pro Arg Pro Pro Thr Pro
625                 630                 635                 640

Ala Pro Thr Ile Ala Ser Gln Pro Leu Ser Leu Arg Pro Glu Ala Cys
                645                 650                 655

Arg Pro Ala Ala Gly Gly Ala Val His Thr Arg Gly Leu Asp Phe Ala
            660                 665                 670

Cys Asp Pro Arg Phe Trp Val Leu Val Val Val Gly Gly Val Leu Ala
        675                 680                 685

Cys Tyr Ser Leu Leu Val Thr Val Ala Phe Ile Ile Phe Trp Val Arg
    690                 695                 700

Ser Lys Arg Ser Arg Leu Leu His Ser Asp Tyr Met Asn Met Thr Pro
705                 710                 715                 720

Arg Arg Pro Gly Pro Thr Arg Lys His Tyr Gln Pro Tyr Ala Pro Pro
                725                 730                 735

Arg Asp Phe Ala Ala Tyr Arg Ser Pro Gly Gly Gly Gly Gly Ser Gly
            740                 745                 750

Gly Gly Gly Ser Gly Gly Gly Gly Ser Met Ser Gln Ser Asn Arg Glu
        755                 760                 765

Leu Val Val Asp Phe Leu Ser Tyr Lys Leu Ser Gln Lys Gly Tyr Ser
    770                 775                 780

Trp Ser Gln Phe Ser Asp Val Glu Glu Asn Arg Thr Glu Ala Pro Glu
785                 790                 795                 800

Gly Thr Glu Ser Glu Ala Val Lys Gln Ala Leu Arg Glu Ala Gly Asp
                805                 810                 815

Glu Phe Glu Leu Arg Tyr Arg Arg Ala Phe Ser Asp Leu Thr Ser Gln
            820                 825                 830
```

```
Leu His Ile Thr Pro Gly Thr Ala Tyr Gln Ser Phe Glu Gln Val Val
        835                 840                 845

Asn Glu Leu Phe Arg Asp Gly Val Asn Trp Gly Arg Ile Val Ala Phe
    850                 855                 860

Phe Ser Phe Gly Gly Ala Leu Cys Val Glu Ser Val Asp Lys Glu Met
865                 870                 875                 880

Gln Val Leu Val Ser Arg Ile Ala Ala Trp Met Ala Thr Tyr Leu Asn
                885                 890                 895

Asp His Leu Glu Pro Trp Ile Gln Glu Asn Gly Gly Trp Asp Thr Phe
            900                 905                 910

Val Glu Leu Tyr Gly Asn Asn Ala Ala Ala Glu Ser Arg Lys Gly Gln
        915                 920                 925

Glu Arg Glu Asp Gly Gly Gly Gly Ser Gly Gly Gly Gly Ser Gly Gly
    930                 935                 940

Gly Gly Ser Met His Arg Val Lys Phe Ser Arg Ser Ala Asp Ala Pro
945                 950                 955                 960

Ala Tyr Gln Gln Gly Gln Asn Gln Leu Tyr Asn Glu Leu Asn Leu Gly
                965                 970                 975

Arg Arg Glu Glu Tyr Asp Val Leu Asp Lys Arg Arg Gly Arg Asp Pro
            980                 985                 990

Glu Met Gly Gly Lys Pro Arg Arg  Lys Asn Pro Gln Glu  Gly Leu Tyr
        995                 1000                 1005

Asn Glu  Leu Gln Lys Asp Lys  Met Ala Glu Ala Tyr  Ser Glu Ile
    1010                 1015                 1020

Gly Met  Lys Gly Glu Arg Arg  Arg Gly Lys Gly His  Asp Gly Leu
    1025                 1030                 1035

Tyr Gln  Gly Leu Ser Thr Ala  Thr Lys Asp Thr Tyr  Asp Ala Leu
    1040                 1045                 1050

His Met  Gln Ala Leu Pro Pro  Arg
    1055                 1060


<210> SEQ ID NO 36
<211> LENGTH: 1061
<212> TYPE: PRT
<213> ORGANISM: Artificial sequence
<220> FEATURE:
<223> OTHER INFORMATION: Homo sapiens

<400> SEQUENCE: 36

Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125
```

-continued

```
Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
```

-continued

```
545                 550                 555                 560

Glu Glu Asn Pro Gly Pro Gly Ser Met Ala Leu Pro Val Thr Ala Leu
                565                 570                 575

Leu Leu Pro Leu Ala Leu Leu Leu His Ala Ala Arg Pro Glu Gln Lys
            580                 585                 590

Leu Ile Ser Glu Glu Asp Leu Gln Thr Thr Pro Gly Glu Arg Ser Ser
        595                 600                 605

Leu Pro Ala Phe Tyr Pro Gly Thr Ser Gly Ser Cys Ser Gly Cys Gly
    610                 615                 620

Ser Leu Ser Leu Pro Thr Thr Thr Pro Ala Pro Arg Pro Pro Thr Pro
625                 630                 635                 640

Ala Pro Thr Ile Ala Ser Gln Pro Leu Ser Leu Arg Pro Glu Ala Cys
                645                 650                 655

Arg Pro Ala Ala Gly Gly Ala Val His Thr Arg Gly Leu Asp Phe Ala
            660                 665                 670

Cys Asp Pro Arg Phe Trp Val Leu Val Val Val Gly Gly Val Leu Ala
        675                 680                 685

Cys Tyr Ser Leu Leu Val Thr Val Ala Phe Ile Ile Phe Trp Val Arg
    690                 695                 700

Ser Lys Arg Ser Arg Leu Leu His Ser Asp Tyr Met Asn Met Thr Pro
705                 710                 715                 720

Arg Arg Pro Gly Pro Thr Arg Lys His Tyr Gln Pro Tyr Ala Pro Pro
                725                 730                 735

Arg Asp Phe Ala Ala Tyr Arg Ser Pro Gly Gly Gly Gly Gly Ser Gly
            740                 745                 750

Gly Gly Gly Ser Gly Gly Gly Gly Ser Met Ser Gln Ser Asn Arg Glu
        755                 760                 765

Leu Val Val Asp Phe Leu Ser Tyr Lys Leu Ser Gln Lys Gly Tyr Ser
    770                 775                 780

Trp Ser Gln Phe Ser Asp Val Glu Glu Asn Arg Thr Glu Ala Pro Glu
785                 790                 795                 800

Gly Thr Glu Ser Glu Ala Val Lys Gln Ala Leu Arg Glu Ala Gly Asp
                805                 810                 815

Asp Phe Glu Leu Arg Tyr Arg Arg Ala Phe Ser Asp Leu Thr Ser Gln
            820                 825                 830

Leu His Ile Thr Pro Gly Thr Ala Tyr Gln Ser Phe Glu Gln Val Val
        835                 840                 845

Asn Glu Leu Phe Arg Asp Gly Val Asn Trp Gly Arg Ile Val Ala Phe
    850                 855                 860

Phe Ser Phe Gly Gly Ala Leu Cys Val Glu Ser Val Asp Lys Glu Met
865                 870                 875                 880

Gln Val Leu Val Ser Arg Ile Ala Ala Trp Met Ala Thr Tyr Leu Asn
                885                 890                 895

Asp His Leu Glu Pro Trp Ile Gln Glu Asn Gly Gly Trp Asp Thr Phe
            900                 905                 910

Val Glu Leu Tyr Gly Asn Asn Ala Ala Ala Glu Ser Arg Lys Gly Gln
        915                 920                 925

Glu Arg Glu Asp Gly Gly Gly Gly Ser Gly Gly Gly Gly Ser Gly Gly
    930                 935                 940

Gly Gly Ser Met His Arg Val Lys Phe Ser Arg Ser Ala Asp Ala Pro
945                 950                 955                 960

Ala Tyr Gln Gln Gly Gln Asn Gln Leu Tyr Asn Glu Leu Asn Leu Gly
                965                 970                 975
```

Arg Arg Glu Glu Tyr Asp Val Leu Asp Lys Arg Arg Gly Arg Asp Pro
980 985 990

Glu Met Gly Gly Lys Pro Arg Arg Lys Asn Pro Gln Glu Gly Leu Tyr
995 1000 1005

Asn Glu Leu Gln Lys Asp Lys Met Ala Glu Ala Tyr Ser Glu Ile
1010 1015 1020

Gly Met Lys Gly Glu Arg Arg Arg Gly Lys Gly His Asp Gly Leu
1025 1030 1035

Tyr Gln Gly Leu Ser Thr Ala Thr Lys Asp Thr Tyr Asp Ala Leu
1040 1045 1050

His Met Gln Ala Leu Pro Pro Arg
1055 1060

<210> SEQ ID NO 37
<211> LENGTH: 1097
<212> TYPE: PRT
<213> ORGANISM: Artificial sequence
<220> FEATURE:
<223> OTHER INFORMATION: Homo sapiens

<400> SEQUENCE: 37

Met Ala Leu Pro Val Thr Ala Leu Leu Leu Pro Leu Ala Leu Leu Leu
1 5 10 15

His Ala Ala Arg Pro Val Gln Leu Gln Gln Ser Gly Pro Glu Leu Val
20 25 30

Lys Pro Gly Thr Ser Val Arg Ile Ser Cys Lys Thr Ser Gly Tyr Thr
35 40 45

Phe Thr Glu Tyr Thr Ile His Trp Val Lys Gln Ser His Gly Lys Ser
50 55 60

Leu Glu Trp Ile Gly Asn Ile Asn Pro Asn Asn Gly Gly Thr Thr Tyr
65 70 75 80

Asn Gln Lys Phe Glu Asp Lys Ala Thr Leu Thr Val Asp Lys Ser Ser
85 90 95

Ser Thr Ala Tyr Met Glu Leu Arg Ser Leu Thr Ser Glu Asp Ser Ala
100 105 110

Val Tyr Tyr Cys Ala Ala Gly Trp Asn Phe Asp Tyr Trp Gly Gln Gly
115 120 125

Thr Thr Val Thr Val Ser Ser Gly Gly Gly Gly Ser Gly Gly Gly Gly
130 135 140

Ser Gly Gly Gly Gly Ser Asp Ile Val Met Thr Gln Ser His Lys Phe
145 150 155 160

Met Ser Thr Ser Val Gly Asp Arg Val Ser Ile Ile Cys Lys Ala Ser
165 170 175

Gln Asp Val Gly Thr Ala Val Asp Trp Tyr Gln Gln Lys Pro Gly Gln
180 185 190

Ser Pro Lys Leu Leu Ile Tyr Trp Ala Ser Thr Arg His Thr Gly Val
195 200 205

Pro Asp Arg Phe Thr Gly Ser Gly Ser Gly Thr Asp Phe Thr Leu Thr
210 215 220

Ile Thr Asn Val Gln Ser Glu Asp Leu Ala Asp Tyr Phe Cys Gln Gln
225 230 235 240

Tyr Asn Ser Tyr Pro Leu Thr Phe Gly Ala Gly Thr Met Leu Asp Leu
245 250 255

Lys Arg Ala Ser Thr Thr Thr Pro Ala Pro Arg Pro Pro Thr Pro Ala
260 265 270

```
Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro Gly Ser Met Ala Leu Pro Val Thr Ala Leu
                565                 570                 575

Leu Leu Pro Leu Ala Leu Leu Leu His Ala Ala Arg Pro Glu Gln Lys
            580                 585                 590

Leu Ile Ser Glu Glu Asp Leu Gln Thr Thr Pro Gly Glu Arg Ser Ser
        595                 600                 605

Leu Pro Ala Phe Tyr Pro Gly Thr Ser Gly Ser Cys Ser Gly Cys Gly
    610                 615                 620

Ser Leu Ser Leu Pro Thr Thr Thr Pro Ala Pro Arg Pro Pro Thr Pro
625                 630                 635                 640

Ala Pro Thr Ile Ala Ser Gln Pro Leu Ser Leu Arg Pro Glu Ala Cys
                645                 650                 655

Arg Pro Ala Ala Gly Gly Ala Val His Thr Arg Gly Leu Asp Phe Ala
            660                 665                 670

Cys Asp Pro Arg Phe Trp Val Leu Val Val Val Gly Gly Val Leu Ala
        675                 680                 685
```

```
Cys Tyr Ser Leu Leu Val Thr Val Ala Phe Ile Ile Phe Trp Val Arg
    690                 695                 700

Ser Lys Arg Ser Arg Leu Leu His Ser Asp Tyr Met Asn Met Thr Pro
705                 710                 715                 720

Arg Arg Pro Gly Pro Thr Arg Lys His Tyr Gln Pro Tyr Ala Pro Pro
                725                 730                 735

Arg Asp Phe Ala Ala Tyr Arg Ser Pro Gly Gly Gly Gly Gly Ser Gly
            740                 745                 750

Gly Gly Gly Ser Gly Gly Gly Gly Ser Met Ala His Ala Gly Arg Thr
        755                 760                 765

Gly Tyr Asp Asn Arg Glu Ile Val Met Lys Tyr Ile His Tyr Lys Leu
    770                 775                 780

Ser Gln Arg Gly Tyr Glu Trp Asp Ala Gly Asp Val Gly Ala Ala Pro
785                 790                 795                 800

Pro Gly Ala Ala Pro Ala Pro Gly Ile Phe Ser Ser Gln Pro Gly His
                805                 810                 815

Thr Pro His Pro Ala Ala Ser Arg Asp Pro Val Ala Arg Thr Ser Pro
            820                 825                 830

Leu Gln Thr Pro Ala Ala Pro Gly Ala Ala Ala Gly Pro Ala Leu Ser
        835                 840                 845

Pro Val Pro Pro Val Val His Leu Thr Leu Arg Gln Ala Gly Asp Asp
    850                 855                 860

Phe Ser Arg Arg Tyr Arg Arg Asp Phe Ala Glu Met Ser Ser Gln Leu
865                 870                 875                 880

His Leu Thr Pro Phe Thr Ala Arg Gly Arg Phe Ala Thr Val Val Glu
                885                 890                 895

Glu Leu Phe Arg Asp Gly Val Asn Trp Gly Arg Ile Val Ala Phe Phe
            900                 905                 910

Glu Phe Gly Gly Val Met Cys Val Glu Ser Val Asn Arg Glu Met Ser
        915                 920                 925

Pro Leu Val Asp Asn Ile Ala Leu Trp Met Thr Glu Tyr Leu Asn Arg
    930                 935                 940

His Leu His Thr Trp Ile Gln Asp Asn Gly Gly Trp Asp Ala Phe Val
945                 950                 955                 960

Glu Leu Tyr Gly Pro Ser Met Arg Gly Gly Gly Gly Ser Gly Gly Gly
                965                 970                 975

Gly Ser Gly Gly Gly Gly Ser Met His Arg Val Lys Phe Ser Arg Ser
            980                 985                 990

Ala Asp Ala Pro Ala Tyr Gln Gln  Gly Gln Asn Gln Leu  Tyr Asn Glu
        995                 1000                1005

Leu Asn  Leu Gly Arg Arg Glu  Glu Tyr Asp Val Leu  Asp Lys Arg
    1010                1015                1020

Arg Gly  Arg Asp Pro Glu Met  Gly Gly Lys Pro Arg  Arg Lys Asn
    1025                1030                1035

Pro Gln  Glu Gly Leu Tyr Asn  Glu Leu Gln Lys Asp  Lys Met Ala
    1040                1045                1050

Glu Ala  Tyr Ser Glu Ile Gly  Met Lys Gly Glu Arg  Arg Arg Gly
    1055                1060                1065

Lys Gly  His Asp Gly Leu Tyr  Gln Gly Leu Ser Thr  Ala Thr Lys
    1070                1075                1080

Asp Thr  Tyr Asp Ala Leu His  Met Gln Ala Leu Pro  Pro Arg
    1085                1090                1095
```

<210> SEQ ID NO 38
<211> LENGTH: 1062
<212> TYPE: PRT
<213> ORGANISM: Artificial sequence
<220> FEATURE:
<223> OTHER INFORMATION: Homo sapiens

<400> SEQUENCE: 38

Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly

```
    370                 375                 380

Ser Gly Gly Gly Gly Ser Gln Gln Arg Trp Glu Leu Ala Leu Gly Arg
385                 390                 395                 400

Phe Leu Ala Tyr Leu Ser Trp Val Ser Thr Leu Ser Glu Gln Val Gln
                405                 410                 415

Glu Glu Leu Leu Ser Ser Gln Val Thr Gln Glu Leu Arg Ala Leu Met
            420                 425                 430

Asp Glu Thr Met Lys Glu Leu Lys Ala Tyr Lys Ser Glu Leu Glu Glu
        435                 440                 445

Gln Leu Thr Pro Val Ala Glu Glu Thr Arg Ala Arg Leu Ser Lys Glu
    450                 455                 460

Leu Gln Ala Ala Gln Ala Arg Leu Gly Ala Asp Met Glu Asp Val Arg
465                 470                 475                 480

Gly Arg Leu Val Gln Tyr Arg Gly Glu Val Gln Ala Met Leu Gly Gln
                485                 490                 495

Ser Thr Glu Glu Leu Arg Val Arg Leu Ala Ser His Leu Ile Ala Leu
            500                 505                 510

Gln Leu Arg Leu Ile Gly Asp Ala Phe Asp Leu Gln Lys Arg Leu Ala
        515                 520                 525

Val Tyr Gln Ala Gly Ala Ala Glu Arg Lys Arg Arg Ser Gly Ser Gly
    530                 535                 540

Arg Ser Gly Ser Gly Glu Gly Arg Gly Ser Leu Leu Thr Cys Gly Asp
545                 550                 555                 560

Val Glu Glu Asn Pro Gly Pro Gly Ser Met Ala Leu Pro Val Thr Ala
                565                 570                 575

Leu Leu Leu Pro Leu Ala Leu Leu Leu His Ala Ala Arg Pro Glu Gln
            580                 585                 590

Lys Leu Ile Ser Glu Glu Asp Leu Gln Thr Thr Pro Gly Glu Arg Ser
        595                 600                 605

Ser Leu Pro Ala Phe Tyr Pro Gly Thr Ser Gly Ser Cys Ser Gly Cys
    610                 615                 620

Gly Ser Leu Ser Leu Pro Thr Thr Thr Pro Ala Pro Arg Pro Pro Thr
625                 630                 635                 640

Pro Ala Pro Thr Ile Ala Ser Gln Pro Leu Ser Leu Arg Pro Glu Ala
                645                 650                 655

Cys Arg Pro Ala Ala Gly Gly Ala Val His Thr Arg Gly Leu Asp Phe
            660                 665                 670

Ala Cys Asp Pro Arg Phe Trp Val Leu Val Val Val Gly Gly Val Leu
        675                 680                 685

Ala Cys Tyr Ser Leu Leu Val Thr Val Ala Phe Ile Ile Phe Trp Val
    690                 695                 700

Arg Ser Lys Arg Ser Arg Leu Leu His Ser Asp Tyr Met Asn Met Thr
705                 710                 715                 720

Pro Arg Arg Pro Gly Pro Thr Arg Lys His Tyr Gln Pro Tyr Ala Pro
                725                 730                 735

Pro Arg Asp Phe Ala Ala Tyr Arg Ser Pro Gly Gly Gly Gly Gly Ser
            740                 745                 750

Gly Gly Gly Gly Ser Gly Gly Gly Gly Ser Met Ser Gln Ser Asn Arg
        755                 760                 765

Glu Leu Val Val Asp Phe Leu Ser Tyr Lys Leu Ser Gln Lys Gly Tyr
    770                 775                 780

Ser Trp Ser Gln Phe Ser Asp Val Glu Glu Asn Arg Thr Glu Ala Pro
785                 790                 795                 800
```

```
Glu Gly Thr Glu Ser Glu Ala Val Lys Gln Ala Leu Arg Glu Ala Gly
                805                 810                 815

Asp Asp Phe Glu Leu Arg Tyr Arg Arg Ala Phe Ser Asp Leu Thr Ser
            820                 825                 830

Gln Leu His Ile Thr Pro Gly Thr Ala Tyr Gln Ser Phe Glu Gln Val
        835                 840                 845

Val Asn Glu Leu Phe Arg Asp Gly Val Asn Trp Gly Arg Ile Val Ala
    850                 855                 860

Phe Phe Ser Phe Gly Gly Ala Leu Cys Val Glu Ser Val Asp Lys Glu
865                 870                 875                 880

Met Gln Val Leu Val Ser Arg Ile Ala Ala Trp Met Ala Thr Tyr Leu
                885                 890                 895

Asn Asp His Leu Glu Pro Trp Ile Gln Glu Asn Gly Gly Trp Asp Thr
            900                 905                 910

Phe Val Glu Leu Tyr Gly Asn Asn Ala Ala Ala Glu Ser Arg Lys Gly
        915                 920                 925

Gln Glu Arg Glu Asp Gly Gly Gly Gly Ser Gly Gly Gly Gly Ser Gly
    930                 935                 940

Gly Gly Gly Ser Met His Arg Val Lys Phe Ser Arg Ser Ala Asp Ala
945                 950                 955                 960

Pro Ala Tyr Gln Gln Gly Gln Asn Gln Leu Tyr Asn Glu Leu Asn Leu
                965                 970                 975

Gly Arg Arg Glu Glu Tyr Asp Val Leu Asp Lys Arg Arg Gly Arg Asp
            980                 985                 990

Pro Glu Met Gly Gly Lys Pro Arg  Arg Lys Asn Pro Gln  Glu Gly Leu
        995                 1000                1005

Tyr Asn  Glu Leu Gln Lys Asp  Lys Met Ala Glu Ala  Tyr Ser Glu
    1010                1015                1020

Ile Gly  Met Lys Gly Glu Arg  Arg Arg Gly Lys Gly  His Asp Gly
    1025                1030                1035

Leu Tyr  Gln Gly Leu Ser Thr  Ala Thr Lys Asp Thr  Tyr Asp Ala
    1040                1045                1050

Leu His  Met Gln Ala Leu Pro  Pro Arg
    1055                1060
```

<210> SEQ ID NO 39
<211> LENGTH: 1062
<212> TYPE: PRT
<213> ORGANISM: Artificial sequence
<220> FEATURE:
<223> OTHER INFORMATION: Homo sapiens

<400> SEQUENCE: 39

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95
```

```
Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Gln Arg Trp Glu Leu Ala Leu Gly Arg
385                 390                 395                 400

Phe Leu Glu Tyr Leu Ser Trp Val Ser Thr Leu Ser Glu Gln Val Gln
                405                 410                 415

Glu Glu Leu Leu Ser Ser Gln Val Thr Gln Glu Leu Arg Ala Leu Met
            420                 425                 430

Asp Glu Thr Met Lys Glu Leu Lys Ala Tyr Lys Ser Glu Leu Glu Glu
        435                 440                 445

Gln Leu Thr Pro Val Ala Glu Glu Thr Arg Ala Arg Leu Ser Lys Glu
    450                 455                 460

Leu Gln Ala Ala Gln Ala Arg Leu Gly Ala Asp Met Glu Asp Val Arg
465                 470                 475                 480

Gly Arg Leu Val Gln Tyr Arg Gly Glu Val Gln Ala Met Leu Gly Gln
                485                 490                 495

Ser Thr Glu Glu Leu Arg Val Arg Leu Ala Ser His Leu Ile Ala Leu
            500                 505                 510
```

-continued

```
Gln Ala Arg Leu Ile Gly Asp Ala Phe Asp Leu Gln Lys Arg Leu Ala
        515                 520                 525

Val Tyr Gln Ala Gly Ala Ala Glu Arg Lys Arg Arg Ser Gly Ser Gly
    530                 535                 540

Arg Ser Gly Ser Gly Glu Gly Arg Gly Ser Leu Leu Thr Cys Gly Asp
545                 550                 555                 560

Val Glu Glu Asn Pro Gly Pro Gly Ser Met Ala Leu Pro Val Thr Ala
                565                 570                 575

Leu Leu Leu Pro Leu Ala Leu Leu Leu His Ala Ala Arg Pro Glu Gln
            580                 585                 590

Lys Leu Ile Ser Glu Glu Asp Leu Gln Thr Thr Pro Gly Glu Arg Ser
        595                 600                 605

Ser Leu Pro Ala Phe Tyr Pro Gly Thr Ser Gly Ser Cys Ser Gly Cys
    610                 615                 620

Gly Ser Leu Ser Leu Pro Thr Thr Thr Pro Ala Pro Arg Pro Pro Thr
625                 630                 635                 640

Pro Ala Pro Thr Ile Ala Ser Gln Pro Leu Ser Leu Arg Pro Glu Ala
                645                 650                 655

Cys Arg Pro Ala Ala Gly Gly Ala Val His Thr Arg Gly Leu Asp Phe
            660                 665                 670

Ala Cys Asp Pro Arg Phe Trp Val Leu Val Val Val Gly Gly Val Leu
        675                 680                 685

Ala Cys Tyr Ser Leu Leu Val Thr Val Ala Phe Ile Ile Phe Trp Val
    690                 695                 700

Arg Ser Lys Arg Ser Arg Leu Leu His Ser Asp Tyr Met Asn Met Thr
705                 710                 715                 720

Pro Arg Arg Pro Gly Pro Thr Arg Lys His Tyr Gln Pro Tyr Ala Pro
                725                 730                 735

Pro Arg Asp Phe Ala Ala Tyr Arg Ser Pro Gly Gly Gly Gly Gly Ser
            740                 745                 750

Gly Gly Gly Gly Ser Gly Gly Gly Gly Ser Met Ser Gln Ser Asn Arg
        755                 760                 765

Glu Leu Val Val Asp Phe Leu Ser Tyr Lys Leu Ser Gln Lys Gly Tyr
    770                 775                 780

Ser Trp Ser Gln Phe Ser Asp Val Glu Glu Asn Arg Thr Glu Ala Pro
785                 790                 795                 800

Glu Gly Thr Glu Ser Glu Ala Val Lys Gln Ala Leu Arg Glu Ala Gly
                805                 810                 815

Asp Asp Phe Glu Leu Arg Tyr Arg Arg Ala Phe Ser Asp Leu Thr Ser
            820                 825                 830

Gln Leu His Ile Thr Pro Gly Thr Ala Tyr Gln Ser Phe Glu Gln Val
        835                 840                 845

Val Asn Glu Leu Phe Arg Asp Gly Val Asn Trp Gly Arg Ile Val Ala
    850                 855                 860

Phe Phe Ser Phe Gly Gly Ala Leu Cys Val Glu Ser Val Asp Lys Glu
865                 870                 875                 880

Met Gln Val Leu Val Ser Arg Ile Ala Ala Trp Met Ala Thr Tyr Leu
                885                 890                 895

Asn Asp His Leu Glu Pro Trp Ile Gln Glu Asn Gly Gly Trp Asp Thr
            900                 905                 910

Phe Val Glu Leu Tyr Gly Asn Asn Ala Ala Ala Glu Ser Arg Lys Gly
        915                 920                 925

Gln Glu Arg Glu Asp Gly Gly Gly Gly Ser Gly Gly Gly Gly Ser Gly
```

```
    930                 935                 940

Gly Gly Gly Ser Met His Arg Val Lys Phe Ser Arg Ser Ala Asp Ala
945                 950                 955                 960

Pro Ala Tyr Gln Gln Gly Gln Asn Gln Leu Tyr Asn Glu Leu Asn Leu
                965                 970                 975

Gly Arg Arg Glu Glu Tyr Asp Val Leu Asp Lys Arg Arg Gly Arg Asp
            980                 985                 990

Pro Glu Met Gly Gly Lys Pro Arg  Arg Lys Asn Pro Gln  Glu Gly Leu
        995                 1000                1005

Tyr Asn  Glu Leu Gln Lys Asp  Lys Met Ala Glu Ala  Tyr Ser Glu
    1010                 1015                1020

Ile Gly  Met Lys Gly Glu Arg  Arg Arg Gly Lys Gly  His Asp Gly
    1025                 1030                1035

Leu Tyr  Gln Gly Leu Ser Thr  Ala Thr Lys Asp Thr  Tyr Asp Ala
    1040                 1045                1050

Leu His  Met Gln Ala Leu Pro  Pro Arg
    1055                 1060


<210> SEQ ID NO 40
<211> LENGTH: 1062
<212> TYPE: PRT
<213> ORGANISM: Artificial sequence
<220> FEATURE:
<223> OTHER INFORMATION: Homo sapiens

<400> SEQUENCE: 40

Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
```

-continued

```
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Gln Arg Trp Glu Leu Ala Leu Gly Arg
385                 390                 395                 400

Phe Leu Glu Tyr Leu Ser Trp Val Ser Thr Leu Ser Glu Gln Val Gln
                405                 410                 415

Glu Glu Leu Leu Ser Ser Gln Val Thr Gln Glu Leu Arg Ala Leu Met
            420                 425                 430

Asp Glu Thr Met Lys Glu Leu Lys Ala Tyr Lys Ser Glu Leu Glu Glu
        435                 440                 445

Gln Leu Thr Pro Val Ala Glu Glu Thr Arg Ala Arg Leu Ser Lys Glu
    450                 455                 460

Leu Gln Ala Ala Gln Ala Arg Leu Gly Ala Asp Met Glu Asp Val Arg
465                 470                 475                 480

Gly Arg Leu Val Gln Tyr Arg Gly Glu Val Gln Ala Met Leu Gly Gln
                485                 490                 495

Ser Thr Glu Glu Leu Arg Val Arg Leu Ala Ser His Leu Ile Ala Leu
            500                 505                 510

Gln Leu Arg Leu Ile Gly Ala Ala Phe Asp Leu Gln Lys Arg Leu Ala
        515                 520                 525

Val Tyr Gln Ala Gly Ala Ala Glu Arg Lys Arg Arg Ser Gly Ser Gly
    530                 535                 540

Arg Ser Gly Ser Gly Glu Gly Arg Gly Ser Leu Leu Thr Cys Gly Asp
545                 550                 555                 560

Val Glu Glu Asn Pro Gly Pro Gly Ser Met Ala Leu Pro Val Thr Ala
                565                 570                 575

Leu Leu Leu Pro Leu Ala Leu Leu Leu His Ala Ala Arg Pro Glu Gln
            580                 585                 590

Lys Leu Ile Ser Glu Glu Asp Leu Gln Thr Thr Pro Gly Glu Arg Ser
        595                 600                 605

Ser Leu Pro Ala Phe Tyr Pro Gly Thr Ser Gly Ser Cys Ser Gly Cys
    610                 615                 620

Gly Ser Leu Ser Leu Pro Thr Thr Thr Pro Ala Pro Arg Pro Pro Thr
625                 630                 635                 640

Pro Ala Pro Thr Ile Ala Ser Gln Pro Leu Ser Leu Arg Pro Glu Ala
                645                 650                 655
```

-continued

```
Cys Arg Pro Ala Ala Gly Gly Ala Val His Thr Arg Gly Leu Asp Phe
            660                 665                 670

Ala Cys Asp Pro Arg Phe Trp Val Leu Val Val Val Gly Gly Val Leu
        675                 680                 685

Ala Cys Tyr Ser Leu Leu Val Thr Val Ala Phe Ile Ile Phe Trp Val
    690                 695                 700

Arg Ser Lys Arg Ser Arg Leu Leu His Ser Asp Tyr Met Asn Met Thr
705                 710                 715                 720

Pro Arg Arg Pro Gly Pro Thr Arg Lys His Tyr Gln Pro Tyr Ala Pro
                725                 730                 735

Pro Arg Asp Phe Ala Ala Tyr Arg Ser Pro Gly Gly Gly Gly Gly Ser
            740                 745                 750

Gly Gly Gly Gly Ser Gly Gly Gly Gly Ser Met Ser Gln Ser Asn Arg
        755                 760                 765

Glu Leu Val Val Asp Phe Leu Ser Tyr Lys Leu Ser Gln Lys Gly Tyr
    770                 775                 780

Ser Trp Ser Gln Phe Ser Asp Val Glu Glu Asn Arg Thr Glu Ala Pro
785                 790                 795                 800

Glu Gly Thr Glu Ser Glu Ala Val Lys Gln Ala Leu Arg Glu Ala Gly
                805                 810                 815

Asp Asp Phe Glu Leu Arg Tyr Arg Arg Ala Phe Ser Asp Leu Thr Ser
            820                 825                 830

Gln Leu His Ile Thr Pro Gly Thr Ala Tyr Gln Ser Phe Glu Gln Val
        835                 840                 845

Val Asn Glu Leu Phe Arg Asp Gly Val Asn Trp Gly Arg Ile Val Ala
    850                 855                 860

Phe Phe Ser Phe Gly Gly Ala Leu Cys Val Glu Ser Val Asp Lys Glu
865                 870                 875                 880

Met Gln Val Leu Val Ser Arg Ile Ala Ala Trp Met Ala Thr Tyr Leu
                885                 890                 895

Asn Asp His Leu Glu Pro Trp Ile Gln Glu Asn Gly Gly Trp Asp Thr
            900                 905                 910

Phe Val Glu Leu Tyr Gly Asn Asn Ala Ala Ala Glu Ser Arg Lys Gly
        915                 920                 925

Gln Glu Arg Glu Asp Gly Gly Gly Gly Ser Gly Gly Gly Gly Ser Gly
    930                 935                 940

Gly Gly Gly Ser Met His Arg Val Lys Phe Ser Arg Ser Ala Asp Ala
945                 950                 955                 960

Pro Ala Tyr Gln Gln Gly Gln Asn Gln Leu Tyr Asn Glu Leu Asn Leu
                965                 970                 975

Gly Arg Arg Glu Glu Tyr Asp Val Leu Asp Lys Arg Arg Gly Arg Asp
            980                 985                 990

Pro Glu Met Gly Gly Lys Pro Arg  Arg Lys Asn Pro Gln  Glu Gly Leu
        995                 1000                1005

Tyr Asn  Glu Leu Gln Lys Asp  Lys Met Ala Glu Ala  Tyr Ser Glu
    1010                1015                1020

Ile Gly  Met Lys Gly Glu Arg  Arg Arg Gly Lys Gly  His Asp Gly
    1025                1030                1035

Leu Tyr  Gln Gly Leu Ser Thr  Ala Thr Lys Asp Thr  Tyr Asp Ala
    1040                1045                1050

Leu His  Met Gln Ala Leu Pro  Pro Arg
    1055                1060
```

<210> SEQ ID NO 41
<211> LENGTH: 1098
<212> TYPE: PRT
<213> ORGANISM: Artificial sequence
<220> FEATURE:
<223> OTHER INFORMATION: Homo sapiens

<400> SEQUENCE: 41

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365
```

-continued

```
Ala Ala Tyr Arg Ser His Met Gly Gly Gly Gly Ser Gly Gly Gly Gly
    370                 375                 380

Ser Gly Gly Gly Gly Ser Gln Gln Arg Trp Glu Leu Ala Leu Gly Arg
385                 390                 395                 400

Phe Leu Ala Tyr Leu Ser Trp Val Ser Thr Leu Ser Glu Gln Val Gln
                405                 410                 415

Glu Glu Leu Leu Ser Ser Gln Val Thr Gln Glu Leu Arg Ala Leu Met
            420                 425                 430

Asp Glu Thr Met Lys Glu Leu Lys Ala Tyr Lys Ser Glu Leu Glu Glu
        435                 440                 445

Gln Leu Thr Pro Val Ala Glu Glu Thr Arg Ala Arg Leu Ser Lys Glu
    450                 455                 460

Leu Gln Ala Ala Gln Ala Arg Leu Gly Ala Asp Met Glu Asp Val Arg
465                 470                 475                 480

Gly Arg Leu Val Gln Tyr Arg Gly Glu Val Gln Ala Met Leu Gly Gln
                485                 490                 495

Ser Thr Glu Glu Leu Arg Val Arg Leu Ala Ser His Leu Ile Ala Leu
            500                 505                 510

Gln Leu Arg Leu Ile Gly Asp Ala Phe Asp Leu Gln Lys Arg Leu Ala
        515                 520                 525

Val Tyr Gln Ala Gly Ala Ala Glu Arg Lys Arg Arg Ser Gly Ser Gly
    530                 535                 540

Arg Ser Gly Ser Gly Glu Gly Arg Gly Ser Leu Leu Thr Cys Gly Asp
545                 550                 555                 560

Val Glu Glu Asn Pro Gly Pro Gly Ser Met Ala Leu Pro Val Thr Ala
                565                 570                 575

Leu Leu Leu Pro Leu Ala Leu Leu Leu His Ala Ala Arg Pro Glu Gln
            580                 585                 590

Lys Leu Ile Ser Glu Glu Asp Leu Gln Thr Thr Pro Gly Glu Arg Ser
        595                 600                 605

Ser Leu Pro Ala Phe Tyr Pro Gly Thr Ser Gly Ser Cys Ser Gly Cys
    610                 615                 620

Gly Ser Leu Ser Leu Pro Thr Thr Thr Pro Ala Pro Arg Pro Pro Thr
625                 630                 635                 640

Pro Ala Pro Thr Ile Ala Ser Gln Pro Leu Ser Leu Arg Pro Glu Ala
                645                 650                 655

Cys Arg Pro Ala Ala Gly Gly Ala Val His Thr Arg Gly Leu Asp Phe
            660                 665                 670

Ala Cys Asp Pro Arg Phe Trp Val Leu Val Val Val Gly Gly Val Leu
        675                 680                 685

Ala Cys Tyr Ser Leu Leu Val Thr Val Ala Phe Ile Ile Phe Trp Val
    690                 695                 700

Arg Ser Lys Arg Ser Arg Leu Leu His Ser Asp Tyr Met Asn Met Thr
705                 710                 715                 720

Pro Arg Arg Pro Gly Pro Thr Arg Lys His Tyr Gln Pro Tyr Ala Pro
                725                 730                 735

Pro Arg Asp Phe Ala Ala Tyr Arg Ser Pro Gly Gly Gly Gly Gly Ser
            740                 745                 750

Gly Gly Gly Gly Ser Gly Gly Gly Gly Ser Met Ala His Ala Gly Arg
        755                 760                 765

Thr Gly Tyr Asp Asn Arg Glu Ile Val Met Lys Tyr Ile His Tyr Lys
    770                 775                 780

Leu Ser Gln Arg Gly Tyr Glu Trp Asp Ala Gly Asp Val Gly Ala Ala
```

```
785                 790                 795                 800

Pro Pro Gly Ala Ala Pro Ala Pro Gly Ile Phe Ser Ser Gln Pro Gly
                805                 810                 815

His Thr Pro His Pro Ala Ala Ser Arg Asp Pro Val Ala Arg Thr Ser
            820                 825                 830

Pro Leu Gln Thr Pro Ala Ala Pro Gly Ala Ala Ala Gly Pro Ala Leu
        835                 840                 845

Ser Pro Val Pro Pro Val Val His Leu Thr Leu Arg Gln Ala Gly Asp
    850                 855                 860

Asp Phe Ser Arg Arg Tyr Arg Arg Asp Phe Ala Glu Met Ser Ser Gln
865                 870                 875                 880

Leu His Leu Thr Pro Phe Thr Ala Arg Gly Arg Phe Ala Thr Val Val
                885                 890                 895

Glu Glu Leu Phe Arg Asp Gly Val Asn Trp Gly Arg Ile Val Ala Phe
            900                 905                 910

Phe Glu Phe Gly Gly Val Met Cys Val Glu Ser Val Asn Arg Glu Met
        915                 920                 925

Ser Pro Leu Val Asp Asn Ile Ala Leu Trp Met Thr Glu Tyr Leu Asn
    930                 935                 940

Arg His Leu His Thr Trp Ile Gln Asp Asn Gly Gly Trp Asp Ala Phe
945                 950                 955                 960

Val Glu Leu Tyr Gly Pro Ser Met Arg Gly Gly Gly Gly Ser Gly Gly
                965                 970                 975

Gly Gly Ser Gly Gly Gly Gly Ser Met His Arg Val Lys Phe Ser Arg
            980                 985                 990

Ser Ala Asp Ala Pro Ala Tyr Gln  Gln Gly Gln Asn Gln  Leu Tyr Asn
        995                 1000                1005

Glu Leu  Asn Leu Gly Arg Arg  Glu Glu Tyr Asp Val  Leu Asp Lys
    1010                1015                1020

Arg Arg  Gly Arg Asp Pro Glu  Met Gly Gly Lys Pro  Arg Arg Lys
    1025                1030                1035

Asn Pro  Gln Glu Gly Leu Tyr  Asn Glu Leu Gln Lys  Asp Lys Met
    1040                1045                1050

Ala Glu  Ala Tyr Ser Glu Ile  Gly Met Lys Gly Glu  Arg Arg Arg
    1055                1060                1065

Gly Lys  Gly His Asp Gly Leu  Tyr Gln Gly Leu Ser  Thr Ala Thr
    1070                1075                1080

Lys Asp  Thr Tyr Asp Ala Leu  His Met Gln Ala Leu  Pro Pro Arg
    1085                1090                1095


<210> SEQ ID NO 42
<211> LENGTH: 1098
<212> TYPE: PRT
<213> ORGANISM: Artificial sequence
<220> FEATURE:
<223> OTHER INFORMATION: Homo sapiens

<400> SEQUENCE: 42

Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
```

```
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Gln Arg Trp Glu Leu Ala Leu Gly Arg
385                 390                 395                 400

Phe Leu Glu Tyr Leu Ser Trp Val Ser Thr Leu Ser Glu Gln Val Gln
                405                 410                 415

Glu Glu Leu Leu Ser Ser Gln Val Thr Gln Glu Leu Arg Ala Leu Met
            420                 425                 430

Asp Glu Thr Met Lys Glu Leu Lys Ala Tyr Lys Ser Glu Leu Glu Glu
        435                 440                 445

Gln Leu Thr Pro Val Ala Glu Glu Thr Arg Ala Arg Leu Ser Lys Glu
    450                 455                 460

Leu Gln Ala Ala Gln Ala Arg Leu Gly Ala Asp Met Glu Asp Val Arg
465                 470                 475                 480
```

```
Gly Arg Leu Val Gln Tyr Arg Gly Glu Val Gln Ala Met Leu Gly Gln
                485                 490                 495

Ser Thr Glu Glu Leu Arg Val Arg Leu Ala Ser His Leu Ile Ala Leu
            500                 505                 510

Gln Ala Arg Leu Ile Gly Asp Ala Phe Asp Leu Gln Lys Arg Leu Ala
        515                 520                 525

Val Tyr Gln Ala Gly Ala Ala Glu Arg Lys Arg Arg Ser Gly Ser Gly
    530                 535                 540

Arg Ser Gly Ser Gly Glu Gly Arg Gly Ser Leu Leu Thr Cys Gly Asp
545                 550                 555                 560

Val Glu Glu Asn Pro Gly Pro Gly Ser Met Ala Leu Pro Val Thr Ala
                565                 570                 575

Leu Leu Leu Pro Leu Ala Leu Leu Leu His Ala Ala Arg Pro Glu Gln
            580                 585                 590

Lys Leu Ile Ser Glu Glu Asp Leu Gln Thr Thr Pro Gly Glu Arg Ser
        595                 600                 605

Ser Leu Pro Ala Phe Tyr Pro Gly Thr Ser Gly Ser Cys Ser Gly Cys
    610                 615                 620

Gly Ser Leu Ser Leu Pro Thr Thr Thr Pro Ala Pro Arg Pro Pro Thr
625                 630                 635                 640

Pro Ala Pro Thr Ile Ala Ser Gln Pro Leu Ser Leu Arg Pro Glu Ala
                645                 650                 655

Cys Arg Pro Ala Ala Gly Gly Ala Val His Thr Arg Gly Leu Asp Phe
            660                 665                 670

Ala Cys Asp Pro Arg Phe Trp Val Leu Val Val Val Gly Gly Val Leu
        675                 680                 685

Ala Cys Tyr Ser Leu Leu Val Thr Val Ala Phe Ile Ile Phe Trp Val
    690                 695                 700

Arg Ser Lys Arg Ser Arg Leu Leu His Ser Asp Tyr Met Asn Met Thr
705                 710                 715                 720

Pro Arg Arg Pro Gly Pro Thr Arg Lys His Tyr Gln Pro Tyr Ala Pro
                725                 730                 735

Pro Arg Asp Phe Ala Ala Tyr Arg Ser Pro Gly Gly Gly Gly Gly Ser
            740                 745                 750

Gly Gly Gly Gly Ser Gly Gly Gly Gly Ser Met Ala His Ala Gly Arg
        755                 760                 765

Thr Gly Tyr Asp Asn Arg Glu Ile Val Met Lys Tyr Ile His Tyr Lys
    770                 775                 780

Leu Ser Gln Arg Gly Tyr Glu Trp Asp Ala Gly Asp Val Gly Ala Ala
785                 790                 795                 800

Pro Pro Gly Ala Ala Pro Ala Pro Gly Ile Phe Ser Ser Gln Pro Gly
                805                 810                 815

His Thr Pro His Pro Ala Ala Ser Arg Asp Pro Val Ala Arg Thr Ser
            820                 825                 830

Pro Leu Gln Thr Pro Ala Ala Pro Gly Ala Ala Ala Gly Pro Ala Leu
        835                 840                 845

Ser Pro Val Pro Pro Val Val His Leu Thr Leu Arg Gln Ala Gly Asp
    850                 855                 860

Asp Phe Ser Arg Arg Tyr Arg Arg Asp Phe Ala Glu Met Ser Ser Gln
865                 870                 875                 880

Leu His Leu Thr Pro Phe Thr Ala Arg Gly Arg Phe Ala Thr Val Val
                885                 890                 895
```

```
Glu Glu Leu Phe Arg Asp Gly Val Asn Trp Gly Arg Ile Val Ala Phe
            900                 905                 910

Phe Glu Phe Gly Gly Val Met Cys Val Glu Ser Val Asn Arg Glu Met
        915                 920                 925

Ser Pro Leu Val Asp Asn Ile Ala Leu Trp Met Thr Glu Tyr Leu Asn
    930                 935                 940

Arg His Leu His Thr Trp Ile Gln Asp Asn Gly Gly Trp Asp Ala Phe
945                 950                 955                 960

Val Glu Leu Tyr Gly Pro Ser Met Arg Gly Gly Gly Gly Ser Gly Gly
                965                 970                 975

Gly Gly Ser Gly Gly Gly Gly Ser Met His Arg Val Lys Phe Ser Arg
            980                 985                 990

Ser Ala Asp Ala Pro Ala Tyr Gln  Gln Gly Gln Asn Gln  Leu Tyr Asn
        995                 1000                 1005

Glu Leu  Asn Leu Gly Arg Arg  Glu Glu Tyr Asp Val  Leu Asp Lys
    1010                 1015                 1020

Arg Arg  Gly Arg Asp Pro Glu  Met Gly Gly Lys Pro  Arg Arg Lys
    1025                 1030                 1035

Asn Pro  Gln Glu Gly Leu Tyr  Asn Glu Leu Gln Lys  Asp Lys Met
    1040                 1045                 1050

Ala Glu  Ala Tyr Ser Glu Ile  Gly Met Lys Gly Glu  Arg Arg Arg
    1055                 1060                 1065

Gly Lys  Gly His Asp Gly Leu  Tyr Gln Gly Leu Ser  Thr Ala Thr
    1070                 1075                 1080

Lys Asp  Thr Tyr Asp Ala Leu  His Met Gln Ala Leu  Pro Pro Arg
    1085                 1090                 1095


<210> SEQ ID NO 43
<211> LENGTH: 1098
<212> TYPE: PRT
<213> ORGANISM: Artificial sequence
<220> FEATURE:
<223> OTHER INFORMATION: Homo sapiens

<400> SEQUENCE: 43

Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160
```

```
Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Gln Arg Trp Glu Leu Ala Leu Gly Arg
385                 390                 395                 400

Phe Leu Glu Tyr Leu Ser Trp Val Ser Thr Leu Ser Glu Gln Val Gln
                405                 410                 415

Glu Glu Leu Leu Ser Ser Gln Val Thr Gln Glu Leu Arg Ala Leu Met
            420                 425                 430

Asp Glu Thr Met Lys Glu Leu Lys Ala Tyr Lys Ser Glu Leu Glu Glu
        435                 440                 445

Gln Leu Thr Pro Val Ala Glu Glu Thr Arg Ala Arg Leu Ser Lys Glu
    450                 455                 460

Leu Gln Ala Ala Gln Ala Arg Leu Gly Ala Asp Met Glu Asp Val Arg
465                 470                 475                 480

Gly Arg Leu Val Gln Tyr Arg Gly Glu Val Gln Ala Met Leu Gly Gln
                485                 490                 495

Ser Thr Glu Glu Leu Arg Val Arg Leu Ala Ser His Leu Ile Ala Leu
            500                 505                 510

Gln Leu Arg Leu Ile Gly Ala Ala Phe Asp Leu Gln Lys Arg Leu Ala
        515                 520                 525

Val Tyr Gln Ala Gly Ala Ala Glu Arg Lys Arg Arg Ser Gly Ser Gly
    530                 535                 540

Arg Ser Gly Ser Gly Glu Gly Arg Gly Ser Leu Leu Thr Cys Gly Asp
545                 550                 555                 560

Val Glu Glu Asn Pro Gly Pro Gly Ser Met Ala Leu Pro Val Thr Ala
                565                 570                 575

Leu Leu Leu Pro Leu Ala Leu Leu Leu His Ala Ala Arg Pro Glu Gln
```

```
            580                 585                 590

Lys Leu Ile Ser Glu Glu Asp Leu Gln Thr Thr Pro Gly Glu Arg Ser
        595                 600                 605

Ser Leu Pro Ala Phe Tyr Pro Gly Thr Ser Gly Ser Cys Ser Gly Cys
    610                 615                 620

Gly Ser Leu Ser Leu Pro Thr Thr Thr Pro Ala Pro Arg Pro Pro Thr
625                 630                 635                 640

Pro Ala Pro Thr Ile Ala Ser Gln Pro Leu Ser Leu Arg Pro Glu Ala
                645                 650                 655

Cys Arg Pro Ala Ala Gly Gly Ala Val His Thr Arg Gly Leu Asp Phe
            660                 665                 670

Ala Cys Asp Pro Arg Phe Trp Val Leu Val Val Val Gly Gly Val Leu
        675                 680                 685

Ala Cys Tyr Ser Leu Leu Val Thr Val Ala Phe Ile Ile Phe Trp Val
    690                 695                 700

Arg Ser Lys Arg Ser Arg Leu Leu His Ser Asp Tyr Met Asn Met Thr
705                 710                 715                 720

Pro Arg Arg Pro Gly Pro Thr Arg Lys His Tyr Gln Pro Tyr Ala Pro
                725                 730                 735

Pro Arg Asp Phe Ala Ala Tyr Arg Ser Pro Gly Gly Gly Gly Gly Ser
            740                 745                 750

Gly Gly Gly Gly Ser Gly Gly Gly Gly Ser Met Ala His Ala Gly Arg
        755                 760                 765

Thr Gly Tyr Asp Asn Arg Glu Ile Val Met Lys Tyr Ile His Tyr Lys
    770                 775                 780

Leu Ser Gln Arg Gly Tyr Glu Trp Asp Ala Gly Asp Val Gly Ala Ala
785                 790                 795                 800

Pro Pro Gly Ala Ala Pro Ala Pro Gly Ile Phe Ser Ser Gln Pro Gly
                805                 810                 815

His Thr Pro His Pro Ala Ala Ser Arg Asp Pro Val Ala Arg Thr Ser
            820                 825                 830

Pro Leu Gln Thr Pro Ala Ala Pro Gly Ala Ala Ala Gly Pro Ala Leu
        835                 840                 845

Ser Pro Val Pro Pro Val Val His Leu Thr Leu Arg Gln Ala Gly Asp
    850                 855                 860

Asp Phe Ser Arg Arg Tyr Arg Arg Asp Phe Ala Glu Met Ser Ser Gln
865                 870                 875                 880

Leu His Leu Thr Pro Phe Thr Ala Arg Gly Arg Phe Ala Thr Val Val
                885                 890                 895

Glu Glu Leu Phe Arg Asp Gly Val Asn Trp Gly Arg Ile Val Ala Phe
            900                 905                 910

Phe Glu Phe Gly Gly Val Met Cys Val Glu Ser Val Asn Arg Glu Met
        915                 920                 925

Ser Pro Leu Val Asp Asn Ile Ala Leu Trp Met Thr Glu Tyr Leu Asn
    930                 935                 940

Arg His Leu His Thr Trp Ile Gln Asp Asn Gly Gly Trp Asp Ala Phe
945                 950                 955                 960

Val Glu Leu Tyr Gly Pro Ser Met Arg Gly Gly Gly Gly Ser Gly Gly
                965                 970                 975

Gly Gly Ser Gly Gly Gly Gly Ser Met His Arg Val Lys Phe Ser Arg
            980                 985                 990

Ser Ala Asp Ala Pro Ala Tyr Gln  Gln Gly Gln Asn Gln  Leu Tyr Asn
        995                 1000                1005
```

```
Glu Leu  Asn Leu Gly Arg Arg  Glu Glu Tyr Asp Val  Leu Asp Lys
    1010                 1015                 1020

Arg Arg  Gly Arg Asp Pro Glu  Met Gly Gly Lys Pro  Arg Arg Lys
    1025                 1030                 1035

Asn Pro  Gln Glu Gly Leu Tyr  Asn Glu Leu Gln Lys  Asp Lys Met
    1040                 1045                 1050

Ala Glu  Ala Tyr Ser Glu Ile  Gly Met Lys Gly Glu  Arg Arg Arg
    1055                 1060                 1065

Gly Lys  Gly His Asp Gly Leu  Tyr Gln Gly Leu Ser  Thr Ala Thr
    1070                 1075                 1080

Lys Asp  Thr Tyr Asp Ala Leu  His Met Gln Ala Leu  Pro Pro Arg
    1085                 1090                 1095


<210> SEQ ID NO 44
<211> LENGTH: 134
<212> TYPE: PRT
<213> ORGANISM: Artificial sequence
<220> FEATURE:
<223> OTHER INFORMATION: Mus musculus

<400> SEQUENCE: 44

Gln Val Gln Leu Gln Gln Ser Gly Ala Ser Met Lys Met Ser Cys Arg
1               5                   10                  15

Ala Ser Gly Tyr Ser Phe Thr Ser Tyr Trp Ile His Trp Leu Lys Gln
            20                  25                  30

Arg Pro Asp Gln Gly Leu Glu Trp Ile Gly Tyr Ile Asp Pro Ala Thr
        35                  40                  45

Ala Tyr Thr Glu Ser Asn Gln Lys Phe Lys Asp Lys Ala Ile Leu Thr
    50                  55                  60

Ala Asp Arg Ser Ser Asn Thr Ala Phe Met Tyr Leu Asn Ser Leu Thr
65                  70                  75                  80

Ser Glu Asp Ser Ala Val Tyr Tyr Cys Ala Arg Glu Ser Pro Arg Leu
                85                  90                  95

Arg Arg Gly Ile Tyr Tyr Tyr Ala Met Asp Tyr Trp Gly Gln Gly Thr
            100                 105                 110

Ser Val Thr Val Ser Ser Ala Pro Gln Ala Lys Ser Ser Gly Ser Gly
        115                 120                 125

Ser Glu Ser Lys Val Asp
    130


<210> SEQ ID NO 45
<211> LENGTH: 107
<212> TYPE: PRT
<213> ORGANISM: Artificial sequence
<220> FEATURE:
<223> OTHER INFORMATION: Mus musculus

<400> SEQUENCE: 45

Asp Ile Gln Met Thr Gln Thr Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
```

```
65                  70                  75                  80

Glu Asp Ile Ala Thr Tyr Phe Cys Gln Gln Gly Asn Thr Leu Pro Pro
                85                  90                  95

Thr Phe Gly Ala Gly Thr Lys Leu Glu Leu Lys
            100                 105


<210> SEQ ID NO 46
<211> LENGTH: 117
<212> TYPE: PRT
<213> ORGANISM: Artificial sequence
<220> FEATURE:
<223> OTHER INFORMATION: Homo sapiens

<400> SEQUENCE: 46

Gly Ser Glu Ser Lys Val Asp Gln Ser Val Val Thr Gln Pro Pro Ser
1               5                   10                  15

Ala Ser Gly Gly Pro Gly Gln Ser Leu Thr Ile Ser Cys Thr Gly Thr
            20                  25                  30

Ser Ser Asp Val Gly Gly Tyr Asn His Val Ser Trp Tyr Gln Gln His
        35                  40                  45

Pro Gly Lys Ala Pro Lys Leu Met Ile Tyr Asp Val Ser Lys Arg Pro
    50                  55                  60

Ser Gly Val Pro His Arg Phe Ser Gly Ser Lys Ser Gly Asn Thr Ala
65                  70                  75                  80

Ser Leu Thr Val Ser Gly Leu Gln Ala Glu Asp Glu Ala Val Tyr Tyr
                85                  90                  95

Cys Ser Ser Tyr Ala Gly Ser Asn Asn Leu Val Phe Gly Gly Gly Thr
            100                 105                 110

Lys Val Thr Val Leu
        115


<210> SEQ ID NO 47
<211> LENGTH: 112
<212> TYPE: PRT
<213> ORGANISM: Artificial sequence
<220> FEATURE:
<223> OTHER INFORMATION: Homo sapiens

<400> SEQUENCE: 47

Gly Ser Glu Ser Lys Val Asp Asp Ile Gln Met Thr Gln Thr Pro Ser
1               5                   10                  15

Ser Leu Ser Ala Ser Val Gly Asp Arg Val Thr Ile Thr Cys Arg Ala
            20                  25                  30

Ser Gln Ser Ile Ser Ser Phe Leu Asn Trp Tyr Gln Gln Lys Pro Gly
        35                  40                  45

Lys Ala Pro Lys Leu Leu Ile Tyr Ala Ala Ser Asn Leu Gln Ser Gly
    50                  55                  60

Val Pro Ser Arg Phe Ser Gly Arg Gly Ser Gly Thr Asp Phe Thr Leu
65                  70                  75                  80

Thr Ile Ser Ser Leu Gln Pro Glu Asp Phe Ala Ala Tyr Tyr Cys Gln
                85                  90                  95

Gln Gly Tyr Thr Thr Pro Leu Thr Phe Gly Gln Gly Thr Lys Leu Glu
            100                 105                 110


<210> SEQ ID NO 48
<211> LENGTH: 115
<212> TYPE: PRT
<213> ORGANISM: Artificial sequence
<220> FEATURE:
```

<223> OTHER INFORMATION: Homo sapiens

<400> SEQUENCE: 48

Gly Ser Glu Ser Lys Val Asp Ser Ser Glu Leu Thr Gln Asp Pro Ala
1 5 10 15

Val Ser Val Ala Leu Gly Gln Thr Val Arg Ile Thr Cys Gln Gly Asp
20 25 30

Ser Leu Arg Ser Tyr Tyr Ala Ser Trp Tyr Gln Gln Lys Pro Gly Gln
35 40 45

Ala Pro Val Leu Val Ile Tyr Gly Lys Asn Asn Arg Pro Ser Gly Ile
50 55 60

Pro Asp Arg Phe Ser Gly Ser Ser Ser Gly Asn Thr Ala Ser Leu Thr
65 70 75 80

Ile Thr Gly Ala Gln Ala Glu Asp Glu Ala Asp Tyr Tyr Cys Asn Ser
85 90 95

Arg Asp Ser Ser Gly Asn His Val Val Phe Gly Gly Gly Thr Lys Leu
100 105 110

Thr Val Leu
115

<210> SEQ ID NO 49
<211> LENGTH: 247
<212> TYPE: PRT
<213> ORGANISM: Artificial sequence
<220> FEATURE:
<223> OTHER INFORMATION: Homo sapiens

<400> SEQUENCE: 49

Gly Ser Asp Ile Gln Met Thr Gln Thr Thr Ser Ser Leu Ser Ala Ser
1 5 10 15

Leu Gly Asp Arg Val Thr Ile Ser Cys Arg Ala Ser Gln Asp Ile Ser
20 25 30

Lys Tyr Leu Asn Trp Tyr Gln Gln Lys Pro Asp Gly Thr Val Lys Leu
35 40 45

Leu Ile Tyr His Thr Ser Arg Leu His Ser Gly Val Pro Ser Arg Phe
50 55 60

Ser Gly Ser Gly Ser Gly Thr Asp Tyr Ser Leu Thr Ile Ser Asn Leu
65 70 75 80

Glu Gln Glu Asp Ile Ala Thr Tyr Phe Cys Gln Gln Gly Asn Thr Leu
85 90 95

Pro Tyr Thr Phe Gly Gly Gly Thr Lys Leu Glu Ile Thr Gly Ser Thr
100 105 110

Ser Gly Ser Gly Lys Pro Gly Ser Gly Glu Gly Ser Thr Lys Gly Glu
115 120 125

Val Lys Leu Gln Glu Ser Gly Pro Gly Leu Val Ala Pro Ser Gln Ser
130 135 140

Leu Ser Val Thr Cys Thr Val Ser Gly Val Ser Leu Pro Asp Tyr Gly
145 150 155 160

Val Ser Trp Ile Arg Gln Pro Pro Arg Lys Gly Leu Glu Trp Leu Gly
165 170 175

Val Ile Trp Gly Ser Glu Thr Thr Tyr Tyr Asn Ser Ala Leu Lys Ser
180 185 190

Arg Leu Thr Ile Ile Lys Asp Asn Ser Lys Ser Gln Val Phe Leu Lys
195 200 205

Met Asn Ser Leu Gln Thr Asp Asp Thr Ala Ile Tyr Tyr Cys Ala Lys
210 215 220

His Tyr Tyr Tyr Gly Gly Ser Tyr Ala Met Asp Tyr Trp Gly Gln Gly
225 230 235 240

Thr Ser Val Thr Val Ser Ser
245

<210> SEQ ID NO 50
<211> LENGTH: 268
<212> TYPE: PRT
<213> ORGANISM: Artificial sequence
<220> FEATURE:
<223> OTHER INFORMATION: Homo sapiens

<400> SEQUENCE: 50

Gln Val Gln Leu Gln Gln Ser Gly Ala Ser Met Lys Met Ser Cys Arg
1 5 10 15

Ala Ser Gly Tyr Ser Phe Thr Ser Tyr Trp Ile His Trp Leu Lys Gln
20 25 30

Arg Pro Asp Gln Gly Leu Glu Trp Ile Gly Tyr Ile Asp Pro Ala Thr
35 40 45

Ala Tyr Thr Glu Ser Asn Gln Lys Phe Lys Asp Lys Ala Ile Leu Thr
50 55 60

Ala Asp Arg Ser Ser Asn Thr Ala Phe Met Tyr Leu Asn Ser Leu Thr
65 70 75 80

Ser Glu Asp Ser Ala Val Tyr Tyr Cys Ala Arg Glu Ser Pro Arg Leu
85 90 95

Arg Arg Gly Ile Tyr Tyr Tyr Ala Met Asp Tyr Trp Gly Gln Gly Thr
100 105 110

Ser Val Thr Val Ser Ser Ala Pro Gln Ala Lys Ser Ser Gly Ser Gly
115 120 125

Ser Glu Ser Lys Val Asp Gln Val Gln Leu Gln Gln Ser Gly Ala Ser
130 135 140

Met Lys Met Ser Cys Arg Ala Ser Gly Tyr Ser Phe Thr Ser Tyr Trp
145 150 155 160

Ile His Trp Leu Lys Gln Arg Pro Asp Gln Gly Leu Glu Trp Ile Gly
165 170 175

Tyr Ile Asp Pro Ala Thr Ala Tyr Thr Glu Ser Asn Gln Lys Phe Lys
180 185 190

Asp Lys Ala Ile Leu Thr Ala Asp Arg Ser Ser Asn Thr Ala Phe Met
195 200 205

Tyr Leu Asn Ser Leu Thr Ser Glu Asp Ser Ala Val Tyr Tyr Cys Ala
210 215 220

Arg Glu Ser Pro Arg Leu Arg Arg Gly Ile Tyr Tyr Tyr Ala Met Asp
225 230 235 240

Tyr Trp Gly Gln Gly Thr Ser Val Thr Val Ser Ser Ala Pro Gln Ala
245 250 255

Lys Ser Ser Gly Ser Gly Ser Glu Ser Lys Val Asp
260 265

<210> SEQ ID NO 51
<211> LENGTH: 283
<212> TYPE: PRT
<213> ORGANISM: Artificial sequence
<220> FEATURE:
<223> OTHER INFORMATION: Homo sapiens

<400> SEQUENCE: 51

Gln Val Gln Leu Gln Gln Ser Gly Ala Ser Met Lys Met Ser Cys Arg

-continued

```
1               5                   10                  15

Ala Ser Gly Tyr Ser Phe Thr Ser Tyr Trp Ile His Trp Leu Lys Gln
            20                  25                  30

Arg Pro Asp Gln Gly Leu Glu Trp Ile Gly Tyr Ile Asp Pro Ala Thr
        35                  40                  45

Ala Tyr Thr Glu Ser Asn Gln Lys Phe Lys Asp Lys Ala Ile Leu Thr
    50                  55                  60

Ala Asp Arg Ser Ser Asn Thr Ala Phe Met Tyr Leu Asn Ser Leu Thr
65                  70                  75                  80

Ser Glu Asp Ser Ala Val Tyr Tyr Cys Ala Arg Glu Ser Pro Arg Leu
                85                  90                  95

Arg Arg Gly Ile Tyr Tyr Tyr Ala Met Asp Tyr Trp Gly Gln Gly Thr
            100                 105                 110

Ser Val Thr Val Ser Ser Ala Pro Gln Ala Lys Ser Ser Gly Ser Gly
        115                 120                 125

Ser Glu Ser Lys Val Asp Gly Gly Gly Gly Ser Gly Gly Gly Gly Ser
    130                 135                 140

Gly Gly Gly Gly Ser Gln Val Gln Leu Gln Gln Ser Gly Ala Ser Met
145                 150                 155                 160

Lys Met Ser Cys Arg Ala Ser Gly Tyr Ser Phe Thr Ser Tyr Trp Ile
                165                 170                 175

His Trp Leu Lys Gln Arg Pro Asp Gln Gly Leu Glu Trp Ile Gly Tyr
            180                 185                 190

Ile Asp Pro Ala Thr Ala Tyr Thr Glu Ser Asn Gln Lys Phe Lys Asp
        195                 200                 205

Lys Ala Ile Leu Thr Ala Asp Arg Ser Ser Asn Thr Ala Phe Met Tyr
    210                 215                 220

Leu Asn Ser Leu Thr Ser Glu Asp Ser Ala Val Tyr Tyr Cys Ala Arg
225                 230                 235                 240

Glu Ser Pro Arg Leu Arg Arg Gly Ile Tyr Tyr Tyr Ala Met Asp Tyr
                245                 250                 255

Trp Gly Gln Gly Thr Ser Val Thr Val Ser Ser Ala Pro Gln Ala Lys
            260                 265                 270

Ser Ser Gly Ser Gly Ser Glu Ser Lys Val Asp
        275                 280


<210> SEQ ID NO 52
<211> LENGTH: 251
<212> TYPE: PRT
<213> ORGANISM: Artificial sequence
<220> FEATURE:
<223> OTHER INFORMATION: Homo sapiens

<400> SEQUENCE: 52

Gln Val Gln Leu Gln Gln Ser Gly Ala Ser Met Lys Met Ser Cys Arg
1               5                   10                  15

Ala Ser Gly Tyr Ser Phe Thr Ser Tyr Trp Ile His Trp Leu Lys Gln
            20                  25                  30

Arg Pro Asp Gln Gly Leu Glu Trp Ile Gly Tyr Ile Asp Pro Ala Thr
        35                  40                  45

Ala Tyr Thr Glu Ser Asn Gln Lys Phe Lys Asp Lys Ala Ile Leu Thr
    50                  55                  60

Ala Asp Arg Ser Ser Asn Thr Ala Phe Met Tyr Leu Asn Ser Leu Thr
65                  70                  75                  80

Ser Glu Asp Ser Ala Val Tyr Tyr Cys Ala Arg Glu Ser Pro Arg Leu
```

```
                85                  90                  95

Arg Arg Gly Ile Tyr Tyr Tyr Ala Met Asp Tyr Trp Gly Gln Gly Thr
            100                 105                 110

Ser Val Thr Val Ser Ser Ala Pro Gln Ala Lys Ser Ser Gly Ser Gly
        115                 120                 125

Ser Glu Ser Lys Val Asp Gly Ser Glu Ser Lys Val Asp Gln Ser Val
    130                 135                 140

Val Thr Gln Pro Pro Ser Ala Ser Gly Gly Pro Gly Gln Ser Leu Thr
145                 150                 155                 160

Ile Ser Cys Thr Gly Thr Ser Ser Asp Val Gly Gly Tyr Asn His Val
                165                 170                 175

Ser Trp Tyr Gln Gln His Pro Gly Lys Ala Pro Lys Leu Met Ile Tyr
            180                 185                 190

Asp Val Ser Lys Arg Pro Ser Gly Val Pro His Arg Phe Ser Gly Ser
        195                 200                 205

Lys Ser Gly Asn Thr Ala Ser Leu Thr Val Ser Gly Leu Gln Ala Glu
    210                 215                 220

Asp Glu Ala Val Tyr Tyr Cys Ser Ser Tyr Ala Gly Ser Asn Asn Leu
225                 230                 235                 240

Val Phe Gly Gly Gly Thr Lys Val Thr Val Leu
                245                 250


<210> SEQ ID NO 53
<211> LENGTH: 266
<212> TYPE: PRT
<213> ORGANISM: Artificial sequence
<220> FEATURE:
<223> OTHER INFORMATION: Homo sapiens

<400> SEQUENCE: 53

Gln Val Gln Leu Gln Gln Ser Gly Ala Ser Met Lys Met Ser Cys Arg
1               5                   10                  15

Ala Ser Gly Tyr Ser Phe Thr Ser Tyr Trp Ile His Trp Leu Lys Gln
            20                  25                  30

Arg Pro Asp Gln Gly Leu Glu Trp Ile Gly Tyr Ile Asp Pro Ala Thr
        35                  40                  45

Ala Tyr Thr Glu Ser Asn Gln Lys Phe Lys Asp Lys Ala Ile Leu Thr
    50                  55                  60

Ala Asp Arg Ser Ser Asn Thr Ala Phe Met Tyr Leu Asn Ser Leu Thr
65                  70                  75                  80

Ser Glu Asp Ser Ala Val Tyr Tyr Cys Ala Arg Glu Ser Pro Arg Leu
                85                  90                  95

Arg Arg Gly Ile Tyr Tyr Tyr Ala Met Asp Tyr Trp Gly Gln Gly Thr
            100                 105                 110

Ser Val Thr Val Ser Ser Ala Pro Gln Ala Lys Ser Ser Gly Ser Gly
        115                 120                 125

Ser Glu Ser Lys Val Asp Gly Gly Gly Gly Ser Gly Gly Gly Gly Ser
    130                 135                 140

Gly Gly Gly Gly Ser Gly Ser Glu Ser Lys Val Asp Gln Ser Val Val
145                 150                 155                 160

Thr Gln Pro Pro Ser Ala Ser Gly Gly Pro Gly Gln Ser Leu Thr Ile
                165                 170                 175

Ser Cys Thr Gly Thr Ser Ser Asp Val Gly Gly Tyr Asn His Val Ser
            180                 185                 190

Trp Tyr Gln Gln His Pro Gly Lys Ala Pro Lys Leu Met Ile Tyr Asp
```

```
        195                 200                 205

Val Ser Lys Arg Pro Ser Gly Val Pro His Arg Phe Ser Gly Ser Lys
    210                 215                 220

Ser Gly Asn Thr Ala Ser Leu Thr Val Ser Gly Leu Gln Ala Glu Asp
225                 230                 235                 240

Glu Ala Val Tyr Tyr Cys Ser Ser Tyr Ala Gly Ser Asn Asn Leu Val
                245                 250                 255

Phe Gly Gly Gly Thr Lys Val Thr Val Leu
            260                 265


<210> SEQ ID NO 54
<211> LENGTH: 246
<212> TYPE: PRT
<213> ORGANISM: Artificial sequence
<220> FEATURE:
<223> OTHER INFORMATION: Homo sapiens

<400> SEQUENCE: 54

Gln Val Gln Leu Gln Gln Ser Gly Ala Ser Met Lys Met Ser Cys Arg
1               5                   10                  15

Ala Ser Gly Tyr Ser Phe Thr Ser Tyr Trp Ile His Trp Leu Lys Gln
            20                  25                  30

Arg Pro Asp Gln Gly Leu Glu Trp Ile Gly Tyr Ile Asp Pro Ala Thr
        35                  40                  45

Ala Tyr Thr Glu Ser Asn Gln Lys Phe Lys Asp Lys Ala Ile Leu Thr
    50                  55                  60

Ala Asp Arg Ser Ser Asn Thr Ala Phe Met Tyr Leu Asn Ser Leu Thr
65                  70                  75                  80

Ser Glu Asp Ser Ala Val Tyr Tyr Cys Ala Arg Glu Ser Pro Arg Leu
                85                  90                  95

Arg Arg Gly Ile Tyr Tyr Tyr Ala Met Asp Tyr Trp Gly Gln Gly Thr
            100                 105                 110

Ser Val Thr Val Ser Ser Ala Pro Gln Ala Lys Ser Ser Gly Ser Gly
        115                 120                 125

Ser Glu Ser Lys Val Asp Gly Ser Glu Ser Lys Val Asp Asp Ile Gln
    130                 135                 140

Met Thr Gln Thr Pro Ser Ser Leu Ser Ala Ser Val Gly Asp Arg Val
145                 150                 155                 160

Thr Ile Thr Cys Arg Ala Ser Gln Ser Ile Ser Ser Phe Leu Asn Trp
                165                 170                 175

Tyr Gln Gln Lys Pro Gly Lys Ala Pro Lys Leu Leu Ile Tyr Ala Ala
            180                 185                 190

Ser Asn Leu Gln Ser Gly Val Pro Ser Arg Phe Ser Gly Arg Gly Ser
        195                 200                 205

Gly Thr Asp Phe Thr Leu Thr Ile Ser Ser Leu Gln Pro Glu Asp Phe
    210                 215                 220

Ala Ala Tyr Tyr Cys Gln Gln Gly Tyr Thr Thr Pro Leu Thr Phe Gly
225                 230                 235                 240

Gln Gly Thr Lys Leu Glu
                245


<210> SEQ ID NO 55
<211> LENGTH: 261
<212> TYPE: PRT
<213> ORGANISM: Artificial sequence
<220> FEATURE:
<223> OTHER INFORMATION: Homo sapiens
```

<400> SEQUENCE: 55

Gln Val Gln Leu Gln Gln Ser Gly Ala Ser Met Lys Met Ser Cys Arg
1               5                   10                  15

Ala Ser Gly Tyr Ser Phe Thr Ser Tyr Trp Ile His Trp Leu Lys Gln
            20                  25                  30

Arg Pro Asp Gln Gly Leu Glu Trp Ile Gly Tyr Ile Asp Pro Ala Thr
        35                  40                  45

Ala Tyr Thr Glu Ser Asn Gln Lys Phe Lys Asp Lys Ala Ile Leu Thr
    50                  55                  60

Ala Asp Arg Ser Ser Asn Thr Ala Phe Met Tyr Leu Asn Ser Leu Thr
65                  70                  75                  80

Ser Glu Asp Ser Ala Val Tyr Tyr Cys Ala Arg Glu Ser Pro Arg Leu
                85                  90                  95

Arg Arg Gly Ile Tyr Tyr Tyr Ala Met Asp Tyr Trp Gly Gln Gly Thr
            100                 105                 110

Ser Val Thr Val Ser Ser Ala Pro Gln Ala Lys Ser Ser Gly Ser Gly
        115                 120                 125

Ser Glu Ser Lys Val Asp Gly Gly Gly Gly Ser Gly Gly Gly Gly Ser
    130                 135                 140

Gly Gly Gly Gly Ser Gly Ser Glu Ser Lys Val Asp Asp Ile Gln Met
145                 150                 155                 160

Thr Gln Thr Pro Ser Ser Leu Ser Ala Ser Val Gly Asp Arg Val Thr
                165                 170                 175

Ile Thr Cys Arg Ala Ser Gln Ser Ile Ser Ser Phe Leu Asn Trp Tyr
            180                 185                 190

Gln Gln Lys Pro Gly Lys Ala Pro Lys Leu Leu Ile Tyr Ala Ala Ser
        195                 200                 205

Asn Leu Gln Ser Gly Val Pro Ser Arg Phe Ser Gly Arg Gly Ser Gly
    210                 215                 220

Thr Asp Phe Thr Leu Thr Ile Ser Ser Leu Gln Pro Glu Asp Phe Ala
225                 230                 235                 240

Ala Tyr Tyr Cys Gln Gln Gly Tyr Thr Thr Pro Leu Thr Phe Gly Gln
                245                 250                 255

Gly Thr Lys Leu Glu
            260

<210> SEQ ID NO 56
<211> LENGTH: 249
<212> TYPE: PRT
<213> ORGANISM: Artificial sequence
<220> FEATURE:
<223> OTHER INFORMATION: Homo sapiens

<400> SEQUENCE: 56

Gln Val Gln Leu Gln Gln Ser Gly Ala Ser Met Lys Met Ser Cys Arg
1               5                   10                  15

Ala Ser Gly Tyr Ser Phe Thr Ser Tyr Trp Ile His Trp Leu Lys Gln
            20                  25                  30

Arg Pro Asp Gln Gly Leu Glu Trp Ile Gly Tyr Ile Asp Pro Ala Thr
        35                  40                  45

Ala Tyr Thr Glu Ser Asn Gln Lys Phe Lys Asp Lys Ala Ile Leu Thr
    50                  55                  60

Ala Asp Arg Ser Ser Asn Thr Ala Phe Met Tyr Leu Asn Ser Leu Thr
65                  70                  75                  80

```
Ser Glu Asp Ser Ala Val Tyr Tyr Cys Ala Arg Glu Ser Pro Arg Leu
                85                  90                  95

Arg Arg Gly Ile Tyr Tyr Tyr Ala Met Asp Tyr Trp Gly Gln Gly Thr
            100                 105                 110

Ser Val Thr Val Ser Ser Ala Pro Gln Ala Lys Ser Ser Gly Ser Gly
        115                 120                 125

Ser Glu Ser Lys Val Asp Gly Ser Glu Ser Lys Val Asp Ser Ser Glu
    130                 135                 140

Leu Thr Gln Asp Pro Ala Val Ser Val Ala Leu Gly Gln Thr Val Arg
145                 150                 155                 160

Ile Thr Cys Gln Gly Asp Ser Leu Arg Ser Tyr Tyr Ala Ser Trp Tyr
                165                 170                 175

Gln Gln Lys Pro Gly Gln Ala Pro Val Leu Val Ile Tyr Gly Lys Asn
            180                 185                 190

Asn Arg Pro Ser Gly Ile Pro Asp Arg Phe Ser Gly Ser Ser Ser Gly
        195                 200                 205

Asn Thr Ala Ser Leu Thr Ile Thr Gly Ala Gln Ala Glu Asp Glu Ala
    210                 215                 220

Asp Tyr Tyr Cys Asn Ser Arg Asp Ser Ser Gly Asn His Val Val Phe
225                 230                 235                 240

Gly Gly Gly Thr Lys Leu Thr Val Leu
                245
```

<210> SEQ ID NO 57
<211> LENGTH: 264
<212> TYPE: PRT
<213> ORGANISM: Artificial sequence
<220> FEATURE:
<223> OTHER INFORMATION: Homo sapiens

<400> SEQUENCE: 57

```
Gln Val Gln Leu Gln Gln Ser Gly Ala Ser Met Lys Met Ser Cys Arg
1               5                   10                  15

Ala Ser Gly Tyr Ser Phe Thr Ser Tyr Trp Ile His Trp Leu Lys Gln
            20                  25                  30

Arg Pro Asp Gln Gly Leu Glu Trp Ile Gly Tyr Ile Asp Pro Ala Thr
        35                  40                  45

Ala Tyr Thr Glu Ser Asn Gln Lys Phe Lys Asp Lys Ala Ile Leu Thr
    50                  55                  60

Ala Asp Arg Ser Ser Asn Thr Ala Phe Met Tyr Leu Asn Ser Leu Thr
65                  70                  75                  80

Ser Glu Asp Ser Ala Val Tyr Tyr Cys Ala Arg Glu Ser Pro Arg Leu
                85                  90                  95

Arg Arg Gly Ile Tyr Tyr Tyr Ala Met Asp Tyr Trp Gly Gln Gly Thr
            100                 105                 110

Ser Val Thr Val Ser Ser Ala Pro Gln Ala Lys Ser Ser Gly Ser Gly
        115                 120                 125

Ser Glu Ser Lys Val Asp Gly Gly Gly Gly Ser Gly Gly Gly Gly Ser
    130                 135                 140

Gly Gly Gly Gly Ser Gly Ser Glu Ser Lys Val Asp Ser Ser Glu Leu
145                 150                 155                 160

Thr Gln Asp Pro Ala Val Ser Val Ala Leu Gly Gln Thr Val Arg Ile
                165                 170                 175

Thr Cys Gln Gly Asp Ser Leu Arg Ser Tyr Tyr Ala Ser Trp Tyr Gln
            180                 185                 190
```

-continued

```
Gln Lys Pro Gly Gln Ala Pro Val Leu Val Ile Tyr Gly Lys Asn Asn
        195                 200                 205

Arg Pro Ser Gly Ile Pro Asp Arg Phe Ser Gly Ser Ser Ser Gly Asn
    210                 215                 220

Thr Ala Ser Leu Thr Ile Thr Gly Ala Gln Ala Glu Asp Glu Ala Asp
225                 230                 235                 240

Tyr Tyr Cys Asn Ser Arg Asp Ser Ser Gly Asn His Val Val Phe Gly
                245                 250                 255

Gly Gly Thr Lys Leu Thr Val Leu
            260
```

<210> SEQ ID NO 58
<211> LENGTH: 118
<212> TYPE: PRT
<213> ORGANISM: Artificial sequence
<220> FEATURE:
<223> OTHER INFORMATION: Mus musculus

<400> SEQUENCE: 58

```
Gly Ser Glu Ser Lys Val Asp Asp Ile Val Met Phe Gln Ser Pro Ala
1               5                   10                  15

Ser Leu Ala Val Ser Leu Gly Gln Arg Ala Thr Ile Ser Cys Arg Ala
            20                  25                  30

Ser Gln Ser Val Ser Ser Ser Ser Tyr Ser Tyr Met His Trp Tyr Gln
        35                  40                  45

Gln Lys Pro Gly Gln Pro Pro Lys Leu Leu Ile Lys Tyr Ala Ser Asn
    50                  55                  60

Leu Glu Ser Gly Val Pro Ala Arg Phe Ser Gly Ser Gly Ser Gly Thr
65                  70                  75                  80

Asp Phe Thr Leu Asn Ile His Pro Val Glu Glu Glu Asp Ala Ala Thr
                85                  90                  95

Tyr Tyr Cys Gln His Ser Arg Asp Val Pro Leu Thr Phe Gly Ala Gly
            100                 105                 110

Thr Lys Leu Glu Ile Lys
        115
```

<210> SEQ ID NO 59
<211> LENGTH: 114
<212> TYPE: PRT
<213> ORGANISM: Artificial sequence
<220> FEATURE:
<223> OTHER INFORMATION: Mus musculus

<400> SEQUENCE: 59

```
Gly Ser Glu Ser Lys Val Asp Asp Ile Gln Met Thr Gln Thr Pro Ser
1               5                   10                  15

Ser Leu Ser Ala Ser Leu Gly Asp Arg Val Thr Ile Ser Cys Arg Ala
            20                  25                  30

Ser Gln Asp Ile Ser Asn Tyr Leu Asn Trp Tyr Gln Gln Lys Pro Asp
        35                  40                  45

Gly Thr Val Lys Leu Leu Ile Val Tyr Thr Ser Arg Leu His Ser Gly
    50                  55                  60

Val Pro Ser Arg Phe Ser Gly Ser Gly Ser Gly Thr Asp Tyr Ser Leu
65                  70                  75                  80

Thr Ile Ser Asn Leu Glu Gln Glu Asp Ile Ala Thr Tyr Phe Cys Gln
                85                  90                  95

Gln Gly Asn Thr Leu Pro Pro Thr Phe Gly Ala Gly Thr Lys Leu Glu
            100                 105                 110
```

Leu Lys

<210> SEQ ID NO 60
<211> LENGTH: 252
<212> TYPE: PRT
<213> ORGANISM: Artificial sequence
<220> FEATURE:
<223> OTHER INFORMATION: Mus musculus

<400> SEQUENCE: 60

```
Gln Val Gln Leu Gln Gln Ser Gly Ala Ser Met Lys Met Ser Cys Arg
1               5                   10                  15

Ala Ser Gly Tyr Ser Phe Thr Ser Tyr Trp Ile His Trp Leu Lys Gln
            20                  25                  30

Arg Pro Asp Gln Gly Leu Glu Trp Ile Gly Tyr Ile Asp Pro Ala Thr
        35                  40                  45

Ala Tyr Thr Glu Ser Asn Gln Lys Phe Lys Asp Lys Ala Ile Leu Thr
    50                  55                  60

Ala Asp Arg Ser Ser Asn Thr Ala Phe Met Tyr Leu Asn Ser Leu Thr
65                  70                  75                  80

Ser Glu Asp Ser Ala Val Tyr Tyr Cys Ala Arg Glu Ser Pro Arg Leu
                85                  90                  95

Arg Arg Gly Ile Tyr Tyr Tyr Ala Met Asp Tyr Trp Gly Gln Gly Thr
            100                 105                 110

Ser Val Thr Val Ser Ser Ala Pro Gln Ala Lys Ser Ser Gly Ser Gly
        115                 120                 125

Ser Glu Ser Lys Val Asp Gly Ser Glu Ser Lys Val Asp Asp Ile Val
    130                 135                 140

Met Phe Gln Ser Pro Ala Ser Leu Ala Val Ser Leu Gly Gln Arg Ala
145                 150                 155                 160

Thr Ile Ser Cys Arg Ala Ser Gln Ser Val Ser Ser Ser Ser Tyr Ser
                165                 170                 175

Tyr Met His Trp Tyr Gln Gln Lys Pro Gly Gln Pro Pro Lys Leu Leu
            180                 185                 190

Ile Lys Tyr Ala Ser Asn Leu Glu Ser Gly Val Pro Ala Arg Phe Ser
        195                 200                 205

Gly Ser Gly Ser Gly Thr Asp Phe Thr Leu Asn Ile His Pro Val Glu
    210                 215                 220

Glu Glu Asp Ala Ala Thr Tyr Tyr Cys Gln His Ser Arg Asp Val Pro
225                 230                 235                 240

Leu Thr Phe Gly Ala Gly Thr Lys Leu Glu Ile Lys
                245                 250
```

<210> SEQ ID NO 61
<211> LENGTH: 267
<212> TYPE: PRT
<213> ORGANISM: Artificial sequence
<220> FEATURE:
<223> OTHER INFORMATION: Mus musculus

<400> SEQUENCE: 61

```
Gln Val Gln Leu Gln Gln Ser Gly Ala Ser Met Lys Met Ser Cys Arg
1               5                   10                  15

Ala Ser Gly Tyr Ser Phe Thr Ser Tyr Trp Ile His Trp Leu Lys Gln
            20                  25                  30

Arg Pro Asp Gln Gly Leu Glu Trp Ile Gly Tyr Ile Asp Pro Ala Thr
        35                  40                  45
```

```
Ala Tyr Thr Glu Ser Asn Gln Lys Phe Lys Asp Lys Ala Ile Leu Thr
    50                  55                  60

Ala Asp Arg Ser Ser Asn Thr Ala Phe Met Tyr Leu Asn Ser Leu Thr
65                  70                  75                  80

Ser Glu Asp Ser Ala Val Tyr Tyr Cys Ala Arg Glu Ser Pro Arg Leu
                85                  90                  95

Arg Arg Gly Ile Tyr Tyr Tyr Ala Met Asp Tyr Trp Gly Gln Gly Thr
            100                 105                 110

Ser Val Thr Val Ser Ser Ala Pro Gln Ala Lys Ser Ser Gly Ser Gly
        115                 120                 125

Ser Glu Ser Lys Val Asp Gly Gly Gly Gly Ser Gly Gly Gly Gly Ser
    130                 135                 140

Gly Gly Gly Gly Ser Gly Ser Glu Ser Lys Val Asp Asp Ile Val Met
145                 150                 155                 160

Phe Gln Ser Pro Ala Ser Leu Ala Val Ser Leu Gly Gln Arg Ala Thr
                165                 170                 175

Ile Ser Cys Arg Ala Ser Gln Ser Val Ser Ser Ser Ser Tyr Ser Tyr
            180                 185                 190

Met His Trp Tyr Gln Gln Lys Pro Gly Gln Pro Pro Lys Leu Leu Ile
        195                 200                 205

Lys Tyr Ala Ser Asn Leu Glu Ser Gly Val Pro Ala Arg Phe Ser Gly
    210                 215                 220

Ser Gly Ser Gly Thr Asp Phe Thr Leu Asn Ile His Pro Val Glu Glu
225                 230                 235                 240

Glu Asp Ala Ala Thr Tyr Tyr Cys Gln His Ser Arg Asp Val Pro Leu
                245                 250                 255

Thr Phe Gly Ala Gly Thr Lys Leu Glu Ile Lys
            260                 265
```

<210> SEQ ID NO 62
<211> LENGTH: 248
<212> TYPE: PRT
<213> ORGANISM: Artificial sequence
<220> FEATURE:
<223> OTHER INFORMATION: Mus musculus

<400> SEQUENCE: 62

```
Gln Val Gln Leu Gln Gln Ser Gly Ala Ser Met Lys Met Ser Cys Arg
1               5                   10                  15

Ala Ser Gly Tyr Ser Phe Thr Ser Tyr Trp Ile His Trp Leu Lys Gln
            20                  25                  30

Arg Pro Asp Gln Gly Leu Glu Trp Ile Gly Tyr Ile Asp Pro Ala Thr
        35                  40                  45

Ala Tyr Thr Glu Ser Asn Gln Lys Phe Lys Asp Lys Ala Ile Leu Thr
    50                  55                  60

Ala Asp Arg Ser Ser Asn Thr Ala Phe Met Tyr Leu Asn Ser Leu Thr
65                  70                  75                  80

Ser Glu Asp Ser Ala Val Tyr Tyr Cys Ala Arg Glu Ser Pro Arg Leu
                85                  90                  95

Arg Arg Gly Ile Tyr Tyr Tyr Ala Met Asp Tyr Trp Gly Gln Gly Thr
            100                 105                 110

Ser Val Thr Val Ser Ser Ala Pro Gln Ala Lys Ser Ser Gly Ser Gly
        115                 120                 125

Ser Glu Ser Lys Val Asp Gly Ser Glu Ser Lys Val Asp Asp Ile Gln
    130                 135                 140
```

Met Thr Gln Thr Pro Ser Ser Leu Ser Ala Ser Leu Gly Asp Arg Val
145 150 155 160

Thr Ile Ser Cys Arg Ala Ser Gln Asp Ile Ser Asn Tyr Leu Asn Trp
165 170 175

Tyr Gln Gln Lys Pro Asp Gly Thr Val Lys Leu Leu Ile Val Tyr Thr
180 185 190

Ser Arg Leu His Ser Gly Val Pro Ser Arg Phe Ser Gly Ser Gly Ser
195 200 205

Gly Thr Asp Tyr Ser Leu Thr Ile Ser Asn Leu Glu Gln Glu Asp Ile
210 215 220

Ala Thr Tyr Phe Cys Gln Gln Gly Asn Thr Leu Pro Pro Thr Phe Gly
225 230 235 240

Ala Gly Thr Lys Leu Glu Leu Lys
245

<210> SEQ ID NO 63
<211> LENGTH: 263
<212> TYPE: PRT
<213> ORGANISM: Artificial sequence
<220> FEATURE:
<223> OTHER INFORMATION: Homo sapiens

<400> SEQUENCE: 63

Gln Val Gln Leu Gln Gln Ser Gly Ala Ser Met Lys Met Ser Cys Arg
1 5 10 15

Ala Ser Gly Tyr Ser Phe Thr Ser Tyr Trp Ile His Trp Leu Lys Gln
20 25 30

Arg Pro Asp Gln Gly Leu Glu Trp Ile Gly Tyr Ile Asp Pro Ala Thr
35 40 45

Ala Tyr Thr Glu Ser Asn Gln Lys Phe Lys Asp Lys Ala Ile Leu Thr
50 55 60

Ala Asp Arg Ser Ser Asn Thr Ala Phe Met Tyr Leu Asn Ser Leu Thr
65 70 75 80

Ser Glu Asp Ser Ala Val Tyr Tyr Cys Ala Arg Glu Ser Pro Arg Leu
85 90 95

Arg Arg Gly Ile Tyr Tyr Tyr Ala Met Asp Tyr Trp Gly Gln Gly Thr
100 105 110

Ser Val Thr Val Ser Ser Ala Pro Gln Ala Lys Ser Ser Gly Ser Gly
115 120 125

Ser Glu Ser Lys Val Asp Gly Gly Gly Gly Ser Gly Gly Gly Gly Ser
130 135 140

Gly Gly Gly Gly Ser Gly Ser Glu Ser Lys Val Asp Asp Ile Gln Met
145 150 155 160

Thr Gln Thr Pro Ser Ser Leu Ser Ala Ser Leu Gly Asp Arg Val Thr
165 170 175

Ile Ser Cys Arg Ala Ser Gln Asp Ile Ser Asn Tyr Leu Asn Trp Tyr
180 185 190

Gln Gln Lys Pro Asp Gly Thr Val Lys Leu Leu Ile Val Tyr Thr Ser
195 200 205

Arg Leu His Ser Gly Val Pro Ser Arg Phe Ser Gly Ser Gly Ser Gly
210 215 220

Thr Asp Tyr Ser Leu Thr Ile Ser Asn Leu Glu Gln Glu Asp Ile Ala
225 230 235 240

Thr Tyr Phe Cys Gln Gln Gly Asn Thr Leu Pro Pro Thr Phe Gly Ala
245 250 255

Gly Thr Lys Leu Glu Leu Lys
260

<210> SEQ ID NO 64
<211> LENGTH: 3192
<212> TYPE: DNA
<213> ORGANISM: Artificial sequence
<220> FEATURE:
<223> OTHER INFORMATION: Homo sapiens

<400> SEQUENCE: 64
actagaaatg gccttaccag tgaccgcctt gctcctgccg ctggccttgc tgctccacgc 60
cgccaggccg gtgcagctgc agcagtcagg acctgaactg gtgaagcctg ggacttcagt 120
gaggatatcc tgcaagactt ctggatacac attcactgaa tataccatac actgggtgaa 180
gcagagccat ggaaagagcc ttgagtggat tggaaacatc aatcctaaca atggtggtac 240
cacctacaat cagaagttcg aggacaaggc cacattgact gtagacaagt cctccagtac 300
agcctacatg gagctccgca gcctaacatc tgaggattct gcagtctatt attgtgcagc 360
tggttggaac tttgactact ggggccaagg gaccacggtc accgtctcct caggtggagg 420
tggatcaggt ggaggtggat ctggtggagg tggatctgac attgtgatga cccagtctca 480
caaattcatg tccacatcag taggagacag ggtcagcatc atctgtaagg ccagtcaaga 540
tgtgggtact gctgtagact ggtatcaaca gaaaccagga caatctccta aactactgat 600
ttattgggca tccactcggc acactggagt ccctgatcgc ttcacaggca gtggatctgg 660
gacagacttc actctcacca ttactaatgt tcagtctgaa gacttggcag attatttctg 720
tcagcaatat aacagctatc ccctcacgtt cggtgctggg accatgctgg acctgaaacg 780
ggctagcaca acaacccctg cccccagacc tcctacccca gcccctacaa ttgccagcca 840
gcctctgagc ctgaggcccg aggcttgtag acctgctgct ggcggagccg tgcacaccag 900
aggactggat ttcgcctgcg acttctgggt gctggtggtc gtgggcggag tgctggcctg 960
ttacagcctg ctcgtgaccg tggccttcat catcttttgg gtgcggagca agagaagcag 1020
actgctgcac agcgactaca tgaacatgac ccccagacgg cctggcccca ccagaaagca 1080
ctaccagcct tacgcccctc ccagagactt cgccgcctac agatctcata tgggaggcgg 1140
aggatctggc ggaggtggaa gtggcggagg cggatctcaa agatgggaac tcgccctggg 1200
cagattcctg gaatacctga gctgggtgtc cacactgagc gaacaggtgc aagaggaact 1260
gctgagcagc caagtgaccc aagagctgag agccctgatg gacgagacaa tgaaggaact 1320
gaaggcctac aagagcgagc tggaagaaca gctgacccct gtggccgagg aaaccagagc 1380
cagactgagc aaagaactgc aggccgctca ggccagactg ggagccgata tggaagatgt 1440
tcggggcaga ctggtgcagt acagaggcga agttcaggcc atgctgggcc agtctaccga 1500
ggaactgaga gtgcggctgg cctctcatct gattgccctg cagctgagac tgatcggcga 1560
cgcattcgac ctgcagaaaa gactggccgt gtaccaggct ggcgctgctg aacggaagcg 1620
gcgcagcggc agcgggcgca gcggcagcgg cgagggcaga ggaagtcttc taacatgcgg 1680
tgacgtggag gagaatcccg gccctggatc catggcctta ccagtgaccg ccttgctcct 1740
gccgctggcc ttgctgctcc acgccgccag gccggaacag aaactcatca gtgaggaaga 1800
tttgcagacg actccaggag agagatcatc actccctgcc ttttaccctg gcacttcagg 1860
ctcttgttcc ggatgtgggt ccctctctct gccgacaaca acccctgccc ccagacctcc 1920
taccccagcc cctacaattg ccagccagcc tctgagcctg aggcccgagg cttgtagacc 1980

```
tgctgctggc ggagccgtgc acaccagagg actggatttc gcctgcgacc taggttctgg   2040

gtgctggtgg tcgtgggcgg agtgctggcc tgttacagcc tgctcgtgac cgtggccttc   2100

atcatctttt gggtgcggag caagagaagc agactgctgc acagcgacta catgaacatg   2160

acccccagac ggcctggccc caccagaaag cactaccagc cttacgcccc tcccagagac   2220

ttcgccgcct acagatctcc cgggggaggc ggaggatctg gcggaggtgg aagtggcgga   2280

ggcggatcta tgagccagag caacagagaa ctggtggtgg acttcctgag ctacaagctg   2340

agccagaagg gctacagctg gtcccagttc agcgacgtgg aagagaacag aacagaggcc   2400

cctgagggca cagagtctga ggctgtgaaa caggccctga gagaagccgg cgacgagttc   2460

gagctgagat acagaagggc cttcagcgac ctgaccagcc agctgcacat cacacctggc   2520

acagcctacc agagcttcga gcaggtcgtg aacgagctgt tcagagatgg cgtgaactgg   2580

ggcagaatcg tggccttctt cagctttggc ggagccctgt gtgtggaaag cgtggacaaa   2640

gaaatgcagg tcctggtgtc cagaatcgcc gcctggatgg ccacctacct gaacgatcat   2700

ctggaaccct ggattcaaga gaacggcggc tgggacacct tcgtggaact gtacggaaac   2760

aacgccgctg ccgagagcag aaagggccaa gaacgagaag atggaggcgg aggatctggc   2820

ggaggtggaa gtggcggagg cggatctatg catagagtga agttcagcag gagcgcagac   2880

gcccccgcgt accagcaggg ccagaaccag ctctataacg agctcaatct aggacgaaga   2940

gaggagtacg atgttttgga caagagacgt ggccgggacc ctgagatggg gggaaagccg   3000

agaaggaaga accctcagga aggcctgtac aatgaactgc agaaagataa gatggcggag   3060

gcctacagtg agattgggat gaaaggcgag cgccggaggg gcaaggggca cgatggcctt   3120

taccagggtc tcagtacagc caccaaggac acctacgacg cccttcacat gcaggccctg   3180

ccccctcgct aa                                                       3192
```

<210> SEQ ID NO 65
<211> LENGTH: 1059
<212> TYPE: PRT
<213> ORGANISM: Artificial sequence
<220> FEATURE:
<223> OTHER INFORMATION: Homo sapiens

<400> SEQUENCE: 65

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140
```

```
Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560
```

```
Glu Glu Asn Pro Gly Pro Gly Ser Met Ala Leu Pro Val Thr Ala Leu
                565                 570                 575

Leu Leu Pro Leu Ala Leu Leu Leu His Ala Ala Arg Pro Glu Gln Lys
            580                 585                 590

Leu Ile Ser Glu Glu Asp Leu Gln Thr Thr Pro Gly Glu Arg Ser Ser
        595                 600                 605

Leu Pro Ala Phe Tyr Pro Gly Thr Ser Gly Ser Cys Ser Gly Cys Gly
    610                 615                 620

Ser Leu Ser Leu Pro Thr Thr Thr Pro Ala Pro Arg Pro Pro Thr Pro
625                 630                 635                 640

Ala Pro Thr Ile Ala Ser Gln Pro Leu Ser Leu Arg Pro Glu Ala Cys
                645                 650                 655

Arg Pro Ala Ala Gly Gly Ala Val His Thr Arg Gly Leu Asp Phe Ala
            660                 665                 670

Cys Asp Pro Arg Phe Trp Val Leu Val Val Val Gly Gly Val Leu Ala
        675                 680                 685

Cys Tyr Ser Leu Leu Val Thr Val Ala Phe Ile Ile Phe Trp Val Arg
    690                 695                 700

Ser Lys Arg Ser Arg Leu Leu His Ser Asp Tyr Met Asn Met Thr Pro
705                 710                 715                 720

Arg Arg Pro Gly Pro Thr Arg Lys His Tyr Gln Pro Tyr Ala Pro Pro
                725                 730                 735

Arg Asp Phe Ala Ala Tyr Arg Ser Pro Gly Gly Gly Gly Gly Ser Gly
            740                 745                 750

Gly Gly Gly Ser Gly Gly Gly Gly Ser Met Ser Gln Ser Asn Arg Glu
        755                 760                 765

Leu Val Val Asp Phe Leu Ser Tyr Lys Leu Ser Gln Lys Gly Tyr Ser
    770                 775                 780

Trp Ser Gln Phe Ser Asp Val Glu Glu Asn Arg Thr Glu Ala Pro Glu
785                 790                 795                 800

Gly Thr Glu Ser Glu Ala Val Lys Gln Ala Leu Arg Glu Ala Gly Asp
                805                 810                 815

Glu Phe Glu Leu Arg Tyr Arg Arg Ala Phe Ser Asp Leu Thr Ser Gln
            820                 825                 830

Leu His Ile Thr Pro Gly Thr Ala Tyr Gln Ser Phe Glu Gln Val Val
        835                 840                 845

Asn Glu Leu Phe Arg Asp Gly Val Asn Trp Gly Arg Ile Val Ala Phe
    850                 855                 860

Phe Ser Phe Gly Gly Ala Leu Cys Val Glu Ser Val Asp Lys Glu Met
865                 870                 875                 880

Gln Val Leu Val Ser Arg Ile Ala Ala Trp Met Ala Thr Tyr Leu Asn
                885                 890                 895

Asp His Leu Glu Pro Trp Ile Gln Glu Asn Gly Gly Trp Asp Thr Phe
            900                 905                 910

Val Glu Leu Tyr Gly Asn Asn Ala Ala Ala Glu Ser Arg Lys Gly Gln
        915                 920                 925

Glu Arg Gly Gly Gly Gly Ser Gly Gly Gly Gly Ser Gly Gly Gly Gly
    930                 935                 940

Ser Met His Arg Val Lys Phe Ser Arg Ser Ala Asp Ala Pro Ala Tyr
945                 950                 955                 960

Gln Gln Gly Gln Asn Gln Leu Tyr Asn Glu Leu Asn Leu Gly Arg Arg
                965                 970                 975

Glu Glu Tyr Asp Val Leu Asp Lys Arg Arg Gly Arg Asp Pro Glu Met
```

```
            980                 985                 990

Gly Gly Lys Pro Arg Arg Lys Asn  Pro Gln Glu Gly Leu  Tyr Asn Glu
        995                 1000                1005

Leu Gln  Lys Asp Lys Met Ala  Glu Ala Tyr Ser Glu  Ile Gly Met
    1010                 1015                 1020

Lys Gly  Glu Arg Arg Arg Gly  Lys Gly His Asp Gly  Leu Tyr Gln
    1025                 1030                 1035

Gly Leu  Ser Thr Ala Thr Lys  Asp Thr Tyr Asp Ala  Leu His Met
    1040                 1045                 1050

Gln Ala  Leu Pro Pro Arg
    1055
```

<210> SEQ ID NO 66
<211> LENGTH: 3198
<212> TYPE: DNA
<213> ORGANISM: Artificial sequence
<220> FEATURE:
<223> OTHER INFORMATION: Homo sapiens

<400> SEQUENCE: 66

```
actagaaatg gccttaccag tgaccgcctt gctcctgccg ctggccttgc tgctccacgc     60

cgccaggccg gtgcagctgc agcagtcagg acctgaactg gtgaagcctg ggacttcagt    120

gaggatatcc tgcaagactt ctggatacac attcactgaa tataccatac actgggtgaa    180

gcagagccat ggaaagagcc ttgagtggat tggaaacatc aatcctaaca atggtggtac    240

cacctacaat cagaagttcg aggacaaggc cacattgact gtagacaagt cctccagtac    300

agcctacatg gagctccgca gcctaacatc tgaggattct gcagtctatt attgtgcagc    360

tggttggaac tttgactact ggggccaagg gaccacggtc accgtctcct caggtggagg    420

tggatcaggt ggaggtggat ctggtggagg tggatctgac attgtgatga cccagtctca    480

caaattcatg tccacatcag taggagacag ggtcagcatc atctgtaagg ccagtcaaga    540

tgtgggtact gctgtagact ggtatcaaca gaaaccagga caatctccta aactactgat    600

ttattgggca tccactcggc acactggagt ccctgatcgc ttcacaggca gtggatctgg    660

gacagacttc actctcacca ttactaatgt tcagtctgaa gacttggcag attatttctg    720

tcagcaatat aacagctatc cctcacgttc ggtgctggg accatgctgg acctgaaacg    780

ggctagcaca acaacccctg cccccagacc tcctaccccca gcccctacaa ttgccagcca    840

gcctctgagc ctgaggcccg aggcttgtag acctgctgct ggcggagccg tgcacaccag    900

aggactggat ttcgcctgcg acttctgggt gctggtggtc gtgggcggag tgctggcctg    960

ttacagcctg ctcgtgaccg tggccttcat catcttttgg gtgcggagca agagaagcag   1020

actgctgcac agcgactaca tgaacatgac ccccagacgg cctggcccca ccagaaagca   1080

ctaccagcct tacgcccctc ccagagactt cgccgcctac agatctcata tgggaggcgg   1140

aggatctggc ggaggtggaa gtggcggagg cggatctcaa agatgggaac tcgccctggg   1200

cagattcctg gaatacctga gctgggtgtc cacactgagc gaacaggtgc aagaggaact   1260

gctgagcagc caagtgaccc aagagctgag agccctgatg gacgagacaa tgaaggaact   1320

gaaggcctac aagagcgagc tggaagaaca gctgacccct gtggccgagg aaaccagagc   1380

cagactgagc aaagaactgc aggccgctca ggccagactg ggagccgata tggaagatgt   1440

tcggggcaga ctggtgcagt acagaggcga agttcaggcc atgctgggcc agtctaccga   1500

ggaactgaga gtgcggctgg cctctcatct gattgccctg cagctgagac tgatcggcga   1560
```

-continued

```
cgcattcgac ctgcagaaaa gactggccgt gtaccaggct ggcgctgctg aacggaagcg   1620

gcgcagcggc agcgggcgca gcggcagcgg cgagggcaga ggaagtcttc taacatgcgg   1680

tgacgtggag gagaatcccg gccctggatc catggcctta ccagtgaccg ccttgctcct   1740

gccgctggcc ttgctgctcc acgccgccag gccggaacag aaactcatca gtgaggaaga   1800

tttgcagacg actccaggag agagatcatc actccctgcc ttttaccctg gcacttcagg   1860

ctcttgttcc ggatgtgggt ccctctctct gccgacaaca acccctgccc ccagacctcc   1920

taccccagcc cctacaattg ccagccagcc tctgagcctg aggcccgagg cttgtagacc   1980

tgctgctggc ggagccgtgc acaccagagg actggatttc gcctgcgacc taggttctgg   2040

gtgctggtgg tcgtgggcgg agtgctggcc tgttacagcc tgctcgtgac cgtggccttc   2100

atcatctttt gggtgcggag caagagaagc agactgctgc acagcgacta catgaacatg   2160

acccccagac ggcctggccc caccagaaag cactaccagc cttacgcccc tcccagagac   2220

ttcgccgcct acagatctcc cgggggaggc ggaggatctg gcggaggtgg aagtggcgga   2280

ggcggatcta tgagccagag caacagagaa ctggtggtgg acttcctgag ctacaagctg   2340

agccagaagg gctacagctg gtcccagttc agcgacgtgg aagagaacag aacagaggcc   2400

cctgagggca cagagtctga ggctgtgaaa caggccctga gagaagccgg cgacgacttc   2460

gagctgagat acagaagggc cttcagcgac ctgaccagcc agctgcacat cacacctggc   2520

acagcctacc agagcttcga gcaggtcgtg aacgagctgt tcagagatgg cgtgaactgg   2580

ggcagaatcg tggccttctt cagctttggc ggagccctgt gtgtggaaag cgtggacaaa   2640

gaaatgcagg tcctggtgtc cagaatcgcc gcctggatgg ccacctacct gaacgatcat   2700

ctggaaccct ggattcaaga gaacggcggc tgggacacct tcgtggaact gtacggaaac   2760

aacgccgctg ccgagagcag aaagggccaa gaacgagaag atgaagatgg aggcggagga   2820

tctggcggag gtggaagtgg cggaggcgga tctatgcata gagtgaagtt cagcaggagc   2880

gcagacgccc ccgcgtacca gcagggccag aaccagctct ataacgagct caatctagga   2940

cgaagagagg agtacgatgt tttggacaag agacgtggcc gggaccctga gatgggggga   3000

aagccgagaa ggaagaaccc tcaggaaggc ctgtacaatg aactgcagaa agataagatg   3060

gcggaggcct acagtgagat tgggatgaaa ggcgagcgcc ggaggggcaa ggggcacgat   3120

ggcctttacc agggtctcag tacagccacc aaggacacct acgacgccct tcacatgcag   3180

gccctgcccc ctcgctaa                                                 3198
```

<210> SEQ ID NO 67
<211> LENGTH: 1061
<212> TYPE: PRT
<213> ORGANISM: Artificial sequence
<220> FEATURE:
<223> OTHER INFORMATION: Homo sapiens

<400> SEQUENCE: 67

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
```

-continued

```
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495
```

```
Thr Glu Glu Leu Arg Val Arg Leu Ala Ser His Leu Ile Ala Leu Gln
            500                 505                 510

Leu Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro Gly Ser Met Ala Leu Pro Val Thr Ala Leu
                565                 570                 575

Leu Leu Pro Leu Ala Leu Leu Leu His Ala Ala Arg Pro Glu Gln Lys
            580                 585                 590

Leu Ile Ser Glu Glu Asp Leu Gln Thr Thr Pro Gly Glu Arg Ser Ser
        595                 600                 605

Leu Pro Ala Phe Tyr Pro Gly Thr Ser Gly Ser Cys Ser Gly Cys Gly
    610                 615                 620

Ser Leu Ser Leu Pro Thr Thr Thr Pro Ala Pro Arg Pro Pro Thr Pro
625                 630                 635                 640

Ala Pro Thr Ile Ala Ser Gln Pro Leu Ser Leu Arg Pro Glu Ala Cys
                645                 650                 655

Arg Pro Ala Ala Gly Gly Ala Val His Thr Arg Gly Leu Asp Phe Ala
            660                 665                 670

Cys Asp Pro Arg Phe Trp Val Leu Val Val Val Gly Gly Val Leu Ala
        675                 680                 685

Cys Tyr Ser Leu Leu Val Thr Val Ala Phe Ile Ile Phe Trp Val Arg
    690                 695                 700

Ser Lys Arg Ser Arg Leu Leu His Ser Asp Tyr Met Asn Met Thr Pro
705                 710                 715                 720

Arg Arg Pro Gly Pro Thr Arg Lys His Tyr Gln Pro Tyr Ala Pro Pro
                725                 730                 735

Arg Asp Phe Ala Ala Tyr Arg Ser Pro Gly Gly Gly Gly Gly Ser Gly
            740                 745                 750

Gly Gly Gly Ser Gly Gly Gly Gly Ser Met Ser Gln Ser Asn Arg Glu
        755                 760                 765

Leu Val Val Asp Phe Leu Ser Tyr Lys Leu Ser Gln Lys Gly Tyr Ser
    770                 775                 780

Trp Ser Gln Phe Ser Asp Val Glu Glu Asn Arg Thr Glu Ala Pro Glu
785                 790                 795                 800

Gly Thr Glu Ser Glu Ala Val Lys Gln Ala Leu Arg Glu Ala Gly Asp
                805                 810                 815

Asp Phe Glu Leu Arg Tyr Arg Arg Ala Phe Ser Asp Leu Thr Ser Gln
            820                 825                 830

Leu His Ile Thr Pro Gly Thr Ala Tyr Gln Ser Phe Glu Gln Val Val
        835                 840                 845

Asn Glu Leu Phe Arg Asp Gly Val Asn Trp Gly Arg Ile Val Ala Phe
    850                 855                 860

Phe Ser Phe Gly Gly Ala Leu Cys Val Glu Ser Val Asp Lys Glu Met
865                 870                 875                 880

Gln Val Leu Val Ser Arg Ile Ala Ala Trp Met Ala Thr Tyr Leu Asn
                885                 890                 895

Asp His Leu Glu Pro Trp Ile Gln Glu Asn Gly Gly Trp Asp Thr Phe
            900                 905                 910
```

```
Val Glu Leu Tyr Gly Asn Asn Ala Ala Ala Glu Ser Arg Lys Gly Gln
        915                 920                 925

Glu Arg Glu Asp Gly Gly Gly Gly Ser Gly Gly Gly Gly Ser Gly Gly
    930                 935                 940

Gly Gly Ser Met His Arg Val Lys Phe Ser Arg Ser Ala Asp Ala Pro
945                 950                 955                 960

Ala Tyr Gln Gln Gly Gln Asn Gln Leu Tyr Asn Glu Leu Asn Leu Gly
                965                 970                 975

Arg Arg Glu Glu Tyr Asp Val Leu Asp Lys Arg Arg Gly Arg Asp Pro
            980                 985                 990

Glu Met Gly Gly Lys Pro Arg Arg  Lys Asn Pro Gln Glu  Gly Leu Tyr
        995                 1000                 1005

Asn Glu  Leu Gln Lys Asp Lys  Met Ala Glu Ala Tyr  Ser Glu Ile
    1010                 1015                 1020

Gly Met  Lys Gly Glu Arg Arg  Arg Gly Lys Gly His  Asp Gly Leu
    1025                 1030                 1035

Tyr Gln  Gly Leu Ser Thr Ala  Thr Lys Asp Thr Tyr  Asp Ala Leu
    1040                 1045                 1050

His Met  Gln Ala Leu Pro Pro  Arg
    1055                 1060
```

<210> SEQ ID NO 68
<211> LENGTH: 3306
<212> TYPE: DNA
<213> ORGANISM: Artificial sequence
<220> FEATURE:
<223> OTHER INFORMATION: Homo sapiens

<400> SEQUENCE: 68

```
actagaaatg gccttaccag tgaccgcctt gctcctgccg ctggccttgc tgctccacgc     60

cgccaggccg gtgcagctgc agcagtcagg acctgaactg gtgaagcctg ggacttcagt    120

gaggatatcc tgcaagactt ctggatacac attcactgaa tataccatac actgggtgaa    180

gcagagccat ggaaagagcc ttgagtggat tggaaacatc aatcctaaca atggtggtac    240

cacctacaat cagaagttcg aggacaaggc cacattgact gtagacaagt cctccagtac    300

agcctacatg gagctccgca gcctaacatc tgaggattct gcagtctatt attgtgcagc    360

tggttggaac tttgactact ggggccaagg gaccacggtc accgtctcct caggtggagg    420

tggatcaggt ggaggtggat ctggtggagg tggatctgac attgtgatga cccagtctca    480

caaattcatg tccacatcag taggagacag ggtcagcatc atctgtaagg ccagtcaaga    540

tgtgggtact gctgtagact ggtatcaaca gaaaccagga caatctccta aactactgat    600

ttattgggca tccactcggc acactggagt ccctgatcgc ttcacaggca gtggatctgg    660

gacagacttc actctcacca ttactaatgt tcagtctgaa gacttggcag attatttctg    720

tcagcaatat aacagctatc cctcacgttc ggtgctgggg accatgctgg acctgaaacg    780

ggctagcaca acaacccctg cccccagacc tcctaccccca gcccctacaa ttgccagcca    840

gcctctgagc ctgaggcccg aggcttgtag acctgctgct ggcggagccg tgcacaccag    900

aggactggat ttcgcctgcg acttctgggt gctggtggtc gtgggcggag tgctggcctg    960

ttacagcctg ctcgtgaccg tggccttcat catcttttgg gtgcggagca agagaagcag   1020

actgctgcac agcgactaca tgaacatgac ccccagacgg cctggcccca ccagaaagca   1080

ctaccagcct tacgcccctc ccagagactt cgccgcctac agatctcata tgggaggcgg   1140

aggatctggc ggaggtggaa gtggcggagg cggatctcaa agatgggaac tcgccctggg   1200
```

```
cagattcctg gaatacctga gctgggtgtc cacactgagc gaacaggtgc aagaggaact   1260

gctgagcagc caagtgaccc aagagctgag agccctgatg gacgagacaa tgaaggaact   1320

gaaggcctac aagagcgagc tggaagaaca gctgacccct gtggccgagg aaaccagagc   1380

cagactgagc aaagaactgc aggccgctca ggccagactg ggagccgata tggaagatgt   1440

tcggggcaga ctggtgcagt acagaggcga agttcaggcc atgctgggcc agtctaccga   1500

ggaactgaga gtgcggctgg cctctcatct gattgccctg cagctgagac tgatcggcga   1560

cgcattcgac ctgcagaaaa gactggccgt gtaccaggct ggcgctgctg aacggaagcg   1620

gcgcagcggc agcgggcgca gcggcagcgg cgagggcaga ggaagtcttc taacatgcgg   1680

tgacgtggag gagaatcccg gccctggatc catggcctta ccagtgaccg ccttgctcct   1740

gccgctggcc ttgctgctcc acgccgccag gccggaacag aaactcatca gtgaggaaga   1800

tttgcagacg actccaggag agagatcatc actccctgcc ttttaccctg gcacttcagg   1860

ctcttgttcc ggatgtgggt ccctctctct gccgacaaca acccctgccc ccagacctcc   1920

taccccagcc cctacaattg ccagccagcc tctgagcctg aggcccgagg cttgtagacc   1980

tgctgctggc ggagccgtgc acaccagagg actggatttc gcctgcgacc taggttctgg   2040

gtgctggtgg tcgtgggcgg agtgctggcc tgttacagcc tgctcgtgac cgtggccttc   2100

atcatctttt gggtgcggag caagagaagc agactgctgc acagcgacta catgaacatg   2160

acccccagac ggcctggccc caccagaaag cactaccagc cttacgcccc tcccagagac   2220

ttcgccgcct acagatctcc cgggggaggc ggaggatctg gcggaggtgg aagtggcgga   2280

ggcggatcta tggcccacgc cggcaggacc ggctacgaca acagggagat cgtgatgaag   2340

tacatccact acaagctgag ccagaggggc tacgagtggg acgccggcga cgtgggcgcc   2400

gcccccccg gcgccgcccc cgcccccggc atcttcagca gccagcccgg ccacaccccc   2460

cacccccgccg ccagcaggga ccccgtggcc aggaccagcc ccctgcagac ccccgccgcc   2520

cccggcgccg ccgccggccc cgccctgagc cccgtgcccc ccgtggtgca cctgaccctg   2580

aggcaggccg gcgacgactt cagcaggagg tacaggaggg acttcgccga gatgagcagc   2640

cagctgcacc tgaccccctt caccgccagg ggcaggttcg ccaccgtggt ggaggagctg   2700

ttcagggacg gcgtgaactg gggcaggatc gtggccttct tcgagttcgg cggcgtgatg   2760

tgcgtggaga gcgtgaacag ggagatgagc cccctggtgg acaacatcgc cctgtggatg   2820

accgagtacc tgaacaggca cctgcacacc tggatccagg acaacggcgg ctgggacgcc   2880

ttcgtggagc tgtacggccc cagcatgagg gaagatggag gcggaggatc tggcggaggt   2940

ggaagtggcg gaggcggatc tatgcataga gtgaagttca gcaggagcgc agacgccccc   3000

gcgtaccagc agggccagaa ccagctctat aacgagctca atctaggacg aagagaggag   3060

tacgatgttt tggacaagag acgtggccgg gaccctgaga tggggggaaa gccgagaagg   3120

aagaaccctc aggaaggcct gtacaatgaa ctgcagaaag ataagatggc ggaggcctac   3180

agtgagattg ggatgaaagg cgagcgccgg aggggcaagg ggcacgatgg cctttaccag   3240

ggtctcagta cagccaccaa ggacacctac gacgcccttc acatgcaggc cctgcccccct   3300

cgctaa                                                              3306
```

<210> SEQ ID NO 69
<211> LENGTH: 1097
<212> TYPE: PRT
<213> ORGANISM: Artificial sequence
<220> FEATURE:

<223> OTHER INFORMATION: Homo sapiens

<400> SEQUENCE: 69

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400
```

-continued

```
Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro Gly Ser Met Ala Leu Pro Val Thr Ala Leu
                565                 570                 575

Leu Leu Pro Leu Ala Leu Leu Leu His Ala Ala Arg Pro Glu Gln Lys
            580                 585                 590

Leu Ile Ser Glu Glu Asp Leu Gln Thr Thr Pro Gly Glu Arg Ser Ser
        595                 600                 605

Leu Pro Ala Phe Tyr Pro Gly Thr Ser Gly Ser Cys Ser Gly Cys Gly
    610                 615                 620

Ser Leu Ser Leu Pro Thr Thr Thr Pro Ala Pro Arg Pro Pro Thr Pro
625                 630                 635                 640

Ala Pro Thr Ile Ala Ser Gln Pro Leu Ser Leu Arg Pro Glu Ala Cys
                645                 650                 655

Arg Pro Ala Ala Gly Gly Ala Val His Thr Arg Gly Leu Asp Phe Ala
            660                 665                 670

Cys Asp Pro Arg Phe Trp Val Leu Val Val Val Gly Gly Val Leu Ala
        675                 680                 685

Cys Tyr Ser Leu Leu Val Thr Val Ala Phe Ile Ile Phe Trp Val Arg
    690                 695                 700

Ser Lys Arg Ser Arg Leu Leu His Ser Asp Tyr Met Asn Met Thr Pro
705                 710                 715                 720

Arg Arg Pro Gly Pro Thr Arg Lys His Tyr Gln Pro Tyr Ala Pro Pro
                725                 730                 735

Arg Asp Phe Ala Ala Tyr Arg Ser Pro Gly Gly Gly Gly Gly Ser Gly
            740                 745                 750

Gly Gly Gly Ser Gly Gly Gly Gly Ser Met Ala His Ala Gly Arg Thr
        755                 760                 765

Gly Tyr Asp Asn Arg Glu Ile Val Met Lys Tyr Ile His Tyr Lys Leu
    770                 775                 780

Ser Gln Arg Gly Tyr Glu Trp Asp Ala Gly Asp Val Gly Ala Ala Pro
785                 790                 795                 800

Pro Gly Ala Ala Pro Ala Pro Gly Ile Phe Ser Ser Gln Pro Gly His
                805                 810                 815

Thr Pro His Pro Ala Ala Ser Arg Asp Pro Val Ala Arg Thr Ser Pro
```

```
            820                 825                 830

Leu Gln Thr Pro Ala Ala Pro Gly Ala Ala Ala Gly Pro Ala Leu Ser
        835                 840                 845

Pro Val Pro Pro Val Val His Leu Thr Leu Arg Gln Ala Gly Asp Asp
    850                 855                 860

Phe Ser Arg Arg Tyr Arg Arg Asp Phe Ala Glu Met Ser Ser Gln Leu
865                 870                 875                 880

His Leu Thr Pro Phe Thr Ala Arg Gly Arg Phe Ala Thr Val Val Glu
                885                 890                 895

Glu Leu Phe Arg Asp Gly Val Asn Trp Gly Arg Ile Val Ala Phe Phe
            900                 905                 910

Glu Phe Gly Gly Val Met Cys Val Glu Ser Val Asn Arg Glu Met Ser
        915                 920                 925

Pro Leu Val Asp Asn Ile Ala Leu Trp Met Thr Glu Tyr Leu Asn Arg
    930                 935                 940

His Leu His Thr Trp Ile Gln Asp Asn Gly Gly Trp Asp Ala Phe Val
945                 950                 955                 960

Glu Leu Tyr Gly Pro Ser Met Arg Gly Gly Gly Gly Ser Gly Gly Gly
                965                 970                 975

Gly Ser Gly Gly Gly Gly Ser Met His Arg Val Lys Phe Ser Arg Ser
            980                 985                 990

Ala Asp Ala Pro Ala Tyr Gln Gln  Gly Gln Asn Gln Leu  Tyr Asn Glu
        995                 1000                1005

Leu Asn  Leu Gly Arg Arg Glu  Glu Tyr Asp Val Leu  Asp Lys Arg
    1010                 1015                 1020

Arg Gly  Arg Asp Pro Glu Met  Gly Gly Lys Pro Arg  Arg Lys Asn
    1025                 1030                 1035

Pro Gln  Glu Gly Leu Tyr Asn  Glu Leu Gln Lys Asp  Lys Met Ala
    1040                 1045                 1050

Glu Ala  Tyr Ser Glu Ile Gly  Met Lys Gly Glu Arg  Arg Arg Gly
    1055                 1060                 1065

Lys Gly  His Asp Gly Leu Tyr  Gln Gly Leu Ser Thr  Ala Thr Lys
    1070                 1075                 1080

Asp Thr  Tyr Asp Ala Leu His  Met Gln Ala Leu Pro  Pro Arg
    1085                 1090                 1095


<210> SEQ ID NO 70
<211> LENGTH: 3193
<212> TYPE: DNA
<213> ORGANISM: Artificial sequence
<220> FEATURE:
<223> OTHER INFORMATION: Homo sapiens

<400> SEQUENCE: 70

actagaaatg gccttaccag tgaccgcctt gctcctgccg ctggccttgc tgctccacgc      60

cgccaggccg gtgcagctgc agcagtcagg acctgaactg gtgaagcctg ggacttcagt     120

gaggatatcc tgcaagactt ctggatacac attcactgaa tataccatac actgggtgaa     180

gcagagccat ggaaagagcc ttgagtggat tggaaacatc aatcctaaca atggtggtac     240

cacctacaat cagaagttcg aggacaaggc cacattgact gtagacaagt cctccagtac     300

agcctacatg gagctccgca gcctaacatc tgaggattct gcagtctatt attgtgcagc     360

tggttggaac tttgactact ggggccaagg gaccacggtc accgtctcct caggtggagg     420

tggatcaggt ggaggtggat ctggtggagg tggatctgac attgtgatga cccagtctca     480
```

-continued

```
caaattcatg tccacatcag taggagacag ggtcagcatc atctgtaagg ccagtcaaga    540
tgtgggtact gctgtagact ggtatcaaca gaaaccagga caatctccta aactactgat    600
ttattgggca tccactcggc acactggagt ccctgatcgc ttcacaggca gtggatctgg    660
gacagacttc actctcacca ttactaatgt tcagtctgaa gacttggcag attatttctg    720
tcagcaatat aacagctatc cctcacgtt cggtgctggg accatgctgg acctgaaacg    780
ggctagcaca acaacccctg cccccagacc tcctacccca gcccctacaa ttgccagcca    840
gcctctgagc ctgaggcccg aggcttgtag acctgctgct ggcggagccg tgcacaccag    900
aggactggat ttcgcctgcg acttctgggt gctggtggtc gtgggcggag tgctggcctg    960
ttacagcctg ctcgtgaccg tggccttcat catcttttgg gtgcggagca agagaagcag   1020
actgctgcac agcgactaca tgaacatgac ccccagacgg cctggcccca ccagaaagca   1080
ctaccagcct tacgcccctc ccagagactt cgccgcctac agatctcata tgggaggcgg   1140
aggatctggc ggaggtggaa gtggcggagg cggatctcca aagatgggaa ctcgccctgg   1200
gcagattcct ggaatacctg agctgggtgt ccacactgag cgaacaggtg caagaggaac   1260
tgctgagcag ccaagtgacc caagagctga gagccctgat ggacgagaca atgaaggaac   1320
tgaaggccta caagagcgag ctggaagaac agctgacccc tgtggccgag gaaaccagag   1380
ccagactgag caaagaactg caggccgctc aggccagact gggagccgat atggaagatg   1440
ttcggggcag actggtgcag tacagaggcg aagttcaggc catgctgggc cagtctaccg   1500
aggaactgag agtgcggctg gcctctcatc tgattgccct gcaggcaaga ctgatcggcg   1560
acgcattcga cctgcagaaa agactggccg tgtaccaggc tggcgctgct gaacggaagc   1620
ggcgcagcgg cagcgggcgc agcggcagcg gcgagggcag aggaagtctt ctaacatgcg   1680
gtgacgtgga ggagaatccc ggccctggat ccatggcctt accagtgacc gccttgctcc   1740
tgccgctggc cttgctgctc cacgccgcca ggccggaaca gaaactcatc agtgaggaag   1800
atttgcagac gactccagga gagagatcat cactccctgc cttttaccct ggcacttcag   1860
gctcttgttc cggatgtggg tccctctctc tgccgacaac aacccctgcc cccagacctc   1920
ctaccccagc ccctacaatt gccagccagc ctctgagcct gaggcccgag gcttgtagac   1980
ctgctgctgg cggagccgtg cacaccagag gactggattt cgcctgcgac ctaggttctg   2040
ggtgctggtg gtcgtgggcg gagtgctggc ctgttacagc ctgctcgtga ccgtggcctt   2100
catcatcttt tgggtgcgga gcaagagaag cagactgctg cacagcgact acatgaacat   2160
gacccccaga cggcctggcc ccaccagaaa gcactaccag ccttacgccc ctcccagaga   2220
cttcgccgcc tacagatctc ccgggggagg cggaggatct ggcggaggtg gaagtggcgg   2280
aggcggatct atgagccaga gcaacagaga actggtggtg gacttcctga gctacaagct   2340
gagccagaag ggctacagct ggtcccagtt cagcgacgtg gaagagaaca gaacagaggc   2400
ccctgagggc acagagtctg aggctgtgaa acaggccctg agagaagccg gcgacgagtt   2460
cgagctgaga tacagaaggg ccttcagcga cctgaccagc cagctgcaca tcacacctgg   2520
cacagcctac cagagcttcg agcaggtcgt gaacgagctg ttcagagatg gcgtgaactg   2580
gggcagaatc gtggccttct tcagctttgg cggagccctg tgtgtggaaa gcgtggacaa   2640
agaaatgcag gtcctggtgt ccagaatcgc cgcctggatg gccacctacc tgaacgatca   2700
tctggaaccc tggattcaag agaacggcgg ctgggacacc ttcgtggaac tgtacggaaa   2760
caacgccgct gccgagagca gaaagggcca agaacgagaa gatggaggcg gaggatctgg   2820
cggaggtgga agtggcggag gcggatctat gcatagagtg aagttcagca ggagcgcaga   2880
```

```
cgcccccgcg taccagcagg gccagaacca gctctataac gagctcaatc taggacgaag   2940

agaggagtac gatgttttgg acaagagacg tggccgggac cctgagatgg ggggaaagcc   3000

gagaaggaag aaccctcagg aaggcctgta caatgaactg cagaaagata agatggcgga   3060

ggcctacagt gagattggga tgaaaggcga gcgccggagg ggcaaggggc acgatggcct   3120

ttaccagggt ctcagtacag ccaccaagga cacctacgac gcccttcaca tgcaggccct   3180

gccccctcgc taa                                                      3193
```

<210> SEQ ID NO 71
<211> LENGTH: 1059
<212> TYPE: PRT
<213> ORGANISM: Artificial sequence
<220> FEATURE:
<223> OTHER INFORMATION: Homo sapiens

<400> SEQUENCE: 71

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300
```

```
Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Ala Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro Gly Ser Met Ala Leu Pro Val Thr Ala Leu
                565                 570                 575

Leu Leu Pro Leu Ala Leu Leu Leu His Ala Ala Arg Pro Glu Gln Lys
            580                 585                 590

Leu Ile Ser Glu Glu Asp Leu Gln Thr Thr Pro Gly Glu Arg Ser Ser
        595                 600                 605

Leu Pro Ala Phe Tyr Pro Gly Thr Ser Gly Ser Cys Ser Gly Cys Gly
    610                 615                 620

Ser Leu Ser Leu Pro Thr Thr Thr Pro Ala Pro Arg Pro Pro Thr Pro
625                 630                 635                 640

Ala Pro Thr Ile Ala Ser Gln Pro Leu Ser Leu Arg Pro Glu Ala Cys
                645                 650                 655

Arg Pro Ala Ala Gly Gly Ala Val His Thr Arg Gly Leu Asp Phe Ala
            660                 665                 670

Cys Asp Pro Arg Phe Trp Val Leu Val Val Val Gly Gly Val Leu Ala
        675                 680                 685

Cys Tyr Ser Leu Leu Val Thr Val Ala Phe Ile Ile Phe Trp Val Arg
    690                 695                 700

Ser Lys Arg Ser Arg Leu Leu His Ser Asp Tyr Met Asn Met Thr Pro
705                 710                 715                 720
```

```
Arg Arg Pro Gly Pro Thr Arg Lys His Tyr Gln Pro Tyr Ala Pro Pro
                725                 730                 735

Arg Asp Phe Ala Ala Tyr Arg Ser Pro Gly Gly Gly Gly Gly Ser Gly
            740                 745                 750

Gly Gly Gly Ser Gly Gly Gly Gly Ser Met Ser Gln Ser Asn Arg Glu
        755                 760                 765

Leu Val Val Asp Phe Leu Ser Tyr Lys Leu Ser Gln Lys Gly Tyr Ser
    770                 775                 780

Trp Ser Gln Phe Ser Asp Val Glu Glu Asn Arg Thr Glu Ala Pro Glu
785                 790                 795                 800

Gly Thr Glu Ser Glu Ala Val Lys Gln Ala Leu Arg Glu Ala Gly Asp
                805                 810                 815

Glu Phe Glu Leu Arg Tyr Arg Arg Ala Phe Ser Asp Leu Thr Ser Gln
            820                 825                 830

Leu His Ile Thr Pro Gly Thr Ala Tyr Gln Ser Phe Glu Gln Val Val
        835                 840                 845

Asn Glu Leu Phe Arg Asp Gly Val Asn Trp Gly Arg Ile Val Ala Phe
    850                 855                 860

Phe Ser Phe Gly Gly Ala Leu Cys Val Glu Ser Val Asp Lys Glu Met
865                 870                 875                 880

Gln Val Leu Val Ser Arg Ile Ala Ala Trp Met Ala Thr Tyr Leu Asn
                885                 890                 895

Asp His Leu Glu Pro Trp Ile Gln Glu Asn Gly Gly Trp Asp Thr Phe
            900                 905                 910

Val Glu Leu Tyr Gly Asn Asn Ala Ala Ala Glu Ser Arg Lys Gly Gln
        915                 920                 925

Glu Arg Gly Gly Gly Gly Ser Gly Gly Gly Gly Ser Gly Gly Gly Gly
    930                 935                 940

Ser Met His Arg Val Lys Phe Ser Arg Ser Ala Asp Ala Pro Ala Tyr
945                 950                 955                 960

Gln Gln Gly Gln Asn Gln Leu Tyr Asn Glu Leu Asn Leu Gly Arg Arg
                965                 970                 975

Glu Glu Tyr Asp Val Leu Asp Lys Arg Arg Gly Arg Asp Pro Glu Met
            980                 985                 990

Gly Gly Lys Pro Arg Arg Lys Asn  Pro Gln Glu Gly Leu  Tyr Asn Glu
        995                 1000                1005

Leu Gln  Lys Asp Lys Met Ala  Glu Ala Tyr Ser Glu  Ile Gly Met
    1010                1015                1020

Lys Gly  Glu Arg Arg Arg Gly  Lys Gly His Asp Gly  Leu Tyr Gln
    1025                1030                1035

Gly Leu  Ser Thr Ala Thr Lys  Asp Thr Tyr Asp Ala  Leu His Met
    1040                1045                1050

Gln Ala  Leu Pro Pro Arg
    1055
```

<210> SEQ ID NO 72
<211> LENGTH: 3191
<212> TYPE: DNA
<213> ORGANISM: Artificial sequence
<220> FEATURE:
<223> OTHER INFORMATION: Homo sapiens

<400> SEQUENCE: 72

```
actagaaatg gccttaccag tgaccgcctt gctcctgccg ctggccttgc tgctccacgc     60

cgccaggccg gtgcagctgc agcagtcagg acctgaactg gtgaagcctg ggacttcagt    120
```

```
gaggatatcc tgcaagactt ctggatacac attcactgaa tataccatac actgggtgaa    180
gcagagccat ggaaagagcc ttgagtggat tggaaacatc aatcctaaca atggtggtac    240
cacctacaat cagaagttcg aggacaaggc cacattgact gtagacaagt cctccagtac    300
agcctacatg gagctccgca gcctaacatc tgaggattct gcagtctatt attgtgcagc    360
tggttggaac tttgactact ggggccaagg gaccacggtc accgtctcct caggtggagg    420
tggatcaggt ggaggtggat ctggtggagg tggatctgac attgtgatga cccagtctca    480
caaattcatg tccacatcag taggagacag ggtcagcatc atctgtaagg ccagtcaaga    540
tgtgggtact gctgtagact ggtatcaaca gaaaccagga caatctccta aactactgat    600
ttattgggca tccactcggc acactggagt ccctgatcgc ttcacaggca gtggatctgg    660
gacagacttc actctcacca ttactaatgt tcagtctgaa gacttggcag attatttctg    720
tcagcaatat aacagctatc cctcacgttt cggtgctggg accatgctgg acctgaaacg    780
ggctagcaca acaacccctg cccccagacc tcctacccca gcccctacaa ttgccagcca    840
gcctctgagc ctgaggcccg aggcttgtag acctgctgct ggcggagccg tgcacaccag    900
aggactggat ttcgcctgcg acttctgggt gctggtggtc gtgggcggag tgctggcctg    960
ttacagcctg ctcgtgaccg tggccttcat catcttttgg gtgcggagca agagaagcag   1020
actgctgcac agcgactaca tgaacatgac ccccagacgg cctggcccca ccagaaagca   1080
ctaccagcct tacgcccctc ccagagactt cgccgcctac agatctcata tgggaggcgg   1140
aggatctggc ggaggtggaa gtggcggagg cggatctcaa agatgggaac tcgccctggg   1200
cagattcctg gaatacctga gctgggtgtc cacactgagc gaacaggtgc aagaggaact   1260
gctgagcagc caagtgaccc aagagctgag agccctgatg gacgagacaa tgaaggaact   1320
gaaggcctac aagagcgagc tggaagaaca gctgacccct gtggccgagg aaaccagagc   1380
cagactgagc aaagaactgc aggccgctca ggccagactg ggagccgata tggaagatgt   1440
tcggggcaga ctggtgcagt acagaggcga agttcaggcc atgctgggcc agtctaccga   1500
ggaactgaga gtgcggctgg cctctcatct gattgccctg cagctgagac tgatcggcgc   1560
agcattcgac ctgcagaaaa gactggccgt gtaccaggct ggcgctctga acggaagcgg   1620
cgcagcggca gcgggcgcag cggcagcggc gagggcagag gaagtcttct aacatgcggt   1680
gacgtggagg agaatcccgg ccctggatcc atggccttac cagtgaccgc cttgctcctg   1740
ccgctggcct tgctgctcca cgccgccagg ccggaacaga aactcatcag tgaggaagat   1800
ttgcagacga ctccaggaga gagatcatca ctccctgcct tttaccctgg cacttcaggc   1860
tcttgttccg gatgtgggtc cctctctctg ccgacaacaa cccctgcccc cagacctcct   1920
accccagccc ctacaattgc cagccagcct ctgagcctga ggcccgaggc ttgtagacct   1980
gctgctggcg gagccgtgca caccagagga ctggatttcg cctgcgacct aggttctggg   2040
tgctggtggt cgtgggcgga gtgctggcct gttacagcct gctcgtgacc gtggccttca   2100
tcatcttttg ggtgcggagc aagagaagca gactgctgca cagcgactac atgaacatga   2160
cccccagacg gcctggcccc accagaaagc actaccagcc ttacgcccct cccagagact   2220
tcgccgccta cagatctccc gggggaggcg gaggatctgg cggaggtgga agtggcggag   2280
gcggatctat gagccagagc aacagagaac tggtggtgga cttcctgagc tacaagctga   2340
gccagaaggg ctacagctgg tcccagttca gcgacgtgga agagaacaga acagaggccc   2400
ctgagggcac agagtctgag gctgtgaaac aggccctgag agaagccggc gacgagttcg   2460
```

```
agctgagata cagaagggcc ttcagcgacc tgaccagcca gctgcacatc acacctggca   2520

cagcctacca gagcttcgag caggtcgtga acgagctgtt cagagatggc gtgaactggg   2580

gcagaatcgt ggccttcttc agctttggcg gagccctgtg tgtggaaagc gtggacaaag   2640

aaatgcaggt cctggtgtcc agaatcgccg cctggatggc cacctacctg aacgatcatc   2700

tggaaccctg gattcaagag aacggcggct gggacacctt cgtggaactg tacggaaaca   2760

acgccgctgc cgagagcaga aagggccaag aacgagaaga tggaggcgga ggatctggcg   2820

gaggtggaag tggcggaggc ggatctatgc atagagtgaa gttcagcagg agcgcagacg   2880

cccccgcgta ccagcagggc cagaaccagc tctataacga gctcaatcta ggacgaagag   2940

aggagtacga tgttttggac aagagacgtg gccgggaccc tgagatgggg ggaaagccga   3000

gaaggaagaa ccctcaggaa ggcctgtaca atgaactgca gaaagataag atggcggagg   3060

cctacagtga gattgggatg aaaggcgagc gccggagggg caaggggcac gatggccttt   3120

accagggtct cagtacagcc accaaggaca cctacgacgc ccttcacatg caggccctgc   3180

cccctcgcta a                                                         3191
```

<210> SEQ ID NO 73
<211> LENGTH: 1059
<212> TYPE: PRT
<213> ORGANISM: Artificial sequence
<220> FEATURE:
<223> OTHER INFORMATION: Homo sapiens

<400> SEQUENCE: 73

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
```

```
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Ala Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro Gly Ser Met Ala Leu Pro Val Thr Ala Leu
                565                 570                 575

Leu Leu Pro Leu Ala Leu Leu Leu His Ala Ala Arg Pro Glu Gln Lys
            580                 585                 590

Leu Ile Ser Glu Glu Asp Leu Gln Thr Thr Pro Gly Glu Arg Ser Ser
        595                 600                 605

Leu Pro Ala Phe Tyr Pro Gly Thr Ser Gly Ser Cys Ser Gly Cys Gly
    610                 615                 620

Ser Leu Ser Leu Pro Thr Thr Thr Pro Ala Pro Arg Pro Pro Thr Pro
625                 630                 635                 640

Ala Pro Thr Ile Ala Ser Gln Pro Leu Ser Leu Arg Pro Glu Ala Cys
                645                 650                 655
```

```
Arg Pro Ala Ala Gly Gly Ala Val His Thr Arg Gly Leu Asp Phe Ala
            660                 665                 670

Cys Asp Pro Arg Phe Trp Val Leu Val Val Val Gly Gly Val Leu Ala
        675                 680                 685

Cys Tyr Ser Leu Leu Val Thr Val Ala Phe Ile Ile Phe Trp Val Arg
    690                 695                 700

Ser Lys Arg Ser Arg Leu Leu His Ser Asp Tyr Met Asn Met Thr Pro
705                 710                 715                 720

Arg Arg Pro Gly Pro Thr Arg Lys His Tyr Gln Pro Tyr Ala Pro Pro
                725                 730                 735

Arg Asp Phe Ala Ala Tyr Arg Ser Pro Gly Gly Gly Gly Gly Ser Gly
            740                 745                 750

Gly Gly Gly Ser Gly Gly Gly Gly Ser Met Ser Gln Ser Asn Arg Glu
        755                 760                 765

Leu Val Val Asp Phe Leu Ser Tyr Lys Leu Ser Gln Lys Gly Tyr Ser
    770                 775                 780

Trp Ser Gln Phe Ser Asp Val Glu Glu Asn Arg Thr Glu Ala Pro Glu
785                 790                 795                 800

Gly Thr Glu Ser Glu Ala Val Lys Gln Ala Leu Arg Glu Ala Gly Asp
                805                 810                 815

Glu Phe Glu Leu Arg Tyr Arg Arg Ala Phe Ser Asp Leu Thr Ser Gln
            820                 825                 830

Leu His Ile Thr Pro Gly Thr Ala Tyr Gln Ser Phe Glu Gln Val Val
        835                 840                 845

Asn Glu Leu Phe Arg Asp Gly Val Asn Trp Gly Arg Ile Val Ala Phe
    850                 855                 860

Phe Ser Phe Gly Gly Ala Leu Cys Val Glu Ser Val Asp Lys Glu Met
865                 870                 875                 880

Gln Val Leu Val Ser Arg Ile Ala Ala Trp Met Ala Thr Tyr Leu Asn
                885                 890                 895

Asp His Leu Glu Pro Trp Ile Gln Glu Asn Gly Gly Trp Asp Thr Phe
            900                 905                 910

Val Glu Leu Tyr Gly Asn Asn Ala Ala Ala Glu Ser Arg Lys Gly Gln
        915                 920                 925

Glu Arg Gly Gly Gly Gly Ser Gly Gly Gly Gly Ser Gly Gly Gly Gly
    930                 935                 940

Ser Met His Arg Val Lys Phe Ser Arg Ser Ala Asp Ala Pro Ala Tyr
945                 950                 955                 960

Gln Gln Gly Gln Asn Gln Leu Tyr Asn Glu Leu Asn Leu Gly Arg Arg
                965                 970                 975

Glu Glu Tyr Asp Val Leu Asp Lys Arg Arg Gly Arg Asp Pro Glu Met
            980                 985                 990

Gly Gly Lys Pro Arg Arg Lys Asn  Pro Gln Glu Gly Leu  Tyr Asn Glu
        995                 1000                1005

Leu Gln  Lys Asp Lys Met Ala  Glu Ala Tyr Ser Glu  Ile Gly Met
    1010                1015                1020

Lys Gly  Glu Arg Arg Arg Gly  Lys Gly His Asp Gly  Leu Tyr Gln
    1025                1030                1035

Gly Leu  Ser Thr Ala Thr Lys  Asp Thr Tyr Asp Ala  Leu His Met
    1040                1045                1050

Gln Ala  Leu Pro Pro Arg
    1055
```

<210> SEQ ID NO 74
<211> LENGTH: 21
<212> TYPE: PRT
<213> ORGANISM: Artificial sequence
<220> FEATURE:
<223> OTHER INFORMATION: Homo sapiens

<400> SEQUENCE: 74

```
Gly Val Leu Ala Gly Ile Val Met Gly Asp Leu Val Leu Thr Val Leu
1               5                   10                  15

Ile Ala Leu Ala Val
            20
```

<210> SEQ ID NO 75
<211> LENGTH: 19
<212> TYPE: PRT
<213> ORGANISM: Artificial sequence
<220> FEATURE:
<223> OTHER INFORMATION: Homo sapiens

<400> SEQUENCE: 75

```
Leu Arg Pro Val Gln Ala Gln Ala Gln Ser Asp Cys Ser Cys Ser Thr
1               5                   10                  15

Val Ser Pro
```

<210> SEQ ID NO 76
<211> LENGTH: 566
<212> TYPE: PRT
<213> ORGANISM: Artificial sequence
<220> FEATURE:
<223> OTHER INFORMATION: Homo sapiens

<400> SEQUENCE: 76

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205
```

```
Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Ala Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro
                565
```

<210> SEQ ID NO 77
<211> LENGTH: 566
<212> TYPE: PRT
<213> ORGANISM: Artificial sequence
<220> FEATURE:
<223> OTHER INFORMATION: Homo sapiens

<400> SEQUENCE: 77

Met Ala Leu Pro Val Thr Ala Leu Leu Leu Pro Leu Ala Leu Leu Leu
1 5 10 15

His Ala Ala Arg Pro Val Gln Leu Gln Gln Ser Gly Pro Glu Leu Val
20 25 30

Lys Pro Gly Thr Ser Val Arg Ile Ser Cys Lys Thr Ser Gly Tyr Thr
35 40 45

Phe Thr Glu Tyr Thr Ile His Trp Val Lys Gln Ser His Gly Lys Ser
50 55 60

Leu Glu Trp Ile Gly Asn Ile Asn Pro Asn Asn Gly Gly Thr Thr Tyr
65 70 75 80

Asn Gln Lys Phe Glu Asp Lys Ala Thr Leu Thr Val Asp Lys Ser Ser
85 90 95

Ser Thr Ala Tyr Met Glu Leu Arg Ser Leu Thr Ser Glu Asp Ser Ala
100 105 110

Val Tyr Tyr Cys Ala Ala Gly Trp Asn Phe Asp Tyr Trp Gly Gln Gly
115 120 125

Thr Thr Val Thr Val Ser Ser Gly Gly Gly Gly Ser Gly Gly Gly Gly
130 135 140

Ser Gly Gly Gly Gly Ser Asp Ile Val Met Thr Gln Ser His Lys Phe
145 150 155 160

Met Ser Thr Ser Val Gly Asp Arg Val Ser Ile Ile Cys Lys Ala Ser
165 170 175

Gln Asp Val Gly Thr Ala Val Asp Trp Tyr Gln Gln Lys Pro Gly Gln
180 185 190

Ser Pro Lys Leu Leu Ile Tyr Trp Ala Ser Thr Arg His Thr Gly Val
195 200 205

Pro Asp Arg Phe Thr Gly Ser Gly Ser Gly Thr Asp Phe Thr Leu Thr
210 215 220

Ile Thr Asn Val Gln Ser Glu Asp Leu Ala Asp Tyr Phe Cys Gln Gln
225 230 235 240

Tyr Asn Ser Tyr Pro Leu Thr Phe Gly Ala Gly Thr Met Leu Asp Leu
245 250 255

Lys Arg Ala Ser Thr Thr Thr Pro Ala Pro Arg Pro Pro Thr Pro Ala
260 265 270

Pro Thr Ile Ala Ser Gln Pro Leu Ser Leu Arg Pro Glu Ala Cys Arg
275 280 285

Pro Ala Ala Gly Gly Ala Val His Thr Arg Gly Leu Asp Phe Ala Cys
290 295 300

Asp Phe Trp Val Leu Val Val Val Gly Gly Val Leu Ala Cys Tyr Ser
305 310 315 320

Leu Leu Val Thr Val Ala Phe Ile Ile Phe Trp Val Arg Ser Lys Arg
325 330 335

Ser Arg Leu Leu His Ser Asp Tyr Met Asn Met Thr Pro Arg Arg Pro
340 345 350

Gly Pro Thr Arg Lys His Tyr Gln Pro Tyr Ala Pro Pro Arg Asp Phe
355 360 365

Ala Ala Tyr Arg Ser His Met Gly Gly Gly Gly Ser Gly Gly Gly Gly
370 375 380

Ser Gly Gly Gly Gly Ser Gln Arg Trp Glu Leu Ala Leu Gly Arg Phe
385 390 395 400

Leu Glu Tyr Leu Ser Trp Val Ser Thr Leu Ser Glu Gln Val Gln Glu
405 410 415

Glu Leu Leu Ser Ser Gln Val Thr Gln Glu Leu Arg Ala Leu Met Asp
420 425 430

Glu Thr Met Lys Glu Leu Lys Ala Tyr Lys Ser Glu Leu Glu Glu Gln
435 440 445

Leu Thr Pro Val Ala Glu Glu Thr Arg Ala Arg Leu Ser Lys Glu Leu
450 455 460

Gln Ala Ala Gln Ala Arg Leu Gly Ala Asp Met Glu Asp Val Arg Gly
465 470 475 480

Arg Leu Val Gln Tyr Arg Gly Glu Val Gln Ala Met Leu Gly Gln Ser
485 490 495

Thr Glu Glu Leu Arg Val Arg Leu Ala Ser His Leu Ile Ala Leu Gln
500 505 510

Leu Arg Leu Ile Gly Ala Ala Phe Asp Leu Gln Lys Arg Leu Ala Val
515 520 525

Tyr Gln Ala Gly Ala Ala Glu Arg Lys Arg Arg Ser Gly Ser Gly Arg
530 535 540

Ser Gly Ser Gly Glu Gly Arg Gly Ser Leu Leu Thr Cys Gly Asp Val
545 550 555 560

Glu Glu Asn Pro Gly Pro
565

<210> SEQ ID NO 78
<211> LENGTH: 493
<212> TYPE: PRT
<213> ORGANISM: Artificial sequence
<220> FEATURE:
<223> OTHER INFORMATION: Homo sapiens

<400> SEQUENCE: 78

Met Ala Leu Pro Val Thr Ala Leu Leu Leu Pro Leu Ala Leu Leu Leu
1 5 10 15

His Ala Ala Arg Pro Glu Gln Lys Leu Ile Ser Glu Glu Asp Leu Gln
20 25 30

Thr Thr Pro Gly Glu Arg Ser Ser Leu Pro Ala Phe Tyr Pro Gly Thr
35 40 45

Ser Gly Ser Cys Ser Gly Cys Gly Ser Leu Ser Leu Pro Thr Thr Thr
50 55 60

Pro Ala Pro Arg Pro Pro Thr Pro Ala Pro Thr Ile Ala Ser Gln Pro
65 70 75 80

Leu Ser Leu Arg Pro Glu Ala Cys Arg Pro Ala Ala Gly Gly Ala Val
85 90 95

His Thr Arg Gly Leu Asp Phe Ala Cys Asp Pro Arg Phe Trp Val Leu
100 105 110

Val Val Val Gly Gly Val Leu Ala Cys Tyr Ser Leu Leu Val Thr Val
115 120 125

Ala Phe Ile Ile Phe Trp Val Arg Ser Lys Arg Ser Arg Leu Leu His
130 135 140

Ser Asp Tyr Met Asn Met Thr Pro Arg Arg Pro Gly Pro Thr Arg Lys
145 150 155 160

His Tyr Gln Pro Tyr Ala Pro Pro Arg Asp Phe Ala Ala Tyr Arg Ser
165 170 175

Pro Gly Gly Gly Gly Gly Ser Gly Gly Gly Gly Ser Gly Gly Gly Gly
180 185 190

Ser Met Ser Gln Ser Asn Arg Glu Leu Val Val Asp Phe Leu Ser Tyr
195 200 205

```
Lys Leu Ser Gln Lys Gly Tyr Ser Trp Ser Gln Phe Ser Asp Val Glu
    210                 215                 220

Glu Asn Arg Thr Glu Ala Pro Glu Gly Thr Glu Ser Glu Ala Val Lys
225                 230                 235                 240

Gln Ala Leu Arg Glu Ala Gly Asp Glu Phe Glu Leu Arg Tyr Arg Arg
                245                 250                 255

Ala Phe Ser Asp Leu Thr Ser Gln Leu His Ile Thr Pro Gly Thr Ala
            260                 265                 270

Tyr Gln Ser Phe Glu Gln Val Val Asn Glu Leu Phe Arg Asp Gly Val
        275                 280                 285

Asn Trp Gly Arg Ile Val Ala Phe Phe Ser Phe Gly Gly Ala Leu Cys
    290                 295                 300

Val Glu Ser Val Asp Lys Glu Met Gln Val Leu Val Ser Arg Ile Ala
305                 310                 315                 320

Ala Trp Met Ala Thr Tyr Leu Asn Asp His Leu Glu Pro Trp Ile Gln
                325                 330                 335

Glu Asn Gly Gly Trp Asp Thr Phe Val Glu Leu Tyr Gly Asn Asn Ala
            340                 345                 350

Ala Ala Glu Ser Arg Lys Gly Gln Glu Arg Glu Asp Gly Gly Gly Gly
        355                 360                 365

Ser Gly Gly Gly Gly Ser Gly Gly Gly Gly Ser Met His Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 79
<211> LENGTH: 493
<212> TYPE: PRT
<213> ORGANISM: Artificial sequence
<220> FEATURE:
<223> OTHER INFORMATION: Homo sapiens

<400> SEQUENCE: 79

Gly Ser Met Ala Leu Pro Val Thr Ala Leu Leu Leu Pro Leu Ala Leu
1               5                   10                  15

Leu Leu His Ala Ala Arg Pro Glu Gln Lys Leu Ile Ser Glu Glu Asp
            20                  25                  30

Leu Gln Thr Thr Pro Gly Glu Arg Ser Ser Leu Pro Ala Phe Tyr Pro
        35                  40                  45

Gly Thr Ser Gly Ser Cys Ser Gly Cys Gly Ser Leu Ser Leu Pro Thr
    50                  55                  60

Thr Thr Pro Ala Pro Arg Pro Pro Thr Pro Ala Pro Thr Ile Ala Ser
65                  70                  75                  80
```

-continued

```
Gln Pro Leu Ser Leu Arg Pro Glu Ala Cys Arg Pro Ala Ala Gly Gly
                85                  90                  95

Ala Val His Thr Arg Gly Leu Asp Phe Ala Cys Asp Pro Arg Phe Trp
            100                 105                 110

Val Leu Val Val Val Gly Gly Val Leu Ala Cys Tyr Ser Leu Leu Val
        115                 120                 125

Thr Val Ala Phe Ile Ile Phe Trp Val Arg Ser Lys Arg Ser Arg Leu
    130                 135                 140

Leu His Ser Asp Tyr Met Asn Met Thr Pro Arg Arg Pro Gly Pro Thr
145                 150                 155                 160

Arg Lys His Tyr Gln Pro Tyr Ala Pro Pro Arg Asp Phe Ala Ala Tyr
                165                 170                 175

Arg Ser Pro Gly Gly Gly Gly Gly Ser Gly Gly Gly Gly Ser Gly Gly
            180                 185                 190

Gly Gly Ser Met Ser Gln Ser Asn Arg Glu Leu Val Val Asp Phe Leu
        195                 200                 205

Ser Tyr Lys Leu Ser Gln Lys Gly Tyr Ser Trp Ser Gln Phe Ser Asp
    210                 215                 220

Val Glu Glu Asn Arg Thr Glu Ala Pro Glu Gly Thr Glu Ser Glu Ala
225                 230                 235                 240

Val Lys Gln Ala Leu Arg Glu Ala Gly Asp Glu Phe Glu Leu Arg Tyr
                245                 250                 255

Arg Arg Ala Phe Ser Asp Leu Thr Ser Gln Leu His Ile Thr Pro Gly
            260                 265                 270

Thr Ala Tyr Gln Ser Phe Glu Gln Val Val Asn Glu Leu Phe Arg Asp
        275                 280                 285

Gly Val Asn Trp Gly Arg Ile Val Ala Phe Phe Ser Phe Gly Gly Ala
    290                 295                 300

Leu Cys Val Glu Ser Val Asp Lys Glu Met Gln Val Leu Val Ser Arg
305                 310                 315                 320

Ile Ala Ala Trp Met Ala Thr Tyr Leu Asn Asp His Leu Glu Pro Trp
                325                 330                 335

Ile Gln Glu Asn Gly Gly Trp Asp Thr Phe Val Glu Leu Tyr Gly Asn
            340                 345                 350

Asn Ala Ala Ala Glu Ser Arg Lys Gly Gln Glu Arg Gly Gly Gly Gly
        355                 360                 365

Ser Gly Gly Gly Gly Ser Gly Gly Gly Gly Ser Met His Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 80
<211> LENGTH: 495
<212> TYPE: PRT
<213> ORGANISM: Artificial sequence
<220> FEATURE:
<223> OTHER INFORMATION: Homo sapiens

<400> SEQUENCE: 80

```
Gly Ser Met Ala Leu Pro Val Thr Ala Leu Leu Leu Pro Leu Ala Leu
1               5                   10                  15

Leu Leu His Ala Ala Arg Pro Glu Gln Lys Leu Ile Ser Glu Glu Asp
            20                  25                  30

Leu Gln Thr Thr Pro Gly Glu Arg Ser Ser Leu Pro Ala Phe Tyr Pro
        35                  40                  45

Gly Thr Ser Gly Ser Cys Ser Gly Cys Gly Ser Leu Ser Leu Pro Thr
    50                  55                  60

Thr Thr Pro Ala Pro Arg Pro Pro Thr Pro Ala Pro Thr Ile Ala Ser
65                  70                  75                  80

Gln Pro Leu Ser Leu Arg Pro Glu Ala Cys Arg Pro Ala Ala Gly Gly
                85                  90                  95

Ala Val His Thr Arg Gly Leu Asp Phe Ala Cys Asp Pro Arg Phe Trp
            100                 105                 110

Val Leu Val Val Val Gly Gly Val Leu Ala Cys Tyr Ser Leu Leu Val
        115                 120                 125

Thr Val Ala Phe Ile Ile Phe Trp Val Arg Ser Lys Arg Ser Arg Leu
    130                 135                 140

Leu His Ser Asp Tyr Met Asn Met Thr Pro Arg Arg Pro Gly Pro Thr
145                 150                 155                 160

Arg Lys His Tyr Gln Pro Tyr Ala Pro Pro Arg Asp Phe Ala Ala Tyr
                165                 170                 175

Arg Ser Pro Gly Gly Gly Gly Gly Ser Gly Gly Gly Gly Ser Gly Gly
            180                 185                 190

Gly Gly Ser Met Ser Gln Ser Asn Arg Glu Leu Val Val Asp Phe Leu
        195                 200                 205

Ser Tyr Lys Leu Ser Gln Lys Gly Tyr Ser Trp Ser Gln Phe Ser Asp
    210                 215                 220

Val Glu Glu Asn Arg Thr Glu Ala Pro Glu Gly Thr Glu Ser Glu Ala
225                 230                 235                 240

Val Lys Gln Ala Leu Arg Glu Ala Gly Asp Asp Phe Glu Leu Arg Tyr
                245                 250                 255

Arg Arg Ala Phe Ser Asp Leu Thr Ser Gln Leu His Ile Thr Pro Gly
            260                 265                 270

Thr Ala Tyr Gln Ser Phe Glu Gln Val Val Asn Glu Leu Phe Arg Asp
        275                 280                 285

Gly Val Asn Trp Gly Arg Ile Val Ala Phe Phe Ser Phe Gly Gly Ala
    290                 295                 300

Leu Cys Val Glu Ser Val Asp Lys Glu Met Gln Val Leu Val Ser Arg
305                 310                 315                 320

Ile Ala Ala Trp Met Ala Thr Tyr Leu Asn Asp His Leu Glu Pro Trp
                325                 330                 335

Ile Gln Glu Asn Gly Gly Trp Asp Thr Phe Val Glu Leu Tyr Gly Asn
            340                 345                 350

Asn Ala Ala Ala Glu Ser Arg Lys Gly Gln Glu Arg Glu Asp Gly Gly
        355                 360                 365

Gly Gly Ser Gly Gly Gly Gly Ser Gly Gly Gly Gly Ser Met His Arg
```

```
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495


<210> SEQ ID NO 81
<211> LENGTH: 531
<212> TYPE: PRT
<213> ORGANISM: Artificial sequence
<220> FEATURE:
<223> OTHER INFORMATION: Homo sapiens

<400> SEQUENCE: 81

Gly Ser Met Ala Leu Pro Val Thr Ala Leu Leu Leu Pro Leu Ala Leu
1               5                   10                  15

Leu Leu His Ala Ala Arg Pro Glu Gln Lys Leu Ile Ser Glu Glu Asp
            20                  25                  30

Leu Gln Thr Thr Pro Gly Glu Arg Ser Ser Leu Pro Ala Phe Tyr Pro
        35                  40                  45

Gly Thr Ser Gly Ser Cys Ser Gly Cys Gly Ser Leu Ser Leu Pro Thr
    50                  55                  60

Thr Thr Pro Ala Pro Arg Pro Pro Thr Pro Ala Pro Thr Ile Ala Ser
65                  70                  75                  80

Gln Pro Leu Ser Leu Arg Pro Glu Ala Cys Arg Pro Ala Ala Gly Gly
                85                  90                  95

Ala Val His Thr Arg Gly Leu Asp Phe Ala Cys Asp Pro Arg Phe Trp
            100                 105                 110

Val Leu Val Val Val Gly Gly Val Leu Ala Cys Tyr Ser Leu Leu Val
        115                 120                 125

Thr Val Ala Phe Ile Ile Phe Trp Val Arg Ser Lys Arg Ser Arg Leu
    130                 135                 140

Leu His Ser Asp Tyr Met Asn Met Thr Pro Arg Arg Pro Gly Pro Thr
145                 150                 155                 160

Arg Lys His Tyr Gln Pro Tyr Ala Pro Pro Arg Asp Phe Ala Ala Tyr
                165                 170                 175

Arg Ser Pro Gly Gly Gly Gly Gly Ser Gly Gly Gly Gly Ser Gly Gly
            180                 185                 190

Gly Gly Ser Met Ala His Ala Gly Arg Thr Gly Tyr Asp Asn Arg Glu
        195                 200                 205

Ile Val Met Lys Tyr Ile His Tyr Lys Leu Ser Gln Arg Gly Tyr Glu
    210                 215                 220

Trp Asp Ala Gly Asp Val Gly Ala Ala Pro Pro Gly Ala Ala Pro Ala
225                 230                 235                 240

Pro Gly Ile Phe Ser Ser Gln Pro Gly His Thr Pro His Pro Ala Ala
```

```
                245                 250                 255

Ser Arg Asp Pro Val Ala Arg Thr Ser Pro Leu Gln Thr Pro Ala Ala
            260                 265                 270

Pro Gly Ala Ala Ala Gly Pro Ala Leu Ser Pro Val Pro Pro Val Val
        275                 280                 285

His Leu Thr Leu Arg Gln Ala Gly Asp Asp Phe Ser Arg Arg Tyr Arg
    290                 295                 300

Arg Asp Phe Ala Glu Met Ser Ser Gln Leu His Leu Thr Pro Phe Thr
305                 310                 315                 320

Ala Arg Gly Arg Phe Ala Thr Val Val Glu Glu Leu Phe Arg Asp Gly
                325                 330                 335

Val Asn Trp Gly Arg Ile Val Ala Phe Phe Glu Phe Gly Gly Val Met
            340                 345                 350

Cys Val Glu Ser Val Asn Arg Glu Met Ser Pro Leu Val Asp Asn Ile
        355                 360                 365

Ala Leu Trp Met Thr Glu Tyr Leu Asn Arg His Leu His Thr Trp Ile
    370                 375                 380

Gln Asp Asn Gly Gly Trp Asp Ala Phe Val Glu Leu Tyr Gly Pro Ser
385                 390                 395                 400

Met Arg Gly Gly Gly Gly Ser Gly Gly Gly Gly Ser Gly Gly Gly Gly
                405                 410                 415

Ser Met His Arg Val Lys Phe Ser Arg Ser Ala Asp Ala Pro Ala Tyr
            420                 425                 430

Gln Gln Gly Gln Asn Gln Leu Tyr Asn Glu Leu Asn Leu Gly Arg Arg
        435                 440                 445

Glu Glu Tyr Asp Val Leu Asp Lys Arg Arg Gly Arg Asp Pro Glu Met
    450                 455                 460

Gly Gly Lys Pro Arg Arg Lys Asn Pro Gln Glu Gly Leu Tyr Asn Glu
465                 470                 475                 480

Leu Gln Lys Asp Lys Met Ala Glu Ala Tyr Ser Glu Ile Gly Met Lys
                485                 490                 495

Gly Glu Arg Arg Arg Gly Lys Gly His Asp Gly Leu Tyr Gln Gly Leu
            500                 505                 510

Ser Thr Ala Thr Lys Asp Thr Tyr Asp Ala Leu His Met Gln Ala Leu
        515                 520                 525

Pro Pro Arg
    530


<210> SEQ ID NO 82
<211> LENGTH: 566
<212> TYPE: PRT
<213> ORGANISM: Artificial sequence
<220> FEATURE:
<223> OTHER INFORMATION: Homo sapiens

<400> SEQUENCE: 82

Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
```

```
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495
```

```
Thr Glu Glu Leu Arg Val Arg Leu Ala Ser His Leu Ile Ala Leu Gln
            500                 505                 510

Leu Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro
                565


<210> SEQ ID NO 83
<211> LENGTH: 495
<212> TYPE: PRT
<213> ORGANISM: Artificial sequence
<220> FEATURE:
<223> OTHER INFORMATION: Homo sapiens

<400> SEQUENCE: 83

Gly Ser Met Ala Leu Pro Val Thr Ala Leu Leu Leu Pro Leu Ala Leu
1               5                   10                  15

Leu Leu His Ala Ala Arg Pro Glu Gln Lys Leu Ile Ser Glu Glu Asp
            20                  25                  30

Leu Gln Thr Thr Pro Gly Glu Arg Ser Ser Leu Pro Ala Phe Tyr Pro
        35                  40                  45

Gly Thr Ser Gly Ser Cys Ser Gly Cys Gly Ser Leu Ser Leu Pro Thr
    50                  55                  60

Thr Thr Pro Ala Pro Arg Pro Pro Thr Pro Ala Pro Thr Ile Ala Ser
65                  70                  75                  80

Gln Pro Leu Ser Leu Arg Pro Glu Ala Cys Arg Pro Ala Ala Gly Gly
                85                  90                  95

Ala Val His Thr Arg Gly Leu Asp Phe Ala Cys Asp Pro Arg Phe Trp
            100                 105                 110

Val Leu Val Val Val Gly Gly Val Leu Ala Cys Tyr Ser Leu Leu Val
        115                 120                 125

Thr Val Ala Phe Ile Ile Phe Trp Val Arg Ser Lys Arg Ser Arg Leu
    130                 135                 140

Leu His Ser Asp Tyr Met Asn Met Thr Pro Arg Arg Pro Gly Pro Thr
145                 150                 155                 160

Arg Lys His Tyr Gln Pro Tyr Ala Pro Pro Arg Asp Phe Ala Ala Tyr
                165                 170                 175

Arg Ser Pro Gly Gly Gly Gly Gly Ser Gly Gly Gly Gly Ser Gly Gly
            180                 185                 190

Gly Gly Ser Met Ser Gln Ser Asn Arg Glu Leu Val Val Asp Phe Leu
        195                 200                 205

Ser Tyr Lys Leu Ser Gln Lys Gly Tyr Ser Trp Ser Gln Phe Ser Asp
    210                 215                 220

Val Glu Glu Asn Arg Thr Glu Ala Pro Glu Gly Thr Glu Ser Glu Ala
225                 230                 235                 240

Val Lys Gln Ala Leu Arg Glu Ala Gly Asp Glu Phe Glu Leu Arg Tyr
                245                 250                 255

Arg Arg Ala Phe Ser Asp Leu Thr Ser Gln Leu His Ile Thr Pro Gly
            260                 265                 270

Thr Ala Tyr Gln Ser Phe Glu Gln Val Val Asn Glu Leu Phe Arg Asp
        275                 280                 285
```

Gly Val Asn Trp Gly Arg Ile Val Ala Phe Phe Ser Phe Gly Gly Ala
290 295 300

Leu Cys Val Glu Ser Val Asp Lys Glu Met Gln Val Leu Val Ser Arg
305 310 315 320

Ile Ala Ala Trp Met Ala Thr Tyr Leu Asn Asp His Leu Glu Pro Trp
325 330 335

Ile Gln Glu Asn Gly Gly Trp Asp Thr Phe Val Glu Leu Tyr Gly Asn
340 345 350

Asn Ala Ala Ala Glu Ser Arg Lys Gly Gln Glu Arg Glu Asp Gly Gly
355 360 365

Gly Gly Ser Gly Gly Gly Gly Ser Gly Gly Gly Gly Ser Met His Arg
370 375 380

Val Lys Phe Ser Arg Ser Ala Asp Ala Pro Ala Tyr Gln Gln Gly Gln
385 390 395 400

Asn Gln Leu Tyr Asn Glu Leu Asn Leu Gly Arg Arg Glu Glu Tyr Asp
405 410 415

Val Leu Asp Lys Arg Arg Gly Arg Asp Pro Glu Met Gly Gly Lys Pro
420 425 430

Arg Arg Lys Asn Pro Gln Glu Gly Leu Tyr Asn Glu Leu Gln Lys Asp
435 440 445

Lys Met Ala Glu Ala Tyr Ser Glu Ile Gly Met Lys Gly Glu Arg Arg
450 455 460

Arg Gly Lys Gly His Asp Gly Leu Tyr Gln Gly Leu Ser Thr Ala Thr
465 470 475 480

Lys Asp Thr Tyr Asp Ala Leu His Met Gln Ala Leu Pro Pro Arg
485 490 495

<210> SEQ ID NO 84
<211> LENGTH: 566
<212> TYPE: PRT
<213> ORGANISM: Artificial sequence
<220> FEATURE:
<223> OTHER INFORMATION: Homo sapiens

<400> SEQUENCE: 84

Met Ala Leu Pro Val Thr Ala Leu Leu Leu Pro Leu Ala Leu Leu Leu
1 5 10 15

His Ala Ala Arg Pro Val Gln Leu Gln Gln Ser Gly Pro Glu Leu Val
20 25 30

Lys Pro Gly Thr Ser Val Arg Ile Ser Cys Lys Thr Ser Gly Tyr Thr
35 40 45

Phe Thr Glu Tyr Thr Ile His Trp Val Lys Gln Ser His Gly Lys Ser
50 55 60

Leu Glu Trp Ile Gly Asn Ile Asn Pro Asn Asn Gly Gly Thr Thr Tyr
65 70 75 80

Asn Gln Lys Phe Glu Asp Lys Ala Thr Leu Thr Val Asp Lys Ser Ser
85 90 95

Ser Thr Ala Tyr Met Glu Leu Arg Ser Leu Thr Ser Glu Asp Ser Ala
100 105 110

Val Tyr Tyr Cys Ala Ala Gly Trp Asn Phe Asp Tyr Trp Gly Gln Gly
115 120 125

Thr Thr Val Thr Val Ser Ser Gly Gly Gly Gly Ser Gly Gly Gly Gly
130 135 140

Ser Gly Gly Gly Gly Ser Asp Ile Val Met Thr Gln Ser His Lys Phe
145 150 155 160

```
Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro
                565
```

<210> SEQ ID NO 85
<211> LENGTH: 493
<212> TYPE: PRT
<213> ORGANISM: Artificial sequence
<220> FEATURE:
<223> OTHER INFORMATION: Homo sapiens

<400> SEQUENCE: 85

```
Gly Ser Met Ala Leu Pro Val Thr Ala Leu Leu Leu Pro Leu Ala Leu
1               5                   10                  15

Leu Leu His Ala Ala Arg Pro Glu Gln Lys Leu Ile Ser Glu Glu Asp
            20                  25                  30

Leu Gln Thr Thr Pro Gly Glu Arg Ser Ser Leu Pro Ala Phe Tyr Pro
        35                  40                  45

Gly Thr Ser Gly Ser Cys Ser Gly Cys Gly Ser Leu Ser Leu Pro Thr
    50                  55                  60

Thr Thr Pro Ala Pro Arg Pro Pro Thr Pro Ala Pro Thr Ile Ala Ser
65                  70                  75                  80

Gln Pro Leu Ser Leu Arg Pro Glu Ala Cys Arg Pro Ala Ala Gly Gly
                85                  90                  95

Ala Val His Thr Arg Gly Leu Asp Phe Ala Cys Asp Pro Arg Phe Trp
            100                 105                 110

Val Leu Val Val Val Gly Gly Val Leu Ala Cys Tyr Ser Leu Leu Val
        115                 120                 125

Thr Val Ala Phe Ile Ile Phe Trp Val Arg Ser Lys Arg Ser Arg Leu
    130                 135                 140

Leu His Ser Asp Tyr Met Asn Met Thr Pro Arg Arg Pro Gly Pro Thr
145                 150                 155                 160

Arg Lys His Tyr Gln Pro Tyr Ala Pro Pro Arg Asp Phe Ala Ala Tyr
                165                 170                 175

Arg Ser Pro Gly Gly Gly Gly Gly Ser Gly Gly Gly Gly Ser Gly Gly
            180                 185                 190

Gly Gly Ser Met Ser Gln Ser Asn Arg Glu Leu Val Val Asp Phe Leu
        195                 200                 205

Ser Tyr Lys Leu Ser Gln Lys Gly Tyr Ser Trp Ser Gln Phe Ser Asp
    210                 215                 220

Val Glu Glu Asn Arg Thr Glu Ala Pro Glu Gly Thr Glu Ser Glu Ala
225                 230                 235                 240

Val Lys Gln Ala Leu Arg Glu Ala Gly Asp Glu Phe Glu Leu Arg Tyr
                245                 250                 255

Arg Arg Ala Phe Ser Asp Leu Thr Ser Gln Leu His Ile Thr Pro Gly
            260                 265                 270

Thr Ala Tyr Gln Ser Phe Glu Gln Val Val Asn Glu Leu Phe Arg Asp
        275                 280                 285

Gly Val Asn Trp Gly Arg Ile Val Ala Phe Phe Ser Phe Gly Gly Ala
    290                 295                 300

Leu Cys Val Glu Ser Val Asp Lys Glu Met Gln Val Leu Val Ser Arg
305                 310                 315                 320

Ile Ala Ala Trp Met Ala Thr Tyr Leu Asn Asp His Leu Glu Pro Trp
                325                 330                 335

Ile Gln Glu Asn Gly Gly Trp Asp Thr Phe Val Glu Leu Tyr Gly Asn
            340                 345                 350

Asn Ala Ala Ala Glu Ser Arg Lys Gly Gln Glu Arg Gly Gly Gly Gly
        355                 360                 365
```

Ser Gly Gly Gly Gly Ser Gly Gly Gly Gly Ser Met His Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 86
<211> LENGTH: 566
<212> TYPE: PRT
<213> ORGANISM: Artificial sequence
<220> FEATURE:
<223> OTHER INFORMATION: Homo sapiens

<400> SEQUENCE: 86

Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
245 250 255

Lys Arg Ala Ser Thr Thr Thr Pro Ala Pro Arg Pro Pro Thr Pro Ala
260 265 270

Pro Thr Ile Ala Ser Gln Pro Leu Ser Leu Arg Pro Glu Ala Cys Arg
275 280 285

Pro Ala Ala Gly Gly Ala Val His Thr Arg Gly Leu Asp Phe Ala Cys
290 295 300

Asp Phe Trp Val Leu Val Val Val Gly Gly Val Leu Ala Cys Tyr Ser
305 310 315 320

Leu Leu Val Thr Val Ala Phe Ile Ile Phe Trp Val Arg Ser Lys Arg
325 330 335

Ser Arg Leu Leu His Ser Asp Tyr Met Asn Met Thr Pro Arg Arg Pro
340 345 350

Gly Pro Thr Arg Lys His Tyr Gln Pro Tyr Ala Pro Pro Arg Asp Phe
355 360 365

Ala Ala Tyr Arg Ser His Met Gly Gly Gly Gly Ser Gly Gly Gly Gly
370 375 380

Ser Gly Gly Gly Gly Ser Gln Arg Trp Glu Leu Ala Leu Gly Arg Phe
385 390 395 400

Leu Glu Tyr Leu Ser Trp Val Ser Thr Leu Ser Glu Gln Val Gln Glu
405 410 415

Glu Leu Leu Ser Ser Gln Val Thr Gln Glu Leu Arg Ala Leu Met Asp
420 425 430

Glu Thr Met Lys Glu Leu Lys Ala Tyr Lys Ser Glu Leu Glu Glu Gln
435 440 445

Leu Thr Pro Val Ala Glu Glu Thr Arg Ala Arg Leu Ser Lys Glu Leu
450 455 460

Gln Ala Ala Gln Ala Arg Leu Gly Ala Asp Met Glu Asp Val Arg Gly
465 470 475 480

Arg Leu Val Gln Tyr Arg Gly Glu Val Gln Ala Met Leu Gly Gln Ser
485 490 495

Thr Glu Glu Leu Arg Val Arg Leu Ala Ser His Leu Ile Ala Leu Gln
500 505 510

Leu Arg Leu Ile Gly Asp Ala Phe Asp Leu Gln Lys Arg Leu Ala Val
515 520 525

Tyr Gln Ala Gly Ala Ala Glu Arg Lys Arg Arg Ser Gly Ser Gly Arg
530 535 540

Ser Gly Ser Gly Glu Gly Arg Gly Ser Leu Leu Thr Cys Gly Asp Val
545 550 555 560

Glu Glu Asn Pro Gly Pro
565

<210> SEQ ID NO 87
<211> LENGTH: 495
<212> TYPE: PRT
<213> ORGANISM: Artificial sequence
<220> FEATURE:
<223> OTHER INFORMATION: Homo sapiens

<400> SEQUENCE: 87

Gly Ser Met Ala Leu Pro Val Thr Ala Leu Leu Leu Pro Leu Ala Leu
1 5 10 15

Leu Leu His Ala Ala Arg Pro Glu Gln Lys Leu Ile Ser Glu Glu Asp
20 25 30

-continued

```
Leu Gln Thr Thr Pro Gly Glu Arg Ser Ser Leu Pro Ala Phe Tyr Pro
        35                  40                  45

Gly Thr Ser Gly Ser Cys Ser Gly Cys Gly Ser Leu Ser Leu Pro Thr
    50                  55                  60

Thr Thr Pro Ala Pro Arg Pro Pro Thr Pro Ala Pro Thr Ile Ala Ser
65                  70                  75                  80

Gln Pro Leu Ser Leu Arg Pro Glu Ala Cys Arg Pro Ala Ala Gly Gly
                85                  90                  95

Ala Val His Thr Arg Gly Leu Asp Phe Ala Cys Asp Pro Arg Phe Trp
            100                 105                 110

Val Leu Val Val Val Gly Gly Val Leu Ala Cys Tyr Ser Leu Leu Val
        115                 120                 125

Thr Val Ala Phe Ile Ile Phe Trp Val Arg Ser Lys Arg Ser Arg Leu
    130                 135                 140

Leu His Ser Asp Tyr Met Asn Met Thr Pro Arg Arg Pro Gly Pro Thr
145                 150                 155                 160

Arg Lys His Tyr Gln Pro Tyr Ala Pro Pro Arg Asp Phe Ala Ala Tyr
                165                 170                 175

Arg Ser Pro Gly Gly Gly Gly Gly Ser Gly Gly Gly Gly Ser Gly Gly
            180                 185                 190

Gly Gly Ser Met Ser Gln Ser Asn Arg Glu Leu Val Val Asp Phe Leu
        195                 200                 205

Ser Tyr Lys Leu Ser Gln Lys Gly Tyr Ser Trp Ser Gln Phe Ser Asp
    210                 215                 220

Val Glu Glu Asn Arg Thr Glu Ala Pro Glu Gly Thr Glu Ser Glu Ala
225                 230                 235                 240

Val Lys Gln Ala Leu Arg Glu Ala Gly Asp Asp Phe Glu Leu Arg Tyr
                245                 250                 255

Arg Arg Ala Phe Ser Asp Leu Thr Ser Gln Leu His Ile Thr Pro Gly
            260                 265                 270

Thr Ala Tyr Gln Ser Phe Glu Gln Val Val Asn Glu Leu Phe Arg Asp
        275                 280                 285

Gly Val Asn Trp Gly Arg Ile Val Ala Phe Phe Ser Phe Gly Gly Ala
    290                 295                 300

Leu Cys Val Glu Ser Val Asp Lys Glu Met Gln Val Leu Val Ser Arg
305                 310                 315                 320

Ile Ala Ala Trp Met Ala Thr Tyr Leu Asn Asp His Leu Glu Pro Trp
                325                 330                 335

Ile Gln Glu Asn Gly Gly Trp Asp Thr Phe Val Glu Leu Tyr Gly Asn
            340                 345                 350

Asn Ala Ala Ala Glu Ser Arg Lys Gly Gln Glu Arg Glu Asp Gly Gly
        355                 360                 365

Gly Gly Ser Gly Gly Gly Gly Ser Gly Gly Gly Gly Ser Met His Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
```

```
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495


<210> SEQ ID NO 88
<211> LENGTH: 566
<212> TYPE: PRT
<213> ORGANISM: Artificial sequence
<220> FEATURE:
<223> OTHER INFORMATION: Homo sapiens

<400> SEQUENCE: 88

Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
```

```
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro
                565


<210> SEQ ID NO 89
<211> LENGTH: 531
<212> TYPE: PRT
<213> ORGANISM: Artificial sequence
<220> FEATURE:
<223> OTHER INFORMATION: Homo sapiens

<400> SEQUENCE: 89

Gly Ser Met Ala Leu Pro Val Thr Ala Leu Leu Leu Pro Leu Ala Leu
1               5                   10                  15

Leu Leu His Ala Ala Arg Pro Glu Gln Lys Leu Ile Ser Glu Glu Asp
            20                  25                  30

Leu Gln Thr Thr Pro Gly Glu Arg Ser Ser Leu Pro Ala Phe Tyr Pro
        35                  40                  45

Gly Thr Ser Gly Ser Cys Ser Gly Cys Gly Ser Leu Ser Leu Pro Thr
    50                  55                  60

Thr Thr Pro Ala Pro Arg Pro Pro Thr Pro Ala Pro Thr Ile Ala Ser
65                  70                  75                  80

Gln Pro Leu Ser Leu Arg Pro Glu Ala Cys Arg Pro Ala Ala Gly Gly
                85                  90                  95

Ala Val His Thr Arg Gly Leu Asp Phe Ala Cys Asp Pro Arg Phe Trp
            100                 105                 110

Val Leu Val Val Val Gly Gly Val Leu Ala Cys Tyr Ser Leu Leu Val
```

-continued

```
        115                 120                 125

Thr Val Ala Phe Ile Ile Phe Trp Val Arg Ser Lys Arg Ser Arg Leu
    130                 135                 140

Leu His Ser Asp Tyr Met Asn Met Thr Pro Arg Arg Pro Gly Pro Thr
145                 150                 155                 160

Arg Lys His Tyr Gln Pro Tyr Ala Pro Pro Arg Asp Phe Ala Ala Tyr
                165                 170                 175

Arg Ser Pro Gly Gly Gly Gly Gly Ser Gly Gly Gly Gly Ser Gly Gly
            180                 185                 190

Gly Gly Ser Met Ala His Ala Gly Arg Thr Gly Tyr Asp Asn Arg Glu
        195                 200                 205

Ile Val Met Lys Tyr Ile His Tyr Lys Leu Ser Gln Arg Gly Tyr Glu
    210                 215                 220

Trp Asp Ala Gly Asp Val Gly Ala Ala Pro Pro Gly Ala Ala Pro Ala
225                 230                 235                 240

Pro Gly Ile Phe Ser Ser Gln Pro Gly His Thr Pro His Pro Ala Ala
                245                 250                 255

Ser Arg Asp Pro Val Ala Arg Thr Ser Pro Leu Gln Thr Pro Ala Ala
            260                 265                 270

Pro Gly Ala Ala Ala Gly Pro Ala Leu Ser Pro Val Pro Pro Val Val
        275                 280                 285

His Leu Thr Leu Arg Gln Ala Gly Asp Asp Phe Ser Arg Arg Tyr Arg
    290                 295                 300

Arg Asp Phe Ala Glu Met Ser Ser Gln Leu His Leu Thr Pro Phe Thr
305                 310                 315                 320

Ala Arg Gly Arg Phe Ala Thr Val Val Glu Glu Leu Phe Arg Asp Gly
                325                 330                 335

Val Asn Trp Gly Arg Ile Val Ala Phe Phe Glu Phe Gly Gly Val Met
            340                 345                 350

Cys Val Glu Ser Val Asn Arg Glu Met Ser Pro Leu Val Asp Asn Ile
        355                 360                 365

Ala Leu Trp Met Thr Glu Tyr Leu Asn Arg His Leu His Thr Trp Ile
    370                 375                 380

Gln Asp Asn Gly Gly Trp Asp Ala Phe Val Glu Leu Tyr Gly Pro Ser
385                 390                 395                 400

Met Arg Gly Gly Gly Gly Ser Gly Gly Gly Gly Ser Gly Gly Gly Gly
                405                 410                 415

Ser Met His Arg Val Lys Phe Ser Arg Ser Ala Asp Ala Pro Ala Tyr
            420                 425                 430

Gln Gln Gly Gln Asn Gln Leu Tyr Asn Glu Leu Asn Leu Gly Arg Arg
        435                 440                 445

Glu Glu Tyr Asp Val Leu Asp Lys Arg Arg Gly Arg Asp Pro Glu Met
    450                 455                 460

Gly Gly Lys Pro Arg Arg Lys Asn Pro Gln Glu Gly Leu Tyr Asn Glu
465                 470                 475                 480

Leu Gln Lys Asp Lys Met Ala Glu Ala Tyr Ser Glu Ile Gly Met Lys
                485                 490                 495

Gly Glu Arg Arg Arg Gly Lys Gly His Asp Gly Leu Tyr Gln Gly Leu
            500                 505                 510

Ser Thr Ala Thr Lys Asp Thr Tyr Asp Ala Leu His Met Gln Ala Leu
        515                 520                 525

Pro Pro Arg
    530
```

<210> SEQ ID NO 90
<211> LENGTH: 566
<212> TYPE: PRT
<213> ORGANISM: Artificial sequence
<220> FEATURE:
<223> OTHER INFORMATION: Homo sapiens

<400> SEQUENCE: 90

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365
```

```
Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Ala Arg Leu Ile Gly Asp Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro
                565


<210> SEQ ID NO 91
<211> LENGTH: 493
<212> TYPE: PRT
<213> ORGANISM: Artificial sequence
<220> FEATURE:
<223> OTHER INFORMATION: Homo sapiens

<400> SEQUENCE: 91

Gly Ser Met Ala Leu Pro Val Thr Ala Leu Leu Leu Pro Leu Ala Leu
1               5                   10                  15

Leu Leu His Ala Ala Arg Pro Glu Gln Lys Leu Ile Ser Glu Glu Asp
            20                  25                  30

Leu Gln Thr Thr Pro Gly Glu Arg Ser Ser Leu Pro Ala Phe Tyr Pro
        35                  40                  45

Gly Thr Ser Gly Ser Cys Ser Gly Cys Gly Ser Leu Ser Leu Pro Thr
    50                  55                  60

Thr Thr Pro Ala Pro Arg Pro Pro Thr Pro Ala Pro Thr Ile Ala Ser
65                  70                  75                  80

Gln Pro Leu Ser Leu Arg Pro Glu Ala Cys Arg Pro Ala Ala Gly Gly
                85                  90                  95

Ala Val His Thr Arg Gly Leu Asp Phe Ala Cys Asp Pro Arg Phe Trp
            100                 105                 110

Val Leu Val Val Val Gly Gly Val Leu Ala Cys Tyr Ser Leu Leu Val
        115                 120                 125

Thr Val Ala Phe Ile Ile Phe Trp Val Arg Ser Lys Arg Ser Arg Leu
    130                 135                 140

Leu His Ser Asp Tyr Met Asn Met Thr Pro Arg Arg Pro Gly Pro Thr
145                 150                 155                 160
```

```
Arg Lys His Tyr Gln Pro Tyr Ala Pro Pro Arg Asp Phe Ala Ala Tyr
                165                 170                 175

Arg Ser Pro Gly Gly Gly Gly Gly Ser Gly Gly Gly Gly Ser Gly Gly
            180                 185                 190

Gly Gly Ser Met Ser Gln Ser Asn Arg Glu Leu Val Val Asp Phe Leu
        195                 200                 205

Ser Tyr Lys Leu Ser Gln Lys Gly Tyr Ser Trp Ser Gln Phe Ser Asp
    210                 215                 220

Val Glu Glu Asn Arg Thr Glu Ala Pro Glu Gly Thr Glu Ser Glu Ala
225                 230                 235                 240

Val Lys Gln Ala Leu Arg Glu Ala Gly Asp Glu Phe Glu Leu Arg Tyr
                245                 250                 255

Arg Arg Ala Phe Ser Asp Leu Thr Ser Gln Leu His Ile Thr Pro Gly
            260                 265                 270

Thr Ala Tyr Gln Ser Phe Glu Gln Val Val Asn Glu Leu Phe Arg Asp
        275                 280                 285

Gly Val Asn Trp Gly Arg Ile Val Ala Phe Phe Ser Phe Gly Gly Ala
    290                 295                 300

Leu Cys Val Glu Ser Val Asp Lys Glu Met Gln Val Leu Val Ser Arg
305                 310                 315                 320

Ile Ala Ala Trp Met Ala Thr Tyr Leu Asn Asp His Leu Glu Pro Trp
                325                 330                 335

Ile Gln Glu Asn Gly Gly Trp Asp Thr Phe Val Glu Leu Tyr Gly Asn
            340                 345                 350

Asn Ala Ala Ala Glu Ser Arg Lys Gly Gln Glu Arg Gly Gly Gly Gly
        355                 360                 365

Ser Gly Gly Gly Gly Ser Gly Gly Gly Gly Ser Met His Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 92
<211> LENGTH: 566
<212> TYPE: PRT
<213> ORGANISM: Artificial sequence
<220> FEATURE:
<223> OTHER INFORMATION: Homo sapiens

<400> SEQUENCE: 92

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30
```

-continued

```
Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445
```

```
Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Ala Ala Phe Asp Leu Gln Lys Arg Leu Ala Val
        515                 520                 525

Tyr Gln Ala Gly Ala Ala Glu Arg Lys Arg Arg Ser Gly Ser Gly Arg
    530                 535                 540

Ser Gly Ser Gly Glu Gly Arg Gly Ser Leu Leu Thr Cys Gly Asp Val
545                 550                 555                 560

Glu Glu Asn Pro Gly Pro
                565


<210> SEQ ID NO 93
<211> LENGTH: 493
<212> TYPE: PRT
<213> ORGANISM: Artificial sequence
<220> FEATURE:
<223> OTHER INFORMATION: Homo sapiens

<400> SEQUENCE: 93

Gly Ser Met Ala Leu Pro Val Thr Ala Leu Leu Leu Pro Leu Ala Leu
1               5                   10                  15

Leu Leu His Ala Ala Arg Pro Glu Gln Lys Leu Ile Ser Glu Glu Asp
            20                  25                  30

Leu Gln Thr Thr Pro Gly Glu Arg Ser Ser Leu Pro Ala Phe Tyr Pro
        35                  40                  45

Gly Thr Ser Gly Ser Cys Ser Gly Cys Gly Ser Leu Ser Leu Pro Thr
    50                  55                  60

Thr Thr Pro Ala Pro Arg Pro Pro Thr Pro Ala Pro Thr Ile Ala Ser
65                  70                  75                  80

Gln Pro Leu Ser Leu Arg Pro Glu Ala Cys Arg Pro Ala Ala Gly Gly
                85                  90                  95

Ala Val His Thr Arg Gly Leu Asp Phe Ala Cys Asp Pro Arg Phe Trp
            100                 105                 110

Val Leu Val Val Val Gly Gly Val Leu Ala Cys Tyr Ser Leu Leu Val
        115                 120                 125

Thr Val Ala Phe Ile Ile Phe Trp Val Arg Ser Lys Arg Ser Arg Leu
    130                 135                 140

Leu His Ser Asp Tyr Met Asn Met Thr Pro Arg Arg Pro Gly Pro Thr
145                 150                 155                 160

Arg Lys His Tyr Gln Pro Tyr Ala Pro Pro Arg Asp Phe Ala Ala Tyr
                165                 170                 175

Arg Ser Pro Gly Gly Gly Gly Gly Ser Gly Gly Gly Gly Ser Gly Gly
            180                 185                 190

Gly Gly Ser Met Ser Gln Ser Asn Arg Glu Leu Val Val Asp Phe Leu
        195                 200                 205

Ser Tyr Lys Leu Ser Gln Lys Gly Tyr Ser Trp Ser Gln Phe Ser Asp
    210                 215                 220

Val Glu Glu Asn Arg Thr Glu Ala Pro Glu Gly Thr Glu Ser Glu Ala
225                 230                 235                 240
```

-continued

```
Val Lys Gln Ala Leu Arg Glu Ala Gly Asp Glu Phe Glu Leu Arg Tyr
                245                 250                 255

Arg Arg Ala Phe Ser Asp Leu Thr Ser Gln Leu His Ile Thr Pro Gly
            260                 265                 270

Thr Ala Tyr Gln Ser Phe Glu Gln Val Val Asn Glu Leu Phe Arg Asp
        275                 280                 285

Gly Val Asn Trp Gly Arg Ile Val Ala Phe Phe Ser Phe Gly Gly Ala
    290                 295                 300

Leu Cys Val Glu Ser Val Asp Lys Glu Met Gln Val Leu Val Ser Arg
305                 310                 315                 320

Ile Ala Ala Trp Met Ala Thr Tyr Leu Asn Asp His Leu Glu Pro Trp
                325                 330                 335

Ile Gln Glu Asn Gly Gly Trp Asp Thr Phe Val Glu Leu Tyr Gly Asn
            340                 345                 350

Asn Ala Ala Ala Glu Ser Arg Lys Gly Gln Glu Arg Gly Gly Gly Gly
        355                 360                 365

Ser Gly Gly Gly Gly Ser Gly Gly Gly Gly Ser Met His Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 94
<211> LENGTH: 1698
<212> TYPE: DNA
<213> ORGANISM: Artificial sequence
<220> FEATURE:
<223> OTHER INFORMATION: Homo sapiens

<400> SEQUENCE: 94

```
atggccttac cagtgaccgc cttgctcctg ccgctggcct tgctgctcca cgccgccagg      60

ccggtgcagc tgcagcagtc aggacctgaa ctggtgaagc ctgggacttc agtgaggata     120

tcctgcaaga cttctggata cacattcact gaatatacca tacactgggt gaagcagagc     180

catggaaaga gccttgagtg gattggaaac atcaatccta acaatggtgg taccacctac     240

aatcagaagt tcgaggacaa ggccacattg actgtagaca agtcctccag tacagcctac     300

atggagctcc gcagcctaac atctgaggat tctgcagtct attattgtgc agctggttgg     360

aactttgact actggggcca agggaccacg gtcaccgtct cctcaggtgg aggtggatca     420

ggtggaggtg gatctggtgg aggtggatct gacattgtga tgacccagtc tcacaaattc     480

atgtccacat cagtaggaga cagggtcagc atcatctgta aggccagtca agatgtgggt     540

actgctgtag actggtatca acagaaacca ggacaatctc ctaaactact gatttattgg     600

gcatccactc ggcacactgg agtccctgat cgcttcacag gcagtggatc tgggacagac     660
```

```
ttcactctca ccattactaa tgttcagtct gaagacttgg cagattattt ctgtcagcaa    720
tataacagct atcccctcac gttcggtgct gggaccatgc tggacctgaa acgggctagc    780
acaacaaccc ctgcccccag acctcctacc ccagccccta caattgccag ccagcctctg    840
agcctgaggc ccgaggcttg tagacctgct gctggcggag ccgtgcacac cagaggactg    900
gatttcgcct gcgacttctg ggtgctggtg gtcgtgggcg gagtgctggc ctgttacagc    960
ctgctcgtga ccgtggcctt catcatcttt tgggtgcgga gcaagagaag cagactgctg   1020
cacagcgact acatgaacat gacccccaga cggcctggcc ccaccagaaa gcactaccag   1080
ccttacgccc ctcccagaga cttcgccgcc tacagatctc atatgggagg cggaggatct   1140
ggcggaggtg gaagtggcgg aggcggatct caaagatggg aactcgccct gggcagattc   1200
ctggaatacc tgagctgggt gtccacactg agcgaacagg tgcaagagga actgctgagc   1260
agccaagtga cccaagagct gagagccctg atggacgaga caatgaagga actgaaggcc   1320
tacaagagcg agctggaaga acagctgacc cctgtggccg aggaaaccag agccagactg   1380
agcaaagaac tgcaggccgc tcaggccaga ctgggagccg atatggaaga tgttcggggc   1440
agactggtgc agtacagagg cgaagttcag gccatgctgg gccagtctac cgaggaactg   1500
agagtgcggc tggcctctca tctgattgcc ctgcagctga gactgatcgg cgacgcattc   1560
gacctgcaga aaagactggc cgtgtaccag gctggcgctg ctgaacggaa gcggcgcagc   1620
ggcagcgggc gcagcggcag cggcgagggc agaggaagtc ttctaacatg cggtgacgtg   1680
gaggagaatc ccggccct                                                 1698
```

<210> SEQ ID NO 95
<211> LENGTH: 1705
<212> TYPE: DNA
<213> ORGANISM: Artificial sequence
<220> FEATURE:
<223> OTHER INFORMATION: Homo sapiens

<400> SEQUENCE: 95

```
tctagaaatg gccttaccag tgaccgcctt gctcctgccg ctggccttgc tgctccacgc     60
cgccaggccg gtgcagctgc agcagtcagg acctgaactg gtgaagcctg ggacttcagt    120
gaggatatcc tgcaagactt ctggatacac attcactgaa tataccatac actgggtgaa    180
gcagagccat ggaaagagcc ttgagtggat tggaaacatc aatcctaaca atggtggtac    240
cacctacaat cagaagttcg aggacaaggc cacattgact gtagacaagt cctccagtac    300
agcctacatg gagctccgca gcctaacatc tgaggattct gcagtctatt attgtgcagc    360
tggttggaac tttgactact ggggccaagg gaccacggtc accgtctcct caggtggagg    420
tggatcaggt ggaggtggat ctggtggagg tggatctgac attgtgatga cccagtctca    480
caaattcatg tccacatcag taggagacag ggtcagcatc atctgtaagg ccagtcaaga    540
tgtgggtact gctgtagact ggtatcaaca gaaaccagga caatctccta aactactgat    600
ttattgggca tccactcggc acactggagt ccctgatcgc ttcacaggca gtggatctgg    660
gacagacttc actctcacca ttactaatgt tcagtctgaa gacttggcag attatttctg    720
tcagcaatat aacagctatc ccctcacgtt cggtgctggg accatgctgg acctgaaacg    780
ggctagcaca acaacccctg cccccagacc tcctacccca gcccctacaa ttgccagcca    840
gcctctgagc ctgaggcccg aggcttgtag acctgctgct ggcggagccg tgcacaccag    900
aggactggat ttcgcctgcg acttctgggt gctggtggtc gtgggcggag tgctggcctg    960
```

```
ttacagcctg ctcgtgaccg tggccttcat catcttttgg gtgcggagca agagaagcag   1020

actgctgcac agcgactaca tgaacatgac ccccagacgg cctggcccca ccagaaagca   1080

ctaccagcct tacgcccctc ccagagactt cgccgcctac agatctcata tgggaggcgg   1140

aggatctggc ggaggtggaa gtggcggagg cggatctcaa agatgggaac tcgccctggg   1200

cagattcctg gaatacctga gctgggtgtc cacactgagc gaacaggtgc aagaggaact   1260

gctgagcagc caagtgaccc aagagctgag agccctgatg gacgagacaa tgaaggaact   1320

gaaggcctac aagagcgagc tggaagaaca gctgacccct gtggccgagg aaaccagagc   1380

cagactgagc aaagaactgc aggccgctca ggccagactg ggagccgata tggaagatgt   1440

tcggggcaga ctggtgcagt acagaggcga agttcaggcc atgctgggcc agtctaccga   1500

ggaactgaga gtgcggctgg cctctcatct gattgccctg cagctgagac tgatcggcga   1560

cgcattcgac ctgcagaaaa gactggccgt gtaccaggct ggcgctgctg aacggaagcg   1620

gcgcagcggc agcgggcgca gcggcagcgg cgagggcaga ggaagtcttc taacatgcgg   1680

tgacgtggag gagaatcccg gccct                                         1705
```

<210> SEQ ID NO 96
<211> LENGTH: 1705
<212> TYPE: DNA
<213> ORGANISM: Artificial sequence
<220> FEATURE:
<223> OTHER INFORMATION: Homo sapiens

<400> SEQUENCE: 96

```
tctagaaatg gccttaccag tgaccgcctt gctcctgccg ctggccttgc tgctccacgc     60

cgccaggccg gtgcagctgc agcagtcagg acctgaactg gtgaagcctg ggacttcagt    120

gaggatatcc tgcaagactt ctggatacac attcactgaa tataccatac actgggtgaa    180

gcagagccat ggaaagagcc ttgagtggat tggaaacatc aatcctaaca atggtggtac    240

cacctacaat cagaagttcg aggacaaggc cacattgact gtagacaagt cctccagtac    300

agcctacatg gagctccgca gcctaacatc tgaggattct gcagtctatt attgtgcagc    360

tggttggaac tttgactact ggggccaagg gaccacggtc accgtctcct caggtggagg    420

tggatcaggt ggaggtggat ctggtggagg tggatctgac attgtgatga cccagtctca    480

caaattcatg tccacatcag taggagacag ggtcagcatc atctgtaagg ccagtcaaga    540

tgtgggtact gctgtagact ggtatcaaca gaaaccagga caatctccta aactactgat    600

ttattgggca tccactcggc acactggagt ccctgatcgc ttcacaggca gtggatctgg    660

gacagacttc actctcacca ttactaatgt tcagtctgaa gacttggcag attatttctg    720

tcagcaatat aacagctatc cctcacgtt cggtgctggg accatgctgg acctgaaacg     780

ggctagcaca acaacccctg cccccagacc tcctacccca gcccctacaa ttgccagcca    840

gcctctgagc ctgaggcccg aggcttgtag acctgctgct ggcggagccg tgcacaccag    900

aggactggat ttcgcctgcg acttctgggt gctggtggtc gtgggcggag tgctggcctg    960

ttacagcctg ctcgtgaccg tggccttcat catcttttgg gtgcggagca agagaagcag   1020

actgctgcac agcgactaca tgaacatgac ccccagacgg cctggcccca ccagaaagca   1080

ctaccagcct tacgcccctc ccagagactt cgccgcctac agatctcata tgggaggcgg   1140

aggatctggc ggaggtggaa gtggcggagg cggatctcaa agatgggaac tcgccctggg   1200

cagattcctg gaatacctga gctgggtgtc cacactgagc gaacaggtgc aagaggaact   1260

gctgagcagc caagtgaccc aagagctgag agccctgatg gacgagacaa tgaaggaact   1320
```

```
gaaggcctac aagagcgagc tggaagaaca gctgacccct gtggccgagg aaaccagagc   1380

cagactgagc aaagaactgc aggccgctca ggccagactg ggagccgata tggaagatgt   1440

tcggggcaga ctggtgcagt acagaggcga agttcaggcc atgctgggcc agtctaccga   1500

ggaactgaga gtgcggctgg cctctcatct gattgccctg cagctgagac tgatcggcga   1560

cgcattcgac ctgcagaaaa gactggccgt gtaccaggct ggcgctgctg aacggaagcg   1620

gcgcagcggc agcgggcgca gcggcagcgg cgagggcaga ggaagtcttc taacatgcgg   1680

tgacgtggag gagaatcccg gccct                                         1705
```

<210> SEQ ID NO 97
<211> LENGTH: 1705
<212> TYPE: DNA
<213> ORGANISM: Artificial sequence
<220> FEATURE:
<223> OTHER INFORMATION: Homo sapiens

<400> SEQUENCE: 97

```
tctagaaatg gccttaccag tgaccgcctt gctcctgccg ctggccttgc tgctccacgc     60

cgccaggccg gtgcagctgc agcagtcagg acctgaactg gtgaagcctg ggacttcagt    120

gaggatatcc tgcaagactt ctggatacac attcactgaa tataccatac actgggtgaa    180

gcagagccat ggaaagagcc ttgagtggat tggaaacatc aatcctaaca atggtggtac    240

cacctacaat cagaagttcg aggacaaggc cacattgact gtagacaagt cctccagtac    300

agcctacatg gagctccgca gcctaacatc tgaggattct gcagtctatt attgtgcagc    360

tggttggaac tttgactact ggggccaagg gaccacggtc accgtctcct caggtggagg    420

tggatcaggt ggaggtggat ctggtggagg tggatctgac attgtgatga cccagtctca    480

caaattcatg tccacatcag taggagacag ggtcagcatc atctgtaagg ccagtcaaga    540

tgtgggtact gctgtagact ggtatcaaca gaaaccagga caatctccta aactactgat    600

ttattgggca tccactcggc acactggagt ccctgatcgc ttcacaggca gtggatctgg    660

gacagacttc actctcacca ttactaatgt tcagtctgaa gacttggcag attatttctg    720

tcagcaatat aacagctatc cctcacgttt cggtgctggg accatgctgg acctgaaacg    780

ggctagcaca acaacccctg cccccagacc tcctacccca gcccctacaa ttgccagcca    840

gcctctgagc ctgaggcccg aggcttgtag acctgctgct ggcggagccg tgcacaccag    900

aggactggat ttcgcctgcg acttctgggt gctggtggtc gtgggcggag tgctggcctg    960

ttacagcctg ctcgtgaccg tggccttcat catcttttgg gtgcggagca agagaagcag   1020

actgctgcac agcgactaca tgaacatgac ccccagacgg cctggcccca ccagaaagca   1080

ctaccagcct tacgcccctc ccagagactt cgccgcctac agatctcata tgggaggcgg   1140

aggatctggc ggaggtggaa gtggcggagg cggatctcaa agatgggaac tcgccctggg   1200

cagattcctg gaatacctga gctgggtgtc cacactgagc gaacaggtgc aagaggaact   1260

gctgagcagc caagtgaccc aagagctgag agccctgatg gacgagacaa tgaaggaact   1320

gaaggcctac aagagcgagc tggaagaaca gctgacccct gtggccgagg aaaccagagc   1380

cagactgagc aaagaactgc aggccgctca ggccagactg ggagccgata tggaagatgt   1440

tcggggcaga ctggtgcagt acagaggcga agttcaggcc atgctgggcc agtctaccga   1500

ggaactgaga gtgcggctgg cctctcatct gattgccctg cagctgagac tgatcggcga   1560

cgcattcgac ctgcagaaaa gactggccgt gtaccaggct ggcgctgctg aacggaagcg   1620
```

gcgcagcggc agcgggcgca gcggcagcgg cgagggcaga ggaagtcttc taacatgcgg 1680
tgacgtggag gagaatcccg gccct 1705

<210> SEQ ID NO 98
<211> LENGTH: 1706
<212> TYPE: DNA
<213> ORGANISM: Artificial sequence
<220> FEATURE:
<223> OTHER INFORMATION: Homo sapiens

<400> SEQUENCE: 98
tctagaaatg gccttaccag tgaccgcctt gctcctgccg ctggccttgc tgctccacgc 60
cgccaggccg gtgcagctgc agcagtcagg acctgaactg gtgaagcctg ggacttcagt 120
gaggatatcc tgcaagactt ctggatacac attcactgaa tataccatac actgggtgaa 180
gcagagccat ggaaagagcc ttgagtggat tggaaacatc aatcctaaca atggtggtac 240
cacctacaat cagaagttcg aggacaaggc cacattgact gtagacaagt cctccagtac 300
agcctacatg gagctccgca gcctaacatc tgaggattct gcagtctatt attgtgcagc 360
tggttggaac tttgactact ggggccaagg gaccacggtc accgtctcct caggtggagg 420
tggatcaggt ggaggtggat ctggtggagg tggatctgac attgtgatga cccagtctca 480
caaattcatg tccacatcag taggagacag ggtcagcatc atctgtaagg ccagtcaaga 540
tgtgggtact gctgtagact ggtatcaaca gaaaccagga caatctccta aactactgat 600
ttattgggca tccactcggc acactggagt ccctgatcgc ttcacaggca gtggatctgg 660
gacagacttc actctcacca ttactaatgt tcagtctgaa gacttggcag attatttctg 720
tcagcaatat aacagctatc cctcacgtt cggtgctggg accatgctgg acctgaaacg 780
ggctagcaca acaacccctg cccccagacc tcctacccca gcccctacaa ttgccagcca 840
gcctctgagc ctgaggcccg aggcttgtag acctgctgct ggcggagccg tgcacaccag 900
aggactggat ttcgcctgcg acttctgggt gctggtggtc gtgggcggag tgctggcctg 960
ttacagcctg ctcgtgaccg tggccttcat catcttttgg gtgcggagca agagaagcag 1020
actgctgcac agcgactaca tgaacatgac ccccagacgg cctggcccca ccagaaagca 1080
ctaccagcct tacgcccctc ccagagactt cgccgcctac agatctcata tgggaggcgg 1140
aggatctggc ggaggtggaa gtggcggagg cggatctcca aagatgggaa ctcgccctgg 1200
gcagattcct ggaatacctg agctgggtgt ccacactgag cgaacaggtg caagaggaac 1260
tgctgagcag ccaagtgacc caagagctga gagccctgat ggacgagaca atgaaggaac 1320
tgaaggccta caagagcgag ctggaagaac agctgacccc tgtggccgag gaaaccagag 1380
ccagactgag caaagaactg caggccgctc aggccagact gggagccgat atggaagatg 1440
ttcggggcag actggtgcag tacagaggcg aagttcaggc catgctgggc cagtctaccg 1500
aggaactgag agtgcggctg gcctctcatc tgattgccct gcaggcaaga ctgatcggcg 1560
acgcattcga cctgcagaaa agactggccg tgtaccaggc tggcgctgct gaacggaagc 1620
ggcgcagcgg cagcgggcgc agcggcagcg gcgagggcag aggaagtctt ctaacatgcg 1680
gtgacgtgga ggagaatccc ggccct 1706

<210> SEQ ID NO 99
<211> LENGTH: 1704
<212> TYPE: DNA
<213> ORGANISM: Artificial sequence
<220> FEATURE:
<223> OTHER INFORMATION: Homo sapiens

<400> SEQUENCE: 99

```
tctagaaatg gccttaccag tgaccgcctt gctcctgccg ctggccttgc tgctccacgc     60
cgccaggccg gtgcagctgc agcagtcagg acctgaactg gtgaagcctg ggacttcagt    120
gaggatatcc tgcaagactt ctggatacac attcactgaa tataccatac actgggtgaa    180
gcagagccat ggaaagagcc ttgagtggat tggaaacatc aatcctaaca atggtggtac    240
cacctacaat cagaagttcg aggacaaggc cacattgact gtagacaagt cctccagtac    300
agcctacatg gagctccgca gcctaacatc tgaggattct gcagtctatt attgtgcagc    360
tggttggaac tttgactact ggggccaagg gaccacggtc accgtctcct caggtggagg    420
tggatcaggt ggaggtggat ctggtggagg tggatctgac attgtgatga cccagtctca    480
caaattcatg tccacatcag taggagacag ggtcagcatc atctgtaagg ccagtcaaga    540
tgtgggtact gctgtagact ggtatcaaca gaaaccagga caatctccta aactactgat    600
ttattgggca tccactcggc acactggagt ccctgatcgc ttcacaggca gtggatctgg    660
gacagacttc actctcacca ttactaatgt tcagtctgaa gacttggcag attatttctg    720
tcagcaatat aacagctatc cctcacgtt cggtgctggg accatgctgg acctgaaacg     780
ggctagcaca acaacccctg cccccagacc tcctacccca gcccctacaa ttgccagcca    840
gcctctgagc ctgaggcccg aggcttgtag acctgctgct ggcggagccg tgcacaccag    900
aggactggat ttcgcctgcg acttctgggt gctggtggtc gtgggcggag tgctggcctg    960
ttacagcctg ctcgtgaccg tggccttcat catcttttgg gtgcggagca agagaagcag   1020
actgctgcac agcgactaca tgaacatgac ccccagacgg cctggcccca ccagaaagca   1080
ctaccagcct tacgcccctc ccagagactt cgccgcctac agatctcata tgggaggcgg   1140
aggatctggc ggaggtggaa gtggcggagg cggatctcaa agatgggaac tcgccctggg   1200
cagattcctg gaatacctga gctgggtgtc cacactgagc gaacaggtgc aagaggaact   1260
gctgagcagc caagtgaccc aagagctgag agccctgatg gacgagacaa tgaaggaact   1320
gaaggcctac aagagcgagc tggaagaaca gctgaccccc gtggccgagg aaaccagagc   1380
cagactgagc aaagaactgc aggccgctca ggccagactg ggagccgata tggaagatgt   1440
tcggggcaga ctggtgcagt acagaggcga agttcaggcc atgctgggcc agtctaccga   1500
ggaactgaga gtgcggctgg cctctcatct gattgccctg cagctgagac tgatcggcgc   1560
agcattcgac ctgcagaaaa gactggccgt gtaccaggct ggcgctctga acggaagcgg   1620
cgcagcggca gcgggcgcag cggcagcggc gagggcagag gaagtcttct aacatgcggt   1680
gacgtggagg agaatcccgg ccct                                           1704
```

<210> SEQ ID NO 100
<211> LENGTH: 1488
<212> TYPE: DNA
<213> ORGANISM: Artificial sequence
<220> FEATURE:
<223> OTHER INFORMATION: Homo sapiens

<400> SEQUENCE: 100

```
ggatccatgg ccttaccagt gaccgccttg ctcctgccgc tggccttgct gctccacgcc     60
gccaggccgg aacagaaact catcagtgag gaagatttgc agacgactcc aggagagaga    120
tcatcactcc ctgcctttta ccctggcact tcaggctctt gttccggatg tgggtccctc    180
tctctgccga caacaacccc tgcccccaga cctcctaccc cagcccctac aattgccagc    240
```

```
cagcctctga gcctgaggcc cgaggcttgt agacctgctg ctggcggagc cgtgcacacc    300
agaggactgg atttcgcctg cgaccctagg ttctgggtgc tggtggtcgt gggcggagtg    360
ctggcctgtt acagcctgct cgtgaccgtg gccttcatca tcttttgggt gcggagcaag    420
agaagcagac tgctgcacag cgactacatg aacatgaccc ccagacggcc tggccccacc    480
agaaagcact accagcctta cgcccctccc agagacttcg ccgcctacag atctcccggg    540
ggaggcggag gatctggcgg aggtggaagt ggcggaggcg gatctatgag ccagagcaac    600
agagaactgg tggtggactt cctgagctac aagctgagcc agaagggcta cagctggtcc    660
cagttcagcg acgtggaaga gaacagaaca gaggcccctg agggcacaga gtctgaggct    720
gtgaaacagg ccctgagaga agccggcgac gagttcgagc tgagatacag aagggccttc    780
agcgacctga ccagccagct gcacatcaca cctggcacag cctaccagag cttcgagcag    840
gtcgtgaacg agctgttcag agatggcgtg aactggggca gaatcgtggc cttcttcagc    900
tttggcggag ccctgtgtgt ggaaagcgtg gacaaagaaa tgcaggtcct ggtgtccaga    960
atcgccgcct ggatggccac ctacctgaac gatcatctgg aaccctggat tcaagagaac   1020
ggcggctggg acaccttcgt ggaactgtac ggaaacaacg ccgctgccga gagcagaaag   1080
ggccaagaac gagaagatgg cggcggtggt tctggtggcg gcggtagtgg tggcggtgga   1140
tcaatgcata gagtgaagtt cagcaggagc gcagacgccc ccgcgtacca gcagggccag   1200
aaccagctct ataacgagct caatctagga cgaagagagg agtacgatgt tttggacaag   1260
agacgtggcc gggaccctga gatgggggga aagccgagaa ggaagaaccc tcaggaaggc   1320
ctgtacaatg aactgcagaa agataagatg gcggaggcct acagtgagat tgggatgaaa   1380
ggcgagcgcc ggaggggcaa ggggcacgat ggcctttacc agggtctcag tacagccacc   1440
aaggacacct acgacgccct tcacatgcag gccctgcccc ctcgctaa                1488
```

```
<210> SEQ ID NO 101
<211> LENGTH: 1487
<212> TYPE: DNA
<213> ORGANISM: Artificial sequence
<220> FEATURE:
<223> OTHER INFORMATION: Homo sapiens

<400> SEQUENCE: 101
```

```
ggatccatgg ccttaccagt gaccgccttg ctcctgccgc tggccttgct gctccacgcc     60
gccaggccgg aacagaaact catcagtgag gaagatttgc agacgactcc aggagagaga    120
tcatcactcc ctgcctttta ccctggcact tcaggctctt gttccggatg tgggtccctc    180
tctctgccga caacaacccc tgcccccaga cctcctaccc cagcccctac aattgccagc    240
cagcctctga gcctgaggcc cgaggcttgt agacctgctg ctggcggagc cgtgcacacc    300
agaggactgg atttcgcctg cgacctaggt tctgggtgct ggtggtcgtg ggcggagtgc    360
tggcctgtta cagcctgctc gtgaccgtgg ccttcatcat cttttgggtg cggagcaaga    420
gaagcagact gctgcacagc gactacatga acatgacccc cagacggcct ggccccacca    480
gaaagcacta ccagccttac gcccctccca gagacttcgc cgcctacaga tctcccgggg    540
gaggcggagg atctggcgga ggtggaagtg gcggaggcgg atctatgagc cagagcaaca    600
gagaactggt ggtggacttc ctgagctaca agctgagcca gaagggctac agctggtccc    660
agttcagcga cgtggaagag aacagaacag aggcccctga gggcacagag tctgaggctg    720
tgaaacaggc cctgagagaa gccggcgacg agttcgagct gagatacaga agggccttca    780
gcgacctgac cagccagctg cacatcacac ctggcacagc ctaccagagc ttcgagcagg    840
```

```
tcgtgaacga gctgttcaga gatggcgtga actggggcag aatcgtggcc ttcttcagct    900

ttggcggagc cctgtgtgtg gaaagcgtgg acaaagaaat gcaggtcctg gtgtccagaa    960

tcgccgcctg gatggccacc tacctgaacg atcatctgga accctggatt caagagaacg   1020

gcggctggga caccttcgtg gaactgtacg gaaacaacgc cgctgccgag agcagaaagg   1080

gccaagaacg agaagatgga ggcggaggat ctggcggagg tggaagtggc ggaggcggat   1140

ctatgcatag agtgaagttc agcaggagcg cagacgcccc cgcgtaccag cagggccaga   1200

accagctcta taacgagctc aatctaggac gaagagagga gtacgatgtt ttggacaaga   1260

gacgtggccg ggaccctgag atgggggggaa agccgagaag gaagaaccct caggaaggcc   1320

tgtacaatga actgcagaaa gataagatgg cggaggccta cagtgagatt gggatgaaag   1380

gcgagcgccg gaggggcaag gggcacgatg gcctttacca gggtctcagt acagccacca   1440

aggacaccta cgacgccctt cacatgcagg ccctgccccc tcgctaa                 1487
```

<210> SEQ ID NO 102
<211> LENGTH: 1493
<212> TYPE: DNA
<213> ORGANISM: Artificial sequence
<220> FEATURE:
<223> OTHER INFORMATION: Homo sapiens

<400> SEQUENCE: 102

```
ggatccatgg ccttaccagt gaccgccttg ctcctgccgc tggccttgct gctccacgcc     60

gccaggccgg aacagaaact catcagtgag gaagatttgc agacgactcc aggagagaga    120

tcatcactcc ctgcctttta ccctggcact tcaggctctt gttccggatg tgggtccctc    180

tctctgccga caacaacccc tgcccccaga cctcctaccc cagcccctac aattgccagc    240

cagcctctga gcctgaggcc cgaggcttgt agacctgctg ctggcggagc cgtgcacacc    300

agaggactgg atttcgcctg cgacctaggt tctgggtgct ggtggtcgtg ggcggagtgc    360

tggcctgtta cagcctgctc gtgaccgtgg ccttcatcat cttttgggtg cggagcaaga    420

gaagcagact gctgcacagc gactacatga acatgacccc cagacggcct ggccccacca    480

gaaagcacta ccagccttac gcccctccca gagacttcgc cgcctacaga tctcccgggg    540

gaggcggagg atctggcgga ggtggaagtg gcggaggcgg atctatgagc cagagcaaca    600

gagaactggt ggtggacttc ctgagctaca agctgagcca gaagggctac agctggtccc    660

agttcagcga cgtggaagag aacagaacag aggcccctga gggcacagag tctgaggctg    720

tgaaacaggc cctgagagaa gccggcgacg acttcgagct gagatacaga agggccttca    780

gcgacctgac cagccagctg cacatcacac ctggcacagc ctaccagagc ttcgagcagg    840

tcgtgaacga gctgttcaga gatggcgtga actggggcag aatcgtggcc ttcttcagct    900

ttggcggagc cctgtgtgtg gaaagcgtgg acaaagaaat gcaggtcctg gtgtccagaa    960

tcgccgcctg gatggccacc tacctgaacg atcatctgga accctggatt caagagaacg   1020

gcggctggga caccttcgtg gaactgtacg gaaacaacgc cgctgccgag agcagaaagg   1080

gccaagaacg agaagatgaa gatggaggcg gaggatctgg cggaggtgga agtggcggag   1140

gcggatctat gcatagagtg aagttcagca ggagcgcaga cgcccccgcg taccagcagg   1200

gccagaacca gctctataac gagctcaatc taggacgaag agaggagtac gatgttttgg   1260

acaagagacg tggccgggac cctgagatgg ggggaaagcc gagaaggaag aaccctcagg   1320

aaggcctgta caatgaactg cagaaagata agatggcgga ggcctacagt gagattggga   1380
```

tgaaaggcga gcgccggagg ggcaaggggc acgatggcct ttaccagggt ctcagtacag 1440
ccaccaagga cacctacgac gcccttcaca tgcaggccct gccccctcgc taa 1493

<210> SEQ ID NO 103
<211> LENGTH: 1601
<212> TYPE: DNA
<213> ORGANISM: Artificial sequence
<220> FEATURE:
<223> OTHER INFORMATION: Homo sapiens

<400> SEQUENCE: 103
ggatccatgg ccttaccagt gaccgccttg ctcctgccgc tggccttgct gctccacgcc 60
gccaggccgg aacagaaact catcagtgag gaagatttgc agacgactcc aggagagaga 120
tcatcactcc ctgcctttta ccctggcact tcaggctctt gttccggatg tgggtccctc 180
tctctgccga caacaacccc tgcccccaga cctcctaccc cagcccctac aattgccagc 240
cagcctctga gcctgaggcc cgaggcttgt agacctgctg ctggcggagc cgtgcacacc 300
agaggactgg atttcgcctg cgacctaggt tctgggtgct ggtggtcgtg ggcggagtgc 360
tggcctgtta cagcctgctc gtgaccgtgg ccttcatcat cttttgggtg cggagcaaga 420
gaagcagact gctgcacagc gactacatga acatgacccc cagacggcct ggccccacca 480
gaaagcacta ccagccttac gcccctccca gagacttcgc cgcctacaga tctcccgggg 540
gaggcggagg atctggcgga ggtggaagtg gcggaggcgg atctatggcc cacgccggca 600
ggaccggcta cgacaacagg gagatcgtga tgaagtacat ccactacaag ctgagccaga 660
ggggctacga gtgggacgcc ggcgacgtgg gcgccgcccc ccccggcgcc gcccccgccc 720
ccggcatctt cagcagccag cccggccaca ccccccaccc cgccgccagc agggaccccg 780
tggccaggac cagccccctg cagacccccg ccgcccccgg cgccgccgcc ggccccgccc 840
tgagccccgt gccccccgtg gtgcacctga ccctgaggca ggccggcgac gacttcagca 900
ggaggtacag gagggacttc gccgagatga gcagccagct gcacctgacc cccttcaccg 960
ccaggggcag gttcgccacc gtggtggagg agctgttcag ggacggcgtg aactggggca 1020
ggatcgtggc cttcttcgag ttcggcggcg tgatgtgcgt ggagagcgtg aacagggaga 1080
tgagccccct ggtggacaac atcgccctgt ggatgaccga gtacctgaac aggcacctgc 1140
acacctggat ccaggacaac ggcggctggg acgccttcgt ggagctgtac ggccccagca 1200
tgagggaaga tggaggcgga ggatctggcg gaggtggaag tggcggaggc ggatctatgc 1260
atagagtgaa gttcagcagg agcgcagacg cccccgcgta ccagcagggc cagaaccagc 1320
tctataacga gctcaatcta ggacgaagag aggagtacga tgttttggac aagagacgtg 1380
gccgggaccc tgagatgggg ggaaagccga gaaggaagaa ccctcaggaa ggcctgtaca 1440
atgaactgca gaaagataag atggcggagg cctacagtga gattgggatg aaaggcgagc 1500
gccggagggg caaggggcac gatggccttt accagggtct cagtacagcc accaaggaca 1560
cctacgacgc ccttcacatg caggccctgc cccctcgcta a 1601

<210> SEQ ID NO 104
<211> LENGTH: 15
<212> TYPE: PRT
<213> ORGANISM: Homo sapiens

<400> SEQUENCE: 104

Glu Pro Lys Ser Cys Asp Lys Thr His Thr Cys Pro Pro Cys Pro
1 5 10 15

<210> SEQ ID NO 105
<211> LENGTH: 12
<212> TYPE: PRT
<213> ORGANISM: Homo sapiens

<400> SEQUENCE: 105

```
Glu Arg Lys Cys Cys Val Glu Cys Pro Pro Cys Pro
1               5                   10
```

<210> SEQ ID NO 106
<211> LENGTH: 62
<212> TYPE: PRT
<213> ORGANISM: Homo sapiens

<400> SEQUENCE: 106

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro
    50                  55                  60
```

<210> SEQ ID NO 107
<211> LENGTH: 12
<212> TYPE: PRT
<213> ORGANISM: Homo sapiens

<400> SEQUENCE: 107

```
Glu Ser Lys Tyr Gly Pro Pro Cys Pro Ser Cys Pro
1               5                   10
```

<210> SEQ ID NO 108
<211> LENGTH: 247
<212> TYPE: PRT
<213> ORGANISM: Artificial sequence
<220> FEATURE:
<223> OTHER INFORMATION: Homo sapiens

<400> SEQUENCE: 108

```
Gly Ser Asp Ile Gln Met Thr Gln Thr Thr Ser Ser Leu Ser Ala Ser
1               5                   10                  15

Leu Gly Asp Arg Val Thr Ile Ser Cys Arg Ala Ser Gln Asp Ile Ser
            20                  25                  30

Lys Tyr Leu Asn Trp Tyr Gln Gln Lys Pro Asp Gly Thr Val Lys Leu
        35                  40                  45

Leu Ile Tyr His Thr Ser Arg Leu His Ser Gly Val Pro Ser Arg Phe
    50                  55                  60

Ser Gly Ser Gly Ser Gly Thr Asp Tyr Ser Leu Thr Ile Ser Asn Leu
65                  70                  75                  80

Glu Gln Glu Asp Ile Ala Thr Tyr Phe Cys Gln Gln Gly Asn Thr Leu
                85                  90                  95

Pro Tyr Thr Phe Gly Gly Gly Thr Lys Leu Glu Ile Thr Gly Ser Thr
            100                 105                 110

Ser Gly Ser Gly Lys Pro Gly Ser Gly Glu Gly Ser Thr Lys Gly Glu
        115                 120                 125

Val Lys Leu Gln Glu Ser Gly Pro Gly Leu Val Ala Pro Ser Gln Ser
    130                 135                 140
```

```
Leu Ser Val Thr Cys Thr Val Ser Gly Val Ser Leu Pro Asp Tyr Gly
145                 150                 155                 160

Val Ser Trp Ile Arg Gln Pro Pro Arg Lys Gly Leu Glu Trp Leu Gly
                165                 170                 175

Val Ile Trp Gly Ser Glu Thr Thr Tyr Tyr Asn Ser Ala Leu Lys Ser
            180                 185                 190

Arg Leu Thr Ile Ile Lys Asp Asn Ser Lys Ser Gln Val Phe Leu Lys
        195                 200                 205

Met Asn Ser Leu Gln Thr Asp Asp Thr Ala Ile Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Ser Val Thr Val Ser Ser
                245


<210> SEQ ID NO 109
<211> LENGTH: 512
<212> TYPE: PRT
<213> ORGANISM: Artificial sequence
<220> FEATURE:
<223> OTHER INFORMATION: Homo sapiens

<400> SEQUENCE: 109

Val Gln Leu Gln Gln Ser Gly Pro Glu Leu Val Lys Pro Gly Thr Ser
1               5                   10                  15

Val Arg Ile Ser Cys Lys Thr Ser Gly Tyr Thr Phe Thr Glu Tyr Thr
            20                  25                  30

Ile His Trp Val Lys Gln Ser His Gly Lys Ser Leu Glu Trp Ile Gly
        35                  40                  45

Asn Ile Asn Pro Asn Asn Gly Gly Thr Thr Tyr Asn Gln Lys Phe Glu
    50                  55                  60

Asp Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Ala Gly Trp Asn Phe Asp Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Asp Ile Val Met Thr Gln Ser His Lys Phe Met Ser Thr Ser Val
    130                 135                 140

Gly Asp Arg Val Ser Ile Ile Cys Lys Ala Ser Gln Asp Val Gly Thr
145                 150                 155                 160

Ala Val Asp Trp Tyr Gln Gln Lys Pro Gly Gln Ser Pro Lys Leu Leu
                165                 170                 175

Ile Tyr Trp Ala Ser Thr Arg His Thr Gly Val Pro Asp Arg Phe Thr
            180                 185                 190

Gly Ser Gly Ser Gly Thr Asp Phe Thr Leu Thr Ile Thr Asn Val Gln
        195                 200                 205

Ser Glu Asp Leu Ala Asp Tyr Phe Cys Gln Gln Tyr Asn Ser Tyr Pro
    210                 215                 220

Leu Thr Phe Gly Ala Gly Thr Met Leu Asp Leu Lys Arg Ala Ser Thr
225                 230                 235                 240

Thr Thr Pro Ala Pro Arg Pro Pro Thr Pro Ala Pro Thr Ile Ala Ser
                245                 250                 255
```

-continued

```
Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

His Met Gly Gly Gly Gly Ser Gly Gly Gly Gly Ser Gly Gly Gly Gly
        355                 360                 365

Ser Gln Arg Trp Glu Leu Ala Leu Gly Arg Phe Leu Glu Tyr Leu Ser
    370                 375                 380

Trp Val Ser Thr Leu Ser Glu Gln Val Gln Glu Glu Leu Leu Ser Ser
385                 390                 395                 400

Gln Val Thr Gln Glu Leu Arg Ala Leu Met Asp Glu Thr Met Lys Glu
                405                 410                 415

Leu Lys Ala Tyr Lys Ser Glu Leu Glu Glu Gln Leu Thr Pro Val Ala
            420                 425                 430

Glu Glu Thr Arg Ala Arg Leu Ser Lys Glu Leu Gln Ala Ala Gln Ala
        435                 440                 445

Arg Leu Gly Ala Asp Met Glu Asp Val Arg Gly Arg Leu Val Gln Tyr
    450                 455                 460

Arg Gly Glu Val Gln Ala Met Leu Gly Gln Ser Thr Glu Glu Leu Arg
465                 470                 475                 480

Val Arg Leu Ala Ser His Leu Ile Ala Leu Gln Leu Arg Leu Ile Gly
                485                 490                 495

Asp Ala Phe Asp Leu Gln Lys Arg Leu Ala Val Tyr Gln Ala Gly Ala
            500                 505                 510


<210> SEQ ID NO 110
<211> LENGTH: 512
<212> TYPE: PRT
<213> ORGANISM: Artificial sequence
<220> FEATURE:
<223> OTHER INFORMATION: Homo sapiens

<400> SEQUENCE: 110

Val Gln Leu Gln Gln Ser Gly Pro Glu Leu Val Lys Pro Gly Thr Ser
1               5                   10                  15

Val Arg Ile Ser Cys Lys Thr Ser Gly Tyr Thr Phe Thr Glu Tyr Thr
            20                  25                  30

Ile His Trp Val Lys Gln Ser His Gly Lys Ser Leu Glu Trp Ile Gly
        35                  40                  45

Asn Ile Asn Pro Asn Asn Gly Gly Thr Thr Tyr Asn Gln Lys Phe Glu
    50                  55                  60

Asp Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Ala Gly Trp Asn Phe Asp Tyr Trp Gly Gln Gly Thr Thr Val Thr Val
            100                 105                 110
```

```
Ser Ser Gly Gly Gly Gly Ser Gly Gly Gly Gly Ser Gly Gly Gly Gly
        115                 120                 125

Ser Asp Ile Val Met Thr Gln Ser His Lys Phe Met Ser Thr Ser Val
    130                 135                 140

Gly Asp Arg Val Ser Ile Ile Cys Lys Ala Ser Gln Asp Val Gly Thr
145                 150                 155                 160

Ala Val Asp Trp Tyr Gln Gln Lys Pro Gly Gln Ser Pro Lys Leu Leu
                165                 170                 175

Ile Tyr Trp Ala Ser Thr Arg His Thr Gly Val Pro Asp Arg Phe Thr
            180                 185                 190

Gly Ser Gly Ser Gly Thr Asp Phe Thr Leu Thr Ile Thr Asn Val Gln
        195                 200                 205

Ser Glu Asp Leu Ala Asp Tyr Phe Cys Gln Gln Tyr Asn Ser Tyr Pro
    210                 215                 220

Leu Thr Phe Gly Ala Gly Thr Met Leu Asp Leu Lys Arg Ala Ser Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

His Met Gly Gly Gly Gly Ser Gly Gly Gly Gly Ser Gly Gly Gly Gly
        355                 360                 365

Ser Gln Arg Trp Glu Leu Ala Leu Gly Arg Phe Leu Ala Tyr Leu Ser
    370                 375                 380

Trp Val Ser Thr Leu Ser Glu Gln Val Gln Glu Glu Leu Leu Ser Ser
385                 390                 395                 400

Gln Val Thr Gln Glu Leu Arg Ala Leu Met Asp Glu Thr Met Lys Glu
                405                 410                 415

Leu Lys Ala Tyr Lys Ser Glu Leu Glu Glu Gln Leu Thr Pro Val Ala
            420                 425                 430

Glu Glu Thr Arg Ala Arg Leu Ser Lys Glu Leu Gln Ala Ala Gln Ala
        435                 440                 445

Arg Leu Gly Ala Asp Met Glu Asp Val Arg Gly Arg Leu Val Gln Tyr
    450                 455                 460

Arg Gly Glu Val Gln Ala Met Leu Gly Gln Ser Thr Glu Glu Leu Arg
465                 470                 475                 480

Val Arg Leu Ala Ser His Leu Ile Ala Leu Gln Leu Arg Leu Ile Gly
                485                 490                 495

Asp Ala Phe Asp Leu Gln Lys Arg Leu Ala Val Tyr Gln Ala Gly Ala
            500                 505                 510
```

<210> SEQ ID NO 111
<211> LENGTH: 512
<212> TYPE: PRT

<213> ORGANISM: Artificial sequence
<220> FEATURE:
<223> OTHER INFORMATION: Homo sapiens

<400> SEQUENCE: 111

```
Val Gln Leu Gln Gln Ser Gly Pro Glu Leu Val Lys Pro Gly Thr Ser
1               5                   10                  15

Val Arg Ile Ser Cys Lys Thr Ser Gly Tyr Thr Phe Thr Glu Tyr Thr
            20                  25                  30

Ile His Trp Val Lys Gln Ser His Gly Lys Ser Leu Glu Trp Ile Gly
        35                  40                  45

Asn Ile Asn Pro Asn Asn Gly Gly Thr Thr Tyr Asn Gln Lys Phe Glu
    50                  55                  60

Asp Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Ala Gly Trp Asn Phe Asp Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Asp Ile Val Met Thr Gln Ser His Lys Phe Met Ser Thr Ser Val
    130                 135                 140

Gly Asp Arg Val Ser Ile Ile Cys Lys Ala Ser Gln Asp Val Gly Thr
145                 150                 155                 160

Ala Val Asp Trp Tyr Gln Gln Lys Pro Gly Gln Ser Pro Lys Leu Leu
                165                 170                 175

Ile Tyr Trp Ala Ser Thr Arg His Thr Gly Val Pro Asp Arg Phe Thr
            180                 185                 190

Gly Ser Gly Ser Gly Thr Asp Phe Thr Leu Thr Ile Thr Asn Val Gln
        195                 200                 205

Ser Glu Asp Leu Ala Asp Tyr Phe Cys Gln Gln Tyr Asn Ser Tyr Pro
    210                 215                 220

Leu Thr Phe Gly Ala Gly Thr Met Leu Asp Leu Lys Arg Ala Ser Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

His Met Gly Gly Gly Gly Ser Gly Gly Gly Gly Ser Gly Gly Gly Gly
        355                 360                 365

Ser Gln Arg Trp Glu Leu Ala Leu Gly Arg Phe Leu Glu Tyr Leu Ser
    370                 375                 380

Trp Val Ser Thr Leu Ser Glu Gln Val Gln Glu Glu Leu Leu Ser Ser
```

```
385                 390                 395                 400

Gln Val Thr Gln Glu Leu Arg Ala Leu Met Asp Glu Thr Met Lys Glu
                405                 410                 415

Leu Lys Ala Tyr Lys Ser Glu Leu Glu Glu Gln Leu Thr Pro Val Ala
            420                 425                 430

Glu Glu Thr Arg Ala Arg Leu Ser Lys Glu Leu Gln Ala Ala Gln Ala
        435                 440                 445

Arg Leu Gly Ala Asp Met Glu Asp Val Arg Gly Arg Leu Val Gln Tyr
    450                 455                 460

Arg Gly Glu Val Gln Ala Met Leu Gly Gln Ser Thr Glu Glu Leu Arg
465                 470                 475                 480

Val Arg Leu Ala Ser His Leu Ile Ala Leu Gln Ala Arg Leu Ile Gly
                485                 490                 495

Asp Ala Phe Asp Leu Gln Lys Arg Leu Ala Val Tyr Gln Ala Gly Ala
            500                 505                 510


<210> SEQ ID NO 112
<211> LENGTH: 512
<212> TYPE: PRT
<213> ORGANISM: Artificial sequence
<220> FEATURE:
<223> OTHER INFORMATION: Homo sapiens

<400> SEQUENCE: 112

Val Gln Leu Gln Gln Ser Gly Pro Glu Leu Val Lys Pro Gly Thr Ser
1               5                   10                  15

Val Arg Ile Ser Cys Lys Thr Ser Gly Tyr Thr Phe Thr Glu Tyr Thr
            20                  25                  30

Ile His Trp Val Lys Gln Ser His Gly Lys Ser Leu Glu Trp Ile Gly
        35                  40                  45

Asn Ile Asn Pro Asn Asn Gly Gly Thr Thr Tyr Asn Gln Lys Phe Glu
    50                  55                  60

Asp Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Ala Gly Trp Asn Phe Asp Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Asp Ile Val Met Thr Gln Ser His Lys Phe Met Ser Thr Ser Val
    130                 135                 140

Gly Asp Arg Val Ser Ile Ile Cys Lys Ala Ser Gln Asp Val Gly Thr
145                 150                 155                 160

Ala Val Asp Trp Tyr Gln Gln Lys Pro Gly Gln Ser Pro Lys Leu Leu
                165                 170                 175

Ile Tyr Trp Ala Ser Thr Arg His Thr Gly Val Pro Asp Arg Phe Thr
            180                 185                 190

Gly Ser Gly Ser Gly Thr Asp Phe Thr Leu Thr Ile Thr Asn Val Gln
        195                 200                 205

Ser Glu Asp Leu Ala Asp Tyr Phe Cys Gln Gln Tyr Asn Ser Tyr Pro
    210                 215                 220

Leu Thr Phe Gly Ala Gly Thr Met Leu Asp Leu Lys Arg Ala Ser Thr
225                 230                 235                 240

Thr Thr Pro Ala Pro Arg Pro Pro Thr Pro Ala Pro Thr Ile Ala Ser
```

```
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

His Met Gly Gly Gly Gly Ser Gly Gly Gly Gly Ser Gly Gly Gly Gly
        355                 360                 365

Ser Gln Arg Trp Glu Leu Ala Leu Gly Arg Phe Leu Glu Tyr Leu Ser
    370                 375                 380

Trp Val Ser Thr Leu Ser Glu Gln Val Gln Glu Glu Leu Leu Ser Ser
385                 390                 395                 400

Gln Val Thr Gln Glu Leu Arg Ala Leu Met Asp Glu Thr Met Lys Glu
                405                 410                 415

Leu Lys Ala Tyr Lys Ser Glu Leu Glu Glu Gln Leu Thr Pro Val Ala
            420                 425                 430

Glu Glu Thr Arg Ala Arg Leu Ser Lys Glu Leu Gln Ala Ala Gln Ala
        435                 440                 445

Arg Leu Gly Ala Asp Met Glu Asp Val Arg Gly Arg Leu Val Gln Tyr
    450                 455                 460

Arg Gly Glu Val Gln Ala Met Leu Gly Gln Ser Thr Glu Glu Leu Arg
465                 470                 475                 480

Val Arg Leu Ala Ser His Leu Ile Ala Leu Gln Leu Arg Leu Ile Gly
                485                 490                 495

Ala Ala Phe Asp Leu Gln Lys Arg Leu Ala Val Tyr Gln Ala Gly Ala
            500                 505                 510


<210> SEQ ID NO 113
<211> LENGTH: 462
<212> TYPE: PRT
<213> ORGANISM: Artificial sequence
<220> FEATURE:
<223> OTHER INFORMATION: Homo sapiens

<400> SEQUENCE: 113

Gln Thr Thr Pro Gly Glu Arg Ser Ser Leu Pro Ala Phe Tyr Pro Gly
1               5                   10                  15

Thr Ser Gly Ser Cys Ser Gly Cys Gly Ser Leu Ser Leu Pro Thr Thr
            20                  25                  30

Thr Pro Ala Pro Arg Pro Pro Thr Pro Ala Pro Thr Ile Ala Ser Gln
        35                  40                  45

Pro Leu Ser Leu Arg Pro Glu Ala Cys Arg Pro Ala Ala Gly Gly Ala
    50                  55                  60

Val His Thr Arg Gly Leu Asp Phe Ala Cys Asp Pro Arg Phe Trp Val
65                  70                  75                  80

Leu Val Val Val Gly Gly Val Leu Ala Cys Tyr Ser Leu Leu Val Thr
                85                  90                  95

Val Ala Phe Ile Ile Phe Trp Val Arg Ser Lys Arg Ser Arg Leu Leu
```

```
            100                 105                 110

His Ser Asp Tyr Met Asn Met Thr Pro Arg Arg Pro Gly Pro Thr Arg
        115                 120                 125

Lys His Tyr Gln Pro Tyr Ala Pro Pro Arg Asp Phe Ala Ala Tyr Arg
    130                 135                 140

Ser Pro Gly Gly Gly Gly Gly Ser Gly Gly Gly Gly Ser Gly Gly Gly
145                 150                 155                 160

Gly Ser Met Ser Gln Ser Asn Arg Glu Leu Val Val Asp Phe Leu Ser
                165                 170                 175

Tyr Lys Leu Ser Gln Lys Gly Tyr Ser Trp Ser Gln Phe Ser Asp Val
            180                 185                 190

Glu Glu Asn Arg Thr Glu Ala Pro Glu Gly Thr Glu Ser Glu Ala Val
        195                 200                 205

Lys Gln Ala Leu Arg Glu Ala Gly Asp Glu Phe Glu Leu Arg Tyr Arg
    210                 215                 220

Arg Ala Phe Ser Asp Leu Thr Ser Gln Leu His Ile Thr Pro Gly Thr
225                 230                 235                 240

Ala Tyr Gln Ser Phe Glu Gln Val Val Asn Glu Leu Phe Arg Asp Gly
                245                 250                 255

Val Asn Trp Gly Arg Ile Val Ala Phe Phe Ser Phe Gly Gly Ala Leu
            260                 265                 270

Cys Val Glu Ser Val Asp Lys Glu Met Gln Val Leu Val Ser Arg Ile
        275                 280                 285

Ala Ala Trp Met Ala Thr Tyr Leu Asn Asp His Leu Glu Pro Trp Ile
    290                 295                 300

Gln Glu Asn Gly Gly Trp Asp Thr Phe Val Glu Leu Tyr Gly Asn Asn
305                 310                 315                 320

Ala Ala Ala Glu Ser Arg Lys Gly Gln Glu Arg Glu Asp Gly Gly Gly
                325                 330                 335

Gly Ser Gly Gly Gly Gly Ser Gly Gly Gly Gly Ser Met His Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460


<210> SEQ ID NO 114
<211> LENGTH: 460
<212> TYPE: PRT
<213> ORGANISM: Artificial sequence
<220> FEATURE:
<223> OTHER INFORMATION: Homo sapiens

<400> SEQUENCE: 114

Gln Thr Thr Pro Gly Glu Arg Ser Ser Leu Pro Ala Phe Tyr Pro Gly
```

-continued

```
1               5                   10                  15

Thr Ser Gly Ser Cys Ser Gly Cys Gly Ser Leu Ser Leu Pro Thr Thr
            20                  25                  30

Thr Pro Ala Pro Arg Pro Pro Thr Pro Ala Pro Thr Ile Ala Ser Gln
        35                  40                  45

Pro Leu Ser Leu Arg Pro Glu Ala Cys Arg Pro Ala Ala Gly Gly Ala
    50                  55                  60

Val His Thr Arg Gly Leu Asp Phe Ala Cys Asp Pro Arg Phe Trp Val
65                  70                  75                  80

Leu Val Val Val Gly Gly Val Leu Ala Cys Tyr Ser Leu Leu Val Thr
                85                  90                  95

Val Ala Phe Ile Ile Phe Trp Val Arg Ser Lys Arg Ser Arg Leu Leu
            100                 105                 110

His Ser Asp Tyr Met Asn Met Thr Pro Arg Arg Pro Gly Pro Thr Arg
        115                 120                 125

Lys His Tyr Gln Pro Tyr Ala Pro Pro Arg Asp Phe Ala Ala Tyr Arg
    130                 135                 140

Ser Pro Gly Gly Gly Gly Gly Ser Gly Gly Gly Gly Ser Gly Gly Gly
145                 150                 155                 160

Gly Ser Met Ser Gln Ser Asn Arg Glu Leu Val Val Asp Phe Leu Ser
                165                 170                 175

Tyr Lys Leu Ser Gln Lys Gly Tyr Ser Trp Ser Gln Phe Ser Asp Val
            180                 185                 190

Glu Glu Asn Arg Thr Glu Ala Pro Glu Gly Thr Glu Ser Glu Ala Val
        195                 200                 205

Lys Gln Ala Leu Arg Glu Ala Gly Asp Glu Phe Glu Leu Arg Tyr Arg
    210                 215                 220

Arg Ala Phe Ser Asp Leu Thr Ser Gln Leu His Ile Thr Pro Gly Thr
225                 230                 235                 240

Ala Tyr Gln Ser Phe Glu Gln Val Val Asn Glu Leu Phe Arg Asp Gly
                245                 250                 255

Val Asn Trp Gly Arg Ile Val Ala Phe Phe Ser Phe Gly Gly Ala Leu
            260                 265                 270

Cys Val Glu Ser Val Asp Lys Glu Met Gln Val Leu Val Ser Arg Ile
        275                 280                 285

Ala Ala Trp Met Ala Thr Tyr Leu Asn Asp His Leu Glu Pro Trp Ile
    290                 295                 300

Gln Glu Asn Gly Gly Trp Asp Thr Phe Val Glu Leu Tyr Gly Asn Asn
305                 310                 315                 320

Ala Ala Ala Glu Ser Arg Lys Gly Gln Glu Arg Gly Gly Gly Gly Ser
                325                 330                 335

Gly Gly Gly Gly Ser Gly Gly Gly Gly Ser Met His Arg Val Lys Phe
            340                 345                 350

Ser Arg Ser Ala Asp Ala Pro Ala Tyr Gln Gln Gly Gln Asn Gln Leu
        355                 360                 365

Tyr Asn Glu Leu Asn Leu Gly Arg Arg Glu Glu Tyr Asp Val Leu Asp
    370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
            420                 425                 430
```

Gly His Asp Gly Leu Tyr Gln Gly Leu Ser Thr Ala Thr Lys Asp Thr
435 440 445

Tyr Asp Ala Leu His Met Gln Ala Leu Pro Pro Arg
450 455 460

<210> SEQ ID NO 115
<211> LENGTH: 462
<212> TYPE: PRT
<213> ORGANISM: Artificial sequence
<220> FEATURE:
<223> OTHER INFORMATION: Homo sapiens

<400> SEQUENCE: 115

Gln Thr Thr Pro Gly Glu Arg Ser Ser Leu Pro Ala Phe Tyr Pro Gly
1 5 10 15

Thr Ser Gly Ser Cys Ser Gly Cys Gly Ser Leu Ser Leu Pro Thr Thr
20 25 30

Thr Pro Ala Pro Arg Pro Pro Thr Pro Ala Pro Thr Ile Ala Ser Gln
35 40 45

Pro Leu Ser Leu Arg Pro Glu Ala Cys Arg Pro Ala Ala Gly Gly Ala
50 55 60

Val His Thr Arg Gly Leu Asp Phe Ala Cys Asp Pro Arg Phe Trp Val
65 70 75 80

Leu Val Val Val Gly Gly Val Leu Ala Cys Tyr Ser Leu Leu Val Thr
85 90 95

Val Ala Phe Ile Ile Phe Trp Val Arg Ser Lys Arg Ser Arg Leu Leu
100 105 110

His Ser Asp Tyr Met Asn Met Thr Pro Arg Arg Pro Gly Pro Thr Arg
115 120 125

Lys His Tyr Gln Pro Tyr Ala Pro Pro Arg Asp Phe Ala Ala Tyr Arg
130 135 140

Ser Pro Gly Gly Gly Gly Gly Ser Gly Gly Gly Gly Ser Gly Gly Gly
145 150 155 160

Gly Ser Met Ser Gln Ser Asn Arg Glu Leu Val Val Asp Phe Leu Ser
165 170 175

Tyr Lys Leu Ser Gln Lys Gly Tyr Ser Trp Ser Gln Phe Ser Asp Val
180 185 190

Glu Glu Asn Arg Thr Glu Ala Pro Glu Gly Thr Glu Ser Glu Ala Val
195 200 205

Lys Gln Ala Leu Arg Glu Ala Gly Asp Asp Phe Glu Leu Arg Tyr Arg
210 215 220

Arg Ala Phe Ser Asp Leu Thr Ser Gln Leu His Ile Thr Pro Gly Thr
225 230 235 240

Ala Tyr Gln Ser Phe Glu Gln Val Val Asn Glu Leu Phe Arg Asp Gly
245 250 255

Val Asn Trp Gly Arg Ile Val Ala Phe Phe Ser Phe Gly Gly Ala Leu
260 265 270

Cys Val Glu Ser Val Asp Lys Glu Met Gln Val Leu Val Ser Arg Ile
275 280 285

Ala Ala Trp Met Ala Thr Tyr Leu Asn Asp His Leu Glu Pro Trp Ile
290 295 300

Gln Glu Asn Gly Gly Trp Asp Thr Phe Val Glu Leu Tyr Gly Asn Asn
305 310 315 320

Ala Ala Ala Glu Ser Arg Lys Gly Gln Glu Arg Glu Asp Gly Gly Gly
325 330 335

```
Gly Ser Gly Gly Gly Gly Ser Gly Gly Gly Gly Ser Met His Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460


<210> SEQ ID NO 116
<211> LENGTH: 460
<212> TYPE: PRT
<213> ORGANISM: Artificial sequence
<220> FEATURE:
<223> OTHER INFORMATION: Homo sapiens

<400> SEQUENCE: 116

Gln Thr Thr Pro Gly Glu Arg Ser Ser Leu Pro Ala Phe Tyr Pro Gly
1               5                   10                  15

Thr Ser Gly Ser Cys Ser Gly Cys Gly Ser Leu Ser Leu Pro Thr Thr
            20                  25                  30

Thr Pro Ala Pro Arg Pro Pro Thr Pro Ala Pro Thr Ile Ala Ser Gln
        35                  40                  45

Pro Leu Ser Leu Arg Pro Glu Ala Cys Arg Pro Ala Ala Gly Gly Ala
    50                  55                  60

Val His Thr Arg Gly Leu Asp Phe Ala Cys Asp Pro Arg Phe Trp Val
65                  70                  75                  80

Leu Val Val Val Gly Gly Val Leu Ala Cys Tyr Ser Leu Leu Val Thr
                85                  90                  95

Val Ala Phe Ile Ile Phe Trp Val Arg Ser Lys Arg Ser Arg Leu Leu
            100                 105                 110

His Ser Asp Tyr Met Asn Met Thr Pro Arg Arg Pro Gly Pro Thr Arg
        115                 120                 125

Lys His Tyr Gln Pro Tyr Ala Pro Pro Arg Asp Phe Ala Ala Tyr Arg
    130                 135                 140

Ser Pro Gly Gly Gly Gly Gly Ser Gly Gly Gly Gly Ser Gly Gly Gly
145                 150                 155                 160

Gly Ser Met Ser Gln Ser Asn Arg Glu Leu Val Val Asp Phe Leu Ser
                165                 170                 175

Tyr Lys Leu Ser Gln Lys Gly Tyr Ser Trp Ser Gln Phe Ser Asp Val
            180                 185                 190

Glu Glu Asn Arg Thr Glu Ala Pro Glu Gly Thr Glu Ser Glu Ala Val
        195                 200                 205

Lys Gln Ala Leu Arg Glu Ala Gly Asp Asp Phe Glu Leu Arg Tyr Arg
    210                 215                 220

Arg Ala Phe Ser Asp Leu Thr Ser Gln Leu His Ile Thr Pro Gly Thr
225                 230                 235                 240
```

```
Ala Tyr Gln Ser Phe Glu Gln Val Val Asn Glu Leu Phe Arg Asp Gly
                245                 250                 255

Val Asn Trp Gly Arg Ile Val Ala Phe Phe Ser Phe Gly Gly Ala Leu
            260                 265                 270

Cys Val Glu Ser Val Asp Lys Glu Met Gln Val Leu Val Ser Arg Ile
        275                 280                 285

Ala Ala Trp Met Ala Thr Tyr Leu Asn Asp His Leu Glu Pro Trp Ile
    290                 295                 300

Gln Glu Asn Gly Gly Trp Asp Thr Phe Val Glu Leu Tyr Gly Asn Asn
305                 310                 315                 320

Ala Ala Ala Glu Ser Arg Lys Gly Gln Glu Arg Gly Gly Gly Gly Ser
                325                 330                 335

Gly Gly Gly Gly Ser Gly Gly Gly Gly Ser Met His Arg Val Lys Phe
            340                 345                 350

Ser Arg Ser Ala Asp Ala Pro Ala Tyr Gln Gln Gly Gln Asn Gln Leu
        355                 360                 365

Tyr Asn Glu Leu Asn Leu Gly Arg Arg Glu Glu Tyr Asp Val Leu Asp
    370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
            420                 425                 430

Gly His Asp Gly Leu Tyr Gln Gly Leu Ser Thr Ala Thr Lys Asp Thr
        435                 440                 445

Tyr Asp Ala Leu His Met Gln Ala Leu Pro Pro Arg
    450                 455                 460
```

<210> SEQ ID NO 117
<211> LENGTH: 498
<212> TYPE: PRT
<213> ORGANISM: Artificial sequence
<220> FEATURE:
<223> OTHER INFORMATION: Homo sapiens

<400> SEQUENCE: 117

```
Gln Thr Thr Pro Gly Glu Arg Ser Ser Leu Pro Ala Phe Tyr Pro Gly
1               5                   10                  15

Thr Ser Gly Ser Cys Ser Gly Cys Gly Ser Leu Ser Leu Pro Thr Thr
            20                  25                  30

Thr Pro Ala Pro Arg Pro Pro Thr Pro Ala Pro Thr Ile Ala Ser Gln
        35                  40                  45

Pro Leu Ser Leu Arg Pro Glu Ala Cys Arg Pro Ala Ala Gly Gly Ala
    50                  55                  60

Val His Thr Arg Gly Leu Asp Phe Ala Cys Asp Pro Arg Phe Trp Val
65                  70                  75                  80

Leu Val Val Val Gly Gly Val Leu Ala Cys Tyr Ser Leu Leu Val Thr
                85                  90                  95

Val Ala Phe Ile Ile Phe Trp Val Arg Ser Lys Arg Ser Arg Leu Leu
            100                 105                 110

His Ser Asp Tyr Met Asn Met Thr Pro Arg Arg Pro Gly Pro Thr Arg
        115                 120                 125

Lys His Tyr Gln Pro Tyr Ala Pro Pro Arg Asp Phe Ala Ala Tyr Arg
    130                 135                 140
```

```
Ser Pro Gly Gly Gly Gly Gly Ser Gly Gly Gly Gly Ser Gly Gly Gly
145                 150                 155                 160

Gly Ser Met Ala His Ala Gly Arg Thr Gly Tyr Asp Asn Arg Glu Ile
                165                 170                 175

Val Met Lys Tyr Ile His Tyr Lys Leu Ser Gln Arg Gly Tyr Glu Trp
            180                 185                 190

Asp Ala Gly Asp Val Gly Ala Ala Pro Pro Gly Ala Ala Pro Ala Pro
        195                 200                 205

Gly Ile Phe Ser Ser Gln Pro Gly His Thr Pro His Pro Ala Ala Ser
    210                 215                 220

Arg Asp Pro Val Ala Arg Thr Ser Pro Leu Gln Thr Pro Ala Ala Pro
225                 230                 235                 240

Gly Ala Ala Ala Gly Pro Ala Leu Ser Pro Val Pro Pro Val Val His
                245                 250                 255

Leu Thr Leu Arg Gln Ala Gly Asp Asp Phe Ser Arg Arg Tyr Arg Arg
            260                 265                 270

Asp Phe Ala Glu Met Ser Ser Gln Leu His Leu Thr Pro Phe Thr Ala
        275                 280                 285

Arg Gly Arg Phe Ala Thr Val Val Glu Glu Leu Phe Arg Asp Gly Val
    290                 295                 300

Asn Trp Gly Arg Ile Val Ala Phe Phe Glu Phe Gly Gly Val Met Cys
305                 310                 315                 320

Val Glu Ser Val Asn Arg Glu Met Ser Pro Leu Val Asp Asn Ile Ala
                325                 330                 335

Leu Trp Met Thr Glu Tyr Leu Asn Arg His Leu His Thr Trp Ile Gln
            340                 345                 350

Asp Asn Gly Gly Trp Asp Ala Phe Val Glu Leu Tyr Gly Pro Ser Met
        355                 360                 365

Arg Gly Gly Gly Gly Ser Gly Gly Gly Gly Ser Gly Gly Gly Gly Ser
    370                 375                 380

Met His Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
    450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg
```

<210> SEQ ID NO 118
<211> LENGTH: 1698
<212> TYPE: DNA
<213> ORGANISM: Artificial sequence
<220> FEATURE:
<223> OTHER INFORMATION: Homo sapiens

<400> SEQUENCE: 118

```
atggccttac cagtgaccgc cttgctcctg ccgctggcct tgctgctcca cgccgccagg     60
ccggtgcagc tgcagcagtc aggacctgaa ctggtgaagc ctgggacttc agtgaggata    120
tcctgcaaga cttctggata cacattcact gaatatacca tacactgggt gaagcagagc    180
catggaaaga gccttgagtg gattggaaac atcaatccta acaatggtgg taccacctac    240
aatcagaagt tcgaggacaa ggccacattg actgtagaca agtcctccag tacagcctac    300
atggagctcc gcagcctaac atctgaggat tctgcagtct attattgtgc agctggttgg    360
aactttgact actggggcca agggaccacg gtcaccgtct cctcaggtgg aggtggatca    420
ggtggaggtg gatctggtgg aggtggatct gacattgtga tgacccagtc tcacaaattc    480
atgtccacat cagtaggaga cagggtcagc atcatctgta aggccagtca agatgtgggt    540
actgctgtag actggtatca acagaaacca ggacaatctc ctaaactact gatttattgg    600
gcatccactc ggcacactgg agtccctgat cgcttcacag gcagtggatc tgggacagac    660
ttcactctca ccattactaa tgttcagtct gaagacttgg cagattattt ctgtcagcaa    720
tataacagct atcccctcac gttcggtgct gggaccatgc tggacctgaa acgggctagc    780
acaacaaccc ctgcccccag acctcctacc ccagccccta caattgccag ccagcctctg    840
agcctgaggc ccgaggcttg tagacctgct gctggcggag ccgtgcacac cagaggactg    900
gatttcgcct gcgacttctg ggtgctggtg gtcgtgggcg gagtgctggc ctgttacagc    960
ctgctcgtga ccgtggcctt catcatcttt tgggtgcgga gcaagagaag cagactgctg   1020
cacagcgact acatgaacat gacccccaga cggcctggcc ccaccagaaa gcactaccag   1080
ccttacgccc ctcccagaga cttcgccgcc tacagatctc atatgggagg cggaggatct   1140
ggcggaggtg gaagtggcgg aggcggatct caaagatggg aactcgccct gggcagattc   1200
ctggaatacc tgagctgggt gtccacactg agcgaacagg tgcaagagga actgctgagc   1260
agccaagtga cccaagagct gagagccctg atggacgaga caatgaagga actgaaggcc   1320
tacaagagcg agctggaaga acagctgacc cctgtggccg aggaaaccag agccagactg   1380
agcaaagaac tgcaggccgc tcaggccaga ctgggagccg atatggaaga tgttcggggc   1440
agactggtgc agtacagagg cgaagttcag gccatgctgg gccagtctac cgaggaactg   1500
agagtgcggc tggcctctca tctgattgcc ctgcagctga gactgatcgg cgacgcattc   1560
gacctgcaga aaagactggc cgtgtaccag gctggcgctg ctgaacggaa gcggcgcagc   1620
ggcagcgggc gcagcggcag cggcgagggc agaggaagtc ttctaacatg cggtgacgtg   1680
gaggagaatc ccggccct                                                 1698
```

<210> SEQ ID NO 119
<211> LENGTH: 1705
<212> TYPE: DNA
<213> ORGANISM: Artificial sequence
<220> FEATURE:
<223> OTHER INFORMATION: Homo sapiens

<400> SEQUENCE: 119

```
tctagaaatg gccttaccag tgaccgcctt gctcctgccg ctggccttgc tgctccacgc     60
cgccaggccg gtgcagctgc agcagtcagg acctgaactg gtgaagcctg ggacttcagt    120
gaggatatcc tgcaagactt ctggatacac attcactgaa tataccatac actgggtgaa    180
gcagagccat ggaaagagcc ttgagtggat tggaaacatc aatcctaaca atggtggtac    240
cacctacaat cagaagttcg aggacaaggc cacattgact gtagacaagt cctccagtac    300
agcctacatg gagctccgca gcctaacatc tgaggattct gcagtctatt attgtgcagc    360
```

tggttggaac tttgactact ggggccaagg gaccacggtc accgtctcct caggtggagg 420
tggatcaggt ggaggtggat ctggtggagg tggatctgac attgtgatga cccagtctca 480
caaattcatg tccacatcag taggagacag ggtcagcatc atctgtaagg ccagtcaaga 540
tgtgggtact gctgtagact ggtatcaaca gaaaccagga caatctccta aactactgat 600
ttattgggca tccactcggc acactggagt ccctgatcgc ttcacaggca gtggatctgg 660
gacagacttc actctcacca ttactaatgt tcagtctgaa gacttggcag attatttctg 720
tcagcaatat aacagctatc cctcacgtt cggtgctggg accatgctgg acctgaaacg 780
ggctagcaca acaacccctg cccccagacc tcctacccca gcccctacaa ttgccagcca 840
gcctctgagc ctgaggcccg aggcttgtag acctgctgct ggcggagccg tgcacaccag 900
aggactggat ttcgcctgcg acttctgggt gctggtggtc gtgggcggag tgctggcctg 960
ttacagcctg ctcgtgaccg tggccttcat catcttttgg gtgcggagca agagaagcag 1020
actgctgcac agcgactaca tgaacatgac ccccagacgg cctggcccca ccagaaagca 1080
ctaccagcct tacgcccctc ccagagactt cgccgcctac agatctcata tgggaggcgg 1140
aggatctggc ggaggtggaa gtggcggagg cggatctcaa agatgggaac tcgccctggg 1200
cagattcctg gaatacctga gctgggtgtc cacactgagc gaacaggtgc aagaggaact 1260
gctgagcagc caagtgaccc aagagctgag agccctgatg gacgagacaa tgaaggaact 1320
gaaggcctac aagagcgagc tggaagaaca gctgacccct gtggccgagg aaaccagagc 1380
cagactgagc aaagaactgc aggccgctca ggccagactg ggagccgata tggaagatgt 1440
tcggggcaga ctggtgcagt acagaggcga agttcaggcc atgctgggcc agtctaccga 1500
ggaactgaga gtgcggctgg cctctcatct gattgccctg cagctgagac tgatcggcga 1560
cgcattcgac ctgcagaaaa gactggccgt gtaccaggct ggcgctgctg aacggaagcg 1620
gcgcagcggc agcgggcgca gcggcagcgg cgagggcaga ggaagtcttc taacatgcgg 1680
tgacgtggag gagaatcccg gccct 1705

<210> SEQ ID NO 120
<211> LENGTH: 1705
<212> TYPE: DNA
<213> ORGANISM: Artificial sequence
<220> FEATURE:
<223> OTHER INFORMATION: Homo sapiens

<400> SEQUENCE: 120
tctagaaatg gccttaccag tgaccgcctt gctcctgccg ctggccttgc tgctccacgc 60
cgccaggccg gtgcagctgc agcagtcagg acctgaactg gtgaagcctg ggacttcagt 120
gaggatatcc tgcaagactt ctggatacac attcactgaa tataccatac actgggtgaa 180
gcagagccat ggaaagagcc ttgagtggat tggaaacatc aatcctaaca atggtggtac 240
cacctacaat cagaagttcg aggacaaggc cacattgact gtagacaagt cctccagtac 300
agcctacatg gagctccgca gcctaacatc tgaggattct gcagtctatt attgtgcagc 360
tggttggaac tttgactact ggggccaagg gaccacggtc accgtctcct caggtggagg 420
tggatcaggt ggaggtggat ctggtggagg tggatctgac attgtgatga cccagtctca 480
caaattcatg tccacatcag taggagacag ggtcagcatc atctgtaagg ccagtcaaga 540
tgtgggtact gctgtagact ggtatcaaca gaaaccagga caatctccta aactactgat 600
ttattgggca tccactcggc acactggagt ccctgatcgc ttcacaggca gtggatctgg 660
gacagacttc actctcacca ttactaatgt tcagtctgaa gacttggcag attatttctg 720
tcagcaatat aacagctatc ccctcacgtt cggtgctggg accatgctgg acctgaaacg 780
ggctagcaca acaacccctg cccccagacc tcctacccca gcccctacaa ttgccagcca 840
gcctctgagc ctgaggcccg aggcttgtag acctgctgct ggcggagccg tgcacaccag 900
aggactggat ttcgcctgcg acttctgggt gctggtggtc gtgggcggag tgctggcctg 960
ttacagcctg ctcgtgaccg tggccttcat catcttttgg gtgcggagca agagaagcag 1020
actgctgcac agcgactaca tgaacatgac ccccagacgg cctggcccca ccagaaagca 1080
ctaccagcct tacgcccctc ccagagactt cgccgcctac agatctcata tgggaggcgg 1140
aggatctggc ggaggtggaa gtggcggagg cggatctcaa agatgggaac tcgccctggg 1200
cagattcctg gaatacctga gctgggtgtc cacactgagc gaacaggtgc aagaggaact 1260
gctgagcagc caagtgaccc aagagctgag agccctgatg gacgagacaa tgaaggaact 1320
gaaggcctac aagagcgagc tggaagaaca gctgacccct gtggccgagg aaaccagagc 1380
cagactgagc aaagaactgc aggccgctca ggccagactg ggagccgata tggaagatgt 1440
tcggggcaga ctggtgcagt acagaggcga agttcaggcc atgctgggcc agtctaccga 1500
ggaactgaga gtgcggctgg cctctcatct gattgccctg cagctgagac tgatcggcga 1560
cgcattcgac ctgcagaaaa gactggccgt gtaccaggct ggcgctgctg aacggaagcg 1620
gcgcagcggc agcgggcgca gcggcagcgg cgagggcaga ggaagtcttc taacatgcgg 1680
tgacgtggag gagaatcccg gccct 1705

<210> SEQ ID NO 121
<211> LENGTH: 1705
<212> TYPE: DNA
<213> ORGANISM: Artificial sequence
<220> FEATURE:
<223> OTHER INFORMATION: Homo sapiens

<400> SEQUENCE: 121
tctagaaatg gccttaccag tgaccgcctt gctcctgccg ctggccttgc tgctccacgc 60
cgccaggccg gtgcagctgc agcagtcagg acctgaactg gtgaagcctg ggacttcagt 120
gaggatatcc tgcaagactt ctggatacac attcactgaa tataccatac actgggtgaa 180
gcagagccat ggaaagagcc ttgagtggat tggaaacatc aatcctaaca atggtggtac 240
cacctacaat cagaagttcg aggacaaggc cacattgact gtagacaagt cctccagtac 300
agcctacatg gagctccgca gcctaacatc tgaggattct gcagtctatt attgtgcagc 360
tggttggaac tttgactact ggggccaagg gaccacggtc accgtctcct caggtggagg 420
tggatcaggt ggaggtggat ctggtggagg tggatctgac attgtgatga cccagtctca 480
caaattcatg tccacatcag taggagacag ggtcagcatc atctgtaagg ccagtcaaga 540
tgtgggtact gctgtagact ggtatcaaca gaaaccagga caatctccta aactactgat 600
ttattgggca tccactcggc acactggagt ccctgatcgc ttcacaggca gtggatctgg 660
gacagacttc actctcacca ttactaatgt tcagtctgaa gacttggcag attatttctg 720
tcagcaatat aacagctatc ccctcacgtt cggtgctggg accatgctgg acctgaaacg 780
ggctagcaca acaacccctg cccccagacc tcctacccca gcccctacaa ttgccagcca 840
gcctctgagc ctgaggcccg aggcttgtag acctgctgct ggcggagccg tgcacaccag 900
aggactggat ttcgcctgcg acttctgggt gctggtggtc gtgggcggag tgctggcctg 960
ttacagcctg ctcgtgaccg tggccttcat catcttttgg gtgcggagca agagaagcag 1020
actgctgcac agcgactaca tgaacatgac ccccagacgg cctggcccca ccagaaagca 1080
ctaccagcct tacgcccctc ccagagactt cgccgcctac agatctcata tgggaggcgg 1140
aggatctggc ggaggtggaa gtggcggagg cggatctcaa agatgggaac tcgccctggg 1200
cagattcctg gaatacctga gctgggtgtc cacactgagc gaacaggtgc aagaggaact 1260
gctgagcagc caagtgaccc aagagctgag agccctgatg gacgagacaa tgaaggaact 1320
gaaggcctac aagagcgagc tggaagaaca gctgacccct gtggccgagg aaaccagagc 1380
cagactgagc aaagaactgc aggccgctca ggccagactg ggagccgata tggaagatgt 1440
tcggggcaga ctggtgcagt acagaggcga agttcaggcc atgctgggcc agtctaccga 1500
ggaactgaga gtgcggctgg cctctcatct gattgccctg cagctgagac tgatcggcga 1560
cgcattcgac ctgcagaaaa gactggccgt gtaccaggct ggcgctgctg aacggaagcg 1620
gcgcagcggc agcgggcgca gcggcagcgg cgagggcaga ggaagtcttc taacatgcgg 1680
tgacgtggag gagaatcccg gccct 1705

<210> SEQ ID NO 122
<211> LENGTH: 1706
<212> TYPE: DNA
<213> ORGANISM: Artificial sequence
<220> FEATURE:
<223> OTHER INFORMATION: Homo sapiens

<400> SEQUENCE: 122
tctagaaatg gccttaccag tgaccgcctt gctcctgccg ctggccttgc tgctccacgc 60
cgccaggccg gtgcagctgc agcagtcagg acctgaactg gtgaagcctg ggacttcagt 120
gaggatatcc tgcaagactt ctggatacac attcactgaa tataccatac actgggtgaa 180
gcagagccat ggaaagagcc ttgagtggat tggaaacatc aatcctaaca atggtggtac 240
cacctacaat cagaagttcg aggacaaggc cacattgact gtagacaagt cctccagtac 300
agcctacatg gagctccgca gcctaacatc tgaggattct gcagtctatt attgtgcagc 360
tggttggaac tttgactact ggggccaagg gaccacggtc accgtctcct caggtggagg 420
tggatcaggt ggaggtggat ctggtggagg tggatctgac attgtgatga cccagtctca 480
caaattcatg tccacatcag taggagacag ggtcagcatc atctgtaagg ccagtcaaga 540
tgtgggtact gctgtagact ggtatcaaca gaaaccagga caatctccta aactactgat 600
ttattgggca tccactcggc acactggagt ccctgatcgc ttcacaggca gtggatctgg 660
gacagacttc actctcacca ttactaatgt tcagtctgaa gacttggcag attatttctg 720
tcagcaatat aacagctatc cctcacgtt cggtgctggg accatgctgg acctgaaacg 780
ggctagcaca acaacccctg cccccagacc tcctacccca gcccctacaa ttgccagcca 840
gcctctgagc ctgaggcccg aggcttgtag acctgctgct ggcggagccg tgcacaccag 900
aggactggat ttcgcctgcg acttctgggt gctggtggtc gtgggcggag tgctggcctg 960
ttacagcctg ctcgtgaccg tggccttcat catcttttgg gtgcggagca agagaagcag 1020
actgctgcac agcgactaca tgaacatgac ccccagacgg cctggcccca ccagaaagca 1080
ctaccagcct tacgcccctc ccagagactt cgccgcctac agatctcata tgggaggcgg 1140
aggatctggc ggaggtggaa gtggcggagg cggatctcca aagatgggaa ctcgccctgg 1200
gcagattcct ggaatacctg agctgggtgt ccacactgag cgaacaggtg caagaggaac 1260
tgctgagcag ccaagtgacc caagagctga gagccctgat ggacgagaca atgaaggaac 1320
tgaaggccta caagagcgag ctggaagaac agctgacccc tgtggccgag gaaaccagag 1380
ccagactgag caaagaactg caggccgctc aggccagact gggagccgat atggaagatg 1440
ttcggggcag actggtgcag tacagaggcg aagttcaggc catgctgggc cagtctaccg 1500
aggaactgag agtgcggctg gcctctcatc tgattgccct gcaggcaaga ctgatcggcg 1560
acgcattcga cctgcagaaa agactggccg tgtaccaggc tggcgctgct gaacggaagc 1620
ggcgcagcgg cagcgggcgc agcggcagcg gcgagggcag aggaagtctt ctaacatgcg 1680
gtgacgtgga ggagaatccc ggccct 1706

<210> SEQ ID NO 123
<211> LENGTH: 1704
<212> TYPE: DNA
<213> ORGANISM: Artificial sequence
<220> FEATURE:
<223> OTHER INFORMATION: Homo sapiens

<400> SEQUENCE: 123
tctagaaatg gccttaccag tgaccgcctt gctcctgccg ctggccttgc tgctccacgc 60
cgccaggccg gtgcagctgc agcagtcagg acctgaactg gtgaagcctg ggacttcagt 120
gaggatatcc tgcaagactt ctggatacac attcactgaa tataccatac actgggtgaa 180
gcagagccat ggaaagagcc ttgagtggat tggaaacatc aatcctaaca atggtggtac 240
cacctacaat cagaagttcg aggacaaggc cacattgact gtagacaagt cctccagtac 300
agcctacatg gagctccgca gcctaacatc tgaggattct gcagtctatt attgtgcagc 360
tggttggaac tttgactact ggggccaagg gaccacggtc accgtctcct caggtggagg 420
tggatcaggt ggaggtggat ctggtggagg tggatctgac attgtgatga cccagtctca 480
caaattcatg tccacatcag taggagacag ggtcagcatc atctgtaagg ccagtcaaga 540
tgtgggtact gctgtagact ggtatcaaca gaaaccagga caatctccta aactactgat 600
ttattgggca tccactcggc acactggagt ccctgatcgc ttcacaggca gtggatctgg 660
gacagacttc actctcacca ttactaatgt tcagtctgaa gacttggcag attatttctg 720
tcagcaatat aacagctatc cctcacgttt cggtgctggg accatgctgg acctgaaacg 780
ggctagcaca acaacccctg cccccagacc tcctacccca gcccctacaa ttgccagcca 840
gcctctgagc ctgaggcccg aggcttgtag acctgctgct ggcggagccg tgcacaccag 900
aggactggat ttcgcctgcg acttctgggt gctggtggtc gtgggcggag tgctggcctg 960
ttacagcctg ctcgtgaccg tggccttcat catcttttgg gtgcggagca agagaagcag 1020
actgctgcac agcgactaca tgaacatgac ccccagacgg cctggcccca ccagaaagca 1080
ctaccagcct tacgcccctc ccagagactt cgccgcctac agatctcata tgggaggcgg 1140
aggatctggc ggaggtggaa gtggcggagg cggatctcaa agatgggaac tcgccctggg 1200
cagattcctg gaatacctga gctgggtgtc cacactgagc gaacaggtgc aagaggaact 1260
gctgagcagc caagtgaccc aagagctgag agccctgatg gacgagacaa tgaaggaact 1320
gaaggcctac aagagcgagc tggaagaaca gctgacccct gtggccgagg aaaccagagc 1380
cagactgagc aaagaactgc aggccgctca ggccagactg ggagccgata tggaagatgt 1440
tcggggcaga ctggtgcagt acagaggcga agttcaggcc atgctgggcc agtctaccga 1500
ggaactgaga gtgcggctgg cctctcatct gattgccctg cagctgagac tgatcggcgc 1560
agcattcgac ctgcagaaaa gactggccgt gtaccaggct ggcgctctga acggaagcgg 1620
cgcagcggca gcgggcgcag cggcagcggc gagggcagag gaagtcttct aacatgcggt 1680
gacgtggagg agaatcccgg ccct 1704

<210> SEQ ID NO 124
<211> LENGTH: 1488
<212> TYPE: DNA
<213> ORGANISM: Artificial sequence
<220> FEATURE:
<223> OTHER INFORMATION: Homo sapiens

<400> SEQUENCE: 124
ggatccatgg ccttaccagt gaccgccttg ctcctgccgc tggccttgct gctccacgcc 60
gccaggccgg aacagaaact catcagtgag gaagatttgc agacgactcc aggagagaga 120
tcatcactcc ctgcctttta ccctggcact tcaggctctt gttccggatg tgggtccctc 180
tctctgccga caacaacccc tgcccccaga cctcctaccc cagcccctac aattgccagc 240
cagcctctga gcctgaggcc cgaggcttgt agacctgctg ctggcggagc cgtgcacacc 300
agaggactgg atttcgcctg cgaccctagg ttctgggtgc tggtggtcgt gggcggagtg 360
ctggcctgtt acagcctgct cgtgaccgtg gccttcatca tcttttgggt gcggagcaag 420
agaagcagac tgctgcacag cgactacatg aacatgaccc ccagacggcc tggccccacc 480
agaaagcact accagcctta cgcccctccc agagacttcg ccgcctacag atctcccggg 540
ggaggcggag gatctggcgg aggtggaagt ggcggaggcg gatctatgag ccagagcaac 600
agagaactgg tggtggactt cctgagctac aagctgagcc agaagggcta cagctggtcc 660
cagttcagcg acgtggaaga gaacagaaca gaggcccctg agggcacaga gtctgaggct 720
gtgaaacagg ccctgagaga agccggcgac gagttcgagc tgagatacag aagggccttc 780
agcgacctga ccagccagct gcacatcaca cctggcacag cctaccagag cttcgagcag 840
gtcgtgaacg agctgttcag agatggcgtg aactggggca gaatcgtggc cttcttcagc 900
tttggcggag ccctgtgtgt ggaaagcgtg gacaaagaaa tgcaggtcct ggtgtccaga 960
atcgccgcct ggatggccac ctacctgaac gatcatctgg aaccctggat tcaagagaac 1020
ggcggctggg acaccttcgt ggaactgtac ggaaacaacg ccgctgccga gagcagaaag 1080
ggccaagaac gagaagatgg cggcggtggt tctggtggcg gcggtagtgg tggcggtgga 1140
tcaatgcata gagtgaagtt cagcaggagc gcagacgccc ccgcgtacca gcagggccag 1200
aaccagctct ataacgagct caatctagga cgaagagagg agtacgatgt tttggacaag 1260
agacgtggcc gggaccctga gatgggggga aagccgagaa ggaagaaccc tcaggaaggc 1320
ctgtacaatg aactgcagaa agataagatg gcggaggcct acagtgagat tgggatgaaa 1380
ggcgagcgcc ggaggggcaa ggggcacgat ggcctttacc agggtctcag tacagccacc 1440
aaggacacct acgacgccct tcacatgcag gccctgcccc ctcgctaa 1488

<210> SEQ ID NO 125
<211> LENGTH: 1487
<212> TYPE: DNA
<213> ORGANISM: Artificial sequence
<220> FEATURE:
<223> OTHER INFORMATION: Homo sapiens

<400> SEQUENCE: 125
ggatccatgg ccttaccagt gaccgccttg ctcctgccgc tggccttgct gctccacgcc 60
gccaggccgg aacagaaact catcagtgag gaagatttgc agacgactcc aggagagaga 120
tcatcactcc ctgcctttta ccctggcact tcaggctctt gttccggatg tgggtccctc 180

```
tctctgccga caacaacccc tgcccccaga cctcctaccc cagcccctac aattgccagc    240
cagcctctga gcctgaggcc cgaggcttgt agacctgctg ctggcggagc cgtgcacacc    300
agaggactgg atttcgcctg cgacctaggt tctgggtgct ggtggtcgtg ggcggagtgc    360
tggcctgtta cagcctgctc gtgaccgtgg ccttcatcat cttttgggtg cggagcaaga    420
gaagcagact gctgcacagc gactacatga acatgacccc cagacggcct ggccccacca    480
gaaagcacta ccagccttac gcccctccca gagacttcgc cgcctacaga tctcccgggg    540
gaggcggagg atctggcgga ggtggaagtg gcggaggcgg atctatgagc cagagcaaca    600
gagaactggt ggtggacttc ctgagctaca agctgagcca gaagggctac agctggtccc    660
agttcagcga cgtggaagag aacagaacag aggcccctga gggcacagag tctgaggctg    720
tgaaacaggc cctgagagaa gccggcgacg agttcgagct gagatacaga agggccttca    780
gcgacctgac cagccagctg cacatcacac ctggcacagc ctaccagagc ttcgagcagg    840
tcgtgaacga gctgttcaga gatggcgtga actggggcag aatcgtggcc ttcttcagct    900
ttggcggagc cctgtgtgtg gaaagcgtgg acaaagaaat gcaggtcctg gtgtccagaa    960
tcgccgcctg gatggccacc tacctgaacg atcatctgga accctggatt caagagaacg   1020
gcggctggga caccttcgtg gaactgtacg gaaacaacgc cgctgccgag agcagaaagg   1080
gccaagaacg agaagatgga ggcggaggat ctggcggagg tggaagtggc ggaggcggat   1140
ctatgcatag agtgaagttc agcaggagcg cagacgcccc cgcgtaccag cagggccaga   1200
accagctcta taacgagctc aatctaggac gaagagagga gtacgatgtt ttggacaaga   1260
gacgtggccg ggaccctgag atgggggggaa agccgagaag gaagaaccct caggaaggcc   1320
tgtacaatga actgcagaaa gataagatgg cggaggccta cagtgagatt gggatgaaag   1380
gcgagcgccg gaggggcaag gggcacgatg gcctttacca gggtctcagt acagccacca   1440
aggacaccta cgacgccctt cacatgcagg ccctgccccc tcgctaa                 1487
```

<210> SEQ ID NO 126
<211> LENGTH: 1493
<212> TYPE: DNA
<213> ORGANISM: Artificial sequence
<220> FEATURE:
<223> OTHER INFORMATION: Homo sapiens

<400> SEQUENCE: 126

```
ggatccatgg ccttaccagt gaccgccttg ctcctgccgc tggccttgct gctccacgcc     60
gccaggccgg aacagaaact catcagtgag gaagatttgc agacgactcc aggagagaga    120
tcatcactcc ctgcctttta ccctggcact tcaggctctt gttccggatg tgggtccctc    180
tctctgccga caacaacccc tgcccccaga cctcctaccc cagcccctac aattgccagc    240
cagcctctga gcctgaggcc cgaggcttgt agacctgctg ctggcggagc cgtgcacacc    300
agaggactgg atttcgcctg cgacctaggt tctgggtgct ggtggtcgtg ggcggagtgc    360
tggcctgtta cagcctgctc gtgaccgtgg ccttcatcat cttttgggtg cggagcaaga    420
gaagcagact gctgcacagc gactacatga acatgacccc cagacggcct ggccccacca    480
gaaagcacta ccagccttac gcccctccca gagacttcgc cgcctacaga tctcccgggg    540
gaggcggagg atctggcgga ggtggaagtg gcggaggcgg atctatgagc cagagcaaca    600
gagaactggt ggtggacttc ctgagctaca agctgagcca gaagggctac agctggtccc    660
agttcagcga cgtggaagag aacagaacag aggcccctga gggcacagag tctgaggctg    720
tgaaacaggc cctgagagaa gccggcgacg acttcgagct gagatacaga agggccttca    780
```

```
gcgacctgac cagccagctg cacatcacac ctggcacagc ctaccagagc ttcgagcagg    840

tcgtgaacga gctgttcaga gatggcgtga actggggcag aatcgtggcc ttcttcagct    900

ttggcggagc cctgtgtgtg gaaagcgtgg acaaagaaat gcaggtcctg gtgtccagaa    960

tcgccgcctg gatggccacc tacctgaacg atcatctgga accctggatt caagagaacg   1020

gcggctggga caccttcgtg gaactgtacg gaaacaacgc cgctgccgag agcagaaagg   1080

gccaagaacg agaagatgaa gatggaggcg gaggatctgg cggaggtgga agtggcggag   1140

gcggatctat gcatagagtg aagttcagca ggagcgcaga cgcccccgcg taccagcagg   1200

gccagaacca gctctataac gagctcaatc taggacgaag agaggagtac gatgttttgg   1260

acaagagacg tggccgggac cctgagatgg ggggaaagcc gagaaggaag aaccctcagg   1320

aaggcctgta caatgaactg cagaaagata agatggcgga ggcctacagt gagattggga   1380

tgaaaggcga gcgccggagg ggcaaggggc acgatggcct ttaccagggt ctcagtacag   1440

ccaccaagga cacctacgac gcccttcaca tgcaggccct gccccctcgc taa          1493
```

<210> SEQ ID NO 127
<211> LENGTH: 1601
<212> TYPE: DNA
<213> ORGANISM: Artificial sequence
<220> FEATURE:
<223> OTHER INFORMATION: Homo sapiens

<400> SEQUENCE: 127

```
ggatccatgg ccttaccagt gaccgccttg ctcctgccgc tggccttgct gctccacgcc     60

gccaggccgg aacagaaact catcagtgag gaagatttgc agacgactcc aggagagaga    120

tcatcactcc ctgcctttta ccctggcact tcaggctctt gttccggatg tgggtccctc    180

tctctgccga caacaacccc tgcccccaga cctcctaccc cagcccctac aattgccagc    240

cagcctctga gcctgaggcc cgaggcttgt agacctgctg ctggcggagc cgtgcacacc    300

agaggactgg atttcgcctg cgacctaggt tctgggtgct ggtggtcgtg ggcggagtgc    360

tggcctgtta cagcctgctc gtgaccgtgg ccttcatcat cttttgggtg cggagcaaga    420

gaagcagact gctgcacagc gactacatga acatgacccc cagacggcct ggccccacca    480

gaaagcacta ccagccttac gcccctccca gagacttcgc cgcctacaga tctcccgggg    540

gaggcggagg atctggcgga ggtggaagtg gcggaggcgg atctatggcc cacgccggca    600

ggaccggcta cgacaacagg gagatcgtga tgaagtacat ccactacaag ctgagccaga    660

ggggctacga gtgggacgcc ggcgacgtgg gcgccgcccc ccccggcgcc gcccccgccc    720

ccggcatctt cagcagccag cccggccaca ccccccaccc cgccgccagc agggaccccg    780

tggccaggac cagccccctg cagacccccg ccgcccccgg cgccgccgcc ggccccgccc    840

tgagccccgt gccccccgtg gtgcacctga ccctgaggca ggccggcgac gacttcagca    900

ggaggtacag gagggacttc gccgagatga gcagccagct gcacctgacc cccttcaccg    960

ccaggggcag gttcgccacc gtggtggagg agctgttcag ggacggcgtg aactggggca   1020

ggatcgtggc cttcttcgag ttcggcggcg tgatgtgcgt ggagagcgtg aacagggaga   1080

tgagccccct ggtggacaac atcgccctgt ggatgaccga gtacctgaac aggcacctgc   1140

acacctggat ccaggacaac ggcggctggg acgccttcgt ggagctgtac ggccccagca   1200

tgagggaaga tggaggcgga ggatctggcg gaggtggaag tggcggaggc ggatctatgc   1260

atagagtgaa gttcagcagg agcgcagacg cccccgcgta ccagcagggc cagaaccagc   1320
```

```
tctataacga gctcaatcta ggacgaagag aggagtacga tgttttggac aagagacgtg   1380
gccgggaccc tgagatgggg ggaaagccga gaaggaagaa ccctcaggaa ggcctgtaca   1440
atgaactgca gaaagataag atggcggagg cctacagtga gattgggatg aaaggcgagc   1500
gccggagggg caaggggcac gatggccttt accagggtct cagtacagcc accaaggaca   1560
cctacgacgc ccttcacatg caggccctgc cccctcgcta a                       1601
```

<210> SEQ ID NO 128
<211> LENGTH: 1487
<212> TYPE: DNA
<213> ORGANISM: Artificial sequence
<220> FEATURE:
<223> OTHER INFORMATION: Homo sapiens

<400> SEQUENCE: 128

```
ggatccatgg ccttaccagt gaccgccttg ctcctgccgc tggccttgct gctccacgcc     60
gccaggccgg aacagaaact catcagtgag gaagatttgc agacgactcc aggagagaga    120
tcatcactcc ctgcctttta ccctggcact tcaggctctt gttccggatg tgggtccctc    180
tctctgccga caacaacccc tgcccccaga cctcctaccc cagcccctac aattgccagc    240
cagcctctga gcctgaggcc cgaggcttgt agacctgctg ctggcggagc cgtgcacacc    300
agaggactgg atttcgcctg cgacctaggt tctgggtgct ggtggtcgtg ggcggagtgc    360
tggcctgtta cagcctgctc gtgaccgtgg ccttcatcat cttttgggtg cggagcaaga    420
gaagcagact gctgcacagc gactacatga acatgacccc cagacggcct ggccccacca    480
gaaagcacta ccagccttac gcccctccca gagacttcgc cgcctacaga tctcccgggg    540
gaggcggagg atctggcgga ggtggaagtg gcggaggcgg atctatgagc cagagcaaca    600
gagaactggt ggtggacttc ctgagctaca agctgagcca gaagggctac agctggtccc    660
agttcagcga cgtggaagag aacagaacag aggcccctga gggcacagag tctgaggctg    720
tgaaacaggc cctgagagaa gccggcgacg agttcgagct gagatacaga agggccttca    780
gcgacctgac cagccagctg cacatcacac ctggcacagc ctaccagagc ttcgagcagg    840
tcgtgaacga gctgttcaga gatggcgtga actggggcag aatcgtggcc ttcttcagct    900
ttggcggagc cctgtgtgtg gaaagcgtgg acaaagaaat gcaggtcctg gtgtccagaa    960
tcgccgcctg gatggccacc tacctgaacg atcatctgga accctggatt caagagaacg   1020
gcggctggga caccttcgtg gaactgtacg gaaacaacgc cgctgccgag agcagaaagg   1080
gccaagaacg agaagatgga ggcggaggat ctggcggagg tggaagtggc ggaggcggat   1140
ctatgcatag agtgaagttc agcaggagcg cagacgcccc cgcgtaccag cagggccaga   1200
accagctcta taacgagctc aatctaggac gaagagagga gtacgatgtt ttggacaaga   1260
gacgtggccg ggaccctgag atggggggaa agccgagaag gaagaaccct caggaaggcc   1320
tgtacaatga actgcagaaa gataagatgg cggaggccta cagtgagatt gggatgaaag   1380
gcgagcgccg gaggggcaag gggcacgatg gcctttacca gggtctcagt acagccacca   1440
aggacaccta cgacgccctt cacatgcagg ccctgccccc tcgctaa                 1487
```

<210> SEQ ID NO 129
<211> LENGTH: 1487
<212> TYPE: DNA
<213> ORGANISM: Artificial sequence
<220> FEATURE:
<223> OTHER INFORMATION: Homo sapiens

<400> SEQUENCE: 129

```
ggatccatgg ccttaccagt gaccgccttg ctcctgccgc tggccttgct gctccacgcc     60

gccaggccgg aacagaaact catcagtgag gaagatttgc agacgactcc aggagagaga    120

tcatcactcc ctgcctttta ccctggcact tcaggctctt gttccggatg tgggtccctc    180

tctctgccga caacaacccc tgcccccaga cctcctaccc cagcccctac aattgccagc    240

cagcctctga gcctgaggcc cgaggcttgt agacctgctg ctggcggagc cgtgcacacc    300

agaggactgg atttcgcctg cgacctaggt tctgggtgct ggtggtcgtg ggcggagtgc    360

tggcctgtta cagcctgctc gtgaccgtgg ccttcatcat cttttgggtg cggagcaaga    420

gaagcagact gctgcacagc gactacatga acatgacccc cagacggcct ggccccacca    480

gaaagcacta ccagccttac gcccctccca gagacttcgc cgcctacaga tctcccgggg    540

gaggcggagg atctggcgga ggtggaagtg gcggaggcgg atctatgagc cagagcaaca    600

gagaactggt ggtggacttc ctgagctaca agctgagcca gaagggctac agctggtccc    660

agttcagcga cgtggaagag aacagaacag aggcccctga gggcacagag tctgaggctg    720

tgaaacaggc cctgagagaa gccggcgacg agttcgagct gagatacaga agggccttca    780

gcgacctgac cagccagctg cacatcacac ctggcacagc ctaccagagc ttcgagcagg    840

tcgtgaacga gctgttcaga gatggcgtga actggggcag aatcgtggcc ttcttcagct    900

ttggcggagc cctgtgtgtg gaaagcgtgg acaaagaaat gcaggtcctg gtgtccagaa    960

tcgccgcctg gatggccacc tacctgaacg atcatctgga accctggatt caagagaacg   1020

gcggctggga caccttcgtg gaactgtacg gaaacaacgc cgctgccgag agcagaaagg   1080

gccaagaacg agaagatgga ggcggaggat ctggcggagg tggaagtggc ggaggcggat   1140

ctatgcatag agtgaagttc agcaggagcg cagacgcccc cgcgtaccag cagggccaga   1200

accagctcta taacgagctc aatctaggac gaagagagga gtacgatgtt ttggacaaga   1260

gacgtggccg ggaccctgag atggggggaa agccgagaag gaagaaccct caggaaggcc   1320

tgtacaatga actgcagaaa gataagatgg cggaggccta cagtgagatt gggatgaaag   1380

gcgagcgccg gaggggcaag gggcacgatg gcctttacca gggtctcagt acagccacca   1440

aggacaccta cgacgccctt cacatgcagg ccctgccccc tcgctaa                 1487
```

```
<210> SEQ ID NO 130
<211> LENGTH: 144
<212> TYPE: PRT
<213> ORGANISM: Artificial Sequence
<220> FEATURE:
<223> OTHER INFORMATION: Homo sapiens

<400> SEQUENCE: 130

Gly Gln Arg Trp Glu Leu Ala Leu Gly Arg Phe Leu Glu Tyr Leu Ser
1               5                   10                  15

Trp Val Ser Thr Leu Ser Glu Gln Val Gln Glu Glu Leu Leu Ser Ser
            20                  25                  30

Gln Val Thr Gln Glu Leu Arg Ala Leu Met Asp Glu Thr Met Lys Glu
        35                  40                  45

Leu Lys Ala Tyr Lys Ser Glu Leu Glu Glu Gln Leu Thr Pro Val Ala
    50                  55                  60

Glu Glu Thr Arg Ala Arg Leu Ser Lys Glu Leu Gln Ala Ala Gln Ala
65                  70                  75                  80

Arg Leu Gly Ala Asp Met Glu Asp Val Arg Gly Arg Leu Val Gln Tyr
                85                  90                  95
```

```
Arg Gly Glu Val Gln Ala Met Leu Gly Gln Ser Thr Glu Glu Leu Arg
            100                 105                 110

Val Arg Leu Ala Ser His Leu Ile Ala Leu Gln Leu Arg Leu Ile Gly
        115                 120                 125

Asp Ala Phe Asp Leu Gln Lys Arg Leu Ala Val Tyr Gln Ala Gly Ala
    130                 135                 140


<210> SEQ ID NO 131
<211> LENGTH: 144
<212> TYPE: PRT
<213> ORGANISM: Artificial sequence
<220> FEATURE:
<223> OTHER INFORMATION: Homo sapiens

<400> SEQUENCE: 131

Gly Gln Arg Trp Glu Leu Ala Leu Gly Arg Phe Leu Ala Tyr Leu Ser
1               5                   10                  15

Trp Val Ser Thr Leu Ser Glu Gln Val Gln Glu Glu Leu Leu Ser Ser
            20                  25                  30

Gln Val Thr Gln Glu Leu Arg Ala Leu Met Asp Glu Thr Met Lys Glu
        35                  40                  45

Leu Lys Ala Tyr Lys Ser Glu Leu Glu Glu Gln Leu Thr Pro Val Ala
    50                  55                  60

Glu Glu Thr Arg Ala Arg Leu Ser Lys Glu Leu Gln Ala Ala Gln Ala
65                  70                  75                  80

Arg Leu Gly Ala Asp Met Glu Asp Val Arg Gly Arg Leu Val Gln Tyr
                85                  90                  95

Arg Gly Glu Val Gln Ala Met Leu Gly Gln Ser Thr Glu Glu Leu Arg
            100                 105                 110

Val Arg Leu Ala Ser His Leu Ile Ala Leu Gln Leu Arg Leu Ile Gly
        115                 120                 125

Asp Ala Phe Asp Leu Gln Lys Arg Leu Ala Val Tyr Gln Ala Gly Ala
    130                 135                 140


<210> SEQ ID NO 132
<211> LENGTH: 144
<212> TYPE: PRT
<213> ORGANISM: Artificial sequence
<220> FEATURE:
<223> OTHER INFORMATION: Homo sapiens

<400> SEQUENCE: 132

Gly Gln Arg Trp Glu Leu Ala Leu Gly Arg Phe Leu Glu Tyr Leu Ser
1               5                   10                  15

Trp Val Ser Thr Leu Ser Glu Gln Val Gln Glu Glu Leu Leu Ser Ser
            20                  25                  30

Gln Val Thr Gln Glu Leu Arg Ala Leu Met Asp Glu Thr Met Lys Glu
        35                  40                  45

Leu Lys Ala Tyr Lys Ser Glu Leu Glu Glu Gln Leu Thr Pro Val Ala
    50                  55                  60

Glu Glu Thr Arg Ala Arg Leu Ser Lys Glu Leu Gln Ala Ala Gln Ala
65                  70                  75                  80

Arg Leu Gly Ala Asp Met Glu Asp Val Arg Gly Arg Leu Val Gln Tyr
                85                  90                  95

Arg Gly Glu Val Gln Ala Met Leu Gly Gln Ser Thr Glu Glu Leu Arg
            100                 105                 110

Val Arg Leu Ala Ser His Leu Ile Ala Leu Gln Ala Arg Leu Ile Gly
        115                 120                 125
```

```
Asp Ala Phe Asp Leu Gln Lys Arg Leu Ala Val Tyr Gln Ala Gly Ala
    130                 135                 140


<210> SEQ ID NO 133
<211> LENGTH: 144
<212> TYPE: PRT
<213> ORGANISM: Artificial sequence
<220> FEATURE:
<223> OTHER INFORMATION: Homo sapiens

<400> SEQUENCE: 133

Gly Gln Arg Trp Glu Leu Ala Leu Gly Arg Phe Leu Glu Tyr Leu Ser
1               5                   10                  15

Trp Val Ser Thr Leu Ser Glu Gln Val Gln Glu Glu Leu Leu Ser Ser
            20                  25                  30

Gln Val Thr Gln Glu Leu Arg Ala Leu Met Asp Glu Thr Met Lys Glu
        35                  40                  45

Leu Lys Ala Tyr Lys Ser Glu Leu Glu Glu Gln Leu Thr Pro Val Ala
    50                  55                  60

Glu Glu Thr Arg Ala Arg Leu Ser Lys Glu Leu Gln Ala Ala Gln Ala
65                  70                  75                  80

Arg Leu Gly Ala Asp Met Glu Asp Val Arg Gly Arg Leu Val Gln Tyr
                85                  90                  95

Arg Gly Glu Val Gln Ala Met Leu Gly Gln Ser Thr Glu Glu Leu Arg
            100                 105                 110

Val Arg Leu Ala Ser His Leu Ile Ala Leu Gln Leu Arg Leu Ile Gly
        115                 120                 125

Ala Ala Phe Asp Leu Gln Lys Arg Leu Ala Val Tyr Gln Ala Gly Ala
    130                 135                 140


<210> SEQ ID NO 134
<211> LENGTH: 273
<212> TYPE: PRT
<213> ORGANISM: Artificial sequence
<220> FEATURE:
<223> OTHER INFORMATION: Homo sapiens

<400> SEQUENCE: 134

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Phe Trp Val
        35                  40                  45

Leu Val Val Val Gly Gly Val Leu Ala Cys Tyr Ser Leu Leu Val Thr
    50                  55                  60

Val Ala Phe Ile Ile Phe Trp Val Arg Ser Lys Arg Ser Arg Leu Leu
65                  70                  75                  80

His Ser Asp Tyr Met Asn Met Thr Pro Arg Arg Pro Gly Pro Thr Arg
                85                  90                  95

Lys His Tyr Gln Pro Tyr Ala Pro Pro Arg Asp Phe Ala Ala Tyr Arg
            100                 105                 110

Ser His Met Gly Gly Gly Gly Ser Gly Gly Gly Gly Ser Gly Gly Gly
        115                 120                 125

Gly Ser Gln Arg Trp Glu Leu Ala Leu Gly Arg Phe Leu Glu Tyr Leu
    130                 135                 140

Ser Trp Val Ser Thr Leu Ser Glu Gln Val Gln Glu Glu Leu Leu Ser
```

145 150 155 160

Ser Gln Val Thr Gln Glu Leu Arg Ala Leu Met Asp Glu Thr Met Lys
165 170 175

Glu Leu Lys Ala Tyr Lys Ser Glu Leu Glu Glu Gln Leu Thr Pro Val
180 185 190

Ala Glu Glu Thr Arg Ala Arg Leu Ser Lys Glu Leu Gln Ala Ala Gln
195 200 205

Ala Arg Leu Gly Ala Asp Met Glu Asp Val Arg Gly Arg Leu Val Gln
210 215 220

Tyr Arg Gly Glu Val Gln Ala Met Leu Gly Gln Ser Thr Glu Glu Leu
225 230 235 240

Arg Val Arg Leu Ala Ser His Leu Ile Ala Leu Gln Leu Arg Leu Ile
245 250 255

Gly Asp Ala Phe Asp Leu Gln Lys Arg Leu Ala Val Tyr Gln Ala Gly
260 265 270

Ala

<210> SEQ ID NO 135
<211> LENGTH: 273
<212> TYPE: PRT
<213> ORGANISM: Artificial sequence
<220> FEATURE:
<223> OTHER INFORMATION: Homo sapiens

<400> SEQUENCE: 135

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp Phe Trp Val
35 40 45

Leu Val Val Val Gly Gly Val Leu Ala Cys Tyr Ser Leu Leu Val Thr
50 55 60

Val Ala Phe Ile Ile Phe Trp Val Arg Ser Lys Arg Ser Arg Leu Leu
65 70 75 80

His Ser Asp Tyr Met Asn Met Thr Pro Arg Arg Pro Gly Pro Thr Arg
85 90 95

Lys His Tyr Gln Pro Tyr Ala Pro Pro Arg Asp Phe Ala Ala Tyr Arg
100 105 110

Ser His Met Gly Gly Gly Gly Ser Gly Gly Gly Gly Ser Gly Gly Gly
115 120 125

Gly Ser Gln Arg Trp Glu Leu Ala Leu Gly Arg Phe Leu Ala Tyr Leu
130 135 140

Ser Trp Val Ser Thr Leu Ser Glu Gln Val Gln Glu Glu Leu Leu Ser
145 150 155 160

Ser Gln Val Thr Gln Glu Leu Arg Ala Leu Met Asp Glu Thr Met Lys
165 170 175

Glu Leu Lys Ala Tyr Lys Ser Glu Leu Glu Glu Gln Leu Thr Pro Val
180 185 190

Ala Glu Glu Thr Arg Ala Arg Leu Ser Lys Glu Leu Gln Ala Ala Gln
195 200 205

Ala Arg Leu Gly Ala Asp Met Glu Asp Val Arg Gly Arg Leu Val Gln
210 215 220

Tyr Arg Gly Glu Val Gln Ala Met Leu Gly Gln Ser Thr Glu Glu Leu
225 230 235 240

Arg Val Arg Leu Ala Ser His Leu Ile Ala Leu Gln Leu Arg Leu Ile
245 250 255

Gly Asp Ala Phe Asp Leu Gln Lys Arg Leu Ala Val Tyr Gln Ala Gly
260 265 270

Ala

<210> SEQ ID NO 136
<211> LENGTH: 273
<212> TYPE: PRT
<213> ORGANISM: Artificial sequence
<220> FEATURE:
<223> OTHER INFORMATION: Homo sapiens

<400> SEQUENCE: 136

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp Phe Trp Val
35 40 45

Leu Val Val Val Gly Gly Val Leu Ala Cys Tyr Ser Leu Leu Val Thr
50 55 60

Val Ala Phe Ile Ile Phe Trp Val Arg Ser Lys Arg Ser Arg Leu Leu
65 70 75 80

His Ser Asp Tyr Met Asn Met Thr Pro Arg Arg Pro Gly Pro Thr Arg
85 90 95

Lys His Tyr Gln Pro Tyr Ala Pro Pro Arg Asp Phe Ala Ala Tyr Arg
100 105 110

Ser His Met Gly Gly Gly Gly Ser Gly Gly Gly Gly Ser Gly Gly Gly
115 120 125

Gly Ser Gln Arg Trp Glu Leu Ala Leu Gly Arg Phe Leu Glu Tyr Leu
130 135 140

Ser Trp Val Ser Thr Leu Ser Glu Gln Val Gln Glu Glu Leu Leu Ser
145 150 155 160

Ser Gln Val Thr Gln Glu Leu Arg Ala Leu Met Asp Glu Thr Met Lys
165 170 175

Glu Leu Lys Ala Tyr Lys Ser Glu Leu Glu Glu Gln Leu Thr Pro Val
180 185 190

Ala Glu Glu Thr Arg Ala Arg Leu Ser Lys Glu Leu Gln Ala Ala Gln
195 200 205

Ala Arg Leu Gly Ala Asp Met Glu Asp Val Arg Gly Arg Leu Val Gln
210 215 220

Tyr Arg Gly Glu Val Gln Ala Met Leu Gly Gln Ser Thr Glu Glu Leu
225 230 235 240

Arg Val Arg Leu Ala Ser His Leu Ile Ala Leu Gln Ala Arg Leu Ile
245 250 255

Gly Asp Ala Phe Asp Leu Gln Lys Arg Leu Ala Val Tyr Gln Ala Gly
260 265 270

Ala

<210> SEQ ID NO 137
<211> LENGTH: 273
<212> TYPE: PRT
<213> ORGANISM: Artificial sequence
<220> FEATURE:
<223> OTHER INFORMATION: Homo sapiens

<400> SEQUENCE: 137

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Phe Trp Val
        35                  40                  45

Leu Val Val Val Gly Gly Val Leu Ala Cys Tyr Ser Leu Leu Val Thr
    50                  55                  60

Val Ala Phe Ile Ile Phe Trp Val Arg Ser Lys Arg Ser Arg Leu Leu
65                  70                  75                  80

His Ser Asp Tyr Met Asn Met Thr Pro Arg Arg Pro Gly Pro Thr Arg
                85                  90                  95

Lys His Tyr Gln Pro Tyr Ala Pro Pro Arg Asp Phe Ala Ala Tyr Arg
            100                 105                 110

Ser His Met Gly Gly Gly Gly Ser Gly Gly Gly Gly Ser Gly Gly Gly
        115                 120                 125

Gly Ser Gln Arg Trp Glu Leu Ala Leu Gly Arg Phe Leu Glu Tyr Leu
    130                 135                 140

Ser Trp Val Ser Thr Leu Ser Glu Gln Val Gln Glu Glu Leu Leu Ser
145                 150                 155                 160

Ser Gln Val Thr Gln Glu Leu Arg Ala Leu Met Asp Glu Thr Met Lys
                165                 170                 175

Glu Leu Lys Ala Tyr Lys Ser Glu Leu Glu Glu Gln Leu Thr Pro Val
            180                 185                 190

Ala Glu Glu Thr Arg Ala Arg Leu Ser Lys Glu Leu Gln Ala Ala Gln
        195                 200                 205

Ala Arg Leu Gly Ala Asp Met Glu Asp Val Arg Gly Arg Leu Val Gln
    210                 215                 220

Tyr Arg Gly Glu Val Gln Ala Met Leu Gly Gln Ser Thr Glu Glu Leu
225                 230                 235                 240

Arg Val Arg Leu Ala Ser His Leu Ile Ala Leu Gln Leu Arg Leu Ile
                245                 250                 255

Gly Ala Ala Phe Asp Leu Gln Lys Arg Leu Ala Val Tyr Gln Ala Gly
            260                 265                 270

Ala

<210> SEQ ID NO 138
<211> LENGTH: 545
<212> TYPE: PRT
<213> ORGANISM: Artificial sequence
<220> FEATURE:
<223> OTHER INFORMATION: Homo sapiens

<400> SEQUENCE: 138

Val Gln Leu Gln Gln Ser Gly Pro Glu Leu Val Lys Pro Gly Thr Ser
1               5                   10                  15

Val Arg Ile Ser Cys Lys Thr Ser Gly Tyr Thr Phe Thr Glu Tyr Thr
            20                  25                  30

Ile His Trp Val Lys Gln Ser His Gly Lys Ser Leu Glu Trp Ile Gly
        35                  40                  45

Asn Ile Asn Pro Asn Asn Gly Gly Thr Thr Tyr Asn Gln Lys Phe Glu
    50                  55                  60

Asp Lys Ala Thr Leu Thr Val Asp Lys Ser Ser Ser Thr Ala Tyr Met

-continued

```
65                  70                  75                  80

Glu Leu Arg Ser Leu Thr Ser Glu Asp Ser Ala Val Tyr Tyr Cys Ala
                85                  90                  95

Ala Gly Trp Asn Phe Asp Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Asp Ile Val Met Thr Gln Ser His Lys Phe Met Ser Thr Ser Val
    130                 135                 140

Gly Asp Arg Val Ser Ile Ile Cys Lys Ala Ser Gln Asp Val Gly Thr
145                 150                 155                 160

Ala Val Asp Trp Tyr Gln Gln Lys Pro Gly Gln Ser Pro Lys Leu Leu
                165                 170                 175

Ile Tyr Trp Ala Ser Thr Arg His Thr Gly Val Pro Asp Arg Phe Thr
            180                 185                 190

Gly Ser Gly Ser Gly Thr Asp Phe Thr Leu Thr Ile Thr Asn Val Gln
        195                 200                 205

Ser Glu Asp Leu Ala Asp Tyr Phe Cys Gln Gln Tyr Asn Ser Tyr Pro
    210                 215                 220

Leu Thr Phe Gly Ala Gly Thr Met Leu Asp Leu Lys Arg Ala Ser Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

His Met Gly Gly Gly Gly Ser Gly Gly Gly Gly Ser Gly Gly Gly Gly
        355                 360                 365

Ser Gln Arg Trp Glu Leu Ala Leu Gly Arg Phe Leu Glu Tyr Leu Ser
    370                 375                 380

Trp Val Ser Thr Leu Ser Glu Gln Val Gln Glu Glu Leu Leu Ser Ser
385                 390                 395                 400

Gln Val Thr Gln Glu Leu Arg Ala Leu Met Asp Glu Thr Met Lys Glu
                405                 410                 415

Leu Lys Ala Tyr Lys Ser Glu Leu Glu Glu Gln Leu Thr Pro Val Ala
            420                 425                 430

Glu Glu Thr Arg Ala Arg Leu Ser Lys Glu Leu Gln Ala Ala Gln Ala
        435                 440                 445

Arg Leu Gly Ala Asp Met Glu Asp Val Arg Gly Arg Leu Val Gln Tyr
    450                 455                 460

Arg Gly Glu Val Gln Ala Met Leu Gly Gln Ser Thr Glu Glu Leu Arg
465                 470                 475                 480

Val Arg Leu Ala Ser His Leu Ile Ala Leu Gln Leu Arg Leu Ile Gly
                485                 490                 495
```

```
Asp Ala Phe Asp Leu Gln Lys Arg Leu Ala Val Tyr Gln Ala Gly Ala
            500                 505                 510

Ala Glu Arg Lys Arg Arg Ser Gly Ser Gly Arg Ser Gly Ser Gly Glu
        515                 520                 525

Gly Arg Gly Ser Leu Leu Thr Cys Gly Asp Val Glu Glu Asn Pro Gly
    530                 535                 540

Pro
545


<210> SEQ ID NO 139
<211> LENGTH: 533
<212> TYPE: PRT
<213> ORGANISM: Artificial sequence
<220> FEATURE:
<223> OTHER INFORMATION: Homo sapiens

<400> SEQUENCE: 139

Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300
```

Asp Phe Trp Val Leu Val Val Val Gly Gly Val Leu Ala Cys Tyr Ser
305 310 315 320

Leu Leu Val Thr Val Ala Phe Ile Ile Phe Trp Val Arg Ser Lys Arg
325 330 335

Ser Arg Leu Leu His Ser Asp Tyr Met Asn Met Thr Pro Arg Arg Pro
340 345 350

Gly Pro Thr Arg Lys His Tyr Gln Pro Tyr Ala Pro Pro Arg Asp Phe
355 360 365

Ala Ala Tyr Arg Ser His Met Gly Gly Gly Gly Ser Gly Gly Gly Gly
370 375 380

Ser Gly Gly Gly Gly Ser Gln Arg Trp Glu Leu Ala Leu Gly Arg Phe
385 390 395 400

Leu Glu Tyr Leu Ser Trp Val Ser Thr Leu Ser Glu Gln Val Gln Glu
405 410 415

Glu Leu Leu Ser Ser Gln Val Thr Gln Glu Leu Arg Ala Leu Met Asp
420 425 430

Glu Thr Met Lys Glu Leu Lys Ala Tyr Lys Ser Glu Leu Glu Glu Gln
435 440 445

Leu Thr Pro Val Ala Glu Glu Thr Arg Ala Arg Leu Ser Lys Glu Leu
450 455 460

Gln Ala Ala Gln Ala Arg Leu Gly Ala Asp Met Glu Asp Val Arg Gly
465 470 475 480

Arg Leu Val Gln Tyr Arg Gly Glu Val Gln Ala Met Leu Gly Gln Ser
485 490 495

Thr Glu Glu Leu Arg Val Arg Leu Ala Ser His Leu Ile Ala Leu Gln
500 505 510

Leu Arg Leu Ile Gly Asp Ala Phe Asp Leu Gln Lys Arg Leu Ala Val
515 520 525

Tyr Gln Ala Gly Ala
530

<210> SEQ ID NO 140
<211> LENGTH: 534
<212> TYPE: PRT
<213> ORGANISM: Artificial sequence
<220> FEATURE:
<223> OTHER INFORMATION: Homo sapiens

<400> SEQUENCE: 140

Met Ala Leu Pro Val Thr Ala Leu Leu Leu Pro Leu Ala Leu Leu Leu
1 5 10 15

His Ala Ala Arg Pro Val Gln Leu Gln Gln Ser Gly Pro Glu Leu Val
20 25 30

Lys Pro Gly Thr Ser Val Arg Ile Ser Cys Lys Thr Ser Gly Tyr Thr
35 40 45

Phe Thr Glu Tyr Thr Ile His Trp Val Lys Gln Ser His Gly Lys Ser
50 55 60

Leu Glu Trp Ile Gly Asn Ile Asn Pro Asn Asn Gly Gly Thr Thr Tyr
65 70 75 80

Asn Gln Lys Phe Glu Asp Lys Ala Thr Leu Thr Val Asp Lys Ser Ser
85 90 95

Ser Thr Ala Tyr Met Glu Leu Arg Ser Leu Thr Ser Glu Asp Ser Ala
100 105 110

Val Tyr Tyr Cys Ala Ala Gly Trp Asn Phe Asp Tyr Trp Gly Gln Gly
115 120 125

-continued

```
Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Gln Arg Trp Glu Leu Ala Leu Gly Arg
385                 390                 395                 400

Phe Leu Ala Tyr Leu Ser Trp Val Ser Thr Leu Ser Glu Gln Val Gln
                405                 410                 415

Glu Glu Leu Leu Ser Ser Gln Val Thr Gln Glu Leu Arg Ala Leu Met
            420                 425                 430

Asp Glu Thr Met Lys Glu Leu Lys Ala Tyr Lys Ser Glu Leu Glu Glu
        435                 440                 445

Gln Leu Thr Pro Val Ala Glu Glu Thr Arg Ala Arg Leu Ser Lys Glu
    450                 455                 460

Leu Gln Ala Ala Gln Ala Arg Leu Gly Ala Asp Met Glu Asp Val Arg
465                 470                 475                 480

Gly Arg Leu Val Gln Tyr Arg Gly Glu Val Gln Ala Met Leu Gly Gln
                485                 490                 495

Ser Thr Glu Glu Leu Arg Val Arg Leu Ala Ser His Leu Ile Ala Leu
            500                 505                 510

Gln Leu Arg Leu Ile Gly Asp Ala Phe Asp Leu Gln Lys Arg Leu Ala
        515                 520                 525

Val Tyr Gln Ala Gly Ala
    530
```

<210> SEQ ID NO 141
<211> LENGTH: 546
<212> TYPE: PRT
<213> ORGANISM: Artificial sequence
<220> FEATURE:
<223> OTHER INFORMATION: Homo sapiens

<400> SEQUENCE: 141

Val Gln Leu Gln Gln Ser Gly Pro Glu Leu Val Lys Pro Gly Thr Ser
1 5 10 15

Val Arg Ile Ser Cys Lys Thr Ser Gly Tyr Thr Phe Thr Glu Tyr Thr
20 25 30

Ile His Trp Val Lys Gln Ser His Gly Lys Ser Leu Glu Trp Ile Gly
35 40 45

Asn Ile Asn Pro Asn Asn Gly Gly Thr Thr Tyr Asn Gln Lys Phe Glu
50 55 60

Asp Lys Ala Thr Leu Thr Val Asp Lys Ser Ser Ser Thr Ala Tyr Met
65 70 75 80

Glu Leu Arg Ser Leu Thr Ser Glu Asp Ser Ala Val Tyr Tyr Cys Ala
85 90 95

Ala Gly Trp Asn Phe Asp Tyr Trp Gly Gln Gly Thr Thr Val Thr Val
100 105 110

Ser Ser Gly Gly Gly Gly Ser Gly Gly Gly Gly Ser Gly Gly Gly Gly
115 120 125

Ser Asp Ile Val Met Thr Gln Ser His Lys Phe Met Ser Thr Ser Val
130 135 140

Gly Asp Arg Val Ser Ile Ile Cys Lys Ala Ser Gln Asp Val Gly Thr
145 150 155 160

Ala Val Asp Trp Tyr Gln Gln Lys Pro Gly Gln Ser Pro Lys Leu Leu
165 170 175

Ile Tyr Trp Ala Ser Thr Arg His Thr Gly Val Pro Asp Arg Phe Thr
180 185 190

Gly Ser Gly Ser Gly Thr Asp Phe Thr Leu Thr Ile Thr Asn Val Gln
195 200 205

Ser Glu Asp Leu Ala Asp Tyr Phe Cys Gln Gln Tyr Asn Ser Tyr Pro
210 215 220

Leu Thr Phe Gly Ala Gly Thr Met Leu Asp Leu Lys Arg Ala Ser Thr
225 230 235 240

Thr Thr Pro Ala Pro Arg Pro Pro Thr Pro Ala Pro Thr Ile Ala Ser
245 250 255

Gln Pro Leu Ser Leu Arg Pro Glu Ala Cys Arg Pro Ala Ala Gly Gly
260 265 270

Ala Val His Thr Arg Gly Leu Asp Phe Ala Cys Asp Phe Trp Val Leu
275 280 285

Val Val Val Gly Gly Val Leu Ala Cys Tyr Ser Leu Leu Val Thr Val
290 295 300

Ala Phe Ile Ile Phe Trp Val Arg Ser Lys Arg Ser Arg Leu Leu His
305 310 315 320

Ser Asp Tyr Met Asn Met Thr Pro Arg Arg Pro Gly Pro Thr Arg Lys
325 330 335

His Tyr Gln Pro Tyr Ala Pro Pro Arg Asp Phe Ala Ala Tyr Arg Ser
340 345 350

His Met Gly Gly Gly Gly Ser Gly Gly Gly Gly Ser Gly Gly Gly Gly
355 360 365

```
Ser Gln Gln Arg Trp Glu Leu Ala Leu Gly Arg Phe Leu Ala Tyr Leu
    370                 375                 380

Ser Trp Val Ser Thr Leu Ser Glu Gln Val Gln Glu Glu Leu Leu Ser
385                 390                 395                 400

Ser Gln Val Thr Gln Glu Leu Arg Ala Leu Met Asp Glu Thr Met Lys
                405                 410                 415

Glu Leu Lys Ala Tyr Lys Ser Glu Leu Glu Glu Gln Leu Thr Pro Val
            420                 425                 430

Ala Glu Glu Thr Arg Ala Arg Leu Ser Lys Glu Leu Gln Ala Ala Gln
        435                 440                 445

Ala Arg Leu Gly Ala Asp Met Glu Asp Val Arg Gly Arg Leu Val Gln
    450                 455                 460

Tyr Arg Gly Glu Val Gln Ala Met Leu Gly Gln Ser Thr Glu Glu Leu
465                 470                 475                 480

Arg Val Arg Leu Ala Ser His Leu Ile Ala Leu Gln Leu Arg Leu Ile
                485                 490                 495

Gly Asp Ala Phe Asp Leu Gln Lys Arg Leu Ala Val Tyr Gln Ala Gly
            500                 505                 510

Ala Ala Glu Arg Lys Arg Arg Ser Gly Ser Gly Arg Ser Gly Ser Gly
        515                 520                 525

Glu Gly Arg Gly Ser Leu Leu Thr Cys Gly Asp Val Glu Glu Asn Pro
    530                 535                 540

Gly Pro
545
```

<210> SEQ ID NO 142
<211> LENGTH: 567
<212> TYPE: PRT
<213> ORGANISM: Artificial sequence
<220> FEATURE:
<223> OTHER INFORMATION: Homo sapiens

<400> SEQUENCE: 142

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175
```

-continued

```
Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Gln Arg Trp Glu Leu Ala Leu Gly Arg
385                 390                 395                 400

Phe Leu Ala Tyr Leu Ser Trp Val Ser Thr Leu Ser Glu Gln Val Gln
                405                 410                 415

Glu Glu Leu Leu Ser Ser Gln Val Thr Gln Glu Leu Arg Ala Leu Met
            420                 425                 430

Asp Glu Thr Met Lys Glu Leu Lys Ala Tyr Lys Ser Glu Leu Glu Glu
        435                 440                 445

Gln Leu Thr Pro Val Ala Glu Glu Thr Arg Ala Arg Leu Ser Lys Glu
    450                 455                 460

Leu Gln Ala Ala Gln Ala Arg Leu Gly Ala Asp Met Glu Asp Val Arg
465                 470                 475                 480

Gly Arg Leu Val Gln Tyr Arg Gly Glu Val Gln Ala Met Leu Gly Gln
                485                 490                 495

Ser Thr Glu Glu Leu Arg Val Arg Leu Ala Ser His Leu Ile Ala Leu
            500                 505                 510

Gln Leu Arg Leu Ile Gly Asp Ala Phe Asp Leu Gln Lys Arg Leu Ala
        515                 520                 525

Val Tyr Gln Ala Gly Ala Ala Glu Arg Lys Arg Arg Ser Gly Ser Gly
    530                 535                 540

Arg Ser Gly Ser Gly Glu Gly Arg Gly Ser Leu Leu Thr Cys Gly Asp
545                 550                 555                 560

Val Glu Glu Asn Pro Gly Pro
                565
```

<210> SEQ ID NO 143
<211> LENGTH: 545
<212> TYPE: PRT

<213> ORGANISM: Artificial sequence
<220> FEATURE:
<223> OTHER INFORMATION: Homo sapiens

<400> SEQUENCE: 143

Val Gln Leu Gln Gln Ser Gly Pro Glu Leu Val Lys Pro Gly Thr Ser
1 5 10 15

Val Arg Ile Ser Cys Lys Thr Ser Gly Tyr Thr Phe Thr Glu Tyr Thr
20 25 30

Ile His Trp Val Lys Gln Ser His Gly Lys Ser Leu Glu Trp Ile Gly
35 40 45

Asn Ile Asn Pro Asn Asn Gly Gly Thr Thr Tyr Asn Gln Lys Phe Glu
50 55 60

Asp Lys Ala Thr Leu Thr Val Asp Lys Ser Ser Ser Thr Ala Tyr Met
65 70 75 80

Glu Leu Arg Ser Leu Thr Ser Glu Asp Ser Ala Val Tyr Tyr Cys Ala
85 90 95

Ala Gly Trp Asn Phe Asp Tyr Trp Gly Gln Gly Thr Thr Val Thr Val
100 105 110

Ser Ser Gly Gly Gly Gly Ser Gly Gly Gly Gly Ser Gly Gly Gly Gly
115 120 125

Ser Asp Ile Val Met Thr Gln Ser His Lys Phe Met Ser Thr Ser Val
130 135 140

Gly Asp Arg Val Ser Ile Ile Cys Lys Ala Ser Gln Asp Val Gly Thr
145 150 155 160

Ala Val Asp Trp Tyr Gln Gln Lys Pro Gly Gln Ser Pro Lys Leu Leu
165 170 175

Ile Tyr Trp Ala Ser Thr Arg His Thr Gly Val Pro Asp Arg Phe Thr
180 185 190

Gly Ser Gly Ser Gly Thr Asp Phe Thr Leu Thr Ile Thr Asn Val Gln
195 200 205

Ser Glu Asp Leu Ala Asp Tyr Phe Cys Gln Gln Tyr Asn Ser Tyr Pro
210 215 220

Leu Thr Phe Gly Ala Gly Thr Met Leu Asp Leu Lys Arg Ala Ser Thr
225 230 235 240

Thr Thr Pro Ala Pro Arg Pro Pro Thr Pro Ala Pro Thr Ile Ala Ser
245 250 255

Gln Pro Leu Ser Leu Arg Pro Glu Ala Cys Arg Pro Ala Ala Gly Gly
260 265 270

Ala Val His Thr Arg Gly Leu Asp Phe Ala Cys Asp Phe Trp Val Leu
275 280 285

Val Val Val Gly Gly Val Leu Ala Cys Tyr Ser Leu Leu Val Thr Val
290 295 300

Ala Phe Ile Ile Phe Trp Val Arg Ser Lys Arg Ser Arg Leu Leu His
305 310 315 320

Ser Asp Tyr Met Asn Met Thr Pro Arg Arg Pro Gly Pro Thr Arg Lys
325 330 335

His Tyr Gln Pro Tyr Ala Pro Pro Arg Asp Phe Ala Ala Tyr Arg Ser
340 345 350

His Met Gly Gly Gly Gly Ser Gly Gly Gly Gly Ser Gly Gly Gly Gly
355 360 365

Ser Gln Arg Trp Glu Leu Ala Leu Gly Arg Phe Leu Glu Tyr Leu Ser
370 375 380

Trp Val Ser Thr Leu Ser Glu Gln Val Gln Glu Glu Leu Leu Ser Ser 385 390 395 400

Gln Val Thr Gln Glu Leu Arg Ala Leu Met Asp Glu Thr Met Lys Glu
405 410 415

Leu Lys Ala Tyr Lys Ser Glu Leu Glu Glu Gln Leu Thr Pro Val Ala
420 425 430

Glu Glu Thr Arg Ala Arg Leu Ser Lys Glu Leu Gln Ala Ala Gln Ala
435 440 445

Arg Leu Gly Ala Asp Met Glu Asp Val Arg Gly Arg Leu Val Gln Tyr
450 455 460

Arg Gly Glu Val Gln Ala Met Leu Gly Gln Ser Thr Glu Glu Leu Arg
465 470 475 480

Val Arg Leu Ala Ser His Leu Ile Ala Leu Gln Ala Arg Leu Ile Gly
485 490 495

Asp Ala Phe Asp Leu Gln Lys Arg Leu Ala Val Tyr Gln Ala Gly Ala
500 505 510

Ala Glu Arg Lys Arg Arg Ser Gly Ser Gly Arg Ser Gly Ser Gly Glu
515 520 525

Gly Arg Gly Ser Leu Leu Thr Cys Gly Asp Val Glu Glu Asn Pro Gly
530 535 540

Pro
545

<210> SEQ ID NO 144
<211> LENGTH: 533
<212> TYPE: PRT
<213> ORGANISM: Artificial sequence
<220> FEATURE:
<223> OTHER INFORMATION: Homo sapiens

<400> SEQUENCE: 144

Met Ala Leu Pro Val Thr Ala Leu Leu Leu Pro Leu Ala Leu Leu Leu
1 5 10 15

His Ala Ala Arg Pro Val Gln Leu Gln Gln Ser Gly Pro Glu Leu Val
20 25 30

Lys Pro Gly Thr Ser Val Arg Ile Ser Cys Lys Thr Ser Gly Tyr Thr
35 40 45

Phe Thr Glu Tyr Thr Ile His Trp Val Lys Gln Ser His Gly Lys Ser
50 55 60

Leu Glu Trp Ile Gly Asn Ile Asn Pro Asn Asn Gly Gly Thr Thr Tyr
65 70 75 80

Asn Gln Lys Phe Glu Asp Lys Ala Thr Leu Thr Val Asp Lys Ser Ser
85 90 95

Ser Thr Ala Tyr Met Glu Leu Arg Ser Leu Thr Ser Glu Asp Ser Ala
100 105 110

Val Tyr Tyr Cys Ala Ala Gly Trp Asn Phe Asp Tyr Trp Gly Gln Gly
115 120 125

Thr Thr Val Thr Val Ser Ser Gly Gly Gly Gly Ser Gly Gly Gly Gly
130 135 140

Ser Gly Gly Gly Gly Ser Asp Ile Val Met Thr Gln Ser His Lys Phe
145 150 155 160

Met Ser Thr Ser Val Gly Asp Arg Val Ser Ile Ile Cys Lys Ala Ser
165 170 175

Gln Asp Val Gly Thr Ala Val Asp Trp Tyr Gln Gln Lys Pro Gly Gln
180 185 190

Ser Pro Lys Leu Leu Ile Tyr Trp Ala Ser Thr Arg His Thr Gly Val

```
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Ala Arg Leu Ile Gly Asp Ala Phe Asp Leu Gln Lys Arg Leu Ala Val
        515                 520                 525

Tyr Gln Ala Gly Ala
    530
```

<210> SEQ ID NO 145
<211> LENGTH: 545
<212> TYPE: PRT
<213> ORGANISM: Artificial sequence
<220> FEATURE:
<223> OTHER INFORMATION: Homo sapiens

<400> SEQUENCE: 145

```
Val Gln Leu Gln Gln Ser Gly Pro Glu Leu Val Lys Pro Gly Thr Ser
1               5                   10                  15

Val Arg Ile Ser Cys Lys Thr Ser Gly Tyr Thr Phe Thr Glu Tyr Thr
```

-continued

```
            20                  25                  30

Ile His Trp Val Lys Gln Ser His Gly Lys Ser Leu Glu Trp Ile Gly
        35                  40                  45

Asn Ile Asn Pro Asn Asn Gly Gly Thr Thr Tyr Asn Gln Lys Phe Glu
    50                  55                  60

Asp Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Ala Gly Trp Asn Phe Asp Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Asp Ile Val Met Thr Gln Ser His Lys Phe Met Ser Thr Ser Val
    130                 135                 140

Gly Asp Arg Val Ser Ile Ile Cys Lys Ala Ser Gln Asp Val Gly Thr
145                 150                 155                 160

Ala Val Asp Trp Tyr Gln Gln Lys Pro Gly Gln Ser Pro Lys Leu Leu
                165                 170                 175

Ile Tyr Trp Ala Ser Thr Arg His Thr Gly Val Pro Asp Arg Phe Thr
            180                 185                 190

Gly Ser Gly Ser Gly Thr Asp Phe Thr Leu Thr Ile Thr Asn Val Gln
        195                 200                 205

Ser Glu Asp Leu Ala Asp Tyr Phe Cys Gln Gln Tyr Asn Ser Tyr Pro
    210                 215                 220

Leu Thr Phe Gly Ala Gly Thr Met Leu Asp Leu Lys Arg Ala Ser Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

His Met Gly Gly Gly Gly Ser Gly Gly Gly Gly Ser Gly Gly Gly Gly
        355                 360                 365

Ser Gln Arg Trp Glu Leu Ala Leu Gly Arg Phe Leu Glu Tyr Leu Ser
    370                 375                 380

Trp Val Ser Thr Leu Ser Glu Gln Val Gln Glu Glu Leu Leu Ser Ser
385                 390                 395                 400

Gln Val Thr Gln Glu Leu Arg Ala Leu Met Asp Glu Thr Met Lys Glu
                405                 410                 415

Leu Lys Ala Tyr Lys Ser Glu Leu Glu Glu Gln Leu Thr Pro Val Ala
            420                 425                 430

Glu Glu Thr Arg Ala Arg Leu Ser Lys Glu Leu Gln Ala Ala Gln Ala
        435                 440                 445
```

```
Arg Leu Gly Ala Asp Met Glu Asp Val Arg Gly Arg Leu Val Gln Tyr
    450                 455                 460

Arg Gly Glu Val Gln Ala Met Leu Gly Gln Ser Thr Glu Glu Leu Arg
465                 470                 475                 480

Val Arg Leu Ala Ser His Leu Ile Ala Leu Gln Leu Arg Leu Ile Gly
                485                 490                 495

Ala Ala Phe Asp Leu Gln Lys Arg Leu Ala Val Tyr Gln Ala Gly Ala
            500                 505                 510

Ala Glu Arg Lys Arg Arg Ser Gly Ser Gly Arg Ser Gly Ser Gly Glu
        515                 520                 525

Gly Arg Gly Ser Leu Leu Thr Cys Gly Asp Val Glu Glu Asn Pro Gly
    530                 535                 540

Pro
545


<210> SEQ ID NO 146
<211> LENGTH: 533
<212> TYPE: PRT
<213> ORGANISM: Artificial sequence
<220> FEATURE:
<223> OTHER INFORMATION: Homo sapiens

<400> SEQUENCE: 146

Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255
```

```
Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Ala Ala Phe Asp Leu Gln Lys Arg Leu Ala Val
        515                 520                 525

Tyr Gln Ala Gly Ala
    530
```

<210> SEQ ID NO 147
<211> LENGTH: 493
<212> TYPE: PRT
<213> ORGANISM: Artificial sequence
<220> FEATURE:
<223> OTHER INFORMATION: Homo sapiens

<400> SEQUENCE: 147

```
Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Gln
            20                  25                  30

Thr Thr Pro Gly Glu Arg Ser Ser Leu Pro Ala Phe Tyr Pro Gly Thr
        35                  40                  45

Ser Gly Ser Cys Ser Gly Cys Gly Ser Leu Ser Leu Pro Thr Thr Thr
    50                  55                  60

Pro Ala Pro Arg Pro Pro Thr Pro Ala Pro Thr Ile Ala Ser Gln Pro
65                  70                  75                  80
```

```
Leu Ser Leu Arg Pro Glu Ala Cys Arg Pro Ala Ala Gly Gly Ala Val
                85                  90                  95

His Thr Arg Gly Leu Asp Phe Ala Cys Asp Pro Arg Phe Trp Val Leu
            100                 105                 110

Val Val Val Gly Gly Val Leu Ala Cys Tyr Ser Leu Leu Val Thr Val
        115                 120                 125

Ala Phe Ile Ile Phe Trp Val Arg Ser Lys Arg Ser Arg Leu Leu His
    130                 135                 140

Ser Asp Tyr Met Asn Met Thr Pro Arg Arg Pro Gly Pro Thr Arg Lys
145                 150                 155                 160

His Tyr Gln Pro Tyr Ala Pro Pro Arg Asp Phe Ala Ala Tyr Arg Ser
                165                 170                 175

Pro Gly Gly Gly Gly Gly Ser Gly Gly Gly Gly Ser Gly Gly Gly Gly
            180                 185                 190

Ser Met Ser Gln Ser Asn Arg Glu Leu Val Val Asp Phe Leu Ser Tyr
        195                 200                 205

Lys Leu Ser Gln Lys Gly Tyr Ser Trp Ser Gln Phe Ser Asp Val Glu
    210                 215                 220

Glu Asn Arg Thr Glu Ala Pro Glu Gly Thr Glu Ser Glu Ala Val Lys
225                 230                 235                 240

Gln Ala Leu Arg Glu Ala Gly Asp Glu Phe Glu Leu Arg Tyr Arg Arg
                245                 250                 255

Ala Phe Ser Asp Leu Thr Ser Gln Leu His Ile Thr Pro Gly Thr Ala
            260                 265                 270

Tyr Gln Ser Phe Glu Gln Val Val Asn Glu Leu Phe Arg Asp Gly Val
        275                 280                 285

Asn Trp Gly Arg Ile Val Ala Phe Phe Ser Phe Gly Gly Ala Leu Cys
    290                 295                 300

Val Glu Ser Val Asp Lys Glu Met Gln Val Leu Val Ser Arg Ile Ala
305                 310                 315                 320

Ala Trp Met Ala Thr Tyr Leu Asn Asp His Leu Glu Pro Trp Ile Gln
                325                 330                 335

Glu Asn Gly Gly Trp Asp Thr Phe Val Glu Leu Tyr Gly Asn Asn Ala
            340                 345                 350

Ala Ala Glu Ser Arg Lys Gly Gln Glu Arg Glu Asp Gly Gly Gly Gly
        355                 360                 365

Ser Gly Gly Gly Gly Ser Gly Gly Gly Gly Ser Met His Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 148
<211> LENGTH: 472
<212> TYPE: PRT
<213> ORGANISM: Artificial sequence
<220> FEATURE:
<223> OTHER INFORMATION: Homo sapiens

<400> SEQUENCE: 148

```
Glu Gln Lys Leu Ile Ser Glu Glu Asp Leu Gln Thr Thr Pro Gly Glu
1               5                   10                  15

Arg Ser Ser Leu Pro Ala Phe Tyr Pro Gly Thr Ser Gly Ser Cys Ser
            20                  25                  30

Gly Cys Gly Ser Leu Ser Leu Pro Thr Thr Thr Pro Ala Pro Arg Pro
        35                  40                  45

Pro Thr Pro Ala Pro Thr Ile Ala Ser Gln Pro Leu Ser Leu Arg Pro
    50                  55                  60

Glu Ala Cys Arg Pro Ala Ala Gly Gly Ala Val His Thr Arg Gly Leu
65                  70                  75                  80

Asp Phe Ala Cys Asp Pro Arg Phe Trp Val Leu Val Val Val Gly Gly
                85                  90                  95

Val Leu Ala Cys Tyr Ser Leu Leu Val Thr Val Ala Phe Ile Ile Phe
            100                 105                 110

Trp Val Arg Ser Lys Arg Ser Arg Leu Leu His Ser Asp Tyr Met Asn
        115                 120                 125

Met Thr Pro Arg Arg Pro Gly Pro Thr Arg Lys His Tyr Gln Pro Tyr
    130                 135                 140

Ala Pro Pro Arg Asp Phe Ala Ala Tyr Arg Ser Pro Gly Gly Gly Gly
145                 150                 155                 160

Gly Ser Gly Gly Gly Gly Ser Gly Gly Gly Gly Ser Met Ser Gln Ser
                165                 170                 175

Asn Arg Glu Leu Val Val Asp Phe Leu Ser Tyr Lys Leu Ser Gln Lys
            180                 185                 190

Gly Tyr Ser Trp Ser Gln Phe Ser Asp Val Glu Glu Asn Arg Thr Glu
        195                 200                 205

Ala Pro Glu Gly Thr Glu Ser Glu Ala Val Lys Gln Ala Leu Arg Glu
    210                 215                 220

Ala Gly Asp Glu Phe Glu Leu Arg Tyr Arg Arg Ala Phe Ser Asp Leu
225                 230                 235                 240

Thr Ser Gln Leu His Ile Thr Pro Gly Thr Ala Tyr Gln Ser Phe Glu
                245                 250                 255

Gln Val Val Asn Glu Leu Phe Arg Asp Gly Val Asn Trp Gly Arg Ile
            260                 265                 270

Val Ala Phe Phe Ser Phe Gly Gly Ala Leu Cys Val Glu Ser Val Asp
        275                 280                 285

Lys Glu Met Gln Val Leu Val Ser Arg Ile Ala Ala Trp Met Ala Thr
    290                 295                 300

Tyr Leu Asn Asp His Leu Glu Pro Trp Ile Gln Glu Asn Gly Gly Trp
305                 310                 315                 320

Asp Thr Phe Val Glu Leu Tyr Gly Asn Asn Ala Ala Ala Glu Ser Arg
                325                 330                 335

Lys Gly Gln Glu Arg Glu Asp Gly Gly Gly Gly Ser Gly Gly Gly Gly
            340                 345                 350

Ser Gly Gly Gly Gly Ser Met His Arg Val Lys Phe Ser Arg Ser Ala
        355                 360                 365
```

```
Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470


<210> SEQ ID NO 149
<211> LENGTH: 491
<212> TYPE: PRT
<213> ORGANISM: Artificial sequence
<220> FEATURE:
<223> OTHER INFORMATION: Homo sapiens

<400> SEQUENCE: 149

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Gln
            20                  25                  30

Thr Thr Pro Gly Glu Arg Ser Ser Leu Pro Ala Phe Tyr Pro Gly Thr
        35                  40                  45

Ser Gly Ser Cys Ser Gly Cys Gly Ser Leu Ser Leu Pro Thr Thr Thr
    50                  55                  60

Pro Ala Pro Arg Pro Pro Thr Pro Ala Pro Thr Ile Ala Ser Gln Pro
65                  70                  75                  80

Leu Ser Leu Arg Pro Glu Ala Cys Arg Pro Ala Ala Gly Gly Ala Val
                85                  90                  95

His Thr Arg Gly Leu Asp Phe Ala Cys Asp Pro Arg Phe Trp Val Leu
            100                 105                 110

Val Val Val Gly Gly Val Leu Ala Cys Tyr Ser Leu Leu Val Thr Val
        115                 120                 125

Ala Phe Ile Ile Phe Trp Val Arg Ser Lys Arg Ser Arg Leu Leu His
    130                 135                 140

Ser Asp Tyr Met Asn Met Thr Pro Arg Arg Pro Gly Pro Thr Arg Lys
145                 150                 155                 160

His Tyr Gln Pro Tyr Ala Pro Pro Arg Asp Phe Ala Ala Tyr Arg Ser
                165                 170                 175

Pro Gly Gly Gly Gly Gly Ser Gly Gly Gly Gly Ser Gly Gly Gly Gly
            180                 185                 190

Ser Met Ser Gln Ser Asn Arg Glu Leu Val Val Asp Phe Leu Ser Tyr
        195                 200                 205

Lys Leu Ser Gln Lys Gly Tyr Ser Trp Ser Gln Phe Ser Asp Val Glu
    210                 215                 220

Glu Asn Arg Thr Glu Ala Pro Glu Gly Thr Glu Ser Glu Ala Val Lys
225                 230                 235                 240

Gln Ala Leu Arg Glu Ala Gly Asp Glu Phe Glu Leu Arg Tyr Arg Arg
                245                 250                 255
```

```
Ala Phe Ser Asp Leu Thr Ser Gln Leu His Ile Thr Pro Gly Thr Ala
            260                 265                 270

Tyr Gln Ser Phe Glu Gln Val Val Asn Glu Leu Phe Arg Asp Gly Val
        275                 280                 285

Asn Trp Gly Arg Ile Val Ala Phe Phe Ser Phe Gly Gly Ala Leu Cys
    290                 295                 300

Val Glu Ser Val Asp Lys Glu Met Gln Val Leu Val Ser Arg Ile Ala
305                 310                 315                 320

Ala Trp Met Ala Thr Tyr Leu Asn Asp His Leu Glu Pro Trp Ile Gln
                325                 330                 335

Glu Asn Gly Gly Trp Asp Thr Phe Val Glu Leu Tyr Gly Asn Asn Ala
            340                 345                 350

Ala Ala Glu Ser Arg Lys Gly Gln Glu Arg Gly Gly Gly Gly Ser Gly
        355                 360                 365

Gly Gly Gly Ser Gly Gly Gly Gly Ser Met His Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 150
<211> LENGTH: 470
<212> TYPE: PRT
<213> ORGANISM: Artificial sequence
<220> FEATURE:
<223> OTHER INFORMATION: Homo sapiens

<400> SEQUENCE: 150

```
Glu Gln Lys Leu Ile Ser Glu Glu Asp Leu Gln Thr Thr Pro Gly Glu
1               5                   10                  15

Arg Ser Ser Leu Pro Ala Phe Tyr Pro Gly Thr Ser Gly Ser Cys Ser
            20                  25                  30

Gly Cys Gly Ser Leu Ser Leu Pro Thr Thr Thr Pro Ala Pro Arg Pro
        35                  40                  45

Pro Thr Pro Ala Pro Thr Ile Ala Ser Gln Pro Leu Ser Leu Arg Pro
    50                  55                  60

Glu Ala Cys Arg Pro Ala Ala Gly Gly Ala Val His Thr Arg Gly Leu
65                  70                  75                  80

Asp Phe Ala Cys Asp Pro Arg Phe Trp Val Leu Val Val Val Gly Gly
                85                  90                  95

Val Leu Ala Cys Tyr Ser Leu Leu Val Thr Val Ala Phe Ile Ile Phe
            100                 105                 110

Trp Val Arg Ser Lys Arg Ser Arg Leu Leu His Ser Asp Tyr Met Asn
        115                 120                 125
```

```
Met Thr Pro Arg Arg Pro Gly Pro Thr Arg Lys His Tyr Gln Pro Tyr
    130                 135                 140

Ala Pro Pro Arg Asp Phe Ala Ala Tyr Arg Ser Pro Gly Gly Gly Gly
145                 150                 155                 160

Gly Ser Gly Gly Gly Gly Ser Gly Gly Gly Gly Ser Met Ser Gln Ser
                165                 170                 175

Asn Arg Glu Leu Val Val Asp Phe Leu Ser Tyr Lys Leu Ser Gln Lys
            180                 185                 190

Gly Tyr Ser Trp Ser Gln Phe Ser Asp Val Glu Glu Asn Arg Thr Glu
        195                 200                 205

Ala Pro Glu Gly Thr Glu Ser Glu Ala Val Lys Gln Ala Leu Arg Glu
    210                 215                 220

Ala Gly Asp Glu Phe Glu Leu Arg Tyr Arg Arg Ala Phe Ser Asp Leu
225                 230                 235                 240

Thr Ser Gln Leu His Ile Thr Pro Gly Thr Ala Tyr Gln Ser Phe Glu
                245                 250                 255

Gln Val Val Asn Glu Leu Phe Arg Asp Gly Val Asn Trp Gly Arg Ile
            260                 265                 270

Val Ala Phe Phe Ser Phe Gly Gly Ala Leu Cys Val Glu Ser Val Asp
        275                 280                 285

Lys Glu Met Gln Val Leu Val Ser Arg Ile Ala Ala Trp Met Ala Thr
    290                 295                 300

Tyr Leu Asn Asp His Leu Glu Pro Trp Ile Gln Glu Asn Gly Gly Trp
305                 310                 315                 320

Asp Thr Phe Val Glu Leu Tyr Gly Asn Asn Ala Ala Ala Glu Ser Arg
                325                 330                 335

Lys Gly Gln Glu Arg Gly Gly Gly Gly Ser Gly Gly Gly Gly Ser Gly
            340                 345                 350

Gly Gly Gly Ser Met His Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470
```

<210> SEQ ID NO 151
<211> LENGTH: 493
<212> TYPE: PRT
<213> ORGANISM: Artificial sequence
<220> FEATURE:
<223> OTHER INFORMATION: Homo sapiens

<400> SEQUENCE: 151

```
Met Ala Leu Pro Val Thr Ala Leu Leu Leu Pro Leu Ala Leu Leu Leu
1               5                   10                  15
```

```
His Ala Ala Arg Pro Glu Gln Lys Leu Ile Ser Glu Glu Asp Leu Gln
            20                  25                  30

Thr Thr Pro Gly Glu Arg Ser Ser Leu Pro Ala Phe Tyr Pro Gly Thr
        35                  40                  45

Ser Gly Ser Cys Ser Gly Cys Gly Ser Leu Ser Leu Pro Thr Thr Thr
    50                  55                  60

Pro Ala Pro Arg Pro Pro Thr Pro Ala Pro Thr Ile Ala Ser Gln Pro
65                  70                  75                  80

Leu Ser Leu Arg Pro Glu Ala Cys Arg Pro Ala Ala Gly Gly Ala Val
                85                  90                  95

His Thr Arg Gly Leu Asp Phe Ala Cys Asp Pro Arg Phe Trp Val Leu
            100                 105                 110

Val Val Val Gly Gly Val Leu Ala Cys Tyr Ser Leu Leu Val Thr Val
        115                 120                 125

Ala Phe Ile Ile Phe Trp Val Arg Ser Lys Arg Ser Arg Leu Leu His
    130                 135                 140

Ser Asp Tyr Met Asn Met Thr Pro Arg Arg Pro Gly Pro Thr Arg Lys
145                 150                 155                 160

His Tyr Gln Pro Tyr Ala Pro Pro Arg Asp Phe Ala Ala Tyr Arg Ser
                165                 170                 175

Pro Gly Gly Gly Gly Gly Ser Gly Gly Gly Gly Ser Gly Gly Gly Gly
            180                 185                 190

Ser Met Ser Gln Ser Asn Arg Glu Leu Val Val Asp Phe Leu Ser Tyr
        195                 200                 205

Lys Leu Ser Gln Lys Gly Tyr Ser Trp Ser Gln Phe Ser Asp Val Glu
    210                 215                 220

Glu Asn Arg Thr Glu Ala Pro Glu Gly Thr Glu Ser Glu Ala Val Lys
225                 230                 235                 240

Gln Ala Leu Arg Glu Ala Gly Asp Asp Phe Glu Leu Arg Tyr Arg Arg
                245                 250                 255

Ala Phe Ser Asp Leu Thr Ser Gln Leu His Ile Thr Pro Gly Thr Ala
            260                 265                 270

Tyr Gln Ser Phe Glu Gln Val Val Asn Glu Leu Phe Arg Asp Gly Val
        275                 280                 285

Asn Trp Gly Arg Ile Val Ala Phe Phe Ser Phe Gly Gly Ala Leu Cys
    290                 295                 300

Val Glu Ser Val Asp Lys Glu Met Gln Val Leu Val Ser Arg Ile Ala
305                 310                 315                 320

Ala Trp Met Ala Thr Tyr Leu Asn Asp His Leu Glu Pro Trp Ile Gln
                325                 330                 335

Glu Asn Gly Gly Trp Asp Thr Phe Val Glu Leu Tyr Gly Asn Asn Ala
            340                 345                 350

Ala Ala Glu Ser Arg Lys Gly Gln Glu Arg Glu Asp Gly Gly Gly Gly
        355                 360                 365

Ser Gly Gly Gly Gly Ser Gly Gly Gly Gly Ser Met His Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
```

-continued

```
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 152
<211> LENGTH: 472
<212> TYPE: PRT
<213> ORGANISM: Artificial sequence
<220> FEATURE:
<223> OTHER INFORMATION: Homo sapiens

<400> SEQUENCE: 152

Glu Gln Lys Leu Ile Ser Glu Glu Asp Leu Gln Thr Thr Pro Gly Glu
1               5                   10                  15

Arg Ser Ser Leu Pro Ala Phe Tyr Pro Gly Thr Ser Gly Ser Cys Ser
            20                  25                  30

Gly Cys Gly Ser Leu Ser Leu Pro Thr Thr Thr Pro Ala Pro Arg Pro
        35                  40                  45

Pro Thr Pro Ala Pro Thr Ile Ala Ser Gln Pro Leu Ser Leu Arg Pro
    50                  55                  60

Glu Ala Cys Arg Pro Ala Ala Gly Gly Ala Val His Thr Arg Gly Leu
65                  70                  75                  80

Asp Phe Ala Cys Asp Pro Arg Phe Trp Val Leu Val Val Val Gly Gly
                85                  90                  95

Val Leu Ala Cys Tyr Ser Leu Leu Val Thr Val Ala Phe Ile Ile Phe
            100                 105                 110

Trp Val Arg Ser Lys Arg Ser Arg Leu Leu His Ser Asp Tyr Met Asn
        115                 120                 125

Met Thr Pro Arg Arg Pro Gly Pro Thr Arg Lys His Tyr Gln Pro Tyr
    130                 135                 140

Ala Pro Pro Arg Asp Phe Ala Ala Tyr Arg Ser Pro Gly Gly Gly Gly
145                 150                 155                 160

Gly Ser Gly Gly Gly Gly Ser Gly Gly Gly Gly Ser Met Ser Gln Ser
                165                 170                 175

Asn Arg Glu Leu Val Val Asp Phe Leu Ser Tyr Lys Leu Ser Gln Lys
            180                 185                 190

Gly Tyr Ser Trp Ser Gln Phe Ser Asp Val Glu Glu Asn Arg Thr Glu
        195                 200                 205

Ala Pro Glu Gly Thr Glu Ser Glu Ala Val Lys Gln Ala Leu Arg Glu
    210                 215                 220

Ala Gly Asp Asp Phe Glu Leu Arg Tyr Arg Arg Ala Phe Ser Asp Leu
225                 230                 235                 240

Thr Ser Gln Leu His Ile Thr Pro Gly Thr Ala Tyr Gln Ser Phe Glu
                245                 250                 255

Gln Val Val Asn Glu Leu Phe Arg Asp Gly Val Asn Trp Gly Arg Ile
            260                 265                 270

Val Ala Phe Phe Ser Phe Gly Gly Ala Leu Cys Val Glu Ser Val Asp
        275                 280                 285

Lys Glu Met Gln Val Leu Val Ser Arg Ile Ala Ala Trp Met Ala Thr
    290                 295                 300

Tyr Leu Asn Asp His Leu Glu Pro Trp Ile Gln Glu Asn Gly Gly Trp
```

```
305                 310                 315                 320

Asp Thr Phe Val Glu Leu Tyr Gly Asn Asn Ala Ala Ala Glu Ser Arg
                325                 330                 335

Lys Gly Gln Glu Arg Glu Asp Gly Gly Gly Gly Ser Gly Gly Gly Gly
            340                 345                 350

Ser Gly Gly Gly Gly Ser Met His Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470


<210> SEQ ID NO 153
<211> LENGTH: 493
<212> TYPE: PRT
<213> ORGANISM: Artificial sequence
<220> FEATURE:
<223> OTHER INFORMATION: Homo sapiens

<400> SEQUENCE: 153

Gly Ser Met Ala Leu Pro Val Thr Ala Leu Leu Leu Pro Leu Ala Leu
1               5                   10                  15

Leu Leu His Ala Ala Arg Pro Glu Gln Lys Leu Ile Ser Glu Glu Asp
            20                  25                  30

Leu Gln Thr Thr Pro Gly Glu Arg Ser Ser Leu Pro Ala Phe Tyr Pro
        35                  40                  45

Gly Thr Ser Gly Ser Cys Ser Gly Cys Gly Ser Leu Ser Leu Pro Thr
    50                  55                  60

Thr Thr Pro Ala Pro Arg Pro Pro Thr Pro Ala Pro Thr Ile Ala Ser
65                  70                  75                  80

Gln Pro Leu Ser Leu Arg Pro Glu Ala Cys Arg Pro Ala Ala Gly Gly
                85                  90                  95

Ala Val His Thr Arg Gly Leu Asp Phe Ala Cys Asp Pro Arg Phe Trp
            100                 105                 110

Val Leu Val Val Val Gly Gly Val Leu Ala Cys Tyr Ser Leu Leu Val
        115                 120                 125

Thr Val Ala Phe Ile Ile Phe Trp Val Arg Ser Lys Arg Ser Arg Leu
    130                 135                 140

Leu His Ser Asp Tyr Met Asn Met Thr Pro Arg Arg Pro Gly Pro Thr
145                 150                 155                 160

Arg Lys His Tyr Gln Pro Tyr Ala Pro Pro Arg Asp Phe Ala Ala Tyr
                165                 170                 175

Arg Ser Pro Gly Gly Gly Gly Gly Ser Gly Gly Gly Gly Ser Gly Gly
            180                 185                 190

Gly Gly Ser Met Ser Gln Ser Asn Arg Glu Leu Val Val Asp Phe Leu
```

```
        195                 200                 205

Ser Tyr Lys Leu Ser Gln Lys Gly Tyr Ser Trp Ser Gln Phe Ser Asp
    210                 215                 220

Val Glu Glu Asn Arg Thr Glu Ala Pro Glu Gly Thr Glu Ser Glu Ala
225                 230                 235                 240

Val Lys Gln Ala Leu Arg Glu Ala Gly Asp Asp Phe Glu Leu Arg Tyr
                245                 250                 255

Arg Arg Ala Phe Ser Asp Leu Thr Ser Gln Leu His Ile Thr Pro Gly
            260                 265                 270

Thr Ala Tyr Gln Ser Phe Glu Gln Val Val Asn Glu Leu Phe Arg Asp
        275                 280                 285

Gly Val Asn Trp Gly Arg Ile Val Ala Phe Phe Ser Phe Gly Gly Ala
    290                 295                 300

Leu Cys Val Glu Ser Val Asp Lys Glu Met Gln Val Leu Val Ser Arg
305                 310                 315                 320

Ile Ala Ala Trp Met Ala Thr Tyr Leu Asn Asp His Leu Glu Pro Trp
                325                 330                 335

Ile Gln Glu Asn Gly Gly Trp Asp Thr Phe Val Glu Leu Tyr Gly Asn
            340                 345                 350

Asn Ala Ala Ala Glu Ser Arg Lys Gly Gln Glu Arg Gly Gly Gly Gly
        355                 360                 365

Ser Gly Gly Gly Gly Ser Gly Gly Gly Gly Ser Met His Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 154
<211> LENGTH: 491
<212> TYPE: PRT
<213> ORGANISM: Artificial sequence
<220> FEATURE:
<223> OTHER INFORMATION: Homo sapiens

<400> SEQUENCE: 154

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Gln
            20                  25                  30

Thr Thr Pro Gly Glu Arg Ser Ser Leu Pro Ala Phe Tyr Pro Gly Thr
        35                  40                  45

Ser Gly Ser Cys Ser Gly Cys Gly Ser Leu Ser Leu Pro Thr Thr Thr
    50                  55                  60

Pro Ala Pro Arg Pro Pro Thr Pro Ala Pro Thr Ile Ala Ser Gln Pro
```

-continued

```
65                  70                  75                  80

Leu Ser Leu Arg Pro Glu Ala Cys Arg Pro Ala Ala Gly Gly Ala Val
                85                  90                  95

His Thr Arg Gly Leu Asp Phe Ala Cys Asp Pro Arg Phe Trp Val Leu
            100                 105                 110

Val Val Val Gly Gly Val Leu Ala Cys Tyr Ser Leu Leu Val Thr Val
        115                 120                 125

Ala Phe Ile Ile Phe Trp Val Arg Ser Lys Arg Ser Arg Leu Leu His
    130                 135                 140

Ser Asp Tyr Met Asn Met Thr Pro Arg Arg Pro Gly Pro Thr Arg Lys
145                 150                 155                 160

His Tyr Gln Pro Tyr Ala Pro Pro Arg Asp Phe Ala Ala Tyr Arg Ser
                165                 170                 175

Pro Gly Gly Gly Gly Gly Ser Gly Gly Gly Gly Ser Gly Gly Gly Gly
            180                 185                 190

Ser Met Ser Gln Ser Asn Arg Glu Leu Val Val Asp Phe Leu Ser Tyr
        195                 200                 205

Lys Leu Ser Gln Lys Gly Tyr Ser Trp Ser Gln Phe Ser Asp Val Glu
    210                 215                 220

Glu Asn Arg Thr Glu Ala Pro Glu Gly Thr Glu Ser Glu Ala Val Lys
225                 230                 235                 240

Gln Ala Leu Arg Glu Ala Gly Asp Asp Phe Glu Leu Arg Tyr Arg Arg
                245                 250                 255

Ala Phe Ser Asp Leu Thr Ser Gln Leu His Ile Thr Pro Gly Thr Ala
            260                 265                 270

Tyr Gln Ser Phe Glu Gln Val Val Asn Glu Leu Phe Arg Asp Gly Val
        275                 280                 285

Asn Trp Gly Arg Ile Val Ala Phe Phe Ser Phe Gly Gly Ala Leu Cys
    290                 295                 300

Val Glu Ser Val Asp Lys Glu Met Gln Val Leu Val Ser Arg Ile Ala
305                 310                 315                 320

Ala Trp Met Ala Thr Tyr Leu Asn Asp His Leu Glu Pro Trp Ile Gln
                325                 330                 335

Glu Asn Gly Gly Trp Asp Thr Phe Val Glu Leu Tyr Gly Asn Asn Ala
            340                 345                 350

Ala Ala Glu Ser Arg Lys Gly Gln Glu Arg Gly Gly Gly Gly Ser Gly
        355                 360                 365

Gly Gly Gly Ser Gly Gly Gly Gly Ser Met His Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 155
<211> LENGTH: 470
<212> TYPE: PRT
<213> ORGANISM: Artificial sequence
<220> FEATURE:
<223> OTHER INFORMATION: Homo sapiens

<400> SEQUENCE: 155

Glu Gln Lys Leu Ile Ser Glu Glu Asp Leu Gln Thr Thr Pro Gly Glu
1 5 10 15

Arg Ser Ser Leu Pro Ala Phe Tyr Pro Gly Thr Ser Gly Ser Cys Ser
20 25 30

Gly Cys Gly Ser Leu Ser Leu Pro Thr Thr Thr Pro Ala Pro Arg Pro
35 40 45

Pro Thr Pro Ala Pro Thr Ile Ala Ser Gln Pro Leu Ser Leu Arg Pro
50 55 60

Glu Ala Cys Arg Pro Ala Ala Gly Gly Ala Val His Thr Arg Gly Leu
65 70 75 80

Asp Phe Ala Cys Asp Pro Arg Phe Trp Val Leu Val Val Val Gly Gly
85 90 95

Val Leu Ala Cys Tyr Ser Leu Leu Val Thr Val Ala Phe Ile Ile Phe
100 105 110

Trp Val Arg Ser Lys Arg Ser Arg Leu Leu His Ser Asp Tyr Met Asn
115 120 125

Met Thr Pro Arg Arg Pro Gly Pro Thr Arg Lys His Tyr Gln Pro Tyr
130 135 140

Ala Pro Pro Arg Asp Phe Ala Ala Tyr Arg Ser Pro Gly Gly Gly Gly
145 150 155 160

Gly Ser Gly Gly Gly Gly Ser Gly Gly Gly Gly Ser Met Ser Gln Ser
165 170 175

Asn Arg Glu Leu Val Val Asp Phe Leu Ser Tyr Lys Leu Ser Gln Lys
180 185 190

Gly Tyr Ser Trp Ser Gln Phe Ser Asp Val Glu Glu Asn Arg Thr Glu
195 200 205

Ala Pro Glu Gly Thr Glu Ser Glu Ala Val Lys Gln Ala Leu Arg Glu
210 215 220

Ala Gly Asp Asp Phe Glu Leu Arg Tyr Arg Arg Ala Phe Ser Asp Leu
225 230 235 240

Thr Ser Gln Leu His Ile Thr Pro Gly Thr Ala Tyr Gln Ser Phe Glu
245 250 255

Gln Val Val Asn Glu Leu Phe Arg Asp Gly Val Asn Trp Gly Arg Ile
260 265 270

Val Ala Phe Phe Ser Phe Gly Gly Ala Leu Cys Val Glu Ser Val Asp
275 280 285

Lys Glu Met Gln Val Leu Val Ser Arg Ile Ala Ala Trp Met Ala Thr
290 295 300

Tyr Leu Asn Asp His Leu Glu Pro Trp Ile Gln Glu Asn Gly Gly Trp
305 310 315 320

Asp Thr Phe Val Glu Leu Tyr Gly Asn Asn Ala Ala Ala Glu Ser Arg
325 330 335

Lys Gly Gln Glu Arg Gly Gly Gly Gly Ser Gly Gly Gly Gly Ser Gly
340 345 350

Gly Gly Gly Ser Met His Arg Val Lys Phe Ser Arg Ser Ala Asp Ala
355 360 365

```
Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470


<210> SEQ ID NO 156
<211> LENGTH: 529
<212> TYPE: PRT
<213> ORGANISM: Artificial sequence
<220> FEATURE:
<223> OTHER INFORMATION: Homo sapiens

<400> SEQUENCE: 156

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Gln
            20                  25                  30

Thr Thr Pro Gly Glu Arg Ser Ser Leu Pro Ala Phe Tyr Pro Gly Thr
        35                  40                  45

Ser Gly Ser Cys Ser Gly Cys Gly Ser Leu Ser Leu Pro Thr Thr Thr
    50                  55                  60

Pro Ala Pro Arg Pro Pro Thr Pro Ala Pro Thr Ile Ala Ser Gln Pro
65                  70                  75                  80

Leu Ser Leu Arg Pro Glu Ala Cys Arg Pro Ala Ala Gly Gly Ala Val
                85                  90                  95

His Thr Arg Gly Leu Asp Phe Ala Cys Asp Pro Arg Phe Trp Val Leu
            100                 105                 110

Val Val Val Gly Gly Val Leu Ala Cys Tyr Ser Leu Leu Val Thr Val
        115                 120                 125

Ala Phe Ile Ile Phe Trp Val Arg Ser Lys Arg Ser Arg Leu Leu His
    130                 135                 140

Ser Asp Tyr Met Asn Met Thr Pro Arg Arg Pro Gly Pro Thr Arg Lys
145                 150                 155                 160

His Tyr Gln Pro Tyr Ala Pro Pro Arg Asp Phe Ala Ala Tyr Arg Ser
                165                 170                 175

Pro Gly Gly Gly Gly Gly Ser Gly Gly Gly Gly Ser Gly Gly Gly Gly
            180                 185                 190

Ser Met Ala His Ala Gly Arg Thr Gly Tyr Asp Asn Arg Glu Ile Val
        195                 200                 205

Met Lys Tyr Ile His Tyr Lys Leu Ser Gln Arg Gly Tyr Glu Trp Asp
    210                 215                 220

Ala Gly Asp Val Gly Ala Ala Pro Pro Gly Ala Ala Pro Ala Pro Gly
225                 230                 235                 240

Ile Phe Ser Ser Gln Pro Gly His Thr Pro His Pro Ala Ala Ser Arg
                245                 250                 255
```

Asp Pro Val Ala Arg Thr Ser Pro Leu Gln Thr Pro Ala Ala Pro Gly
260 265 270

Ala Ala Ala Gly Pro Ala Leu Ser Pro Val Pro Pro Val Val His Leu
275 280 285

Thr Leu Arg Gln Ala Gly Asp Asp Phe Ser Arg Arg Tyr Arg Arg Asp
290 295 300

Phe Ala Glu Met Ser Ser Gln Leu His Leu Thr Pro Phe Thr Ala Arg
305 310 315 320

Gly Arg Phe Ala Thr Val Val Glu Glu Leu Phe Arg Asp Gly Val Asn
325 330 335

Trp Gly Arg Ile Val Ala Phe Phe Glu Phe Gly Gly Val Met Cys Val
340 345 350

Glu Ser Val Asn Arg Glu Met Ser Pro Leu Val Asp Asn Ile Ala Leu
355 360 365

Trp Met Thr Glu Tyr Leu Asn Arg His Leu His Thr Trp Ile Gln Asp
370 375 380

Asn Gly Gly Trp Asp Ala Phe Val Glu Leu Tyr Gly Pro Ser Met Arg
385 390 395 400

Gly Gly Gly Gly Ser Gly Gly Gly Gly Ser Gly Gly Gly Gly Ser Met
405 410 415

His Arg Val Lys Phe Ser Arg Ser Ala Asp Ala Pro Ala Tyr Gln Gln
420 425 430

Gly Gln Asn Gln Leu Tyr Asn Glu Leu Asn Leu Gly Arg Arg Glu Glu
435 440 445

Tyr Asp Val Leu Asp Lys Arg Arg Gly Arg Asp Pro Glu Met Gly Gly
450 455 460

Lys Pro Arg Arg Lys Asn Pro Gln Glu Gly Leu Tyr Asn Glu Leu Gln
465 470 475 480

Lys Asp Lys Met Ala Glu Ala Tyr Ser Glu Ile Gly Met Lys Gly Glu
485 490 495

Arg Arg Arg Gly Lys Gly His Asp Gly Leu Tyr Gln Gly Leu Ser Thr
500 505 510

Ala Thr Lys Asp Thr Tyr Asp Ala Leu His Met Gln Ala Leu Pro Pro
515 520 525

Arg

<210> SEQ ID NO 157
<211> LENGTH: 508
<212> TYPE: PRT
<213> ORGANISM: Artificial sequence
<220> FEATURE:
<223> OTHER INFORMATION: Homo sapiens

<400> SEQUENCE: 157

Glu Gln Lys Leu Ile Ser Glu Glu Asp Leu Gln Thr Thr Pro Gly Glu
1 5 10 15

Arg Ser Ser Leu Pro Ala Phe Tyr Pro Gly Thr Ser Gly Ser Cys Ser
20 25 30

Gly Cys Gly Ser Leu Ser Leu Pro Thr Thr Thr Pro Ala Pro Arg Pro
35 40 45

Pro Thr Pro Ala Pro Thr Ile Ala Ser Gln Pro Leu Ser Leu Arg Pro
50 55 60

Glu Ala Cys Arg Pro Ala Ala Gly Gly Ala Val His Thr Arg Gly Leu
65 70 75 80

```
Asp Phe Ala Cys Asp Pro Arg Phe Trp Val Leu Val Val Val Gly Gly
                85                  90                  95

Val Leu Ala Cys Tyr Ser Leu Leu Val Thr Val Ala Phe Ile Ile Phe
            100                 105                 110

Trp Val Arg Ser Lys Arg Ser Arg Leu Leu His Ser Asp Tyr Met Asn
        115                 120                 125

Met Thr Pro Arg Arg Pro Gly Pro Thr Arg Lys His Tyr Gln Pro Tyr
    130                 135                 140

Ala Pro Pro Arg Asp Phe Ala Ala Tyr Arg Ser Pro Gly Gly Gly Gly
145                 150                 155                 160

Gly Ser Gly Gly Gly Gly Ser Gly Gly Gly Gly Ser Met Ala His Ala
                165                 170                 175

Gly Arg Thr Gly Tyr Asp Asn Arg Glu Ile Val Met Lys Tyr Ile His
            180                 185                 190

Tyr Lys Leu Ser Gln Arg Gly Tyr Glu Trp Asp Ala Gly Asp Val Gly
        195                 200                 205

Ala Ala Pro Pro Gly Ala Ala Pro Ala Pro Gly Ile Phe Ser Ser Gln
    210                 215                 220

Pro Gly His Thr Pro His Pro Ala Ala Ser Arg Asp Pro Val Ala Arg
225                 230                 235                 240

Thr Ser Pro Leu Gln Thr Pro Ala Ala Pro Gly Ala Ala Ala Gly Pro
                245                 250                 255

Ala Leu Ser Pro Val Pro Pro Val Val His Leu Thr Leu Arg Gln Ala
            260                 265                 270

Gly Asp Asp Phe Ser Arg Arg Tyr Arg Arg Asp Phe Ala Glu Met Ser
        275                 280                 285

Ser Gln Leu His Leu Thr Pro Phe Thr Ala Arg Gly Arg Phe Ala Thr
    290                 295                 300

Val Val Glu Glu Leu Phe Arg Asp Gly Val Asn Trp Gly Arg Ile Val
305                 310                 315                 320

Ala Phe Phe Glu Phe Gly Gly Val Met Cys Val Glu Ser Val Asn Arg
                325                 330                 335

Glu Met Ser Pro Leu Val Asp Asn Ile Ala Leu Trp Met Thr Glu Tyr
            340                 345                 350

Leu Asn Arg His Leu His Thr Trp Ile Gln Asp Asn Gly Gly Trp Asp
        355                 360                 365

Ala Phe Val Glu Leu Tyr Gly Pro Ser Met Arg Gly Gly Gly Gly Ser
    370                 375                 380

Gly Gly Gly Gly Ser Gly Gly Gly Gly Ser Met His Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
```

500 505

<210> SEQ ID NO 158
<211> LENGTH: 114
<212> TYPE: PRT
<213> ORGANISM: Homo sapiens

<400> SEQUENCE: 158

Ser Gly Pro Gly Leu Val Ala Pro Ser Gln Ser Leu Ser Val Thr Cys
1 5 10 15

Thr Val Ser Gly Val Ser Leu Pro Asp Tyr Gly Val Ser Trp Ile Arg
20 25 30

Gln Pro Pro Arg Lys Gly Leu Glu Trp Leu Gly Val Ile Trp Gly Ser
35 40 45

Glu Thr Thr Tyr Tyr Asn Ser Ala Leu Lys Ser Arg Leu Thr Ile Ile
50 55 60

Lys Asp Asn Ser Lys Ser Gln Val Phe Leu Lys Met Asn Ser Leu Gln
65 70 75 80

Thr Asp Asp Thr Ala Ile Tyr Tyr Cys Ala Lys His Tyr Tyr Tyr Gly
85 90 95

Gly Ser Tyr Ala Met Asp Tyr Trp Gly Gln Gly Thr Ser Val Thr Val
100 105 110

Ser Ser

<210> SEQ ID NO 159
<211> LENGTH: 545
<212> TYPE: PRT
<213> ORGANISM: Artificial sequence
<220> FEATURE:
<223> OTHER INFORMATION: Homo sapiens

<400> SEQUENCE: 159

Val Gln Leu Gln Gln Ser Gly Pro Glu Leu Val Lys Pro Gly Thr Ser
1 5 10 15

Val Arg Ile Ser Cys Lys Thr Ser Gly Tyr Thr Phe Thr Glu Tyr Thr
20 25 30

Ile His Trp Val Lys Gln Ser His Gly Lys Ser Leu Glu Trp Ile Gly
35 40 45

Asn Ile Asn Pro Asn Asn Gly Gly Thr Thr Tyr Asn Gln Lys Phe Glu
50 55 60

Asp Lys Ala Thr Leu Thr Val Asp Lys Ser Ser Ser Thr Ala Tyr Met
65 70 75 80

Glu Leu Arg Ser Leu Thr Ser Glu Asp Ser Ala Val Tyr Tyr Cys Ala
85 90 95

Ala Gly Trp Asn Phe Asp Tyr Trp Gly Gln Gly Thr Thr Val Thr Val
100 105 110

Ser Ser Gly Gly Gly Gly Ser Gly Gly Gly Gly Ser Gly Gly Gly Gly
115 120 125

Ser Asp Ile Val Met Thr Gln Ser His Lys Phe Met Ser Thr Ser Val
130 135 140

Gly Asp Arg Val Ser Ile Ile Cys Lys Ala Ser Gln Asp Val Gly Thr
145 150 155 160

Ala Val Asp Trp Tyr Gln Gln Lys Pro Gly Gln Ser Pro Lys Leu Leu
165 170 175

Ile Tyr Trp Ala Ser Thr Arg His Thr Gly Val Pro Asp Arg Phe Thr
180 185 190

```
Gly Ser Gly Ser Gly Thr Asp Phe Thr Leu Thr Ile Thr Asn Val Gln
        195                 200                 205

Ser Glu Asp Leu Ala Asp Tyr Phe Cys Gln Gln Tyr Asn Ser Tyr Pro
    210                 215                 220

Leu Thr Phe Gly Ala Gly Thr Met Leu Asp Leu Lys Arg Ala Ser Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

His Met Gly Gly Gly Gly Ser Gly Gly Gly Gly Ser Gly Gly Gly Gly
        355                 360                 365

Ser Gln Arg Trp Glu Leu Ala Leu Gly Arg Phe Leu Glu Tyr Leu Ser
    370                 375                 380

Trp Val Ser Thr Leu Ser Glu Gln Val Gln Glu Glu Leu Leu Ser Ser
385                 390                 395                 400

Gln Val Thr Gln Glu Leu Arg Ala Leu Met Asp Glu Thr Met Lys Glu
                405                 410                 415

Leu Lys Ala Tyr Lys Ser Glu Leu Glu Glu Gln Leu Thr Pro Val Ala
            420                 425                 430

Glu Glu Thr Arg Ala Arg Leu Ser Lys Glu Leu Gln Ala Ala Gln Ala
        435                 440                 445

Arg Leu Gly Ala Asp Met Glu Asp Val Arg Gly Arg Leu Val Gln Tyr
    450                 455                 460

Arg Gly Glu Val Gln Ala Met Leu Gly Gln Ser Thr Glu Glu Leu Arg
465                 470                 475                 480

Val Arg Leu Ala Ser His Leu Ile Ala Leu Gln Leu Arg Leu Ile Gly
                485                 490                 495

Asp Ala Phe Asp Leu Gln Lys Arg Leu Ala Val Tyr Gln Ala Gly Ala
            500                 505                 510

Ala Glu Arg Lys Arg Arg Ser Gly Ser Gly Arg Ser Gly Ser Gly Glu
        515                 520                 525

Gly Arg Gly Ser Leu Leu Thr Cys Gly Asp Val Glu Glu Asn Pro Gly
    530                 535                 540

Pro
545
```

<210> SEQ ID NO 160
<211> LENGTH: 533
<212> TYPE: PRT
<213> ORGANISM: Artificial sequence
<220> FEATURE:
<223> OTHER INFORMATION: Homo sapiens

<400> SEQUENCE: 160

-continued

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Val
            20                  25                  30

Lys Pro Gly Thr Ser Val Arg Ile Ser Cys Lys Thr Ser Gly Tyr Thr
        35                  40                  45

Phe Thr Glu Tyr Thr Ile His Trp Val Lys Gln Ser His Gly Lys Ser
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
```

```
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Asp Ala Phe Asp Leu Gln Lys Arg Leu Ala Val
        515                 520                 525

Tyr Gln Ala Gly Ala
    530


<210> SEQ ID NO 161
<211> LENGTH: 545
<212> TYPE: PRT
<213> ORGANISM: Artificial sequence
<220> FEATURE:
<223> OTHER INFORMATION: Homo sapiens

<400> SEQUENCE: 161

Val Gln Leu Gln Gln Ser Gly Pro Glu Leu Val Lys Pro Gly Thr Ser
1               5                   10                  15

Val Arg Ile Ser Cys Lys Thr Ser Gly Tyr Thr Phe Thr Glu Tyr Thr
            20                  25                  30

Ile His Trp Val Lys Gln Ser His Gly Lys Ser Leu Glu Trp Ile Gly
        35                  40                  45

Asn Ile Asn Pro Asn Asn Gly Gly Thr Thr Tyr Asn Gln Lys Phe Glu
    50                  55                  60

Asp Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Ala Gly Trp Asn Phe Asp Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Asp Ile Val Met Thr Gln Ser His Lys Phe Met Ser Thr Ser Val
    130                 135                 140

Gly Asp Arg Val Ser Ile Ile Cys Lys Ala Ser Gln Asp Val Gly Thr
145                 150                 155                 160

Ala Val Asp Trp Tyr Gln Gln Lys Pro Gly Gln Ser Pro Lys Leu Leu
                165                 170                 175

Ile Tyr Trp Ala Ser Thr Arg His Thr Gly Val Pro Asp Arg Phe Thr
            180                 185                 190

Gly Ser Gly Ser Gly Thr Asp Phe Thr Leu Thr Ile Thr Asn Val Gln
        195                 200                 205

Ser Glu Asp Leu Ala Asp Tyr Phe Cys Gln Gln Tyr Asn Ser Tyr Pro
    210                 215                 220

Leu Thr Phe Gly Ala Gly Thr Met Leu Asp Leu Lys Arg Ala Ser Thr
225                 230                 235                 240

Thr Thr Pro Ala Pro Arg Pro Pro Thr Pro Ala Pro Thr Ile Ala Ser
```

-continued 245 250 255

Gln Pro Leu Ser Leu Arg Pro Glu Ala Cys Arg Pro Ala Ala Gly Gly
260 265 270

Ala Val His Thr Arg Gly Leu Asp Phe Ala Cys Asp Phe Trp Val Leu
275 280 285

Val Val Val Gly Gly Val Leu Ala Cys Tyr Ser Leu Leu Val Thr Val
290 295 300

Ala Phe Ile Ile Phe Trp Val Arg Ser Lys Arg Ser Arg Leu Leu His
305 310 315 320

Ser Asp Tyr Met Asn Met Thr Pro Arg Arg Pro Gly Pro Thr Arg Lys
325 330 335

His Tyr Gln Pro Tyr Ala Pro Pro Arg Asp Phe Ala Ala Tyr Arg Ser
340 345 350

His Met Gly Gly Gly Gly Ser Gly Gly Gly Gly Ser Gly Gly Gly Gly
355 360 365

Ser Gln Arg Trp Glu Leu Ala Leu Gly Arg Phe Leu Glu Tyr Leu Ser
370 375 380

Trp Val Ser Thr Leu Ser Glu Gln Val Gln Glu Glu Leu Leu Ser Ser
385 390 395 400

Gln Val Thr Gln Glu Leu Arg Ala Leu Met Asp Glu Thr Met Lys Glu
405 410 415

Leu Lys Ala Tyr Lys Ser Glu Leu Glu Glu Gln Leu Thr Pro Val Ala
420 425 430

Glu Glu Thr Arg Ala Arg Leu Ser Lys Glu Leu Gln Ala Ala Gln Ala
435 440 445

Arg Leu Gly Ala Asp Met Glu Asp Val Arg Gly Arg Leu Val Gln Tyr
450 455 460

Arg Gly Glu Val Gln Ala Met Leu Gly Gln Ser Thr Glu Glu Leu Arg
465 470 475 480

Val Arg Leu Ala Ser His Leu Ile Ala Leu Gln Ala Arg Leu Ile Gly
485 490 495

Asp Ala Phe Asp Leu Gln Lys Arg Leu Ala Val Tyr Gln Ala Gly Ala
500 505 510

Ala Glu Arg Lys Arg Arg Ser Gly Ser Gly Arg Ser Gly Ser Gly Glu
515 520 525

Gly Arg Gly Ser Leu Leu Thr Cys Gly Asp Val Glu Glu Asn Pro Gly
530 535 540

Pro
545

<210> SEQ ID NO 162
<211> LENGTH: 533
<212> TYPE: PRT
<213> ORGANISM: Artificial sequence
<220> FEATURE:
<223> OTHER INFORMATION: Homo sapiens

<400> SEQUENCE: 162

Met Ala Leu Pro Val Thr Ala Leu Leu Leu Pro Leu Ala Leu Leu Leu
1 5 10 15

His Ala Ala Arg Pro Val Gln Leu Gln Gln Ser Gly Pro Glu Leu Val
20 25 30

Lys Pro Gly Thr Ser Val Arg Ile Ser Cys Lys Thr Ser Gly Tyr Thr
35 40 45

Phe Thr Glu Tyr Thr Ile His Trp Val Lys Gln Ser His Gly Lys Ser

-continued

```
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Ser
                85                  90                  95

Ser Thr Ala Tyr Met Glu Leu Arg Ser Leu Thr Ser Glu Asp Ser Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480
```

```
Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Ala Arg Leu Ile Gly Asp Ala Phe Asp Leu Gln Lys Arg Leu Ala Val
        515                 520                 525

Tyr Gln Ala Gly Ala
    530
```

<210> SEQ ID NO 163
<211> LENGTH: 545
<212> TYPE: PRT
<213> ORGANISM: Artificial sequence
<220> FEATURE:
<223> OTHER INFORMATION: Homo sapiens

<400> SEQUENCE: 163

```
Val Gln Leu Gln Gln Ser Gly Pro Glu Leu Val Lys Pro Gly Thr Ser
1               5                   10                  15

Val Arg Ile Ser Cys Lys Thr Ser Gly Tyr Thr Phe Thr Glu Tyr Thr
            20                  25                  30

Ile His Trp Val Lys Gln Ser His Gly Lys Ser Leu Glu Trp Ile Gly
        35                  40                  45

Asn Ile Asn Pro Asn Asn Gly Gly Thr Thr Tyr Asn Gln Lys Phe Glu
    50                  55                  60

Asp Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Ala Gly Trp Asn Phe Asp Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Asp Ile Val Met Thr Gln Ser His Lys Phe Met Ser Thr Ser Val
    130                 135                 140

Gly Asp Arg Val Ser Ile Ile Cys Lys Ala Ser Gln Asp Val Gly Thr
145                 150                 155                 160

Ala Val Asp Trp Tyr Gln Gln Lys Pro Gly Gln Ser Pro Lys Leu Leu
                165                 170                 175

Ile Tyr Trp Ala Ser Thr Arg His Thr Gly Val Pro Asp Arg Phe Thr
            180                 185                 190

Gly Ser Gly Ser Gly Thr Asp Phe Thr Leu Thr Ile Thr Asn Val Gln
        195                 200                 205

Ser Glu Asp Leu Ala Asp Tyr Phe Cys Gln Gln Tyr Asn Ser Tyr Pro
    210                 215                 220

Leu Thr Phe Gly Ala Gly Thr Met Leu Asp Leu Lys Arg Ala Ser Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Phe Trp Val Leu
        275                 280                 285

Val Val Val Gly Gly Val Leu Ala Cys Tyr Ser Leu Leu Val Thr Val
    290                 295                 300
```

Ala Phe Ile Ile Phe Trp Val Arg Ser Lys Arg Ser Arg Leu Leu His
305 310 315 320

Ser Asp Tyr Met Asn Met Thr Pro Arg Arg Pro Gly Pro Thr Arg Lys
325 330 335

His Tyr Gln Pro Tyr Ala Pro Pro Arg Asp Phe Ala Ala Tyr Arg Ser
340 345 350

His Met Gly Gly Gly Gly Ser Gly Gly Gly Gly Ser Gly Gly Gly Gly
355 360 365

Ser Gln Arg Trp Glu Leu Ala Leu Gly Arg Phe Leu Glu Tyr Leu Ser
370 375 380

Trp Val Ser Thr Leu Ser Glu Gln Val Gln Glu Glu Leu Leu Ser Ser
385 390 395 400

Gln Val Thr Gln Glu Leu Arg Ala Leu Met Asp Glu Thr Met Lys Glu
405 410 415

Leu Lys Ala Tyr Lys Ser Glu Leu Glu Glu Gln Leu Thr Pro Val Ala
420 425 430

Glu Glu Thr Arg Ala Arg Leu Ser Lys Glu Leu Gln Ala Ala Gln Ala
435 440 445

Arg Leu Gly Ala Asp Met Glu Asp Val Arg Gly Arg Leu Val Gln Tyr
450 455 460

Arg Gly Glu Val Gln Ala Met Leu Gly Gln Ser Thr Glu Glu Leu Arg
465 470 475 480

Val Arg Leu Ala Ser His Leu Ile Ala Leu Gln Leu Arg Leu Ile Gly
485 490 495

Ala Ala Phe Asp Leu Gln Lys Arg Leu Ala Val Tyr Gln Ala Gly Ala
500 505 510

Ala Glu Arg Lys Arg Arg Ser Gly Ser Gly Arg Ser Gly Ser Gly Glu
515 520 525

Gly Arg Gly Ser Leu Leu Thr Cys Gly Asp Val Glu Glu Asn Pro Gly
530 535 540

Pro
545

<210> SEQ ID NO 164
<211> LENGTH: 533
<212> TYPE: PRT
<213> ORGANISM: Artificial sequence
<220> FEATURE:
<223> OTHER INFORMATION: Homo sapiens

<400> SEQUENCE: 164

Met Ala Leu Pro Val Thr Ala Leu Leu Leu Pro Leu Ala Leu Leu Leu
1 5 10 15

His Ala Ala Arg Pro Val Gln Leu Gln Gln Ser Gly Pro Glu Leu Val
20 25 30

Lys Pro Gly Thr Ser Val Arg Ile Ser Cys Lys Thr Ser Gly Tyr Thr
35 40 45

Phe Thr Glu Tyr Thr Ile His Trp Val Lys Gln Ser His Gly Lys Ser
50 55 60

Leu Glu Trp Ile Gly Asn Ile Asn Pro Asn Asn Gly Gly Thr Thr Tyr
65 70 75 80

Asn Gln Lys Phe Glu Asp Lys Ala Thr Leu Thr Val Asp Lys Ser Ser
85 90 95

Ser Thr Ala Tyr Met Glu Leu Arg Ser Leu Thr Ser Glu Asp Ser Ala
100 105 110

-continued

```
Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Arg Ala Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser His Met Gly Gly Gly Gly Ser Gly Gly Gly Gly
    370                 375                 380

Ser Gly Gly Gly Gly Ser Gln Arg Trp Glu Leu Ala Leu Gly Arg Phe
385                 390                 395                 400

Leu Glu Tyr Leu Ser Trp Val Ser Thr Leu Ser Glu Gln Val Gln Glu
                405                 410                 415

Glu Leu Leu Ser Ser Gln Val Thr Gln Glu Leu Arg Ala Leu Met Asp
            420                 425                 430

Glu Thr Met Lys Glu Leu Lys Ala Tyr Lys Ser Glu Leu Glu Glu Gln
        435                 440                 445

Leu Thr Pro Val Ala Glu Glu Thr Arg Ala Arg Leu Ser Lys Glu Leu
    450                 455                 460

Gln Ala Ala Gln Ala Arg Leu Gly Ala Asp Met Glu Asp Val Arg Gly
465                 470                 475                 480

Arg Leu Val Gln Tyr Arg Gly Glu Val Gln Ala Met Leu Gly Gln Ser
                485                 490                 495

Thr Glu Glu Leu Arg Val Arg Leu Ala Ser His Leu Ile Ala Leu Gln
            500                 505                 510

Leu Arg Leu Ile Gly Ala Ala Phe Asp Leu Gln Lys Arg Leu Ala Val
        515                 520                 525
```

```
Tyr Gln Ala Gly Ala
    530


<210> SEQ ID NO 165
<211> LENGTH: 472
<212> TYPE: PRT
<213> ORGANISM: Artificial sequence
<220> FEATURE:
<223> OTHER INFORMATION: Homo sapiens

<400> SEQUENCE: 165

Glu Gln Lys Leu Ile Ser Glu Glu Asp Leu Gln Thr Thr Pro Gly Glu
1               5                   10                  15

Arg Ser Ser Leu Pro Ala Phe Tyr Pro Gly Thr Ser Gly Ser Cys Ser
            20                  25                  30

Gly Cys Gly Ser Leu Ser Leu Pro Thr Thr Thr Pro Ala Pro Arg Pro
        35                  40                  45

Pro Thr Pro Ala Pro Thr Ile Ala Ser Gln Pro Leu Ser Leu Arg Pro
    50                  55                  60

Glu Ala Cys Arg Pro Ala Ala Gly Gly Ala Val His Thr Arg Gly Leu
65                  70                  75                  80

Asp Phe Ala Cys Asp Pro Arg Phe Trp Val Leu Val Val Val Gly Gly
                85                  90                  95

Val Leu Ala Cys Tyr Ser Leu Leu Val Thr Val Ala Phe Ile Ile Phe
            100                 105                 110

Trp Val Arg Ser Lys Arg Ser Arg Leu Leu His Ser Asp Tyr Met Asn
        115                 120                 125

Met Thr Pro Arg Arg Pro Gly Pro Thr Arg Lys His Tyr Gln Pro Tyr
    130                 135                 140

Ala Pro Pro Arg Asp Phe Ala Ala Tyr Arg Ser Pro Gly Gly Gly Gly
145                 150                 155                 160

Gly Ser Gly Gly Gly Gly Ser Gly Gly Gly Gly Ser Met Ser Gln Ser
                165                 170                 175

Asn Arg Glu Leu Val Val Asp Phe Leu Ser Tyr Lys Leu Ser Gln Lys
            180                 185                 190

Gly Tyr Ser Trp Ser Gln Phe Ser Asp Val Glu Glu Asn Arg Thr Glu
        195                 200                 205

Ala Pro Glu Gly Thr Glu Ser Glu Ala Val Lys Gln Ala Leu Arg Glu
    210                 215                 220

Ala Gly Asp Glu Phe Glu Leu Arg Tyr Arg Arg Ala Phe Ser Asp Leu
225                 230                 235                 240

Thr Ser Gln Leu His Ile Thr Pro Gly Thr Ala Tyr Gln Ser Phe Glu
                245                 250                 255

Gln Val Val Asn Glu Leu Phe Arg Asp Gly Val Asn Trp Gly Arg Ile
            260                 265                 270

Val Ala Phe Phe Ser Phe Gly Gly Ala Leu Cys Val Glu Ser Val Asp
        275                 280                 285

Lys Glu Met Gln Val Leu Val Ser Arg Ile Ala Ala Trp Met Ala Thr
    290                 295                 300

Tyr Leu Asn Asp His Leu Glu Pro Trp Ile Gln Glu Asn Gly Gly Trp
305                 310                 315                 320

Asp Thr Phe Val Glu Leu Tyr Gly Asn Asn Ala Ala Ala Glu Ser Arg
                325                 330                 335

Lys Gly Gln Glu Arg Glu Asp Gly Gly Gly Gly Ser Gly Gly Gly Gly
            340                 345                 350
```

```
Ser Gly Gly Gly Gly Ser Met His Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470


<210> SEQ ID NO 166
<211> LENGTH: 470
<212> TYPE: PRT
<213> ORGANISM: Artificial sequence
<220> FEATURE:
<223> OTHER INFORMATION: Homo sapiens

<400> SEQUENCE: 166

Glu Gln Lys Leu Ile Ser Glu Glu Asp Leu Gln Thr Thr Pro Gly Glu
1               5                   10                  15

Arg Ser Ser Leu Pro Ala Phe Tyr Pro Gly Thr Ser Gly Ser Cys Ser
            20                  25                  30

Gly Cys Gly Ser Leu Ser Leu Pro Thr Thr Thr Pro Ala Pro Arg Pro
        35                  40                  45

Pro Thr Pro Ala Pro Thr Ile Ala Ser Gln Pro Leu Ser Leu Arg Pro
    50                  55                  60

Glu Ala Cys Arg Pro Ala Ala Gly Gly Ala Val His Thr Arg Gly Leu
65                  70                  75                  80

Asp Phe Ala Cys Asp Pro Arg Phe Trp Val Leu Val Val Val Gly Gly
                85                  90                  95

Val Leu Ala Cys Tyr Ser Leu Leu Val Thr Val Ala Phe Ile Ile Phe
            100                 105                 110

Trp Val Arg Ser Lys Arg Ser Arg Leu Leu His Ser Asp Tyr Met Asn
        115                 120                 125

Met Thr Pro Arg Arg Pro Gly Pro Thr Arg Lys His Tyr Gln Pro Tyr
    130                 135                 140

Ala Pro Pro Arg Asp Phe Ala Ala Tyr Arg Ser Pro Gly Gly Gly Gly
145                 150                 155                 160

Gly Ser Gly Gly Gly Gly Ser Gly Gly Gly Gly Ser Met Ser Gln Ser
                165                 170                 175

Asn Arg Glu Leu Val Val Asp Phe Leu Ser Tyr Lys Leu Ser Gln Lys
            180                 185                 190

Gly Tyr Ser Trp Ser Gln Phe Ser Asp Val Glu Glu Asn Arg Thr Glu
        195                 200                 205

Ala Pro Glu Gly Thr Glu Ser Glu Ala Val Lys Gln Ala Leu Arg Glu
    210                 215                 220

Ala Gly Asp Glu Phe Glu Leu Arg Tyr Arg Arg Ala Phe Ser Asp Leu
225                 230                 235                 240
```

```
Thr Ser Gln Leu His Ile Thr Pro Gly Thr Ala Tyr Gln Ser Phe Glu
                245                 250                 255

Gln Val Val Asn Glu Leu Phe Arg Asp Gly Val Asn Trp Gly Arg Ile
            260                 265                 270

Val Ala Phe Phe Ser Phe Gly Gly Ala Leu Cys Val Glu Ser Val Asp
        275                 280                 285

Lys Glu Met Gln Val Leu Val Ser Arg Ile Ala Ala Trp Met Ala Thr
    290                 295                 300

Tyr Leu Asn Asp His Leu Glu Pro Trp Ile Gln Glu Asn Gly Gly Trp
305                 310                 315                 320

Asp Thr Phe Val Glu Leu Tyr Gly Asn Asn Ala Ala Ala Glu Ser Arg
                325                 330                 335

Lys Gly Gln Glu Arg Gly Gly Gly Gly Ser Gly Gly Gly Gly Ser Gly
            340                 345                 350

Gly Gly Gly Ser Met His Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470


<210> SEQ ID NO 167
<211> LENGTH: 472
<212> TYPE: PRT
<213> ORGANISM: Artificial sequence
<220> FEATURE:
<223> OTHER INFORMATION: Homo sapiens

<400> SEQUENCE: 167

Glu Gln Lys Leu Ile Ser Glu Glu Asp Leu Gln Thr Thr Pro Gly Glu
1               5                   10                  15

Arg Ser Ser Leu Pro Ala Phe Tyr Pro Gly Thr Ser Gly Ser Cys Ser
            20                  25                  30

Gly Cys Gly Ser Leu Ser Leu Pro Thr Thr Thr Pro Ala Pro Arg Pro
        35                  40                  45

Pro Thr Pro Ala Pro Thr Ile Ala Ser Gln Pro Leu Ser Leu Arg Pro
    50                  55                  60

Glu Ala Cys Arg Pro Ala Ala Gly Gly Ala Val His Thr Arg Gly Leu
65                  70                  75                  80

Asp Phe Ala Cys Asp Pro Arg Phe Trp Val Leu Val Val Val Gly Gly
                85                  90                  95

Val Leu Ala Cys Tyr Ser Leu Leu Val Thr Val Ala Phe Ile Ile Phe
            100                 105                 110

Trp Val Arg Ser Lys Arg Ser Arg Leu Leu His Ser Asp Tyr Met Asn
        115                 120                 125
```

```
Met Thr Pro Arg Arg Pro Gly Pro Thr Arg Lys His Tyr Gln Pro Tyr
    130                 135                 140

Ala Pro Pro Arg Asp Phe Ala Ala Tyr Arg Ser Pro Gly Gly Gly Gly
145                 150                 155                 160

Gly Ser Gly Gly Gly Gly Ser Gly Gly Gly Gly Ser Met Ser Gln Ser
                165                 170                 175

Asn Arg Glu Leu Val Val Asp Phe Leu Ser Tyr Lys Leu Ser Gln Lys
            180                 185                 190

Gly Tyr Ser Trp Ser Gln Phe Ser Asp Val Glu Glu Asn Arg Thr Glu
        195                 200                 205

Ala Pro Glu Gly Thr Glu Ser Glu Ala Val Lys Gln Ala Leu Arg Glu
    210                 215                 220

Ala Gly Asp Asp Phe Glu Leu Arg Tyr Arg Arg Ala Phe Ser Asp Leu
225                 230                 235                 240

Thr Ser Gln Leu His Ile Thr Pro Gly Thr Ala Tyr Gln Ser Phe Glu
                245                 250                 255

Gln Val Val Asn Glu Leu Phe Arg Asp Gly Val Asn Trp Gly Arg Ile
            260                 265                 270

Val Ala Phe Phe Ser Phe Gly Gly Ala Leu Cys Val Glu Ser Val Asp
        275                 280                 285

Lys Glu Met Gln Val Leu Val Ser Arg Ile Ala Ala Trp Met Ala Thr
    290                 295                 300

Tyr Leu Asn Asp His Leu Glu Pro Trp Ile Gln Glu Asn Gly Gly Trp
305                 310                 315                 320

Asp Thr Phe Val Glu Leu Tyr Gly Asn Asn Ala Ala Ala Glu Ser Arg
                325                 330                 335

Lys Gly Gln Glu Arg Glu Asp Gly Gly Gly Gly Ser Gly Gly Gly Gly
            340                 345                 350

Ser Gly Gly Gly Gly Ser Met His Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470
```

<210> SEQ ID NO 168
<211> LENGTH: 508
<212> TYPE: PRT
<213> ORGANISM: Artificial sequence
<220> FEATURE:
<223> OTHER INFORMATION: Homo sapiens

<400> SEQUENCE: 168

```
Glu Gln Lys Leu Ile Ser Glu Glu Asp Leu Gln Thr Thr Pro Gly Glu
1               5                   10                  15
```

```
Arg Ser Ser Leu Pro Ala Phe Tyr Pro Gly Thr Ser Gly Ser Cys Ser
            20                  25                  30

Gly Cys Gly Ser Leu Ser Leu Pro Thr Thr Thr Pro Ala Pro Arg Pro
        35                  40                  45

Pro Thr Pro Ala Pro Thr Ile Ala Ser Gln Pro Leu Ser Leu Arg Pro
    50                  55                  60

Glu Ala Cys Arg Pro Ala Ala Gly Gly Ala Val His Thr Arg Gly Leu
65                  70                  75                  80

Asp Phe Ala Cys Asp Pro Arg Phe Trp Val Leu Val Val Val Gly Gly
                85                  90                  95

Val Leu Ala Cys Tyr Ser Leu Leu Val Thr Val Ala Phe Ile Ile Phe
            100                 105                 110

Trp Val Arg Ser Lys Arg Ser Arg Leu Leu His Ser Asp Tyr Met Asn
        115                 120                 125

Met Thr Pro Arg Arg Pro Gly Pro Thr Arg Lys His Tyr Gln Pro Tyr
    130                 135                 140

Ala Pro Pro Arg Asp Phe Ala Ala Tyr Arg Ser Pro Gly Gly Gly Gly
145                 150                 155                 160

Gly Ser Gly Gly Gly Gly Ser Gly Gly Gly Gly Ser Met Ala His Ala
                165                 170                 175

Gly Arg Thr Gly Tyr Asp Asn Arg Glu Ile Val Met Lys Tyr Ile His
            180                 185                 190

Tyr Lys Leu Ser Gln Arg Gly Tyr Glu Trp Asp Ala Gly Asp Val Gly
        195                 200                 205

Ala Ala Pro Pro Gly Ala Ala Pro Ala Pro Gly Ile Phe Ser Ser Gln
    210                 215                 220

Pro Gly His Thr Pro His Pro Ala Ala Ser Arg Asp Pro Val Ala Arg
225                 230                 235                 240

Thr Ser Pro Leu Gln Thr Pro Ala Ala Pro Gly Ala Ala Ala Gly Pro
                245                 250                 255

Ala Leu Ser Pro Val Pro Pro Val Val His Leu Thr Leu Arg Gln Ala
            260                 265                 270

Gly Asp Asp Phe Ser Arg Arg Tyr Arg Arg Asp Phe Ala Glu Met Ser
        275                 280                 285

Ser Gln Leu His Leu Thr Pro Phe Thr Ala Arg Gly Arg Phe Ala Thr
    290                 295                 300

Val Val Glu Glu Leu Phe Arg Asp Gly Val Asn Trp Gly Arg Ile Val
305                 310                 315                 320

Ala Phe Phe Glu Phe Gly Gly Val Met Cys Val Glu Ser Val Asn Arg
                325                 330                 335

Glu Met Ser Pro Leu Val Asp Asn Ile Ala Leu Trp Met Thr Glu Tyr
            340                 345                 350

Leu Asn Arg His Leu His Thr Trp Ile Gln Asp Asn Gly Gly Trp Asp
        355                 360                 365

Ala Phe Val Glu Leu Tyr Gly Pro Ser Met Arg Gly Gly Gly Gly Ser
    370                 375                 380

Gly Gly Gly Gly Ser Gly Gly Gly Gly Ser Met His Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
```

```
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505


<210> SEQ ID NO 169
<211> LENGTH: 18
<212> TYPE: PRT
<213> ORGANISM: Artificial sequence
<220> FEATURE:
<223> OTHER INFORMATION: Synthetic peptide

<400> SEQUENCE: 169

Glu Gly Arg Gly Ser Leu Leu Thr Cys Gly Asp Val Glu Glu Asn Pro
1               5                   10                  15

Gly Pro


<210> SEQ ID NO 170
<211> LENGTH: 21
<212> TYPE: PRT
<213> ORGANISM: Artificial sequence
<220> FEATURE:
<223> OTHER INFORMATION: Synthetic Peptide

<400> SEQUENCE: 170

Gly Ser Gly Glu Gly Arg Gly Ser Leu Leu Thr Cys Gly Asp Val Glu
1               5                   10                  15

Glu Asn Pro Gly Pro
            20


<210> SEQ ID NO 171
<211> LENGTH: 63
<212> TYPE: PRT
<213> ORGANISM: Foot and mouth disease virus

<400> SEQUENCE: 171

Gly Ser Gly Ser Arg Val Thr Glu Leu Leu Tyr Arg Met Lys Arg Ala
1               5                   10                  15

Glu Thr Tyr Cys Pro Arg Pro Leu Leu Ala Ile His Pro Thr Glu Ala
            20                  25                  30

Arg His Lys Gln Lys Ile Val Ala Pro Val Lys Gln Leu Leu Asn Phe
        35                  40                  45

Asp Leu Leu Lys Leu Ala Gly Asp Val Glu Ser Asn Pro Gly Pro
    50                  55                  60


<210> SEQ ID NO 172
<211> LENGTH: 19
<212> TYPE: PRT
<213> ORGANISM: Amphimedon queenslandica

<400> SEQUENCE: 172

Leu Leu Cys Phe Leu Leu Leu Leu Leu Ser Gly Asp Val Glu Leu Asn
1               5                   10                  15

Pro Gly Pro
```

<210> SEQ ID NO 173
<211> LENGTH: 20
<212> TYPE: PRT
<213> ORGANISM: Amphimedon queenslandica

<400> SEQUENCE: 173

His His Phe Met Phe Leu Leu Leu Leu Leu Ala Gly Asp Ile Glu Leu
1 5 10 15

Asn Pro Gly Pro
20

<210> SEQ ID NO 174
<211> LENGTH: 20
<212> TYPE: PRT
<213> ORGANISM: Saccoglossus kowalevskii

<400> SEQUENCE: 174

Trp Phe Leu Val Leu Leu Ser Phe Ile Leu Ser Gly Asp Ile Glu Val
1 5 10 15

Asn Pro Gly Pro
20

<210> SEQ ID NO 175
<211> LENGTH: 20
<212> TYPE: PRT
<213> ORGANISM: Branchiostoma floridae

<400> SEQUENCE: 175

Lys Asn Cys Ala Met Tyr Met Leu Leu Leu Ser Gly Asp Val Glu Thr
1 5 10 15

Asn Pro Gly Pro
20

<210> SEQ ID NO 176
<211> LENGTH: 20
<212> TYPE: PRT
<213> ORGANISM: Branchiostoma floridae

<400> SEQUENCE: 176

Met Val Ile Ser Gln Leu Met Leu Lys Leu Ala Gly Asp Val Glu Glu
1 5 10 15

Asn Pro Gly Pro
20

<210> SEQ ID NO 177
<211> LENGTH: 22
<212> TYPE: PRT
<213> ORGANISM: porcine teschovirus-1

<400> SEQUENCE: 177

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 178
<211> LENGTH: 23
<212> TYPE: PRT
<213> ORGANISM: equine rhinitis A virus

<400> SEQUENCE: 178

Gly Ser Gly Gln Cys Thr Asn Tyr Ala Leu Leu Lys Leu Ala Gly Asp
1 5 10 15

-continued

```
Val Glu Ser Asn Pro Gly Pro
            20


<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (10)..(11)
<223> OTHER INFORMATION: Any amino acid

<400> SEQUENCE: 179

Ile Ala Xaa Xaa Leu Xaa Xaa Ile Gly Xaa Xaa Phe
1               5                   10
```

HETERODIMERIC INACTIVATABLE CHIMERIC ANTIGEN RECEPTORS

CROSS-REFERENCE TO RELATED APPLICATIONS

This application is a U.S. National Phase of International Patent Application No. PCT/EP2019/059576, filed on Apr. 12, 2019, which claims priority to U.S. Provisional Application Ser. No. 62/657,534, filed Apr. 13, 2018, and U.S. Provisional Application Ser. No. 62/832,767, filed Apr. 11, 2019, each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 8, 2024, is named 252457_000016_SL.txt and is 588,252 bytes in size.

FIELD OF THE INVENTION

The invention relates to heterodimeric inactivatable chimeric antigen receptors (CARs) and their use for treatment.

BACKGROUND

Chimeric antigen receptors (CARs) are hybrid molecules comprising a tumor antigen-targeting moiety, typically a scFv, followed by a linker, transmembrane (TM) domain, and various endodomains (EDs) involved in T-cell activation. First generation CARs include the ED of CD3-zeta (CD3ζ) only, required for "signal 1" of T cell activation, while second and third generation CARs also have one or more co-stimulatory EDs, respectively, such as CD28 and 4-1BB, to provide "signal 2".

The adoptive transfer of scFv-directed T lymphocytes, so-called CAR-T cells, has emerged as a potent treatment against various advanced cancers. For example, recent clinical trials with CD19-targeted CAR T cells have yielded up to 90% complete remission rates for patients suffering advanced acute lymphoblastic leukemia (ALL), a 'liquid' tumor[1-3]. 'Solid' tumors, however, remain a significant challenge to CAR therapy. This is in part due to the fact that there are few bona fide tumor antigens that are not found on healthy tissue, and as such important 'on-target/off-tumor' toxicities have occurred in CAR T-cell treated patients, and in some instances even leading to death[4]. Early strategies to address this included drug-inducible 'suicide genes'[5,6], and 'split-signaling' approaches, which require two receptors specific for two different antigens to be co-engaged for full T-cell activation to occur[7]. More recently, a study demonstrated 'remote-control' T cell activation via administration of a small-molecule drug[8], in which the authors developed a split architecture ON-switch CAR comprising two chains that separate tumor antigen recognition from T cell signaling. In this instance, they could only dimerize in the presence of a small molecule. Aspects of this ON-switch system, however, including the short half-life of the molecule required for chain dimerization, limit its clinical translation.

Thus, there remains a need for inactivatable CAR system for safety-enhanced cancer immunotherapy.

SUMMARY OF THE INVENTION

In one aspect, the invention provides a heterodimeric inactivatable chimeric antigen receptor (CAR) comprising:

a) a first polypeptide chain comprising:
 i) an extracellular target-binding region;
 ii) a first transmembrane (TM) region;
 iii) a first co-stimulatory endodomain (ED), and
 iv) a first member of a dimerization pair; and
b) a second polypeptide chain comprising:
 i) a second TM region;
 ii) optionally, a second co-stimulatory ED;
 iii) a second member of a dimerization pair; and
 iv) an intracellular signaling ED, wherein the first and second member of the dimerization pair form a heterodimer.

In one embodiment, the second polypeptide chain comprises an extracellular region which does not comprise the target-binding capacity.

In one embodiment, the first polypeptide chain does not comprise an intracellular signaling ED.

In one embodiment, the CAR comprises:

a) a first polypeptide chain consisting essentially of in the direction from the N terminus to the C terminus:
 i) an extracellular target-binding region;
 ii) a first linker region;
 iii) a first transmembrane (TM) region;
 iv) a first co-stimulatory endodomain (ED), and
 v) a first member of a dimerization pair; and
b) a second polypeptide chain consisting essentially of in the direction from the N terminus to the C terminus:
 i) an extracellular region which does not comprise the target-binding capacity;
 ii) a second linker region;
 iii) a second TM region;
 iv) a second co-stimulatory ED;
 v) a second member of the dimerization pair; and
 vi) an intracellular signaling ED, wherein the first and second member of the dimerization pair form a heterodimer and the first polypeptide chain does not comprise an intracellular signaling ED.

In one embodiment, the first and second member of the dimerization pair are derived from proteins that do not interact in vivo.

In one embodiment, the heterodimer formed by the first and second member of the dimerization pair can be disrupted by an inhibitory molecule (e.g., a small molecule or a polypeptide) resulting in inhibition of CAR-mediated signaling. In one specific embodiment, the inhibitory molecule binds to the first or second member of the dimerization pair with a higher affinity than the first and second member of the dimerization pair bind to each other.

In one embodiment, the first polypeptide chain comprises a linker region interposed between the extracellular target-binding region and the first TM region. In one embodiment, the second polypeptide chain comprises a linker region interposed between the extracellular region and the second TM region. Non-limiting examples of useful linker regions include, e.g., an immunoglobulin hinge region or a linker region derived from CD8, CD8α, or CD28.

In one embodiment, the extracellular target-binding region of the CAR is an antigen-binding polypeptide. In a specific embodiment, the antigen recognized by the antigen-binding polypeptide is selected from a cancer cell associated antigen, an infection-associated antigen and an auto-antigen. Non-limiting examples of antigen-binding polypeptides include antibodies and antibody fragments, such as, e.g., murine antibodies, rabbit antibodies, human antibodies, humanized antibodies, single chain variable fragments (scFv), camelid antibody variable domains and humanized versions, shark antibody variable domains and humanized versions, single domain antibody variable domains, nanobodies (VHHs), and camelized antibody variable domains. Non-limiting examples of antigens which can be recognized by the antigen-binding polypeptide include, e.g., CD19, CD20, CD38, CD30, Her2/neu, ERBB2, CA125, MUC-1, prostate-specific membrane antigen (PSMA), PSA, CD44 surface adhesion molecule, mesothelin, carcinoembryonic antigen (CEA), CEACAM5, CEACAM6, epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, carbonic anhydrase EX, alpha-fetoprotein, A3, antigen specific for A33 antibody, Ba 733, BrE3-antigen, CA125, CD1, CDIa, CD3, CD5, CD15, CD16, CD19, CD20, CD21, CD22, CD23, CD25, CD30, CD33, CD38, CD45, CD74, CD79a, CD80, CD138, colon-specific antigen-p (CSAp), CSAp, EGP-I, EGP-2, Ep-CAM, FIt-I, Flt-3, folate receptor, HLA-DR, human chorionic gonadotropin (HCG) and its subunits, hypoxia inducible factor (HIF-I), Ia, IL-2, IL-6, IL-8, insulin growth factor-1 (IGF-I), KC4-antigen, KS-1-antigen, KS1-4, Le-Y, macrophage inhibition factor (MIF), MAGE, MUC1, MUC2, MUC3, MUC4, NCA66, NCA95, NCA90, tyrosinase, PRAME, EBNA, KLK3, HPV E7, LMP2, NY-ESO-1, PAP, reverse transcriptase, nucleophosmin, PRTN3/ELANE, CT83/KKLC1, MUC16, DNTT, antigen specific for PAM-4 antibody, placental growth factor, p53, prostatic acid phosphatase, RS5, S100, TAC, TAG-72, tenascin, TRAIL receptors, Tn antigen, Thomson-Friedenreich antigens, tumor necrosis antigens, VEGF, ED-B fibronectin, 17-1A-antigen, NeuGcGM3, N-glycolyl GM3 ganglioside, Neu5Gc, GM3-Ganglioside, GD3, GM2, carbohydrate antigens, ganglioside antigens, Lewis Y, Lewis B, CD123, or Kappa chain of immunoglobulin. In a specific embodiment, the cancer cell associated antigen is PSMA. In a specific embodiment, the cancer cell associated antigen is associated with a solid tumor. In a specific embodiment, the antigen recognized by the antigen-binding polypeptide is CD19. In a specific embodiment, the antigen recognized by the antigen-binding polypeptide is NeuGcGM3.

In one embodiment, the extracellular target-binding region is a natural ligand for a target cell antigen or receptor. In one embodiment, the natural ligand for a target cell antigen or receptor is an NKG2D ectodomain. In one embodiment, the extracellular target-binding region is a T-cell receptor (TCR) based recognition domain. In one embodiment, the TCR based recognition domain is a single chain TCR.

In one embodiment, the first and/or second transmembrane (TM) region is derived from CD8, CD8α, CD4, CD3-zeta, CD3-epsilon, CD28, CD45, CD4, CD5, CD7, CD9, CD16, CD22, CD33, CD37, CD40, CD64, CD80, CD86, CD134 (OX-40), CD137, CD154, DAP10, or DAP12.

In one embodiment, the first and second TM regions are the same.

In one embodiment, the first and second TM regions are derived from CD28.

In one embodiment, the extracellular region which does not comprise the target-binding capacity is a stabilizing domain. In one embodiment, the extracellular region which does not comprise the target-binding capacity is derived from DAP10 or DAP12.

In one embodiment, the first and/or second co-stimulatory ED is derived from 4-1BB (CD137), CD28, ICOS, CD134 (OX-40), BTLA, CD27, CD30, GITR, CD226, or HVEM.

In a specific embodiment, the first and second co-stimulatory EDs are derived from CD28.

In one embodiment, the intracellular signaling ED is derived from DAP10, DAP12, Fc epsilon receptor I gamma chain (FCER1G), FcR beta CD3-delta, CD3-epsilon, CD3-gamma, CD3-zeta, CD226, CD66d, CD79A, or CD79B. In a specific embodiment, the intracellular signaling ED is derived from CD3-zeta.

In certain embodiments, the first and/or second polypeptide chain further comprises one or more additional polypeptide sequences. In a specific embodiment, the one or more additional polypeptide sequences are selected from one or more additional co-stimulatory EDs, signal sequences, separation sequences, epitope tags, and polypeptides that produce a detectable signal. In a specific embodiment, the signal sequence is CD8α. In a specific embodiment, the epitope tag is cMyc. In a specific embodiment, the separation sequence is T2A.

In one embodiment, the first member of the dimerization pair comprises:

```
i)
                                        (SEQ ID NO: 2)
QRWELALGRFLEYLSWVSTLSEQVQEELLSSQVTQELRALMDETMKELKA

YKSELEEQLTPVAEETRARLSKELQAAQARLGADMEDVRGRLVQYRGEVQ

AMLGQSTEELRVRLASHLIALQLRLIGDAFDLQKRLAVYQAGA;

ii)
                                        (SEQ ID NO: 3)
QRWELALGRFLEYLSWVSTLSEQVQEELLSSQVTQELRALMDETMKELKA

YKSELEEQLTPVAEETRARLSKELQAAQARLGADMEDVRGRLVQYRGEVQ

AMLGQSTEELRVRLASHLIALQARLIGDAFDLQKRLAVYQAGA;

iii)
                                        (SEQ ID NO: 4)
QRWELALGRFLEYLSWVSTLSEQVQEELLSSQVTQELRALMDETMKELKA

YKSELEEQLTPVAEETRARLSKELQAAQARLGADMEDVRGRLVQYRGEVQ

AMLGQSTEELRVRLASHLIALQLRLIGAAFDLQKRLAVYQAGA;
or

iv)
                                       (SEQ ID NO: 19)
QRWELALGRFLAYLSWVSTLSEQVQEELLSSQVTQELRALMDETMKELKA

YKSELEEQLTPVAEETRARLSKELQAAQARLGADMEDVRGRLVQYRGEVQ

AMLGQSTEELRVRLASHLIALQLRLIGDAFDLQKRLAVYQAGA.
```

In one embodiment, the second member of the dimerization pair comprises:

```
i)
                                        (SEQ ID NO: 5)
MSQSNRELVVDFLSYKLSQKGYSWSQFSDVEENRTEAPEGTESEAVKQAL

REAGDEFELRYRRAFSDLTSQLHITPGTAYQSFEQVVNELFRDGVNWGRI

VAFFSFGGALCVESVDKEMQVLVSRIAAWMATYLNDHLEPWIQENGGWDT

FVELYGNNAAAESRKGQERED;

ii)
                                       (SEQ ID NO: 22)
MSQSNRELVVDFLSYKLSQKGYSWSQFSDVEENRTEAPEGTESEAVKQAL

REAGDEFELRYRRAFSDLTSQLHITPGTAYQSFEQVVNELFRDGVNWGRI

VAFFSFGGALCVESVDKEMQVLVSRIAAWMATYLNDHLEPWIQENGGWDT
```

-continued

FVELYGNNAAAESRKGQER;
or iii)
(SEQ ID NO: 30)
MSQSNRELVVDFLSYKLSQKGYSWSQFSDVEENRTEAPEGTESEAVKQAL
REAGDDFELRYRRAFSDLTSQLFETTPGTAYQSFEQVVNELFRDGVNWGR
IVAFFSFGGALCVESVDKEMQVINSRIAAWMATYLNDHLEPWIQENCICA
VDTEVEINGNNAAAESRKGQERED;

iv)
(SEQ ID NO: 23)
MSQSNRELVVDFLSYKLSQKGYSWSQFSDVEENRTEAPEGTESEAVKQAL
REAGDDFELRYRRAFSDLTSQLHITPGTAYQSFEQVVNELFRDGVNWGRI
VAFFSFGGALCVESVDKEMQVLVSRIAAWMATYLNDHLEPWIQENGGWDT
FVELYGNNAAAESRKGQER;

v)
(SEQ ID NO: 24)
MAHAGRTGYDNREIVMKYIHYKLSQRGYEWDAGDVGAAPPGAAPAPGIFS
SQPGHTPHPAASRDPVARTSPLQTPAAPGAAAGPALSPVPPVVHLTLRQA
GDDFSRRYRRDFAEMSSQLHLTPFTARGRFATVVEELFRDGVNWGRIVAF
FEFGGVMCVESVNREMSPLVDNIALWMTEYLNRHLHTWIQDNGGWDAFVE
LYGPSMR.

In one embodiment, the extracellular target-binding region comprises:

i)
(SEQ ID NO: 6)
VQLQQSGPELVKPGTSVRISCKTSGYTFTEYTIHWVKQSHGKSLEWIGNI
NPNNGGTTYNQKFEDKATLTVDKSSSTAYMELRSLTSEDSAVYYCAAGWN
FDYWGQGTTVTVSSGGGGSGGGGSGGGGSDIVMTQSHKFMSTSVGDRVSI
ICKASQDVGTAVDWYQQKPGQSPKLLIYWASTRHTGVPDRFTGSGSGTDF
TLTITNVQSEDLADYFCQQYNSYPLTFGAGTMLDLKR;
or ii)
(SEQ ID NO: 49)
GSDIQMTQTTSSLSASLGDRVTISCRASQDISKYLNWYQQKPDGTVKLLI
YHTSRLHSGVPSRFSGSGSGTDYSLTISNLEQEDIATYFCQQGNTLPYTF
GGGTKLEITGSTSGSGKPGSGEGSTKGEVKLQESGPGLVAPSQSLSVTCT
VSGVSLPDYGVSWIRQPPRKGLEWLGVIWGSETTYYNSALKSRLTIIKDN
SKSQVFLKMNSLQTDDTAIYYCAKHYYYGGSYAMDYWGQGTSVTVSS.

In one embodiment, the intracellular signaling ED comprises the sequence (SEQ ID NO: 7)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR.

In one embodiment, the extracellular region which does not comprise the target-binding capacity comprises the sequence QTTPGERSSLPAFYPGTSGSCSGCGSLSLP (SEQ ID NO: 8) or GVLAGIVMGDLVLTVLIALAV (SEQ ID NO: 74). In a specific embodiment, the extracellular region which does not comprise the target-binding capacity comprises the sequence of SEQ ID NO: 8.

In one embodiment, the first and/or second linker region comprises the sequence (SEQ ID NO: 9)
TTTPAPRPPTPAPTIASQPLSLRPEACRPAAGGAVHTRGLDFACD.

In one embodiment, the first and/or second TM region comprises the sequence FWVLVVVGGVLACYSLLVTVAFIIFWV (SEQ ID NO: 10).

In one embodiment, the first and/or second co-stimulatory ED comprises the sequence RSKRSRLLHSDYMNMTPRRPGPTRKHYQPYAPPRDFAAYRS (SEQ ID NO: 11).

In one embodiment, the first polypeptide chain comprises, consists of, or consists essentially of the sequence (SEQ ID NO: 109)
VQLQQSGPELVKPGTSVRISCKTSGYTFTEYTIHWVKQSHGKSLEWIGNI
NPNNGGTTYNQKFEDKATLTVDKSSSTAYMELRSLTSEDSAVYYCAAGWN
FDYWGQGTTVTVSSGGGGSGGGGSGGGGSDIVMTQSHKFMSTSVGDRVSI
ICKASQDVGTAVDWYQQKPGQSPKLLIYWASTRHTGVPDRFTGSGSGTDF
TLTITNVQSEDLADYFCQQYNSYPLTFGAGTMLDLKRASTTTPAPRPPTP
APTIASQPLSLRPEACRPAAGGAVHTRGLDFACDFWVLVVVGGVLACYSL
LVTVAFIIFWVRSKRSRLLHSDYMNMTPRRPGPTRKHYQPYAPPRDFAAY
RSHMGGGGSGGGGSGGGGSQRWELALGRFLEYLSWVSTLSEQVQEELLSS
QVTQELRALMDETMKELKAYKSELEEQLTPVAEETRARLSKELQAAQARL
GADMEDVRGRLVQYRGEVQAMLGQSTEELRVRLASHLIALQLRLIGDAFD
LQKRLAVYQAGA.

In one embodiment, the first polypeptide chain comprises, consists of, or consists essentially of the sequence VQLQQSGPELVKPGTSVRISCK-TSGYTFTEYTIHWVKQSHGKSLEWIGNINPNNGGTT (SEQ ID NO: 110)
VQLQQSGPELVKPGTSVRISCKTSGYTFTEYTIHWVKQSHGKSLEWIGNI
NPNNGGTTYNQKFEDKATLTVDKSSSTAYMELRSLTSEDSAVYYCAAGWN
FDYWGQGTTVTVSSGGGGSGGGGSGGGGSDIVMTQSHKFMSTSVGDRVSI
ICKASQDVGTAVDWYQQKPGQSPKLLIYWASTRHTGVPDRFTGSGSGTDF
TLTITNVQSEDLADYFCQQYNSYPLTFGAGTMLDLKRASTTTPAPRPPTP
APTIASQPLSLRPEACRPAAGGAVHTRGLDFACDFWVLVVVGGVLACYSL
LVTVAFIIFWVRSKRSRLLHSDYMNMTPRRPGPTRKHYQPYAPPRDFAAY
RSHMGGGGSGGGGSGGGGSQRWELALGRFLAYLSWVSTLSEQVQEELLSS
QVTQELRALMDETMKELKAYKSELEEQLTPVAEETRARLSKELQAAQARL
GADMEDVRGRLVQYRGEVQAMLGQSTEELRVRLASHLIALQLRLIGDAFD
LQKRLAVYQAGA.

In one embodiment, the first polypeptide chain comprises, consists of, or consists essentially of the sequence (SEQ ID NO: 111)
VQLQQSGPELVKPGTSVRISCKTSGYTFTEYTIHWVKQSHGKSLEWIGN
INPNNGGTTYNQKFEDKATLTVDKSSSTAYMELRSLTSEDSAVYYCAAG
WNFDYWGQGTTVTVSSGGGGSGGGGSGGGGSDIVMTQSHKFMSTSVGDR
VSIICKASQDVGTAVDWYQQKPGQSPKLLIYWASTRHTGVPDRFTGSGS
GTDFTLTITNVQSEDLADYFCQQYNSYPLTFGAGTMLDLKRASTTTPAP
RPPTPAPTIASQPLSLRPEACRPAAGGAVHTRGLDFACDFWVLVVVGGV
LACYSLLVTVAFIIFWVRSKRSRLLHSDYMNMTPRRPGPTRKHYQPYAP
PRDFAAYRSHMGGGGSGGGGSGGGGSQRWELALGRFLEYLSWVSTLSEQ
VQEELLSSQVTQELRALMDETMKELKAYKSELEEQLTPVAEETRARLSK
ELQAAQARLGADMEDVRGRLVQYRGEVQAMLGQSTEELRVRLASHLIAL
QARLIGDAFDLQKRLAVYQAGA.

In one embodiment, the first polypeptide chain comprises, consists of, or consists essentially of the sequence (SEQ ID NO: 112)
VQLQQSGPELVKPGTSVRISCKTSGYTFTEYTIHWVKQSHGKSLEWIGN
INPNNGGTTYNQKFEDKATLTVDKSSSTAYMELRSLTSEDSAVYYCAAG
WNFDYWGQGTTVTVSSGGGGSGGGGSGGGGSDIVMTQSHKFMSTSVGDR
VSIICKASQDVGTAVDWYQQKPGQSPKLLIYWASTRHTGVPDRFTGSGS
GTDFTLTITNVQSEDLADYFCQQYNSYPLTFGAGTMLDLKRASTTTPAP
RPPTPAPTIASQPLSLRPEACRPAAGGAVHTRGLDFACDFWVLVVVGGV
LACYSLLVTVAFIIFWVRSKRSRLLHSDYMNMTPRRPGPTRKHYQPYAP
PRDFAAYRSHMGGGGSGGGGSGGGGSQRWELALGRFLEYLSWVSTLSEQ
VQEELLSSQVTQELRALMDETMKELKAYKSELEEQLTPVAEETRARLSK
ELQAAQARLGADMEDVRGRLVQYRGEVQAMLGQSTEELRVRLASHLIAL
QLRLIGAAFDLQKRLAVYQAGA.

In one embodiment, the second polypeptide chain comprises, consists of, or consists essentially of the sequence (SEQ ID NO: 113)
QTTPGERSSLPAFYPGTSGSCSGCGSLSLPTTTPAPRPPTPAPTIASQP
LSLRPEACRPAAGGAVHTRGLDFACDPRFWVLVVVGGVLACYSLLVTVA
FIIFWVRSKRSRLLHSDYMNMTPRRPGPTRKHYQPYAPPRDFAAYRSPG
GGGGSGGGGSGGGGSMSQSNRELVVDFLSYKLSQKGYSWSQFSDVEENR
TEAPEGTESEAVKQALREAGDEFELRYRRAFSDLTSQLHITPGTAYQSF
EQVVNELFRDGVNWGRIVAFFSFGGALCVESVDKEMQVLVSRIAAWMAT
YLNDHLEPWIQENGGWDTFVELYGNNAAAESRKGQEREDGGGGSGGGGS
GGGGSMHRVKFSRSADAPAYQQGQNQLYNELNLGRREEYDVLDKRRGRD
PEMGGKPRRKNPQEGLYNELQKDKMAEAYSEIGMKGERRRGKGHDGLYQ
GLSTATKDTYDALHMQALPPR.

In one embodiment, the second polypeptide chain comprises, consists of, or consists essentially of the sequence (SEQ ID NO: 114)
QTTPGERSSLPAFYPGTSGSCSGCGSLSLPTTTPAPRPPTPAPTIASQPL
SLRPEACRPAAGGAVHTRGLDFACDPRFWVLVVVGGVLACYSLLVTVAFI
IFWVRSKRSRLLHSDYMNMTPRRPGPTRKHYQPYAPPRDFAAYRSPGGGG
GSGGGGSGGGGSMSQSNRELVVDFLSYKLSQKGYSWSQFSDVEENRTEAP
EGTESEAVKQALREAGDEFELRYRRAFSDLTSQLHITPGTAYQSFEQVVN
ELFRDGVNWGRIVAFFSFGGALCVESVDKEMQVLVSRIAAWMATYLNDHL
EPWIQENGGWDTFVELYGNNAAAESRKGQERGGGGSGGGGSGGGGSMHRV
KFSRSADAPAYQQGQNQLYNELNLGRREEYDVLDKRRGRDPEMGGKPRRK
NPQEGLYNELQKDKMAEAYSEIGMKGERRRGKGHDGLYQGLSTATKDTYD
ALHMQALPPR.

In one embodiment, the second polypeptide chain comprises, consists of, or consists essentially of the sequence (SEQ ID NO: 115)
QTTPGERSSLPAFYPGTSGSCSGCGSLSLPTTTPAPRPPTPAPTIASQP
LSLRPEACRPAAGGAVHTRGLDFACDPRFWVLVVVGGVLACYSLLVTVA
FIIFWVRSKRSRLLHSDYMNMTPRRPGPTRKHYQPYAPPRDFAAYRSPG
GGGGSGGGGSGGGGSMSQSNRELVVDFLSYKLSQKGYSWSQFSDVEENR
TEAPEGTESEAVKQALREAGDDFELRYRRAFSDLTSQLHITPGTAYQSF
EQVVNELFRDGVNWGRIVAFFSFGGALCVESVDKEMQVLVSRIAAWMAT
YLNDHLEPWIQENGGWDTFVELYGNNAAAESRKGQEREDGGGGSGGGGS
GGGGSMHRVKFSRSADAPAYQQGQNQLYNELNLGRREEYDVLDKRRGRD
PEMGGKPRRKNPQEGLYNELQKDKMAEAYSEIGMKGERRRGKGHDGLYQ
GLSTATKDTYDALHMQALPPR.

In one embodiment, the second polypeptide chain comprises, consists of, or consists essentially of the sequence (SEQ ID NO: 116)
QTTPGERSSLPAFYPGTSGSCSGCGSLSLPTTTPAPRPPTPAPTIASQP
LSLRPEACRPAAGGAVHTRGLDFACDPRFWVLVVVGGVLACYSLLVTVA
FIIFWVRSKRSRLLHSDYMNMTPRRPGPTRKHYQPYAPPRDFAAYRSPG
GGGGSGGGGSGGGGSMSQSNRELVVDFLSYKLSQKGYSWSQFSDVEENR
TEAPEGTESEAVKQALREAGDDFELRYRRAFSDLTSQLHITPGTAYQSF
EQVVNELFRDGVNWGRIVAFFSFGGALCVESVDKEMQVLVSRIAAWMAT
YLNDHLEPWIQENGGWDTFVELYGNNAAAESRKGQERGGGGSGGGGSGG
GGSMHRVKFSRSADAPAYQQGQNQLYNELNLGRREEYDVLDKRRGRDPE
MGGKPRRKNPQEGLYNELQKDKMAEAYSEIGMKGERRRGKGHDGLYQGL
STATKDTYDALHMQALPPR.

In one embodiment, the second polypeptide chain comprises, consists of, or consists essentially of the sequence (SEQ ID NO: 117)
QTTPGERSSLPAFYPGTSGSCSGCGSLSLPTTTPAPRPPTPAPTIASQP
LSLRPEACRPAAGGAVHTRGLDFACDPRFWVLVVVGGVLACYSLLVTVA -continued

FIIFWVRSKRSRLLHSDYMNMTPRRPGPTRKHYQPYAPPRDFAAYRSPG

GGGGSGGGGSGGGGSMAHAGRTGYDNREIVMKYIHYKLSQRGYEWDAGD

VGAAPPGAAPAPGIFSSQPGHTPHPAASRDPVARTSPLQTPAAPGAAAG

PALSPVPPVVHLTLRQAGDDFSRRYRRDFAEMSSQLHLTPFTARGRFAT

VVEELFRDGVNWGRIVAFFEFGGVMCVESVNREMSPLVDNIALWMTEYL

NRHLHTWIQDNGGWDAFVELYGPSMRGGGGSGGGGSGGGGSMHRVKFSR

SADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDAL

HMQALPPR.

In one embodiment, the inactivatable chimeric antigen receptor (CAR) comprises: a) a first polypeptide chain comprises, consists of, or consists essentially of the sequence of any one of SEQ ID Nos: 12, 76, 77, 109-112, or 134-146, and b) a second polypeptide chain comprises, consists of, or consists essentially of the sequence of any one of SEQ ID Nos: 13, 79, 80, 81, 113-117,147-156.

In another aspect is provided a nucleic acid molecule comprising a nucleotide sequence encoding any of the above heterodimeric inactivatable chimeric antigen receptors (CARs).

In another related aspect is provided a nucleic acid molecule comprising a nucleotide sequence encoding the first polypeptide chain of any of the above heterodimeric inactivatable chimeric antigen receptors (CARs).

In one specific embodiment, the nucleotide sequence encoding the first polypeptide chain of the CAR is (SEQ ID NO: 118)

atggccttaccagtgaccgccttgctcctgccgctggccttgctgctcca cgccgccaggccggtgcagctgcagcagtcaggacctgaactggtgaagc ctgggacttcagtgaggatatcctgcaagacttctggatacacattcact gaatataccatacactgggtgaagcagagccatggaaagagccttgagtg gattggaaacatcaatcctaacaatggtggtaccacctacaatcagaagt tcgaggacaaggccacattgactgtagacaagtcctccagtacagcctac atggagctccgcagcctaacatctgaggattctgcagtctattattgtgc agctggttggaactttgactactggggccaagggaccacggtcaccgtct cctcaggtggaggtggatcaggtggaggtggatctggtggaggtggatct gacattgtgatgacccagtctcacaaattcatgtccacatcagtaggaga cagggtcagcatcatctgtaaggccagtcaagatgtgggtactgctgtag actggtatcaacagaaaccaggacaatctcctaaactactgatttattgg gcatccactcggcacactggagtccctgatcgcttcacaggcagtggatc tgggacagacttcactctcaccattactaatgttcagtctgaagacttgg cagattatttctgtcagcaatataacagctatcccctcacgttcggtgct gggaccatgctggacctgaaacgggctagcacaacaacccctgcccccag acctcctaccccagcccctacaattgccagccagcctctgagcctgaggc ccgaggcttgtagacctgctgctggcggagccgtgcacaccagaggactg gatttcgcctgcgacttctgggtgctggtggtcgtgggcggagtgctggc -continued ctgttacagcctgctcgtgaccgtggccttcatcatcttttgggtgcgga gcaagagaagcagactgctgcacagcgactacatgaacatgacccccaga cggcctggccccaccagaaagcactaccagccttacgcccctcccagaga cttcgccgcctacagatctcatatgggaggcggaggatctggcggaggtg gaagtggcggaggcggatctcaaagatgggaactcgccctgggcagattc ctggaatacctgagctgggtgtccacactgagcgaacaggtgcaagagga actgctgagcagccaagtgacccaagagctgagagccctgatggacgaga caatgaaggaactgaaggcctacaagagcgagctggaagaacagctgacc cctgtggccgaggaaaccagagccagactgagcaaagaactgcaggccgc tcaggccagactgggagccgatatggaagatgttcggggcagactggtgc agtacagaggcgaagttcaggccatgctgggccagtctaccgaggaactg agagtgcggctggcctctcatctgattgccctgcagctgagactgatcgg cgacgcattcgacctgcagaaaagactggccgtgtaccaggctggcgctg ctgaacggaagcggcgcagcggcagcgggcgcagcggcagcggcgagggc agaggaagtcttctaacatgcggtgacgtggaggagaatcccggccct.

In one specific embodiment, the nucleotide sequence encoding the first polypeptide chain of the CAR is (SEQ ID NO: 119)

tctagaaatggccttaccagtgaccgccttgctcctgccgctggccttgc tgctccacgccgccaggccggtgcagctgcagcagtcaggacctgaactg gtgaagcctgggacttcagtgaggatatcctgcaagacttctggatacac attcactgaatataccatacactgggtgaagcagagccatggaaagagcc ttgagtggattggaaacatcaatcctaacaatggtggtaccacctacaat cagaagttcgaggacaaggccacattgactgtagacaagtcctccagtac agcctacatggagctccgcagcctaacatctgaggattctgcagtctatt attgtgcagctggttggaactttgactactggggccaagggaccacggtc accgtctcctcaggtggaggtggatcaggtggaggtggatctggtggagg tggatctgacattgtgatgacccagtctcacaaattcatgtccacatcag taggagacagggtcagcatcatctgtaaggccagtcaagatgtgggtact gctgtagactggtatcaacagaaaccaggacaatctcctaaactactgat ttattgggcatccactcggcacactggagtccctgatcgcttcacaggca gtggatctgggacagacttcactctcaccattactaatgttcagtctgaa gacttggcagattatttctgtcagcaatataacagctatcccctcacgtt cggtgctgggaccatgctggacctgaaacgggctagcacaacaacccctg cccccagacctcctaccccagcccctacaattgccagccagcctctgagc ctgaggcccgaggcttgtagacctgctgctggcggagccgtgcacaccag aggactggatttcgcctgcgacttctgggtgctggtggtcgtgggcggag tgctggcctgttacagcctgctcgtgaccgtggccttcatcatcttttgg gtgcggagcaagagaagcagactgctgcacagcgactacatgaacatgac ccccagacggcctggccccaccagaaagcactaccagccttacgcccctc -continued ccagagacttcgccgcctacagatctcatatgggaggcggaggatctggc
ggaggtggaagtggcggaggcggatctcaaagatgggaactcgccctggg
cagattcctggaatacctgagctgggtgtccacactgagcgaacaggtgc
aagaggaactgctgagcagccaagtgacccaagagctgagagccctgatg
gacgagacaatgaaggaactgaaggcctacaagagcgagctggaagaaca
gctgacccctgtggccgaggaaaccagagccagactgagcaaagaactgc
aggccgctcaggccagactgggagccgatatggaagatgttcggggcaga
ctggtgcagtacagaggcgaagttcaggccatgctgggccagtctaccga
ggaactgagagtgcggctggcctctcatctgattgccctgcagctgagac
tgatcggcgacgcattcgacctgcagaaaagactggccgtgtaccaggct
ggcgctgctgaacggaagcggcgcagcggcagcgggcgcagcggcagcgg
cgagggcagaggaagtcttctaacatgcggtgacgtggaggagaatcccg
gccct.

In one specific embodiment, the nucleotide sequence encoding the first polypeptide chain of the CAR is (SEQ ID NO: 120)
tctagaaatggccttaccagtgaccgccttgctcctgccgctggccttgc
tgctccacgccgccaggccggtgcagctgcagcagtcaggacctgaactg
gtgaagcctgggacttcagtgaggatatcctgcaagacttctggatacac
attcactgaatataccatacactgggtgaagcagagccatggaaagagcc
ttgagtggattggaaacatcaatcctaacaatggtggtaccacctacaat
cagaagttcgaggacaaggccacattgactgtagacaagtcctccagtac
agcctacatggagctccgcagcctaacatctgaggattctgcagtctatt
attgtgcagctggttggaactttgactactggggccaagggaccacggtc
accgtctcctcaggtggaggtggatcaggtggaggtggatctggtggagg
tggatctgacattgtgatgacccagtctcacaaattcatgtccacatcag
taggagacagggtcagcatcatctgtaaggccagtcaagatgtgggtact
gctgtagactggtatcaacagaaaccaggacaatctcctaaactactgat
ttattgggcatccactcggcacactggagtccctgatcgcttcacaggca
gtggatctgggacagacttcactctcaccattactaatgttcagtctgaa
gacttggcagattatttctgtcagcaatataacagctatcccctcacgtt
cggtgctgggaccatgctggacctgaaacgggctagcacaacaacccctg
cccccagacctcctaccccagcccctacaattgccagccagcctctgagc
ctgaggcccgaggcttgtagacctgctgctggcggagccgtgcacaccag
aggactggatttcgcctgcgacttctgggtgctggtggtcgtgggcggag
tgctggcctgttacagcctgctcgtgaccgtggccttcatcatcttttgg
gtgcggagcaagagaagcagactgctgcacagcgactacatgaacatgac
cccccagacggcctggccccaccagaaagcactaccagccttacgcccctc
ccagagacttcgccgcctacagatctcatatgggaggcggaggatctggc
ggaggtggaagtggcggaggcggatctcaaagatgggaactcgccctggg
cagattcctggaatacctgagctgggtgtccacactgagcgaacaggtgc -continued aagaggaactgctgagcagccaagtgacccaagagctgagagccctgatg
gacgagacaatgaaggaactgaaggcctacaagagcgagctggaagaaca
gctgacccctgtggccgaggaaaccagagccagactgagcaaagaactgc
aggccgctcaggccagactgggagccgatatggaagatgttcggggcaga
ctggtgcagtacagaggcgaagttcaggccatgctgggccagtctaccga
ggaactgagagtgcggctggcctctcatctgattgccctgcagctgagac
tgatcggcgacgcattcgacctgcagaaaagactggccgtgtaccaggct
ggcgctgctgaacggaagcggcgcagcggcagcgggcgcagcggcagcgg
cgagggcagaggaagtcttctaacatgcggtgacgtggaggagaatcccg
gccct.

In one specific embodiment, the nucleotide sequence encoding the first polypeptide chain of the CAR is (SEQ ID NO: 121)
tctagaaatggccttaccagtgaccgccttgctcctgccgctggccttg
ctgctccacgccgccaggccggtgcagctgcagcagtcaggacctgaac
tggtgaagcctgggacttcagtgaggatatcctgcaagacttctggata
cacattcactgaatataccatacactgggtgaagcagagccatggaaag
agccttgagtggattggaaacatcaatcctaacaatggtggtaccacct
acaatcagaagttcgaggacaaggccacattgactgtagacaagtcctc
cagtacagcctacatggagctccgcagcctaacatctgaggattctgca
gtctattattgtgcagctggttggaactttgactactggggccaaggga
ccacggtcaccgtctcctcaggtggaggtggatcaggtggaggtggatc
tggtggaggtggatctgacattgtgatgacccagtctcacaaattcatg
tccacatcagtaggagacagggtcagcatcatctgtaaggccagtcaag
atgtgggtactgctgtagactggtatcaacagaaaccaggacaatctcc
taaactactgatttattgggcatccactcggcacactggagtccctgat
cgcttcacaggcagtggatctgggacagacttcactctcaccattacta
atgttcagtctgaagacttggcagattatttctgtcagcaatataacag
ctatcccctcacgttcggtgctgggaccatgctggacctgaaacgggct
agcacaacaacccctgcccccagacctcctaccccagcccctacaattg
ccagccagcctctgagcctgaggcccgaggcttgtagacctgctgctgg
cggagccgtgcacaccagaggactggatttcgcctgcgacttctgggtg
ctggtggtcgtgggcggagtgctggcctgttacagcctgctcgtgaccg
tggccttcatcatcttttgggtgcggagcaagagaagcagactgctgca
cagcgactacatgaacatgaccccccagacggcctggccccaccagaaag
cactaccagccttacgcccctcccagagacttcgccgcctacagatctc
atatgggaggcggaggatctggcggaggtggaagtggcggaggcggatc
tcaaagatgggaactcgccctgggcagattcctggaatacctgagctgg
gtgtccacactgagcgaacaggtgcaagaggaactgctgagcagccaag
tgacccaagagctgagagccctgatggacgagacaatgaaggaactgaa -continued

```
ggcctacaagagcgagctggaagaacagctgacccctgtggccgaggaa
accagagccagactgagcaaagaactgcaggccgctcaggccagactgg
gagccgatatggaagatgttcggggcagactggtgcagtacagaggcga
agttcaggccatgctgggccagtctaccgaggaactgagagtgcggctg
gcctctcatctgattgccctgcagctgagactgatcggcgacgcattcg
acctgcagaaaagactggccgtgtaccaggctggcgctgctgaacggaa
gcggcgcagcggcagcgggcgcagcggcagcggcgagggcagaggaagt
cttctaacatgcggtgacgtggaggagaatcccggccct.
```

In one specific embodiment, the nucleotide sequence encoding the first polypeptide chain of the CAR is

```
                                        (SEQ ID NO: 122)
tctagaaatggccttaccagtgaccgccttgctcctgccgctggccttg
ctgctccacgccgccaggccggtgcagctgcagcagtcaggacctgaac
tggtgaagcctgggacttcagtgaggatatcctgcaagacttctggata
cacattcactgaatataccatacactgggtgaagcagagccatggaaag
agccttgagtggattggaaacatcaatcctaacaatggtggtaccacct
acaatcagaagttcgaggacaaggccacattgactgtagacaagtcctc
cagtacagcctacatggagctccgcagcctaacatctgaggattctgca
gtctattattgtgcagctggttggaactttgactactggggccaaggga
ccacggtcaccgtctcctcaggtggaggtggatcaggtggaggtggatc
tggtggaggtggatctgacattgtgatgacccagtctcacaaattcatg
tccacatcagtaggagacagggtcagcatcatctgtaaggccagtcaag
atgtgggtactgctgtagactggtatcaacagaaaccaggacaatctcc
taaactactgatttattgggcatccactcggcacactggagtccctgat
cgcttcacaggcagtggatctgggacagacttcactctcaccattacta
atgttcagtctgaagacttggcagattatttctgtcagcaatataacag
ctatcccctcacgttcggtgctgggaccatgctggacctgaaacgggct
agcacaacaacccctgcccccagacctcctaccccagcccctacaattg
ccagccagcctctgagcctgaggcccgaggcttgtagacctgctgctgg
cggagccgtgcacaccagaggactggatttcgcctgcgacttctgggtg
ctggtggtcgtgggcggagtgctggcctgttacagcctgctcgtgaccg
tggccttcatcatcttttgggtgcggagcaagagaagcagactgctgca
cagcgactacatgaacatgacccccagacggcctggccccaccagaaag
cactaccagccttacgcccctcccagagacttcgccgcctacagatctc
atatgggaggcggaggatctggcggaggtggaagtggcggaggcggatc
tccaaagatgggaactcgccctgggcagattcctggaatacctgagctg
ggtgtccacactgagcgaacaggtgcaagaggaactgctgagcagccaa
gtgacccaagagctgagagccctgatggacgagacaatgaaggaactga
aggcctacaagagcgagctggaagaacagctgacccctgtggccgagga
aaccagagccagactgagcaaagaactgcaggccgctcaggccagactg
ggagccgatatggaagatgttcggggcagactggtgcagtacagaggcg
```

-continued

```
aagttcaggccatgctgggccagtctaccgaggaactgagagtgcggct
ggcctctcatctgattgccctgcaggcaagactgatcggcgacgcattc
gacctgcagaaaagactggccgtgtaccaggctggcgctgctgaacgga
agcggcgcagcggcagcgggcgcagcggcagcggcgagggcagaggaag
tcttctaacatgcggtgacgtggaggagaatcccggccct.
```

In one specific embodiment, the nucleotide sequence encoding the first polypeptide chain of the CAR is

```
                                        (SEQ ID NO: 123)
tctagaaatggccttaccagtgaccgccttgctcctgccgctggccttg
ctgctccacgccgccaggccggtgcagctgcagcagtcaggacctgaac
tggtgaagcctgggacttcagtgaggatatcctgcaagacttctggata
cacattcactgaatataccatacactgggtgaagcagagccatggaaag
agccttgagtggattggaaacatcaatcctaacaatggtggtaccacct
acaatcagaagttcgaggacaaggccacattgactgtagacaagtcctc
cagtacagcctacatggagctccgcagcctaacatctgaggattctgca
gtctattattgtgcagctggttggaactttgactactggggccaaggga
ccacggtcaccgtctcctcaggtggaggtggatcaggtggaggtggatc
tggtggaggtggatctgacattgtgatgacccagtctcacaaattcatg
tccacatcagtaggagacagggtcagcatcatctgtaaggccagtcaag
atgtgggtactgctgtagactggtatcaacagaaaccaggacaatctcc
taaactactgatttattgggcatccactcggcacactggagtccctgat
cgcttcacaggcagtggatctgggacagacttcactctcaccattacta
atgttcagtctgaagacttggcagattatttctgtcagcaatataacag
ctatcccctcacgttcggtgctgggaccatgctggacctgaaacgggct
agcacaacaacccctgcccccagacctcctaccccagcccctacaattg
ccagccagcctctgagcctgaggcccgaggcttgtagacctgctgctgg
cggagccgtgcacaccagaggactggatttcgcctgcgacttctgggtg
ctggtggtcgtgggcggagtgctggcctgttacagcctgctcgtgaccg
tggccttcatcatcttttgggtgcggagcaagagaagcagactgctgca
cagcgactacatgaacatgacccccagacggcctggccccaccagaaag
cactaccagccttacgcccctcccagagacttcgccgcctacagatctc
atatgggaggcggaggatctggcggaggtggaagtggcggaggcggatc
tcaaagatgggaactcgccctgggcagattcctggaatacctgagctgg
gtgtccacactgagcgaacaggtgcaagaggaactgctgagcagccaag
tgacccaagagctgagagccctgatggacgagacaatgaaggaactgaa
ggcctacaagagcgagctggaagaacagctgacccctgtggccgaggaa
accagagccagactgagcaaagaactgcaggccgctcaggccagactgg
gagccgatatggaagatgttcggggcagactggtgcagtacagaggcga
agttcaggccatgctgggccagtctaccgaggaactgagagtgcggctg
gcctctcatctgattgccctgcagctgagactgatcggcgcagcattcg
```

-continued acctgcagaaaagactggccgtgtaccaggctggcgctctgaacggaag cggcgcagcggcagcgggcgcagcggcagcggcgagggcagaggaagtc ttctaacatgcggtgacgtggaggagaatcccggccct.

In another aspect is provided a nucleic acid molecule comprising a nucleotide sequence encoding the second polypeptide chain of any of the above heterodimeric chimeric antigen receptors (CARs).

In one specific embodiment, the nucleotide sequence encoding the second polypeptide chain of the CAR is (SEQ ID NO: 15)

ggatccatggccttaccagtgaccgccttgctcctgccgctggccttgc tgctccacgccgccaggccggaacagaaactcatcagtgaggaagattt gcagacgactccaggagagagatcatcactccctgccttttaccctggc acttcaggctcttgttccggatgtgggtccctctctctgccgacaacaa cccctgcccccagacctcctaccccagcccctacaattgccagccagcc tctgagcctgaggcccgaggcttgtagacctgctgctggcggagccgtg cacaccagaggactggatttcgcctgcgaccctaggttctgggtgctgg tggtcgtgggcggagtgctggcctgttacagcctgctcgtgaccgtggc cttcatcatcttttgggtgcggagcaagagaagcagactgctgcacagc gactacatgaacatgacccccagacggcctggccccaccagaaagcact accagccttacgcccctcccagagacttcgccgcctacagatctcccgg gggaggcggaggatctggcggaggtggaagtggcggaggcggatctatg agccagagcaacagagaactggtggtggacttcctgagctacaagctga gccagaagggctacagctggtcccagttcagcgacgtggaagagaacag aacagaggcccctgagggcacagagtctgaggctgtgaaacaggccctg agagaagccggcgacgagttcgagctgagatacagaagggccttcagcg acctgaccagccagctgcacatcacacctggcacagcctaccagagctt cgagcaggtcgtgaacgagctgttcagagatggcgtgaactggggcaga atcgtggccttcttcagctttggcggagccctgtgtgtggaaagcgtgg acaaagaaatgcaggtcctggtgtccagaatcgccgcctggatggccac ctacctgaacgatcatctggaaccctggattcaagagaacggcggctgg gacaccttcgtggaactgtacggaaacaacgccgctgccgagagcagaa agggccaagaacgagaagatggcggcggtggttctggtggcggcggtag tggtggcggtggatcaatgcatagagtgaagttcagcaggagcgcagac gcccccgcgtaccagcagggccagaaccagctctataacgagctcaatc taggacgaagagaggagtacgatgttttggacaagagacgtggccggga ccctgagatggggggaaagccgagaaggaagaaccctcaggaaggcctg tacaatgaactgcagaaagataagatggcggaggcctacagtgagattg ggatgaaaggcgagcgccggaggggcaaggggcacgatggcctttacca gggtctcagtacagccaccaaggacacctacgacgcccttcacatgcag gccctgccccctcgctaa.

In one specific embodiment, the nucleotide sequence encoding the second polypeptide chain of the CAR is (SEQ ID NO: 125)

ggatccatggccttaccagtgaccgccttgctcctgccgctggccttgc tgctccacgccgccaggccggaacagaaactcatcagtgaggaagattt gcagacgactccaggagagagatcatcactccctgccttttaccctggc acttcaggctcttgttccggatgtgggtccctctctctgccgacaacaa cccctgcccccagacctcctaccccagcccctacaattgccagccagcc tctgagcctgaggcccgaggcttgtagacctgctgctggcggagccgtg cacaccagaggactggatttcgcctgcgacctaggttctgggtgctggt ggtcgtgggcggagtgctggcctgttacagcctgctcgtgaccgtggcc ttcatcatcttttgggtgcggagcaagagaagcagactgctgcacagcg actacatgaacatgacccccagacggcctggccccaccagaaagcacta ccagccttacgcccctcccagagacttcgccgcctacagatctcccggg ggaggcggaggatctggcggaggtggaagtggcggaggcggatctatga gccagagcaacagagaactggtggtggacttcctgagctacaagctgag ccagaagggctacagctggtcccagttcagcgacgtggaagagaacaga acagaggcccctgagggcacagagtctgaggctgtgaaacaggccctga gagaagccggcgacgagttcgagctgagatacagaagggccttcagcga cctgaccagccagctgcacatcacacctggcacagcctaccagagcttc gagcaggtcgtgaacgagctgttcagagatggcgtgaactggggcagaa tcgtggccttcttcagctttggcggagccctgtgtgtggaaagcgtgga caaagaaatgcaggtcctggtgtccagaatcgccgcctggatggccacc tacctgaacgatcatctggaaccctggattcaagagaacggcggctggg acaccttcgtggaactgtacggaaacaacgccgctgccgagagcagaaa gggccaagaacgagaagatggaggcggaggatctggcggaggtggaagt ggcggaggcggatctatgcatagagtgaagttcagcaggagcgcagacg cccccgcgtaccagcagggccagaaccagctctataacgagctcaatct aggacgaagagaggagtacgatgttttggacaagagacgtggccgggac cctgagatggggggaaagccgagaaggaagaaccctcaggaaggcctgt acaatgaactgcagaaagataagatggcggaggcctacagtgagattgg gatgaaaggcgagcgccggaggggcaaggggcacgatggcctttaccag ggtctcagtacagccaccaaggacacctacgacgcccttcacatgcagg ccctgccccctcgctaa.

In one specific embodiment, the nucleotide sequence encoding the second polypeptide chain of the CAR is (SEQ ID NO: 126)

ggatccatggccttaccagtgaccgccttgctcctgccgctggccttgct gctccacgccgccaggccggaacagaaactcatcagtgaggaagatttgc agacgactccaggagagagatcatcactccctgccttttaccctggcact tcaggctcttgttccggatgtgggtccctctctctgccgacaacaacccc tgcccccagacctcctaccccagcccctacaattgccagccagcctctga gcctgaggcccgaggcttgtagacctgctgctggcggagccgtgcacacc -continued agaggactggatttcgcctgcgacctaggttctgggtgctggtggtcgtg
ggcggagtgctggcctgttacagcctgctcgtgaccgtggccttcatcat
cttttgggtgcggagcaagagaagcagactgctgcacagcgactacatga
acatgacccccagacggcctggccccaccagaaagcactaccagccttac
gcccctcccagagacttcgccgcctacagatctcccgggggaggcggagg
atctggcggaggtggaagtggcggaggcggatctatgagccagagcaaca
gagaactggtggtggacttcctgagctacaagctgagccagaagggctac
agctggtcccagttcagcgacgtggaagagaacagaacagaggcccctga
gggcacagagtctgaggctgtgaaacaggccctgagagaagccggcgacg
acttcgagctgagatacagaagggccttcagcgacctgaccagccagctg
cacatcacacctggcacagcctaccagagcttcgagcaggtcgtgaacga
gctgttcagagatggcgtgaactggggcagaatcgtggccttcttcagct
ttggcggagccctgtgtgtggaaagcgtggacaaagaaatgcaggtcctg
gtgtccagaatcgccgcctggatggccacctacctgaacgatcatctgga
accctggattcaagagaacggcggctgggacaccttcgtggaactgtacg
gaaacaacgccgctgccgagagcagaaagggccaagaacgagaagatgaa
gatggaggcggaggatctggcggaggtggaagtggcggaggcggatctat
gcatagagtgaagttcagcaggagcgcagacgcccccgcgtaccagcagg
gccagaaccagctctataacgagctcaatctaggacgaagagaggagtac
gatgttttggacaagagacgtggccgggaccctgagatggggggaaagcc
gagaaggaagaaccctcaggaaggcctgtacaatgaactgcagaaagata
agatggcggaggcctacagtgagattgggatgaaaggcgagcgccggagg
ggcaaggggcacgatggcctttaccagggtctcagtacagccaccaagga
cacctacgacgcccttcacatgcaggccctgccccctcgctaa.

In one specific embodiment, the nucleotide sequence encoding the second polypeptide chain of the CAR is (SEQ ID NO: 127)

ggatccatggccttaccagtgaccgccttgctcctgccgctggccttgct
gctccacgccgccaggccggaacagaaactcatcagtgaggaagatttgc
agacgactccaggagagagatcatcactccctgccttttaccctggcact
tcaggctcttgttccggatgtgggtccctctctctgccgacaacaacccc
tgcccccagacctcctaccccagcccctacaattgccagccagcctctga
gcctgaggcccgaggcttgtagacctgctgctggcggagccgtgcacacc
agaggactggatttcgcctgcgacctaggttctgggtgctggtggtcgtg
ggcggagtgctggcctgttacagcctgctcgtgaccgtggccttcatcat
cttttgggtgcggagcaagagaagcagactgctgcacagcgactacatga
acatgacccccagacggcctggccccaccagaaagcactaccagccttac
gcccctcccagagacttcgccgcctacagatctcccgggggaggcggagg
atctggcggaggtggaagtggcggaggcggatctatggcccacgccggca
ggaccggctacgacaacagggagatcgtgatgaagtacatccactacaag
ctgagccagaggggctacgagtgggacgccggcgacgtgggcgccgcccc
ccccggcgccgcccccgcccccggcatcttcagcagccagcccggccaca
ccccccaccccgccgccagcagggaccccgtggccaggaccagccccctg
cagacccccgccgcccccggcgccgccgccggcccccgccctgagccccgt
gccccccgtggtgcacctgaccctgaggcaggccggcgacgacttcagca
ggaggtacaggagggacttcgccgagatgagcagccagctgcacctgacc
cccttcaccgccaggggcaggttcgccaccgtggtggaggagctgttcag
ggacggcgtgaactggggcaggatcgtggccttcttcgagttcggcggcg
tgatgtgcgtggagagcgtgaacagggagatgagcccccctggtggacaac
atcgccctgtggatgaccgagtacctgaacaggcacctgcacacctggat
ccaggacaacggcggctgggacgccttcgtggagctgtacggccccagca
tgagggaagatggaggcggaggatctggcggaggtggaagtggcggaggc
ggatctatgcatagagtgaagttcagcaggagcgcagacgcccccgcgta
ccagcagggccagaaccagctctataacgagctcaatctaggacgaagag
aggagtacgatgttttggacaagagacgtggccgggaccctgagatgggg
ggaaagccgagaaggaagaaccctcaggaaggcctgtacaatgaactgca
gaaagataagatggcggaggcctacagtgagattgggatgaaaggcgagc
gccggaggggcaaggggcacgatggcctttaccagggtctcagtacagcc
accaaggacacctacgacgcccttcacatgcaggccctgccccctcgcta
a.

In one specific embodiment, the nucleotide sequence encoding the second polypeptide chain of the CAR is (SEQ ID NO: 128)

ggatccatggccttaccagtgaccgccttgctcctgccgctggccttgct
gctccacgccgccaggccggaacagaaactcatcagtgaggaagatttgc
agacgactccaggagagagatcatcactccctgccttttaccctggcact
tcaggctcttgttccggatgtgggtccctctctctgccgacaacaacccc
tgcccccagacctcctaccccagcccctacaattgccagccagcctctga
gcctgaggcccgaggcttgtagacctgctgctggcggagccgtgcacacc
agaggactggatttcgcctgcgacctaggttctgggtgctggtggtcgtg
ggcggagtgctggcctgttacagcctgctcgtgaccgtggccttcatcat
cttttgggtgcggagcaagagaagcagactgctgcacagcgactacatga
acatgacccccagacggcctggccccaccagaaagcactaccagccttac
gcccctcccagagacttcgccgcctacagatctcccgggggaggcggagg
atctggcggaggtggaagtggcggaggcggatctatgagccagagcaaca
gagaactggtggtggacttcctgagctacaagctgagccagaagggctac
agctggtcccagttcagcgacgtggaagagaacagaacagaggcccctga
gggcacagagtctgaggctgtgaaacaggccctgagagaagccggcgacg
agttcgagctgagatacagaagggccttcagcgacctgaccagccagctg
cacatcacacctggcacagcctaccagagcttcgagcaggtcgtgaacga
gctgttcagagatggcgtgaactggggcagaatcgtggccttcttcagct -continued ttggcggagccctgtgtgtggaaagcgtggacaaagaaatgcaggtcctg gtgtccagaatcgccgcctggatggccacctacctgaacgatcatctgga accctggattcaagagaacggcggctgggacaccttcgtggaactgtacg gaaacaacgccgctgccgagagcagaaagggccaagaacgagaagatgga ggcggaggatctggcggaggtggaagtggcggaggcggatctatgcatag agtgaagttcagcaggagcgcagacgcccccgcgtaccagcagggccaga accagctctataacgagctcaatctaggacgaagagaggagtacgatgtt ttggacaagagacgtggccgggaccctgagatggggggaaagccgagaag gaagaaccctcaggaaggcctgtacaatgaactgcagaaagataagatgg cggaggcctacagtgagattgggatgaaaggcgagcgccggaggggcaag gggcacgatggcctttaccagggtctcagtacagccaccaaggacaccta cgacgcccttcacatgcaggccctgccccctcgctaa.

In one specific embodiment, the nucleotide sequence encoding the second polypeptide chain of the CAR is (SEQ ID NO: 129)

ggatccatggccttaccagtgaccgccttgctcctgccgctggccttgct gctccacgccgccaggccggaacagaaactcatcagtgaggaagatttgc agacgactccaggagagagatcatcactccctgcctttttaccctggcact tcaggctcttgttccggatgtgggtccctctctctgccgacaacaacccc tgcccccagacctcctaccccagccccctacaattgccagccagcctctga gcctgaggcccgaggcttgtagacctgctgctggcggagccgtgcacacc agaggactggatttcgcctgcgacctaggttctgggtgctggtggtcgtg ggcggagtgctggcctgttacagcctgctcgtgaccgtggccttcatcat cttttgggtgcggagcaagagaagcagactgctgcacagcgactacatga acatgacccccagacggcctggccccaccagaaagcactaccagccttac gcccctcccagagacttcgccgcctacagatctcccgggggaggcggagg atctggcggaggtggaagtggcggaggcggatctatgagccagagcaaca gagaactggtggtggacttcctgagctacaagctgagccagaagggctac agctggtcccagttcagcgacgtggaagagaacagaacagaggcccctga gggcacagagtctgaggctgtgaaacaggccctgagagaagccggcgacg agttcgagctgagatacagaagggccttcagcgacctgaccagccagctg cacatcacacctggcacagcctaccagagcttcgagcaggtcgtgaacga gctgttcagagatggcgtgaactggggcagaatcgtggccttcttcagct ttggcggagccctgtgtgtggaaagcgtggacaaagaaatgcaggtcctg gtgtccagaatcgccgcctggatggccacctacctgaacgatcatctgga accctggattcaagagaacggcggctgggacaccttcgtggaactgtacg gaaacaacgccgctgccgagagcagaaagggccaagaacgagaagatgga ggcggaggatctggcggaggtggaagtggcggaggcggatctatgcatag agtgaagttcagcaggagcgcagacgcccccgcgtaccagcagggccaga accagctctataacgagctcaatctaggacgaagagaggagtacgatgtt ttggacaagagacgtggccgggaccctgagatggggggaaagccgagaag -continued gaagaaccctcaggaaggcctgtacaatgaactgcagaaagataagatgg cggaggcctacagtgagattgggatgaaaggcgagcgccggaggggcaag gggcacgatggcctttaccagggtctcagtacagccaccaaggacaccta cgacgcccttcacatgcaggccctgccccctcgctaa.

In one embodiment, the nucleotide sequence encoding the first polypeptide chain of the CAR is operably linked to a first promoter. In one embodiment, the nucleotide sequence encoding the second polypeptide chain of the CAR is operably linked to a second promoter. In one embodiment, the nucleotide sequence encoding the first polypeptide chain of the CAR is operably linked to a first promoter, the nucleotide sequence encoding the second polypeptide chain of the CAR is operably linked to a second promoter, and the first and second promoters are the same.

In one specific embodiment, the nucleotide sequence encoding the first polypeptide chain of the CAR is operably linked to a first promoter, the nucleotide sequence encoding the second polypeptide chain of the CAR is operably linked to a second promoter, and the first and second promoters are different.

In one specific embodiment, the nucleotide sequences encoding the first and second polypeptide chains of the CAR are operably linked to a single promoter.

In one embodiment, the first and/or second promoter is a T lymphocyte-specific promoter or an NK cell-specific promoter. In one specific embodiment, the nucleic acid molecule is a DNA molecule. In one specific embodiment, the nucleic acid molecule is a RNA molecule.

In another aspect is provided a recombinant vector comprising any of the above nucleic acid molecules. In one embodiment, the vector is a viral vector (e.g., a retroviral vector, a lentiviral vector, an adenoviral vector, an adeno-associated virus vector, an alphaviral vector, a herpes virus vector, and a vaccinia virus vector). In one specific embodiment, the vector is a lentiviral vector.

In a further related aspect is provided an isolated host cell comprising any of the above heterodimeric inactivatable chimeric antigen receptors (CARs) or any of the above CAR-encoding nucleic acid molecules or vectors. In one embodiment, the host cell is a mammalian cell. In one embodiment, the host cell is selected from a cytotoxic cell (e.g., a cytotoxic T cell or a natural killer (NK) cell), a T cell (e.g., T-helper cells, cytotoxic T-cells, T-regulatory cells (Treg), and gamma-delta T cells), a stem cell, a progenitor cell, and a cell derived from a stem cell or a progenitor cell. In one embodiment, the host cell is an allogeneic cell. In one embodiment, the host cell is an autologous cell. In one specific embodiment, the autologous host cell has been isolated from a subject (e.g., human) having a disease.

In a related aspect, the invention provides a pharmaceutical composition comprising any of the above host cells a pharmaceutically acceptable carrier and/or excipient.

In another related aspect, the invention provides a method for producing a host cell of the invention comprising genetically modifying said cell with a nucleic acid molecule or a vector of the invention. In one embodiment, the genetic modification is conducted ex vivo. In one embodiment, the method further comprises activation and/or expansion of the cell ex vivo.

In a further aspect, the invention provides a method for stimulating elimination of a cell comprising an antigen in a subject in need thereof, said method comprising administering to the subject an effective amount of cytotoxic T cells or natural killer (NK) cells comprising a heterodimeric inactivatable chimeric antigen receptor (CAR) of the invention, wherein the extracellular target-binding region of said CAR binds to said antigen. In one embodiment, the antigen is selected from a cancer cell associated antigen, an infection-associated antigen and an auto-antigen. In one specific embodiment, the antigen is a cancer cell associated antigen associated with a solid tumor. In one specific embodiment, the antigen is prostate-specific membrane antigen (PSMA). In one specific embodiment, the antigen is an infection-associated antigen. In one specific embodiment, the antigen is an auto-antigen. In one specific embodiment, the antigen is CD19.

In another aspect is provided a method for stimulating elimination of a cell comprising PSMA in a subject in need thereof, said method comprising administering to the subject an effective amount of cytotoxic T cells or NK cells comprising the any of the above heterodimeric inactivatable CARs.

In another aspect, the invention provides a method for treating a cancer in a subject in need thereof, said method comprising administering to the subject a therapeutically effective amount of cytotoxic T cells or natural killer (NK) cells comprising a heterodimeric inactivatable chimeric antigen receptor (CAR) of the invention, wherein the extracellular target-binding region of said CAR binds to an antigen associated with said cancer. In one embodiment, the cancer is from a solid tumor (e.g., carcinoma, melanoma, prostate cancer, sarcoma, glioma, astrocytoma, medulloblastoma, craniopharyngioma, ependymoma, pinealoma, hemangioblastoma, acoustic neuroma, oligodendroglioma, menangioma, neuroblastoma, or retinoblastoma). In one embodiment, the cancer is a leukemia or a lymphoma.

In a related aspect is provided a method for treating prostate cancer in a subject in need thereof, said method comprising administering to the subject a therapeutically effective amount of cytotoxic T cells or natural killer (NK) cells comprising a heterodimeric inactivatable chimeric antigen receptor (CAR) of the invention.

In yet another aspect, the invention provides a method for treating an infection in a subject in need thereof, said method comprising administering to the subject a therapeutically effective amount of cytotoxic T cells or natural killer (NK) cells comprising a heterodimeric inactivatable chimeric antigen receptor (CAR) of the invention, wherein the extracellular target-binding region of said CAR binds to an antigen associated with said infection.

In yet another aspect, the invention provides a method for treating an inflammatory condition or an autoimmune disease in a subject in need thereof, said method comprising administering to the subject a therapeutically effective amount of T-helper cells or Treg cells comprising a heterodimeric inactivatable chimeric antigen receptor (CAR) of the invention, wherein the extracellular target-binding region of said CAR binds to an antigen associated with said inflammatory condition or an autoimmune disease. In one embodiment, the method results in reducing an immune response to a transplanted organ or tissue.

In one embodiment of any of the above methods involving administration to a subject, the method comprises:

a) isolating T cells or NK cells from the subject;
b) genetically modifying said T cells or NK cells ex vivo with any of the above nucleic acid molecules or vectors;
c) optionally, expanding and/or activating said T cells or NK cells before, after or during step (b); and
d) introducing the genetically modified T cells or NK cells into the subject.

In one embodiment, the method comprises a) isolating T cells or NK cells from the subject;
b) genetically modifying said T cells or NK cells ex vivo with any of the above nucleic acid molecules or vectors;
c) optionally, expanding and/or activating said T cells or NK cells before, after or during step (b); and
d) introducing the genetically modified T cells or NK cells into the subject.

In one embodiment of any of the above methods involving administration to a subject, the method further comprises inhibiting the activity of the CAR by administering to the subject an effective amount of an inhibitory molecule, wherein the inhibitory molecule disrupts the heterodimer formed by the first and second member of the dimerization pair within the CAR resulting in inhibition of CAR-mediated signaling.

In one embodiment of any of the above methods involving administration to a subject, the subject is human.

In a further aspect, the invention provides a method for inhibiting the activity of a heterodimeric inactivatable chimeric antigen receptor (CAR) of the invention in a host cell, comprising contacting the host cell with an inhibitory molecule, wherein the inhibitory molecule disrupts the heterodimer formed by the first and second member of the dimerization pair within the CAR resulting in inhibition of CAR-mediated signaling.

In one embodiment of any of the methods involving an inhibitory molecule, the inhibitory molecule is a small molecule or a polypeptide.

In one embodiment of any of the methods involving an inhibitory molecule, the inhibitory molecule binds to the first or second member of the dimerization pair with higher affinity than the first and second member of the dimerization pair bind to each other.

In one embodiment of any of the methods involving an inhibitory molecule, the inhibitory molecule binds to the first member of the dimerization pair.

In one embodiment of any of the methods involving an inhibitory molecule, the inhibitory molecule binds to the second member of the dimerization pair.

In one embodiment of any of the methods involving an inhibitory molecule, the first or the second member of the dimerization pair comprises a BCL-xL sequence, a BCL-2 sequence, or a mutant of either and the inhibitory molecule is a BCL-xL and/or a BCL-2 inhibitor.

In one embodiment, the inhibitory molecule is navitoclax, A-1331852, A-1155463, venetoclax, ABT-199 (GDC-0199), obatoclax mesylate (GX15-070), HA14-1, ABT-737, TW-37, AT101, sabutoclax, gambogic acid, ARRY 520 trifluoroacetate, iMAC2, maritoclax, methylprednisolone, MIM1, ML 311, glossypol, BH3I-1, or 2-methoxy-antimycin A3). In one specific embodiment, the inhibitory molecule is A-1331852. In one specific embodiment, the inhibitory molecule is A-1155463. In one specific embodiment, the inhibitory molecule is venetoclax.

These and other aspects of the present invention will be apparent to those of ordinary skill in the art in the following description, claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) The OFF-CAR comprises two chains that assemble in the cell-surface membrane via a high affinity interaction between Protein A (computationally designed 1LE4A) and Protein B (BCL-xL). The first chain (Chain A) comprises a tumor-binding scFv followed by a spacer/linker region derived from CD8α, the transmembrane domain (TM) and the endodomain (ED) derived from CD28, and Protein A. The second chain (Chain B) comprises an extracellular region including the ectodomain of DAP10 and a myc tag, followed by the TM and ED of CD28, Protein B, and CD3 that can confer signal 1 for T cell activation. In the presence of high-affinity drugs specific for BCL-xL, these two chains are split, thus, abrogating signaling. (FIG. 1B) A classic second generation CAR, which only encompasses one non-inactivatable chain having a tumor-specific scFv followed by a spacer/linker, a TM region, and both CD3 ζ for signal 1 and a co-stimulatory endodomain for signal 2 of T cell activation.

FIGS. 2A-2C show a three-dimensional model of the heterodimerizing Protein B domain BCL-xL (B cell lymphoma extra-large) in complex with its natural binding partner BimBH3 (FIG. 2A), rationally designed Protein A domain (ApoE mutant derivative 1LE4A) (FIG. 2B), or inhibitory molecule (e.g., Navitoclax) (FIG. 2C). (FIG. 2A) BimBH3 (in dark grey) is a peptide that is able to bind to all of the BCL2 family anti-apoptotic proteins, including BCL-xL[11]. (FIG. 2B) A database search identified Apolipoprotein E4 (ApoE4) as comprising a structure similar to BimBH3. Residues in ApoE4 were then selectively mutated to ones found in BimBH3 that bind to BCL-xL. The resultant protein was named 1LE4A (in dark grey) and was shown to bind with picomolar affinity to BCL-xL. (FIG. 2C) A drug (e.g., a small molecule drug such as A-1331852, A-1155463, or navitoclax) with affinity for Protein B and known to compete for binding at the binding site of Protein A, when administered will out-compete the heterodimerizing interaction. In certain embodiments, the affinity of the drug is higher for Protein B than the affinity of Protein A for Protein B, to allow for the drug to more easily out compete the Protein A and B interaction.

FIGS. 4A-4B provide non-limiting exemplary sequences of OFF-CAR Chain A. The extracellular target-binding domain is a single chain variable fragment (scFv) specific for prostate-specific membrane antigen (PSMA). (FIG. 4A) A non-limiting example of an amino acid sequence of an OFF-CAR Chain A. (FIG. 4B) A non-limiting example of a nucleic acid sequence encoding the amino acid sequence of the OFF-CAR Chain A of FIG. 4A.

FIGS. 5A-5B provide non-limiting exemplary sequences of OFF-CAR Chain B. The DAP10 ectodomain was used to stabilize cell-surface expression of Chain B. (FIG. 5A) A non-limiting example of an amino acid sequence of an OFF-CAR Chain B. (FIG. 5B) A non-limiting example of a nucleic acid sequence encoding the amino acid sequence of the OFF-CAR Chain B of FIG. 5A.

FIG. 7 demonstrates co-localization of about 91% for the exemplary OFF-CAR Chain A (CAR1) and OFF-CAR Chain B (CAR2) upon expression in T cells (as determined using AMNIS® imaging flow cytometry). xi and yi are the per-pixel intensity values of the two images. X and Y are the corresponding mean intensity values.

(FIG. 8A) OFF-CAR transduced Jurkat cells were stained with fluorescently-labeled anti-human Fab mAb and anti-myc mAb to detect Chains A and B, respectively, by flow cytometry. (FIG. 8B) Flow cytometric analysis of the engineered Jurkat cells demonstrated stability of both chains over a ten day period. Chain 1 is the R-chain, and Chain 2 is the S-chain. STOP-CAR stability (left chain-1, right chain-2) were monitored in Jurkat cells at day 5 (black bar), day 15 (dark grey bar), day 30 (light grey bar) (experimental replicate n=2). Briefly, Jurkat cells were transduced with STOP-CAR lentivirus and then kept in culture for 30 days. The cells were monitored for STOP-CAR cell-surface expression stability by flow cytometric analysis. No decrease in expression of either Chain-1 or Chain-2 was observed over time, thus confirming stability. (FIG. 8C) Amnis® imaging of stained Jurkat cells (FITC-anti-human Fab mAb and PE-anti-myc mAb) revealed co-localization of the two OFF-CAR chains. (FIG. 8D) OFF-CAR NFAT-mcherry reporter Jurkat cells, and second generation CAR (Pz-1) NFAT-mcherry reporter Jurkat cells, were co-cultured with $PSMA^+$ target cells and % activation was determined by the proportion of Jurkat cells that turned red.

(FIG. 9A) Transduction efficiency of Chains A and B of the OFF-CAR is approximately 40% and 17%, respectively, on primary T cells as determined by flow cytometric analysis. (FIG. 9B) Untransduced (UTD) and OFF-CAR engineered primary T cells expand at a similar rate thus indicating that the forced expression of the chains does not impair function. (FIG. 9C-9D) OFF-CAR primary T cells co-cultured with target cells produce both IL2 (FIG. 9C) and IFN-γ (FIG. 9D) at similar levels as classic second generation CAR T cells targeting the same antigen (Pz-1).

FIGS. 10A-10C show the abrogation of OFF-CAR primary T cell killing capacity using small inhibitor drug treatment (Drug 1=A-1331852 or Drug 2=A-1155463, at 10 μM) and provide a comparison of the exemplary OFF-CAR T cell cytotoxicity versus second-generation CAR (Pz1), as measured by IncuCyte® assay. The red dye/area (darker areas on the pictures) is a cytotoxicity dye that labels cells (tumor cells) being killed by the CAR-containing T cells.

FIG. 11 demonstrates that the addition of a competitive small molecule (Drug 1=A-1331852 or Drug 2=A-1155463, at 10 μM) inhibits the activity of T cells expressing an exemplary OFF-CAR. Shown are the IncuCyte® assay plots where the total red area/$mm^2$ is used as a measure of cytotoxicity/killing capacity of the OFF-CAR-transduced T cells. Both A-1331852 and A-1155463 eliminate the killing capacity of the exemplary OFF-CAR. Killing, as measured by total red area per mm2 is shown over 52 hours.

FIG. 12 depicts lower affinity 1LE4A Protein A sequences that are suitable for use in some embodiments of the invention.

FIGS. 15A-15C show a protein design protocol and sequence alignment of designed scaffolds. In FIG. 15A, a 12-residue amino acid fragment from the BIM-BH3 interaction was matched against a database of >11000 proteins using the MotifGraft protocol.

Grafted scaffolds were then designed, with their amino acid identities restricted to common mutations according to a BLOSUM62 matrix. Designed scaffolds were filtered by three criteria: proteins with a human origin (or with a close human homologue), globularity, and packing of the BH3 motif within the scaffold. FIG. 15B shows a table of designs and scores for the scoring/filtering criteria. Scaffold PDB id: Protein Databank id for the protein that was used as a scaffold to design each binder. Scaffold protein name: Brief name of the protein that was used as a scaffold. Organism of scaffold: Special origin of the scaffold. Rosetta ddG: Computed delta-delta G interaction energy between LD[1-3] and Bcl-XL. Globularity: Globularity score for each design. vdW Dots to scaffold: Number of vdW contacts between the grafted motif and the scaffold. SASA of seed: Empirical score that denotes the buried surface area of the grafted motif in the scaffold. #manual reversions to WT: Number of designed positions that were reverted to the scaffold identity. Total #mutations on scaffold: Final number of residues in the scaffold that were mutated to a different amino acid identity during the design process. FIG. 15C shows a sequence alignment of the three designed scaffolds. A helical 12-residue fragment with the sequence IAXXLXXIGXXF (SEQ ID NO: 179) (hotspot residues in light grey) was grafted onto three different scaffolds for LD1, LD2, and LD3 respectively: Syntaxin 6 (Syn6, PDB ID: 1LVF); human focal adhesion targeting domain of Pyk2 (pyk2, PDB ID: 3GM2); and Apolipoprotein E (ApoE, PDB ID: 1LE4). Hotspot residues are shown in light grey while designed residues are shown in bold. The sequence of BIM BH3 is shown as a reference in the third line.

FIGS. 16A-16G show structure-based computational design of a high-affinity chemically-disruptable heterodimer (CDH) to control CAR T-cell activity. FIG. 16A shows the domain architecture of the classical second generation (2G)-CAR and the STOP-CAR. The CDH spontaneously assembles by the drug-binding module (cyan) and the binder (dark blue), and it monomerizes in the presence of the drug disruptor. FIG. 16B shows a 12-residue amino acid fragment from the BIM-BH3 interaction was matched against a database of >11,000 proteins using the MotifGraft program. Grafted scaffolds were then designed, with their amino acid identities restricted to common mutations according to the BLOSUM62 matrix. Designed scaffolds were filtered by three criteria: proteins with globularity, human origin (or with a close human homologue), and packing of the BH3 motif within the scaffold. FIG. 16C shows SPR measurements for LD3:Bcl-XL binding interaction, sensorgrams and fitted curves are shown in black and red, respectively. FIG. 16D shows apparent IC50s of the LD3:Bcl-XL complex for the two drugs determined by SPR. Two Bcl-XL inhibitors were selected as candidates for the CDH disruption. FIG. 16E shows a crystal structure of LD3 (pale green) in complex with the protein Bcl-2 (white) is in close agreement with the computational model of LD3 (dark blue) in complex with Bcl-XL (not shown), interface RMSD of 1.35 Å. In FIG. 16F, interface residues of LD3 are labeled and shown as sticks in the model (dark blue) and the crystal structure (pale green). In FIG. 16G, the crystal structure of LD3 (pale green) versus the BIM-BH3 peptide (orange) with the hotspot residues shown as sticks.

FIG. 17A shows SPR sensorgrams results of the three designs injected over immobilized Bcl-XL. Black dashed curves show the sensorgrams and the red curves show the associated kinetic fits (2-state model was used to fit LD1, and 1:1 model was used to fit LD3). For LD1, the concentrations of analyte tested ranged from 1 μM to 31.25 nM varied in 2-fold dilutions. No binding was detected for LD2 upon the injection of concentrations up to 2 μM. LD3 binds to Bcl-XL with a $K_D$ of 3.9 μM, following injections of analyte ranging from 250 nM to 7.8125 nM varied in 2-fold dilutions. In FIG. 17B, LD3 analysed using Circular Dichroism spectroscopy showed a spectrum typical of a helical protein. The melting temperature of LD3 was 59° C. In FIG. 17C, SEC-MALS analysis showed that the Bcl-XL and LD3 are monomers in solution (left and center panels). Bcl-XL and LD3 were pre-incubated with DMSO or 10 μM of Drug-2 (right panel). Bcl-XL:LD3 mixed with DMSO form a heterodimer (black trace), while Bcl-XL:LD3 mixed with Drug-2 resulted in no complex formation with the two proteins eluting in the monomeric state. In FIG. 17D, apparent $IC_{50}$s were measured with SPR. Different drug dilutions were pre-incubated with LD3, and the mixture was injected over immobilized Bcl-XL. Apparent $IC_{50}$s were calculated by using the RU measurement at 120 seconds.

FIGS. 18A-18C show a LD3:Bcl-2 crystal structure comparison with the model, data collection, and refinement statistics. FIG. 18A shows a comparison of crystal density of LD3 (green mesh) with the LD3 model (blue tubes). The molecular surface of Bcl-2 from the crystal structure is shown in white. FIG. 18B shows a comparison of the grafted 12-amino acid motif between crystal density (green mesh) and model (blue). Bcl-2 from the crystal structure is shown in white tubes. FIG. 18C shows crystallographic data collection and refinementstatistics.

FIGS. 19A-19H show computationally designed heterodimeric STOP-CARs are stably expressed on the surface of Jurkat and primary human T-cells. FIG. 19A shows the architecture of the STOP-CAR. The left panel is a cartoon depicting the different components and the designed CDH formed by LD3 (cyan) and Bcl-XL (dark blue) in the monomeric form due to the presence of drug disruptor. The right panel is a schematic of the R- and S-chains encoded in a single lentiviral vector, each led by CD8a leader sequence and separated by the T2A ribosome skipping sequence. FIG. 19B shows flow cytometric evaluation of R- and S-chain expression on Jurkat cells stained with anti-human F(ab)-Ab-APC and anti-cMyc-Ab-APC, respectively. Cell surface co-localization of R- and S-chains, labeled with anti-human F(ab)-Ab-FITC and anti-cMyc-Ab-APC, respectively, as measured by Amnis® imaging (4 different Jurkat cells are reported). FIG. 19C shows STOP-CAR stability on Jurkat cells by flow cytometric analysis post-transduction. FIG. 19D shows percent activation of the STOP-CAR-engineered Jurkat reporter cell line as measured by mCherry expression (PMA/ionomyocin-stimulated cells were set at 100%; experimental replicates n=2) in presence of MS1-PSMA+ target cell line, 1:1 E:T Ratio. FIG. 19E shows transduction efficiency of primary human T cells with a second generation anti-PSMA (2G)-CAR and STOP-CAR (n=13 donors). In FIG. 19F, the expression of both STOP-CAR chains is stable over 15 days (n=5), and in FIG. 19G, there is no difference in fold-expansion of untransduced (UTD)-Ts and STOP-CAR-Ts (n=5). In FIG. 19H, STOP-CAR-Ts and 2G-CAR-Ts have a similar memory phenotype (n=4) ($T_{CM}$=Central Memory, $T_N$=T Naïve, $T_{EMRA}$=terminally differentiated effector memory cells, $T_{EM}$=T effector Memory).

FIG. 20A is a schematic of R- and S-chains for the first STOP-CAR prototype-1 (Proto-1) tested, and their cell-surface expression on Jurkat reporter cells following transfection with a single lentiviral vector encoding both chains. FIG. 20B shows cell-surface localization of 91% of Proto-1 chains on the surface of Jurkat cells as determined by Amnis® imaging following staining with anti-human-F(ab)-Ab-FITC and anti-cMyc-mAb-FITC (for R- and S-chains, respectively). FIG. 20C shows activation of Proto-1 STOP-CAR-Jurkat cells (6×NFAT-mCherry-Jurkat engineered cell line) in the presence of PSMA+-MS1 cells or resulting from PMA/Ionomyocin stimulation as measured by percent mCherry expression, and FIG. 20D shows IL2 production.

Representative flow cytometry plots of the mCherry-expressing activated Jurkat cells are shown. A comparison is made with UTD cells, R-chain and S-chain co-expressed from the same vector (R-T2A-S), R- and S-chains expressed individually, and from co-transfection with two vectors (R+S-chain). The percent mCherry expression and relative IL2 production was normalized with respect to PMA/IONO stimulation which was set at 100% and 1, respectively, for each transfection-type. FIG. 20E shows Proto-1 stability in Jurkat cells and AMNIS® analysis at day 30. FIG. 20F shows transduction efficiency of R- and S-chains of Proto-1 on primary T cells averaged (n=3) 80% and 4%, respectively, as determined by flow cytometric analysis. FIG. 20G shows a vector scheme of prototype-2 (Proto-2), and their cell-surface expression on Jurkat reporter cells. FIG. 20H shows Proto-2 transduction efficiency of R- and S-chains on primary T cells averaged (n=2) 4% and 6%, respectively, as determined by flow cytometric analysis.

FIG. 21A shows a schematic of the experiment in which $CD4^+$ and $CD8^+$ T-cells bead-enriched by negative selection were stimulated overnight with anti-CD3/anti-CD28 beads in the presence of hIL2 and then lentivirally transduced. On day 5, the beads were removed and hIL7/IL15 was added to the culture. Assays were performed on day 10. FIG. 21B shows STOP-CAR cell-surface expression by Jurkat reporter cells on days 15 and 30 as determined by flow cytometric analysis of R- and S-chain staining with anti-F(Ab)-Ab-APC and anti-cMyc-Ab-APC staining, respectively. FIG. 21C shows STOP-CAR expression by primary human T-cells at day 15 (as described for Jurkat cells, n=13 total). FIG. 21D shows 2G-CAR and STOP-CAR expression on $CD4^+$ and $CD8^+$ human T-cells at day 5. STOP-CAR transduction efficiency is similar for $CD8^+$ and $CD4^+$ T-cells measured by flow cytometric analysis of stained cells, as described above (n=6). FIG. 21E shows flow cytometric analysis on day 10 of $CD3^+$ CCR7 and CD45RA mAb-stained STOP-CAR T-cells in order to delineate percentages of naive ($T_N$), central memory ($T_{CM}$), effector memory ($T_E$) and the $CCR7^-$ effector memory subset ($T_{EMRA}$), as compared to UTD and 2G-CAR-Ts (n=4 total). FIG. 21F is a representative dot plot for PSMA antigen expression level in PC3-PIP cells, measured by flow cytometry.

In FIG. 22A, PSMA expression on PC3-PIP tumor cells assessed by flow cytometric analysis. In FIG. 22B, killing of PC3-PIP tumor cells by STOP-CAR-Ts (IncuCyte® measurement, calculated from total red area/$mm^2$) is impaired in the presence of 10 μM Drug-2 ($p<0.0001$, n=5 donors, E:T Ratio 2:1), while killing by 2G-CAR-Ts is unaffected (STOP: STOP-CAR; UTD: untransduced T cells; 2G: second generation CAR). In FIG. 22C, killing of PC3-PIP tumor cells (IncuCyte®) by STOP-CAR-Ts is impaired in the continued presence of 10 μM Drug-2, while STOP-CAR-Ts recover cytolytic activity after Drug-2 is discontinued for 48 h (pre=pre-treated with Drug, n=3 donors). In FIG. 22D, IFNγ production of STOP-CAR-Ts is significantly impaired by continuous exposure to Drug-2 (p=0.0026, n=3, Unpaired Student's t-test), while it recovers following discontinuation of exposure (pre-Drug). FIG. 22E shows a Winn assay in which NSG mice were inoculated subcutaneously with $5\times10^6$ PC3-PIP tumor cells and on day 5, received 1 dose of $2\times10^6$ CAR-Ts or UTD-Ts, +/−daily peri-tumor injections of 10 μM Drug-2, or vehicle (saline, 2% DMSO). Drug-2 significantly impaired tumor control by STOP-CAR-Ts ($p<0.0001$), but did not affect 2G-CAR-Ts (n=5 mice/group). In FIG. 22F, NSG mice were inoculated subcutaneously with $5\times10^6$ PC3-PIP tumor cells and on day 5, received 1 dose of $2\times10^6$ CAR-Ts or UTD-Ts. Dynamic addition of removal of 10 μM Drug-2 was tested starting from day 11. Drug-2 significantly impaired tumor control by STOP-CAR-Ts ($p<0.0001$) (n=7 mice/group). Day 11 Drug removal significantly turned from uncontrolled growth to tumor control at Day 17 (Tumor control not significantly different from STOP-CAR-Ts) (n=7 mice/group), while the Day 11 Drug addition caused the switch from previous tumor control to tumor establishment ($p<0.0130$) (n=7 mice/group). Unless otherwise noted, statistical significance was determined by Two-Way ANOVA and Post-hoc Tukey test.

In FIG. 23A, IncuCyte® measurements of tumor cell death (as measured by total red area/$mm^2$) for PC3-PIP cells over 24 h co-incubation with increasing concentrations of Drug-1 and -2. Representative images of tumor cell death under the different conditions at 24 h (Scale=300 μm). In FIG. 23B, IncuCyte® measurements of CD4+ and CD8+ T cell death (as measured by total red area/$mm^2$) over 24 h co-incubation with increasing concentrations of Drug-1 and -2 (n=4). FIG. 23C shows Fold-expansion and cell diameter of CD4+ and CD8+ T cells following 24 h exposure to 10 μM Drug-2 does not significantly decrease with respect to untreated cells (p=0.555, Two-way ANOVA with Post-hoc Tukey test, p=0.222, n=3, Mann-Whitney U-test, respectively). At 100 μM and 1.5 mM physical properties of T-cells are significantly impaired as compared to untreated, or 10 μM Drug-2 treated cells.

In FIG. 24A, IncuCyte® analysis reveals that 10μM Drug-1 does not impair STOP-CAR-T cytotoxicity (n=5). In FIG. 24B, 5 μM Drug-2 does not significantly abrogate cytotoxicity of STOP-CAR-Ts or 2G-CAR-Ts (n=5).

In FIG. 25A, flow cytometric analysis of anti-PSMA-Ab-PE stained 22Rv1 cells shows that approximately 65% of the cells are antigen-positive. FIG. 25B shows mCherry expression in UTD, 2G-CAR and STOP-CAR-engineered Jurkat reporter cells following 48 h co-culture with 22Rv1 cells (E:T ratio 2:1, experimental replicates=2). FIG. 25C shows IncuCyte® evaluation of 22Rv1 cell-death by STOP-CAR-Ts and 2G-CAR-Ts in the absence and presence of 10 μM Drug-2 over 28 h (E:T ratio 2:1, n=3). Representative images of STOP-CAR-T and 2G-CAR-T killing at 0 and 28 h in the absence of drug (Scale=300 μm) are shown. FIG. 25D shows relative IFNγ and IL-2 production by STOP-CAR-Ts and 2G-CAR-Ts upon co-culture with 22Rv1 cells (24 h, n=2). Cytokine production was normalized as a ratio relative to the maximum quantity produced by each donor.

In FIG. 26A, flow cytometric analysis of PC3 cells stained with anti-PSMA-Ab-PE shows that they are $PSMA^-$. In FIG. 26B, IncuCyte® analysis reveals that there is no killing of PC3 cells by the STOP-CAR-Ts, 2G-CAR-Ts or UTD-Ts (n=5). In FIG. 26C, No IFNγ is produced by STOP-CAR-Ts, 2G-CAR-Ts or UTD-Ts in the presence of PC3 cells (n=5).

In FIG. 27A, no toxicity was observed in 8-12 week-old male NSG mice injected daily for 5 days with Drug-2 at 1.5 mg/kg and 2.5 mg/kg (n=5 mice/group) as assessed by body weight (as well as behavioral and physical observations). In FIG. 27B, there was no impairment in subcutaneous PC3-PIP tumor growth in male NSG mice receiving 1 week of daily Drug-2 injections (from day 4 post-inoculation of $5\times10^6$ PC3-PIP cells) of up to 5 mg/kg. Statistical significance was determined by Two-way ANOVA. FIG. 27C shows results of a Winn assay in which NSG mice were co-injected with $3\times10^6$ CAR-Ts and $3\times10^6$ tumor cells, revealed complete tumor control by both STOP-CAR-Ts and 2G-Ts, as compared to UTD-T treated mice (p=0.003, n=5 mice/group).

FIG. 31A shows the cytotoxicity of STOP-CAR-Ts and 2G-CAR-Ts cultured in the presence of 10 μM Drug-2 for 24 h, which was then removed. Black arrows indicate the time of drug removal. FIG. 31B shows relative IFNγ production by STOP-CAR-Ts and 2G-CAR-Ts conditioned with 10 μM Drug-2 for 24 h. FIG. 31C shows the cytotoxicity of STOP-CAR-Ts and 2G-CAR-Ts cultured in the presence of 5 μM Drug-2 for 24 h. FIG. 31D shows relative IFNγ production by STOP-CAR-Ts and 2G-CAR-Ts conditioned with 5 μM Drug-2 for 24 h.

FIGS. 32A-32C show the sequences of individual components of the polypeptides described herein.

FIG. 33A shows the amino acid sequence of the original anti-PSMA STOP CAR. The first underlined sequence is the CD8 leader (SEQ ID NO: 25). The first non-underlined sequence is the PZ1 scFv (SEQ ID NO: 6). The “AS” sequence in bold is a restriction site. The second underlined sequence is the CD8 hinge (SEQ ID NO: 9). The second non-underlined sequence is the CD28 transmembrane domain (SEQ ID NO: 10). The third underlined sequence is the CD28 intracellular domain (SEQ ID NO: 11). The subsequent “HM” sequence is a restriction site. The first bold sequence is the Ser/Gly linker (SEQ ID NO: 26). The subsequent sequence in italics is the Des3 sequence (SEQ ID NO: 2). The subsequent bold underlined sequence is the T2A peptide sequence (SEQ ID NO: 27). The subsequent "GS" sequence is a restriction site. The subsequent underlined sequence is the CD8 leader sequence (SEQ ID NO: 25). The subsequent non-underlined sequence is the cMyc-tag (SEQ ID NO: 28). The subsequent bold sequence is the DAP10 Ecto-domain (SEQ ID NO: 8). The subsequent underlined sequence is the CD8 hinge (SEQ ID NO: 9). The subsequent "PR" sequence is a restriction site. The subsequent bold sequence is the CD28 intracellular domain (SEQ ID NO: 11). The subsequent "PG" sequence is a restriction site. The subsequent bold sequence is the Ser/Gly linker (SEQ ID NO: 26). The subsequent underlined sequence is BCLXL wildtype (SEQ ID NO: 5). The subsequent bold sequence is the Ser/Gly linker (SEQ ID NO: 26). The subsequent "MH" sequence is a restriction site. The last underlined sequence is the CD3 zeta domain (SEQ ID NO: 7).

FIG. 33B shows the amino acid sequence of the anti-PSMA STOP CAR (DES3 WT+BCL-XL Mut) that binds venetoclax. The first underlined sequence is the CD8 leader (SEQ ID NO: 25). The first non-underlined sequence is the PZ1 scFv (SEQ ID NO: 6). The "AS" sequence in bold is a restriction site. The second underlined sequence is the CD8 hinge (SEQ ID NO: 9). The second non-underlined sequence is the CD28 transmembrane domain (SEQ ID NO: 10). The third underlined sequence is the CD28 intracellular domain (SEQ ID NO: 11). The subsequent "HM" sequence is a restriction site. The first bold sequence is the Ser/Gly linker (SEQ ID NO: 26). The subsequent sequence in italics is the Des3 sequence (SEQ ID NO: 2). The subsequent bold underlined sequence is the T2A peptide sequence (SEQ ID NO: 27). The subsequent "GS" sequence is a restriction site. The subsequent underlined sequence is the CD8 leader sequence (SEQ ID NO: 25). The subsequent non-underlined sequence is the cMyc-tag (SEQ ID NO: 28). The subsequent bold sequence is the DAP10 Ecto-domain (SEQ ID NO: 8). The subsequent underlined sequence is the CD8 hinge (SEQ ID NO: 9). The subsequent "PR" sequence is a restriction site. The subsequent bold sequence is the CD28 intracellular domain (SEQ ID NO: 11). The subsequent "PG" sequence is a restriction site. The subsequent bold sequence is the Ser/Gly linker (SEQ ID NO: 26). The subsequent underlined sequence is BCL-XL mutant sequence (SEQ ID NO: 30). The subsequent bold sequence is the Ser/Gly linker (SEQ ID NO: 26). The subsequent "MH" sequence is a restriction site. The last underlined sequence is the CD3 zeta domain (SEQ ID NO: 7).

FIG. 33C shows the amino acid sequence of the anti-PSMA STOP CAR (DES3 WT+BCL-2) that binds venetoclax. The first underlined sequence is the CD8 leader (SEQ ID NO: 25). The first non-underlined sequence is the PZ1 scFv (SEQ ID NO: 6). The "AS" sequence in bold is a restriction site. The second underlined sequence is the CD8 hinge (SEQ ID NO: 9). The second non-underlined sequence is the CD28 transmembrane domain (SEQ ID NO: 10). The third underlined sequence is the CD28 intracellular domain (SEQ ID NO: 11). The subsequent "HM" sequence is a restriction site. The first bold sequence is the Ser/Gly linker (SEQ ID NO: 26). The subsequent sequence in italics is the Des3 sequence (SEQ ID NO: 2). The subsequent bold underlined sequence is the T2A peptide sequence (SEQ ID NO: 27). The subsequent "GS" sequence is a restriction site. The subsequent underlined sequence is the CD8 leader sequence (SEQ ID NO: 25). The subsequent non-underlined sequence is the cMyc-tag (SEQ ID NO: 28). The subsequent bold sequence is the DAP10 Ecto-domain (SEQ ID NO: 8). The subsequent underlined sequence is the CD8 hinge (SEQ ID NO: 9). The subsequent "PR" sequence is a restriction site. The subsequent bold sequence is the CD28 intracellular domain (SEQ ID NO: 11). The subsequent "PG" sequence is a restriction site. The subsequent bold sequence is the Ser/Gly linker (SEQ ID NO: 26). The subsequent underlined sequence is BCL-2 sequence (SEQ ID NO: 24). The subsequent bold sequence is the Ser/Gly linker (SEQ ID NO: 26). The subsequent "MH" sequence is a restriction site. The last underlined sequence is the CD3 zeta domain (SEQ ID NO: 7).

FIG. 33D shows the amino acid sequence of the anti-PSMA STOP CAR (DES3 a +BCL-XL Mut) that binds venetoclax. The first underlined sequence is the CD8 leader (SEQ ID NO: 25). The first non-underlined sequence is the PZ1 scFv (SEQ ID NO: 6). The "AS" sequence in bold is a restriction site. The second underlined sequence is the CD8 hinge (SEQ ID NO: 9). The second non-underlined sequence is the CD28 transmembrane domain (SEQ ID NO: 10). The third underlined sequence is the CD28 intracellular domain (SEQ ID NO: 11). The subsequent "HM" sequence is a restriction site. The first bold sequence is the Ser/Gly linker (SEQ ID NO: 26). The subsequent sequence in italics is the Des3-A sequence (SEQ ID NO: 19). The subsequent bold underlined sequence is the T2A peptide sequence (SEQ ID NO: 27). The subsequent "GS" sequence is a restriction site. The subsequent underlined sequence is the CD8 leader sequence (SEQ ID NO: 25). The subsequent non-underlined sequence is the cMyc-tag (SEQ ID NO: 28). The subsequent bold sequence is the DAP10 Ecto-domain (SEQ ID NO: 8). The subsequent underlined sequence is the CD8 hinge (SEQ ID NO: 9). The subsequent "PR" sequence is a restriction site. The subsequent bold sequence is the CD28 intracellular domain (SEQ ID NO: 11). The subsequent "PG" sequence is a restriction site. The subsequent bold sequence is the Ser/Gly linker (SEQ ID NO: 26). The subsequent underlined sequence is BCL-XL mutant sequence (SEQ ID NO: 30). The subsequent bold sequence is the Ser/Gly linker (SEQ ID NO: 26). The subsequent "MH" sequence is a restriction site. The last underlined sequence is the CD3 zeta domain (SEQ ID NO: 7).

FIG. 33E shows the amino acid sequence of the anti-PSMA STOP CAR (DES3 b +BCL-XL Mut) that binds venetoclax. The first underlined sequence is the CD8 leader (SEQ ID NO: 25). The first non-underlined sequence is the PZ1 scFv (SEQ ID NO: 6). The "AS" sequence in bold is a restriction site. The second underlined sequence is the CD8 hinge (SEQ ID NO: 9). The second non-underlined sequence is the CD28 transmembrane domain (SEQ ID NO: 10). The third underlined sequence is the CD28 intracellular domain (SEQ ID NO: 11). The subsequent "HM" sequence is a restriction site. The first bold sequence is the Ser/Gly linker (SEQ ID NO: 26). The subsequent sequence in italics is the Des3-B sequence (SEQ ID NO: 3). The subsequent bold underlined sequence is the T2A peptide sequence (SEQ ID NO: 27). The subsequent "GS" sequence is a restriction site. The subsequent underlined sequence is the CD8 leader sequence (SEQ ID NO: 25). The subsequent non-underlined sequence is the cMyc-tag (SEQ ID NO: 28). The subsequent bold sequence is the DAP10 Ecto-domain (SEQ ID NO: 8). The subsequent underlined sequence is the CD8 hinge (SEQ ID NO: 9). The subsequent "PR" sequence is a restriction site. The subsequent bold sequence is the CD28 intracellular domain (SEQ ID NO: 11). The subsequent "PG" sequence is a restriction site. The subsequent bold sequence is the Ser/Gly linker (SEQ ID NO: 26). The subsequent underlined sequence is BCL-XL mutant sequence (SEQ ID NO: 30). The subsequent bold sequence is the Ser/Gly linker (SEQ ID NO: 26). The subsequent "MH" sequence is a restriction site. The last underlined sequence is the CD3 zeta domain (SEQ ID NO: 7).

FIG. 33F shows the amino acid sequence of the anti-PSMA STOP CAR (DES3 c +BCL-XL Mut) that binds venetoclax. The first underlined sequence is the CD8 leader (SEQ ID NO: 25). The first non-underlined sequence is the PZ1 scFv (SEQ ID NO: 6). The "AS" sequence in bold is a restriction site. The second underlined sequence is the CD8 hinge (SEQ ID NO: 9). The second non-underlined sequence is the CD28 transmembrane domain (SEQ ID NO: 10). The third underlined sequence is the CD28 intracellular domain (SEQ ID NO: 11). The subsequent "HM" sequence is a restriction site. The first bold sequence is the Ser/Gly linker (SEQ ID NO: 26). The subsequent sequence in italics is the Des3-C sequence (SEQ ID NO: 4). The subsequent bold underlined sequence is the T2A peptide sequence (SEQ ID NO: 27). The subsequent "GS" sequence is a restriction site. The subsequent underlined sequence is the CD8 leader sequence (SEQ ID NO: 25). The subsequent non-underlined sequence is the cMyc-tag (SEQ ID NO: 28). The subsequent bold sequence is the DAP10 Ecto-domain (SEQ ID NO: 8). The subsequent underlined sequence is the CD8 hinge (SEQ ID NO: 9). The subsequent "PR" sequence is a restriction site. The subsequent bold sequence is the CD28 intracellular domain (SEQ ID NO: 11). The subsequent "PG" sequence is a restriction site. The subsequent bold sequence is the Ser/Gly linker (SEQ ID NO: 26). The subsequent underlined sequence is BCL-XL mutant sequence (SEQ ID NO: 30). The subsequent bold sequence is the Ser/Gly linker (SEQ ID NO: 26). The subsequent "MH" sequence is a restriction site. The last underlined sequence is the CD3 zeta domain (SEQ ID NO: 7).

FIG. 33G shows the amino acid sequence of the anti-PSMA STOP CAR (DES3 a +BCL2) that binds venetoclax. The first underlined sequence is the CD8 leader (SEQ ID NO: 25). The first non-underlined sequence is the PZ1 scFv (SEQ ID NO: 6). The "AS" sequence in bold is a restriction site. The second underlined sequence is the CD8 hinge (SEQ ID NO: 9). The second non-underlined sequence is the CD28 transmembrane domain (SEQ ID NO: 10). The third underlined sequence is the CD28 intracellular domain (SEQ ID NO: 11). The subsequent "HM" sequence is a restriction site. The first bold sequence is the Ser/Gly linker (SEQ ID NO: 26). The subsequent sequence in italics is the Des3-A sequence (SEQ ID NO: 19). The subsequent bold underlined sequence is the T2A peptide sequence (SEQ ID NO: 27). The subsequent "GS" sequence is a restriction site. The subsequent underlined sequence is the CD8 leader sequence (SEQ ID NO: 25). The subsequent non-underlined sequence is the cMyc-tag (SEQ ID NO: 28). The subsequent bold sequence is the DAP10 Ecto-domain (SEQ ID NO: 8). The subsequent underlined sequence is the CD8 hinge (SEQ ID NO: 9). The subsequent "PR" sequence is a restriction site. The subsequent bold sequence is the CD28 intracellular domain (SEQ ID NO: 11). The subsequent "PG" sequence is a restriction site. The subsequent bold sequence is the Ser/Gly linker (SEQ ID NO: 26). The subsequent underlined sequence is BCL2 sequence (SEQ ID NO: 24). The subsequent bold sequence is the Ser/Gly linker (SEQ ID NO: 26). The subsequent "MH" sequence is a restriction site. The last underlined sequence is the CD3 zeta domain (SEQ ID NO: 7).

FIG. 33H shows the amino acid sequence of the anti-PSMA STOP CAR (DES3 b +BCL2) that binds venetoclax. The first underlined sequence is the CD8 leader (SEQ ID NO: 25). The first non-underlined sequence is the PZ1 scFv (SEQ ID NO: 6). The "AS" sequence in bold is a restriction site. The second underlined sequence is the CD8 hinge (SEQ ID NO: 9). The second non-underlined sequence is the CD28 transmembrane domain (SEQ ID NO: 10). The third underlined sequence is the CD28 intracellular domain (SEQ ID NO: 11). The subsequent "HM" sequence is a restriction site. The first bold sequence is the Ser/Gly linker (SEQ ID NO: 26). The subsequent sequence in italics is the Des3-B sequence (SEQ ID NO: 3). The subsequent bold underlined sequence is the T2A peptide sequence (SEQ ID NO: 27). The subsequent "GS" sequence is a restriction site. The subsequent underlined sequence is the CD8 leader sequence (SEQ ID NO: 25). The subsequent non-underlined sequence is the cMyc-tag (SEQ ID NO: 28). The subsequent bold sequence is the DAP10 Ecto-domain (SEQ ID NO: 8). The subsequent underlined sequence is the CD8 hinge (SEQ ID NO: 9). The subsequent "PR" sequence is a restriction site. The subsequent bold sequence is the CD28 intracellular domain (SEQ ID NO: 11). The subsequent "PG" sequence is a restriction site. The subsequent bold sequence is the Ser/Gly linker (SEQ ID NO: 26). The subsequent underlined sequence is BCL2 sequence (SEQ ID NO: 24). The subsequent bold sequence is the Ser/Gly linker (SEQ ID NO: 26). The subsequent "MH" sequence is a restriction site. The last underlined sequence is the CD3 zeta domain (SEQ ID NO: 7).

FIG. 33I shows the amino acid sequence of the anti-PSMA STOP CAR (DES3 c+BCL2) that binds venetoclax. The first underlined sequence is the CD8 leader (SEQ ID NO: 25). The first non-underlined sequence is the PZ1 scFv (SEQ ID NO: 6). The "AS" sequence in bold is a restriction site. The second underlined sequence is the CD8 hinge (SEQ ID NO: 9). The second non-underlined sequence is the CD28 transmembrane domain (SEQ ID NO: 10). The third underlined sequence is the CD28 intracellular domain (SEQ ID NO: 11). The subsequent "HM" sequence is a restriction site. The first bold sequence is the Ser/Gly linker (SEQ ID NO: 26). The subsequent sequence in italics is the Des3-C sequence (SEQ ID NO: 4). The subsequent bold underlined sequence is the T2A peptide sequence (SEQ ID NO: 27). The subsequent "GS" sequence is a restriction site. The subsequent underlined sequence is the CD8 leader sequence (SEQ ID NO: 25). The subsequent non-underlined sequence is the cMyc-tag (SEQ ID NO: 28). The subsequent bold sequence is the DAP10 Ecto-domain (SEQ ID NO: 8). The subsequent underlined sequence is the CD8 hinge (SEQ ID NO: 9). The subsequent "PR" sequence is a restriction site. The subsequent bold sequence is the CD28 intracellular domain (SEQ ID NO: 11). The subsequent "PG" sequence is a restriction site. The subsequent bold sequence is the Ser/Gly linker (SEQ ID NO: 26). The subsequent underlined sequence is BCL2 sequence (SEQ ID NO: 24). The subsequent bold sequence is the Ser/Gly linker (SEQ ID NO: 26). The subsequent "MH" sequence is a restriction site. The last underlined sequence is the CD3 zeta domain (SEQ ID NO: 7).

FIGS. 34A-34D show the sequences of components of Anti-NGcGM3 14F7-derived CARs, and scFv component sequences. FIG. 34A shows a list of single components, and their sequences, i.e. VH murine 14F7, Ser/Gly linker, VL murine 3FMmut, 7AH human VL 14F7, 7BH human VL 14F7, and 8BH human VL 14F7. FIGS. 34B-34D show a list of possible scFv, i.e. CD19scfv, anti-14F7-VHVH, anti-14F7-VHVH with linker, anti-14F7-VH-7AH, anti-14F7-VH-linker-7AH, anti-14F7-VH-7BH, anti-14F7-VH-linker-7BH, anti-14F7-VH-8BH, anti-14F7-VH-linker-8BH, 2aM murine VL 14F7, 3fM murine VL 14F7, Murine VH-2aM murine VL (14F7), Murine VH-Linker-2aM murine VL (14F7), Murine VH-3fM murine VL (14F7), and Murine VH-Linker-3fM murine VL (14F7). FIG. 34E shows examples of anti-NGcGM3 14F7-derived CARs and functional 14F7 derived scFv variants.

FIG. 35A depicts a nucleic acid sequence of STOP-CAR original version (DES high affinity with wildtype BCL-XL), along with a diagram showing the domains and components of the nucleic acid sequence (as underlined or in bold) in order. FIG. 35B depicts the amino acid sequence of STOP-CAR original version (DES high affinity with wildtype BCL-XL), along with a diagram showing the domains and components of the amino acid sequence (as underlined or in bold) in order. FIG. 35C depicts a nucleic acid sequence of STOP-CAR BCL-XL sensitive to venetoclax (DES3 high affinity+ Mutated BCL-XL which can bind Venetoclax), along with a diagram showing the domains and components of the nucleic acid sequence (as underlined or in bold) in order. FIG. 35D depicts the amino acid sequence of STOP-CAR BCL-XL sensitive to venetoclax (DES3 high affinity+ Mutated BCL-XL which can bind Venetoclax), along with a diagram showing the domains and components of the amino acid sequence (as underlined or in bold) in order. FIG. 35E depicts a nucleic acid sequence of STOP-CAR Ventoclax high affinity (DES3 high affinity+WT BCL2), along with a diagram showing the domains and components of the nucleic acid sequence (as underlined or in bold) in order. FIG. 35F depicts the amino acid sequence of STOP-CAR Ventoclax high affinity (DES3 high affinity+WT BCL2), along with a diagram showing the domains and components of the amino acid sequence (as underlined or in bold) in order. FIG. 35G depicts a nucleic acid sequence of STOP-CAR (DES3 medium affinity+WT BCL-XL), along with a diagram showing the domains and components of the nucleic acid sequence (as underlined or in bold) in order. FIG. 35H depicts the amino acid sequence of STOP-CAR (DES3 medium affinity+WT BCL-XL), along with a diagram showing the domains and components of the amino acid sequence (as underlined or in bold) in order. FIG. 35I depicts a nucleic acid sequence of STOP-CAR (DES3 weakest affinity+WT BCL-XL), along with a diagram showing the domains and components of the nucleic acid sequence (as underlined or in bold) in order. FIG. 35J depicts the amino acid sequence of STOP-CAR (DES3 weakest affinity+WT BCL-XL), along with a diagram showing the domains and components of the amino acid sequence (as underlined or in bold) in order.

DETAILED DESCRIPTION

Figures 1A, 1B:
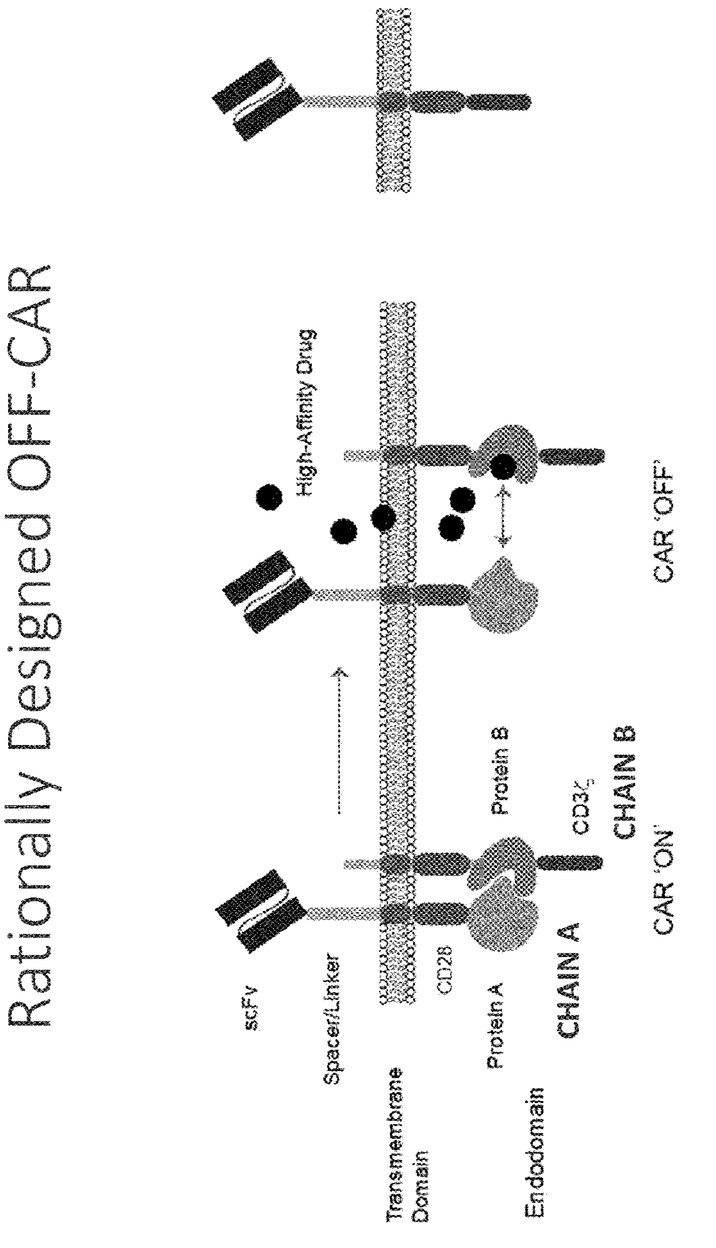
FIGS. 1A-1B are schematic representations of heterodimeric inactivatable chimeric antigen receptors (CARs) (OFF-CAR) according to some embodiments of the invention, and its disassembly in the presence of an inhibitory drug versus a classic second generation CAR.

The present invention is based on the development of heterodimeric inactivatable chimeric antigen receptors (CARs) ("OFF-switch CARs" or "OFF-CARs") which effectively and selectively kill target cells (e.g., cancer cells) upon expression by engineered T cells and provide enhanced safety due to their ability to be inactivated by heterodimer-disrupting molecules. In one non-limiting embodiment, OFF-CAR comprises two polypeptide chains, wherein an extracellular target-binding domain (e.g., scFv) and intracellular signaling endodomain (ED) (e.g., CD3-zeta) are present on different polypeptide chains, and wherein the two chains heterodimerize via intracellular Protein A-Protein B domain interaction resulting in T-cell activation upon target (e.g., tumor antigen) binding. The addition of an inhibitor (e.g., a small molecule drug) which interacts with Protein A domain or Protein B domain with high affinity separates the chains thereby inhibiting CAR-mediated signaling. In certain embodiments, Protein A and Protein B domains are located at approximately equal distances from the cell membrane. See FIGS. 1 and 16A for schematic representations of OFF-CAR and its inhibition. To develop the binding pairs described herein, computational methods have been used to develop heterodimerizing Protein A-Protein B pairs which do not natively interact in vivo and can be selectively disrupted with clinically approved small-molecule drugs having a long half-life.

Figure 13:
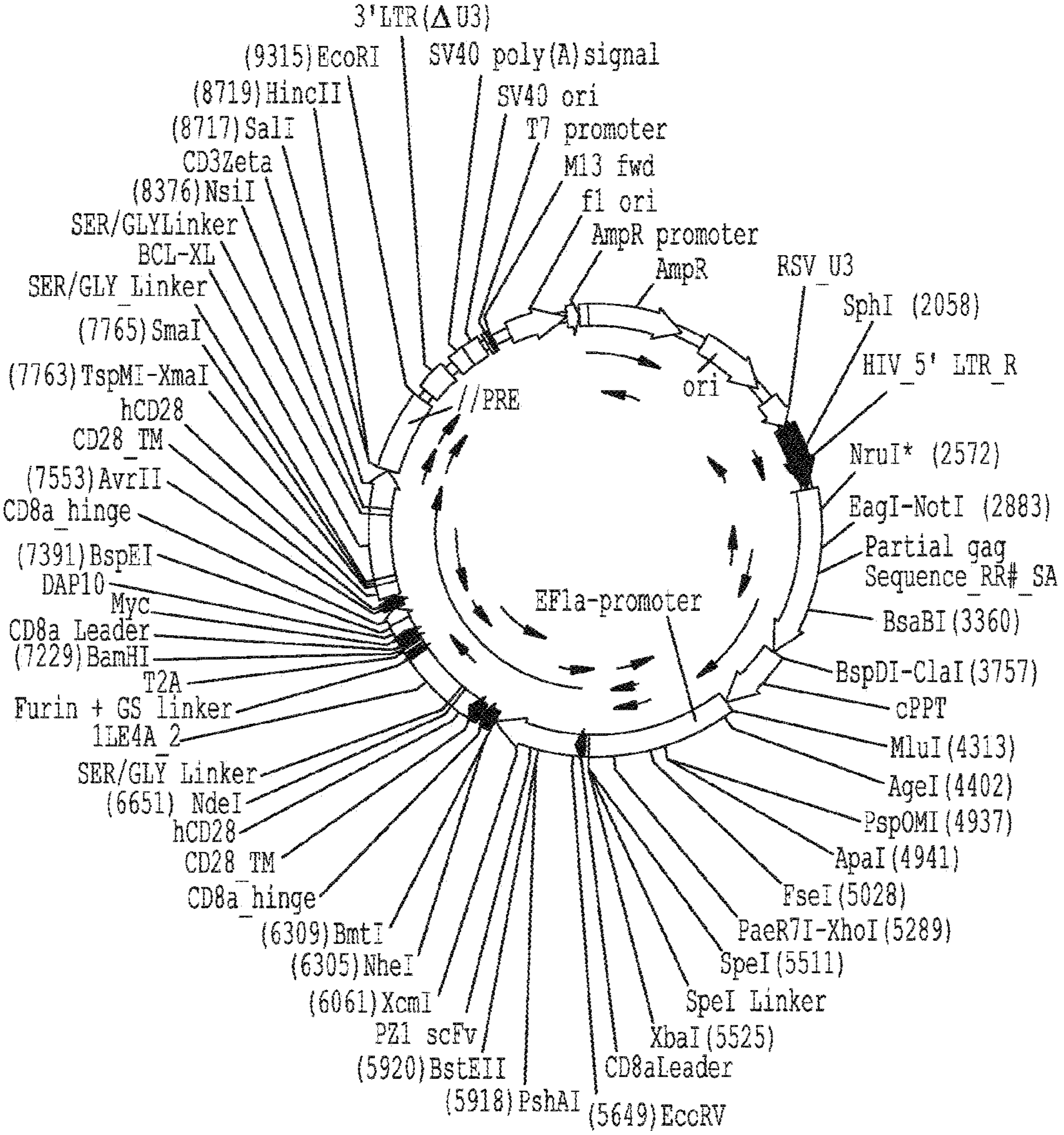
FIG. 13 is a schematic of the pELNS OFF-CAR Map.
Figure 14A:
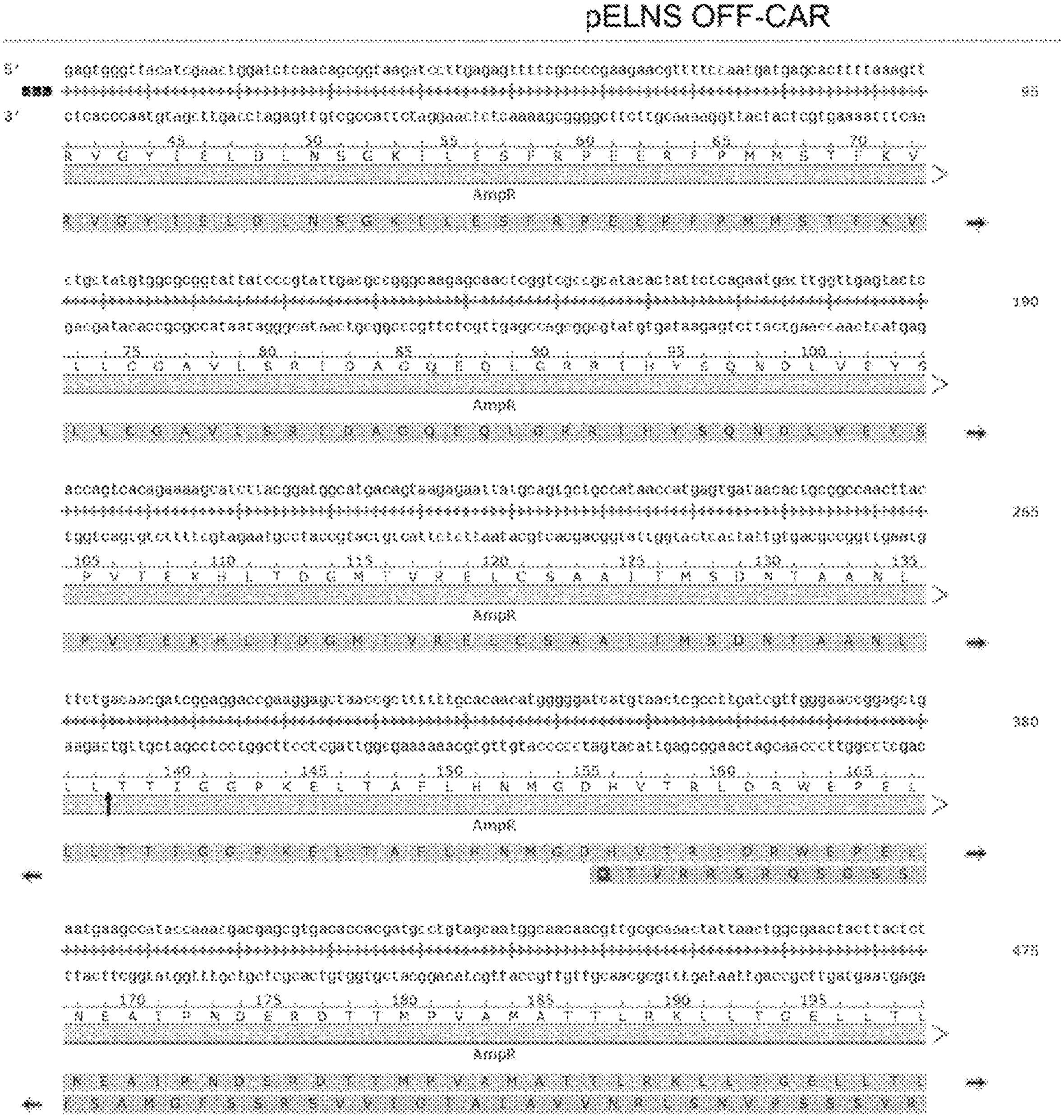
FIGS. 14A-14T depict the nucleic acid sequence of the pELNS OFF-CAR vector, and the amino acid sequence in which it encodes.
Figure 14B:
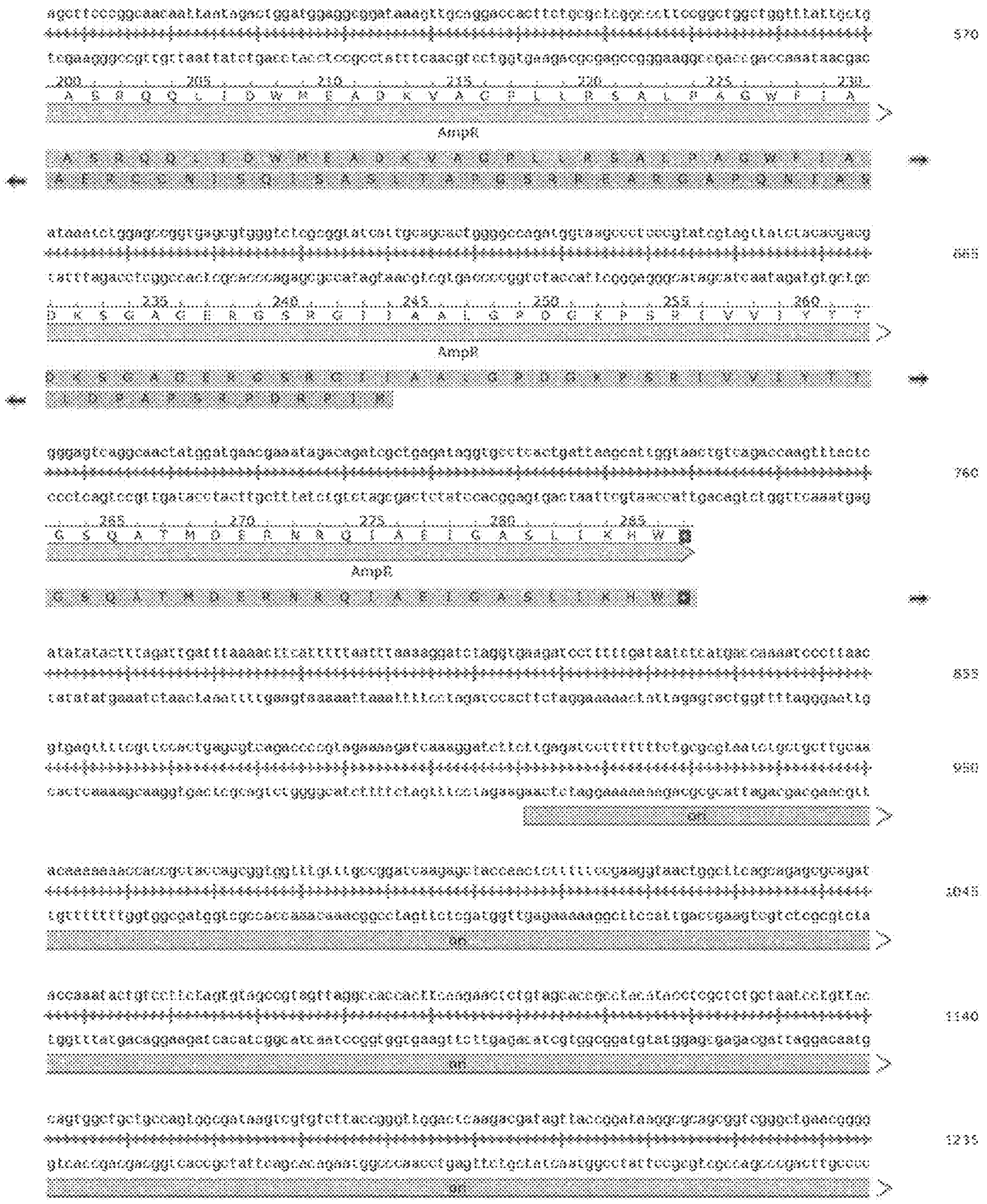
Figure 14C:
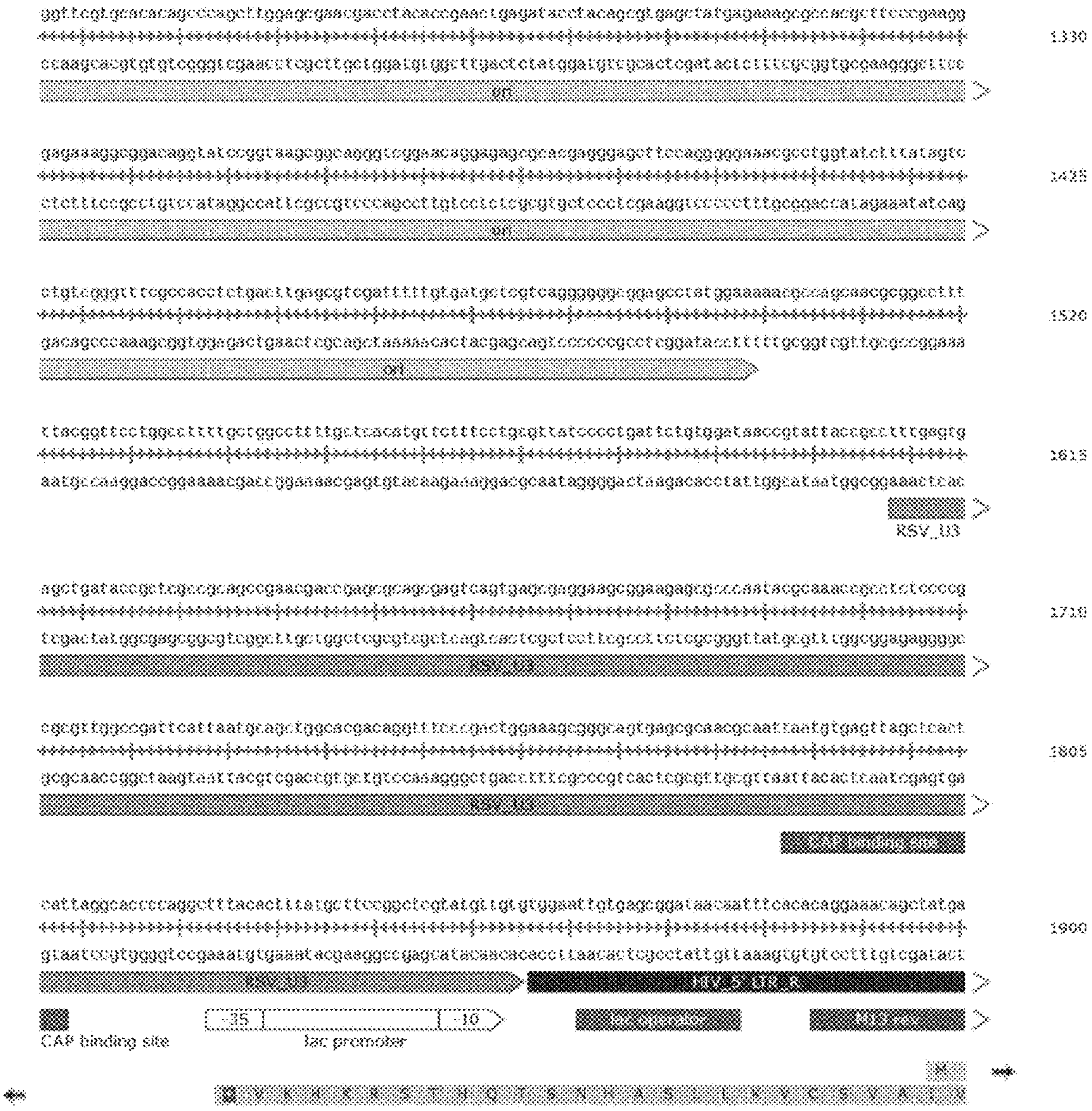
Figure 14D:
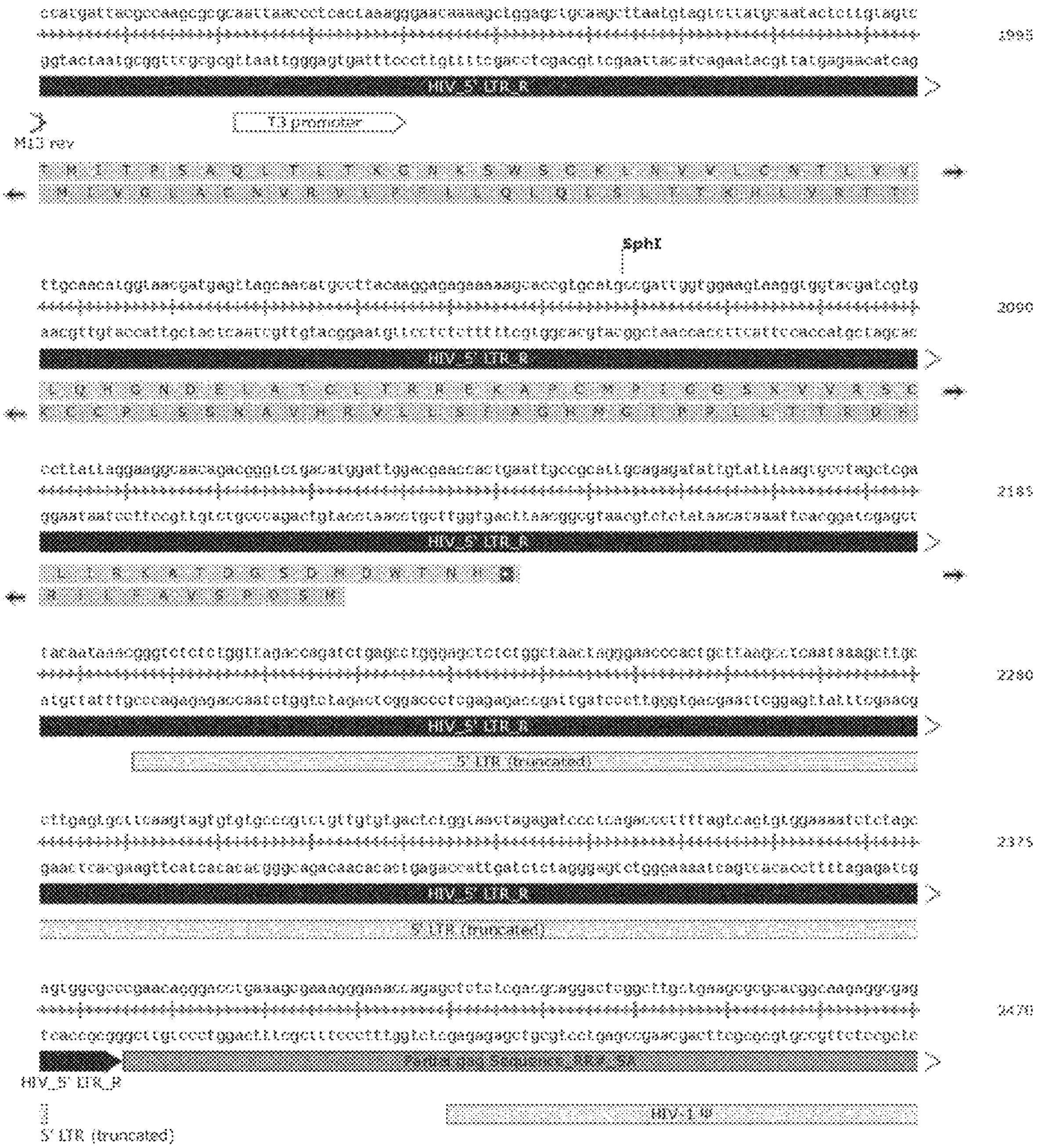
Figure 14E:
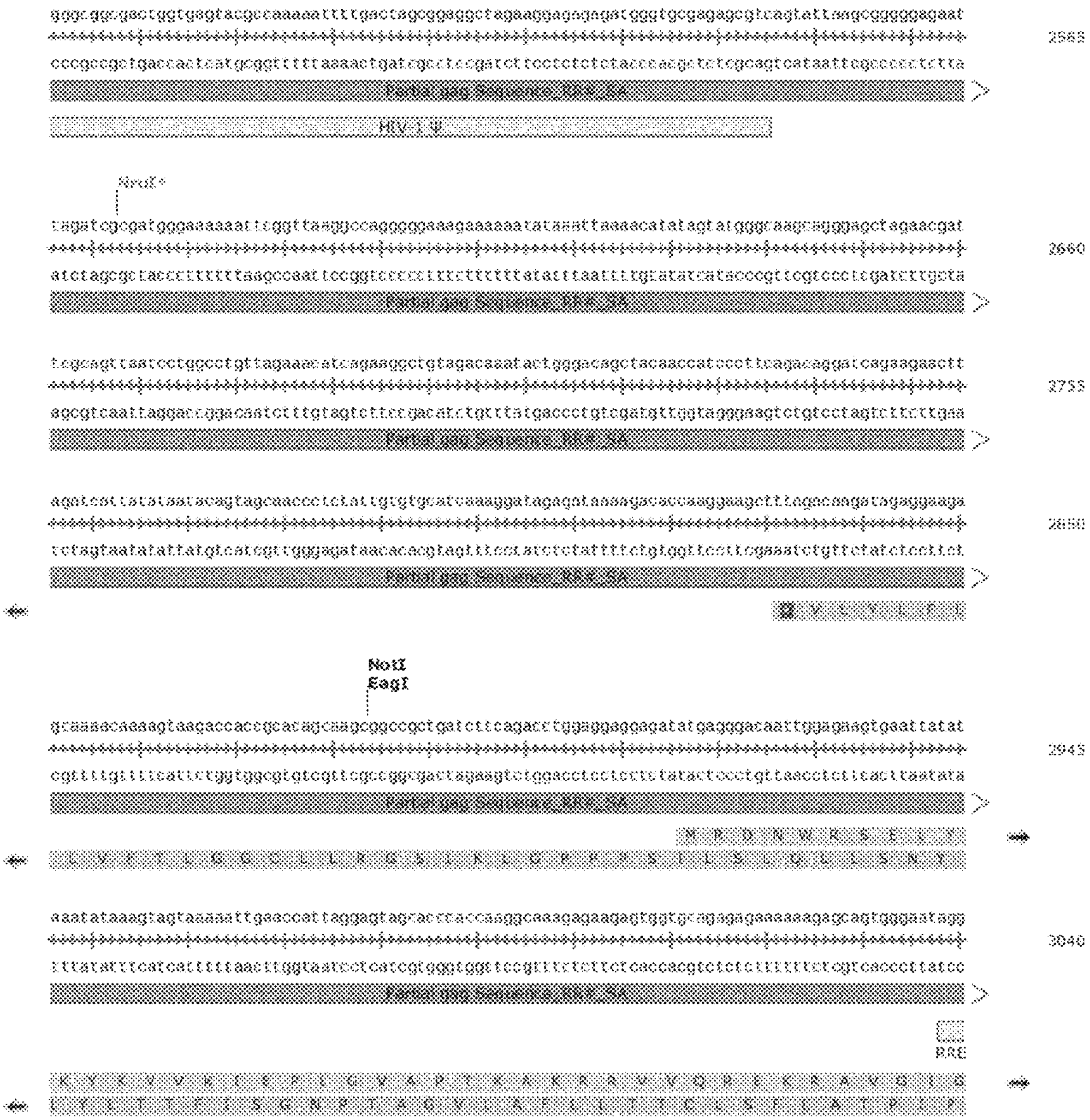
Figure 14F:
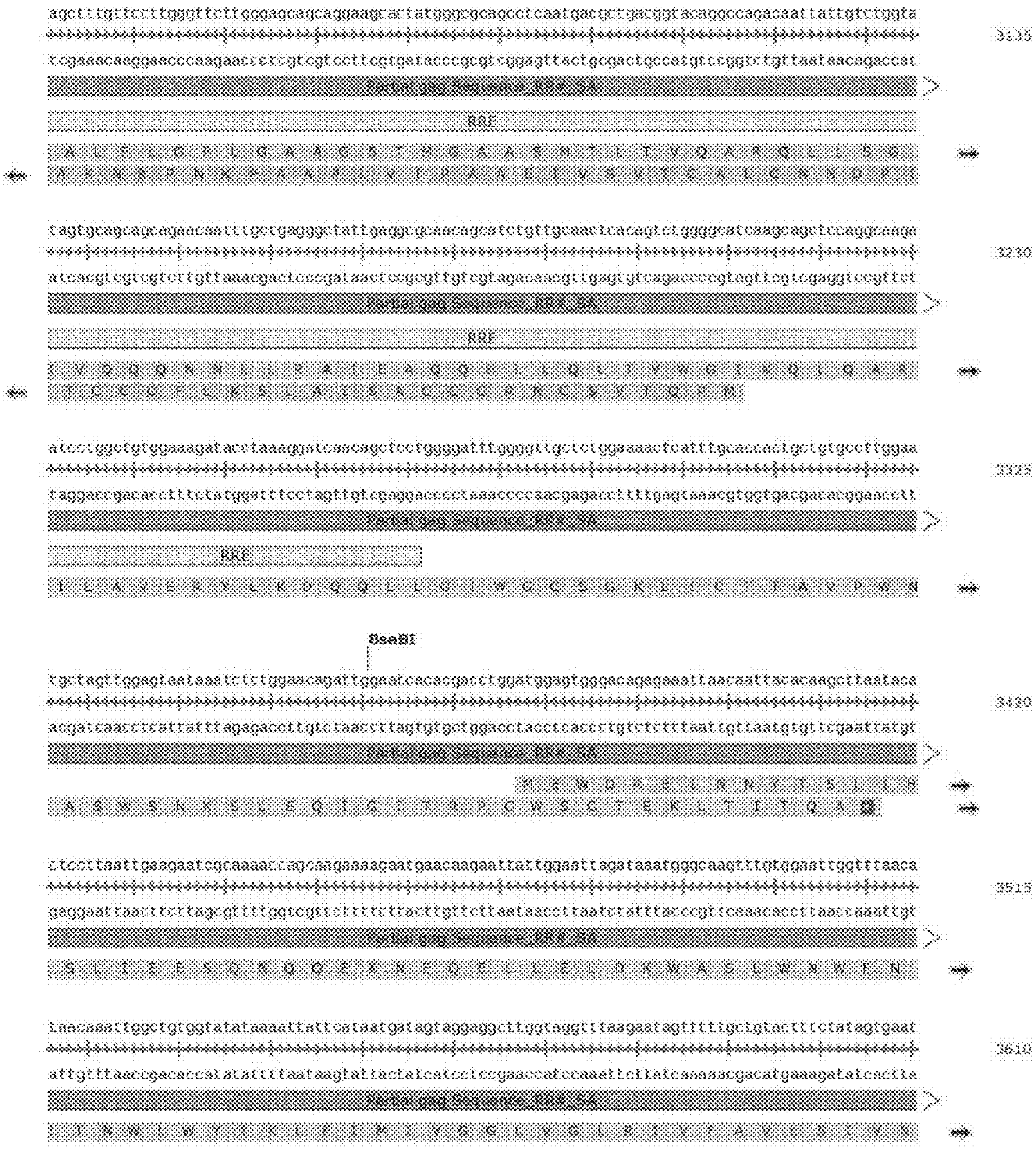
Figure 14G:
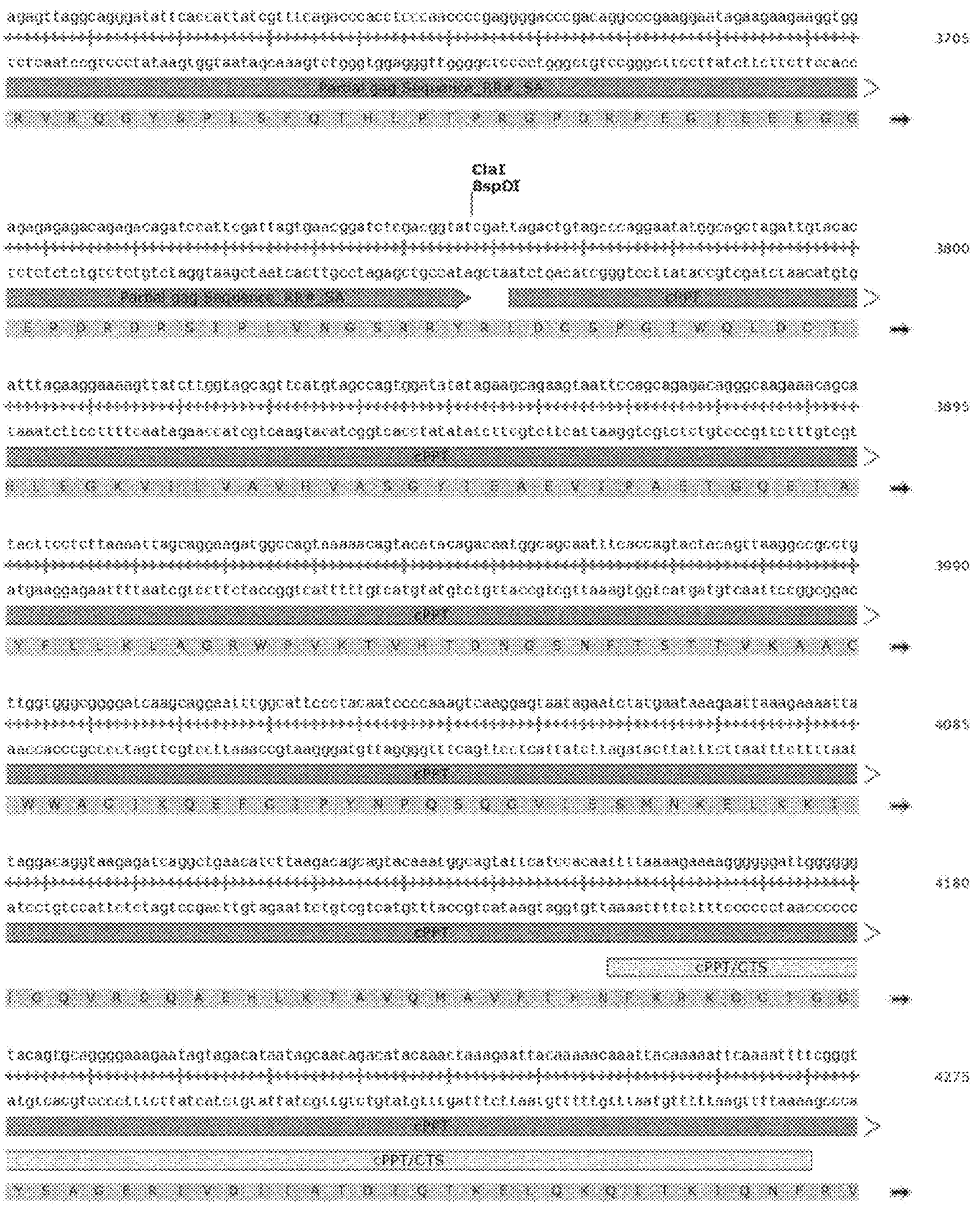
Figure 14H:
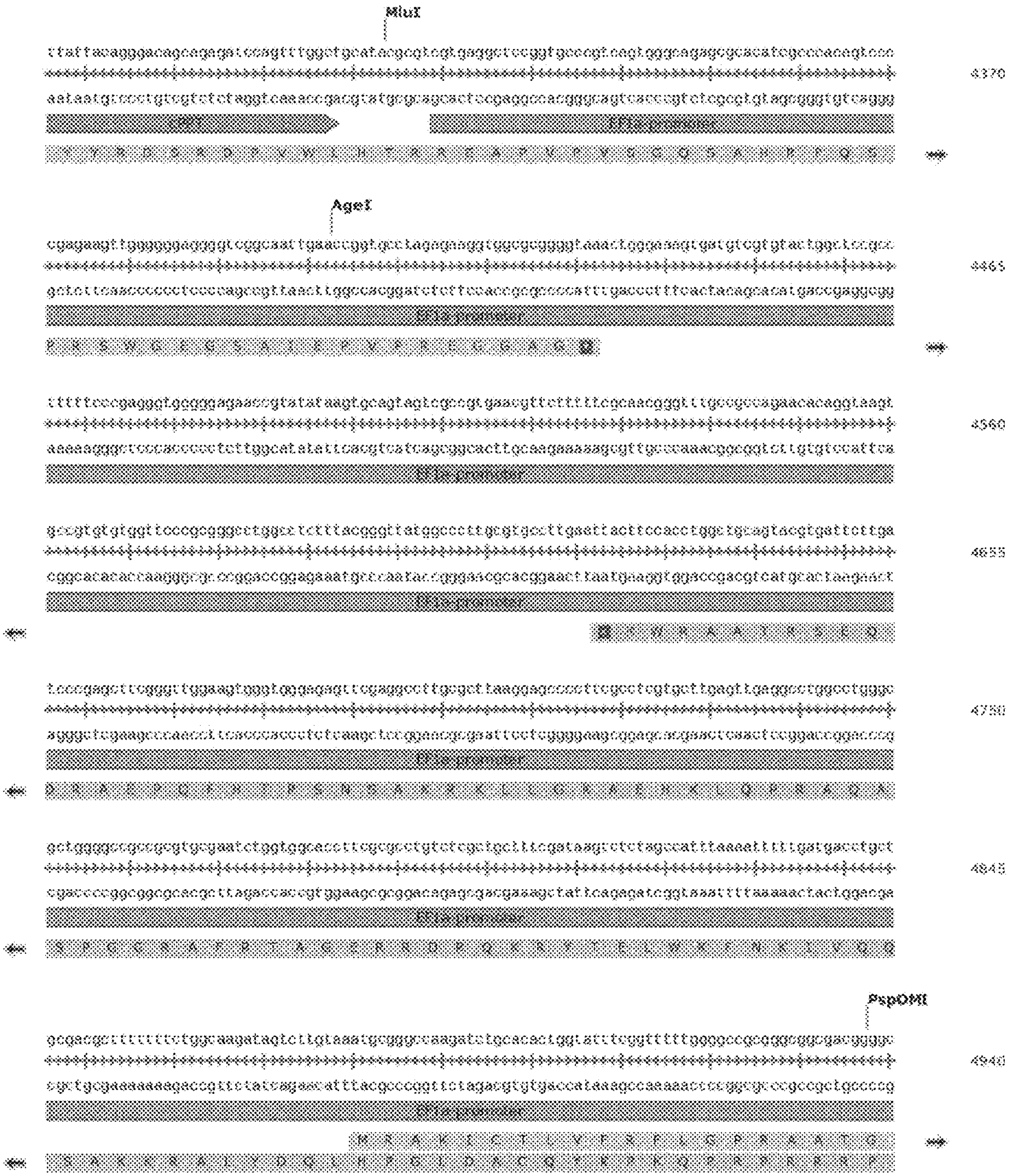
Figure 14I:
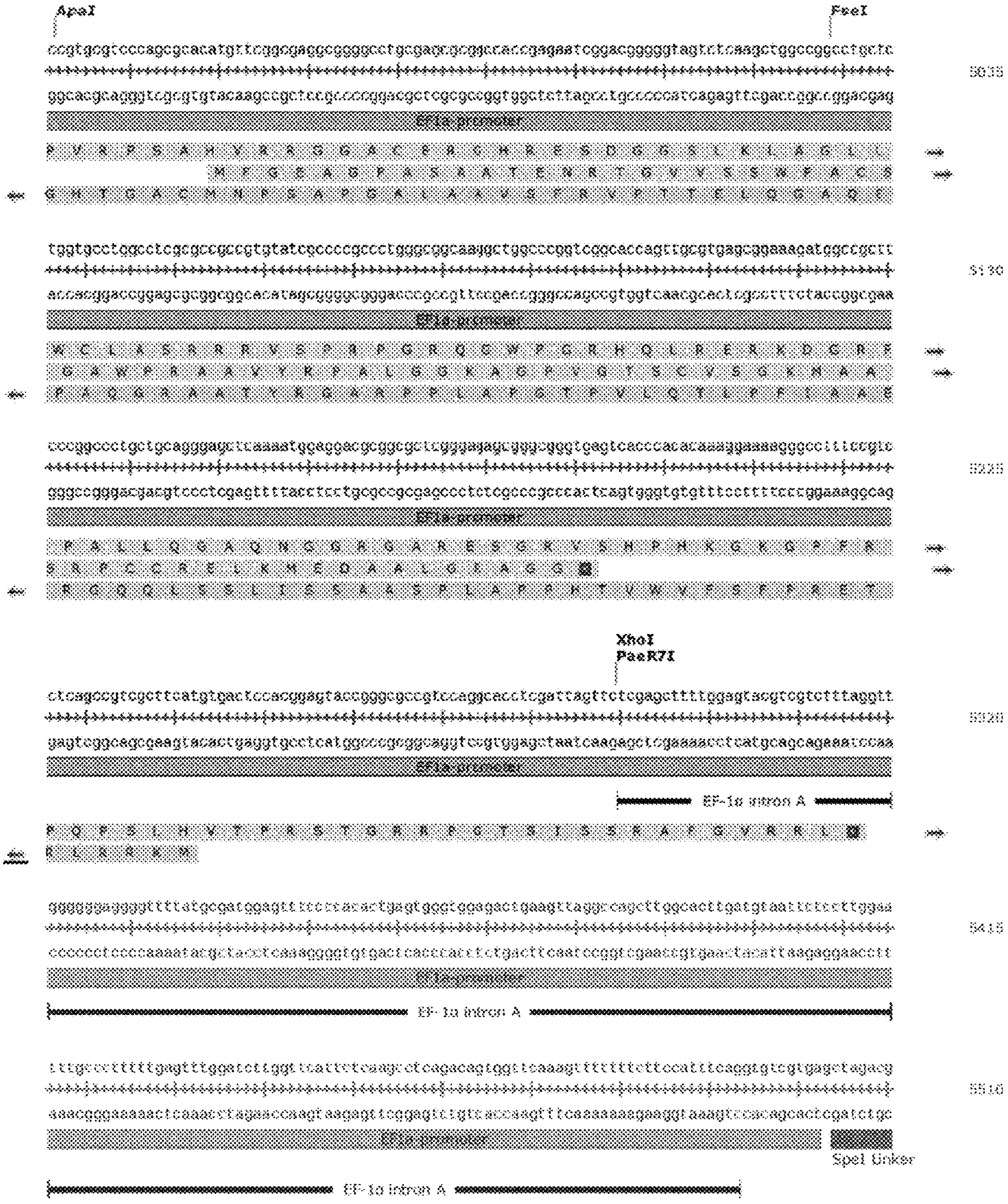
Figure 14J:
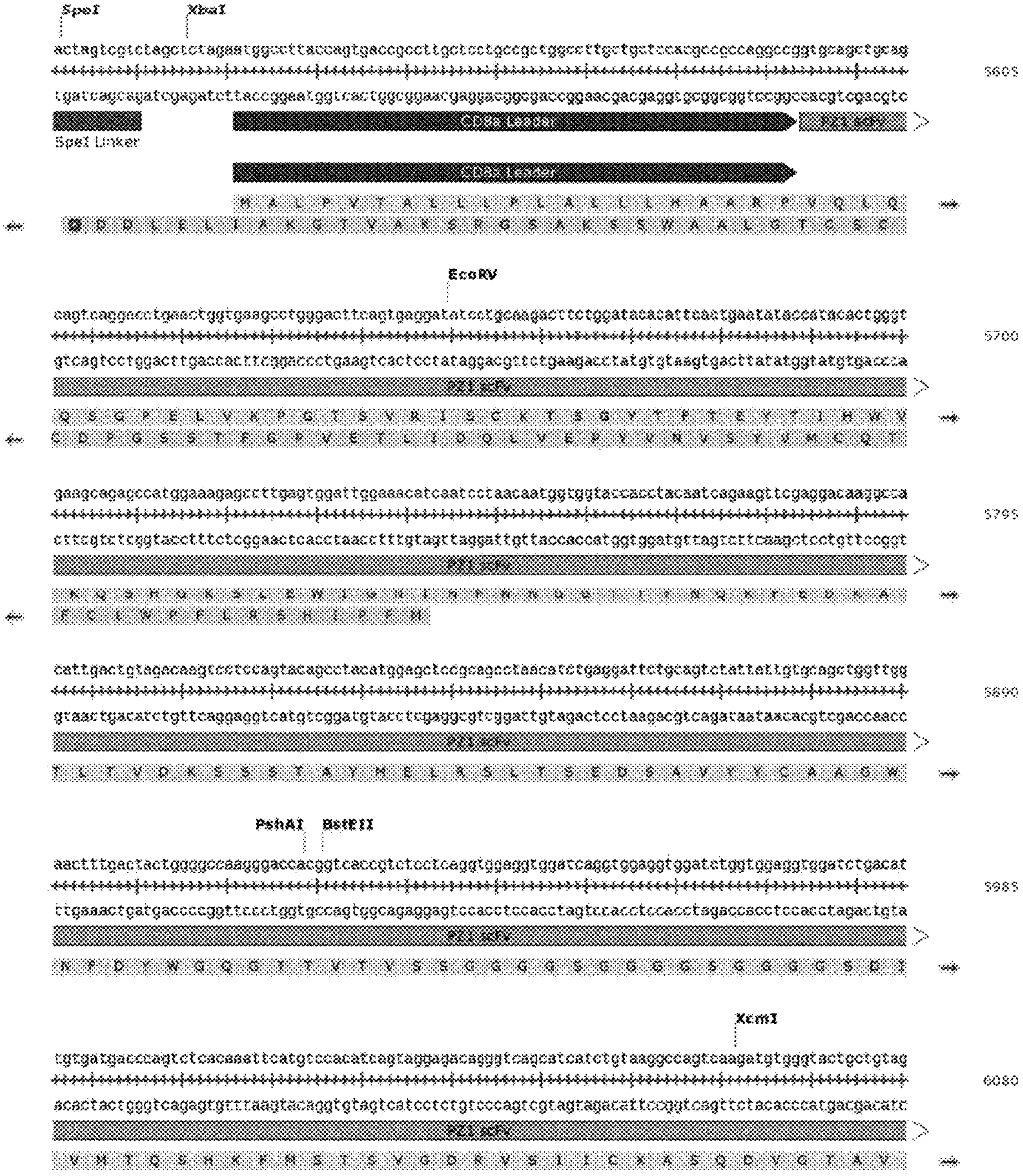
Figure 14K:
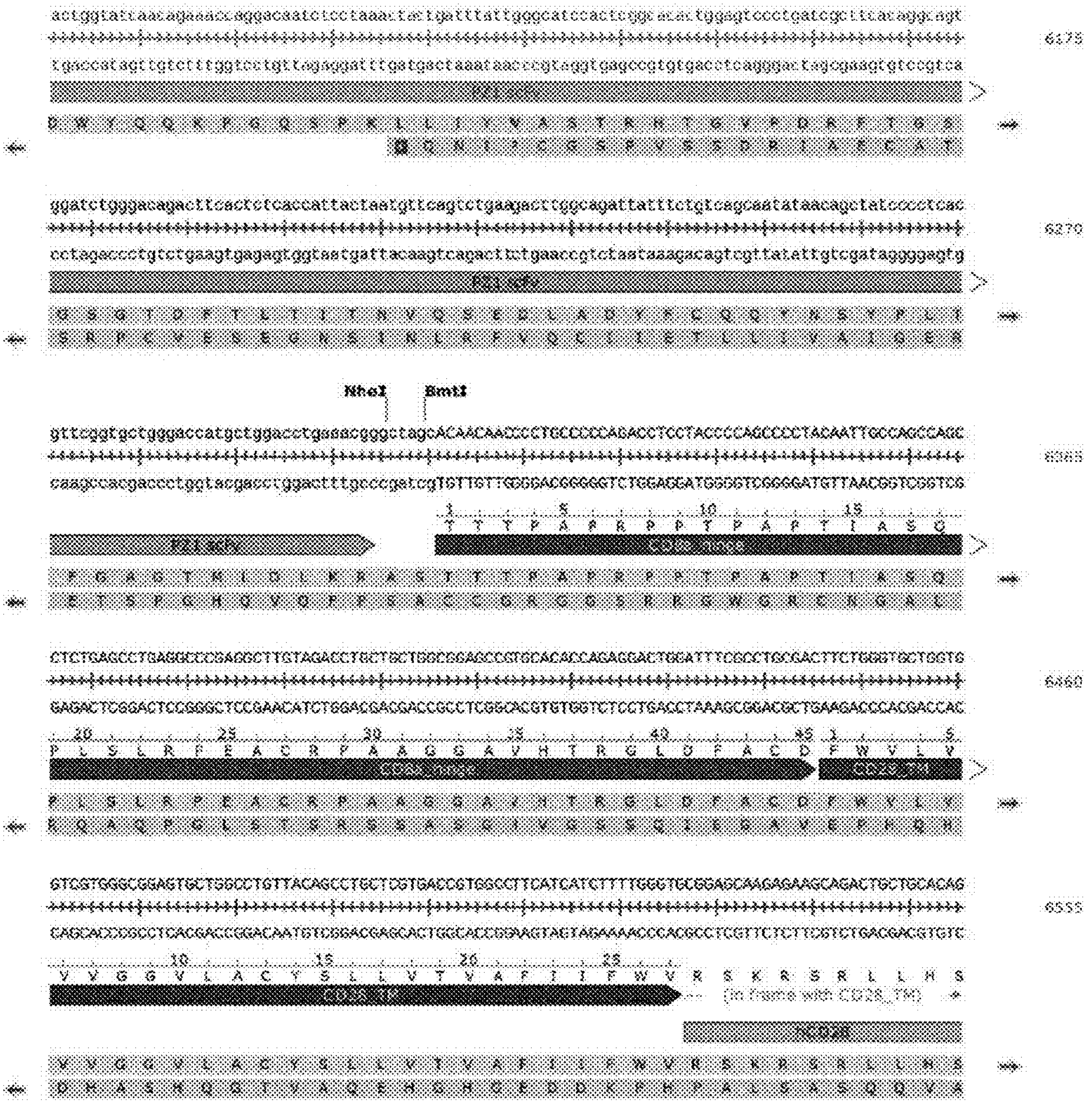
Figure 14L:
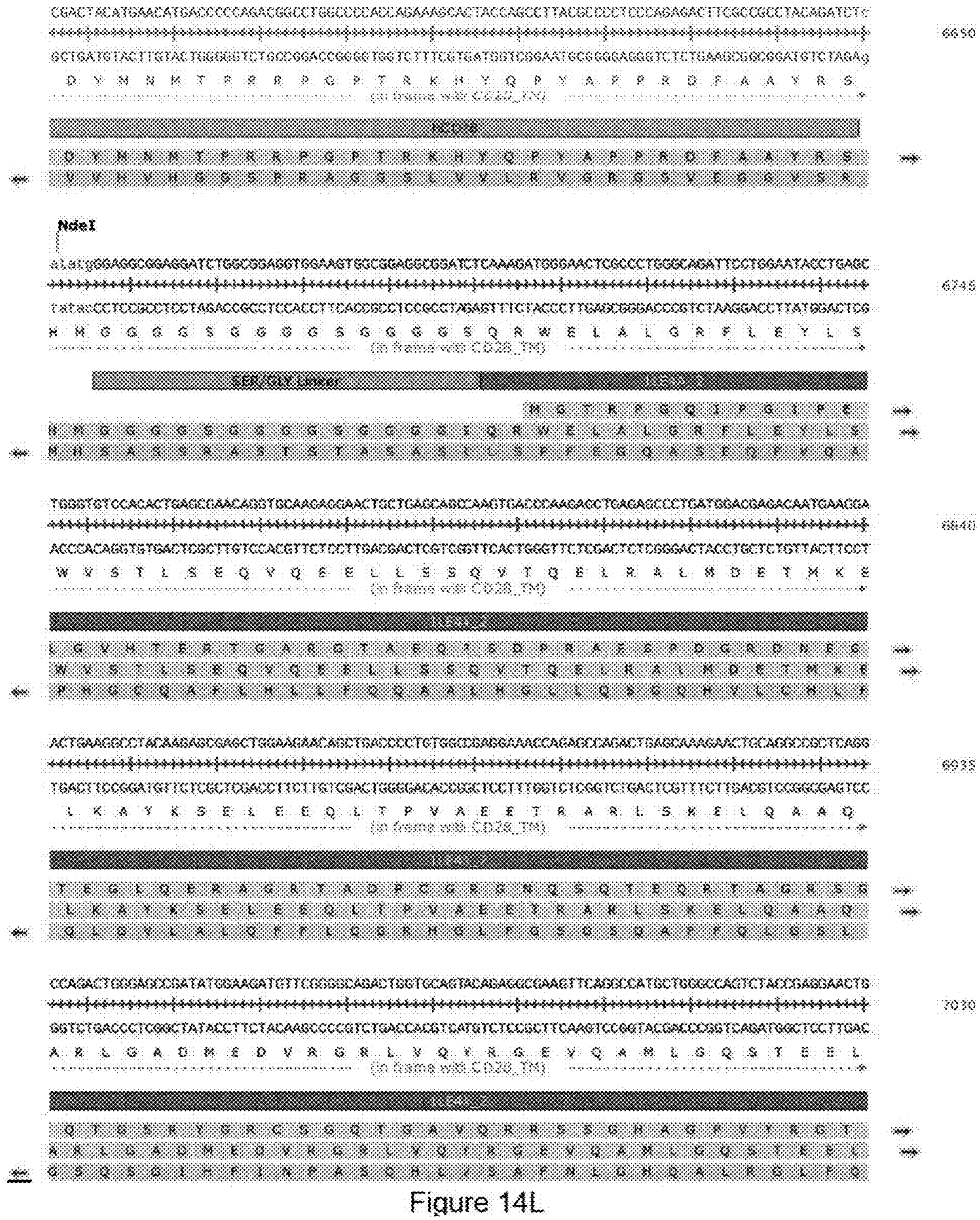
Figure 14M:
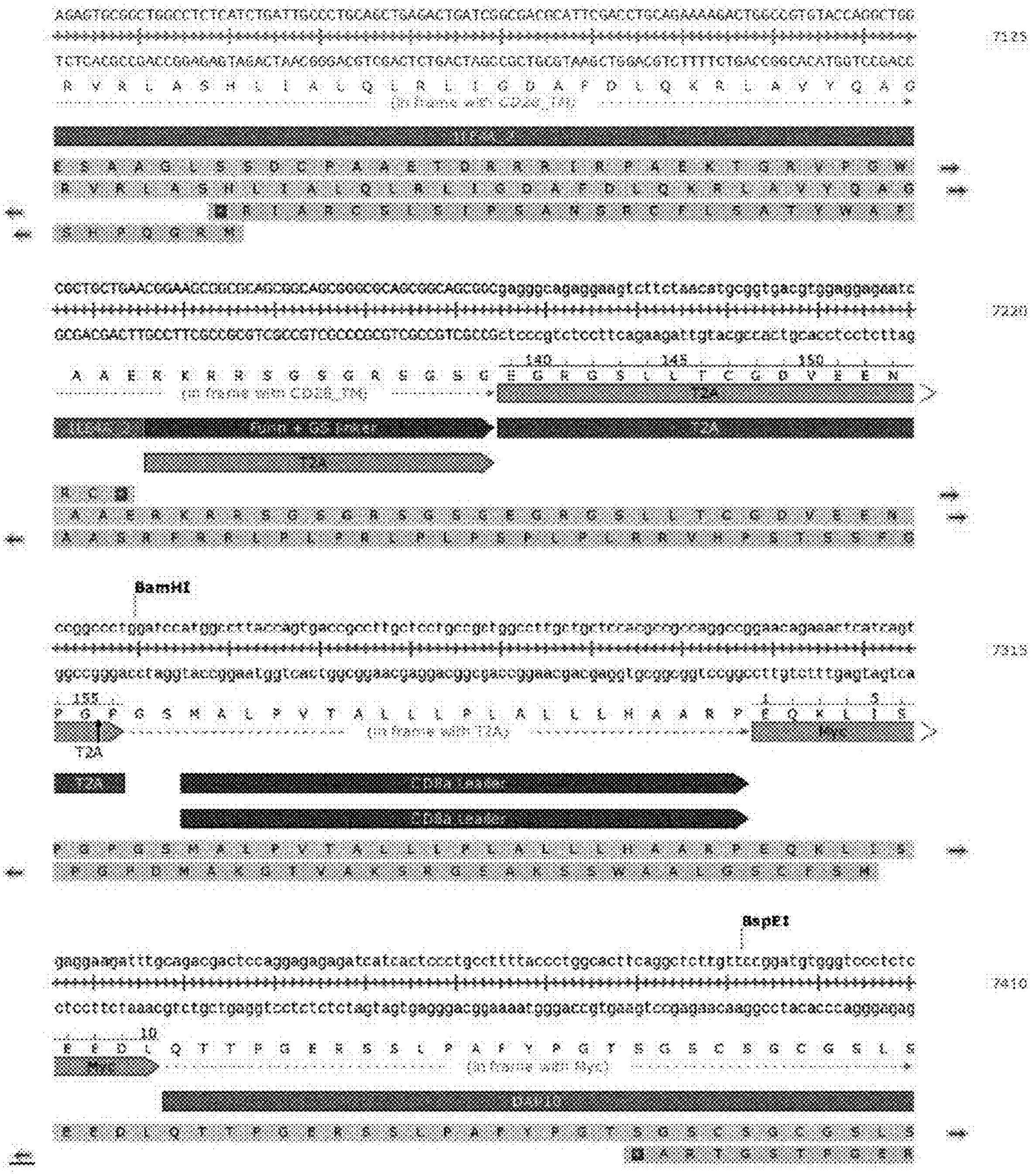
Figure 14N:
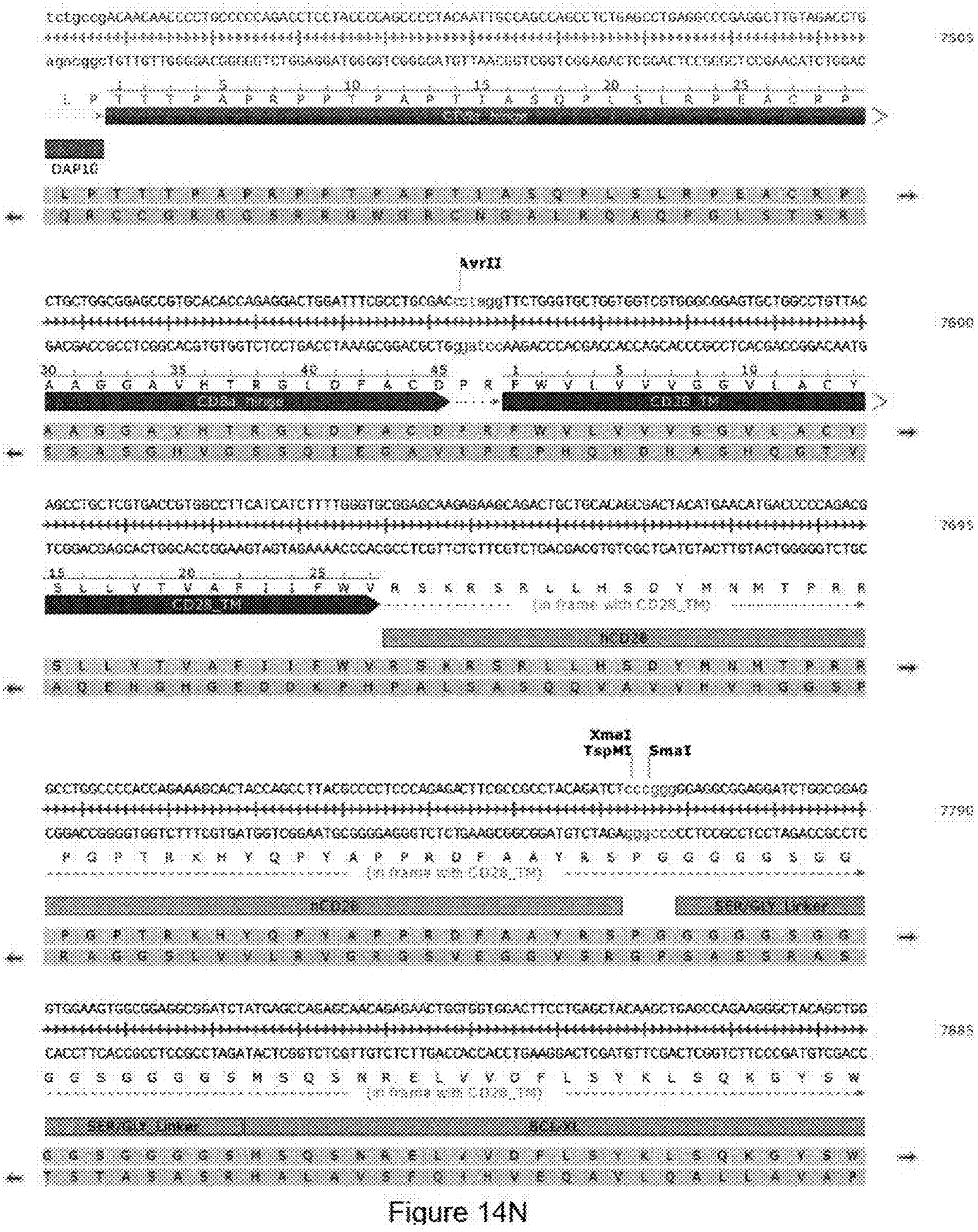
Figure 14O:
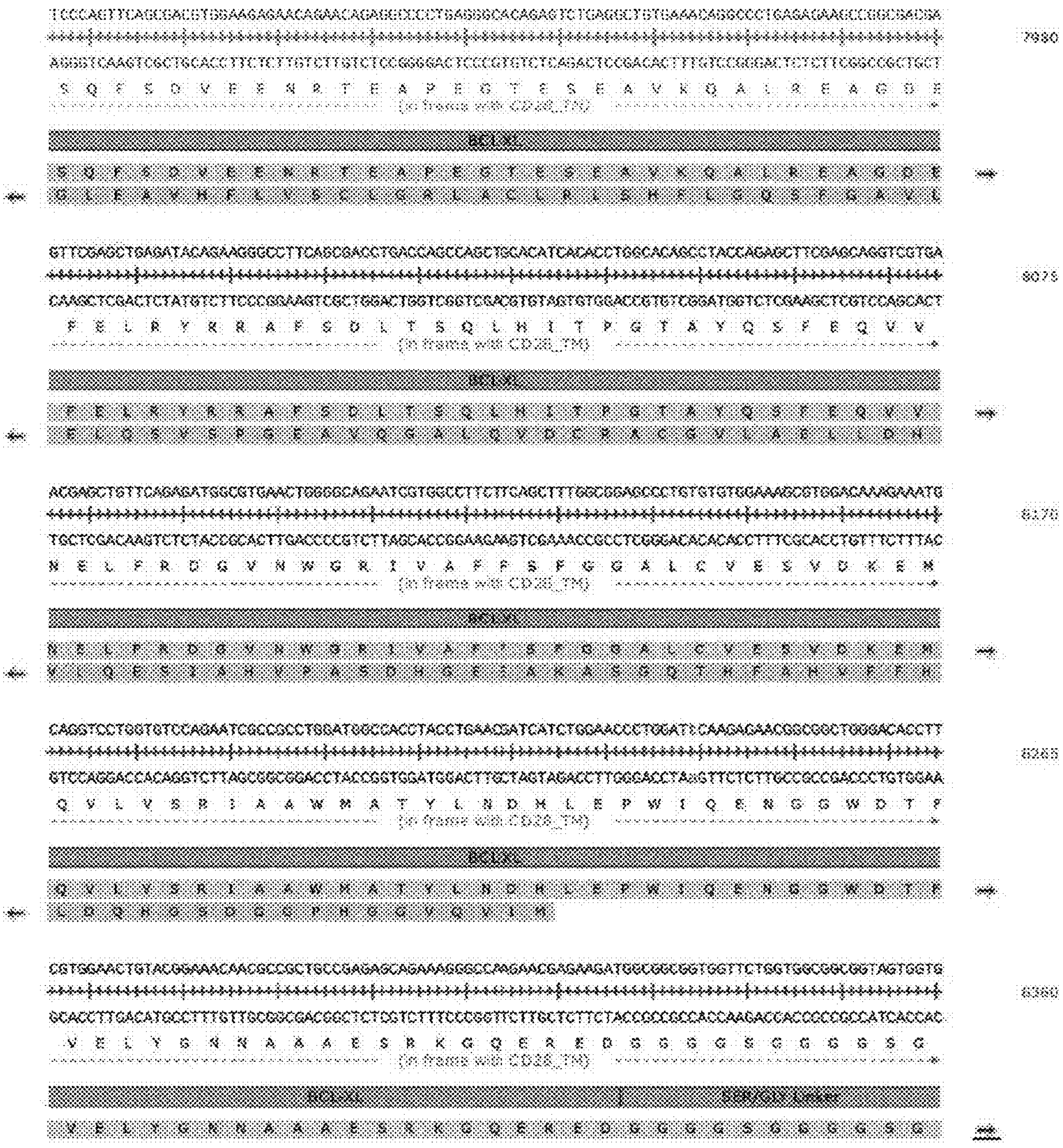
Figure 14P:
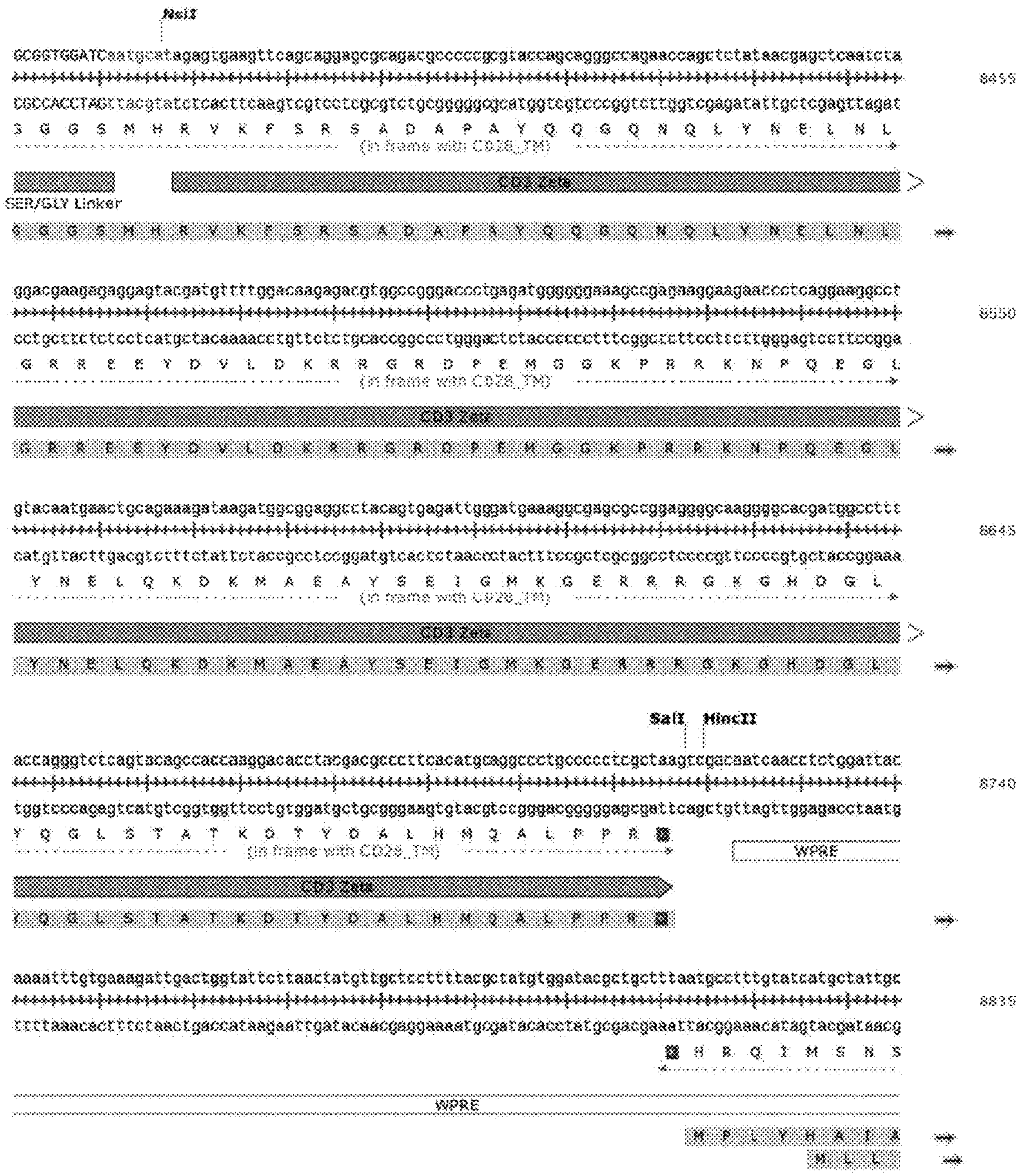
Figure 14Q:
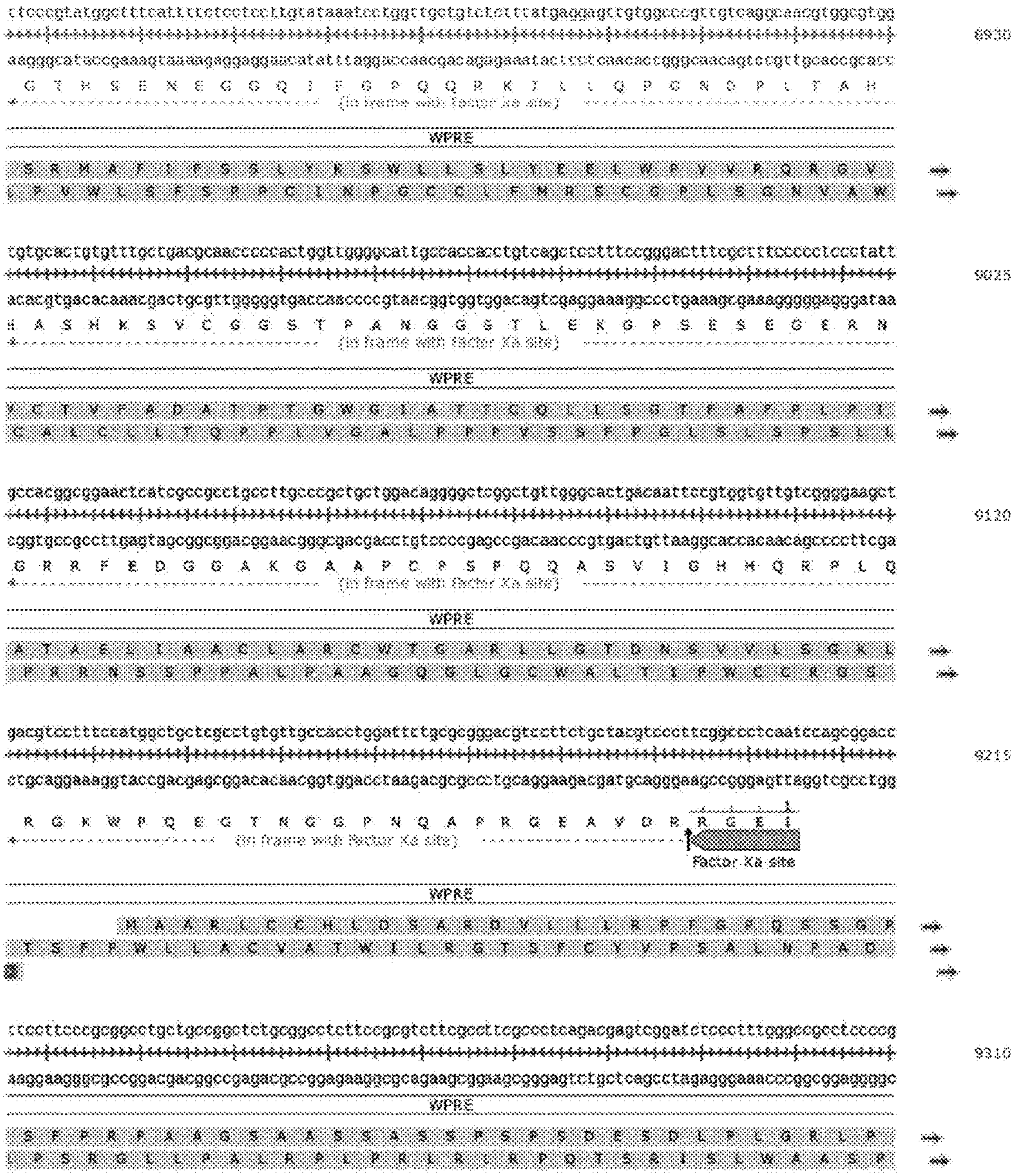
Figure 14R:
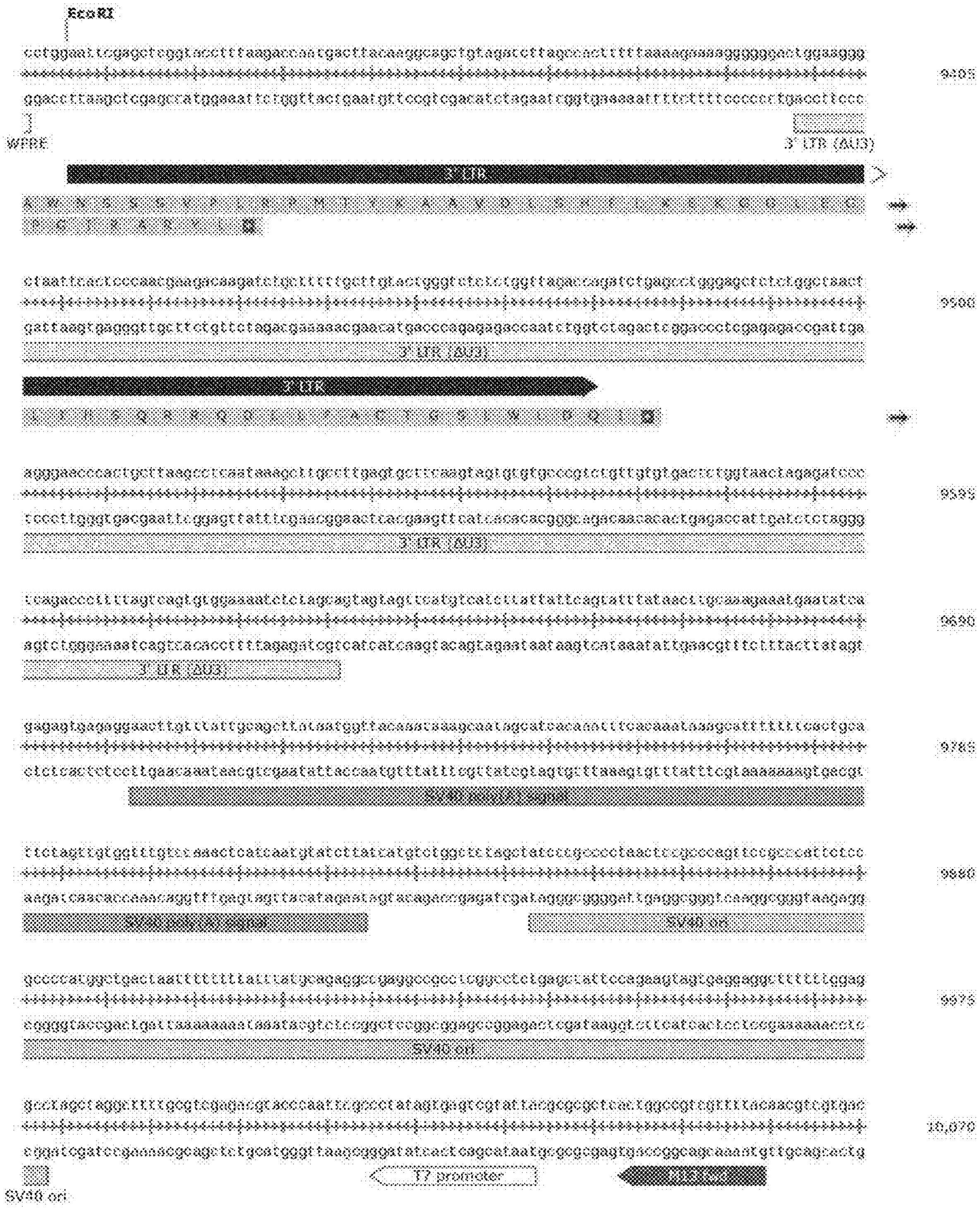
Figure 14S:
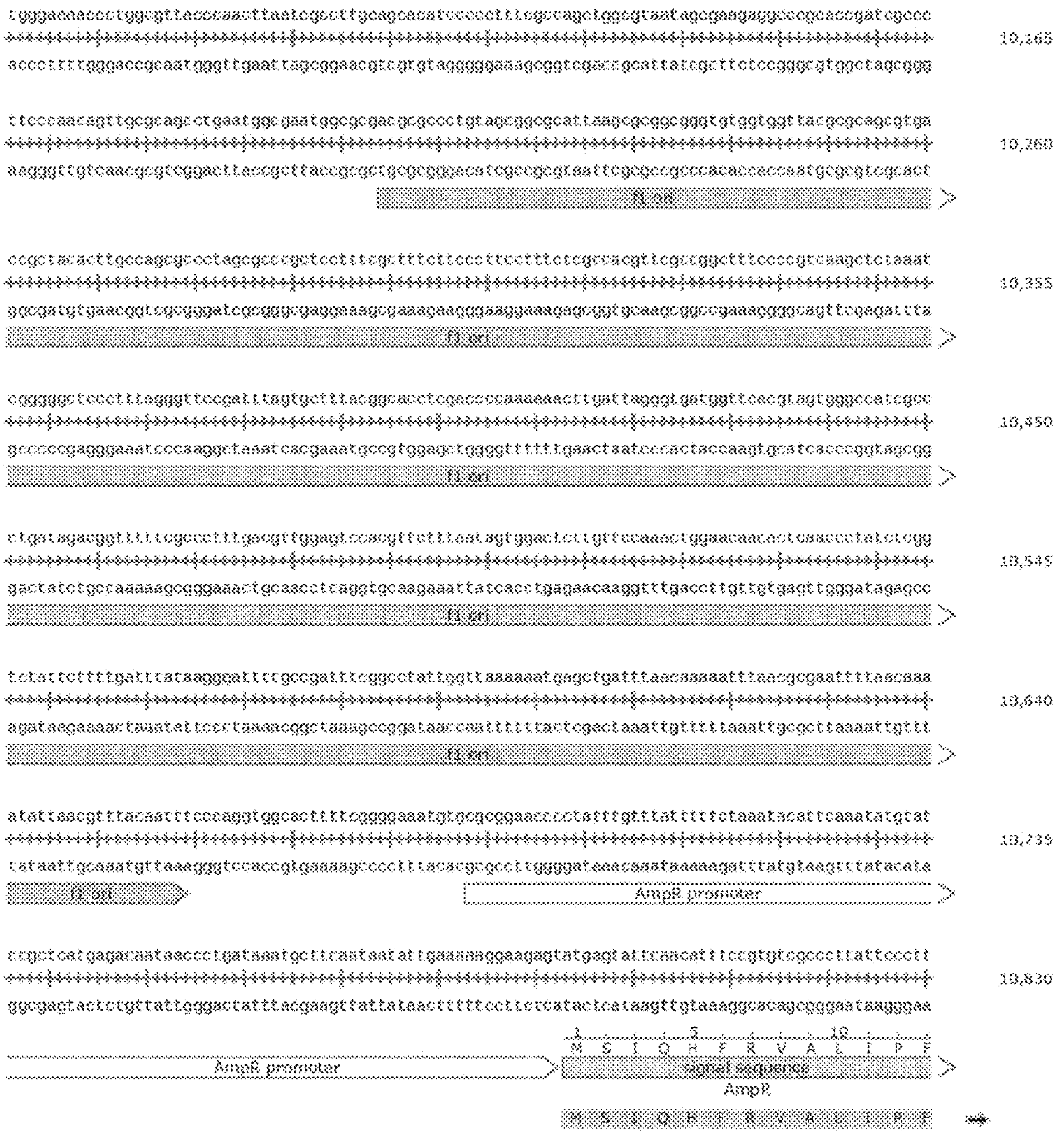
Figure 14T:
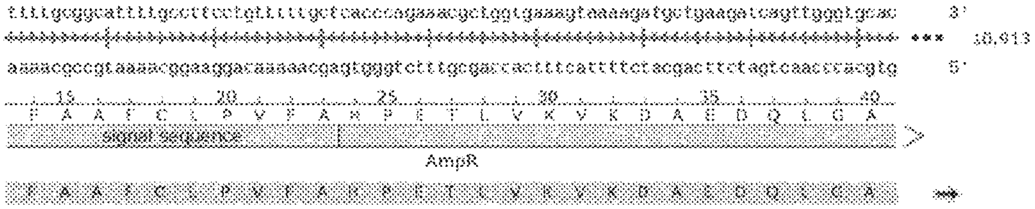

By way of example, but not limitation, OFF-CAR Chain A can comprise a target-binding domain (e.g., a scFv binding to a tumor-specific antigen), followed by a linker, a transmembrane (TM) domain, one or more co-stimulatory endodomains (EDs) required for signal 2 of T cell activation (e.g., CD28, 4-1BB), and the Protein A domain (which can comprise sequences, e.g., as shown in FIGS. 4 and 12-14 and SEQ ID Nos: 1-4, 19, and 130-133); and OFF-CAR Chain B can optionally comprise an extracellular region (ectodomain) having no target-binding capacity (e.g., DAP10 ectodomain) and comprise a TM domain, one or more co-stimulatory EDs (e.g., CD28, 4-1BB), Protein B domain (which can comprise sequence, e.g., as shown in FIGS. 5, 13, and 14 and SEQ ID Nos: 5, 22, 30, 23, and 24), and an intracellular signaling ED required for signal 1 of T cell activation (e.g., CD3-zeta).

In a clinical setting, STOP-CARs may be a powerful tool to temporarily abrogate T-cell activity in the event of an adverse patient response, while not permanently eliminating the T-cells as is the case with previous safety designs incorporating a suicide switch.

The term "chimeric antigen receptor" or "CAR" as used herein is defined as a cell-surface receptor comprising an extracellular target-binding domain, a transmembrane domain and a cytoplasmic domain, comprising a lymphocyte activation domain and optionally at least one co-stimulatory signaling domain, all in a combination that is not naturally found together on a single protein. This particularly includes receptors wherein the extracellular domain and the cytoplasmic domain are not naturally found together on a single receptor protein. The chimeric antigen receptors of the present invention are intended primarily for use with lymphocytes such as T cells and natural killer (NK) cells.

The terms "T cell" and "T lymphocyte" are interchangeable and used synonymously herein. As used herein, T cells include thymocytes, naive T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), a tumor infiltrating cytotoxic T cell (TIL; CD8+ T cell), CD4+CD8+ T cell, or any other subset of T cells. Other illustrative populations of T cells suitable for use in particular embodiments include naive T cells and memory T cells. Also included are "NKT cells", which refer to a specialized population of T cells that express a semi-invariant αβ T-cell receptor, but also express a variety of molecular markers that are typically associated with NK cells, such as NK1. 1. NKT cells include NK1.1+ and NK1. 1", as well as CD4+, CD4", CD8+ and CD8" cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (γδ T cells)," which refer to a specialized population that to a small subset of T cells possessing a distinct TCR on their surface, and unlike the majority of T cells in which the TCR is composed of two glycoprotein chains designated α- and β-TCR chains, the TCR in γδ T cells is made up of a γ-chain and a δ-chain. γδ T cells can play a role in immunosurveillance and immunoregulation, and were found to be an important source of IL-17 and to induce robust CD8+ cytotoxic T cell response. Also included are "regulatory T cells" or "Tregs", which refer to T cells that suppress an abnormal or excessive immune response and play a role in immune tolerance. Tregs are typically transcription factor Foxp3-positive CD4+T cells and can also include transcription factor Foxp3-negative regulatory T cells that are IL-10-producing CD4+ T cells.

As used herein, the term "antigen" refers to any agent (e.g., protein, peptide, polysaccharide, glycoprotein, glycolipid, nucleic acid, portions thereof, or combinations thereof) or molecule capable of being bound by a T-cell receptor. An antigen is also able to provoke an immune response. An example of an immune response may involve, without limitation, antibody production, or the activation of specific immunologically competent cells, or both. A skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to, a tissue sample, a tumor sample, a cell or a fluid with other biological components, organisms, subunits of proteins/antigens, killed or inactivated whole cells or lysates.

The term "tumor-targeting moiety" refers to a target-specific binding element that may be any ligand that binds to the antigen of interest or a polypeptide or fragment thereof, wherein the ligand is either naturally derived or synthetic. Examples of tumor-targeting moieties include, but are not limited to, antibodies; polypeptides derived from antibodies, such as, for example, single chain variable fragments (scFv), Fab, Fab', F(ab')2, and Fv fragments; polypeptides derived from T Cell receptors, such as, for example, TCR variable domains; secreted factors (e.g., cytokines, growth factors) that can be artificially fused to signaling domains (e.g., "zytokines"); and any ligand or receptor fragment (e.g., CD27, NKG2D) that binds to the antigen of interest. Combinatorial libraries could also be used to identify peptides binding with high affinity to the therapeutic target.

Host cells of the present invention include T cells and natural killer cells that contain the DNA or RNA sequences encoding the CAR and express the CAR on the cell surface. Host cells may be used for enhancing T cell activity, natural killer cell activity, treatment of cancer, and treatment of autoimmune disease.

The terms "activation" or "stimulation" means to induce a change in their biologic state by which the cells (e.g., T cells and NK cells) express activation markers, produce cytokines, proliferate and/or become cytotoxic to target cells. All these changes can be produced by primary stimulatory signals. Co-stimulatory signals can amplify the magnitude of the primary signals and suppress cell death following initial stimulation resulting in a more durable activation state and thus a higher cytotoxic capacity. A "co-stimulatory signal" refers to a signal, which in combination with a primary signal, such as TCR/CD3 ligation, leads to T cell and/or NK cell proliferation and/or upregulation or downregulation of key molecules.

The term "proliferation" refers to an increase in cell division, either symmetric or asymmetric division of cells. The term "expansion" refers to the outcome of cell division and cell death.

The term "linker", "linker region", "hinge" or "linker domain" as used herein generally means any oligo- or polypeptide that functions to link the antigen-binding moiety to the transmembrane domain.

The term "differentiation" refers to a method of decreasing the potency or proliferation of a cell or moving the cell to a more developmentally restricted state.

The terms "express" and "expression" mean allowing or causing the information in a gene or DNA sequence to become produced, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or transmembrane.

The term "transfection" means the introduction of a "foreign" (i.e., extrinsic or extracellular) nucleic acid into a cell using recombinant DNA technology. The term "genetic modification" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences operably linked to polynucleotide encoding the chimeric antigen receptor, such as start, stop, promoter, signal, secretion, or other sequences used by a cell's genetic machinery. The gene or sequence may include nonfunctional sequences or sequences with no known function. A host cell that receives and expresses introduced DNA or RNA has been "genetically engineered." The DNA or RNA introduced to a host cell can come from any source, including cells of the same genus or species as the host cell, or from a different genus or species.

The term "transduction" means the introduction of a foreign nucleic acid into a cell using a viral vector.

The terms "genetically modified" or "genetically engineered" refers to the addition of extra genetic material in the form of DNA or RNA into a cell.

As used herein, the term "derivative" in the context of proteins or polypeptides (e.g., CAR constructs or domains thereof) refer to: (a) a polypeptide that has at least 40%, 45%, 50%, 55%, 60%, 65%, 70%, 75%, 80%, 85%, 90%, 95%, 98% or 99% sequence identity to the polypeptide it is a derivative of; (b) a polypeptide encoded by a nucleotide sequence that has at least 40%, 45%, 50%, 55%, 60%, 65%, 70%, 75%, 80%, 85%, 90%, 95%, 98% or 99% sequence identity to a nucleotide sequence encoding the polypeptide it is a derivative of; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to the polypeptide it is a derivative of; (d) a polypeptide encoded by nucleic acids can hybridize under high, moderate or typical stringency hybridization conditions to nucleic acids encoding the polypeptide it is a derivative of; (e) a polypeptide encoded by a nucleotide sequence that can hybridize under high, moderate or typical stringency hybridization conditions to a nucleotide sequence encoding a fragment of the polypeptide, it is a derivative of, of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids; or (f) a fragment of the polypeptide it is a derivative of.

Percent sequence identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wisconsin).

Information regarding hybridization conditions (e.g., high, moderate, and typical stringency conditions) have been described, see, e.g., U.S. Patent Application Publication No. US 2005/0048549 (e.g., paragraphs 72-73).

The terms "vector", "cloning vector" and "expression vector" mean the vehicle by which a DNA or RNA sequence (e.g., a foreign gene) can be introduced into a host cell, so as to genetically modify the host and promote expression (e.g., transcription and translation) of the introduced sequence. Vectors include plasmids, synthesized RNA and DNA molecules, phages, viruses, etc. In certain embodiments, the vector is a viral vector such as, but not limited to, viral vector is an adenoviral, adeno-associated, alphaviral, herpes, lentiviral, retroviral, or vaccinia vector.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The terms "patient", "individual", "subject", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

By "enhance" or "promote," or "increase" or "expand" or "improve" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, effector function, persistence, and/or an increase in cancer cell death killing ability, among others apparent from the understanding in the art and the description herein. In certain embodiments, an "increased" or "enhanced" amount can be a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. In certain embodiments, a "decrease" or "reduced" amount can be a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "protein" is used herein encompasses all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The terms "nucleic acid", "nucleotide", and "polynucleotide" encompass both DNA and RNA unless specified otherwise. By a "nucleic acid sequence" or "nucleotide sequence" is meant the nucleic acid sequence encoding an amino acid, the term may also refer to the nucleic acid sequence including the portion coding for any amino acids added as an artifact of cloning, including any amino acids coded for by linkers Singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The practice of the present invention employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ.

The technology illustratively described herein suitably may be practiced in the absence of any element(s) not specifically disclosed herein.

The terms and expressions which have been employed are used as terms of description and not of limitation, and use of such terms and expressions do not exclude any equivalents of the features shown and described or portions thereof, and various modifications are possible within the scope of the technology claimed.

Chimeric Antigen Receptors

In one aspect is provided a heterodimeric inactivatable chimeric antigen receptor (CAR) that comprises a first polypeptide chain and a second polypeptide chain. The first polypeptide chain comprises: i) an extracellular target-binding region; ii) a first transmembrane (TM) region; iii) a first co-stimulatory endodomain (ED), and iv) a first member of a dimerization pair. The second polypeptide chain comprises: i) a second transmembrane (TM) region; ii) optionally, a second co-stimulatory endodomain (ED); iii) a second member of a dimerization pair; and iv) an intracellular signaling endodomain (ED). The first and second member of the dimerization pair form a heterodimer.

The second polypeptide chain of the CAR may comprise an extracellular region which does not comprise the target-binding capacity.

The first polypeptide chain of the CAR may not comprise an intracellular signaling endodomain (ED).

Without wishing to be bound by theory, neither the first polypeptide chain nor the second polypeptide chains, as individual monomers, would be sufficient to stimulate a T cell or Natural Killer (NK) cell response. However, if the first polypeptide chain and the second polypeptide chain are associated with one another, the signal would propagate. Throughout the application are described embodiments in which the association of the first and second polypeptide chains are regulated, such as by drugs that disrupt the interaction. Such drugs can be administered to a patient to turn off the CAR response, or to otherwise tune the response.

In another aspect is provided a heterodimeric inactivatable chimeric antigen receptor (CAR) that comprises a first polypeptide chain and a second polypeptide chain. In certain embodiments, the first polypeptide chain consists essentially of, in the direction from the N terminus to the C terminus: i) an extracellular target-binding region; ii) a first linker region; iii) a first transmembrane (TM) region; iv) a first co-stimulatory endodomain (ED), and v) a first member of a dimerization pair. In certain embodiments, the second polypeptide chain consists essentially of, in the direction from the N terminus to the C terminus: i) an extracellular region which does not comprise the target-binding capacity; ii) a second linker region; iii) a second transmembrane (TM) region; iv) a second co-stimulatory endodomain (ED); v) a second member of the dimerization pair; and vi) an intracellular signaling endodomain (ED). The first and second member of the dimerization pair form a heterodimer. In certain embodiments, the first polypeptide chain does not comprise an intracellular signaling endodomain (ED).

In either of the above aspects, the first and second member of the dimerization pair may be derived from proteins that do not natively interact in vivo.

In either of the above aspects, the heterodimer formed by the first and second member of the dimerization pair can be disrupted by an inhibitory molecule. The disruption can result in inhibition of CAR-mediated signaling. In certain embodiments, the inhibitory molecule can be a small molecule. In certain embodiments, the inhibitory molecule can be a polypeptide.

The inhibitory molecule may bind to the first or second member of the dimerization pair with a higher affinity than the first and second member of the dimerization pair bind to each other.

The first polypeptide chain may comprise a linker region interposed between the extracellular target-binding region and the first transmembrane (TM) region. The second polypeptide chain may comprise a linker region interposed between the extracellular region and the second transmembrane (TM) region. The linker region may be an immunoglobulin hinge region. The linker region may be derived from CD8 or CD8α. In certain embodiments, the linker region may be SEQ ID NO: 9). Linker regions are described in greater detail below.

The extracellular target-binding region may be an antigen-binding polypeptide, a receptor, or a natural ligand for a target cell antigen or receptor. The extracellular target-binding region may be an antigen-binding polypeptide. Exemplary antigen-binding polypeptides include, but are not limited to, antibodies and antibody fragments. For example, the antigen-binding polypeptide can be a murine antibody, a rabbit antibody, a human antibody, a humanized antibody, a single chain variable fragment (scFv), a camelid antibody variable domain, a humanized version of a camelid antibody variable domain, a shark antibody variable domain, a humanized version of a shark antibody variable domain, a single domain antibody variable domain, a nanobody (VHHs), and a camelized antibody variable domain.

The antigen recognized by the antigen-binding polypeptide may be a cancer cell associated antigen, an infection-associated antigen, or an auto-antigen. The cancer cell associated antigen may be associated with a solid tumor. In certain embodiments, the cancer cell associated antigen is PSMA. In certain embodiments, the cancer cell associated antigen is CD19.

In some embodiments, the antigen recognized by the antigen-binding polypeptide is selected from CD19, CD20, CD38, CD30, Her2/neu, ERBB2, CA125, MUC-1, PSMA, PSA, CD44 surface adhesion molecule, mesothelin, carcinoembryonic antigen (CEA), CEACAM5, CEACAM6, epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, carbonic anhydrase EX, alpha-fetoprotein, A3, antigen specific for A33 antibody, Ba 733, BrE3-antigen, CA125, CD1, CDIa, CD3, CD5, CD15, CD16, CD19, CD20, CD21, CD22, CD23, CD25, CD30, CD33, CD38, CD45, CD74, CD79a, CD80, CD 138, colon-specific antigen-p (CSAp), CSAp, EGP-I, EGP-2, Ep-CAM, FIt-I, Flt-3, folate receptor, HLA-DR, human chorionic gonadotropin (HCG) and its subunits, hypoxia inducible factor (HIF-I), Ia, IL-2, IL-6, IL-8, insulin growth factor-1 (IGF-I), KC4-antigen, KS-1-antigen, KS1-4, Le-Y, macrophage inhibition factor (MIF), MAGE, MUC1, MUC2, MUC3, MUC4, NCA66, NCA95, NCA90, tyrosinase, PRAME, EBNA, KLK3, HPV E7, LMP2, NY-ESO-1, PAP, reverse transcriptase, nucleophosmin, PRTN3/ELANE, CT83/KKLC1, MUC16, DNTT, antigen specific for PAM-4 antibody, placental growth factor, p53, prostatic acid phosphatase, RS5, S100, TAC, TAG-72, tenascin, TRAIL receptors, Tn antigen, Thomson-Friedenreich antigens, tumor necrosis antigens, VEGF, ED-B fibronectin, 17-1A-antigen, NeuGcGM3, N-glycolyl GM3 ganglioside, NeuGcGM3, N-glycolyl GM3 ganglioside, Neu5Gc, GM3-Ganglioside, GD3, GM2, carbohydrate antigens, ganglioside antigens, Lewis Y, Lewis B, CD123 or Kappa chain of immunoglobulin. In certain embodiments, the antigen recognized by the antigen-binding polypeptide is PSMA. In certain embodiments, the PSMA antigen-binding polypeptide is SEQ ID NO: 6. In certain embodiments, the antigen recognized by the antigen-binding polypeptide is CD19. In certain embodiments, the CD19 antigen-binding polypeptide is SEQ ID NO: 49. In certain embodiments, antigen recognized by the antigen-binding polypeptide is NeuGcGM3. In certain embodiments, the NeuGcGM3 antigen-binding polypeptide is SEQ ID NO: 44-48 or 50-63.

The antigen recognized by the antigen-binding polypeptide may be PSMA. PSMA i s a type II membrane protein originally characterized by the murine monoclonal antibody (mAb) 7E11-C5.3 and is expressed in all forms of prostate tissue, including carcinoma. PSMA helps fuel the development of prostate cancer cells. Indeed, prostate cancer cells have high levels of PSMA.

The antigen recognized by the antigen-binding polypeptide may be CD19. The human CD19 antigen is a 95 kD transmembrane glycoprotein belonging to the immunoglobulin superfamily. CD19 is classified as a type I transmembrane protein, with a single transmembrane domain, a cytoplasmic C-terminus, and extracellular N-terminus. CD19 is a biomarker for normal and neoplastic B cells, as well as follicular dendritic cells. CD19 is involved in establishing intrinsic B cell signaling thresholds through modulating both B cell receptor-dependent and independent signaling. CD19 can function as a dominant signaling component of a multimolecular complex on the surface of mature B cells, alongside complement receptor CD21, and the tetraspanin membrane protein CD81 (TAPA-1), as well as CD225. Without wishing to be bound by theory, through study of CD19 transgenic and knockout mouse models, CD19 can play a role in maintaining the balance between humoral, antigen-induced response and tolerance induction.

Since CD19 is a marker of B cells, CD19 has been used to diagnose cancers that arise from B cells, notably B cell lymphomas, acute lymphoblastic leukemia (ALL), and chronic lymphocytic leukemia (CLL). Leukemia & Lymphoma, 1995, 18(5-6):385-397. The majority of B cell malignancies express normal to high levels of CD19. The most current experimental anti-CD19 immunotoxins in development work by exploiting the widespread presence of CD19 on B cells, with expression highly conserved in most neoplastic B cells, to direct treatment specifically towards B-cell cancers. Arthritis Res. & Ther., 2012, 14 Suppl. 5 (5):S1 and Nature Reviews Rheumatology, 2011, 7(3):170-178. However, it is now emerging that the protein plays an active role in driving the growth of these cancers, most intriguingly by stabilizing the concentrations of the MYC oncoprotein. This suggests that CD19 and its downstream signaling may be a more attractive therapeutic target than initially suspected. Journ. Clin. Invest., 2012, 122(6):2257-66 and J. Immunol., 2012, 189(5):2318-25. The targeting of CD19, a cell surface molecule expressed in the vast majority of leukemias and lymphomas, has been successfully translated in the clinic. (Mol. Ther. 2017 May 3; 25(5):1117-1124. doi: 10.1016/j.ymthe.2017.03.034. Epub 2017 Apr. 26. Chimeric Antigen Receptors: A Cell and Gene Therapy Perspective. Riviére Il, Sadelain M2.).

CD19-targeted therapies based on T cells that express CD19-specific chimeric antigen receptors (CARs) have been utilized for their antitumor abilities inpatients with CD19+ lymphoma and leukemia, first against Non-Hodgkins Lymphoma (NHL), then against CLL in 2011, and then against ALL in 2013. Leukemia & Lymphoma, 1995, 18(5-6):385-397; New England J. Med., 2011, 365(8):725-33; Cell, 2017, 171(7):1471; and Clinical Trial Number NCT01493453 at clinicaltrials.gov. Two CD-19-CART therapies have been approved: Gilead Sciences' Yescarta® (axicabtagene ciloleucel, KTE-C19) for third line or later (3L+) large B-cell lymphoma and Novartis' Kymriah® (tisagenlecleucel, CTL019) for acute lymphocytic leukemia (ALL) and diffuse large B-cell lymphoma (DLBCL). CAR-19 T cells are genetically modified T cells that express a targeting moiety on their surface that confers T cell receptor (TCR) specificity towards CD19+ cells. CD19 activates the TCR signaling cascade that leads to proliferation, cytokine production, and ultimately lysis of the target cells, which in this case are CD19+ B cells. CAR-19 T cells are more effective than anti-CD19 immunotoxins because they can proliferate and remain in the body for a longer period of time.

The extracellular target-binding region may be a natural ligand for a target cell antigen or receptor.

The natural ligand for a target cell antigen or receptor may be an NKG2D ectodomain.

The extracellular target-binding region may be a T-cell receptor (TCR) based recognition domain.

The TCR based recognition domain may be a single chain TCR.

The first and/or second transmembrane (TM) region may be derived from CD8, CD8α, CD4, CD3-zeta, CD3-epsilon, CD28, CD45, CD4, CD5, CD7, CD9, CD16, CD22, CD33, CD37, CD40, CD64, CD80, CD86, CD134 (OX-40), CD137, CD154, DAP10, or DAP12. The first and second transmembrane (TM) regions of the first and second polypeptide may be the same. The first and second transmembrane (TM) regions of the first and second polypeptide may be different. In some embodiments, the first and second transmembrane (TM) regions are derived from CD28. In certain embodiments, the transmembrane domain may be SED ID NO: 10.

The extracellular region which does not comprise the target-binding capacity may be a stabilizing domain.

In some embodiments, the extracellular region which does not comprise the target-binding capacity is derived from DAP10. Examples of extracellular regions derived from DAP10 include, but are not limited to, the DAP10 ectodomain, and the transmembrane domain. The DAP12 extracellular region derived from the DAP12 ectodomain may comprise the sequence of SEQ ID NO: 8. In some embodiments, the extracellular region which does not comprise the target-binding capacity is derived from DAP12. Examples of extracellular regions derived from DAP12 include, but are not limited to, the DAP12 ectodomain, and the transmembrane domain. The DAP12 extracellular region derived from the DAP12 ectodomain may comprise the sequence of GVLAGIVMGDLVLTVLIALAV (SEQ ID NO: 74). The DAP12 extracellular region derived from the DAP12 transmembrane domain may comprise the amino acid sequence of LRPVQAQAQSDCSCSTVSP (SEQ ID NO: 75).

The first and/or second co-stimulatory endodomain (ED) of the CAR may be derived from 4-1BB (CD137), CD28, ICOS, CD134 (OX-40), BTLA, CD27, CD30, GITR, CD226, or HVEM. In some embodiments, the first co-stimulatory endodomains (ED) is derived from CD28. In some embodiments, the second co-stimulatory ED is derived from CD28. In some embodiments, the first and/or second co-stimulatory EDs are derived from CD28. In certain embodiments, the co-stimulatory ED may be SEQ ID NO: 11.

The intracellular signaling ED of the CAR is derived from DAP10, DAP12, Fc epsilon receptor I gamma chain (FCER1G), FcR beta CD3-delta, CD3-epsilon, CD3-gamma, CD3-zeta, CD226, CD66d, CD79A, or CD79B. In some embodiments, the intracellular signaling endodomain (ED) is derived from CD3-zeta. In certain embodiments, the intracellular signaling ED may be SEQ ID NO: 7.

In some embodiments, the first and/or second polypeptide chain further comprises one or more additional polypeptide sequences. Exemplary additional polypeptide sequences include, but are not limited to, additional co-stimulatory endodomains (EDs), signal sequences, epitope tags, and polypeptides that produce a detectable signal. In some embodiments, the signal sequence is CD8α. In some embodiments, the epitope tag is cMyc.

Dimerization Pair Sequences

In some embodiments, the first member of the dimerization pair of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to

```
                                    (SEQ ID NO: 1)
QRWELALGRFLEYLSWVSTLSEQVQEELLSSQVTQELRALMDETMKELKA
YKSELEEQLTPVAEETRARLSKELQAAQARLGADMEDVRGRLVQYRGEVQ
AMLGQSTEELRVRLASHLIALQLRLIGDAFDLQKRLAVYQAGAAE.
```

In some embodiments, the first member of the dimerization pair of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to

```
                                    (SEQ ID NO: 2)
QRWELALGRFLEYLSWVSTLSEQVQEELLSSQVTQELRALMDETMKELKA
YKSELEEQLTPVAEETRARLSKELQAAQARLGADMEDVRGRLVQYRGEVQ
AMLGQSTEELRVRLASHLIALQLRLIGDAFDLQKRLAVYQAGA.
```

In some embodiments, the first member of the dimerization pair of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to

```
                                    (SEQ ID NO: 3)
QRWELALGRFLEYLSWVSTLSEQVQEELLSSQVTQELRALMDETMKELKA
YKSELEEQLTPVAEETRARLSKELQAAQARLGADMEDVRGRLVQYRGEVQ
AMLGQSTEELRVRLASHLIALQARLIGDAFDLQKRLAVYQAGA.
```

In some embodiments, the first member of the dimerization pair of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to

```
                                    (SEQ ID NO: 4)
QRWELALGRFLEYLSWVSTLSEQVQEELLSSQVTQELRALMDETMKELKA
YKSELEEQLTPVAEETRARLSKELQAAQARLGADMEDVRGRLVQYRGEVQ
AMLGQSTEELRVRLASHLIALQLRLIGAAFDLQKRLAVYQAGA.
```

In some embodiments, the first member of the dimerization pair of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 19)
QRWELALGRFLAYLSWVSTLSEQVQEELLSSQVTQELRALMDETMKELKA
YKSELEEQLTPVAEETRARLSKELQAAQARLGADMEDVRGRLVQYRGEVQ
AMLGQSTEELRVRLASHLIALQLRLIGDAFDLQKRLAVYQAGA.

In some embodiments, the second member of the dimerization pair of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 5)
MSQSNRELVVDFLSYKLSQKGYSWSQFSDVEENRTEAPEGTESEAVKQAL
REAGDEFELRYRRAFSDLTSQLHITPGTAYQSFEQVVNELFRDGVNWGRI
VAFFSFGGALCVESVDKEMQVLVSRIAAWMATYLNDHLEPWIQENGGWDT
FVELYGNNAAAESRKGQERED.

In some embodiments, the second member of the dimerization pair of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 22)
MSQSNRELVVDFLSYKLSQKGYSWSQFSDVEENRTEAPEGTESEAVKQAL
REAGDEFELRYRRAFSDLTSQLHITPGTAYQSFEQVVNELFRDGVNWGRI
VAFFSFGGALCVESVDKEMQVLVSRIAAWMATYLNDHLEPWIQENGGWDT
FVELYGNNAAAESRKGQER.

In some embodiments, the second member of the dimerization pair of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 30)
MSQSNRELVVDFLSYKLSQKGYSWSQFSDVEENRTEAPEGTESEAVKQAL
REAGDDFELRYRRAFSDLTSQLHITPGTAYQSFEQVVNELFRDGVNWGRIV
AFFSFGGALCVESVDKEMQVLVSRIAAWMATYLNDHLEPWIQENGGWD
TFVELYGNNAAAESRKGQERED.

In some embodiments, the second member of the dimerization pair of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 23)
MSQSNRELVVDFLSYKLSQKGYSWSQFSDVEENRTEAPEGTESEAVKQAL
REAGDDFELRYRRAFSDLTSQLHITPGTAYQSFEQVVNELFRDGVNWGRI
VAFFSFGGALCVESVDKEMQVLVSRIAAWMATYLNDHLEPWIQENGGWDT
FVELYGNNAAAESRKGQER.

In some embodiments, the second member of the dimerization pair of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 24)
MAHAGRTGYDNREIVMKYIHYKLSQRGYEWDAGDVGAAPPGAAPAPGIFS
SQPGHTPHPAASRDPVARTSPLQTPAAPGAAAGPALSPVPPVVHLTLRQA
GDDFSRRYRRDFAEMSSQLHLTPFTARGRFATVVEELFRDGVNWGRIVAF
FEFGGVMCVESVNREMSPLVDNIALWMTEYLNRHLHTWIQDNGGWDAFVE
LYGPSMR.

Additional Sequences

In some embodiments, the extracellular target-binding region of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 6)
VQLQQSGPELVKPGTSVRISCKTSGYTFTEYTIHWVKQSHGKSLEWIGNI
NPNNGGTTYNQKFEDKATLTVDKSSSTAYMELRSLTSEDSAVYYCAAGWN
FDYWGQGTTVTVSSGGGGSGGGGSGGGGSDIVMTQSHKFMSTSVGDRVSI
ICKASQDVGTAVDWYQQKPGQSPKLLIYWASTRHTGVPDRFTGSGSGTDF
TLTITNVQSEDLADYFCQQYNSYPLTFGAGTMLDLKR.

In some embodiments, the extracellular target-binding region of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 49)
GSDIQMTQTTSSLSASLGDRVTISCRASQDISKYLNWYQQKPDGTVKLLI
YHTSRLHSGVPSRFSGSGSGTDYSLTISNLEQEDIATYFCQQGNTLPYTF
GGGTKLEITGSTSGSGKPGSGEGSTKGEVKLQESGPGLVAPSQSLSVTCT
VSGVSLPDYGVSWIRQPPRKGLEWLGVIWGSETTYYNSALKSRLTIIKDN
SKSQVFLKMNSLQTDDTAIYYCAKHYYYGGSYAMDYWGQGTSVTVSS.

In some embodiments, the intracellular signaling ED of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 7)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR.

In some embodiments, the extracellular target-binding region of the CAR comprises the sequence (SEQ ID NO: 49)
GSDIQMTQTTSSLSASLGDRVTISCRASQDISKYLNWYQQKPDGTVKLLI
YHTSRLHSGVPSRFSGSGSGTDYSLTISNLEQEDIATYFCQQGNTLPYTF
GGGTKLEITGSTSGSGKPGSGEGSTKGEVKLQESGPGLVAPSQSLSVTCT
VSGVSLPDYGVSWIRQPPRKGLEWLGVIWGSETTYYNSALKSRLTIIKDN
SKSQVFLKMNSLQTDDTAIYYCAKHYYYGGSYAMDYWGQGTSVTVSS.

In some embodiments, the intracellular signaling ED of the CAR comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to

```
                                        (SEQ ID NO: 7)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR.
```

In some embodiments, the extracellular region which does not comprise the target-binding capacity comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to

```
                                        (SEQ ID NO: 8)
QTTPGERSSLPAFYPGTSGSCSGCGSLSLP.
```

In some embodiments, the extracellular region which does not comprise the target-binding capacity comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 74 or SEQ ID NO: 75.

In some embodiments, the first and/or second linker region comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to

```
                                        (SEQ ID NO: 9)
TTTPAPRPPTPAPTIASQPLSLRPEACRPAAGGAVHTRGLDFACD.
```

In some embodiments, the first and/or second transmembrane (TM) region comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to

```
                                        (SEQ ID NO: 10)
FWVLVVVGGVLACYSLLVTVAFIIFWV.
```

In some embodiments, the first and/or second co-stimulatory endodomain (ED) comprises the sequence at least 81%, 82%, 83%, 84%, 85%, 86%, 87%, 88%, 89%, 90%, 91%, 92%, 93%, 94%, 95%, 96%, 97%, 98%, 99% or 100% identical to

```
                                        (SEQ ID NO: 11)
RSKRSRLLHSDYMNMTPRRPGPTRKHYQPYAPPRDFAAYRS.
```

In some embodiments, the first polypeptide chain comprises, consists of, or consists essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 12, 76, 77, 109-112, or 134-146.

In some embodiments, the second polypeptide chain comprises, consists of, or consists essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 13, 79-81, 113-117, or 147-157.

Combinations of First and Second Polypeptide Chain Sequences

In one aspect, the inactivatable chimeric antigen receptor (CAR) comprises: a) a first polypeptide chain comprises, consists of, or consists essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to any one of SEQ ID Nos: 12, 76, 77, 109-112, or 134-146, and b) a second polypeptide chain comprises, consists of, or consists essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to any one of SEQ ID Nos: 13, 79, 80, 81, 113-117, 147-156.

In another aspect is provided a heterodimeric inactivatable CAR comprising:

a) a first polypeptide chain comprising, consisting of, or consisting essentially of, the sequence at least 81%, 82%, 83%, 84%, 85%, 86%, 87%, 88%, 89%, 90%, 91%, 92%, 93%, 94%, 95%, 96%, 97%, 98%, 99% or 100% identical to MALPVTALLLPLALLL-HAARPVQLQQSGPELVKPGTSVRISCK-TSGYTFTEYTIHWV KQSHGKSLEWIGN-INPNNGGTTYNQKFEDKATLTVDKSSSTAYMEL RSLTSEDSAVY YCAAGWNFDYWGQGTTVTVSSGGGGSGGGGS GGGGSDIVMTQSHKFMSTSVGDR VSIICK-ASQDVGTAVDWYQQKPGQSPKLLIYWAST-RHTGVPDRFTGSGSGTDFTLTIT NVQSEDLA-DYFCQQYNSYPLTFGAGTMLDLKRASTTTPAPR PPTPAPTIASQPLSLRP EACRPAAGGAVHTRGLD-FACDFWVLVVVGGVLACYSLLVTVAFIIFWVR-SKRSRLL HSDYMNMTPRRPGPTRKHYQPYAP-PRDFAAYRSHMGGGGSGGGGSGGGGSQRWE LALGRFLEYLSWVSTLSEQVQEELLSSQVTQEL-RALMDETMKELKAYKSELEEQLTP VAEETRARLSKELQAAQARLGADMEDVR-GRLVQYRGEVQAMLGQSTEELRVRLAS HLIALQLRLIGDAFDLQKRLAVYQAGAAER-KRRSGSGRSGSGEGRGSLLTCGDVEEN PGP (SEQ ID NO: 82), wherein the anti-PSMA domain can be replaced with any extracellular target-binding region of interest including those as disclosed herein, and b) a second polypeptide chain comprising, consisting of, or consisting essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to

```
                                        (SEQ ID NO: 83)
GSMALPVTALLLPLALLLHAARPEQKLISEEDLQTTPGERSSLPAFYPGT

SGSCSGCGSLSLPTTTPAPRPPTPAPTIASQPLSLRPEACRPAAGGAVHT

RGLDFACDPRFWVLVVVGGVLACYSLLVTVAFIIFWVRSKRSRLLHSDYM

NMTPRRPGPTRKHYQPYAPPRDFAAYRSPGGGGGSGGGGSGGGGSMSQSN

RELVVDFLSYKLSQKGYSWSQFSDVEENRTEAPEGTESEAVKQALREAGD

EFELRYRRAFSDLTSQLHITPGTAYQSFEQVVNELFRDGVNWGRIVAFFS

FGGALCVESVDKEMQVLVSRIAAWMATYLNDHLEPWIQENGGWDTFVELY

GNNAAAESRKGQEREDGGGGSGGGGSGGGGSMHRVKFSRSADAPAYQQGQ

NQLYNELNLGRREEYDVLDKRRGRDPEMGGKPRRKNPQEGLYNELQKDKM

AEAYSEIGMKGERRRGKGHDGLYQGLSTATKDTYDALHMQALPPR.
```

In another aspect is provided a heterodimeric inactivatable CAR comprising:

a) a first polypeptide chain comprising, consisting of, or consisting essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to MALPVTALLLPLALLL-HAARPVQLQQSGPELVKPGTSVRISCK-TSGYTFTEYTIHWV KQSHGKSLEWIGN-INPNNGGTTYNQKFEDKATLTVDKSSSTAYMEL RSLTSEDSAVY YCAAGWNFDYWGQGTTVTVSSGGGGSGGGGS GGGGSDIVMTQSHKFMSTSVGDR VSIICK-ASQDVGTAVDWYQQKPGQSPKLLIYWAST-RHTGVPDRFTGSGSGTDFTLTIT NVQSEDLA-DYFCQQYNSYPLTFGAGTMLDLKRASTTTPAPR PPTPAPTIASQPLSLRP EACRPAAGGAVHTRGLD-FACDFWVLVVVGGVLACYSLLVTVAFIIFWVR-SKRSRLL HSDYMNMTPRRPGPTRKHYQPYAP-PRDFAAYRSHMGGGGSGGGGSGGGGSQRWE LALGRFLEYLSWVSTLSEQVQEELLSSQVTQEL-RALMDETMKELKAYKSELEEQLTP VAEETRARLSKELQAAQARLGADMEDVR-GRLVQYRGEVQAMLGQSTEELRVRLAS HLIALQLRLIGDAFDLQKRLAVYQAGAAER-KRRSGSGRSGSGEGRGSLLTCGDVEEN PGP (SEQ ID NO: 84), wherein the anti-PSMA domain can be replaced with any extracellular target-binding region of interest including those as disclosed herein, and b) a second polypeptide chain comprising, consisting of, or consisting essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 85)
GSMALPVTALLLPLALLLHAARPEQKLISEEDLQTTPGERSSLPAFYPGT
SGSCSGCGSLSLPTTTPAPRPPTPAPTIASQPLSLRPEACRPAAGGAVHT
RGLDFACDPRFWVLVVVGGVLACYSLLVTVAFIIFWVRSKRSRLLHSDYM
NMTPRRPGPTRKHYQPYAPPRDFAAYRSPGGGGGSGGGGSGGGGSMSQSN
RELVVDFLSYKLSQKGYSWSQFSDVEENRTEAPEGTESEAVKQALREAGD
EFELRYRRAFSDLTSQLHITPGTAYQSFEQVVNELFRDGVNWGRIVAFFS
FGGALCVESVDKEMQVLVSRIAAWMATYLNDHLEPWIQENGGWDTFVELY
GNNAAAESRKGQERGGGGSGGGGSGGGGSMHRVKFSRSADAPAYQQGQNQ
LYNELNLGRREEYDVLDKRRGRDPEMGGKPRRKNPQEGLYNELQKDKMAE
AYSEIGMKGERRRGKGHDGLYQGLSTATKDTYDALHMQALPPR.

In another aspect is provided a heterodimeric inactivatable CAR comprising:

a) a first polypeptide chain comprising, consisting of, or consisting essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to MALPVTALLLPLALLL-HAARPVQLQQSGPELVKPGTSVRISCK-TSGYTFTEYTIHWV KQSHGKSLEWIGN-INPNNGGTTYNQKFEDKATLTVDKSSSTAYMEL RSLTSEDSAVY YCAAGWNFDYWGQGTTVTVSSGGGGSGGGGS GGGGSDIVMTQSHKFMSTSVGDR VSIICK-ASQDVGTAVDWYQQKPGQSPKLLIYWAST-RHTGVPDRFTGSGSGTDFTLTIT NVQSEDLA-DYFCQQYNSYPLTFGAGTMLDLKRASTTTPAP RPPTPAPTIASQPLSLRP EACRPAAGGAVHTR-GLDFACDFWVLVVVGGVLACYSLL-VTVAFIIFWVRSKRSRLL HSDYMNMTPRRPGP-TRKHYQPYAPPRDFAAYRSHMGGGGSGGGGSG GGGSQRWE LALGRFLEYLSWVSTLSE-QVQEELLSSQVTQELRALMDETMKEL-KAYKSELEEQLTP VAEETRARLSKELQAAQARL-GADMEDVRGRLVQYRGEVQAMLGQSTEELRVR-LAS HLIALQLRLIGDAFDLQKRLAVYQAGAAER-KRRSGSGRSGSGEGRGSLLTCGDVEEN PGP (SEQ ID NO: 86), wherein the anti-PSMA domain can be replaced with any extracellular target-binding region of interest including those as disclosed herein, and b) a second polypeptide chain comprising, consisting of, or consisting essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 87)
GSMALPVTALLLPLALLLHAARPEQKLISEEDLQTTPGERSSLPAFYPGT
SGSCSGCGSLSLPTTTPAPRPPTPAPTIASQPLSLRPEACRPAAGGAVHT
RGLDFACDPRFWVLVVVGGVLACYSLLVTVAFIIFWVRSKRSRLLHSDYM
NMTPRRPGPTRKHYQPYAPPRDFAAYRSPGGGGGSGGGGSGGGGSMSQSN
RELVVDFLSYKLSQKGYSWSQFSDVEENRTEAPEGTESEAVKQALREAGD
DFELRYRRAFSDLTSQLHITPGTAYQSFEQVVNELFRDGVNWGRIVAFFS
FGGALCVESVDKEMQVLVSRIAAWMATYLNDHLEPWIQENGGWDTFVELY
GNNAAAESRKGQEREDGGGGSGGGGSGGGGSMHRVKFSRSADAPAYQQGQ
NQLYNELNLGRREEYDVLDKRRGRDPEMGGKPRRKNPQEGLYNELQKDKM
AEAYSEIGMKGERRRGKGHDGLYQGLSTATKDTYDALHMQALPPR.

In another aspect is provided a heterodimeric inactivatable CAR comprising:

a) a first polypeptide chain comprising, consisting of, or consisting essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to MALPVTALLLPLALLL-HAARPVQLQQSGPELVKPGTSVRISCK-TSGYTFTEYTIHWV KQSHGKSLEWIGN-INPNNGGTTYNQKFEDKATLTVDKSSSTAYMEL RSLTSEDSAVY YCAAGWNFDYWGQGTTVTVSSGGGGSGGGGS GGGGSDIVMTQSHKFMSTSVGDR VSIICK-ASQDVGTAVDWYQQKPGQSPKLLIYWAST-RHTGVPDRFTGSGSGTDFTLTIT NVQSEDLA-DYFCQQYNSYPLTFGAGTMLDLKRASTTTPAPR PPTPAPTIASQPLSLRP EACRPAAGGAVHTRGLD-FACDFWVLVVVGGVLACYSLLVTVAFIIFWVR-SKRSRLL HSDYMNMTPRRPGPTRKHYQPYAP-PRDFAAYRSHMGGGGSGGGGSGGGGSQRWE LALGRFLEYLSWVSTLSEQVQEELLSSQVTQEL-RALMDETMKELKAYKSELEEQLTP VAEETRARLSKELQAAQARLGADMEDVR-GRLVQYRGEVQAMLGQSTEELRVRLAS HLIALQLRLIGDAFDLQKRLAVYQAGAAER-KRRSGSGRSGSGEGRGSLLTCGDVEEN PGP (SEQ ID NO: 88), wherein the anti-PSMA domain can be replaced with any extracellular target-binding region of interest including those as disclosed herein, and b) a second polypeptide chain comprising, consisting of, or consisting essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 89)
GSMALPVTALLLPLALLLHAARPEQKLISEEDLQTTPGERSSLPAFYPGT
SGSCSGCGSLSLPTTTPAPRPPTPAPTIASQPLSLRPEACRPAAGGAVHT
RGLDFACDPRFWVLVVVGGVLACYSLLVTVAFIIFWVRSKRSRLLHSDYM
NMTPRRPGPTRKHYQPYAPPRDFAAYRSPGGGGGSGGGGSGGGGSMAHAG
RTGYDNREIVMKYIHYKLSQRGYEWDAGDVGAAPPGAAPAPGIFSSQPGH
TPHPAASRDPVARTSPLQTPAAPGAAAGPALSPVPPVVHLTLRQAGDDFS
RRYRRDFAEMSSQLHLTPFTARGRFATVVEELFRDGVNWGRIVAFFEFGG
VMCVESVNREMSPLVDNIALWMTEYLNRHLHTWIQDNGGWDAFVELYGPS
MRGGGGSGGGGSGGGGSMHRVKFSRSADAPAYQQGQNQLYNELNLGRREE
YDVLDKRRGRDPEMGGKPRRKNPQEGLYNELQKDKMAEAYSEIGMKGERR
RGKGHDGLYQGLSTATKDTYDALHMQALPPR.

In another aspect is provided a heterodimeric inactivatable CAR comprising:

a) a first polypeptide chain comprising, consisting of, or consisting essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to MALPVTALLLPLALLLHAARPVQLQQSGPELVKPGTSVRISCKTSGYTFTEYTIHWV KQSHGKSLEWIGNINPNNGGTTYNQKFEDKATLTVDKSSSTAYMEL RSLTSEDSAVY YCAAGWNFDYWGQGTTVTVSSGGGGSGGGGS GGGGSDIVMTQSHKFMSTSVGDR VSIICKASQDVGTAVDWYQQKPGQSPKLLIYWASTRHTGVPDRFTGSGSGTDFTLTIT NVQSEDLADYFCQQYNSYPLTFGAGTMLDLKRASTTTPAPR PPTPAPTIASQPLSLRP EACRPAAGGAVHTRGLDFACDFWVLVVVGGVLACYSLLVTVAFIIFWVRSKRSRLL HSDYMNMTPRRPGPTRKHYQPYAPRDFAAYRSHMGGGGSGGGGSGGGGSQRWE LALGRFLEYLSWVSTLSEQVQEELLSSQVTQELRALMDETMKELKAYKSELEEQLTP VAEETRARLSKELQAAQARLGADMEDVRGRLVQYRGEVQAMLGQSTEELRVRLAS HLIALQARLIGDAFDLQKRLAVYQAGAAERKRRSGSGRSGSGEGRGSLLTCGDVEE NPGP (SEQ ID NO: 90), wherein the anti-PSMA domain can be replaced with any extracellular target-binding region of interest including those as disclosed herein, and b) a second polypeptide chain comprising, consisting of, or consisting essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 91)
GSMALPVTALLLPLALLLHAARPEQKLISEEDLQTTPGERSSLPAFYPGT
SGSCSGCGSLSLPTTTPAPRPPTPAPTIASQPLSLRPEACRPAAGGAVHT
RGLDFACDPRFWVLVVVGGVLACYSLLVTVAFIIFWVRSKRSRLLHSDYM -continued
NMTPRRPGPTRKHYQPYAPPRDFAAYRSPGGGGGSGGGGSGGGGSMSQSN
RELVVDFLSYKLSQKGYSWSQFSDVEENRTEAPEGTESEAVKQALREAGD
EFELRYRRAFSDLTSQLHITPGTAYQSFEQVVNELFRDGVNWGRIVAFFS
FGGALCVESVDKEMQVLVSRIAAWMATYLNDHLEPWIQENGGWDTFVELY
GNNAAAESRKGQERGGGGSGGGGSGGGGSMHRVKFSRSADAPAYQQGQNQ
LYNELNLGRREEYDVLDKRRGRDPEMGGKPRRKNPQEGLYNELQKDKMAE
AYSEIGMKGERRRGKGHDGLYQGLSTATKDTYDALHMQALPPR.

In another aspect is provided a heterodimeric inactivatable CAR comprising:

a) a first polypeptide chain comprising, consisting of, or consisting essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to MALPVTALLLPLALLLHAARPVQLQQSGPELVKPGTSVRISCKTSGYTFTEYTIHWV KQSHGKSLEWIGNINPNNGGTTYNQKFEDKATLTVDKSSSTAYMEL RSLTSEDSAVY YCAAGWNFDYWGQGTTVTVSSGGGGSGGGGS GGGGSDIVMTQSHKFMSTSVGDR VSIICKASQDVGTAVDWYQQKPGQSPKLLIYWASTRHTGVPDRFTGSGSGTDFTLTIT NVQSEDLADYFCQQYNSYPLTFGAGTMLDLKRASTTTPAPR PPTPAPTIASQPLSLRP EACRPAAGGAVHTRGLDFACDFWVLVVVGGVLACYSLLVTVAFIIFWVRSKRSRLL HSDYMNMTPRRPGPTRKHYQPYAPRDFAAYRSHMGGGGSGGGGSGGGGSQRWE LALGRFLEYLSWVSTLSEQVQEELLSSQVTQELRALMDETMKELKAYKSELEEQLTP VAEETRARLSKELQAAQARLGADMEDVRGRLVQYRGEVQAMLGQSTEELRVRLAS HLIALQLRLIGAAFDLQKRLAVYQAGAAERKRRSGSGRSGSGEGRGSLLTCGDVEEN PGP (SEQ ID NO: 92), wherein the anti-PSMA domain can be replaced with any extracellular target-binding region of interest including those as disclosed herein, and b) a second polypeptide chain comprising, consisting of, or consisting essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 93)
GSMALPVTALLLPLALLLHAARPEQKLISEEDLQTTPGERSSLPAFYPGT
SGSCSGCGSLSLPTTTPAPRPPTPAPTIASQPLSLRPEACRPAAGGAVHT
RGLDFACDPRFWVLVVVGGVLACYSLLVTVAFIIFWVRSKRSRLLHSDYM
NMTPRRPGPTRKHYQPYAPPRDFAAYRSPGGGGGSGGGGSGGGGSMSQSN
RELVVDFLSYKLSQKGYSWSQFSDVEENRTEAPEGTESEAVKQALREAGD
EFELRYRRAFSDLTSQLHITPGTAYQSFEQVVNELFRDGVNWGRIVAFFS
FGGALCVESVDKEMQVLVSRIAAWMATYLNDHLEPWIQENGGWDTFVELY
GNNAAAESRKGQERGGGGSGGGGSGGGGSMHRVKFSRSADAPAYQQGQNQ
LYNELNLGRREEYDVLDKRRGRDPEMGGKPRRKNPQEGLYNELQKDKMAE -continued

AYSEIGMKGERRRGKGHDGLYQGLSTATKDTYDALHMQALPPR.

In various embodiments, a linker region (a.k.a linker domain) can be used to provide more flexibility and accessibility for the antigen-binding moiety. A linker region may comprise up to 300 amino acids, preferably 10 to 100 amino acids and most preferably 25 to 50 amino acids. A linker region may be derived from all or part of naturally occurring molecules, such as from all or part of the extracellular region of CD8, CD4 or CD28, or from all or part of an antibody constant region. Alternatively, the linker region may be a synthetic sequence that corresponds to a naturally occurring linker region sequence, or may be an entirely synthetic linker domain sequence. Non-limiting examples of linker region which may be used in accordance to the invention include a part of human CD8 a chain, partial extracellular domain of CD28, FcγRllla receptor, IgG, IgM, IgA, IgD, IgE, an Ig hinge, or functional fragment thereof. In certain embodiments, additional linking amino acids are added to the linker region to ensure that the antigen-binding moiety is an optimal distance from the transmembrane domain. In certain embodiments, when the linker is derived from an Ig, the linker may be mutated to prevent Fc receptor binding.

In certain embodiments, the linker region comprises an immunoglobulin IgG hinge or functional fragment thereof. In certain embodiments, the IgG hinge is from IgG1, IgG2, IgG3, IgG4, IgM1, IgM2, IgA1, IgA2, IgD, IgE, or a chimera thereof. In certain embodiments, the linker region comprises the CH1, CH2, CH3 and/or hinge region of the immunoglobulin.

In certain embodiments, the linker region comprises the core hinge region of the immunoglobulin. The term "core hinge" can be used interchangeably with the term "short hinge" (a.k.a "SH"). Non-limiting examples of suitable linker region are the core immunoglobulin hinge regions listed in Table 1 (see also Wypych et al., *JBC* 2008 283(23): 16194-16205, which is incorporated herein by reference in its entirety for all purposes). In certain embodiments, the linker region is a fragment of the immunoglobulin hinge.

TABLE 1

Amino Acid Sequence of Core Hinge Regions of IgG Immunoglobulins

| IgG Subtype | Core Hinge Sequence |
|---|---|
| IgG1 | EPKSCDKTHTCPPCP (SEQ ID NO: 104) |
| IgG2 | ERKCCVECPPCP (SEQ ID NO: 105) |
| IgG3 | ELKTPLGDTTHTCPRCP(EPKSCDTPPPCPRCP)$_3$ (SEQ ID NO: 106) |
| IgG4 | ESKYGPPCPSCP (SEQ ID NO: 107) |

In certain embodiments, the linker region comprises an IgG1 hinge, or a variant thereof. In certain embodiments, the linker region comprises the core hinge structure of IgG1 or a variant thereof. In certain embodiments, the linker region comprises an IgG2 hinge, or a variant thereof. In certain embodiments, the linker region comprises the core hinge structure of IgG2 or a variant thereof.

Transmembrane Domain

In certain embodiments, the transmembrane domain is fused in frame between the extracellular target-binding domain and the cytoplasmic domain. The transmembrane domain may be derived from the protein contributing to the extracellular target-binding domain, the protein contributing the signaling or co-signaling domain, or by a totally different protein. In some instances, the transmembrane domain can be selected or modified by amino acid substitution, deletions, or insertions to minimize interactions with other members of the CAR complex. In some instances, the transmembrane domain can be selected or modified by amino acid substitution, deletions, or insertions to avoid-binding of proteins naturally associated with the transmembrane domain. In certain embodiments, the transmembrane domain includes additional amino acids to allow for flexibility and/or optimal distance between the domains connected to the transmembrane domain.

The transmembrane domain may be derived either from a natural or from a synthetic source. Where the source is natural, the domain may be derived from any membrane-bound or transmembrane protein. Non-limiting examples of transmembrane domains of particular use in this invention may be derived from (i.e. comprise at least the transmembrane region(s) of) the α, β or ζ chain of the T-cell receptor, CD28, CD3 epsilon, CD45, CD4, CD5, CD8, CD9, CD16, CD22, CD33, CD37, CD40, CD64, CD80, CD86, CD134, CD137, CD154. Alternatively, the transmembrane domain may be synthetic, in which case it will comprise predominantly hydrophobic residues such as leucine and valine. For example, a triplet of phenylalanine, tryptophan and/or valine can be found at each end of a synthetic transmembrane domain.

In certain embodiments, it will be desirable to utilize the transmembrane domain of the ζ, η or FcεR1γ chains which contain a cysteine residue capable of disulfide bonding, so that the resulting chimeric protein will be able to form disulfide linked dimers with itself, or with unmodified versions of the ζ, η or FcεR1γ chains or related proteins. In some instances, the transmembrane domain will be selected or modified by amino acid substitution to avoid-binding of such domains to the transmembrane domains of the same or different surface membrane proteins to minimize interactions with other members of the receptor complex. In other cases, it will be desirable to employ the transmembrane domain of ζ, η or FcεR1γ and -β, MB1 (Igα.), B29 or CD3-γ, ζ, or η, in order to retain physical association with other members of the receptor complex.

In certain embodiments, the transmembrane domain in the CAR of the invention is derived from the CD28 transmembrane domain. In certain embodiments, the transmembrane domain in the CAR of the invention is derived from the CD8a transmembrane domain.

Cytoplasmic Domain

In certain embodiments, the cytoplasmic domain comprises one or more of a lymphocyte activation domain, a MyD88 polypeptide or functional fragment thereof, and a CD40 cytoplasmic polypeptide region or a functional fragment thereof.

In certain embodiments, the lymphocyte activation domain and co-stimulatory domains can be in any order. The cytoplasmic domain, which comprises the lymphocyte activation domain of the CAR of the invention, is responsible for activation of at least one of the normal effector functions of the lymphocyte in which the CAR has been placed in. The term "effector function" refers to a specialized function of a cell. Effector function of a T cell, for example, may be cytolytic activity or helper activity including the secretion of cytokines. Thus, the term "lymphocyte activation domain" refers to the portion of a protein which transduces the effector function signal and directs the cell to perform a specialized function. While usually the entire lymphocyte activation domain is present, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the lymphocyte activation domain sufficient to transduce the effector function signal.

Non-limiting examples of lymphocyte activation domains which can be used in the CARs of the invention include, e.g., lymphocyte activation domains derived from DAP10, DAP12, Fc epsilon receptor I gamma chain (FCER1G), FcR β, CD3δ, CD3ε, CD3γ, CD3ζ, CD5, CD22, CD226, CD66d, CD79A, and CD79B.

In certain embodiments, the lymphocyte activation domain in the CAR of the invention is designed to comprise the signaling domain of CD3ζ. It is known that signals generated through the TCR alone are insufficient for full activation of lymphocytes and that a secondary or co-stimulatory signal is also required. Thus, lymphocyte activation can be said to be mediated by two distinct classes of cytoplasmic signaling sequence: those that initiate antigen-dependent primary activation through the TCR (primary lymphocyte activation sequences (as discussed above)) and those that act in an antigen-independent manner to provide a secondary or co-stimulatory signal (secondary cytoplasmic signaling sequences).

Cluster of differentiation 40 (CD40) is a co-stimulatory protein found on antigen presenting cells. The protein receptor encoded by the CD40 gene is a member of the TNF-receptor superfamily and is found to be essential in mediating a broad variety of immune and inflammatory responses including T cell-dependent immunoglobulin class switching, memory B cell development, and germinal center formation. See e.g., Grewal, IS; Flavell, RA (1998). *Annual Review of Immunology*. 16: 111-35; An et al., JBC 2011 286(13): 11226-11235; and Chen et. al., *Cellular & Molecular Immunology*, 2006 3(3):163-169, each of which are incorporated by reference herein in their entirety for all purposes. A CD40 polypeptide or functional fragment thereof is a polypeptide product of CD40. An example of CD40 polypeptide, includes but is not limited to, the human CD40 (e.g., NCBI Gene ID 958; X60592.1). A functional fragment of CD40, refers to a CD40 nucleic acid fragment, variant, or analog, refers to a nucleic acid that codes for a CD40 polypeptide, or a CD40 polypeptide, that stimulates an immune response. A non-limiting example of a CD40 functional fragment includes a CD40 polypeptide that is lacking the extracellular domain, but is capable of amplifying the lymphocyte immune response. In certain embodiments, the CD40 is a functional fragment (i.e., the protein is not full length and may lack, for example, a domain, but still functions as a co-stimulatory domain). For example, a CD40 functional fragment may lack its transmembrane and/or extracellular domain but is capable of amplifying the lymphocyte immune response. In certain embodiments, the CD40 functional fragment includes the transmembrane domain. In certain embodiments, the CD40 functional fragment includes the transmembrane domain and a portion of the extracellular domain, wherein the extracellular domain does not interact with natural or synthetic ligands of CD40. In certain embodiments, the CD40 functional fragment interacts with Jak3, TRAF2, TRAF3, and/or TRAF6. By a nucleotide sequence coding for a CD40 functional fragment is meant the nucleotide sequence coding for the CD40 functional fragment peptide, the term may also refer to the nucleic acid sequence including the portion coding for any amino acids added as an artifact of cloning, including any amino acids coded for by the linkers. It is understood that where a method or construct refers to a CD40 functional fragment polypeptide, the method may also be used, or the construct designed to refer to another CD40 polypeptide, such as a full length CD40 polypeptide. Where a method or construct refers to a full length CD40 polypeptide, the method may also be used, or the construct designed to refer to a CD40 functional fragment polypeptide.

In certain embodiments, the CARs of the invention can include additional co-stimulatory domains. Non-limiting co-stimulatory domains include, but are not limited to, 4-1BB (CD137), CD28, ICOS, CD134 (OX-40), BTLA, CD27, CD30, GITR, CD226, and HVEM.

Accessory Genes

In addition to the CAR construct, the CAR may further comprise an accessory gene that encodes an accessory peptide. Examples of accessory genes can include a transduced host cell selection marker, an in vivo tracking marker, a cytokine, a suicide gene, or some other functional gene. For example, the constructs depicted in FIG. 1A comprise the EphA2-CAR, a 2A sequence, and the accessory gene for truncated CD19 (tCD19). In certain embodiments, the tCD19 can be used as a tag. For example, expression of tCD19 can help determine transduction efficiency. In certain embodiments, the CAR comprises the tCD19 construct. In certain embodiments, the CAR does not include the tCD19 construct. In certain embodiments, the tCD19 can be replaced with a functional accessory gene to enhance the effector function of the CAR (e.g., EphA2-CAR) containing host cells. In certain embodiments, the functional accessory gene can increase the safety of the CAR. In certain embodiments, the CAR comprises at least one accessory gene. In certain embodiments, the CAR comprises one accessory gene. In other embodiments, the CAR comprises two accessory genes. In yet another embodiment, the CAR comprises three accessory genes.

Non-limiting examples of classes of accessory genes that can be used to increase the effector function of CAR containing host cells, include i) secretable cytokines (e.g., but not limited to, IL-7, IL-12, IL-15, IL-18), ii) membrane bound cytokines (e.g., but not limited to, IL-15), iii) chimeric cytokine receptors (e.g., but not limited to, IL-2/IL-7, IL-4/IL-7), iv) constitutive active cytokine receptors (e.g., but not limited to, C7R), v) dominant negative receptors (DNR; e.g., but not limited to TGFRII DNR), vi) ligands of costimulatory molecules (e.g., but not limited to, CD80, 4-1BBL), vii) antibodies, including fragments thereof and bispecific antibodies (e.g., but not limited to, bispecific T-cell engagers (BiTEs)), or vii) a second CAR.

In certain embodiments, the functional accessory gene can be a suicide gene. A suicide gene is a recombinant gene that will cause the host cell that the gene is expressed in to undergo programmed cell death or antibody mediated clearance at a desired time. Suicide genes can function to increase the safety of the CAR. In another embodiment, the accessory gene is an inducible suicide gene. Non-limiting examples of suicide genes include i) molecules that are expressed on the cell surface and can be targeted with a clinical grade monoclonal antibody including CD20, EGFR or a fragment thereof, HER2 or a fragment thereof, and ii) inducible suicide genes (e.g., but not limited to inducible caspase 9 (see Straathof et al. (2005) Blood. 105(11): 4247-4254; US Publ. No. 2011/0286980, each of which are incorporated herein by reference in their entirety for all purposes)).

CD19 could also be replaced with two accessory genes separated by a separation sequence (e.g., a 2A sequence) using a combination of the classes of molecules listed above (e.g., CAR-2A-CD20-2A-IL15). In addition, the use of two separation sequences (e.g., 2A sequences) would allow the expression of TCR (e.g., CAR-2A-TCRα-2A-TCRβ). In the constructs with a CAR and two or three accessory genes, the order of the CAR and the second or third transgene could be switched.

A "separation sequence" refers to a peptide sequence that causes a ribosome to release the growing polypeptide chain that it is being synthesizes without dissociation from the mRNA. In this respect, the ribosome continues translating and therefore produces a second polypeptide. Non-limiting examples of separation sequences includes T2A (EGRGSLLTCGDVEENPGP (SEQ ID NO: 169) or GSGEGRGSLLTCGDVEENPGP (SEQ ID NO: 170)) the foot and mouth disease virus (FMDV) 2A sequence (GSGSRVTELLYRMKRAETYCPRPLLAIHPTEAR-HKQKIVAPVKQLLNFDLLKLAGD VESNPGP (SEQ ID NO: 171)), Sponge (Amphimedon queenslandica) 2A sequence (LLCFLLLLLSGDVELNPGP (SEQ ID NO: 172); or HHFMFLLLLLAGDIELNPGP (SEQ ID NO: 173)); acorn worm (Saccoglossus kowalevskii) (WFLVLLSFILSGDIEVNPGP (SEQ ID NO: 174)) 2A sequence; amphioxus (Branchiostoma floridae) (KN-CAMYMLLLLSGDVETNPGP (SEQ ID NO: 175); or MVISQLMLKLAGDVEENPGP (SEQ ID NO: 176)) 2A sequence porcine teschovirus-1 (GSGATNFSLLKQAGD-VEENPGP (SEQ ID NO: 177)) 2A sequence; and equine rhinitis A virus (GSGQCTNYALLKLAGDVESNPGP (SEQ ID NO: 178)) 2A sequence. In some embodiments, the separation sequence is a naturally occurring or synthetic sequence. In certain embodiments, the separation sequence includes the 2A consensus sequence D-X-E-X-NPGP, in which X is any amino acid residue.

Nucleic Acid Molecules

In one aspect is provided a nucleic acid molecule comprising a nucleotide sequence encoding any heterodimeric inactivatable chimeric antigen receptor (CAR) described herein.

In a specific embodiment, the nucleic acid molecule may comprise, or consist of the sequence at least 81%, 82%, 83%, 84%, 85%, 86%, 87%, 88%, 89%, 90%, 91%, 92%, 93%, 94%, 95%, 96%, 97%, 98%, 99% or 100% identical to
atggccttaccagtgaccgccttgctcctgccgctggccttgctgctc-
cacgccgccaggccggtgcagctgcagcagtcaggacct gaactggt-
gaagcctgggacttcagtgaggatatcctgcaagacttctggatacacattcact-
gaatataccatacactgggtgaagca
gagccatggaaagagccttgagtggattggaaacat-
caatcctaacaatggtggtaccacctacaatcagaagttcgaggacaaggc
cacattgactgtagacaagtcctccagtacagcctacatggagctccgcagcctaa-
catctgaggattctgcagtctattattgtgcagct ggttggaactttgac-
tactggggccaagggaccacggtcaccgtctcctcaggtggaggtg-
gatcaggtggaggtggatctggtgga
ggtggatctgacattgtgatgacccagtctcacaaattcatgtccacatcagtagga-
gacagggtcagcatcatctgtaaggccagtca agatgtgggtactgctgta-
gactggtatcaacagaaaccaggacaatctcctaaactactgatttattgggcatc-
cactcggcacactgg
agtccctgatcgcttcacaggcagtggatctgggacagacttcactctcaccat-
tactaatgttcagtctgaagacttggcagattattct gtcagcaatataacagc-
tatcccctcacgttcggtgctgggaccatgctggacct-
gaaacgggctagcacaacaacccctgcccccca
gacctcctaccccagcccctacaattgccagccagcctctgagcct-
gaggcccgaggcttgtagacctgctgctggcggagccgtgc
acaccagaggactggatttcgcctgcgacttctgggtgctggtggtcgtgggcg-
gagtgctggcctgttacagcctgctcgtgaccgt ggccttcat-
catcttttgggtgcggagcaagagaagcagactgctgcacagcgactacatgaa-
catgacccccagacggcctggccc
caccagaaagcactaccagccttacgcccctcccagagacttcgccgcctaca-
gatctcatatgggaggcggaggatctggcggag gtggaagtggcggaggcg-
gatctcaaagatgggaactcgccctgggcagattcctggaatacct-
gagctgggtgtccacactgagc
gaacaggtgcaagaggaactgctgagcagccaagtgacccaagagct-
gagagccctgatggacgagacaatgaaggaactgaag gccta-
caagagcgagctggaagaacagctgacccctgtggccgag-
gaaaccagagccagactgagcaaagaactgcaggccgct
caggccagactgggagccgatatggaagatgttcggggcagactggtgcagta-
cagaggcgaagttcaggccatgctgggccagt ctaccgaggaact-
gagagtgcggctggcctctcatctgattgccctgcagctgagact-
gatcggcgacgcattcgacctgcagaaaa
gactggccgtgtaccaggctggcgctgctgaacg-
gaagcggcgcagcggcagcgggcgcagcggcagcggcgagggcagagg
aagtcttctaacatgcggtgacgtggaggagaatcccggccct (SEQ ID NO: 94), wherein the anti-PSMA domain can be replaced with any extracellular target-binding region of interest including those as disclosed herein.

In some embodiments, the nucleotide sequence encoding the first polypeptide chain of the CAR is at least 81%, 82%, 83%, 84%, 85%, 86%, 87%, 88%, 89%, 90%, 91%, 92%, 93%, 94%, 95%, 96%, 97%, 98%, 99% or 100% identical to
tctagaaatggccttaccagtgaccgccttgctcctgccgctggccttgctgctc-
cacgccgccaggccggtgcagctgcagcagtca ggacctgaactggt-
gaagcctgggacttcagtgaggatatcctgcaagacttctggatacacattcact-
gaatataccatacactgggtg
aagcagagccatggaaagagccttgagtggattggaaacat-
caatcctaacaatggtggtaccacctacaatcagaagttcgaggac aaggcca-
cattgactgtagacaagtcctccagtacagcctacatggagctccgcagcctaa-
catctgaggattctgcagtctattattgt
gcagctggttggaactttgactactggggccaagggaccacggt-
caccgtctcctcaggtggaggtggatcaggtggaggtggatct ggtggaggtg-
gatctgacattgtgatgacccagtctcacaaattcatgtccacatcagtagga-
gacagggtcagcatcatctgtaaggc
cagtcaagatgtgggtactgctgtagactggtat-
caacagaaaccaggacaatctcctaaactactgatttattgggcatccactcggca
cactggagtccctgatcgcttcacaggcagtggatctgggacagacttcactct-
caccattactaatgttcagtctgaagacttggcagat tat-
ttctgtcagcaatataacagctatcccctcacgttcggtgctgggac-
catgctggacctgaaacgggctagcacaacaacccctgc
ccccagacctcctaccccagcccctacaattgccagccagcctctgagcct-
gaggcccgaggcttgtagacctgctgctggcggagc
cgtgcacaccagaggactggat-
ttcgcctgcgacttctgggtgctggtggtcgtgggcggagtgctggcctgtta-
cagcctgctcgtg accgtggccttcatcatcttttgggtgcg-
gagcaagagaagcagactgctgcacagcgactacatgaacatgacccccagac
ggcct ggccccaccagaaagcactaccagccttacgcccctcccaga-
gacttcgccgcctacagatctcatatgggaggcggaggatctgg cggaggtg-
gaagtggcggaggcggatctcaaagatgggaactcgccctgggcagattcctg-
gaatacctgagctgggtgtccacac
tgagcgaacaggtgcaagaggaactgctgagcagccaagtgacccaagagct-
gagagccctgatggacgagacaatgaaggaac tgaaggccta-
caagagcgagctggaagaacagctgacccctgtggccgag-
gaaaccagagccagactgagcaaagaactgcagg
ccgctcaggccagactgggagccgatatggaagatgttcggggca-
gactggtgcagtacagaggcgaagttcaggccatgctggg ccagtctaccgag-
gaactgagagtgcggctggcctctcatctgattgccctgcagctgagact-
gatcggcgacgcattcgacctgcag
aaaagactggccgtgtaccaggctggcgctgctgaacg-
gaagcggcgcagcggcagcgggcgcagcggcagcggcgagggca gag-
gaagtcttctaacatgcggtgacgtggaggagaatcccggccct (SEQ ID NO: 95), wherein the anti-PSMA domain can be replaced with any extracellular target-binding region of interest including those as disclosed herein.

In some embodiments, the nucleotide sequence encoding the first polypeptide chain of the CAR is at least 81%, 82%, 83%, 84%, 85%, 86%, 87%, 88%, 89%, 90%, 91%, 92%, 93%, 94%, 95%, 96%, 97%, 98%, 99% or 100% identical to tctagaaatggccttaccagtgaccgccttgctcctgccgctggccttgctgctc- cacgccgccaggccggtgcagctgcagcagtca ggacctgaactggt- gaagcctgggacttcagtgaggatatcctgcaagacttctggatacacattcact- gaatataccatacactgggtg aagcagagccatggaaagagccttgagtggattggaaacat- caatcctaacaatggtggtaccacctacaatcagaagttcgaggac aaggcca- cattgactgtagacaagtcctccagtacagcctacatggagctccgcagcctaa- catctgaggattctgcagtctattattgt gcagctggttggaactttgactactggggccaagggaccacggt- caccgtctcctcaggtggaggtggatcaggtggaggtggatct ggtggaggtg- gatctgacattgtgatgacccagtctcacaaattcatgtccacatcagtagga- gacagggtcagcatcatctgtaaggc cagtcaagatgtgggtactgctgtagactggtat- caacagaaaccaggacaatctcctaaactactgatttattgggcatccactcggca cactggagtccctgatcgcttcacaggcagtggatctgggacagacttcactct- caccattactaatgttcagtctgaagacttggcagat tat- ttctgtcagcaatataacagctatcccctcacgttcggtgctgggac- catgctggacctgaaacgggctagcacaacaacccctgc ccccagacctcctaccccagcccctacaattgccagccagcctctgagcct- gaggcccgaggcttgtagacctgctgctggcggagc cgtgcacaccagaggactggat- ttcgcctgcgacttctgggtgctggtggtcgtgggcggagtgctggcctgtta- cagcctgctcgtg accgtggccttcatcatcttttgggtgcg- gagcaagagaagcagactgctgcacagcgactacatgaacatgacccccagac ggcct ggccccaccagaaagcactaccagccttacgcccctcccaga- gacttcgccgcctacagatctcatatgggaggcggaggatctgg cggaggtg- gaagtggcggaggcggatctcaaagatgggaactcgccctgggcagattcctg- gaatacctgagctgggtgtccacac tgagcgaacaggtgcaagaggaactgctgagcagccaagtgacccaagagct- gagagccctgatggacgagacaatgaaggaac tgaaggccta- caagagcgagctggaagaacagctgacccctgtggccgag- gaaaccagagccagactgagcaaagaactgcagg ccgctcaggccagactgggagccgatatggaagatgttcggggca- gactggtgcagtacagaggcgaagttcaggccatgctggg ccagtctaccgag- gaactgagagtgcggctggcctctcatctgattgccctgcagctgagact- gatcggcgacgcattcgacctgcag aaaagactggccgtgtaccaggctggcgctgctgaacg- gaagcggcgcagcggcagcgggcgcagcggcagcggcgagggca gag- gaagtcttctaacatgcggtgacgtggaggagaatcccggccct (SEQ ID NO: 96), wherein the anti-PSMA domain can be replaced with any extracellular target-binding region of interest including those as disclosed herein.

In some embodiments, the nucleotide sequence encoding the first polypeptide chain of the CAR is at least 81%, 82%, 83%, 84%, 85%, 86%, 87%, 88%, 89%, 90%, 91%, 92%, 93%, 94%, 95%, 96%, 97%, 98%, 99% or 100% identical to tctagaaatggccttaccagtgaccgccttgctcctgccgctggccttgctgctc- cacgccgccaggccggtgcagctgcagcagtca ggacctgaactggt- gaagcctgggacttcagtgaggatatcctgcaagacttctggatacacattcact- gaatataccatacactgggtg aagcagagccatggaaagagccttgagtggattggaaacat- caatcctaacaatggtggtaccacctacaatcagaagttcgaggac aaggcca- cattgactgtagacaagtcctccagtacagcctacatggagctccgcagcctaa- catctgaggattctgcagtctattattgt gcagctggttggaactttgactactggggccaagggaccacggt- caccgtctcctcaggtggaggtggatcaggtggaggtggatct ggtggaggtg- gatctgacattgtgatgacccagtctcacaaattcatgtccacatcagtagga- gacagggtcagcatcatctgtaaggc cagtcaagatgtgggtactgctgtagactggtat- caacagaaaccaggacaatctcctaaactactgatttattgggcatccactcggca cactggagtccctgatcgcttcacaggcagtggatctgggacagacttcactct- caccattactaatgttcagtctgaagacttggcagat tat- ttctgtcagcaatataacagctatcccctcacgttcggtgctgggac- catgctggacctgaaacgggctagcacaacaacccctgc ccccagacctcctaccccagcccctacaattgccagccagcctctgagcct- gaggcccgaggcttgtagacctgctgctggcggagc cgtgcacaccagaggactggat- ttcgcctgcgacttctgggtgctggtggtcgtgggcggagtgctggcctgtta- cagcctgctcgtg accgtggccttcatcatcttttgggtgcg- gagcaagagaagcagactgctgcacagcgactacatgaacatgacccccagac ggcct ggccccaccagaaagcactaccagccttacgcccctcccaga- gacttcgccgcctacagatctcatatgggaggcggaggatctgg cggaggtg- gaagtggcggaggcggatctcaaagatgggaactcgccctgggcagattcctg- gaatacctgagctgggtgtccacac tgagcgaacaggtgcaagaggaactgctgagcagccaagtgacccaagagct- gagagccctgatggacgagacaatgaaggaac tgaaggccta- caagagcgagctggaagaacagctgacccctgtggccgag- gaaaccagagccagactgagcaaagaactgcagg ccgctcaggccagactgggagccgatatggaagatgttcggggca- gactggtgcagtacagaggcgaagttcaggccatgctggg ccagtctaccgag- gaactgagagtgcggctggcctctcatctgattgccctgcagctgagact- gatcggcgacgcattcgacctgcag aaaagactggccgtgtaccaggctggcgctgctgaacg- gaagcggcgcagcggcagcgggcgcagcggcagcggcgagggca gag- gaagtcttctaacatgcggtgacgtggaggagaatcccggccct (SEQ ID NO: 97), wherein the anti-PSMA domain can be replaced with any extracellular target-binding region of interest including those as disclosed herein.

In some embodiments, the nucleotide sequence encoding the first polypeptide chain of the CAR is at least 81%, 82%, 83%, 84%, 85%, 86%, 87%, 88%, 89%, 90%, 91%, 92%, 93%, 94%, 95%, 96%, 97%, 98%, 99% or 100% identical to tctagaaatggccttaccagtgaccgccttgctcctgccgctggccttgctgctc- cacgccgccaggccggtgcagctgcagcagtca ggacctgaactggt- gaagcctgggacttcagtgaggatatcctgcaagacttctggatacacattcact- gaatataccatacactgggtg aagcagagccatggaaagagccttgagtggattggaaacat- caatcctaacaatggtggtaccacctacaatcagaagttcgaggac aaggcca- cattgactgtagacaagtcctccagtacagcctacatggagctccgcagcctaa- catctgaggattctgcagtctattattgt gcagctggttggaactttgactactggggccaagggaccacggt- caccgtctcctcaggtggaggtggatcaggtggaggtggatct ggtggaggtg- gatctgacattgtgatgacccagtctcacaaattcatgtccacatcagtagga- gacagggtcagcatcatctgtaaggc cagtcaagatgtgggtactgctgtagactggtat- caacagaaaccaggacaatctcctaaactactgatttattgggcatccactcggca cactggagtccctgatcgcttcacaggcagtggatctgggacagacttcactct- caccattactaatgttcagtctgaagacttggcagat tat- ttctgtcagcaatataacagctatcccctcacgttcggtgctgggac- catgctggacctgaaacgggctagcacaacaacccctgc ccccagacctcctaccccagcccctacaattgccagccagcctctgagcct- gaggcccgaggcttgtagacctgctgctggcggagc cgtgcacaccagaggactggat- ttcgcctgcgacttctgggtgctggtggtcgtgggcggagtgctggcctgtta- cagcctgctcgtg accgtggccttcatcatcttttgggtgcg- gagcaagagaagcagactgctgcacagcgactacatgaacatgacccccagacg gcct ggccccaccagaaagcactaccagccttacgcccctcccaga- gacttcgccgcctacagatctcatatgggaggcggaggatctgg cggaggtg- gaagtggcggaggcggatctccaaagatgggaactcgccctgggcagattcctg- gaatacctgagctgggtgtccaca ctgagcgaacaggtgcaagaggaactgctgagcagccaagtgacccaagagct- gagagccctgatggacgagacaatgaaggaa ctgaaggccta- caagagcgagctggaagaacagctgacccctgtggccgag- gaaaccagagccagactgagcaaagaactgcag gccgctcaggccagactgggagccgatatggaagatgttcggggca- gactggtgcagtacagaggcgaagttcaggccatgctgg gccagtctaccgag- gaactgagagtgcggctggcctctcatctgattgccctgcaggcaagact- gatcggcgacgcattcgacctgc agaaaagactggccgtgtaccaggctggcgctgctgaacg- gaagcggcgcagcggcagcgggcgcagcggcagcggcgaggg cagaggaagtcttctaacatgcggtgacgtggaggagaatcccggccct (SEQ ID NO: 98), wherein the anti-PSMA domain can be replaced with any extracellular target-binding region of interest including those as disclosed herein.

In some embodiments, the nucleotide sequence encoding the first polypeptide chain of the CAR is at least 81%, 82%, 83%, 84%, 85%, 86%, 87%, 88%, 89%, 90%, 91%, 92%, 93%, 94%, 95%, 96%, 97%, 98%, 99% or 100% identical to
tctagaaatggccttaccagtgaccgccttgctcctgccgctggccttgctgctc-
cacgccgccaggccggtgcagctgcagcagtca ggacctgaactggt-
gaagcctgggacttcagtgaggatatcctgcaagacttctggatacacattcact-
gaatataccatacactgggtg
aagcagagccatggaaagagccttgagtggattggaaacat-
caatcctaacaatggtggtaccacctacaatcagaagttcgaggac aaggcca-
cattgactgtagacaagtcctccagtacagcctacatggagctccgcagcctaa-
catctgaggattctgcagtctattattgt
gcagctggttggaactttgactactggggccaagggaccacggt-
caccgtctcctcaggtggaggtggatcaggtggaggtggatct ggtggaggtg-
gatctgacattgtgatgacccagtctcacaaattcatgtccacatcagtagga-
gacagggtcagcatcatctgtaaggc
cagtcaagatgtgggtactgctgtagactggtat-
caacagaaaccaggacaatctcctaaactactgatttattgggcatccactcggca
cactggagtccctgatcgcttcacaggcagtggatctgggacagacttcactct-
caccattactaatgttcagtctgaagacttggcagat tat-
ttctgtcagcaatataacagctatcccctcacgttcggtgctgggac-
catgctggacctgaaacgggctagcacaacaacccctgc
cccccagacctcctaccccagcccctacaattgccagccagcctctgagcct-
gaggcccgaggcttgtagacctgctgctggcggagc
cgtgcacaccagaggactggat-
ttcgcctgcgacttctgggtgctggtggtcgtgggcggagtgctggcctgtta-
cagcctgctcgtg accgtggccttcatcatcttttgggtgcg-
gagcaagagaagcagactgctgcacagcgactacatgaacatgacccccagacg
gcct ggccccaccagaaagcactaccagccttacgcccctcccaga-
gacttcgccgcctacagatctcatatgggaggcggaggatctgg cggaggtg-
gaagtggcggaggcggatctcaaagatgggaactcgccctgggcagattcctg-
gaatacctgagctgggtgtccacac
tgagcgaacaggtgcaagaggaactgctgagcagccaagtgacccaagagct-
gagagccctgatggacgagacaatgaaggaac tgaaggccta-
caagagcgagctggaagaacagctgacccctgtggccgag-
gaaaccagagccagactgagcaaagaactgcagg
ccgctcaggccagactgggagccgatatggaagatgttcggggca-
gactggtgcagtacagaggcgaagttcaggccatgctggg ccagtctaccgag-
gaactgagagtgcggctggcctctcatctgattgccctgcagctgagact-
gatcggcgcagcattcgacctgcag
aaaagactggccgtgtaccaggctggcgctctgaacg-
gaagcggcgcagcggcagcgggcgcagcggcagcggcgagggcag
aggaagtcttctaacatgcggtgacgtggaggagaatcccggccct (SEQ ID NO: 99), wherein the anti-PSMA domain can be replaced with any extracellular target-binding region of interest including those as disclosed herein.

The nucleic acid molecule may comprise a nucleotide sequence encoding the second polypeptide chain of any heterodimeric inactivatable chimeric antigen receptor (CAR) described herein.

In some embodiments, the nucleotide sequence encoding the second polypeptide chain of the CAR is at least 81%, 82%, 83%, 84%, 85%, 86%, 87%, 88%, 89%, 90%, 91%, 92%, 93%, 94%, 95%, 96%, 97%, 98%, 99% or 100% identical to

```
                                           (SEQ ID NO: 100)
ggatccatggccttaccagtgaccgccttgctcctgccgctggccttgct

gctccacgccgccaggccggaacagaaactcatcagtgaggaagatttgc

agacgactccaggagagagatcatcactccctgccttttaccctggcact
```

-continued

```
tcaggctcttgttccggatgtgggtccctctctctgccgacaacaacccc

tgcccccagacctcctaccccagcccctacaattgccagccagcctctga

gcctgaggcccgaggcttgtagacctgctgctggcggagccgtgcacacc

agaggactggatttcgcctgcgaccctaggttctgggtgctggtggtcgt

gggcggagtgctggcctgttacagcctgctcgtgaccgtggccttcatca

tcttttgggtgcggagcaagagaagcagactgctgcacagcgactacatg

aacatgacccccagacggcctggccccaccagaaagcactaccagcctta

cgcccctcccagagacttcgccgcctacagatctcccgggggaggcggag

gatctggcggaggtggaagtggcggaggcggatctatgagccagagcaac

agagaactggtggtggacttcctgagctacaagctgagccagaagggcta

cagctggtcccagttcagcgacgtggaagagaacagaacagaggcccctg

agggcacagagtctgaggctgtgaaacaggccctgagagaagccggcgac

gagttcgagctgagatacagaagggccttcagcgacctgaccagccagct

gcacatcacacctggcacagcctaccagagcttcgagcaggtcgtgaacg

agctgttcagagatggcgtgaactggggcagaatcgtggccttcttcagc

tttggcggagccctgtgtgtggaaagcgtggacaaagaaatgcaggtcct

ggtgtccagaatcgccgcctggatggccacctacctgaacgatcatctgg

aaccctggattcaagagaacggcggctgggacaccttcgtggaactgtac

ggaaacaacgccgctgccgagagcagaaagggccaagaacgagaagatgg

cggcggtggttctggtggcggcggtagtggtggcggtggatcaatgcata

gagtgaagttcagcaggagcgcagacgcccccgcgtaccagcagggccag

aaccagctctataacgagctcaatctaggacgaagagaggagtacgatgt

tttggacaagagacgtggccgggaccctgagatgggggaaagccgagaa

ggaagaaccctcaggaaggcctgtacaatgaactgcagaaagataagatg

gcggaggcctacagtgagattgggatgaaaggcgagcgccggaggggcaa

ggggcacgatggcctttaccagggtctcagtacagccaccaaggacacct

acgacgcccttcacatgcaggccctgccccctcgctaa.
```

In some embodiments, the nucleotide sequence encoding the second polypeptide chain of the CAR is at least 81%, 82%, 83%, 84%, 85%, 86%, 87%, 88%, 89%, 90%, 91%, 92%, 93%, 94%, 95%, 96%, 97%, 98%, 99% or 100% identical to

```
                                           (SEQ ID NO: 101)
ggatccatggccttaccagtgaccgccttgctcctgccgctggccttgct

gctccacgccgccaggccggaacagaaactcatcagtgaggaagatttgc

agacgactccaggagagagatcatcactccctgccttttaccctggcact

tcaggctcttgttccggatgtgggtccctctctctgccgacaacaacccc

tgcccccagacctcctaccccagcccctacaattgccagccagcctctga

gcctgaggcccgaggcttgtagacctgctgctggcggagccgtgcacacc

agaggactggatttcgcctgcgacctaggttctgggtgctggtggtcgtg

ggcggagtgctggcctgttacagcctgctcgtgaccgtggccttcatcat
```

-continued

```
cttttgggtgcggagcaagagaagcagactgctgcacagcgactacatga
acatgacccccagacggcctggccccaccagaaagcactaccagccttac
gcccctcccagagacttcgccgcctacagatctcccgggggaggcggagg
atctggcggaggtggaagtggcggaggcggatctatgagccagagcaaca
gagaactggtggtggacttcctgagctacaagctgagccagaagggctac
agctggtcccagttcagcgacgtggaagagaacagaacagaggcccctga
gggcacagagtctgaggctgtgaaacaggccctgagagaagccggcgacg
agttcgagctgagatacagaagggccttcagcgacctgaccagccagctg
cacatcacacctggcacagcctaccagagcttcgagcaggtcgtgaacga
gctgttcagagatggcgtgaactggggcagaatcgtggccttcttcagct
ttggcggagccctgtgtgtggaaagcgtggacaaagaaatgcaggtcctg
gtgtccagaatcgccgcctggatggccacctacctgaacgatcatctgga
accctggattcaagagaacggcggctgggacaccttcgtggaactgtacg
gaaacaacgccgctgccgagagcagaaagggccaagaacgagaagatgga
ggcggaggatctggcggaggtggaagtggcggaggcggatctatgcatag
agtgaagttcagcaggagcgcagacgcccccgcgtaccagcagggccaga
accagctctataacgagctcaatctaggacgaagagaggagtacgatgtt
ttggacaagagacgtggccgggaccctgagatggggggaaagccgagaag
gaagaaccctcaggaaggcctgtacaatgaactgcagaaagataagatgg
cggaggcctacagtgagattgggatgaaaggcgagcgccggaggggcaag
gggcacgatggcctttaccagggtctcagtacagccaccaaggacaccta
cgacgcccttcacatgcaggccctgccccctcgctaa.
```

In some embodiments, the nucleotide sequence encoding the second polypeptide chain of the CAR is at least 81%, 82%, 83%, 84%, 85%, 86%, 87%, 88%, 89%, 90%, 91%, 92%, 93%, 94%, 95%, 96%, 97%, 98%, 99% or 100% identical to

```
                                          (SEQ ID NO: 102)
ggatccatggccttaccagtgaccgccttgctcctgccgctggccttgct
gctccacgccgccaggccggaacagaaactcatcagtgaggaagatttgc
agacgactccaggagagagatcatcactccctgccttttaccctggcact
tcaggctcttgttccggatgtgggtccctctctctgccgacaacaacccc
tgcccccagacctcctaccccagcccctacaattgccagccagcctctga
gcctgaggcccgaggcttgtagacctgctgctggcggagccgtgcacacc
agaggactggatttcgcctgcgacctaggttctgggtgctggtggtcgtg
ggcggagtgctggcctgttacagcctgctcgtgaccgtggccttcatcat
cttttgggtgcggagcaagagaagcagactgctgcacagcgactacatga
acatgacccccagacggcctggccccaccagaaagcactaccagccttac
gcccctcccagagacttcgccgcctacagatctcccgggggaggcggagg
atctggcggaggtggaagtggcggaggcggatctatgagccagagcaaca
gagaactggtggtggacttcctgagctacaagctgagccagaagggctac
agctggtcccagttcagcgacgtggaagagaacagaacagaggcccctga
gggcacagagtctgaggctgtgaaacaggccctgagagaagccggcgacg
acttcgagctgagatacagaagggccttcagcgacctgaccagccagctg
cacatcacacctggcacagcctaccagagcttcgagcaggtcgtgaacga
gctgttcagagatggcgtgaactggggcagaatcgtggccttcttcagct
ttggcggagccctgtgtgtggaaagcgtggacaaagaaatgcaggtcctg
gtgtccagaatcgccgcctggatggccacctacctgaacgatcatctgga
accctggattcaagagaacggcggctgggacaccttcgtggaactgtacg
gaaacaacgccgctgccgagagcagaaagggccaagaacgagaagatgaa
gatggaggcggaggatctggcggaggtggaagtggcggaggcggatctat
gcatagagtgaagttcagcaggagcgcagacgcccccgcgtaccagcagg
gccagaaccagctctataacgagctcaatctaggacgaagagaggagtac
gatgttttggacaagagacgtggccgggaccctgagatggggggaaagcc
gagaaggaagaaccctcaggaaggcctgtacaatgaactgcagaaagata
agatggcggaggcctacagtgagattgggatgaaaggcgagcgccggagg
ggcaaggggcacgatggcctttaccagggtctcagtacagccaccaagga
cacctacgacgcccttcacatgcaggccctgccccctcgctaa.
```

In some embodiments, the nucleotide sequence encoding the second polypeptide chain of the CAR is at least 81%, 82%, 83%, 84%, 85%, 86%, 87%, 88%, 89%, 90%, 91%, 92%, 93%, 94%, 95%, 96%, 97%, 98%, 99% or 100% identical to

```
                                          (SEQ ID NO: 103)
ggatccatggccttaccagtgaccgccttgctcctgccgctggccttgct
gctccacgccgccaggccggaacagaaactcatcagtgaggaagatttgc
agacgactccaggagagagatcatcactccctgccttttaccctggcact
tcaggctcttgttccggatgtgggtccctctctctgccgacaacaacccc
tgcccccagacctcctaccccagcccctacaattgccagccagcctctga
gcctgaggcccgaggcttgtagacctgctgctggcggagccgtgcacacc
agaggactggatttcgcctgcgacctaggttctgggtgctggtggtcgtg
ggcggagtgctggcctgttacagcctgctcgtgaccgtggccttcatcat
cttttgggtgcggagcaagagaagcagactgctgcacagcgactacatga
acatgacccccagacggcctggccccaccagaaagcactaccagccttac
gcccctcccagagacttcgccgcctacagatctcccgggggaggcggagg
atctggcggaggtggaagtggcggaggcggatctatggcccacgccggca
ggaccggctacgacaacagggagatcgtgatgaagtacatccactacaag
ctgagccagaggggctacgagtgggacgccggcgacgtgggcgccgcccc
ccccggcgccgcccccgcccccggcatcttcagcagccagcccggccaca
cccccaccccgccgccagcagggaccccgtggccaggaccagccccctg
cagacccccgccgcccccggcgccgccgccggccccgccctgagccccgt
gcccccccgtggtgcacctgaccctgaggcaggccggcgacgacttcagca
ggaggtacaggagggacttcgccgagatgagcagccagctgcacctgacc
```

-continued cccttcaccgccaggggcaggttcgccaccgtggtggaggagctgttcag ggacggcgtgaactggggcaggatcgtggccttcttcgagttcggcggcg tgatgtgcgtggagagcgtgaacagggagatgagcccccctggtggacaac atcgccctgtggatgaccgagtacctgaacaggcacctgcacacctggat ccaggacaacggcggctgggacgccttcgtggagctgtacggccccagca tgagggaagatggaggcggaggatctggcggaggtggaagtggcggaggc ggatctatgcatagagtgaagttcagcaggagcgcagacgcccccgcgta ccagcagggccagaaccagctctataacgagctcaatctaggacgaagag aggagtacgatgttttggacaagagacgtggccgggaccctgagatgggg ggaaagccgagaaggaagaaccctcaggaaggcctgtacaatgaactgca gaaagataagatggcggaggcctacagtgagattgggatgaaaggcgagc gccggaggggcaaggggcacgatggcctttaccagggtctcagtacagcc accaaggacacctacgacgcccttcacatgcaggccctgccccctcgcta a.

In some embodiments, the nucleotide sequence encoding the second polypeptide chain of the CAR is at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 20)

ggatccatggccttaccagtgaccgccttgctcctgccgctggccttgct gctccacgccgccaggccggaacagaaactcatcagtgaggaagatttgc agacgactccaggagagagatcatcactccctgccttttaccctggcact tcaggctcttgttccggatgtgggtccctctctctgccgacaacaacccc tgcccccagacctcctaccccagcccctacaattgccagccagcctctga gcctgaggcccgaggcttgtagacctgctgctggcggagccgtgcacacc agaggactggatttcgcctgcgacctaggttctgggtgctggtggtcgtg ggcggagtgctggcctgttacagcctgctcgtgaccgtggccttcatcat cttttgggtgcggagcaagagaagcagactgctgcacagcgactacatga acatgacccccagacggcctggccccaccagaaagcactaccagccttac gcccctcccagagacttcgccgcctacagatctcccgggggaggcggagg atctggcggaggtggaagtggcggaggcggatctatgagccagagcaaca gagaactggtggtggacttcctgagctacaagctgagccagaagggctac agctggtcccagttcagcgacgtggaagagaacagaacagaggcccctga gggcacagagtctgaggctgtgaaacaggccctgagagaagccggcgacg agttcgagctgagatacagaagggccttcagcgacctgaccagccagctg cacatcacacctggcacagcctaccagagcttcgagcaggtcgtgaacga gctgttcagagatggcgtgaactggggcagaatcgtggccttcttcagct ttggcggagccctgtgtgtggaaagcgtggacaaagaaatgcaggtcctg gtgtccagaatcgccgcctggatggccacctacctgaacgatcatctgga accctggattcaagagaacggcggctgggacaccttcgtggaactgtacg gaaacaacgccgctgccgagagcagaaagggccaagaacgagaagatgga -continued ggcggaggatctggcggaggtggaagtggcggaggcggatctatgcatag agtgaagttcagcaggagcgcagacgcccccgcgtaccagcagggccaga accagctctataacgagctcaatctaggacgaagagaggagtacgatgtt ttggacaagagacgtggccgggaccctgagatggggggaaagccgagaag gaagaaccctcaggaaggcctgtacaatgaactgcagaaagataagatgg cggaggcctacagtgagattgggatgaaaggcgagcgccggaggggcaag gggcacgatggcctttaccagggtctcagtacagccaccaaggacaccta cgacgcccttcacatgcaggccctgccccctcgctaa.

In some embodiments, the nucleotide sequence encoding the second polypeptide chain of the CAR is at least 81%, 82%, 83%, 84%, 85%, 86%, 87%, 88%, 89%, 90%, 91%, 92%, 93%, 94%, 95%, 96%, 97%, 98%, 99% or 100% identical to (SEQ ID NO: 21)

ggatccatggccttaccagtgaccgccttgctcctgccgctggccttgct gctccacgccgccaggccggaacagaaactcatcagtgaggaagatttgc agacgactccaggagagagatcatcactccctgccttttaccctggcact tcaggctcttgttccggatgtgggtccctctctctgccgacaacaacccc tgcccccagacctcctaccccagcccctacaattgccagccagcctctga gcctgaggcccgaggcttgtagacctgctgctggcggagccgtgcacacc agaggactggatttcgcctgcgacctaggttctgggtgctggtggtcgtg ggcggagtgctggcctgttacagcctgctcgtgaccgtggccttcatcat cttagggtgcggagcaagagaagcagactgctgcacagcgactacatgaa catgacccccagacggcctggccccaccagaaagcactaccagccttacg cccctcccagagacttcgccgcctacagatctcccgggggaggcggagga tctggcggaggtggaagtggcggaggcggatctatgagccagagcaacag agaactggtggtggacttcctgagctacaagctgagccagaagggctaca gctggtcccagttcagcgacgtggaagagaacagaacagaggcccctgag ggcacagagtctgaggctgtgaaacaggccctgagagaagccggcgacga gttcgagctgagatacagaagggccttcagcgacctgaccagccagctgc acatcacacctggcacagcctaccagagcttcgagcaggtcgtgaacgag ctgttcagagatggcgtgaactggggcagaatcgtggccttcttcagctt tggcggagccctgtgtgtggaaagcgtggacaaagaaatgcaggtcctgg tgtccagaatcgccgcctggatggccacctacctgaacgatcatctggaa ccctggattcaagagaacggcggctgggacaccttcgtggaactgtacgg aaacaacgccgctgccgagagcagaaagggccaagaacgagaagatggag gcggaggatctggcggaggtggaagtggcggaggcggatctatgcataga gtgaagttcagcaggagcgcagacgcccccgcgtaccagcagggccagaa ccagctctataacgagctcaatctaggacgaagagaggagtacgatgttt tggacaagagacgtggccgggaccctgagatggggggaaagccgagaagg aagaaccctcaggaaggcctgtacaatgaactgcagaaagataagatggc -continued

```
ggaggcctacagtgagattgggatgaaaggcgagcgccggaggggcaagg
ggcacgatggcctttaccagggtctcagtacagccaccaaggacacctac
gacgcccttcacatgcaggccctgccccctcgctaa.
```

In various embodiments, the nucleotide sequence encoding the first polypeptide chain of the CAR is operably linked to a first promoter. In various embodiments, the nucleotide sequence encoding the second polypeptide chain of the CAR is operably linked to a second promoter. In various embodiments, the nucleotide sequence encoding the first polypeptide chain of the CAR is operably linked to a first promoter, the nucleotide sequence encoding the second polypeptide chain of the CAR is operably linked to a second promoter, and the first and second promoters are the same. In various embodiments, the nucleotide sequence encoding the first polypeptide chain of the CAR is operably linked to a first promoter, the nucleotide sequence encoding the second polypeptide chain of the CAR is operably linked to a second promoter, and the first and second promoters are different.

In various embodiments, the nucleotide sequences encoding the first and second polypeptide chains of the CAR are operably linked to a single promoter. In various embodiments, the first and/or second promoter is a T lymphocyte-specific promoter or an NK cell-specific promoter. In various embodiments, the nucleic acid molecule is a DNA molecule.

In various embodiments, the nucleic acid molecule is an RNA molecule.

Vectors

In one aspect is provided a recombinant vector comprising any nucleic acid molecule described herein, or any nucleic acid encoding any polypeptide described herein. In some embodiments, the recombinant vector is a viral vector. The vector may be a retroviral vector, a lentiviral vector, an adenoviral vector, an adeno-associated virus vector, an alphaviral vector, a herpes virus vector, or a vaccinia virus vector. In some embodiments, the vector is a lentiviral vector.

In one embodiment, the recombinant vector comprises (SEQ ID NO: 18)

```
gagtgggttacatcgaactggatctcaacagcggtaagatccttgagagt
tttcgccccgaagaacgttttccaatgatgagcacttttaaagttctgct
atgtggcgcggtattatcccgtattgacgccgggcaagagcaactcggtc
gccgcatacactattctcagaatgacttggttgagtactcaccagtcaca
gaaaagcatcttacggatggcatgacagtaagagaattatgcagtgctgc
cataaccatgagtgataacactgcggccaacttacttctgacaacgatcg
gaggaccgaaggagctaaccgctatagcacaacatggggggatcatgtaac
tcgccttgatcgttgggaaccggagctgaatgaagccataccaaacgacg
agcgtgacaccacgatgcctgtagcaatggcaacaacgttgcgcaaacta
ttaactggcgaactacttactctagcttcccggcaacaattaatagactg
gatggaggcggataaagttgcaggaccacttctgcgctcggcccttccgg
ctggctggtttattgctgataaatctggagccggtgagcgtgggtctcgc
ggtatcattgcagcactggggccagatggtaagccctcccgtatcgtagt
tatctacacgacggggagtcaggcaactatggatgaacgaaatagacaga
```

-continued

```
tcgctgagataggtgcctcactgattaagcattggtaactgtcagaccaa
gtttactcatatatactttagattgatttaaaacttcatttttaatttaa
aaggatctaggtgaagatcctattgataatctcatgaccaaaatccctta
acgtgagttttcgttccactgagcgtcagaccccgtagaaaagatcaaag
gatcttcttgagatcctttttttctgcgcgtaatctgctgcttgcaaaca
aaaaaaccaccgctaccagcggtggtttgtagccggatcaagagctacca
actcataccgaaggtaactggcttcagcagagcgcagataccaaatactg
tccttctagtgtagccgtagttaggccaccacttcaagaactctgtagca
ccgcctacatacctcgctctgctaatcctgttaccagtggctgctgccag
tggcgataagtcgtgtcttaccgggttggactcaagacgatagttaccgg
ataaggcgcagcggtcgggctgaacggggggttcgtgcacacagcccagc
ttggagcgaacgacctacaccgaactgagatacctacagcgtgagctatg
agaaagcgccacgcttcccgaagggagaaaggcggacaggtatccggtaa
gcggcagggtcggaacaggagagcgcacgagggagcttccagggggaaac
gcctggtatctttatagtcctgtcgggtacgccacctctgacttgagcgt
cgatttttgtgatgctcgtcaggggggcggagcctatggaaaaacgccag
caacgcggcctttttacggttcctggccttttgctggccttttgctcaca
tgttctttcctgcgttatcccctgattctgtggataaccgtattaccgcc
tttgagtgagctgataccgctcgccgcagccgaacgaccgagcgcagcga
gtcagtgagcgaggaagcggaagagcgcccaatacgcaaaccgcctctcc
ccgcgcgttggccgattcattaatgcagctggcacgacaggtttcccgac
tggaaagcgggcagtgagcgcaacgcaattaatgtgagttagctcactca
ttaggcaccccaggctttacactttatgcttccggctcgtatgttgtgtg
gaattgtgagcggataacaatttcacacaggaaacagctatgaccatgat
tacgccaagcgcgcaattaaccctcactaaagggaacaaaagctggagct
gcaagcttaatgtagtcttatgcaatactcttgtagtcttgcaacatggt
aacgatgagttagcaacatgccttacaaggagagaaaaagcaccgtgcat
gccgattggtggaagtaaggtggtacgatcgtgccttattaggaaggcaa
cagacgggtctgacatggattggacgaaccactgaattgccgcattgcag
agatattgtatttaagtgcctagctcgatacaataaacgggtctctctgg
ttagaccagatctgagcctgggagctctctggctaactagggaacccact
gcttaagcctcaataaagcttgccttgagtgcttcaagtagtgtgtgccc
gtctgttgtgtgactctggtaactagagatccctcagacccttttagtca
gtgtggaaaatctctagcagtggcgcccgaacagggacctgaaagcgaaa
gggaaaccagagctctctcgacgcaggactcggcttgctgaagcgcgcac
ggcaagaggcgaggggcggcgactggtgagtacgccaaaaattttgacta
gcggaggctagaaggagagagatgggtgcgagagcgtcagtattaagcgg
gggagaattagatcgcgatgggaaaaaattcggttaaggccagggggaaa
gaaaaaatataaattaaaacatatagtatgggcaagcagggagctagaac
gattcgcagttaatcctggcctgttagaaacatcagaaggctgtagacaa
atactgggacagctacaaccatcccttcagacaggatcagaagaacttag
```

-continued atcattatataatacagtagcaaccctctattgtgtgcatcaaaggatag agataaaagacaccaaggaagctttagacaagatagaggaagagcaaaac aaaagtaagaccaccgcacagcaagcggccgctgatcttcagacctggag gaggagatatgagggacaattggagaagtgaattatataaatataaagta gtaaaaattgaaccattaggagtagcacccaccaaggcaaagagaagagt ggtgcagagagaaaaaagagcagtgggaataggagctttgttccttgggt tcttgggagcagcaggaagcactatgggcgcagcctcaatgacgctgacg gtacaggccagacaattattgtctggtatagtgcagcagcagaacaattt gctgagggctattgaggcgcaacagcatctgttgcaactcacagtctggg gcatcaagcagctccaggcaagaatcctggctgtggaaagatacctaaag gatcaacagctcctggggatttggggttgctctggaaaactcatttgcac cactgctgtgccttggaatgctagttggagtaataaatctctggaacaga ttggaatcacacgacctggatggagtgggacagagaaattaacaattaca caagcttaatacactccttaattgaagaatcgcaaaaccagcaagaaaag aatgaacaagaattattggaattagataaatgggcaagtttgtggaattg gtttaacataacaaattggctgtggtatataaaattattcataatgatag taggaggcttggtaggtttaagaatagtatttgctgtactttctatagtga atagagttaggcagggatattcaccattatcgtttcagacccacctccca accccgaggggacccgacaggcccgaaggaatagaagaagaaggtggaga gagagacagagacagatccattcgattagtgaacggatctcgacggtatc gattagactgtagcccaggaatatggcagctagattgtacacatttagaa ggaaaagttatcttggtagcagttcatgtagccagtggatatatagaagc agaagtaattccagcagagacagggcaagaaacagcatacttcctcttaa aattagcaggaagatggccagtaaaaacagtacatacagacaatggcagc aatttcaccagtactacagttaaggccgcctgttggtgggcggggatcaa gcaggaatttggcattccctacaatccccaaagtcaaggagtaatagaat ctatgaataaagaattaaagaaaattataggacaggtaagagatcaggct gaacatcttaagacagcagtacaaatggcagtattcatccacaattttaa aagaaaaggggggattggggggtacagtgcaggggaaagaatagtagaca taatagcaacagacatacaaactaaagaattacaaaaacaaattacaaaa attcaaaattttcgggtttattacagggacagcagagatccagtttggct gcatacgcgtcgtgaggctccggtgcccgtcagtgggcagagcgcacatc gcccacagtccccgagaagttggggggaggggtcggcaattgaaccggtg cctagagaaggtggcgcggggtaaactgggaaagtgatgtcgtgtactgg ctccgcctttttcccgagggtgggggagaaccgtatataagtgcagtagt cgccgtgaacgttatttcgcaacgggtttgccgccagaacacaggtaagt gccgtgtgtggttcccgcgggcctggcctctttacgggttatggcccttg cgtgccttgaattacttccacctggctgcagtacgtgattcttgatcccg agcttcgggttggaagtgggtgggagagttcgaggccttgcgcttaagga gccccttcgcctcgtgcttgagttgaggcctggcctgggcgctggggccg -continued ccgcgtgcgaatctggtggcaccttcgcgcctgtctcgctgctttcgata agtctctagccatttaaaatttttgatgacctgctgcgacgctttttttc tggcaagatagtcttgtaaatgcgggccaagatctgcacactggtatttc ggtttttggggccgcgggcggcgacggggcccgtgcgtcccagcgcacat gttcggcgaggcggggcctgcgagcgcggccaccgagaatcggacggggg tagtctcaagctggccggcctgctctggtgcctggcctcgcgccgccgtg tatcgccccgccctgggcggcaaggctggcccggtcggcaccagttgcgt gagcggaaagatggccgcttcccggccctgctgcagggagctcaaaatgg aggacgcggcgctcgggagagcgggcgggtgagtcacccacacaaaggaa aagggcattccgtcctcagccgtcgcttcatgtgactccacggagtaccg ggcgccgtccaggcacctcgattagttctcgagcttttggagtacgtcgt ctttaggttggggggaggggttttatgcgatggagtttccccacactgag tgggtggagactgaagttaggccagcttggcacttgatgtaattctcctt ggaatttgccctattgagtttggatcttggttcattctcaagcctcagac agtggttcaaagtttttttcttccatttcaggtgtcgtgagctagacgac tagtcgtctagctctagaatggccttaccagtgaccgccttgctcctgcc gctggccttgctgctccacgccgccaggccggtgcagctgcagcagtcag gacctgaactggtgaagcctgggacttcagtgaggatatcctgcaagact tctggatacacattcactgaatataccatacactgggtgaagcagagcca tggaaagagccttgagtggattggaaacatcaatcctaacaatggtggta ccacctacaatcagaagttcgaggacaaggccacattgactgtagacaag tcctccagtacagcctacatggagctccgcagcctaacatctgaggattc tgcagtctattattgtgcagctggttggaactttgactactggggccaag ggaccacggtcaccgtctcctcaggtggaggtggatcaggtggaggtgga tctggtggaggtggatctgacattgtgatgacccagtctcacaaattcat gtccacatcagtaggagacagggtcagcatcatctgtaaggccagtcaag atgtgggtactgctgtagactggtatcaacagaaaccaggacaatctcct aaactactgatttattgggcatccactcggcacactggagtccctgatcg cttcacaggcagtggatctgggacagacttcactctcaccattactaatg ttcagtctgaagacttggcagattatttctgtcagcaatataacagctat cccctcacgttcggtgctgggaccatgctggacctgaaacgggctagcAC

AACAACCCCTGCCCCCAGACCTCCTACCCCAGCCCCTACAATTGCCAGCC

AGCCTCTGAGCCTGAGGCCCGAGGCTTGTAGACCTGCTGCTGGCGGAGCC

GTGCACACCAGAGGACTGGATTTCGCCTGCGACTTCTGGGTGCTGGTGGT

CGTGGGCGGAGTGCTGGCCTGTTACAGCCTGCTCGTGACCGTGGCCTTCA

TCATCTTTTGGGTGCGGAGCAAGAGAAGCAGACTGCTGCACAGCGACTAC

ATGAACATGACCCCCAGACGGCCTGGCCCCACCAGAAAGCACTACCAGCC

TTACGCCCCTCCCAGAGACTTCGCCGCCTACAGATCTcatatgGGAGGCG

GAGGATCTGGCGGAGGTGGAAGTGGCGGAGGCGGATCTCAAAGATGGGAA

CTCGCCCTGGGCAGATTCCTGGAATACCTGAGCTGGGTGTCCACACTGAG

CGAACAGGTGCAAGAGGAACTGCTGAGCAGCCAAGTGACCCAAGAGCTGA

-continued

```
GAGCCCTGATGGACGAGACAATGAAGGAACTGAAGGCCTACAAGAGCGAG
CTGGAAGAACAGCTGACCCCTGTGGCCGAGGAAACCAGAGCCAGACTGAG
CAAAGAACTGCAGGCCGCTCAGGCCAGACTGGGAGCCGATATGGAAGATG
TTCGGGGCAGACTGGTGCAGTACAGAGGCGAAGTTCAGGCCATGCTGGGC
CAGTCTACCGAGGAACTGAGAGTGCGGCTGGCCTCTCATCTGATTGCCCT
GCAGCTGAGACTGATCGGCGACGCATTCGACCTGCAGAAAAGACTGGCCG
TGTACCAGGCTGGCGCTGCTGAACGGAAGCGGCGCAGCGGCAGCGGGCGC
AGCGGCAGCGGCgagggcagaggaagtcttctaacatgcggtgacgtgga
ggagaatcccggccctggatccatggccttaccagtgaccgccttgctcc
tgccgctggccttgctgctccacgccgccaggccggaacagaaactcatc
agtgaggaagatttgcagacgactccaggagagagatcatcactccctgc
cttttaccctggcacttcaggctcttgttccggatgtgggtccctctctc
tgccgACAACAACCCCTGCCCCCAGACCTCCTACCCCAGCCCCTACAATT
GCCAGCCAGCCTCTGAGCCTGAGGCCCGAGGCTTGTAGACCTGCTGCTGG
CGGAGCCGTGCACACCAGAGGACTGGATTTCGCCTGCGACcctaggTTCT
GGGTGCTGGTGGTCGTGGGCGGAGTGCTGGCCTGTTACAGCCTGCTCGTG
ACCGTGGCCTTCATCATCTTTTGGGTGCGGAGCAAGAGAAGCAGACTGCT
GCACAGCGACTACATGAACATGACCCCCAGACGGCCTGGCCCCACCAGAA
AGCACTACCAGCCTTACGCCCCTCCCAGAGACTTCGCCGCCTACAGATCT
cccgggGGAGGCGGAGGATCTGGCGGAGGTGGAAGTGGCGGAGGCGGATC
TATGAGCCAGAGCAACAGAGAACTGGTGGTGGACTTCCTGAGCTACAAGC
TGAGCCAGAAGGGCTACAGCTGGTCCCAGTTCAGCGACGTGGAAGAGAAC
AGAACAGAGGCCCCTGAGGGCACAGAGTCTGAGGCTGTGAAACAGGCCCT
GAGAGAAGCCGGCGACGAGTTCGAGCTGAGATACAGAAGGGCCTTCAGCG
ACCTGACCAGCCAGCTGCACATCACACCTGGCACAGCCTACCAGAGCTTC
GAGCAGGTCGTGAACGAGCTGTTCAGAGATGGCGTGAACTGGGGCAGAAT
CGTGGCCTTCTTCAGCTTTGGCGGAGCCCTGTGTGTGGAAAGCGTGGACA
AAGAAATGCAGGTCCTGGTGTCCAGAATCGCCGCCTGGATGGCCACCTAC
CTGAACGATCATCTGGAACCCTGGATtCAAGAGAACGGCGGCTGGGACAC
CTTCGTGGAACTGTACGGAAACAACGCCGCTGCCGAGAGCAGAAAGGGCC
AAGAACGAGAAGATGGCGGCGGTGGTTCTGGTGGCGGCGGTAGTGGTGGC
GGTGGATCaatgcatagagtgaagttcagcaggagcgcagacgcccccgc
gtaccagcagggccagaaccagctctataacgagctcaatctaggacgaa
gagaggagtacgatgttttggacaagagacgtggccgggaccctgagatg
gggggaaagccgagaaggaagaaccctcaggaaggcctgtacaatgaact
gcagaaagataagatggcggaggcctacagtgagattgggatgaaaggcg
agcgccggaggggcaaggggcacgatggcctttaccagggtctcagtaca
gccaccaaggacacctacgacgcccttcacatgcaggccctgccccctcg
ctaagtcgacaatcaacctctggattacaaaatttgtgaaagattgactg
gtattcttaactatgttgctccttttacgctatgtggatacgctgcttta
```

-continued

```
atgcctttgtatcatgctattgcttcccgtatggctttcattttctcctc
cttgtataaatcctggttgctgtctctttatgaggagttgtggcccgttg
tcaggcaacgtggcgtggtgtgcactgtgtttgctgacgcaacccccact
ggttggggcattgccaccacctgtcagctcattccgggactttcgctacc
ccctccctattgccacggcggaactcatcgccgcctgccttgcccgctgc
tggacaggggctcggctgttgggcactgacaattccgtggtgttgtcggg
gaagctgacgtcctttccatggctgctcgcctgtgttgccacctggattc
tgcgcgggacgtccttctgctacgtcccttcggccctcaatccagcggac
cttccttcccgcggcctgctgccggctctgcggcctcttccgcgtcttcg
ccttcgccctcagacgagtcggatctccctttgggccgcctccccgcctg
gaattcgagctcggtacctttaagaccaatgacttacaaggcagctgtag
atcttagccactattaaaagaaaaggggggactggaagggctaattcact
cccaacgaagacaagatctgcttttttgcttgtactgggtctctctggtta
gaccagatctgagcctgggagctctctggctaactagggaacccactgct
taagcctcaataaagcttgccttgagtgcttcaagtagtgtgtgcccgtc
tgttgtgtgactctggtaactagagatccctcagacccttttagtcagtg
tggaaaatctctagcagtagtagttcatgtcatcttattattcagtattt
ataacttgcaaagaaatgaatatcagagagtgagaggaacttgtttattg
cagcttataatggttacaaataaagcaatagcatcacaaatttcacaaat
aaagcatttttttcactgcattctagttgtggtttgtccaaactcatcaa
tgtatcttatcatgtctggctctagctatcccgcccctaactccgcccag
ttccgcccattctccgccccatggctgactaattttttttatttatgcag
aggccgaggccgcctcggcctctgagctattccagaagtagtgaggaggc
ttttttggaggcctagctaggcttttgcgtcgagacgtacccaattcg
ccctatagtgagtcgtattacgcgcgctcactggccgtcgttttacaacg
tcgtgactgggaaaaccctggcgttacccaacttaatcgccttgcagcac
atccccctttcgccagctggcgtaatagcgaagaggcccgcaccgatcgc
ccttcccaacagttgcgcagcctgaatggcgaatggcgcgacgcgccctg
tagcggcgcattaagcgcggcgggtgtggtggttacgcgcagcgtgaccg
ctacacttgccagcgccctagcgcccgctcctttcgctttcttcccttcc
tttctcgccacgttcgccggctttccccgtcaagctctaaatcgggggct
ccctttagggttccgatttagtgctttacggcacctcgaccccaaaaaac
ttgattagggtgatggttcacgtagtgggccatcgccctgatagacggtt
tttcgccctttgacgttggagtccacgttctttaatagtggactcttgtt
ccaaactggaacaacactcaaccctatctcggtctattcttttgatttat
aagggattttgccgatttcggcctattggttaaaaaatgagctgatttaa
caaaaatttaacgcgaattttaacaaaatattaacgtttacaatttccca
ggtggcacttttcggggaaatgtgcgcggaacccctatttgtttattttt
ctaaatacattcaaatatgtatccgctcatgagacaataaccctgataaa
tgcttcaataatattgaaaaaggaagagtatgagtattcaacatttccgt
```

-continued

```
gtcgcccttattcccttttttgcggcattttgccttcctgtttttgctca

cccagaaacgctggtgaaagtaaaagatgctgaagatcagttgggtgcac
```

Host Cells

In another aspect is provided an isolated host cell comprising any heterodimeric inactivatable CAR described herein. The isolated host cell may comprise any nucleic acid molecule described herein. The isolated host cell may comprise any vector described herein. The host cell may be a mammalian cell. Exemplary host cells include, but are not limited to, cytotoxic cells, T cells, stem cells, progenitor cells, and cells derived from a stem cell or a progenitor cell. The T cell may be a T-helper cell, a cytotoxic T-cell, a T-regulatory cell (Treg), or a gamma-delta T cell. The cytotoxic cell may be a cytotoxic T cell or a natural killer (NK) cell. The host cell may be activated ex vivo and/or expanded ex vivo. The host cell may be an allogeneic cell. The host cell may be an autologous cell. The host cell may be isolated from a subject having a disease. In various embodiments, the subject is human.

Also provided is a method for producing any of the above host cells. The method comprises genetically modifying the cell with any nucleic acid molecule or any vector described herein. The genetic modification may be conducted ex vivo. The method may further comprise activation and/or expansion of the cell ex vivo.

The polypeptides disclosed herein, or nucleic acids encoding such, may be introduced into the host cells using transfection and/or transduction techniques known in the art. The nucleic acid may be integrated into the host cell DNA or may be maintained extrachromosomally. The nucleic acid may be maintained transiently or may be a stable introduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transduction refers to the delivery of a gene(s) using a viral or retroviral vector by means of viral infection rather than by transfection. In certain embodiments, retroviral vectors are transduced by packaging the vectors into virions prior to contact with a cell. For example, a nucleic acid encoding a transmembrane polypeptide carried by a retroviral vector can be transduced into a cell through infection and pro virus integration.

In certain embodiments, the nucleic acid or viral vector is transferred via ex vivo transformation. Methods for transfecting vascular cells and tissues removed from an organism in an ex vivo setting are known to those of skill in the art. Thus, it is contemplated that cells or tissues may be removed and transfected ex vivo using the polynucleotides presented herein. In particular aspects, the transplanted cells or tissues may be placed into an organism. Thus, it is well within the knowledge of one skilled in the art to isolate antigen-presenting cells (e.g., T-cells or NK cells) from an animal (e.g., human), transfect the cells with the expression vector and then administer the transfected or transformed cells back to the animal.

In certain embodiments, the nucleic acid or viral vector is transferred via injection. In certain embodiments, a polynucleotide is introduced into an organelle, a cell, a tissue or an organism via electroporation. In certain embodiments, a polynucleotide is delivered into a cell using DEAE-dextran followed by polyethylene glycol. In certain embodiments, the polynucleotides encode any of the first and second transmembrane polypeptides described herein, and are inserted into a vector or vectors. The vector is a vehicle into which a polynucleotide encoding a protein may be covalently inserted so as to bring about the expression of that protein and/or the cloning of the polynucleotide. Expression vectors have the ability to incorporate and express heterologous or modified nucleic acid sequences coding for at least part of a gene product capable of being transcribed in a cell. In most cases, RNA molecules are then translated into a protein.

Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well. An expression vector may comprise additional elements, for example, the expression vector may have two replication systems, thus allowing it to be maintained in two organisms, for example in human cells for expression and in a prokaryotic host for cloning and amplification. The expression vector may have additional sequence such as 6×-histidine, c-Myc, and FLAG tags which are incorporated into the expressed polypeptides. In various embodiments, the vectors are plasmid, autonomously replicating sequences, and transposable elements.

In certain embodiments, the nucleic acids encoding the transmembrane polypeptides of the present invention are provided in a viral vector. In certain embodiments, the viral vector is a retroviral vector or a lentiviral vector. The term “retroviral vector” refers to a vector containing structural and functional genetic elements that are primarily derived from a retrovirus. The term “lentiviral vector” refers to a vector containing structural and functional genetic elements outside the LTRs that are primarily derived from a lentivirus.

In certain embodiments, the present disclosure provides isolated host cells (e.g., T-cells) containing the vectors provided herein. The host cells containing the vector may be useful in expression or cloning of the polynucleotide contained in the vector.

Pharmaceutical Compositions

In another aspect is provided a pharmaceutical composition comprising any host cell described herein, and a pharmaceutically acceptable carrier and/or excipient. Exemplary carriers include, but are not limited to, sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in “Remington’s Pharmaceutical Sciences” by E. W. Martin.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432).

The pharmaceutical composition may be used in combination with other therapies. It is contemplated that when used to treat various diseases, the compositions and methods can be combined with other therapeutic agents suitable for the same or similar diseases. Also, two or more embodiments described herein may be also co-administered to generate additive or synergistic effects. When co-administered with a second therapeutic agent, the embodiment described herein and the second therapeutic agent may be simultaneously or sequentially (in any order). Suitable therapeutically effective dosages for each agent may be lowered due to the additive action or synergy.

As a non-limiting example, the methods described herein can be combined with other therapies that block inflammation (e.g., via blockage of IL1, INFα/β, IL6, TNF, IL13, IL23, etc.).

In some embodiments, the compositions and methods disclosed herein are useful to enhance the efficacy of vaccines directed to tumors or infections. Thus, the compositions and methods described herein can be administered to a subject either simultaneously with or before (e.g., 1-30 days before) a reagent (including but not limited to small molecules, antibodies, or cellular reagents) that acts to elicit an immune response (e.g., to treat cancer or an infection) is administered to the subject.

The compositions and methods described herein can be also administered in combination with an anti-tumor antibody or an antibody directed at a pathogenic antigen or allergen.

The compositions and methods described herein can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41BB, OX40, etc.). The inhibitory treatments described herein can be also combined with other treatments that possess the ability to modulate NKT function or stability, including but not limited to CD1d, CD1d-fusion proteins, CD1d dimers or larger polymers of CDT d either unloaded or loaded with antigens, CDT d-chimeric antigen receptors (CD1d-CAR), or any other of the five known CD1 isomers exisiting in humans (CD1a, CD1b, CD1c, CD1e), in any of the aforementioned forms or formulations, alone or in combination with each other or other agents.

Therapeutic methods described herein can be combined with additional immunotherapies and therapies. For example, when used for treating cancer, NKT cells described herein can be used in combination with conventional cancer therapies, such as, e.g., surgery, radiotherapy, chemotherapy or combinations thereof, depending on type of the tumor, patient condition, other health issues, and a variety of factors. In certain aspects, other therapeutic agents useful for combination cancer therapy with the inhibitors described herein include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In some embodiments, the inhibitors described herein can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

The present invention provides methods which comprise administering a pharmaceutical composition comprising any of the exemplary heterodimeric inactivatable CAR described herein in combination with one or more additional therapeutic agents. Exemplary additional therapeutic agents that may be combined with or administered in combination with a heterodimeric inactivatable CAR include, e.g., an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2, anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET anagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody), a VEGF antagonist (e.g., a VEGF-Trap, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 (PSMA) antagonist, a PRLR antagonist (e.g., an anti-PRLR antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin antibody), etc. Other agents that may be beneficially administered in combination with a heterodimeric inactivatable CAR include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions of the present invention may also be administered as part of a therapeutic regimen comprising one or more therapeutic combinations selected from "ICE": ifosfamide (e.g., Ifex®), carboplatin (e.g., Paraplatin®), etoposide (e.g., Etopophos®, Toposar®, VePesid®, VP-16); "DHAP": dexamethasone (e.g., Decadron®), cytarabine (e.g., Cytosar-U®, cytosine arabinoside, ara-C), cisplatin (e.g., Platinol®-AQ); and "ESHAP": etoposide (e.g., Etopophos®, Toposar®, VePesid®, VP-16), methylprednisolone (e.g., Medrol®), high-dose cytarabine, cisplatin (e.g., Platinol®-AQ).

The present invention also includes therapeutic combinations comprising any of the antigen-binding molecules mentioned herein and an inhibitor of one or more of VEGF, Ang2, DLL4, EGFR, ErbB2, ErbB3, ErbB4, EGFRvIII, cMet, IGF1R, B-raf, PDGFR-α, PDGFR-β, FOLH1 (PSMA), PRLR, STEAP1, STEAP2, TMPRSS2, MSLN, CA9, uroplakin, or any of the aforementioned cytokines, wherein the inhibitor is an aptamer, an antisense molecule, a ribozyme, an siRNA, a peptibody, a nanobody or an antibody fragment (e.g., Fab fragment; F(ab')2 fragment; Fd fragment; Fv fragment; scFv; dAb fragment; or other engineered molecules, such as diabodies, triabodies, tetrabodies, minibodies and minimal recognition units). The heterodimeric inactivatable CAR may also be administered and/or co-formulated in combination with antivirals, antibiotics, analgesics, corticosteroids and/or NSAIDs. The antigen-binding molecules of the invention may also be administered as part of a treatment regimen that also includes radiation treatment and/or conventional chemotherapy.

Non-limiting examples of chemotherapeutic compounds which can be used in combination treatments include, for example, aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as *vinca* alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

For treatment of infections, a combined therapy may be used. The combined therapy can encompass co-administering compositions and methods described herein with an antibiotic, an anti-fungal drug, an anti-viral drug, an anti-parasitic drug, an anti-protozoal drug, or a combination thereof.

Non-limiting examples of useful antibiotics include lincosamides (clindomycin); chloramphenicols; tetracyclines (such as Tetracycline, Chlortetracycline, Demeclocycline, Methacycline, Doxycycline, Minocycline); aminoglycosides (such as Gentamicin, Tobramycin, Netilmicin, Amikacin, Kanamycin, Streptomycin, Neomycin); beta-lactams (such as penicillins, cephalosporins, Imipenem, Aztreonam); vancomycins; bacitracins; macrolides (erythromycins), amphotericins; sulfonamides (such as Sulfanilamide, Sulfamethoxazole, Sulfacetamide, Sulfadiazine, Sulfisoxazole, Sulfacytine, Sulfadoxine, Mafenide, p-Aminobenzoic Acid, Trimethoprim-Sulfamethoxazole); Methenamin; Nitrofurantoin; Phenazopyridine; trimethoprim; rifampicins; metronidazoles; cefazolins; Lincomycin; Spectinomycin; mupirocins; quinolones (such as Nalidixic Acid, Cinoxacin, Norfloxacin, Ciprofloxacin, Perfloxacin, Ofloxacin, Enoxacin, Fleroxacin, Levofloxacin); novobiocins; polymixins; gramicidins; and antipseudomonals (such as Carbenicillin, Carbenicillin Indanyl, Ticarcillin, Azlocillin, Mezlocillin, Piperacillin) or any salts or variants thereof. See also Physician's Desk Reference, $59^{th}$ edition, (2005), Thomson P D R, Montvale N.J.; Gennaro et al., Eds. Remington's The Science and Practice of Pharmacy, 20th edition, (2000), Lippincott Williams and Wilkins, Baltimore Md.; Braunwald et al., Eds. Harrison's Principles of Internal Medicine, 15th edition, (2001), McGraw Hill, NY; Berkow et al., Eds. The Merck Manual of Diagnosis and Therapy, (1992), Merck Research Laboratories, Rahway N.J. Such antibiotics can be obtained commercially, e.g., from Daiichi Sankyo, Inc. (Parsipanny, N.J.), Merck (Whitehouse Station, N.J.), Pfizer (New York, N.Y.), Glaxo Smith Kline (Research Triangle Park, N.C.), Johnson & Johnson (New Brunswick, N.J.), AstraZeneca (Wilmington, Del.), Novartis (East Hanover, N.J.), and Sanofi-Aventis (Bridgewater, N.J.). The antibiotic used will depend on the type of bacterial infection.

Non-limiting examples of useful anti-fungal agents include imidazoles (such as griseofulvin, miconazole, terbinafine, fluconazole, ketoconazole, voriconazole, and itraconizole); polyenes (such as amphotericin B and nystatin); Flucytosines; and candicidin or any salts or variants thereof.

See also Physician's Desk Reference, 59th edition, (2005), Thomson P D R, Montvale N.J.; Gennaro et al., Eds. Remington's The Science and Practice of Pharmacy 20th edition, (2000), Lippincott Williams and Wilkins, Baltimore Md.; Braunwald et al., Eds. Harrison's Principles of Internal Medicine, 15th edition, (2001), McGraw Hill, NY; Berkow et al., Eds. The Merck Manual of Diagnosis and Therapy, (1992), Merck Research Laboratories, Rahway N.J.

Non-limiting examples of useful anti-viral drugs include interferon alpha, beta or gamma, didanosine, lamivudine, zanamavir, lopanivir, nelfinavir, efavirenz, indinavir, valacyclovir, zidovudine, amantadine, rimantidine, ribavirin, ganciclovir, foscarnet, and acyclovir or any salts or variants thereof. See also Physician's Desk Reference, 59th edition, (2005), Thomson P D R, Montvale N.J.; Gennaro et al., Eds. Remington's The Science and Practice of Pharmacy 20th edition, (2000), Lippincott Williams and Wilkins, Baltimore Md.; Braunwald et al., Eds. Harrison's Principles of Internal Medicine, 15th edition, (2001), McGraw Hill, NY; Berkow et al., Eds. The Merck Manual of Diagnosis and Therapy, (1992), Merck Research Laboratories, Rahway N.J.

Non-limiting examples of useful anti-parasitic agents include chloroquine, mefloquine, quinine, primaquine, atovaquone, sulfasoxine, and pyrimethamine or any salts or variants thereof. See also Physician's Desk Reference, 59th edition, (2005), Thomson P D R, Montvale N.J.; Gennaro et al., Eds. Remington's The Science and Practice of Pharmacy 20th edition, (2000), Lippincott Williams and Wilkins, Baltimore Md.; Braunwald et al., Eds. Harrison's Principles of Internal Medicine, 15th edition, (2001), McGraw Hill, NY; Berkow et al., Eds. The Merck Manual of Diagnosis and Therapy, (1992), Merck Research Laboratories, Rahway N.J.

Non-limiting examples of useful anti-protozoal drugs include metronidazole, diloxanide, iodoquinol, trimethoprim, sufamethoxazole, pentamidine, clindamycin, primaquine, pyrimethamine, and sulfadiazine or any salts or variants thereof. See also Physician's Desk Reference, 59th edition, (2005), Thomson P D R, Montvale N.J.; Gennaro et al., Eds. Remington's The Science and Practice of Pharmacy 20th edition, (2000), Lippincott Williams and Wilkins, Baltimore Md.; Braunwald et al., Eds. Harrison's Principles of Internal Medicine, 15th edition, (2001), McGraw Hill, NY; Berkow et al., Eds. The Merck Manual of Diagnosis and Therapy, (1992), Merck Research Laboratories, Rahway N.J.

The additional therapeutically active component(s) may be administered just prior to, concurrent with, or shortly after the administration of a heterodimeric inactivatable CAR (for purposes of the present disclosure, such administration regimens are considered the administration of a heterodimeric inactivatable CAR "in combination with" an additional therapeutically active component).

The present invention includes pharmaceutical compositions in which a heterodimeric inactivatable CAR is co-formulated with one or more of the additional therapeutically active component(s) as described elsewhere herein.

Therapeutic Uses

The present invention includes methods comprising administering to a subject in need thereof a therapeutic composition comprising a heterodimeric inactivatable CAR as described herein. The therapeutic composition can comprise any of the heterodimeric inactivatable CAR as disclosed herein and a pharmaceutically acceptable carrier or diluent. As used herein, the expression "a subject in need thereof" means a human or non-human animal that exhibits one or more symptoms or indicia of an infection (e.g., a subject suffering from a bacterial or viral infection, including any of those mentioned herein) cancer (e.g., a subject expressing a tumor or suffering from any of the cancers mentioned herein), an autoimmune disorder (e.g., a subject suffering from any of the autoimmune diseases or disorders mentioned herein), inflammatory diseases, or who otherwise would benefit from enhancement or suppression of T cell activity.

In another aspect, described herein is a method of treating a disorder in a subject in need thereof comprising administering to said subject an effective amount of a heterodimeric inactivatable CARs described herein, wherein the heterodimeric inactivatable CAR binds to an antigen-specific TCR and wherein the antigen recognized by the TCR is associated with the disorder.

The heterodimeric inactivatable CARs of the invention (and therapeutic compositions comprising the same) are useful, inter alia, for treating any disease or disorder in which stimulation or suppression of an immune response (via T cell modulation) targeted against a specific antigen would be beneficial. In particular, the heterodimeric inactivatable CARs of the present invention may be used for the treatment and prevention of infections, cancers or autoimmune disorders.

Where the heterodimeric inactivatable CAR described herein includes a second molecule comprising a domain that specifically binds a T-cell immunomodulatory molecule that is an activating polypeptide, transduction of the T cell with the heterodimeric inactivatable CAR activates the epitope-specific T cell. In some instances, the epitope-specific T cell is a T cell that is specific for an epitope present on a cancer cell, and contacting the epitope-specific T cell with the heterodimeric inactivatable CAR increases cytotoxic activity of the T cell toward the cancer cell. In some embodiments, the epitope-specific T cell is a T cell that is specific for an epitope present on a cancer cell, and contacting the epitope-specific T cell with the heterodimeric inactivatable CAR increases the number of the epitope-specific T cells.

In some embodiments, the epitope-specific T cell is a T cell that is specific for an epitope present on a virus-infected cell, and contacting the epitope-specific T cell with the heterodimeric inactivatable CAR increases cytotoxic activity of the T cell toward the virus-infected cell. In some instances, the epitope-specific T cell is a T cell that is specific for an epitope present on a virus-infected cell, and contacting the epitope-specific T cell with the heterodimeric inactivatable CAR increases the number of the epitope-specific T cells.

Where the heterodimeric inactivatable CAR includes a second molecule comprising a domain that specifically binds a T-cell immunomodulatory molecule that is an inhibiting polypeptide, contacting the T cell with the heterodimeric inactivatable CAR inhibits the epitope-specific T cell. In some instances, the epitope-specific T cell is a self-reactive T cell that is specific for an epitope present in a self antigen, and the contacting reduces the number of the self-reactive T cells.

The interaction of a T cell with the heterodimeric inactivatable CARs described herein can result in, e.g., activation, induction of anergy, or death of a T cell that occurs when the TCR of the T cell is bound by a TCR-binding pMHC complex. "Activation of a T cell" refers to induction of signal transduction pathways in the T cell resulting in production of cellular products (e.g., interleukin-2) by that T cell. "Anergy" refers to the diminished reactivity by a T cell to an antigen. Activation and anergy can be measured by, for example, measuring the amount of IL-2 produced by a T cell after an pMHC complex has bound to the TcR. Anergic cells will have decreased IL-2 production when compared with stimulated T cells. Another method for measuring the diminished activity of anergic T cells includes measuring intracellular and/or extracellular calcium mobilization by a T cell upon engagement of its TCR's. "T cell death" refers to the permanent cessation of substantially all functions of the T cell.

T-cell phenotypes may be evaluated using well-known methods, e.g., by measuring changes in the level of expression of cytokines and/or T cell activation markers, and/or the induction of antigen-specific proliferating cells. Techniques known to those of skill in the art, include, but not limited to, immunoprecipitation followed by Western blot analysis, ELISAs, flow cytometry, Northern blot analysis, and RT-PCR can be used to measure the expression cytokines and T cell activation markers. Cytokine release may be measured by measuring secretion of cytokines including but not limited to Interleukin-2 (IL-2), Interleukin-4 (IL-4), Interleukin-6 (IL-6), Interleukin-12 (IL-12), Interleukin-16 (IL-16), PDGF, TGF-α, TGF-β, TNF-α, TNF-β, GCSF, GM-CSF, MCSF, IFN-α, IFN-β, IFN-γ, TFN-γ, IGF-I, and IGF-II (see, e.g., Isaacs et al., 2001, Rheumatology, 40: 724-738; Soubrane et al., 1993, Blood, 81(1): 15-19).

T cell modulation may also be evaluated by measuring (e.g., proliferation) by, for example, 3H-thymidine incorporation, trypan blue cell counts, and fluorescence activated cell sorting (FACS™).

The anti-tumor responses of T cells after exposure to the heterodimeric inactivatable CAR may be determined in xenograft tumor models. Tumors may be established using any human cancer cell line expressing the tumor associated antigen presented by the heterodimeric inactivatable CAR. In order to establish xenograft tumor models, about 5 $\times10^6$ viable cells, may be injected, e.g., s.c., into nude athymic mice using for example Matrigel® (Becton Dickinson). The endpoint of the xenograft tumor models can be determined based on the size of the tumors, weight of animals, survival time and histochemical and histopathological examination of the cancer, using methods known to one skilled in the art.

The anergic state or death of T cells after exposure to the heterodimeric inactivatable CARs described herein, e.g., which may be useful for treatment of inflammatory and autoimmune disorders, can be tested in vitro or in vivo by, e.g., 51Cr-release assays. The ability to mediate the depletion of peripheral blood T cells can be assessed by, e.g., measuring T cell counts using flow cytometry analysis.

Non-limiting examples of useful animal models for analyzing the effect of the exposure of T cells to the heterodimeric inactivatable CARs described herein on inflammatory diseases include adjuvant-induced arthritis rat models, collagen-induced arthritis rat and mouse models and antigen-induced arthritis rat, rabbit and hamster models (see, e.g., Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993); Trenthorn et al., 1977, J. Exp. Med. 146:857; Courtenay et al., 1980, Nature 283:665; Cathcart et at, 1986, Lab. Invest. 54:26; Holmdahl, R., 1999, Curr. Biol. 15:R528-530). Other useful animal models of inflammatory diseases include animal models of inflammatory bowel disease, ulcerative cholitis and Crohn's disease induced, e.g., by sulfated polysaccharides (e.g., amylopectin, carrageen, amylopectin sulfate, dextran sulfate) or chemical irritants (e.g., trinitrobenzenesulphonic acid (TNBS) or acetic acid). See, e.g., Kim et al., 1992, Scand. J. Gastroentrol. 27:529-537; Strober, 1985, Dig. Dis. Sci. 30(12 Suppl):3S-10S).

Additional useful models are animal models for asthma such as, e.g., adoptive transfer model in which aeroallergen provocation of TH1 or TH2 recipient mice results in TH effector cell migration to the airways and is associated with an intense neutrophilic (TH1) and eosinophilic (TH2) lung mucosal inflammatory response (see, e.g., Cohn et al., 1997, J. Exp. Med. 1861737-1747). Useful animal models of studying the effect of the heterodimeric inactivatable CARs of the invention on multiple sclerosis (MS) include an experimental allergic encephalomyelitis (EAE) model (see, e.g., Zamvil et al, 1990, Ann. Rev, Immunol. 8:579). Animal models which can be used for analyzing the effect of the heterodimeric inactivatable CARs of the invention on autoimmune disorders such as type 1 diabetes, thyroid autoimmunity, systemic lupus eruthematosus, and glomerulonephritis have been also developed (see, e.g., Bluestone et al., 2004, PNAS 101:14622-14626; Flanders et al., 1999, Autoimmunity 29:235-246; Krogh et al., 1999, Biochimie 81:511-515; Foster, 1999, Semin. Nephrol. 19:12-24).

Efficacy of a heterodimeric inactivatable CAR to downregulate immune responses in treating an autoimmune disorder may be evaluated, e.g., by detecting their ability to reduce one or more symptoms of the autoimmune disorder, to reduce mean absolute lymphocyte counts, to decrease T cell activation, to decrease T cell proliferation, to reduce cytokine production, or to modulate one or more particular cytokine profiles (e.g., Interleukin-2 (IL-2). Interleukin-4 (IL-4), Interleukin-6 (IL-6), Interleukin-12 (IL-12), Interleukin-16 (IL-16), PDGF, TGF-α, TGF-β, TNF-α, TNF-β, GCSF, GM-CSF, MCSF, IFN-α, IFN-β, IFN-γ, TFN-γ, IGF-I, and IGF-II) (see, e.g., Isaacs et al., 2001, Rheumatology, 40: 724-738; Soubrane et al., 1993, Blood, 81(1): 15-19).

Efficacy of the heterodimeric inactivatable CARs for use in treating diabetes may be evaluated, e.g. by the ability of the heterodimeric inactivatable CARs to reduce one or more symptoms of diabetes, to preserve the C-peptide response to MMTT, to reduce the level HAT or HA1c, to reduce the daily requirement for insulin, or to decrease T cell activation in pancreatic islet tissue. Efficacy in treating arthritis may be assessed through tender and swollen joint counts, determination of a global scores for pain and disease activity, ESRICRP, determination of progression of structural joint damage (e.g., by quantitative scoring of X-rays of hands, wrists, and feet (Sharp method)), determination of changes in functional status (e.g., evaluated using the Health Assessment Questionnaire (HAQ)), or determination of quality of life changes (assessed, e.g., using SF-36).

In a related aspect, disclosed herein is a method of treating a disorder in a subject in need thereof comprising administering to said subject an effective amount of the heterodimeric inactivatable CAR, wherein the heterodimeric inactivatable CAR binds to an antigen-specific TCR and wherein the antigen is associated with the disorder. In some embodiments, the disorder is an inflammatory or an autoimmune disorder, and the administration results in a downregulation of an inflammatory or autoimmune response. In one specific embodiment, the disorder is celiac disease or gluten sensitivity. In one specific embodiment, the antigen comprises a gliadin or a fragment thereof (e.g., (i) α-gliadin fragment corresponding to amino acids 57-73 or (ii) γ-gliadin fragment corresponding to amino acids 139-153 or (iii) ω-gliadin fragment corresponding to amino acids 102-118). In one specific embodiment, the heterodimeric inactivatable CAR presents a peptide derived from the antigen in the context of a class II MHC. In some embodiments, the disorder is a tumor and the administration results in an upregulation of an anti-tumor immune response.

CAR T cells comprising the heterodimeric inactivatable CARs described herein can eliminate auto-reactive B cells. CAR T cells comprising the heterodimeric inactivatable CARs described herein can be used to dampen immune responses, which may be useful in the context of GVHD, autoimmunity or transplantation tolerance.

In a recent study, permanent and profound B cell depletion by CD19-targeted CAR T cells lead to lasting remission of experimental lupus. In two mouse strains that are reliable models of SLE and that differ in the underlying genetic mechanisms leading to autoimmunity, sustained CD19+ B cell depletion prevented autoantibody production, alleviated manifestations of lupus pathogenesis, and lengthened life spans. Kansal et al., Sci. Transl. Med., 2019, eaav1648.

In another embodiment, the disorder is an infection caused by an infectious agent and the administration results in an upregulation of an immune response against the infectious agent. In one specific embodiment, the infectious agent is selected from the group consisting of a virus, a bacterium, a fungus, a protozoa, a parasite, a helminth, and an ectoparasite. In one specific embodiment, the infectious agent is lymphocytic choriomeningitis virus (LCMV) and the antigen is gp33 protein. In one specific embodiment, the heterodimeric inactivatable CAR presents a peptide derived from the antigen in the context of a class I MHC. In some embodiments, the subject is a mammal (e.g., human).

According to certain aspects, a heterodimeric inactivatable CAR may be used to treat a cancer in which the tumor cells express a tumor-associated antigen, for example, a tumor-associated antigen selected from the group consisting of adipophilin, AIM-2, ALDH1A1, alpha-actinin-4, alpha-fetoprotein ("AFP"), ARTC1, ALK, BAGE proteins (e.g., BAGE-1), BIRC5 (survivin), BIRC7, β-catenin, BRCA1, BORIS, B-RAF, BCLX (L), BCR-ABL fusion protein b3a2, beta-catenin, BING-4, CA-125, CALCA, carcinoembryonic antigen ("CEA"), CAGE-1 to 8, CASP-5, CASP-8, CD274, CD45, Cdc27, CDK12, CDK4, CDKN2A, CEA, CLPP, COA-1, CPSF, CSNK1A1, CTAG1, CTAG2, cyclin D1, Cyclin-A1, CA9, carbonic anhydrase IX, caspase-8, CALR, CCR5, CD19, CD20 (MS4A1), CD22, CD40, CD70, CDK4, cyclin-B1, CYP1B1, dek-can fusion protein, DKK1, EFTUD2, Elongation factor 2, ENAH (hMena), EphA3, epithelial tumor antigen ("ETA"), EGFR, EGFRvIII, ErbB2/Her2, ErbB3, ErbB4, ETV6-AML1 fusion protein, EpCAM, EphA2, EZH2, FGF5, FLT3-ITD, FN1, Fra-1, FOLR1, G250/MN/CAIX, GAGE proteins (e.g., GAGE-1-8), GD2, GD3, GloboH, glypican-3, GM3, gp100, GAS7, GnTV, gp100/Pme117, GPNMB, GnTV, HAUS3, Hepsin, HERV-K-MEL, HLA-All, HLA-A2, HLA-DOB, hsp70-2, HPV E2, HPV E6, HPV E7, HPV EG, Her2/neu, HLA/B-raf, HLA/k-ras, HLA/MAGE-A3, hTERT, IDO1, IGF2B3, IL13Ralpha2, Intestinal carboxyl esterase, K-ras, Kallikrein 4, KIF20A, KK-LC-1, KKLC1, KM-HN-1, KMHN1 also known as CCDC110, LAGE-1, LDLR-fucosyltransferase AS fusion protein, Lengsin, LMP2, M-CSF, MAGE proteins (e.g., MAGE-A1, -A2, -A3, -A4, -A6, -A9, -A10, -A12, -C1, and -C2), malic enzyme, mammaglobin-A, MART-1, MART-2, MATN, MC1R, MCSP, mdm-2, ME1, Melan-A/MART-1, Meloe, Midkine, MMP-2, MMP-7, mesothelin, ML-IAP, Muc1, Muc2, Muc3, Muc4, Muc5, Muc16 (CA-125), MUC5AC, MUM-1, MUM-2, MUM-3, Myosin, Myosin class I, N-raw, NA88-A, neo-PAP, NFYC, NA17, NA-88, NY-BR1, NY-BR62, NY-BR85, NY-ESO1/LAGE-2, OA1, OGT, OS-9, P polypeptide, p15, p53, PAP, PAX3, PAX5, PCTA-1, PLAC1, PRLR, PRAME, PSMA (FOLH1), PBF, pml-RARalpha fusion protein, polymorphic epithelial mucin ("PEM"), PPP1R3B, PRDX5, PSA, PSMA, PTPRK, RAB38/NY-MEL-1, RBAF600, RGS5, RhoC, RNF43, RU2AS, RAGE proteins (e.g., RAGE-1), Ras, RGS5, Rho, SART-1, SART-3, STEAP1, STEAP2, SAGE, secernin 1, SIRT2, SNRPD1, SOX10, Sp17, SPA17, SSX-2, SSX-4, STEAP1, survivin, SYT-SSX1 or -SSX2 fusion protein, TAG-1, TAG-2, TAG-72, TGF-β, TMPRSS2, Thompson-nouvelle antigen (Tn), TRP-1/gp75, TRP-2, TRP2-INT2, tyrosinase, Telomerase, TPBG, TRAG-3, Triosephosphate isomerase, uroplakin-3, VEGF, XAGE-lb/GAGED2a, WT-1, NeuGcGM3, N-glycolyl GM3 ganglioside, Neu5Gc, GM3-Ganglioside, GD3, GM2, carbohydrate antigens, ganglioside antigens, Lewis Y, and Lewis B, CD123 and Kappa chain of immunoglobulin. In some embodiments, the peptide is a neo-antigen. In some embodiments, the peptide is a tumor specific antigen.

Specific cancers/tumors treatable by the methods and heterodimeric inactivatable CARs of the present invention include, without limitation, various solid malignancies, carcinomas, lymphomas, sarcomas, blastomas, and leukemias. Non-limiting specific examples, include, for example, breast cancer, pancreatic cancer, liver cancer, lung cancer, prostate cancer, colon cancer, renal cancer, bladder cancer, head and neck carcinoma, thyroid carcinoma, soft tissue sarcoma, ovarian cancer, primary or metastatic melanoma, squamous cell carcinoma, basal cell carcinoma, brain cancers of all histopathologic types, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, Ewing's tumor, leiomyosarcoma, Ewing's sarcoma, rhabdomyosarcoma, carcinoma of unknown primary (CUP), squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, cervical cancer, testicular tumor, glioma, glioblastoma, astrocytoma, medulloblastoma, craniopharyngioma, ependymoma, pinealoma, hemangioblastoma, acoustic neuroma, oligodendroglioma, meningioma, retinoblastoma, leukemia, neuroblastoma, small cell lung carcinoma, bladder carcinoma, lymphoma, multiple myeloma, medullary carcinoma, B cell lymphoma, T cell lymphoma, NK cell lymphoma, large granular lymphocytic lymphoma or leukemia, gamma-delta T cell lymphoma or gamma-delta T cell leukemia, mantle cell lymphoma, myeloma, leukemia, chronic myeloid leukemia, acute myeloid leukemia, chronic lymphocytic leukemia, acute lymphocytic leukemia, hairy cell leukemia, hematopoietic neoplasias, thymoma, sarcoma, non-Hodgkin's lymphoma, Hodgkin's lymphoma, Epstein-Barr virus (EBV) induced malignancies of all typies including but not limited to EBV-associated Hodkin's and non-Hodgkin's lymphoma, all forms of post-transplant lymphomas including post-transplant lymphoproliferative disorder (PTLD), uterine cancer, renal cell carcinoma, hepatoma, hepatoblastoma, Cancers that may treated by methods and compositions described herein include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The present invention also includes methods for treating residual cancer in a subject. As used herein, the term "residual cancer" means the existence or persistence of one or more cancerous cells in a subject following treatment with an anti-cancer therapy.

Non-limiting examples of the inflammatory and autoimmune diseases include, but are not limited to, inflammatory bowel disease (IBD), ulcerative colitis (UC), Crohn's disease, diabetes (e.g., diabetes mellitus type 1), multiple sclerosis, arthritis (e.g., rheumatoid arthritis), Graves' disease, lupus erythematosus, ankylosing spondylitis, psoriasis, Behcet's disease, autistic enterocolitis, Guillain-Barre Syndrome, myasthenia gravis, pemphigus vulgaris, acute disseminated encephalomyelitis (ADEM), transverse myelitis autoimmune cardiomyopathy, Celiac disease, dermatomyositis, Wegener's granulomatosis, allergy, asthma, contact dermatitis, atherosclerosis (or any other inflammatory condition affecting the heart or vascular system), autoimmune uveitis, as well as other autoimmune skin conditions, autoimmune kidney, lung, or liver conditions, autoimmune neuropathies, asthma, allergy, celiac disease, systemic lupus erythematosis (SLE), scleroderma, sarcoidosis, thyroiditis, multiple sclerosis, spondylitis, periarteritis, eczema, atopic dermatitis, myasthenia gravis, insulin-dependent diabetes mellitus, Crohn's disease, Guillain-Barre syndrome, Graves' disease, glomerulonephritis, ulcerative colitis, Crohn's disease, sprue, autoimmune arthritis, rheumatoid arthritis, osteoarthritis, juvenile chronic arthritis, psoriatic arthritis, reactive arthritis, spondyloarthropathy, psoriasis, acute or chronic immune disease associated with organ transplantation, an inflammatory disease, skin or organ transplantation rejection, graft-versus-host disease (GVHD), or autoimmune diseases, comprising administering to a subject a pharmaceutical composition described herein (e.g., a pharmaceutic composition comprising a heterodimeric inactivatable CAR described herein. Examples of autoimmune diseases include, for example, glomerular nephritis, arthritis, dilated cardiomyopathy-like disease, ulceous colitis, Sjogren syndrome, Crohn's disease, systemic erythematodes, chronic rheumatoid arthritis, multiple sclerosis, psoriasis, allergic contact dermatitis, polymyosiis, pachyderma, periarteritis nodosa, rheumatic fever, vitiligo vulgaris, insulin dependent diabetes mellitus, Behcet disease, Hashimoto disease, Addison disease, dermatomyositis, myasthenia gravis, Reiter syndrome, Graves' disease, anaemia perniciosa, sterility disease, chronic active hepatitis, pemphigus, autoimmune thrombopenic purpura, and autoimmune hemolytic anemia, active chronic hepatitis, Addison's disease, antiphospholipid syndrome, atopic allergy, autoimmune atrophic gastritis, achlorhydra autoimmune, celiac disease, Cushing's syndrome, dermatomyositis, discoid lupus, erythematosis, Goodpasture's syndrome, Hashimoto's thyroiditis, idiopathic adrenal atrophy, idiopathic thrombocytopenia, insulin-dependent diabetes, Lambert-Eaton syndrome, lupoid hepatitis, some embodiments of lymphopenia, mixed connective tissue disease, pemphigoid, pemphigus vulgaris, pernicious anemia, phacogenic uveitis, polyarteritis nodosa, polyglandular autosyndromes, primary biliary cirrhosis, primary sclerosing cholangitis, Raynaud's syndrome, relapsing polychondritis, Schmidt's syndrome, limited scleroderma (or crest syndrome), sympathetic ophthalmia, systemic lupus erythematosis, Takayasu's arteritis, temporal arteritis, thyrotoxicosis, type b insulin resistance, ulcerative colitis and Wegener's granulomatosis.

In another embodiment, the methods described herein are used for treating or preventing a transplantation-related condition. In another embodiment, the methods described herein are used for treating or preventing graft-versus-host disease. In another embodiment, the methods described herein are used for treating or preventing a post-transplant lymphoproliferative disorder.

According to certain aspects, the heterodimeric inactivatable CAR may be used to treat an infection, such as a bacterial infection (e.g.. a bacterial infection resistant to conventional antibiotics) or a viral infection. In particular embodiments, the heterodimeric inactivatable CAR is designed to present a peptide derived from a viral antigen or a bacterial antigen. In some embodiments, the viral antigen is derived from a virus selected from the group consisting of adenovirus, astrovirus, chikungunya, cytomegalovirus, dengue, ebola, EBV, hantavirus, HBsAg, hepatitis A, hepatitis B, hepatitis C, hepatitis D, hepatitis E, herpes, HIV, HPIV, HTLV, influenza, Japanese encephalitis virus, lassa, measles, metapneumovirus, mumps, norovirus, oropauche, HPV, parvovirus, rotavirus, RSV, rubella, SARS, TBEV, usutu, vaccina, varicella, West Nile, yellow fever, and zika. In some embodiments, the bacterial antigen is derived from a bacterium selected from the group consisting of methicillin-resistant *Staphylococcus Aureus* (MRSA), *Clostridium Difficile*, carbapenum-resistant Enterobacteriaceae, drug-resistant *Neisseria Gonorrhoeae*, multidrug-resistant *Acinetobacter*, drug-resistant *Campylobacter*, Fluconazole-resistant *Candida*, extended-spectrum β-lactamase producing bacteria, Vancomycin-resistant *enterococcus*, multidrug-resistant *pseudomonas Aeruginosa*, drug-resistant non-typhoidal *Salmonella*, drug-resistant *Salmonella* serotype *typhi*, drug-resistant *Shigella*, drug-resistant *Streptococcus Pneumoniae*, drug-resistant tuberculosis, Vancomycin-resistant *Staphylococcus Aureus*, Erythomycin-resistant group A *Streptococcus*, and Clindamycin-resistant group B *Streptococcus*.

Heterodimeric inactivatable CARs designed to treat cancer or an infection may include an antigen-binding domain (e.g., a one-arm antibody) on the second binding molecule that specifically binds a T-cell co-stimulatory molecule (e.g., CD28) to induce activation, proliferation (e.g., clonal expansion) and/or survival of T cells (e.g., CD8+ T cells) specific for the peptide presented on the first binding molecule. In some embodiments, T cell activation is revived. In some embodiments, naïve T-cells are activated or caused to proliferate. Such T cells can enhance or stimulate an immune response against cells (e.g., tumor cells or infected cells) expressing a protein comprising the peptide presented on the first binding molecule of the heterodimeric inactivatable CAR. In various embodiments, the heterodimeric inactivatable CARs do not induce proliferation of non-specific T cells (i.e., T cells that are not specific for the peptide presented on the first binding molecule).

According to certain aspects, the heterodimeric inactivatable CAR may be used to treat, prevent, or ameliorate an autoimmune disease or disorder by targeting the activity of T cells with specificity for a peptide corresponding to an antigen associated with the autoimmune disease or disorder. For example, the antigen may be selected from the group consisting of gliadin (celiac disease; e.g., (i) α-gliadin fragment corresponding to amino acids 57-73 or (ii) γ-gliadin fragment corresponding to amino acids 139 153 or (iii) w-gliadin fragment corresponding to amino acids 102-118), GAD 65, IA-2 and insulin B chain (for type 1-diabetes), glatiramer acetate (GA) (for multiple sclerosis), achetylcholine receptor (AChR) (for myasthenia gravis), p205, insulin, thyroid-stimulating hormone, tyrosinase, TRP1, and myelin antigens (including myelin basic protein (MBP) and proteolipid protein (PLP)). In some embodiments, the antigen may be IL-4R, IL-6R, or DLL4.

Heterodimeric inactivatable CARs designed to treat an autoimmune disorder may include an antigen-binding domain (e.g., a one-arm antibody) on the second binding molecule that specifically binds a T-cell co-inhibitory molecule (e.g., CTLA-4, LAG3, PD1, etc.) to suppress the activity of T cells (e.g., CD4+ T cells) specific for the peptide presented on the first binding molecule. Inhibition or suppression of such T cell activity can treat, alleviate, or prevent recurrence of, autoimmune diseases or disorders in which the cells targeted by the individual's immune system express a protein comprising the peptide presented on the first binding molecule of the heterodimeric inactivatable CAR. In some embodiments, administration of a heterodimeric inactivatable CAR of the present invention can be used to make an individual's T cells tolerant of a self-antigen for which the T cells are specific.

The present invention also includes use of the heterodimeric inactivatable CARs herein in the manufacture of a medicament for preventing, treating and/or ameliorating an infection, a cancer, or an autoimmune disorder (e.g., as discussed herein).

In one aspect is provided a method for stimulating elimination of a cell comprising an antigen in a subject in need thereof. The method comprises administering to the subject an effective amount of cytotoxic T cells or natural killer (NK) cells comprising any heterodimeric CAR described herein, wherein the extracellular target-binding region of said CAR binds to said antigen.

The antigen may be a cancer cell associated antigen, an infection-associated antigen or an auto-antigen. The antigen may be a cancer cell associated antigen. The cancer cell associated antigen may be associated with a solid tumor. The cancer cell associated antigen may be a prostate-specific membrane antigen (PSMA). The antigen may be an infection-associated antigen. The antigen may be an auto-antigen. The antigen may be CD19. The antigen may be NeuGcGM3 or N-glycolyl GM3 ganglioside.

In another aspect is provided a method for stimulating elimination of a cell comprising prostate-specific membrane antigen (PSMA) in a subject in need thereof. The method comprises administering to the subject an effective amount of cytotoxic T cells or natural killer (NK) cells comprising a heterodimeric inactivatable CAR described herein.

In another aspect is provided a method for treating a cancer in a subject in need thereof. The method comprises administering to the subject a therapeutically effective amount of cytotoxic T cells or natural killer (NK) cells comprising any heterodimeric inactivatable chimeric antigen receptor (CAR) described herein, wherein the extracellular target-binding region of said CAR binds to an antigen associated with said cancer. The cancer may be from a solid tumor. The cancer may be carcinoma, melanoma, prostate cancer, sarcoma, glioma, astrocytoma, medulloblastoma, craniopharyngioma, ependymoma, pinealoma, hemangioblastoma, acoustic neuroma, oligodendroglioma, menangioma, neuroblastoma, or retinoblastoma. The cancer may be a leukemia or a lymphoma.

In another aspect is provided a method for treating prostate cancer in a subject in need thereof. The method comprises administering to the subject a therapeutically effective amount cytotoxic T cells or natural killer (NK) cells comprising any heterodimeric inactivatable CAR described herein. In some embodiments, the extracellular target-binding region of said CAR binds to an antigen associated with said infection.

In another aspect is provided a method for treating an inflammatory condition or an autoimmune disease in a subject in need thereof. The method comprises administering to the subject a therapeutically effective amount of T-helper cells or Treg cells comprising any heterodimeric inactivatable CAR described herein. The extracellular target-binding region of the CAR binds to an antigen associated with said inflammatory condition or an autoimmune disease. The method may result in reducing an immune response to a transplanted organ or tissue.

The method may comprise a) isolating T cells or NK cells from the subject; b) genetically modifying said T cells or NK cells ex vivo with any nucleic acid molecule or any vector described herein. The T cells or NK cells may be expanded or activated before, after or during step (b). The genetically modified T cells or NK cells are introduced into the subject.

The above methods may further comprise inhibiting the activity of the CAR by administering to the subject an effective amount of an inhibitory molecule that disrupts the heterodimer formed by the first and second member of the dimerization pair within the CAR resulting in inhibition of CAR-mediated signaling.

In various embodiments, the subject is human.

According to certain embodiments of the present invention, multiple doses of a heterodimeric inactivatable CAR may be administered to a subject over a defined time course. The methods according to this aspect of the invention comprise sequentially administering to a subject multiple doses of a heterodimeric inactivatable CAR of the invention. As used herein, "sequentially administering" means that each dose of a heterodimeric inactivatable CAR is administered to the subject at a different point in time, e.g., on different days separated by a predetermined interval (e.g., hours, days, weeks or months). The present invention includes methods which comprise sequentially administering to the patient a single initial dose of a heterodimeric inactivatable CAR, followed by one or more secondary doses of the heterodimeric inactivatable CAR, and optionally followed by one or more tertiary doses of the heterodimeric inactivatable CAR.

The terms "initial dose," "secondary doses," and "tertiary doses," refer to the temporal sequence of administration of the heterodimeric inactivatable CAR. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the heterodimeric inactivatable CAR, but generally may differ from one another in terms of frequency of administration. In certain embodiments, however, the amount of a heterodimeric inactivatable CAR contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of heterodimeric inactivatable CAR which is administered to a patient prior to the administration of the very next dose in the sequence with no intervening doses.

The methods according to this aspect of the invention may comprise administering to a patient any number of secondary and/or tertiary doses of a heterodimeric inactivatable CAR. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Inhibition of CAR Activity

Also provided is a method for inhibiting the activity of the heterodimeric inactivatable chimeric antigen receptor (CAR) in any host cell described herein. The method comprises contacting the host cell with an inhibitory molecule that disrupts the heterodimer formed by the first and second member of the dimerization pair within the CAR, resulting in inhibition of CAR-mediated signaling. The inhibitory molecule may be a small molecule or a polypeptide. The inhibitory molecule may bind to the first or second member of the dimerization pair with higher affinity than the first and second member of the dimerization pair bind to each other. In some embodiments, the inhibitory molecule binds to the first member of the dimerization pair. In some embodiments, the inhibitory molecule binds to the second member of the dimerization pair. In some embodiments, the inhibitory molecule is a BcL-xL and/or BCL-2 inhibitor. The first or the second member of the dimerization pair may comprise a BCL-xL sequence, a BCL-2 sequence, or a mutant of either, and the inhibitory molecule is a BcL-xL and/or BCL-2 inhibitor.

In various embodiments, the BCL-xL inhibitor or mutants thereof is navitoclax, A-1331852, A-1155463, venetoclax, ABT-199 (GDC-0199), obatoclax mesylate (GX15-070), HA14-1, ABT-737, TW-37, AT101, sabutoclax, gambogic acid, ARRY 520 trifluoroacetate, iMAC2, maritoclax, methylprednisolone, MIM1, ML 311, glossypol, BH3I-1, or 2-methoxy-antimycin A3 or derivatives thereof. In some embodiments, the BCL-xL or mutants thereof, inhibitor is A-1331852 or A-1155463 or derivatives thereof. In various embodiments, the BCL-2, or mutants thereof, inhibitor is navitoclax, A-1331852, A-1155463, venetoclax, ABT-199 (GDC-0199), obatoclax mesylate (GX15-070), HA14-1, ABT-737, TW-37, AT101, sabutoclax, gambogic acid, ARRY 520 trifluoroacetate, iMAC2, maritoclax, methylprednisolone, MIM1, ML 311, glossypol, BH3I-1, or 2-methoxy-antimycin A3 or derivatives thereof. In some embodiments, the BCL-2, or mutants thereof, inhibitor is A-1331852 or A-1155463 or derivatives thereof.

In some embodiments, the BCL-xL, or mutants thereof, inhibitor is venetoclax or derivatives thereof. In some embodiments, the BCL-2, or mutants thereof, inhibitor is venetoclax or derivatives thereof. Venetoclax is an orally bioavailable, selective small molecule inhibitor of the anti-apoptotic protein Bcl-2, with potential antineoplastic activity. Venetoclax is an antineoplastic agent used in the therapy of refractory chronic lymphocytic leukemia (CLL). The IUPAC name for venetoclax is 4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo[2,3-b]pyridin-5-yloxy)benzamide. The chemical structure of venetoclax is as follows:

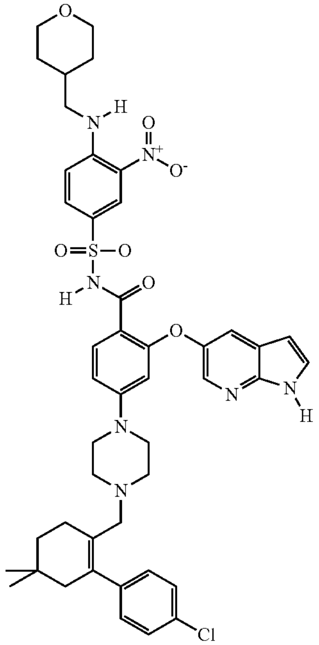

Without wishing to be bound by theory venetoclax mimics BH3-only proteins, the native ligands of Bcl-2 and apoptosis activators, by binding to the hydrophobic groove of Bcl-2 proteins thereby repressing Bcl-2 activity and restoring apoptotic processes in tumor cells. Bcl-2 protein is overexpressed in some cancers and plays an important role in the regulation of apoptosis; its expression is associated with increased drug resistance and tumor cell survival. Compared to the Bcl-2 inhibitor navitoclax, venetoclax does not inhibit bcl-XL and does not cause bcl-XL-mediated thrombocytopenia.

ScFv

In various embodiments, the scFV comprises an anti-PSMA scFv. An exemplary anti-PSMA scFV sequence comprises, consists of, or consists essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 6.

In various embodiments, the scFV comprises an anti-CD19 scFv. An exemplary anti-CD19 scFV sequence comprises, consists of, or consists essentially of the sequence at least 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 49.

In some embodiments, the scFV comprises a 14F7-derived scFv that targets NGcGM3. Additional information on 14F7 can be found in Bjerregaard-Andersen, K., Sci. Rep. 2018, 10836, incorporated by reference herein in its entirety. Exemplary scFV include, but are not limited to, those comprising: (i) a VH domain fused to a second VH domain, (ii) a VH domain fused to a linker, wherein the linker is fused to a second VH, (iii) a VH domain fused to a 7AH domain, (iv) a VH domain fused to a linker, wherein the linker is fused to a 7AH domain, (v) a VH domain fused to a 7BH domain, (vi) a VH domain fused to a linker, wherein the linker is fused to a 7BH domain, (vii) a VH domain fused to an 8BH domain, (viii) a VH domain fused to a linker, wherein the linker is fused to an 8BH domain, (ix) a VH domain fused to a 2Am domain, (x) a VH domain fused to a linker, wherein the linker is fused to a 2Am domain, (xi) a VH domain fused to a 3Fm domain, and (xii) a VH domain fused to a linker, wherein the linker is fused to a 3Fm domain. The VH domain may be a murine domain. 2Am and 3Fm are murine domains; 7AH, 7BH and 8BH are human domains. Exemplary components are listed in FIGS. 34A-34D and SEQ ID Nos: 44-48 and 50-63.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

A schematic representation of OFF-switch CAR (OFF-CAR) and its inhibition by a heterodimer disrupting molecule is shown in FIG. 1. The amino acid sequences and domains for OFF-CAR Chain A and Chain B used in the experiments are provided in FIG. 4 and FIG. 5, respectively.

BCL-xL (B cell lymphoma extra large) protein was used as an example of Protein B domain. Natural binding partner of BCL-xL is BimBH3. A search was conducted to identify proteins that do not interact with BCL-xL in vivo but include a similar structural conformation to the BimBH3 motif that interacts with BCL-xL. One of the identified proteins was Apolipoprotein E (ApoE). Residues in ApoE were then mutated so that it would have the same residues as BimBH3 in this binding domain in addition to other residues that are in the interface and might contribute to binding. The resulting mutant was named 1LE4A and represents an example of Protein A domain. Basically, 1LE4A is the BimBH3 binding domain on an ApoE scaffold. FIG. 2 shows BimBH3 binding domain in purple as well as 1LE4A in orange. KD of 1LE4A-BCL-xL binding is about 400 pM. Small molecule drug navitoclax which binds to BCL-xL with $K_D$ of about 10 pM (see FIG. 2) can be used as a possible inhibitor of the Protein A-Protein B (1LE4A-BCL-xL) interaction as it will out-compete the heterodimerizing interaction between 1LE4A and BCL-xL. It was also demonstrated by surface plasmon resonance that BCL-xL and 1LE4A could be disrupted by two potent and selective BCL-xL inhibitors, A1331852 and A1155463 (both have picomolar binding affinity for BCL-xL; Ki less than 0.01 nM according to abcam).

Lentiviral constructs encoding OFF-CAR chains (FIGS. 13 and 14) were used to transduce both a Jurkat NFAT promoter-mCherry reporter line (Jurkat), and primary human T cells obtained from healthy donors (HD18, HD19, HD20, and HD21) following activation with anti-CD3/anti-CD28 beads.

Figure 6A:
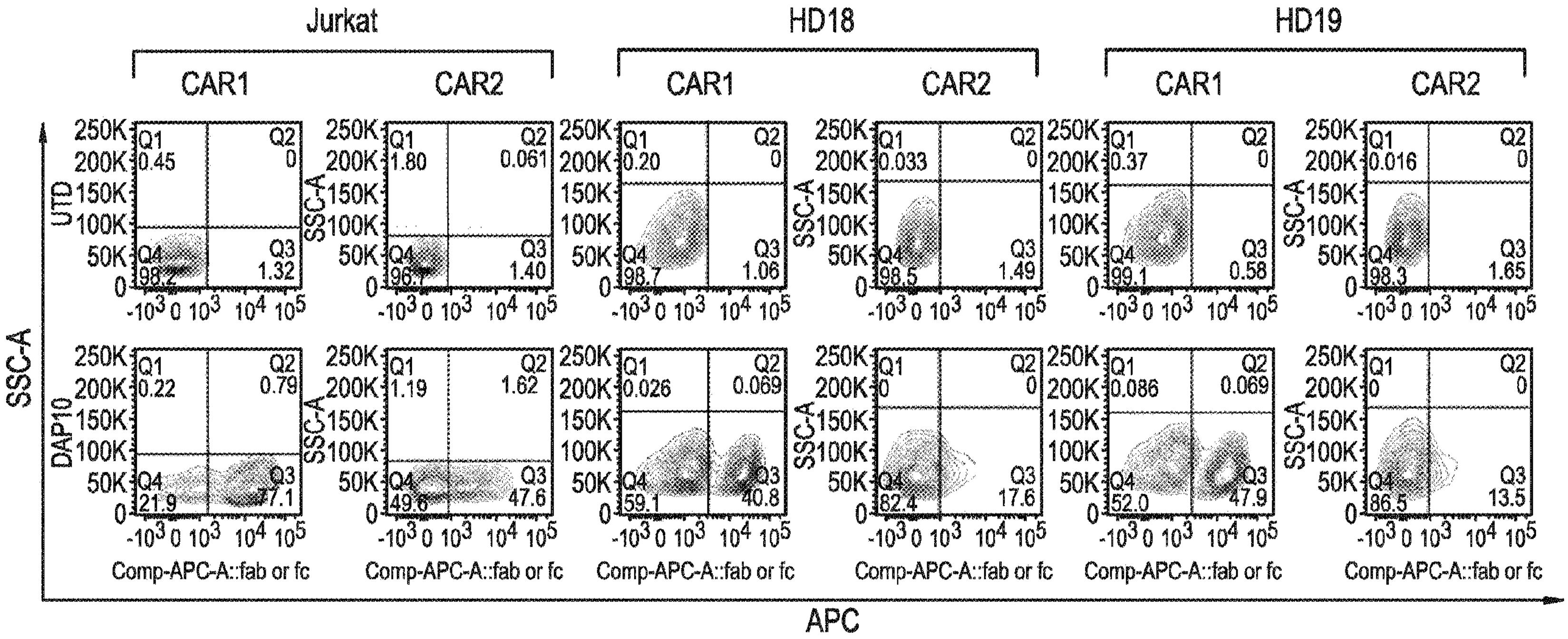
FIGS. 6A-6B show expression of the exemplary OFF-CAR by transduced Jurkat cells and primary T cells from healthy donors (HD). Both OFF-CAR Chain A (CAR1) and OFF-CAR Chain B (CAR2) were labeled with antibodies conjugated to APC, so their presence is denoted as the population on the right-hand side of the gate (more positive APC population). UTD=untransduced, control. HD=healthy donor (these are primary human T cells)
Figure 6B:
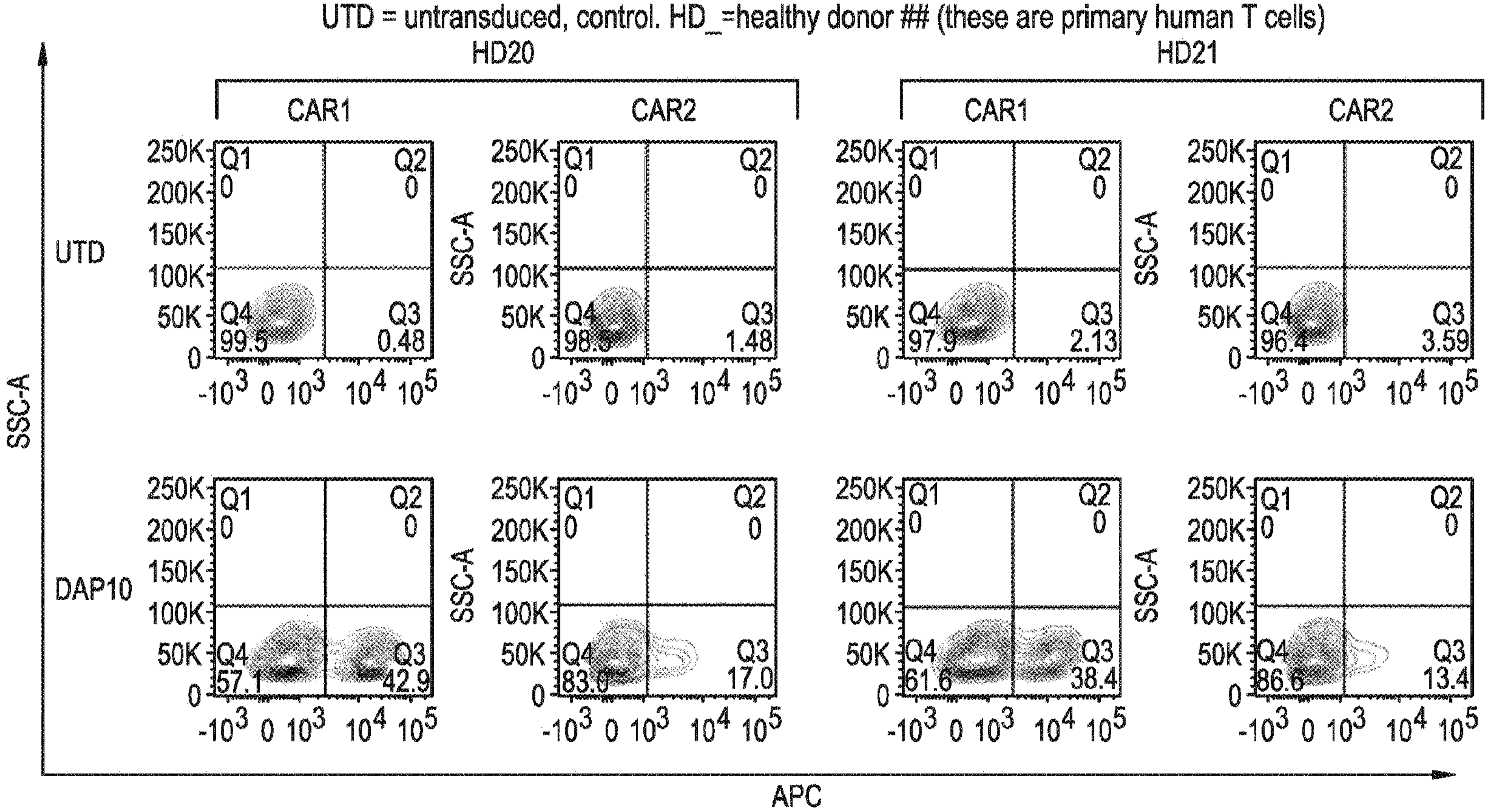

Flow cytometry was used to assess OFF-CAR cell-surface expression (FIGS. 6A-6B).

Figures 8A, 8B, 8C, 8D:
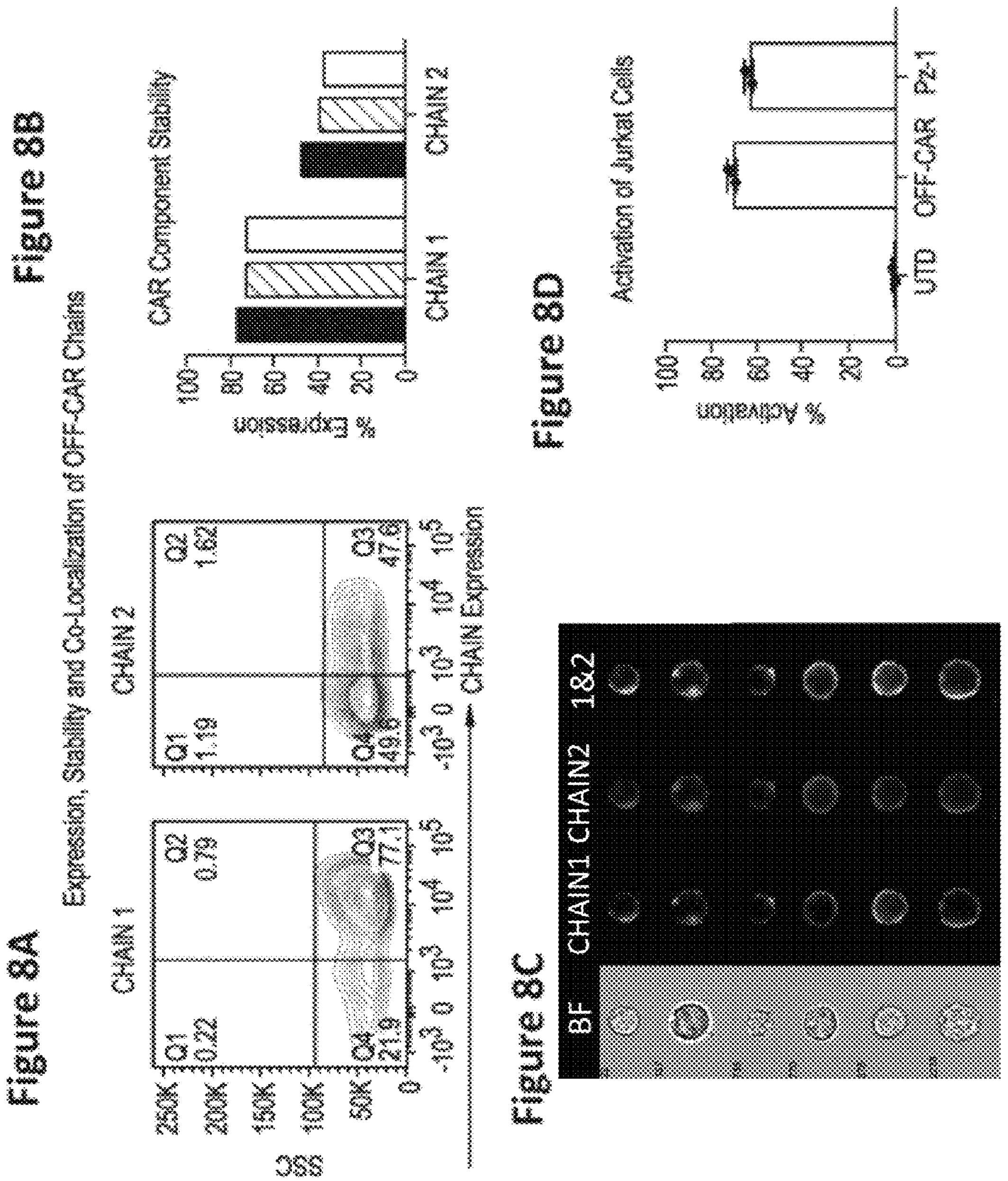
FIGS. 8A-8D show the cell-surface expression and function of OFF-CAR in Jurkat T cells.

AMNIS® imaging was used to visualize co-localization of OFF-CAR Chain A and Chain B (FIG. 7 and bottom left panel of FIG. 8). The degree of colocalization between two fluorescent probes can be assessed in a quantitative manner by performing cross-correlation analysis of the bright regions of pairs of images of the same cell. The Similarity score quantifies the degree of similarity between any two channels images on a pixel-by-pixel and cell-by-cell basis. This score is derived from the Pearson's correlation coefficient (PCC, p), which is based on a linear regression analysis of pairs of values taken from different data sources. A histogram was then created to depict the frequency of the similarity scores and then based on the distribution of the histogram the program calculates a gated colocalized population, leading to a percent colocalization, which was 910% for the tested OFF-CAR chains.

Figures 9A, 9B, 9C, 9D:
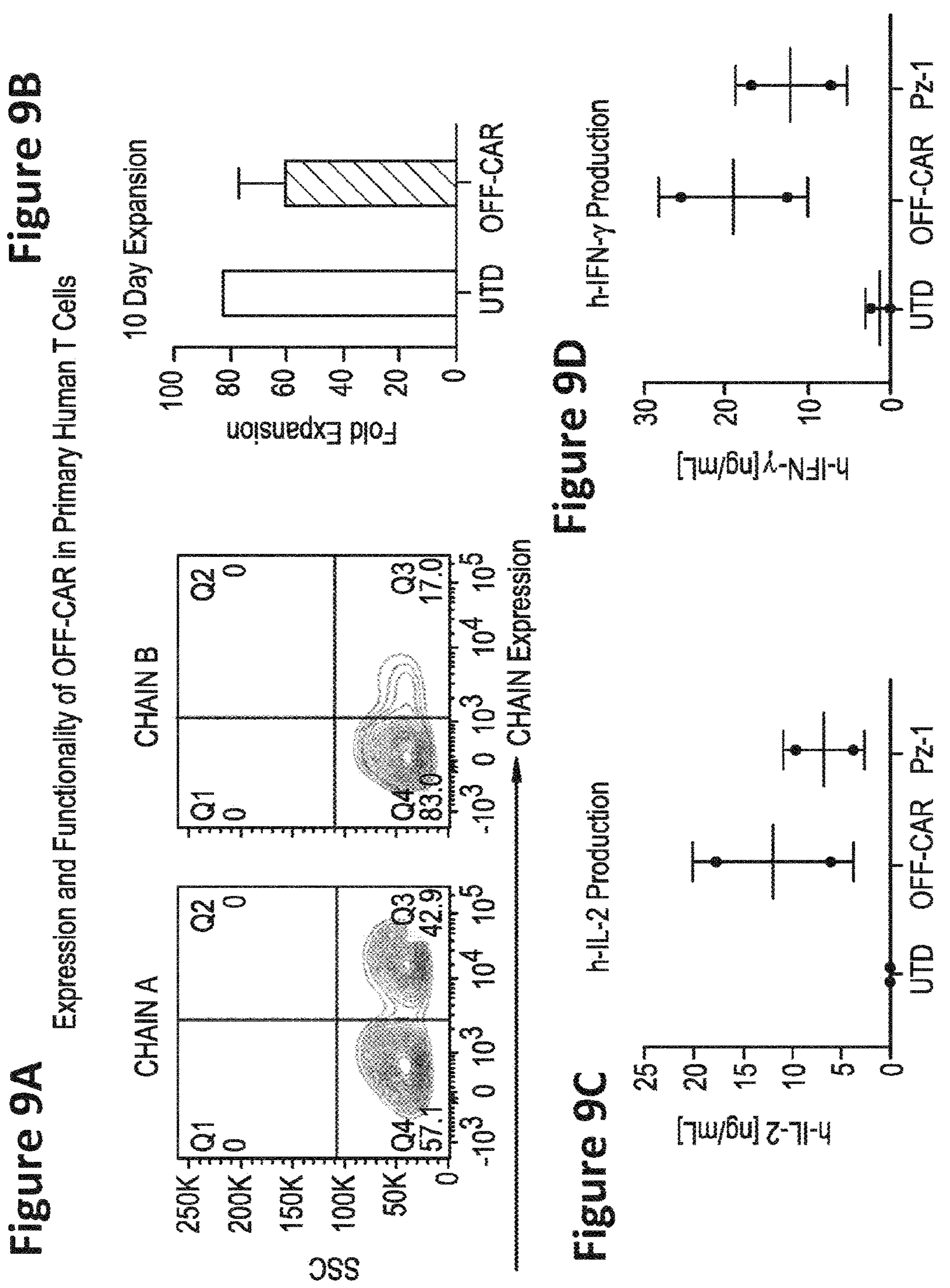
FIGS. 9A-9D show the cell-surface expression and function of OFF-CAR in primary human T cells.

Expression, stability and co-localization of the OFF-CAR Chain A and Chain B in Jurkat cells and primary human T cells were demonstrated (FIG. 8) by flow cytometry and AMNIS® imaging. The functionality of OFF-CAR-containing T cells was confirmed by assessing IL-2 and IFN-gamma production (FIG. 9). The OFF-CAR-containing T cells had comparable activity levels (similar cytotoxic effects) to classic second-generation CAR (Pz1)-containing T cells targeting the same antigen (prostate-specific membrane antigen (PSMA)).

FIGS. 10B-10C demonstrate that the cytotoxicity of the OFF-CAR T cells (but not of classic second-generation CAR (Pz1)-containing T cells) was inhibited by the addition of competitive small molecule inhibitors A-1331852 (FIG. 10B) and A-1155463 (FIG. 10C). The IncuCyte® instrument was used to measure tumor target cell killing by anti-PSMA OFF-CAR T cells versus second generation CAR T cells over time. Tumor cells are labeled with Cyotoxic Red reagent and turn red upon death. At 0 hours there was minimal tumor cell death in the plate wells, while at 48 hours there was significant tumor cell death caused by the OFF-CAR T cells and second generation CAR T cells. In the presence of two different inhibitory drugs (selective BCL-xL inhibitors, A1331852 and A1155463), target cell killing by the OFF-CAR T cells was abrogated, while the activity of second generation CAR T cells is less affected. FIG. 11 demonstrates that the addition of small molecule drugs that competitively bind to OFF-CAR Chain B (Drug 1=A-1331852 or Drug 2=A-1155463, at 10 μM) inhibits OFF-CAR T-cell mediated killing. There was no tumor cell killing by untransduced (UTD) T cells, and killing by the OFF-CARs was immediately abolished in the presence of inhibitory drugs.

Materials and Methods

OFF-CAR Construction

The two OFF-CAR chains (Chain A and Chain B) were synthesized as GeneArt™ gene-strings (Thermo Fischer Scientific) and cloned into a third-generation self-inactivating lentiviral expression vector, pELNS (FIG. 13), with expression driven by the elongation factor-1a (EF-1α) promoter. The anti-PSMA scFv derived from monoclonal antibody J591 was used as the tumor-targeting moiety on Chain A[52,53]. Chain A comprises a CD8a leader, the anti-PSMA scFv, CD8α hinge, CD28 TM, CD28 ED, a serine/glycine (SG) linker, protein A (1LE4A), and an SG linker. Chain B comprises CD8α linker, cMyc, DAP10 ectodomain, CD8a hinge, CD28 TM, CD28 ED, SG linker, Protein B (BCL-XL), SG linker, and CD3ζ.

Recombinant Lentivirus Production

High-titer replication-defective lentivirus were produced and concentrated for primary T cell transduction. Briefly, 24 hours before transfection, 293T human embryonic kidney (HEK) cells were seeded at $10\times10^6$ in T-150 tissue culture flask. All plasmid DNA was purified using the Endo-free Maxiprep kit (Invitrogen, Life Technologies). HEK cells were transfected with 7 μg pVSV-G (VSV glycoprotein expression plasmid), 18 μg of μg R874 (Rev and Gag/Pol expression plasmid), and 15 μg of pELNS transgene plasmid using a mix of Turbofect™ (Thermo Fisher Scientific AG) and Optimem media (Invitrogen, Life Technologies). The viral supernatant was harvested at 48 hours post-transfection. Viral particles were concentrated and resuspended in 0.4 ml by ultracentrifugation for 2.5 hours at 25,000 rpm followed by immediate snap freezing in dry ice.

Jurkat Cell Transduction

For Jurkat cell transduction, the cells were suspended at $1\times10^6$ cell/ml and seeded into 48-well plates at 500 μl/well. For each transfection, 50 μl of virus supernatant was mixed with protamine sulfate for a final concentration of 10 μg/ml. The cells were then incubated for 24 hours at 37° C. before replacement of half of the media and incubated for an additional 72 hours at 37° C.

Primary Human T Cell Transduction

Primary human T cells were isolated from the peripheral blood mononuclear cells (PBMCs) of healthy donors (prepared as buffycoats). All blood samples were collected with informed consent of the donors, and genetically-engineered with Ethics Approval from the Canton of Vaud to the laboratory of Dr. G. Coukos. Total PBMCs were obtained via Lymphoprep™ (Axonlab) separation solution, using a standard protocol of centrifugation, and CD4+ and CD8+ T cells were isolated using a negative selection kit coupled with magnetic beads separation (easySEP™, Stem Cell technology). T cells were then cultured in complete media (RPMI 1640 with Glutamax, supplemented with 10% heat-inactivated fetal bovine serum, 100 U/ml penicillin, 100 μg/ml streptomycin sulfate (Invitrogen, Life Technologies)), and stimulated with anti-CD3 and anti-CD28 mAbs coated beads (Life Technologies) in a ratio of 1:2, T cells: Beads. Twelve to twenty-four hours after activation, T cells were transduced with lentivirus particles at multiplicity of infection of ~5-10. The CD4+ and CD8+ T cells used for in vitro and in vivo experiments were mixed at a 1:1 ratio, activated, and transduced. Human recombinant interleukin-2 (h-IL2; Glaxo) was added every other day to obtain a 50 IU/ml final concentration until 5 days post stimulation (day +5). At day +5, magnetic beads were removed and h-IL2 was switched to h-IL15 at 10 ng/mL (Miltenyi Biotec GmbH). A cell density of 0.5-1×$10^6$ cells/ml was maintained for expansion. Rested engineered T cells were adjusted for identical transgene expression before all functional assays.

Cell Lines 293T, 22Rv1, and Jurkat cell lines were purchased from ATCC® and cultured in RPMI-1640 supplemented with 10% heat-inactivated FBS, 2 mmol/l L-glutamine, and 100 μg/ml penicillin, and 100 U/ml streptomycin. The 293T cell line was used for lentiviral packaging and preparation. 22Rv1 is a human prostate carcinoma cell line that expresses prostate-specific membrane antigen (PSMA). The Jurkat cell line was engineered to express a 6×NFAT-mCherry-reporter system such that upon activation the cells turn red.

Cytokine Release Assays

Cytokine release assays were performed by co-culture of 5×$10^4$ T cells with 5×$10^4$ target cells per well in duplicate in 96-well round bottom plates in a final volume of 200 μl of RPMI media. After 24 hours, co-culture supernatants were harvested and tested for presence of IFN-γ and IL2 using an ELISA Kit, according to the manufacturer's protocol (Biolegend).

The reported values represent the mean of OFF-CAR engineered T cells derived from four healthy donors (HD).

Cytotoxicity Assays

Cytotoxicity assays were performed using the IncuCyte® System (Essen Bioscience). Briefly, 1.5×$10^4$ target cells were seeded 18 hours before the co-culture set up, in flat bottom 96well plates (Costar, Vitaris). The following day, rested T cells (no cytokine addition for 48 hours) were counted and seeded at 3 ×$10^4$/well, at a ratio 1:2, target:T cells in complete media. No exogenous cytokine was added in the assay medium during the co-culture period. Cytotox Red reagent (Essen Bioscience) was added at a final concentration of 125 nM in a total volume of 200 ul. Internal experimental negative controls were included in all assays, including co-incubation of untransduced (UTD) and tumor cells, as well as tumor cells alone in the presence of Cytotoxic Red reagent to monitor spontaneous cell death over time. As a positive control, tumor cells alone were treated with 1% Triton™ solution to represent maximal killing in the assay. Images of total number of red cells or total red area/well were collected every two hours of the co-culture for a total of three days. The total number of red cells or total red area/well was obtained by using the software provided by the IncuCyte® manufacturer. Data are expressed as mean of four different HDs +/−standard deviation.

Flow Cytometric Analysis

To detect cell-surface expression of the two OFF-CAR chains, transduced cells were stained with fluorescently-labeled anti-human Fab mAb (to detect Chain 1) and fluorescently-labeled anti-human cMyc mAb and (to detect Chain 2). Aqua live Dye BV510 was used for viability staining. All mAbs were purchased from BD Biosciences. Tumor cell surface expression of PSMA was quantified by fluorescently-labeled anti-PSMA mAb and its comparative isotype. Acquisition and analysis was performed using a BD™ FACS LRSII with FACS DIVA™ software (BD Biosciences). AMNIS® imaging was used to evaluate the level of co-localization of the two OFF-CAR Chains. The FITC anti-human Fab, APC anti-human cMyc, and DAPI dead stain were used. IDEAs software was used to analyze the data and perform the co-localization analysis after gating on the live, single-cell, double-positive for FITC and APC lymphocytes.

Statistical Analysis

Student's t-test was used to evaluate differences in absolute numbers of transferred T cells, cytokine secretion, and specific cytolysis. Kaplan-Meier survival curves were compared using the log-rank test. GraphPad Prism 4.0 (GraphPad Software, La Jolla, CA) was used for statistical calculations. $P<0.05$ was considered significant.

Example 2

Chimeric antigen receptor (CAR) T cells have made remarkable advances in cancer therapy but unexpected toxicity and other adverse side-effects remain an important issue. To engineer safety, a synthetic high-affinity protein interface was computationally designed with minimal amino acid deviation from wild-type, which self-assembles but can be disrupted by a small molecule. The designed chemically disruptable heterodimer (CDH) was incorporated into a synthetic receptor, dubbed STOP-CAR, featuring an antigen-recognition chain and a CD3ζ-endodomain signaling chain. STOP-CAR-T cells exhibited similar activity to classic second-generation (2G) CAR-T cells in vitro and in vivo against tumors, while administration of the small-molecule drug disruptor, specifically inactivated the STOP-CAR-T cells. STOP-CARs may hold important clinical promise, and provide the potential for rational, structure-based design to implement novel, controllable elements into synthetic cellular therapies.

T cells engineered with CARs, hybrid molecules linking antigen-binding to T-cell signaling endodomains (EDs), have mediated potent and durable responses against both chronic and acute B cell leukemias[12-15]. While the efficacy of CAR-T cells (CAR-Ts) for leukemia has been striking, this therapy is frequently associated with life-threatening side-effects including cytokine release syndrome and neurotoxicity. The clinical development of CAR-T cells (CAR-Ts) against solid tumors has proven challenging, however, there is great optimism that next-generation CAR-Ts will bring benefit to a broader range of cancer patients[16]. Indeed, it is now well-understood that physical and immunometabolic barriers upregulated in solid tumor microenvironment can impair T-cell function[17]. Innovative engineering strategies, such as the expression of cytokines, chemokines, decoy molecules, or stimulatory ligands, etc., are being developed to overcome these barriers, and have shown favorable preclinical responses[17-19]. Safety, however, remains an important barrier to clinical entry, since most solid tumor antigens targeted to date are also found in healthy tissues, sometimes leading to serious adverse events in patients[20]. The ability to control on command CAR-T activity will greatly accelerate the clinical development of CAR-T therapies.

Figure 15A:
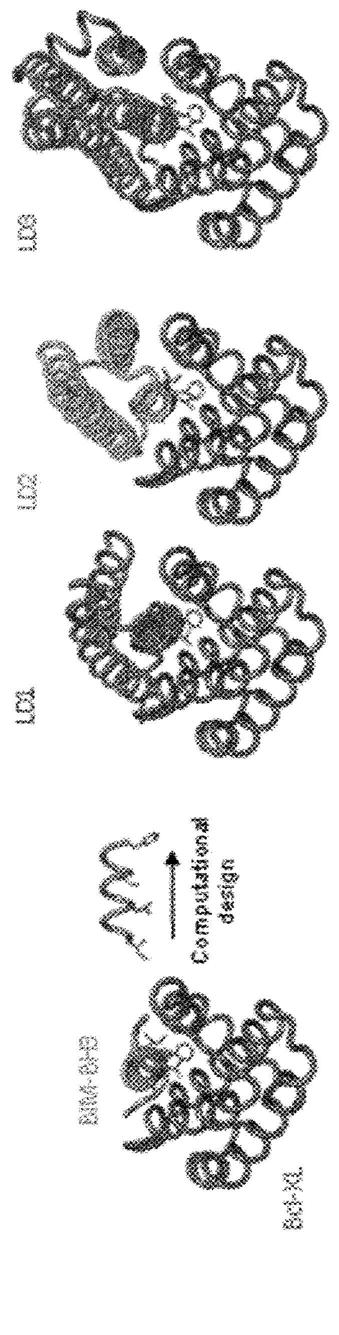

The above considerations have driven the development of CAR-T control/safety systems[16], such as drug-inducible suicide switches[21, 22], negative regulatory co-receptors (iCARs) that upon engagement with specific antigens will stop effector function[23], and split-signaling CAR-Ts that require co-engagement of two ligands for full T-cell activation[24]. More recently, the feasibility of ON-switch CARs, requiring small molecule-mediated heterodimerization to enable T-cell activation in the presence of antigen, has been demonstrated[25], and SUPRA (split, universal and programmable) CARs have been developed that can sense and logically respond to multiple antigens[26]. Presented herein is a novel computationally designed STOP-switch CAR-T control system in which antigen binding and T-cell activation are encoded by two chains, the recognition (R) and the signaling (S) chains, respectively. These chains spontaneously dimerize into a functional heterodimer via a computationally designed protein pair, inserted in the CAR heterodimer, which can be specifically disrupted by administration of a small molecule (depicted in FIG. 15A). Thus, STOP-CARs can be used to temporarily tune down effector function in the event of excessive activity levels causing toxicity, rather than eliminating the therapy as in the case of a suicide switch.

With the aim of developing STOP-CARs having potential for clinical translation, the inventors sought to develop a CDH (i.e. a protein heterodimer that can be dissociated into two monomers by a small molecule disruptor), comprising proteins of human origin with a minimal number of mutations to minimize the risk of transgene immune rejection in patients[27, 28, 29]. In addition, well-folded globular domains from proteins were used that should not interfere with synapse-proximal T-cell signaling. Finally, the CDH design based on the availability of disruptive small molecules was initiated, clinically approved, that have a long half-life (about 10 hrs) and are well-tolerated in humans. Previously described CDH-like systems have not met these requirements, either because the proteins were not of human origin, were modulated by endogenous molecules such as biotin[30]; or had weak binding affinity[31].

The inventors identified the interaction between human Bcl-XL (B-cell lymphoma-extra-large; a transmembrane mitochondrial protein with anti-apoptotic activity) and the unstructured BH3 domain (Bcl-2 homology; a short peptide motif found in certain Bcl-2 family proteins that have pro-apoptotic activity)[32] of BIM (Bcl-2-interacting mediator of cell death; a pro-apoptotic molecule) as a promising starting point for the CDH design. Several drugs with clinical potential are available that can inhibit their interaction[33]. The inventors sought to transplant the BH3 binding motif from the intrinsically disordered BH3 segment of BIM protein[34] onto a human globular domain in order to bind Bcl-XL with high affinity. Notably, an important challenge is that the affinity of BH3 domains and Bcl-2 family proteins (Bcl-XL, Bcl-2, etc.) depends not only on helical residues that form the interface hydrophobic core, but also on polar residues pointing away from it. Indeed, all previous attempts to design Bcl-2-family binding proteins by engrafting the BH3 domain onto pre-existing scaffolds have yielded weaker binders than the native, unstructured BH3 domain itself[35-37].

Figure 15C:
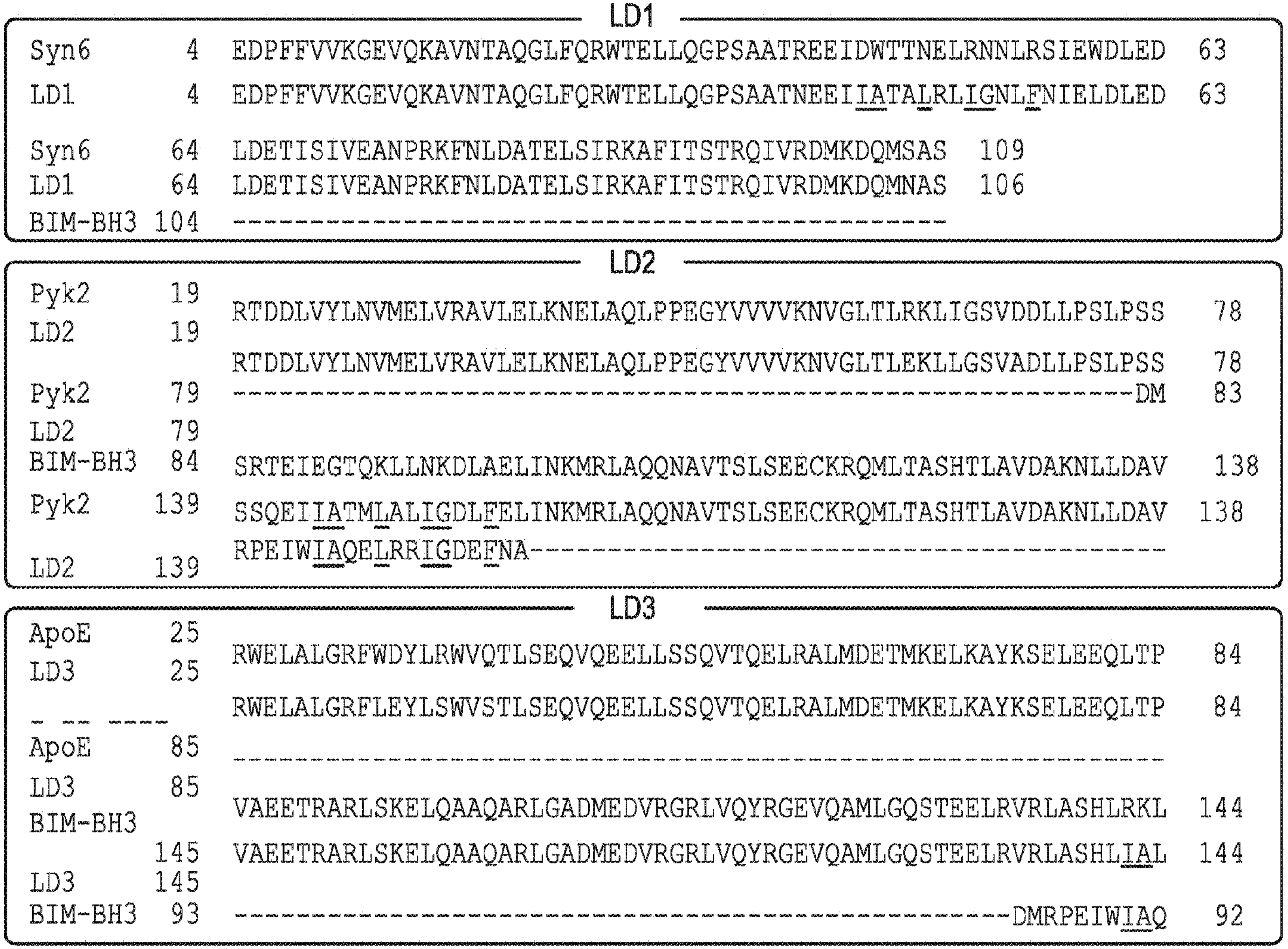

To develop the novel CDH, Rosetta MotifGraft[38], a computational protocol, was used to redesign existing monomeric proteins to bind to Bcl-XL. MotifGraft was used to identify scaffolds having backbone similarity to a binding motif, as well as structural compatibility to a given binding partner (FIG. 15). Subsequently, MotifGraft transplanted critical binding residues and was used to perform additional design at interface residues. The structure of Bcl-XL in complex with BIM-BH3 (PDB ID: 3FDL) (FIG. 16B) was used as the input, and the 12-amino acid helical segment from BIM-BH3 (FIG. 16B), IAXXLXXIGXXF, was used as the binding motif (hot-spot residues are underlined)[34].

Figure 16A:
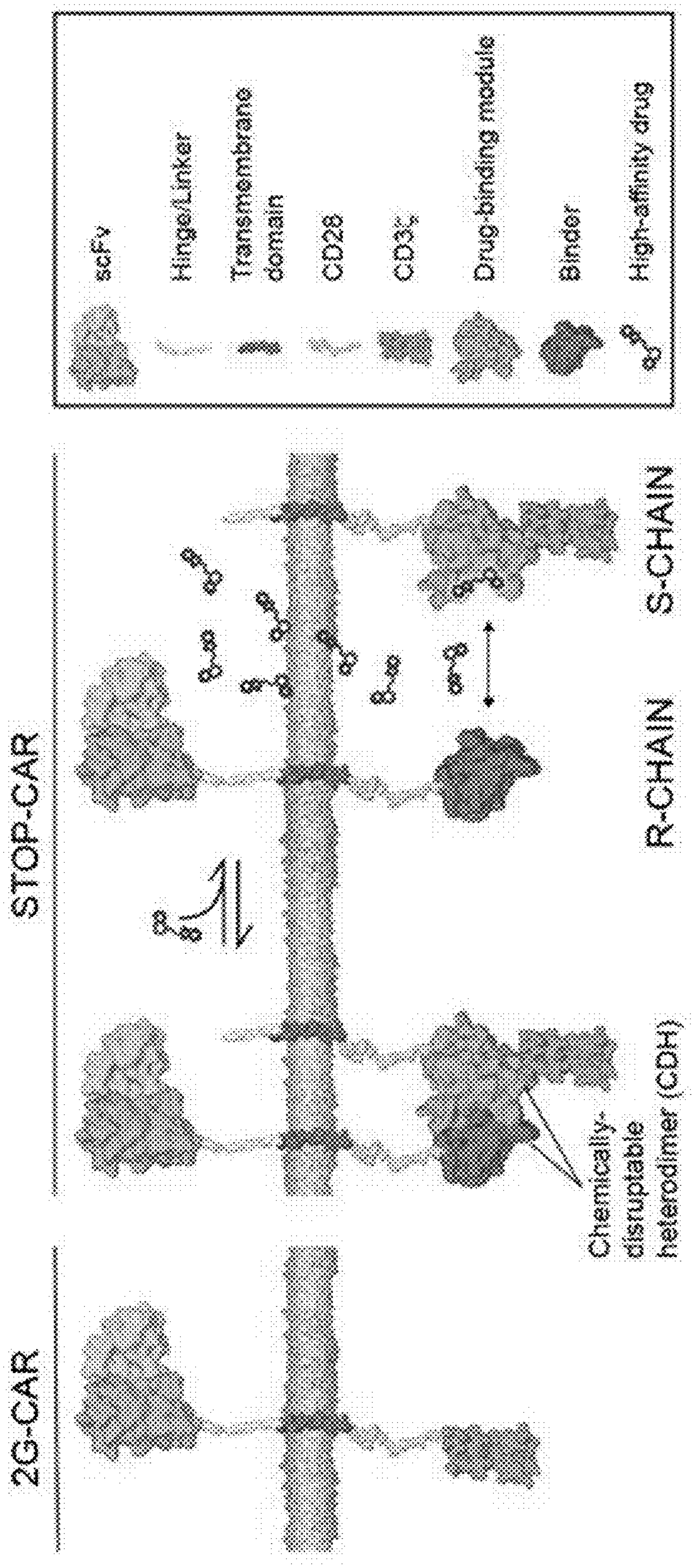
Figure 16B:
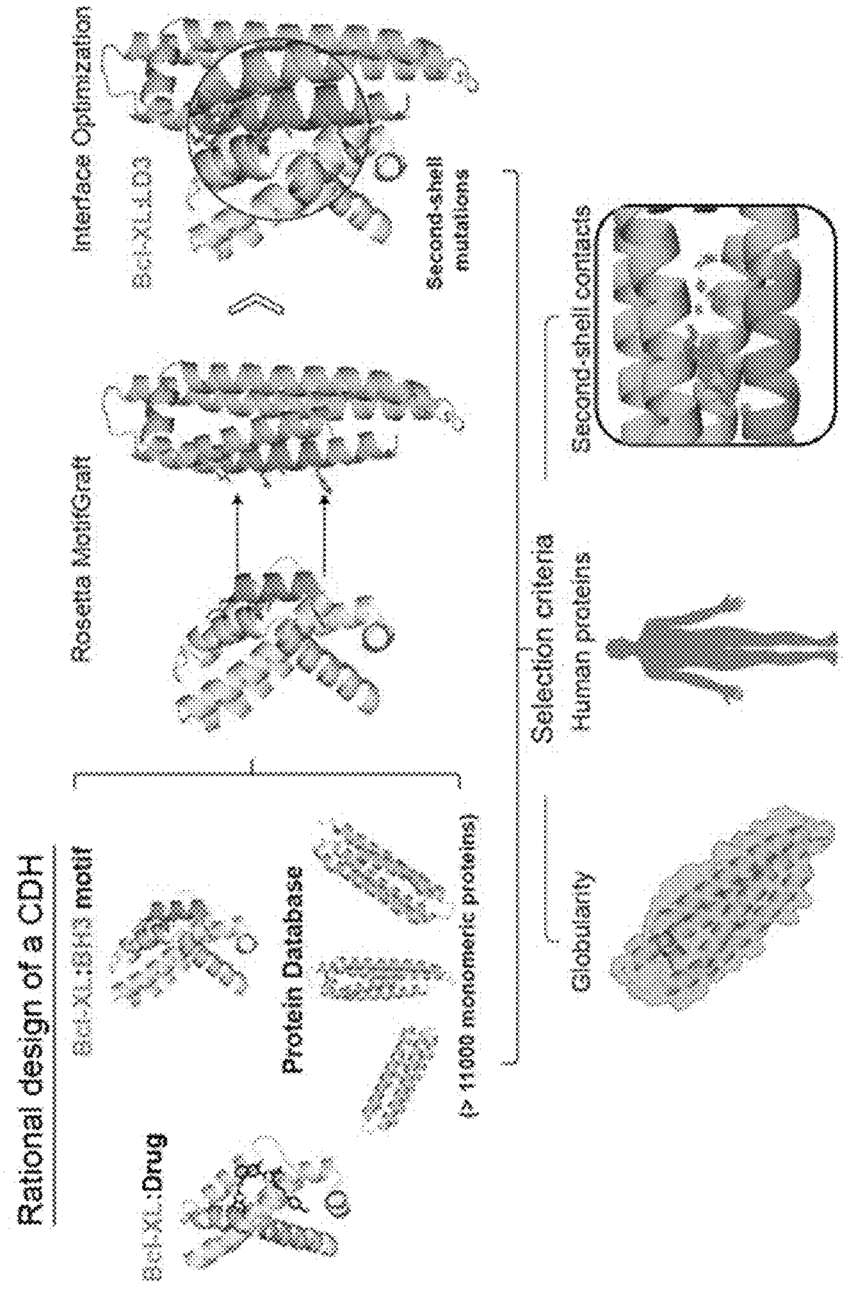

Residues within 6 Å of Bcl-XL were conservatively designed, allowing only favorable mutations according to the BLOSUM62 matrix. Designs that passed an initial steric filter were ranked by a predicted interaction energy (ΔΔG), filtered for globularity of the scaffold and packing of the binding motif against the scaffold. Three lead designs (LD) were generated: a rat protein with a close human homologue, Syntaxin 6 (LD1), as well as two human proteins, human focal adhesion targeting domain of Pyk2 (LD2), and human apolipoprotein E4 (LD3) (FIG. 16B). The designs carried between 11 and 13 mutations relative to the native proteins, which included 6 hot-spot residues (FIG. 15).

Figure 16C:
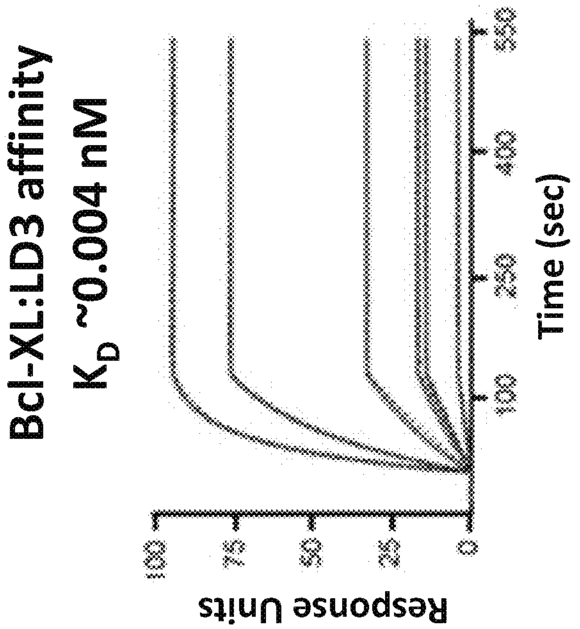
Figure 16E:
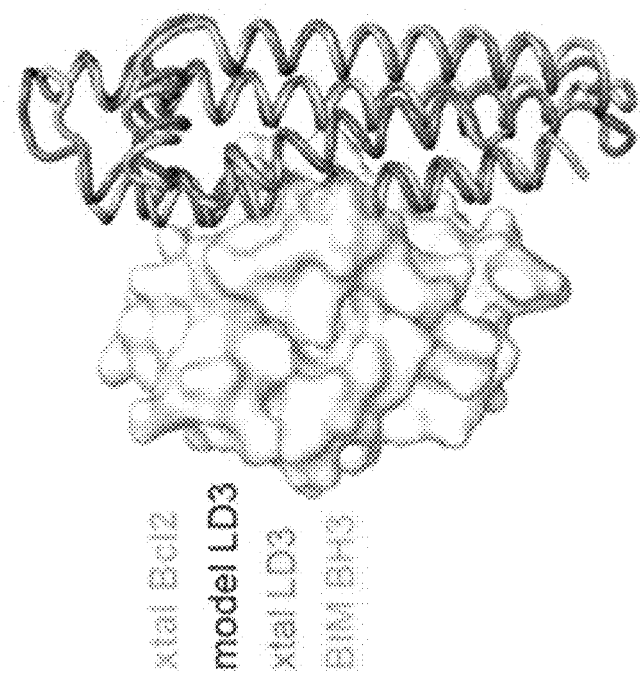
Figure 16F:
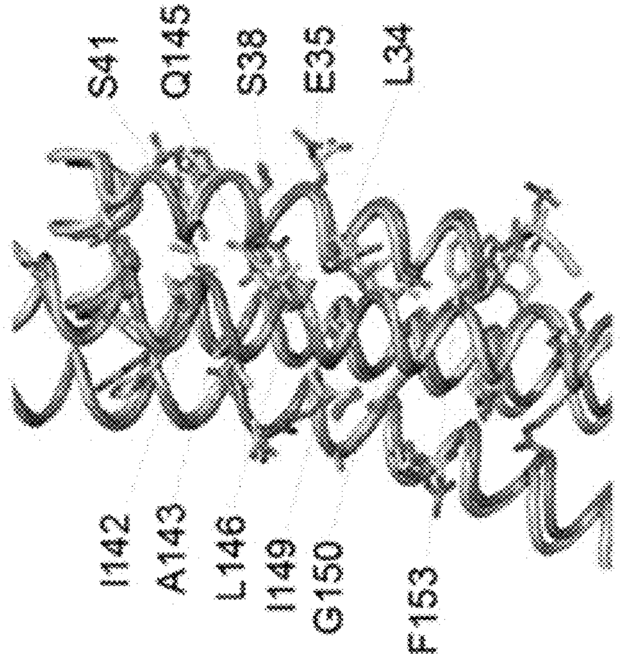
Figure 16G:
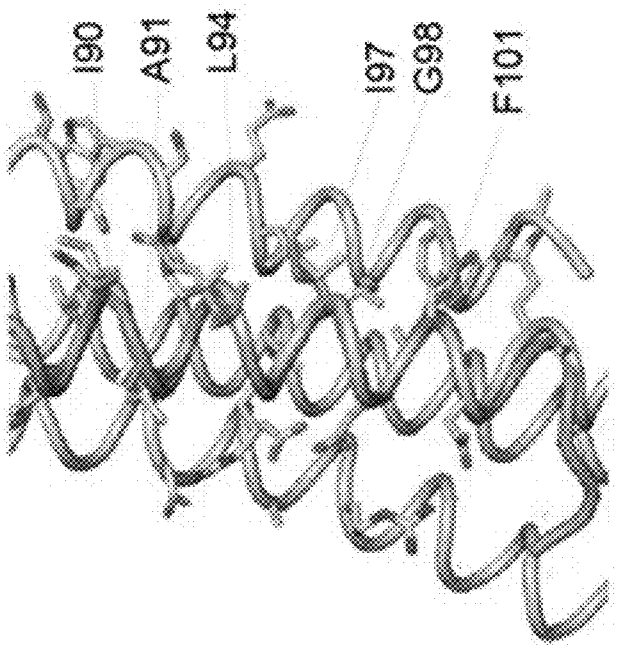
Figure 17A:
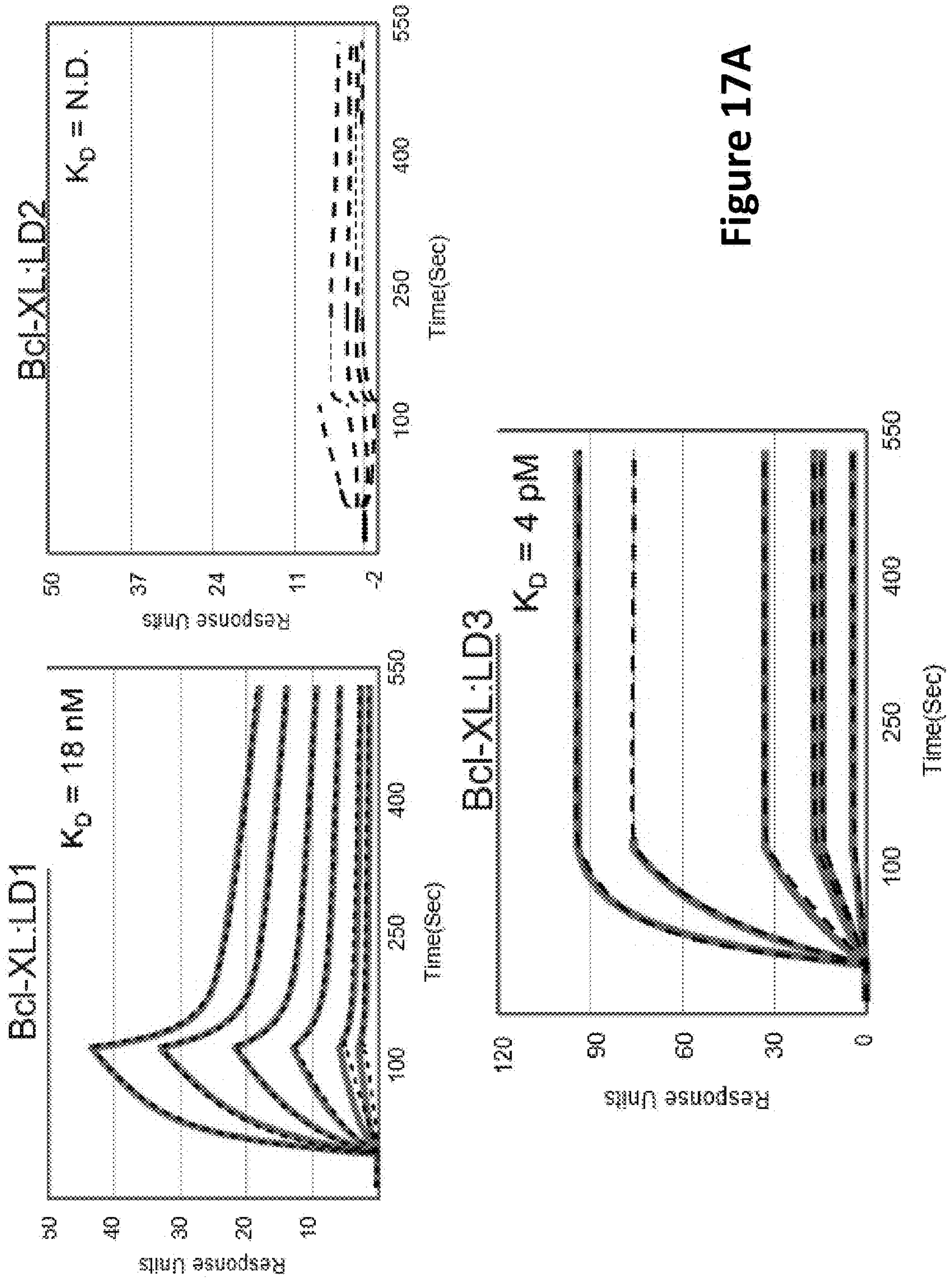
FIGS. 17A-17D show biochemical characterization of computationally designed binders.
Figure 17B:
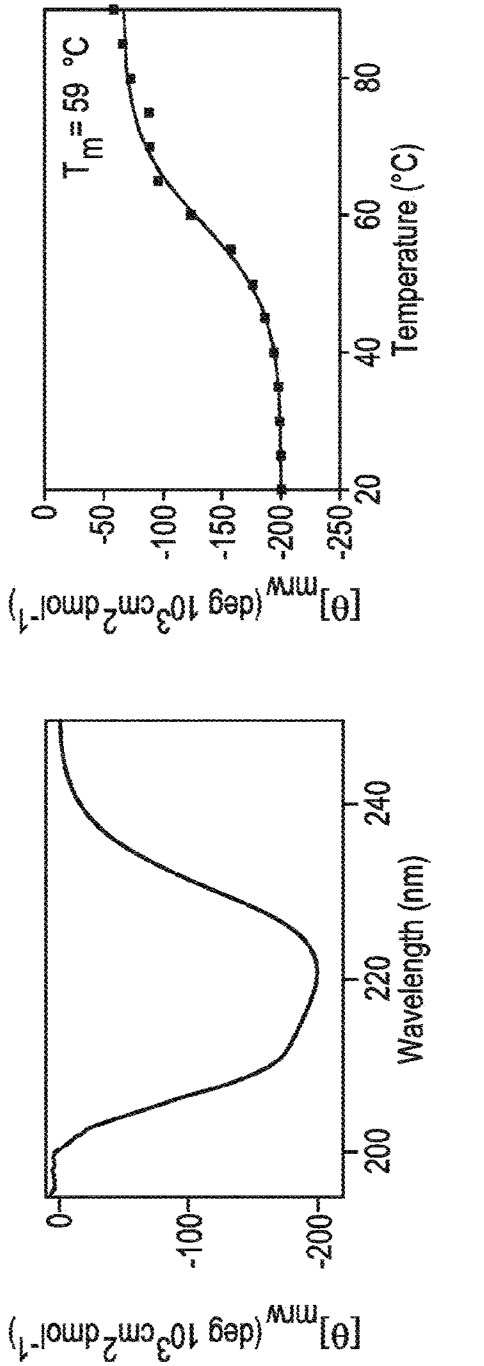
Figure 17C:
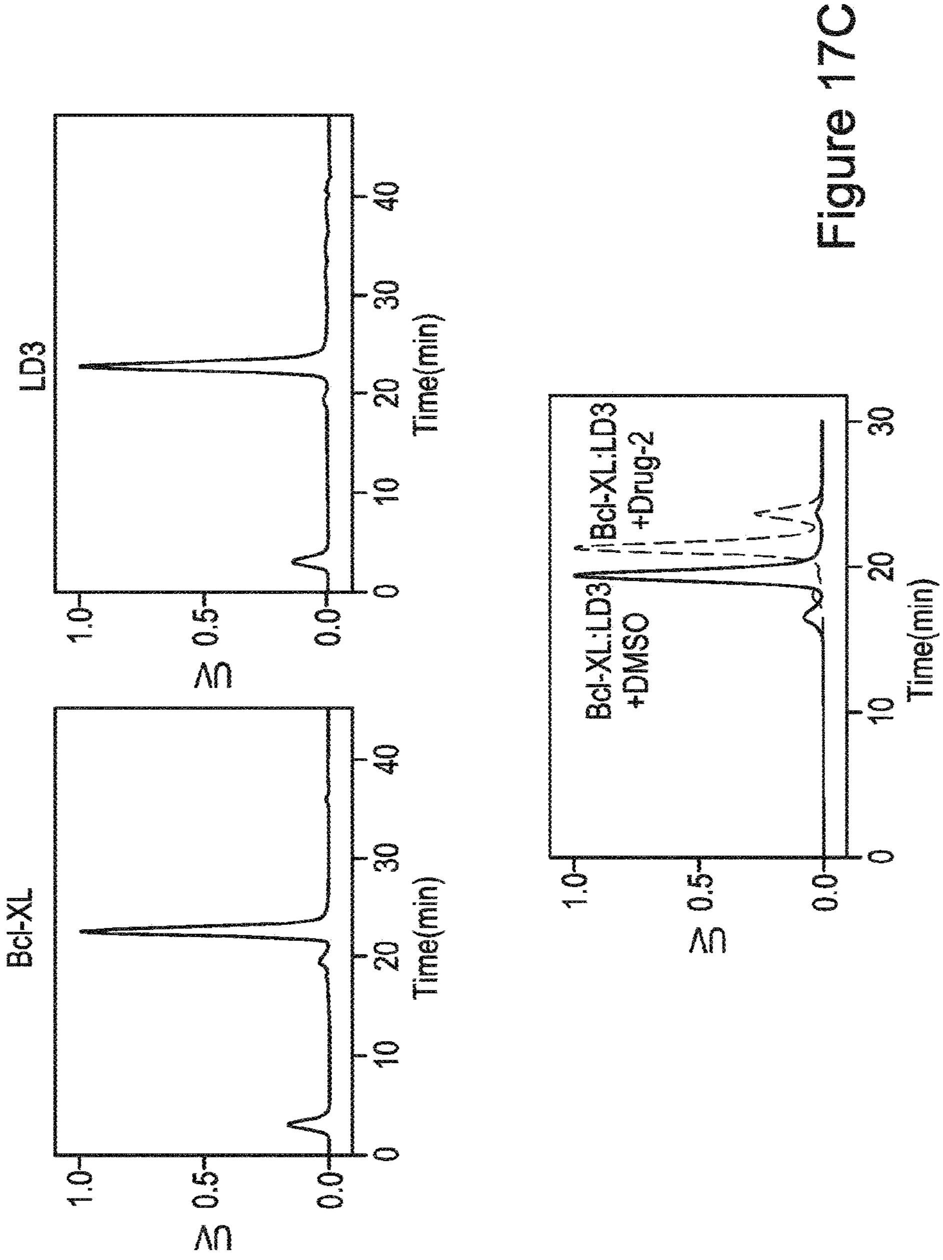
Figure 17D:
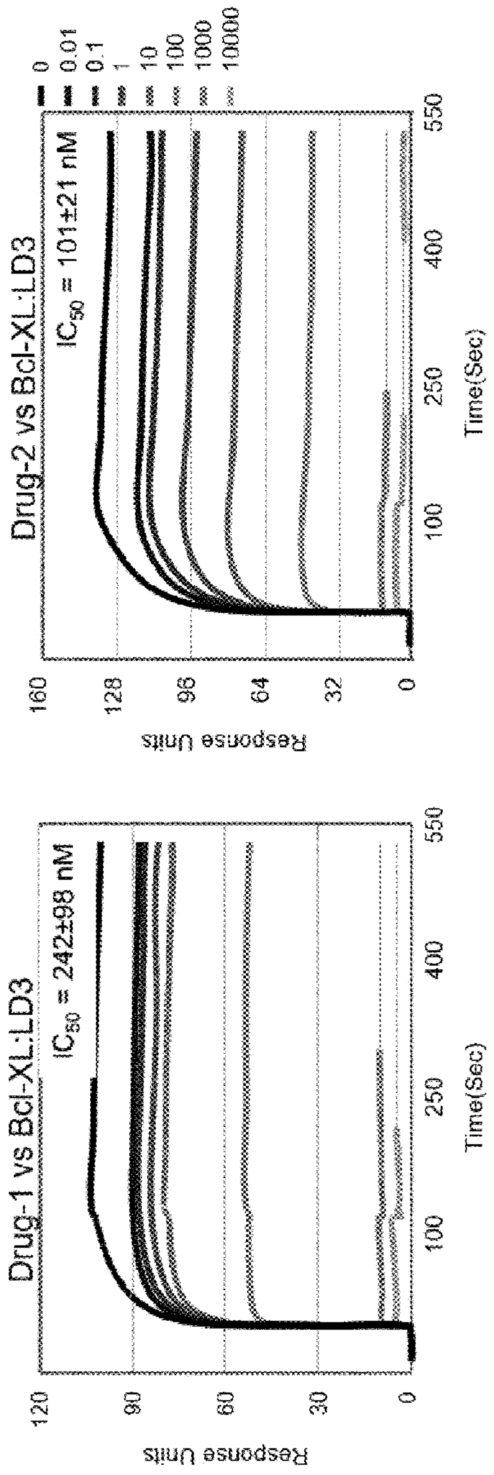
Figure 18A:
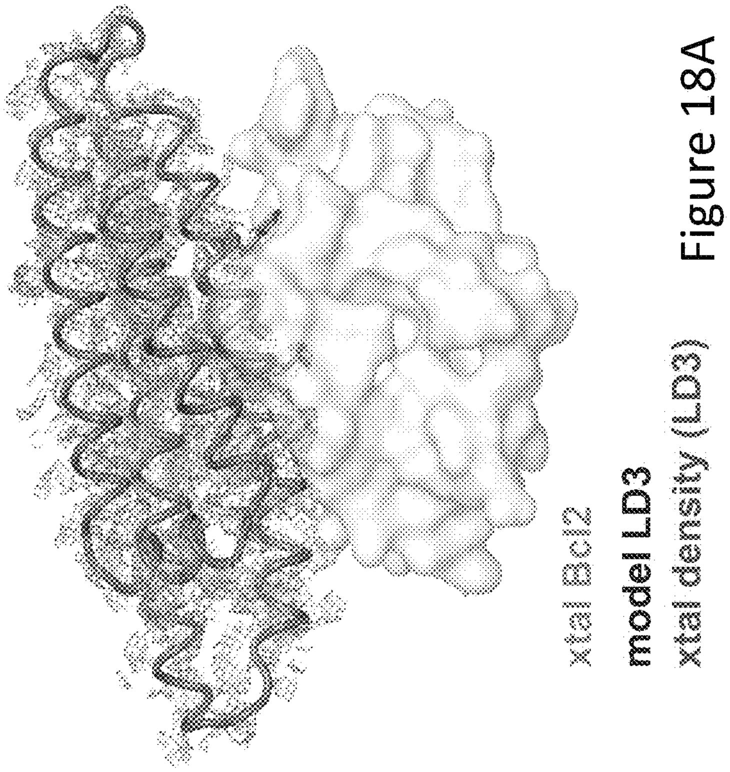
Figure 18B:
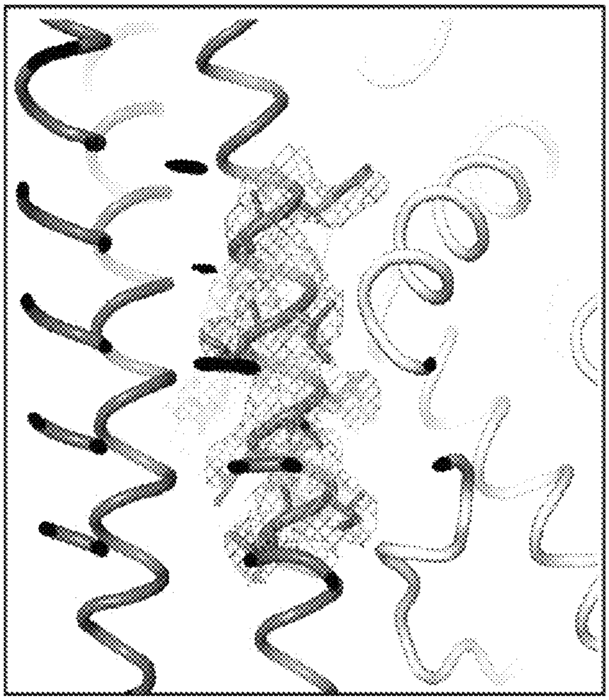

The three computationally designed proteins were recombinantly produced, and their dissociation constants ($K_D$s) for Bcl-XL assessed by surface plasmon resonance (SPR). LD1 and LD3 bound with KDs of 17 nM and 3.9 pM, respectively, while there was no detectable binding by LD2 (FIG. 16C and FIG. 17). In comparison, previously reported $K_D$s for the wild-type Bcl-XL:BIM-BH3 interaction are in the range of 6 nM[39]. Two known small molecules, A-1331852 and A-1155463 (abbreviated Drug-1 and Drug-2), have been reported to bind to Bcl-XL at less than 10 pM[33], and were shown by SPR to dissociate Bcl-XL from LD3 (FIG. 16D), with apparent $IC_{50}$ values of 115 nM and 25 nM (FIG. 16D and FIG. 17), respectively. Based on its favorable properties as a CDH, LD3, was chosen for further study. While it was not possible to obtain crystals of the LD3:Bcl-XL complex suitable for diffraction, a 2.5 Å crystal structure of LD3: Bcl-2 (a close homologue of Bcl-XL) was solved (FIG. 16E and FIG. 18). The structure validated the computational model, as the two proteins showed a root mean square deviation (RMSD) of 1.3 Å for the $C_\alpha$ atoms of the complex, 1.35 Å for the side chains of the designed interface atoms (FIG. 16F) and 1.2 Å RMSD over the helical residues of the binding motif (FIG. 16G).

The CDH was then incorporated into a STOP-CAR design under the hypothesis that the R and S chains would form a fully functional heterodimer, but in the presence of a Bcl-XL inhibitor, LD3 would be displaced and T-cell activity would be disrupted. Indeed, the separation of antigen recognition from signal-transducing elements on separate receptors is a common feature of both the innate and adaptive immune system, as it enables genes encoding the ligand-binding receptor to diversify while maintaining signaling features[40].

For protein expression and purification, the gene sequences of Bcl-XL and all the designed proteins were flanked with an N-terminal 6×His-tag and synthesized by GenScript. Genes were cloned into a pET-11b expression vector by using Gibson assembly (New England Biolabs, E2611S). The sequence-confirmed plasmid was transformed into *Escherichia coli* BL21 (DE3) (Thermo Fisher), and a single clone was used to inoculate 700 ml of Terrific Broth (#101629, Merck Millipore) containing Ampicillin (100 μg/ml). The culture was grown at 37° C. until $OD_{600}$ reached around 1.0, and protein expression induced with 1 mM IPTG (Fisher Scientific) at 20° C. After overnight induction, cells were harvested by centrifugation at 4000 rpm, and the bacterial pellet was resuspended in 40 ml lysis buffer (50 mM Tris, 500 mM NaCl and 5% Glycerol at pH 7.5) containing 100 μg/ml PMSF (ROTH, 6376.2) and 1 mg/ml lysozyme (#10837059001, Sigma-Aldrich). The cells were disrupted by sonication, and lysates were cleared by centrifuging at 20000 g for 20 min. Cleared lysate was loaded onto an AKTA purifier (GE Healthcare) for Ni-NTA affinity purification. The column was washed with five column values of equilibration buffer (50 mM Tris, 500 mM NaCl and 20 mM imidazole), and the protein was eluted in equilibration buffer supplemented with 300 mM imidazole. The eluent was further purified by gel filtration with a Superdex 75 10/300 GL column (GE Healthcare) in phosphate buffer, pH 7.4. The purified proteins were concentrated, aliquoted and stored at −80° C.

For all designs tested, for the R-chain a single chain variable antibody fragment (scFv) targeting the prostate-specific membrane antigen (PSMA) was incorporated along with an antigen expressed in a large proportion of advanced prostate adenocarcinomas, on the vascular endothelium of many solid tumors, but also in normal organs such as the 41,42 duodenum and salivary glands[41, 42]. The R-chain comprised also a hinge/linker (H/L), a transmembrane domain (TMD) and co-stimulatory ED from CD28, followed by LD3. For the S-chain, however, three variations were tested, all of which incorporated the H/L, TMD and co-stimulatory ED from CD28, followed by Bcl-XL, and finally the ED of CD3ζ at its terminus, with variations in the ectodomain only (FIG. 19A).

Figure 20A:
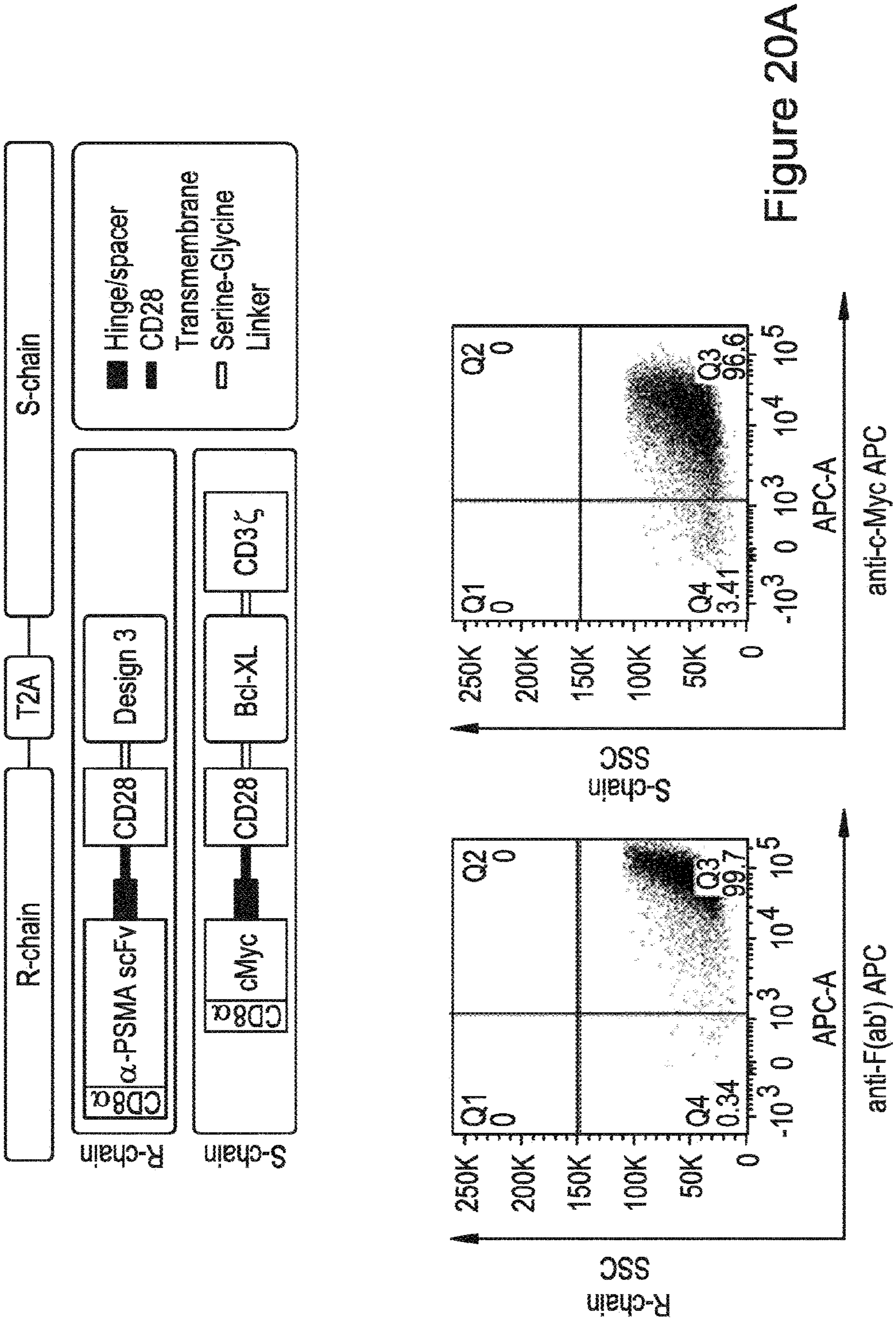
FIGS. 20A-20H show the first two STOP-CAR prototypes comprising either cMyc alone or cMyc plus the CH2-CH3 linker region in the ectodomain of the S-chain, yielded low transduction efficiencies in primary human T-cells.
Figure 20B:
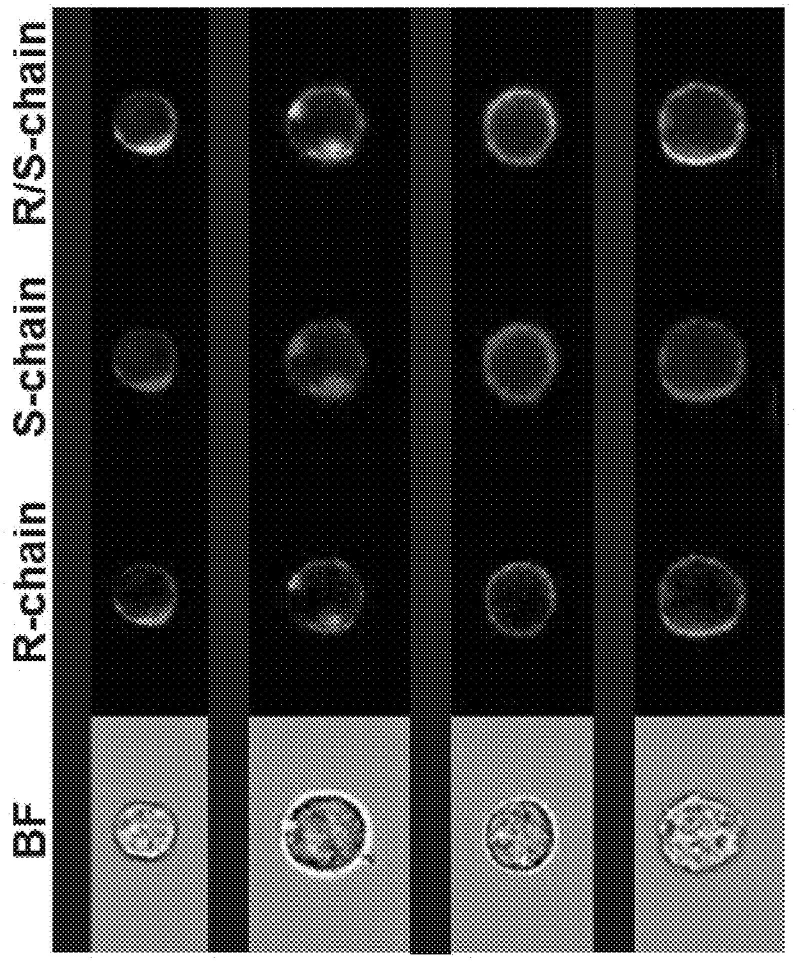
Figure 20C:
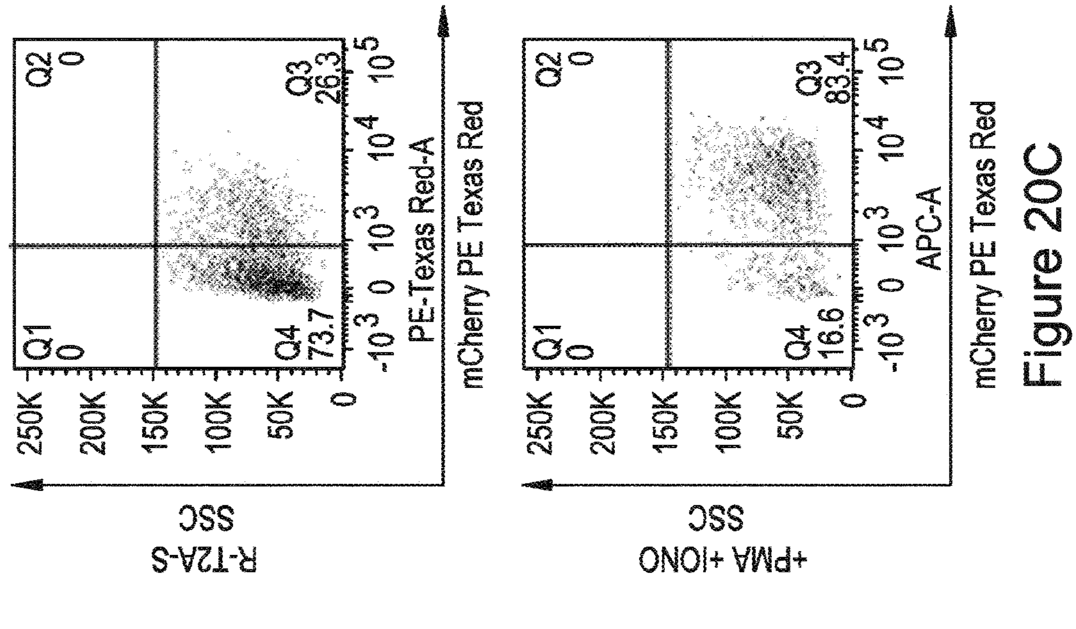
Figure 20D:
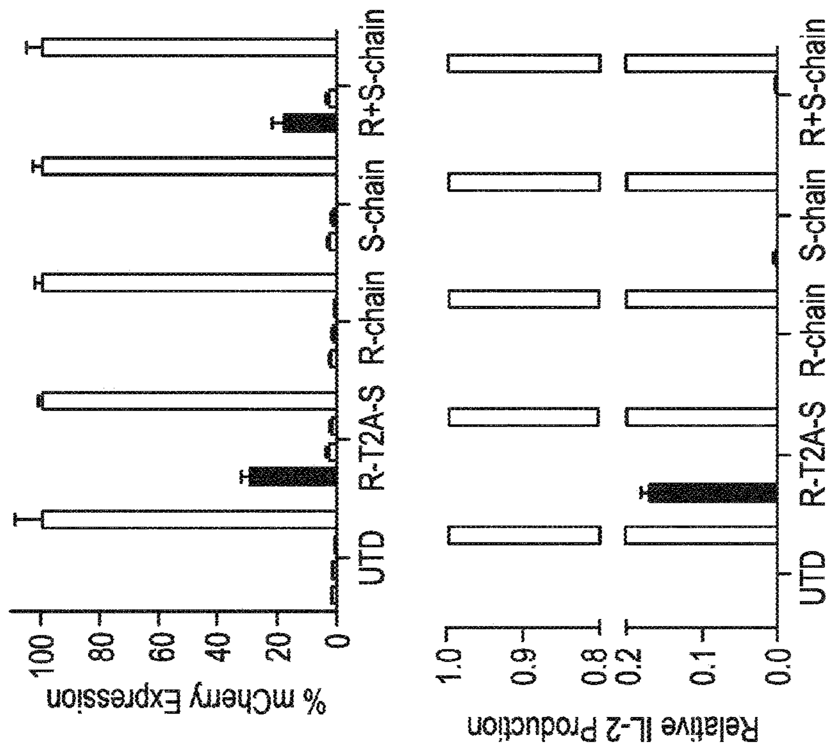
Figure 20E:
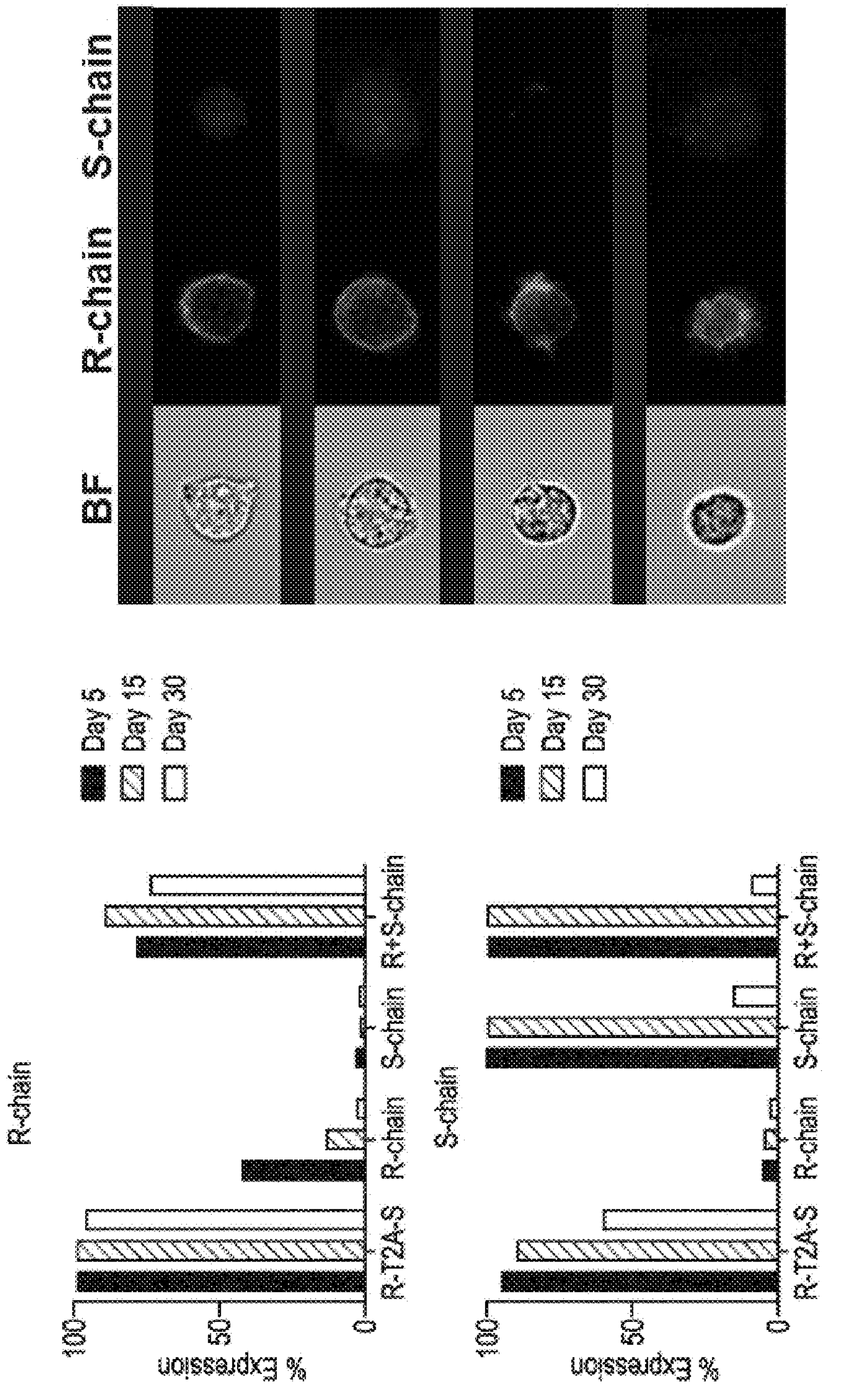
Figure 20F:
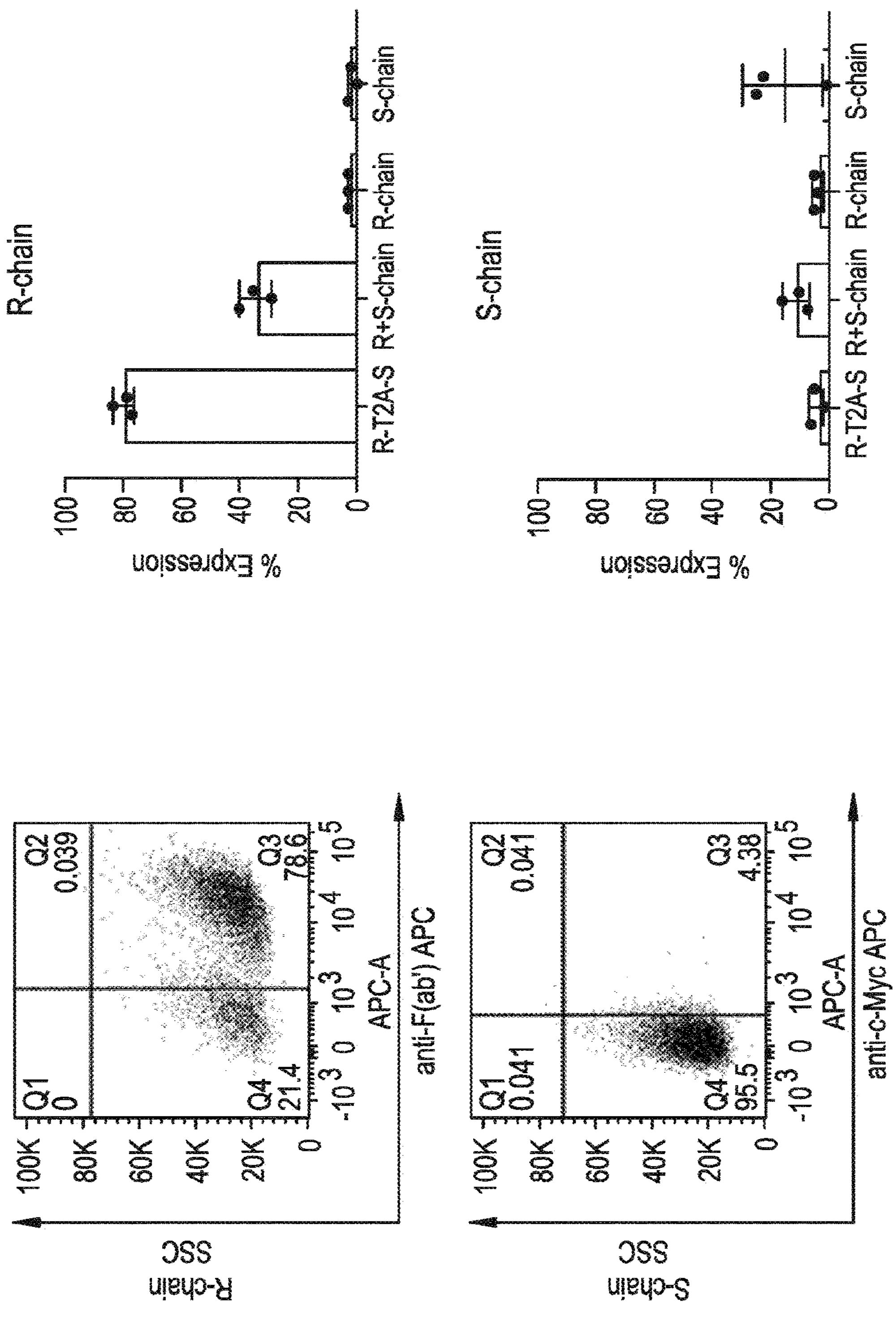
Figure 20G:
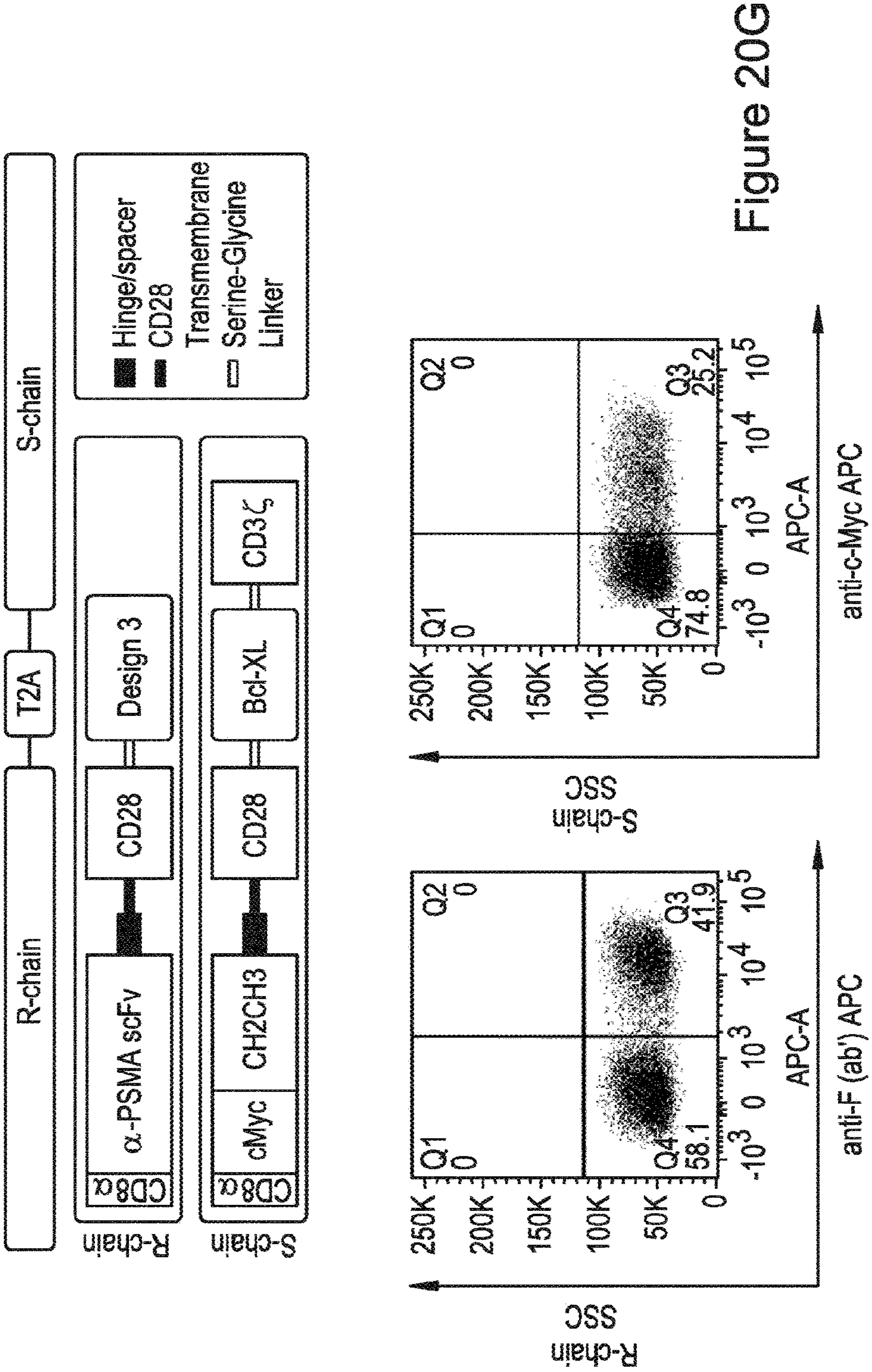
Figure 20H:
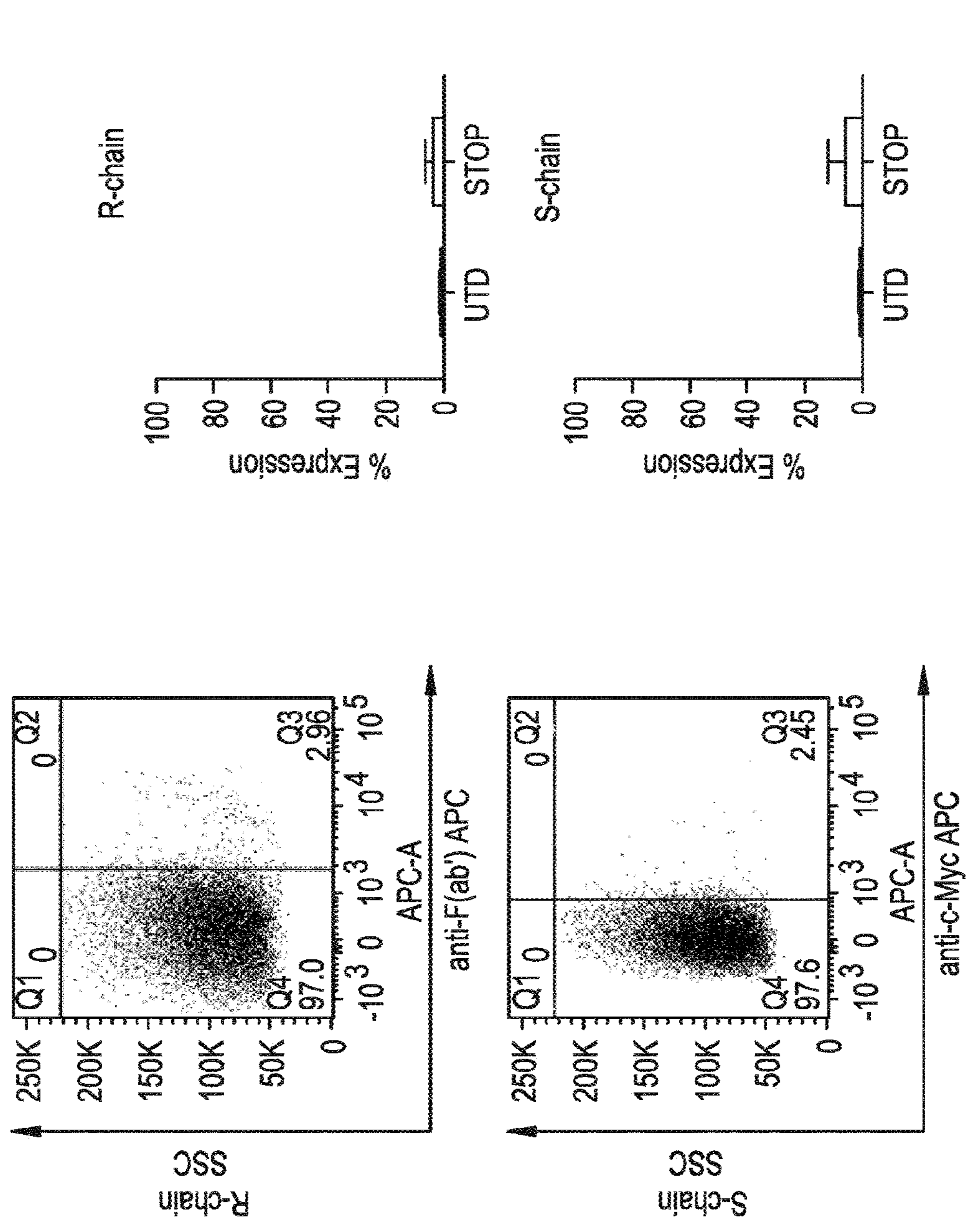
Figure 21A:
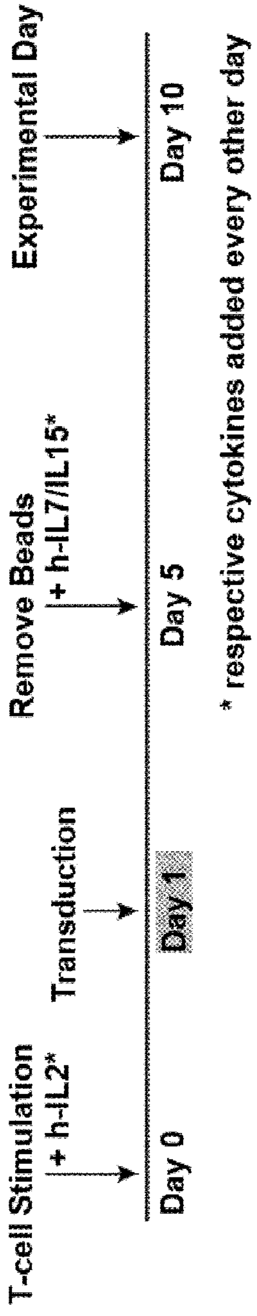
FIGS. 21A-21F show representative flow cytometric analysis of the third STOP-CAR prototype comprising the DAP10 ectodomain on the S-chain showing efficient and stable expression on the surface of Jurkat and primary human T-cells over time.
Figure 21B:
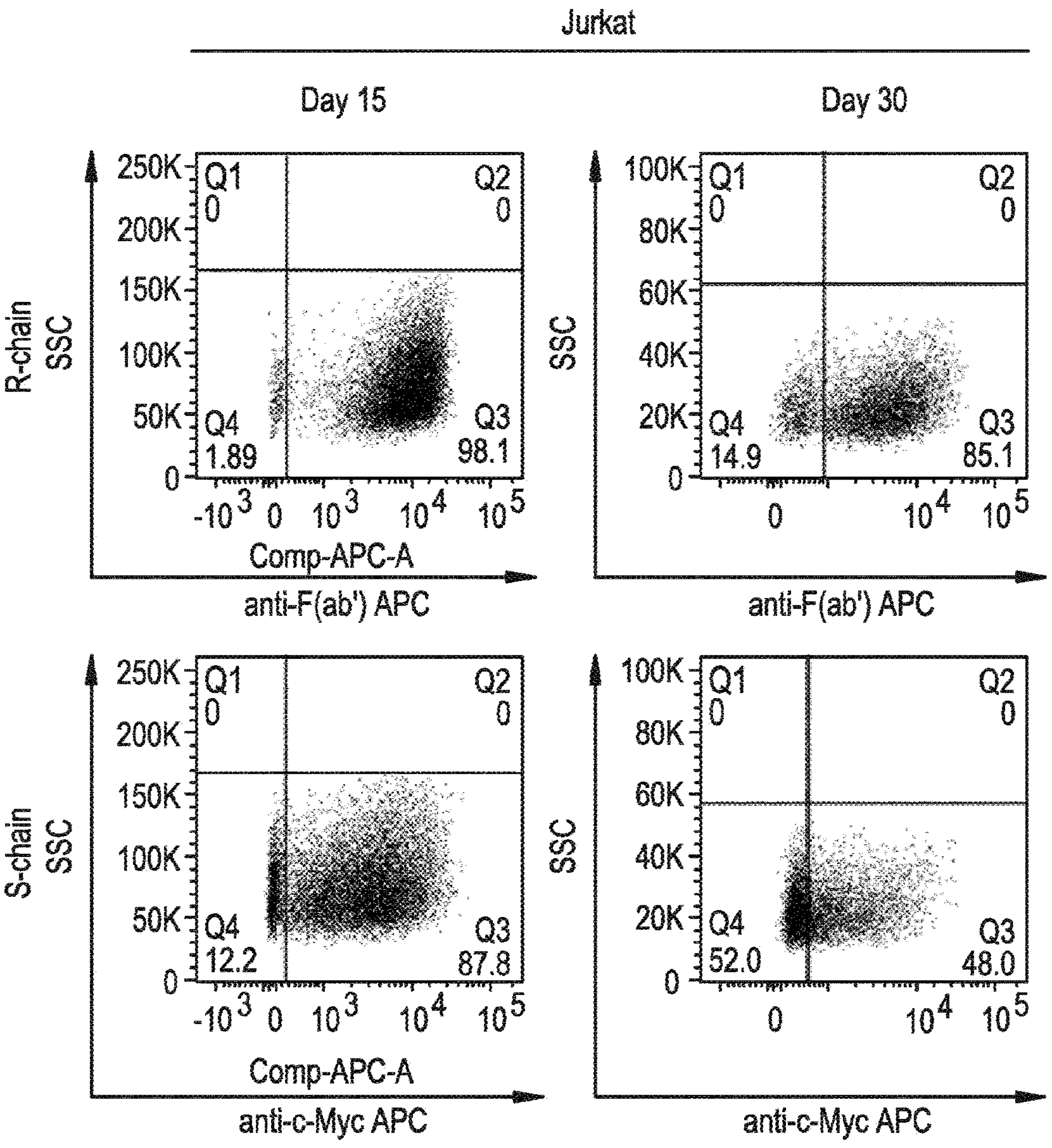
Figure 21C:
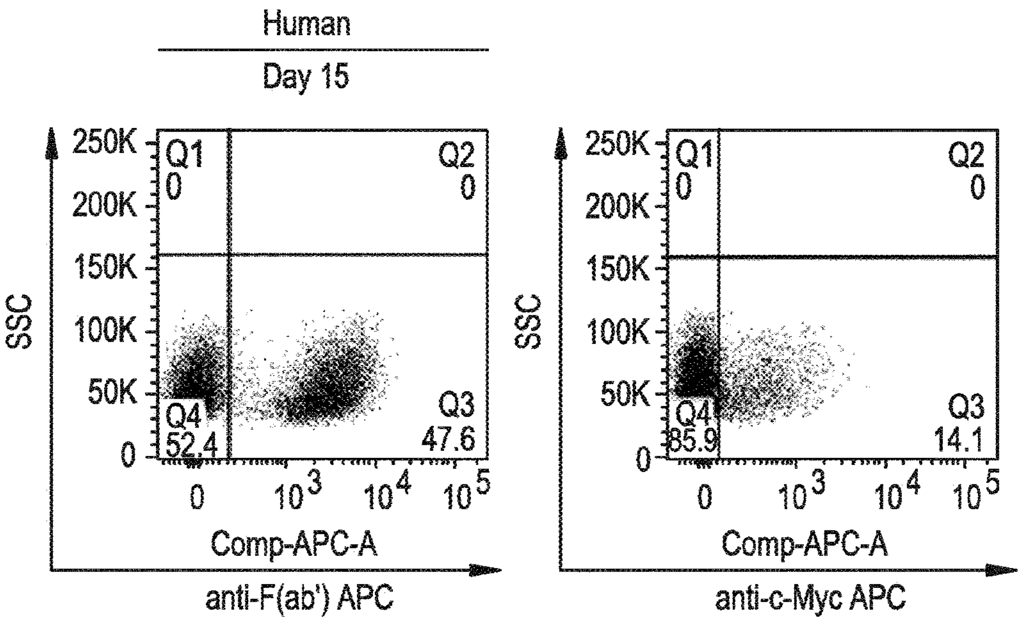
Figure 21D:
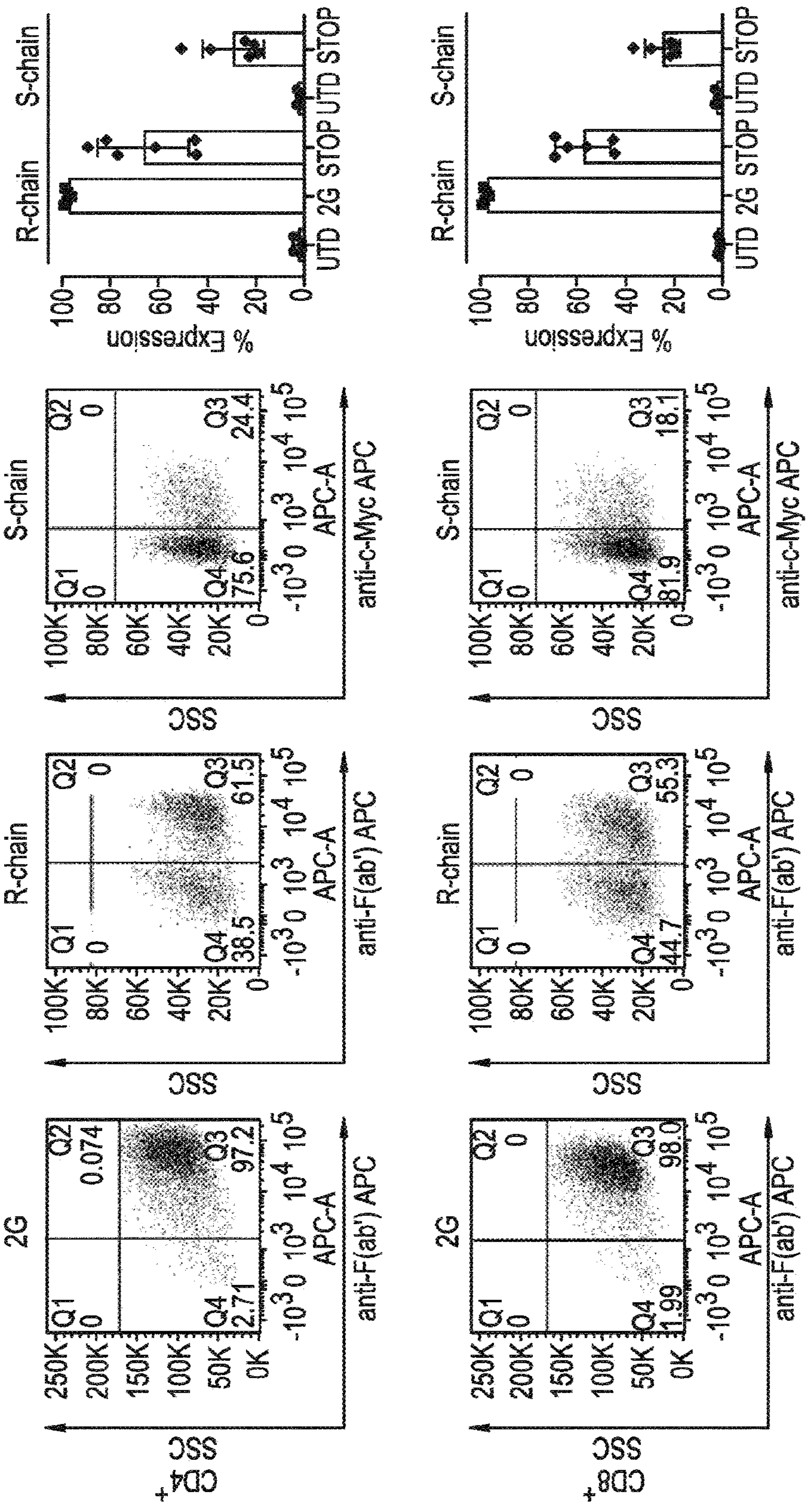
Figure 21E:
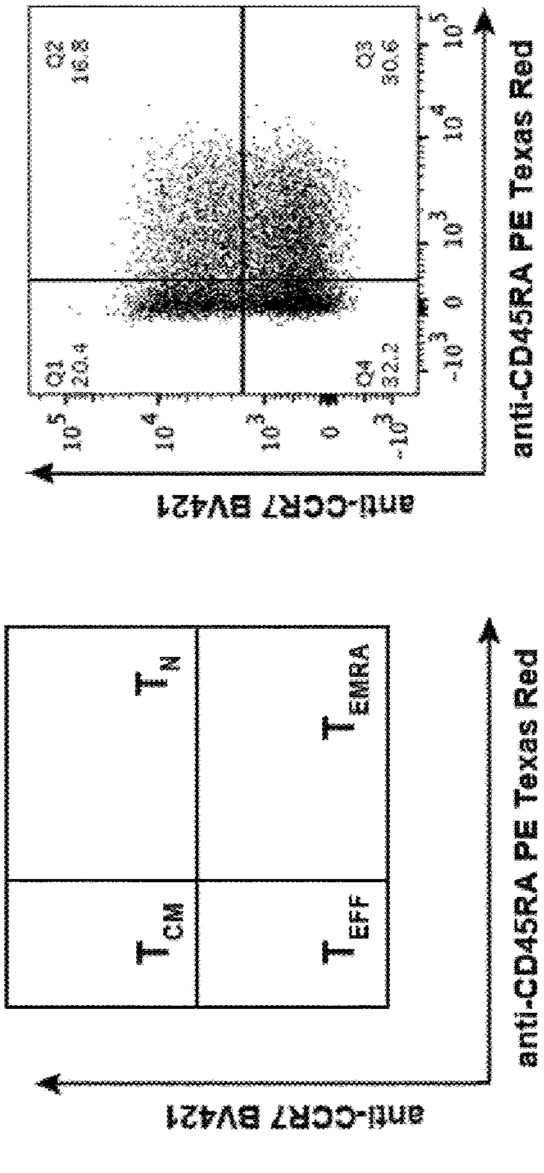
Figure 21F:
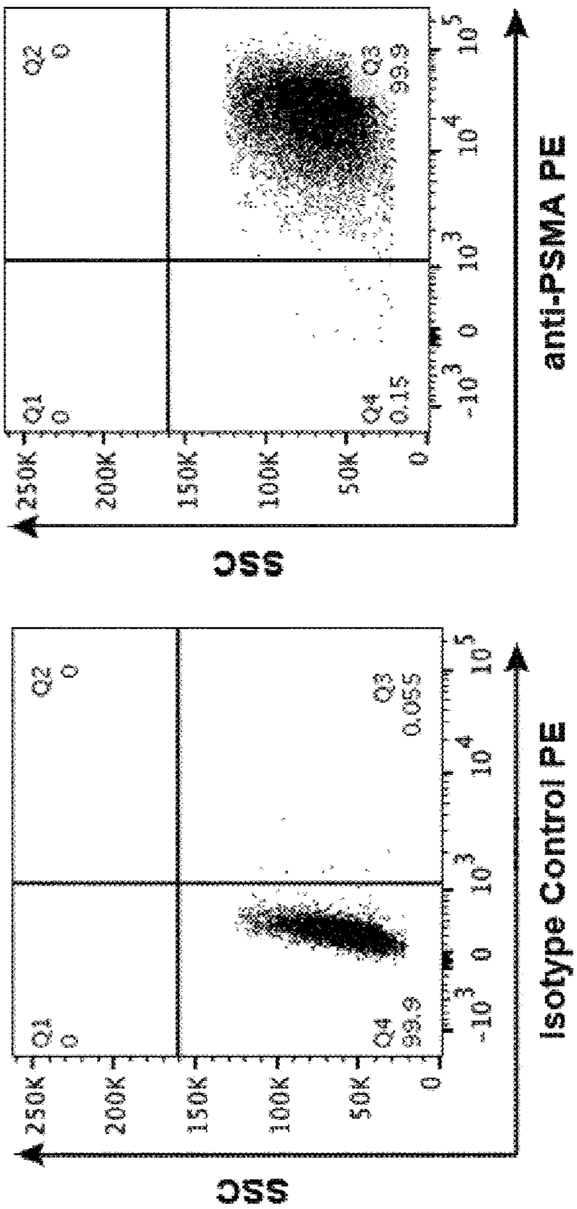

In the first STOP-CAR prototype described in FIG. 20A, the S-chain ectodomain comprised a cMyc-tag, revealing high and stable transfection of Jurkat 6×NFAT-mCherry reporter cells (about 100% expression at day 15) using a single lentiviral vector encoding both chains (FIGS. 20 and S5). The chains localized on the cell membrane. Jurkat cells transduced with both STOP-CAR chains were specifically activated in the presence of $PSMA^+$ target cells, while expression of either single chain alone did not enable activation. However, transduction of primary human T-cells was poor for the S-chain (<5%). The CH2-CH3 linker was incorporated on the assumption that the ectodomain of S-chain (i.e., a short cMyc-tag) was responsible for chain instability (FIG. 20). This construct, however, was expressed at lower levels on Jurkat cells, and was nearly undetectable on transduced primary T-cells (<3% expression).

Figure 19A:
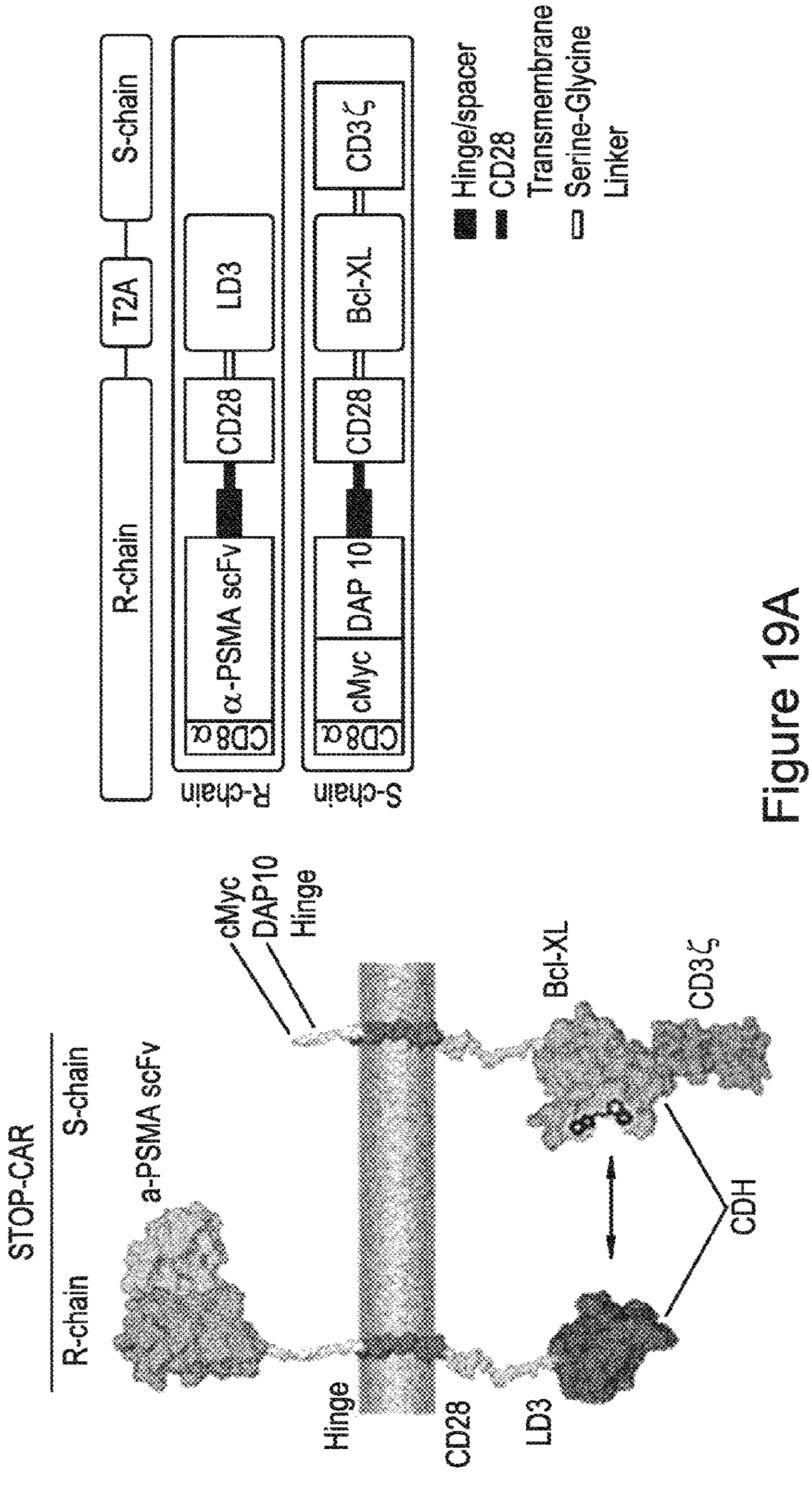
Figure 19C:
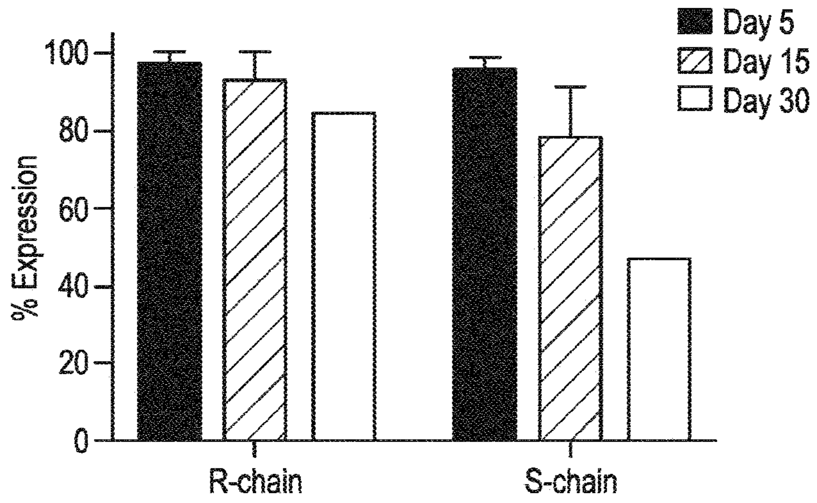
Figure 19D:
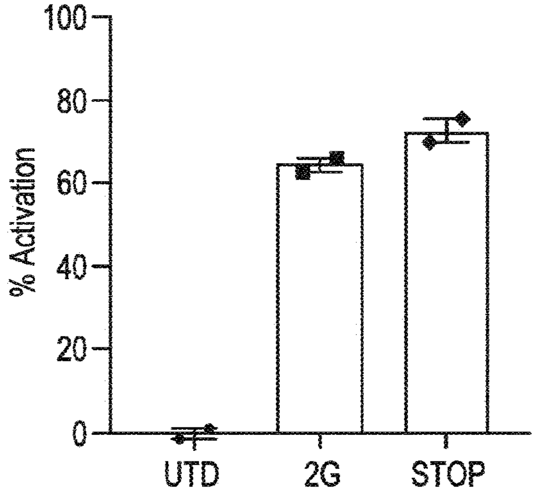
Figure 19E:
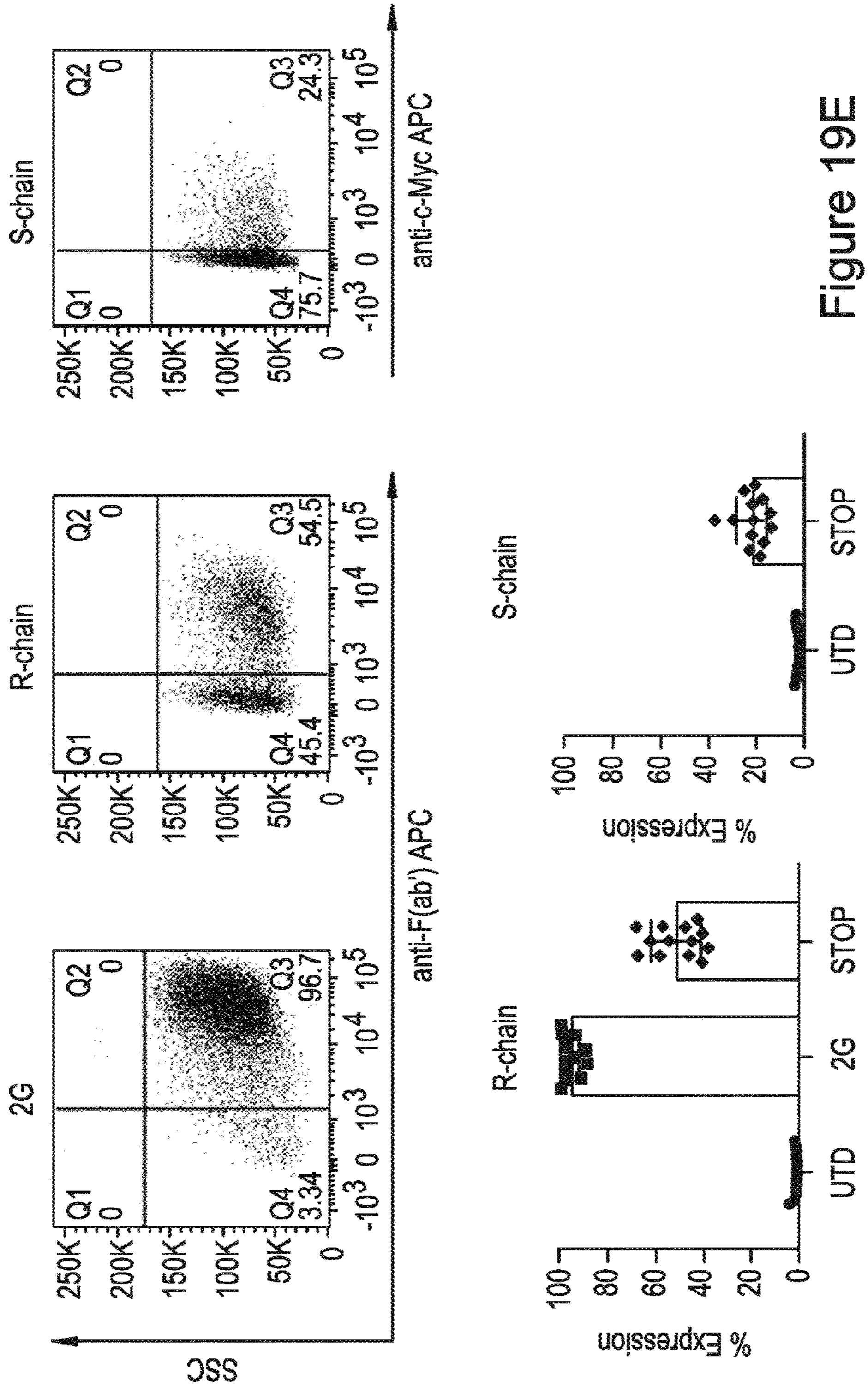
Figure 19F:
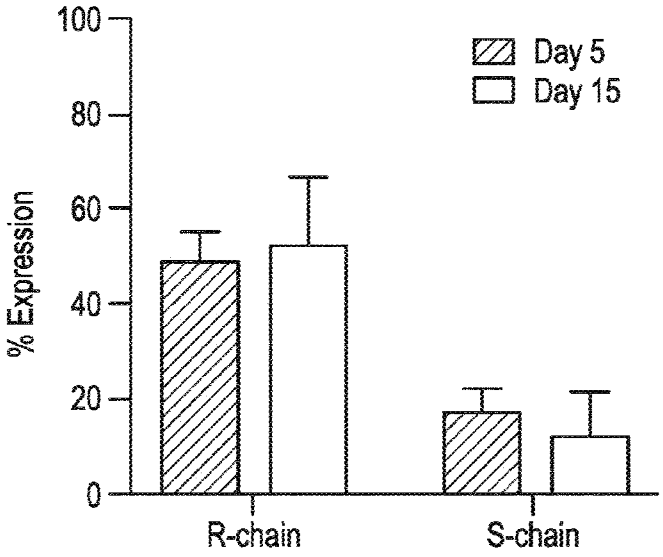
Figure 19G:
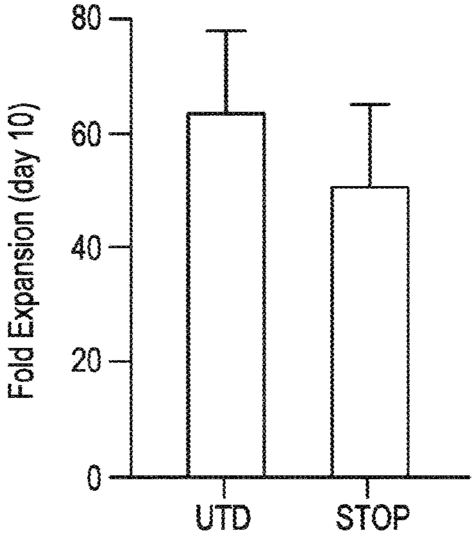
Figure 19H:
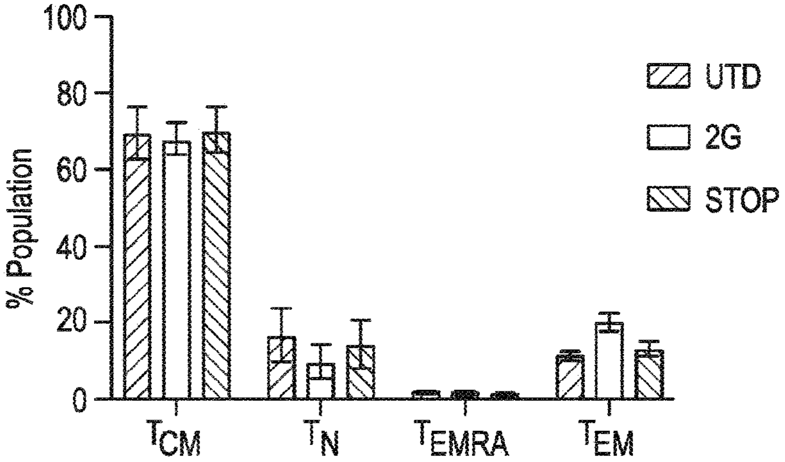

In a next attempt to improve S-chain expression, the inventors incorporated the ectodomain of DAP10, a signaling subunit that is broadly expressed by both adaptive and innate immune cells[40.] (FIG. 19A). Here, high levels of co-expression (about 100%, both chains) were detected on the surface of Jurkat reporter cells (FIG. 19B), and relative stability of both chains over time (FIG. 19C). In addition, specific activation of the engineered cells in the presence of PSMA+ target cells was observed, similar to control second generation 2G-CAR (comprising a CD28 endodomain) targeting PSMA (FIG. 19D). This design enabled acceptable transduction efficiencies in primary human CD8+ and CD4+ T-cells that were stable over 15 days, with an average of 52% for R-chain and 21% for S-chain (50:50 $CD8^+$ and $CD4^+$ T-cell population, n=13 donors) (FIG. 19E and FIG. 21). The inventors observed that the proliferative capacity of the STOP-CAR-Ts was similar to untransduced (UTD) T-cells (FIG. 19G). Finally, phenotypic analysis of the human STOP-CAR-Ts revealed effector/memory differentiation similar to that of 2G-CAR-Ts (FIG. 19H and FIG. 21).

Having established stable cell-surface expression of a heterodimeric STOP-CAR in primary human T cells, the ability of the STOP-CAR to specifically activate engineered CAR-Ts in vitro and in vivo was assessed. Also tested was whether the administration of Drug-1 or Drug-2 could disrupt effector function, and if the STOP-CAR-Ts would re-activate upon drug removal. Drug-2 (A1155463, Chemietek CT-A115) and Drug-1 (A1331852, Chemietek CT-A133) were directly used without further purification. A1155463 and A1331852 were each dissolved in DMSO as 10 mM stocks. Stocks were aliquoted and stored at −20° C. until use.

Figure 22A:
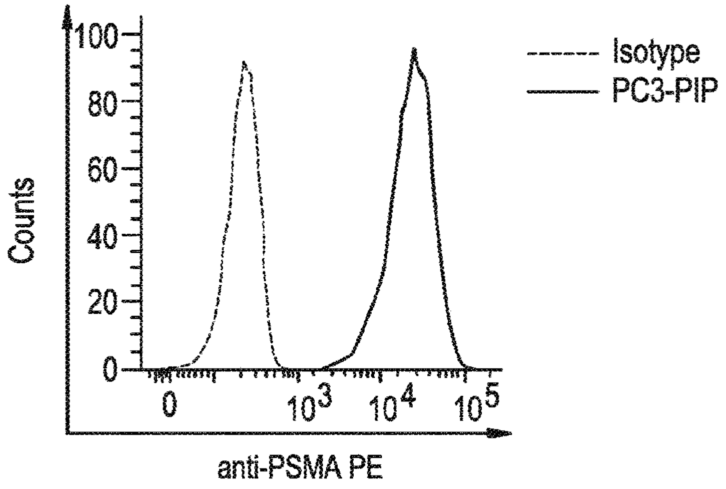
FIGS. 22A-22F show STOP-CARs are functional in primary human T-cells, both in vitro and in vivo, and activity can be abrogated in a drug-dependent manner. showing drug-dependent activity.
Figure 23A:
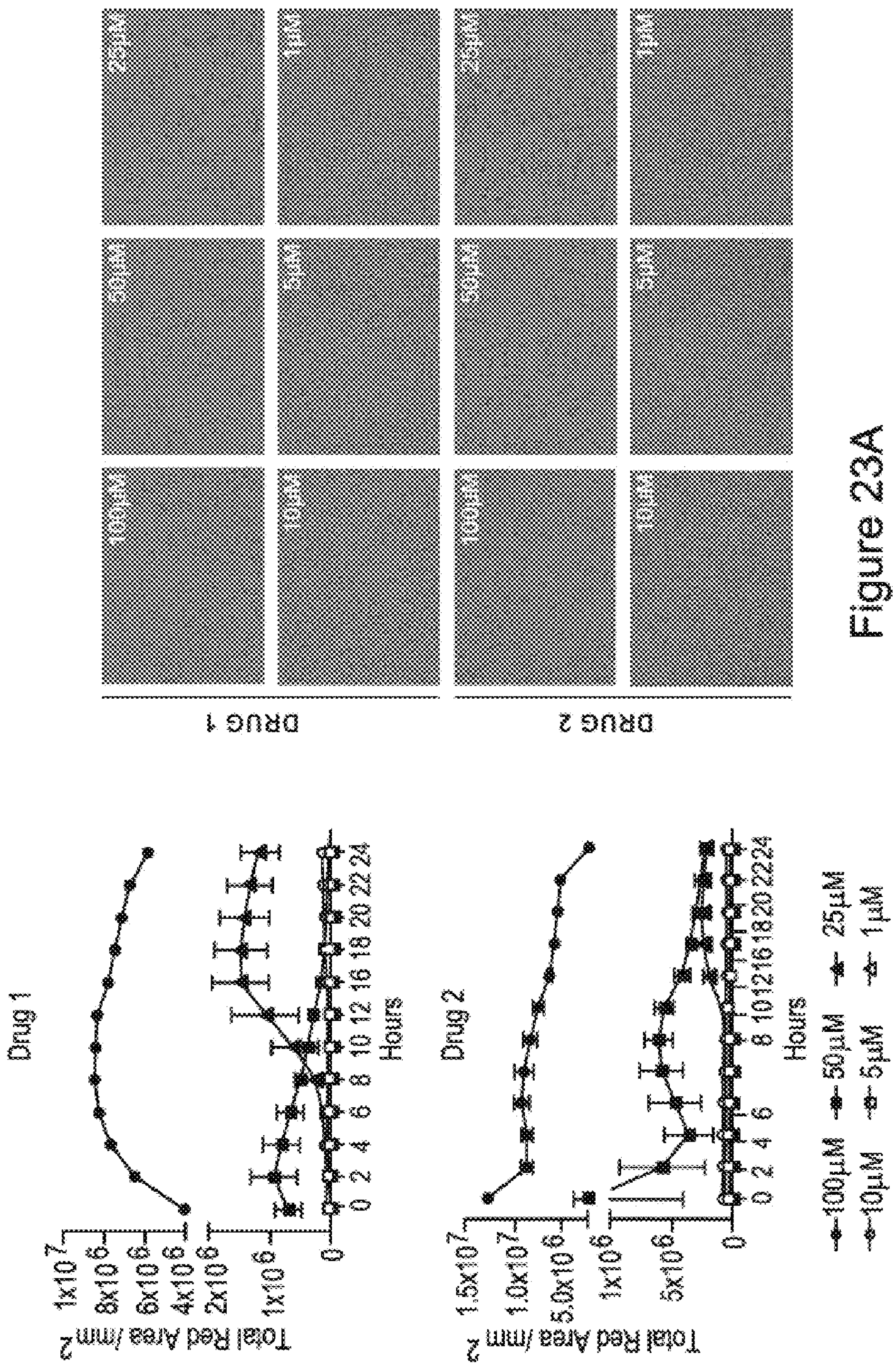
FIGS. 23A-23C show that concentrations of greater than 10 μM, both Drug-1 and -2 are toxic in vitro to PC3-PIP tumor cells and impair primary human T-cells function.
Figure 23B:
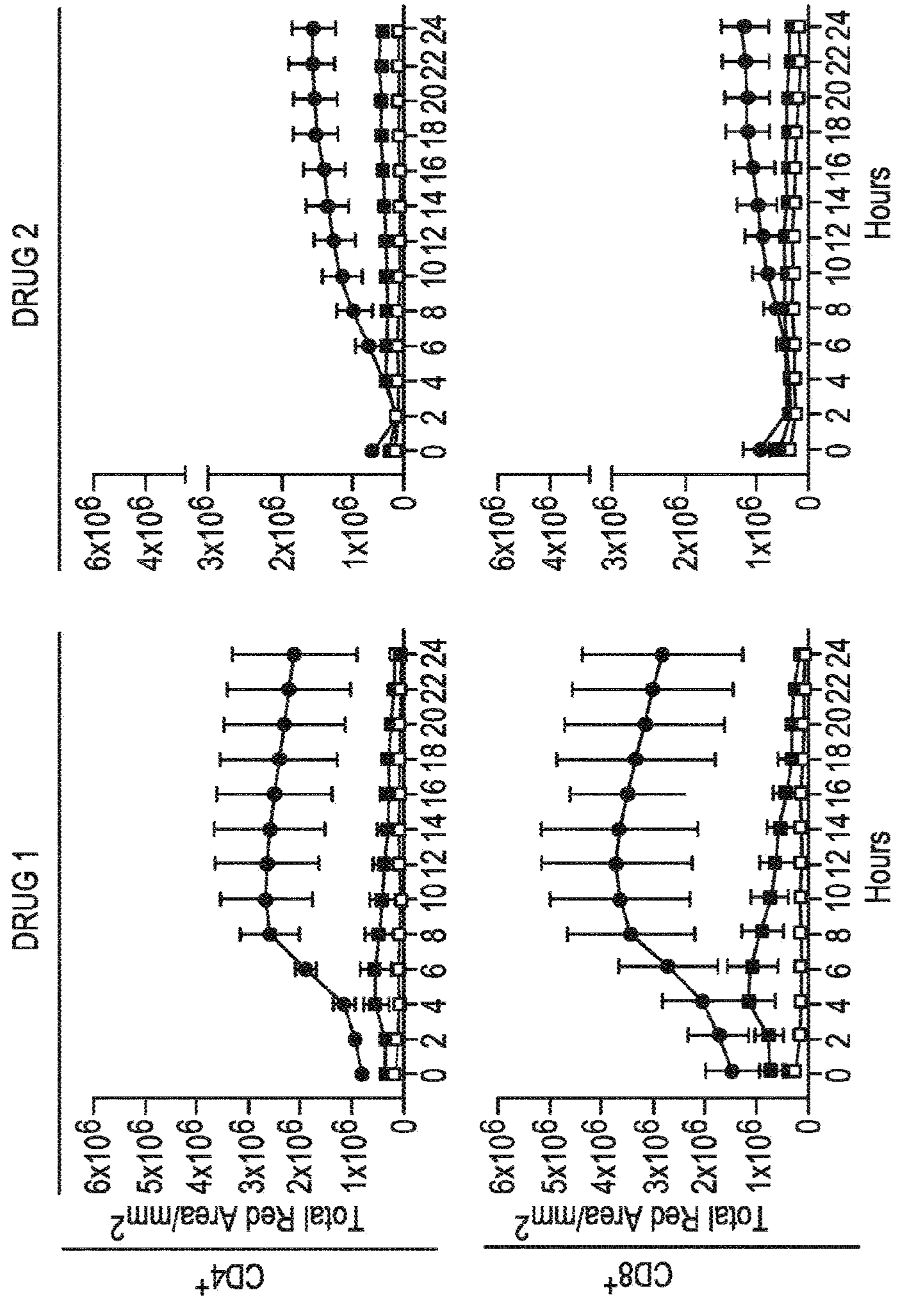
Figure 23C:
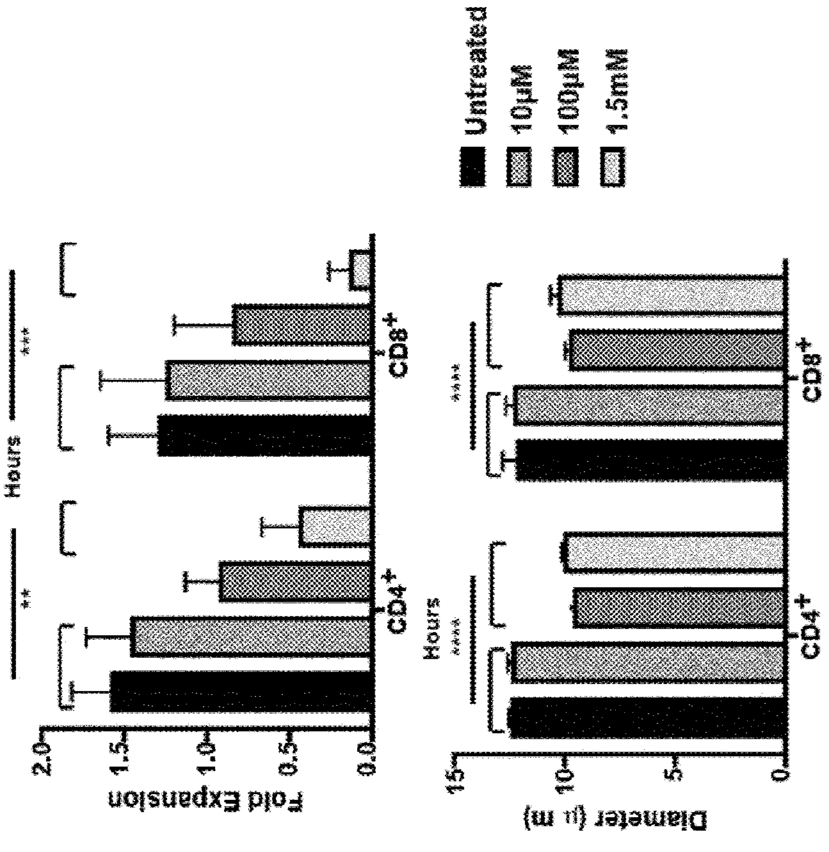

For these assays, PC3 and PC3-PIP cell lines were employed, the latter modified to stably overexpress human PSMA (FIGS. 22A and 21)[43]. 10 μM was identified as the maximal dose of Drug-1 and Drug-2 that did not cause direct toxicity on tumor and T-cells (FIG. 23).

Figure 22B:
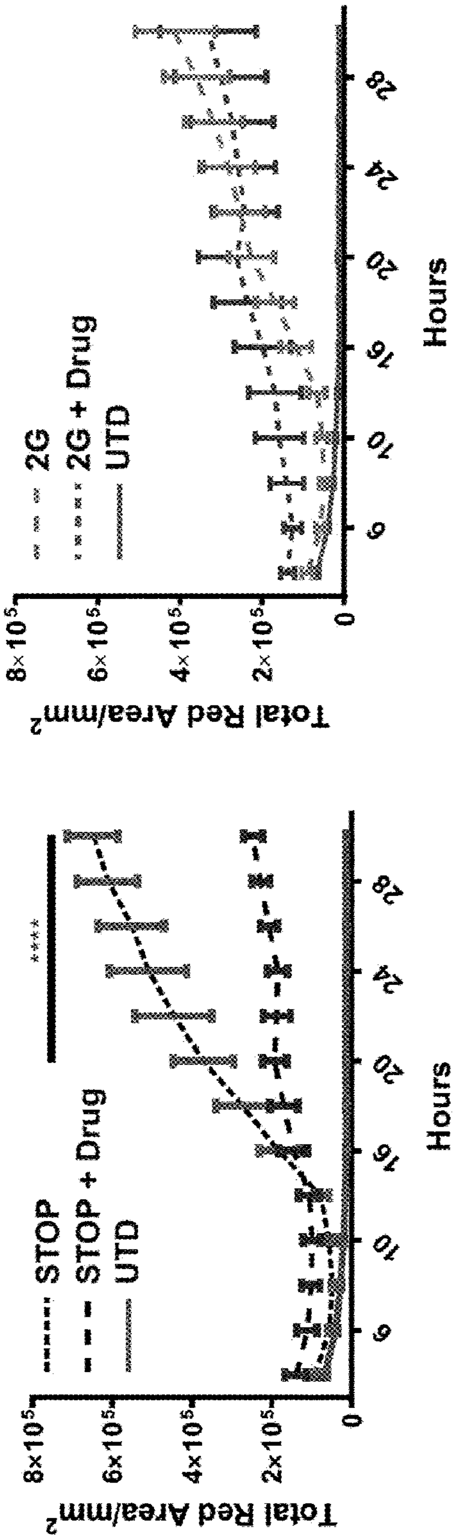
Figure 24A:
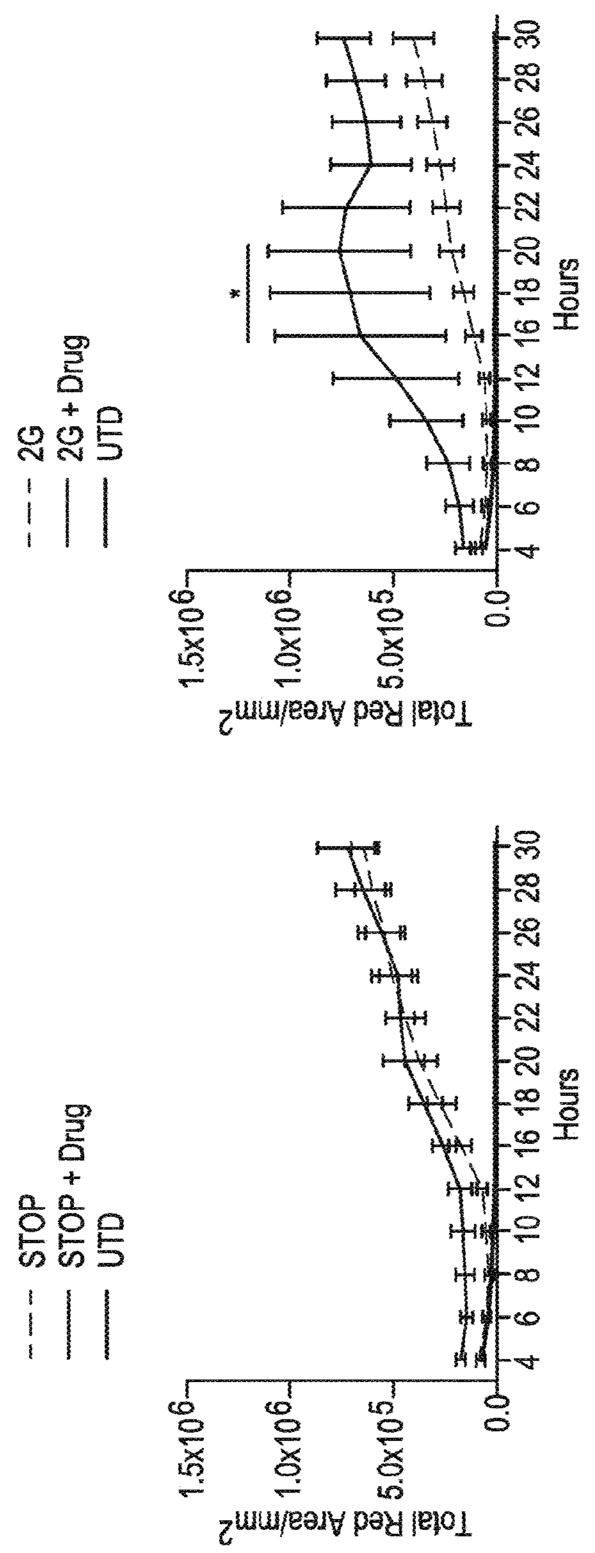
FIGS. 24A-24B show that STOP-CAR-T cytotoxicity is not significantly attenuated in the presence of 10 μM Drug-1 or lower doses of Drug-2.
Figure 24B:
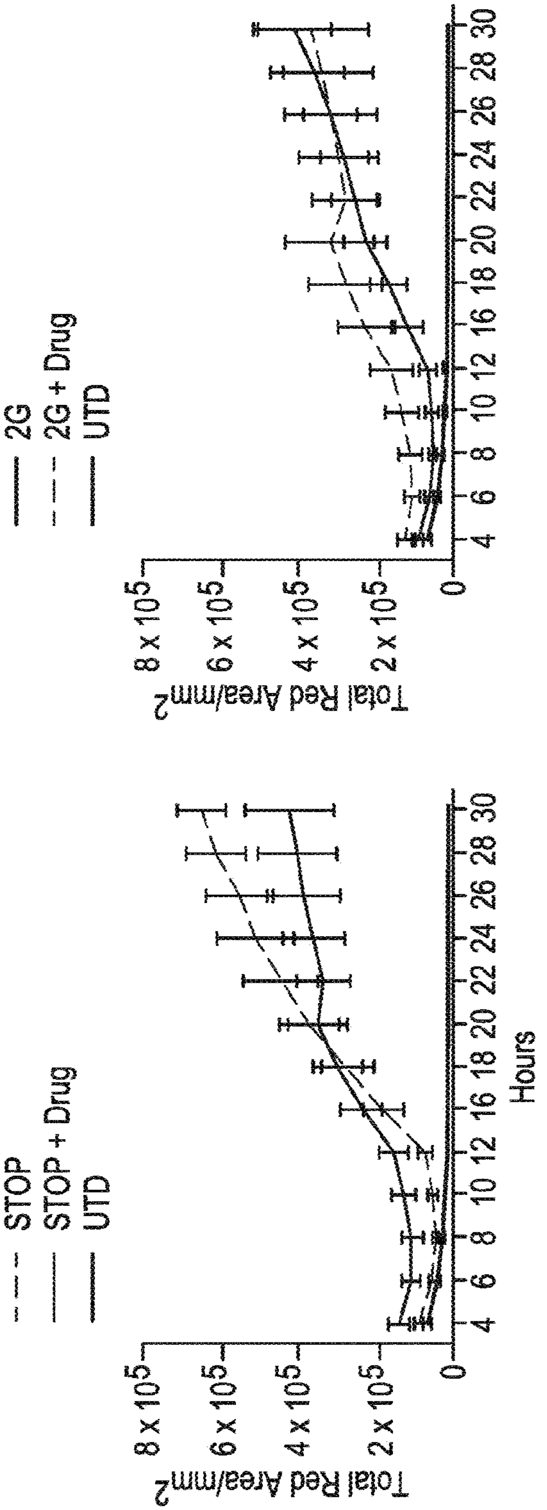
Figure 25A:
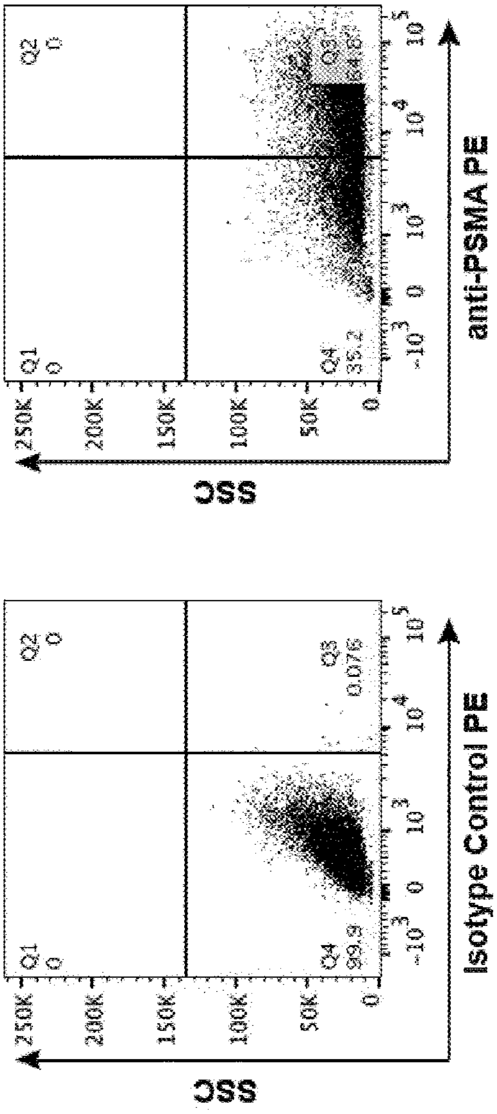
FIGS. 25A-25D show that STOP-CAR-Ts recognize and respond to PSMA+22Rv1 tumor cells.
Figure 25B:
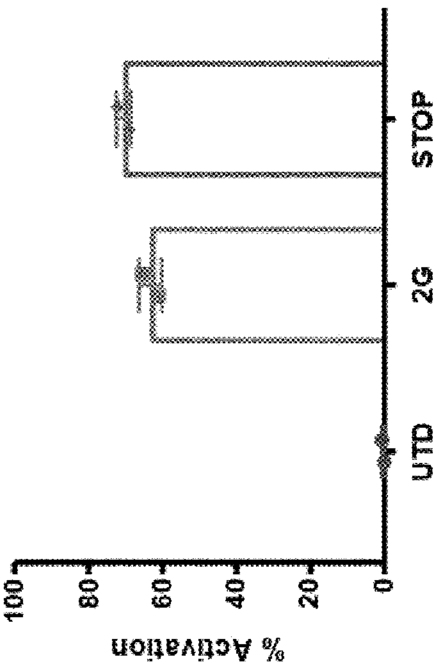
Figure 25C:
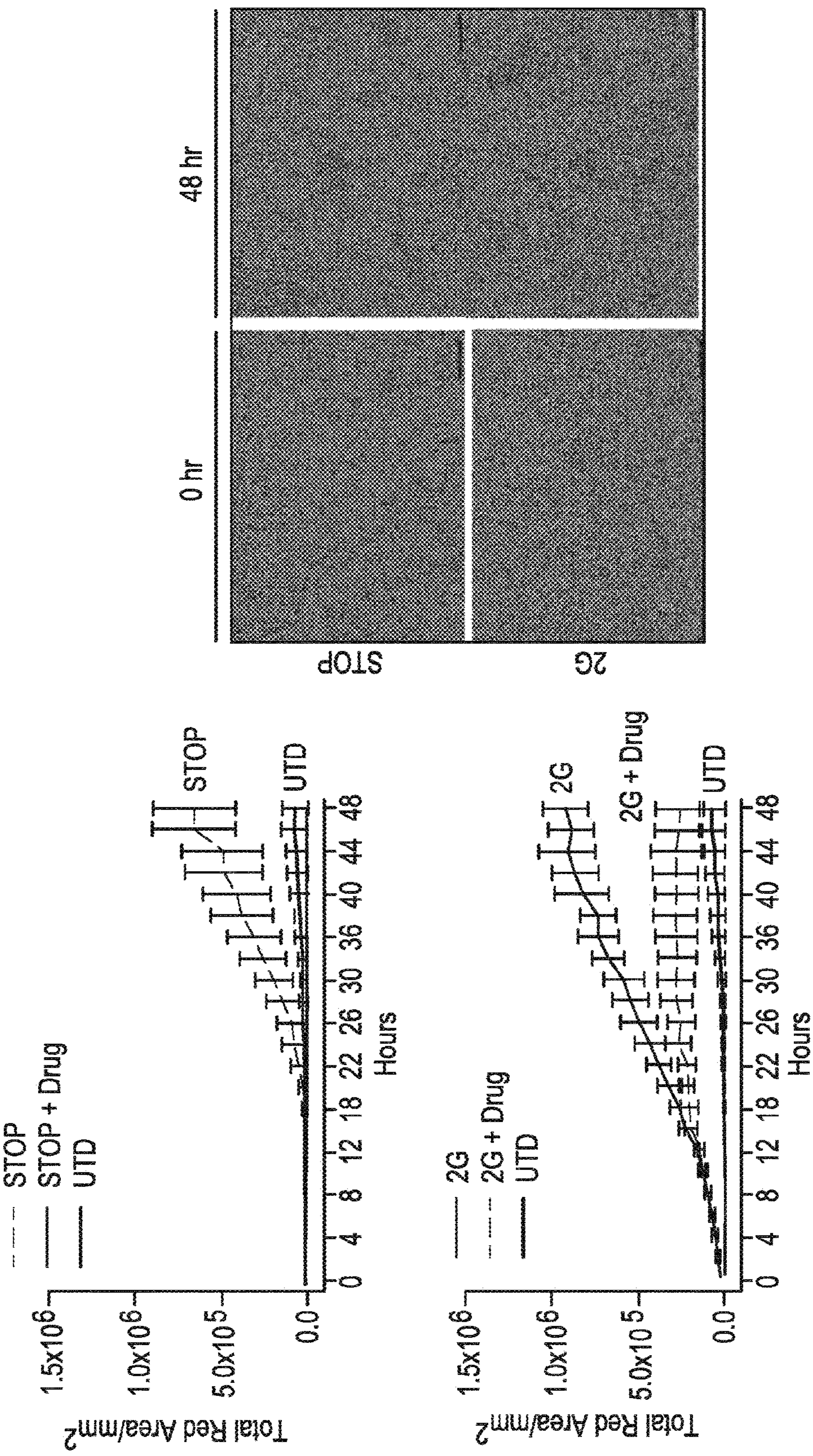
Figure 25D:
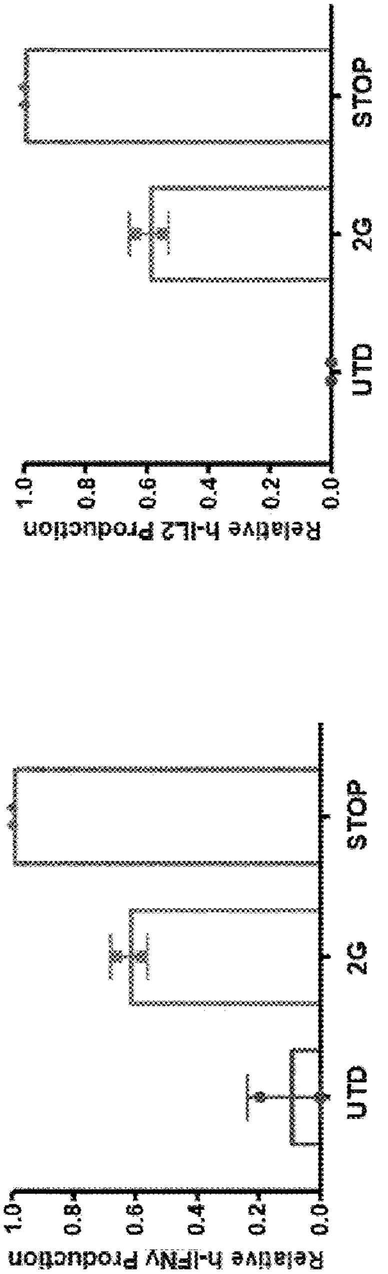
Figure 26A:
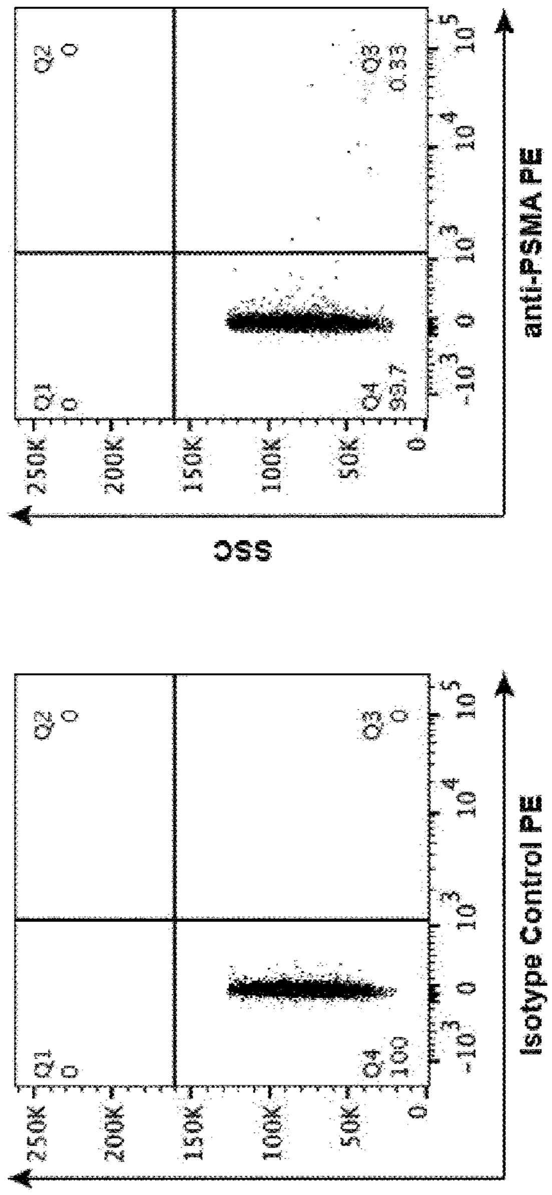
FIGS. 26A-26C show that STOP-CAR-Ts and 2G-CAR-Ts targeting PSMA are not activated in the presence of $PSMA^-$PC3 tumor cells.
Figure 26B:
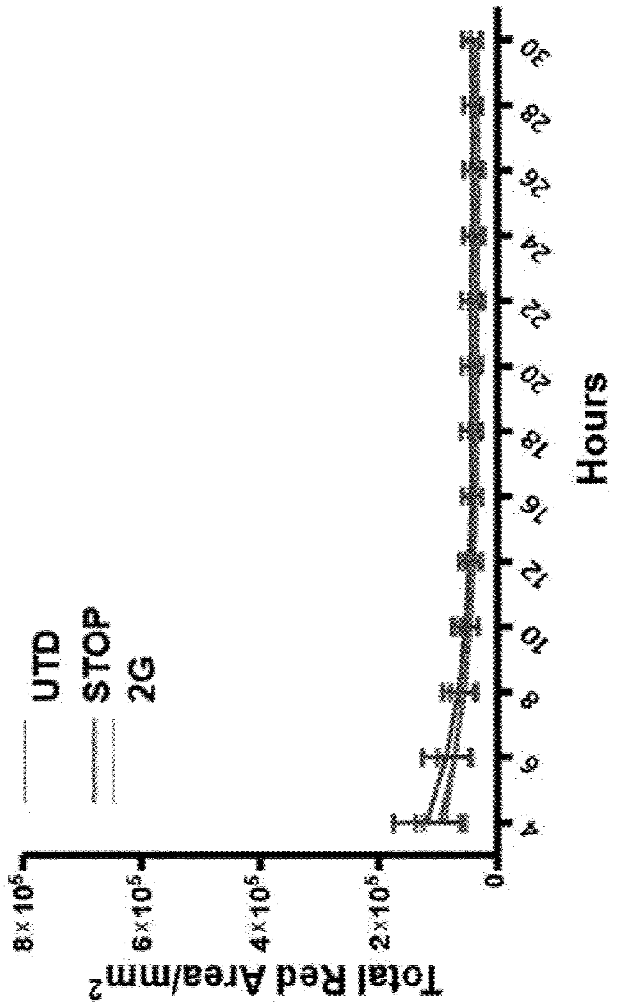
Figure 26C:
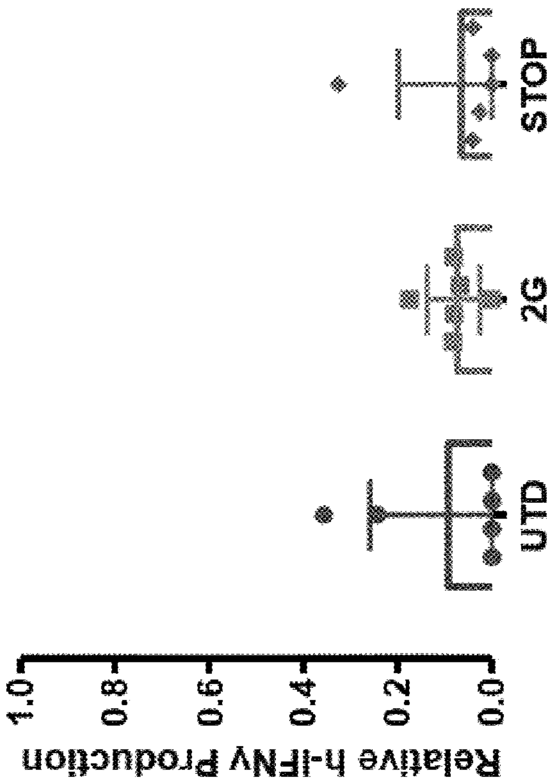

In all in vitro assays, 2G and STOP-CAR-Ts, normalized for equivalent cell surface expression, displayed similar cytolytic activity towards PC3-PIP cells. Addition of 10 μM Drug-2 specifically impaired the cytotoxicity of STOP-CAR-Ts, but not of 2G-CAR-Ts (FIG. 22B). However, Drug-1 was not effective at this concentration, as expected based on $IC_{50}$ in dissociating Bcl-XL from LD3. Similarly, lower concentrations of Drug-2 did not block cytotoxicity of STOP-CAR T cells (FIG. 24). Thus, all further in vitro tests, aside from controls, were performed with 10 μM Drug-2. Primary human STOP-CAR-Ts and 2G-CAR-Ts were also activated against 22Rv1 cells, a prostate cell line with natural expression of PSMA, as measured by cytotoxicity and cytokine production (IFNγ and IL-2), and activity of STOP-CARs was abrogated by 10 μM Drug-2 (FIG. 25). Finally, the activation of the CAR-Ts was antigen-specific, as there was no reactivity of either CAR-Ts against $PSMA^-$ PC3 cells (FIG. 26).

Figure 22C:
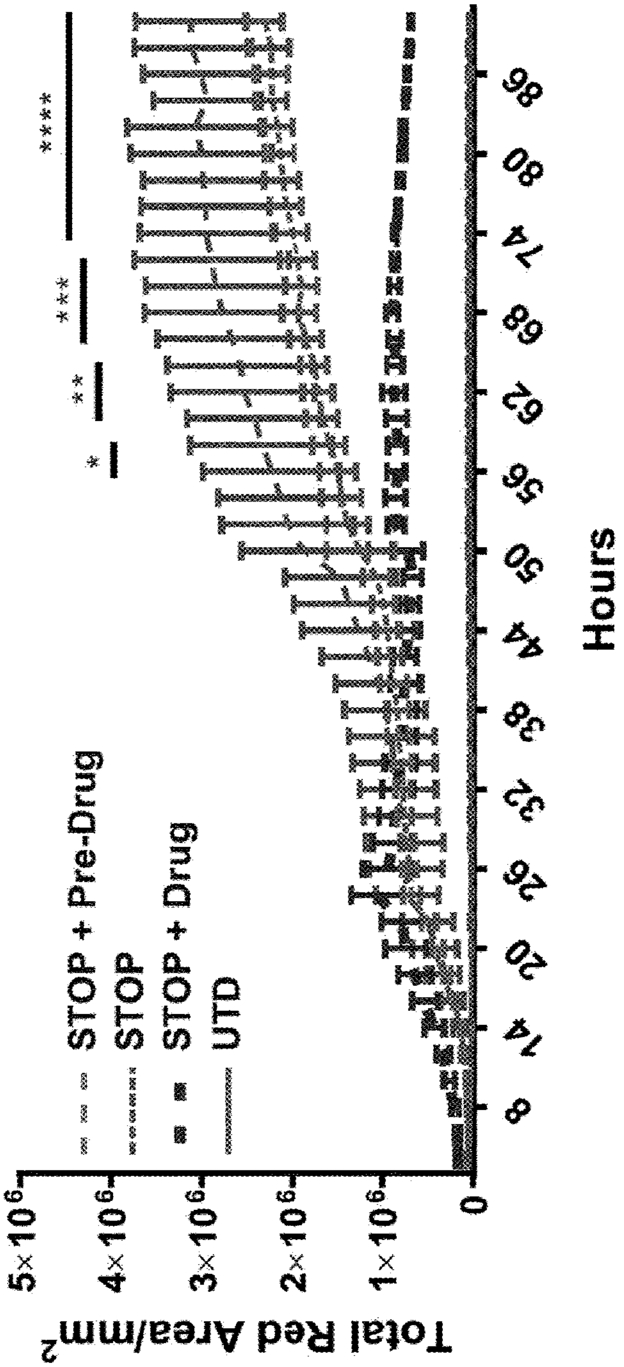
Figure 22D:
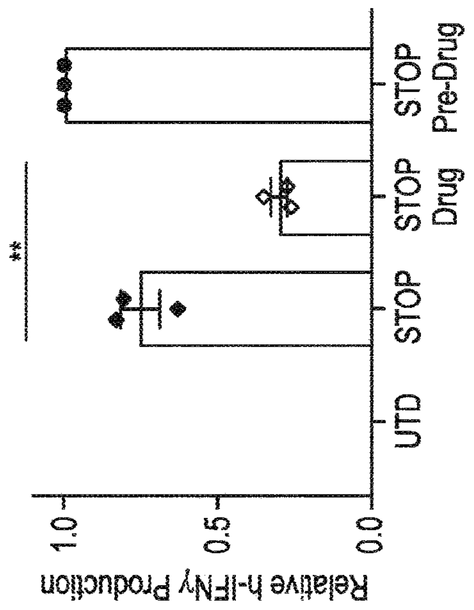

Next, STOP-CAR-Ts were assayed to determine if they would reactivate, i.e. become functionally active again upon heterodimerization of the chains, following drug withdrawal. CAR-Ts pre-cultured with 10 μM Drug-2 for 24 hours regained cytotoxicity and IFNγ production 48 hours following drug removal (FIGS. 22C and 22D). Thus, activation of STOP-CAR-Ts is antigen-specific, can be abrogated by Drug-2 in vitro and is fully restored following drug withdrawal.

To further evaluate the feasibility of the newly generated CDH, an anti-human CD19-STOP-CAR, derived from the previously validated FMC63 (J Immunother. 2009, September; 32(7): 689-702) and here after referred as 19-STOP-CAR, was also engineered. (FIG. 28). The same architecture containing the DAP10 dimerization domain was used, which enabled acceptable transduction efficiency in primary human $CD4^+$ and $CD8^+$ with an average R-chain/S-chain co-expression of 42% and 32% respectively, n=6 donors) (FIG. 28). It was observed the proliferative capacity of the 19-STOP-CAR-Ts was similar to UTD T-cells and phenotypic analysis revealed effector/memory differentiation similar to that of 19-2G-CAR-Ts (FIG. 28). When redirected against CD19+ target cells, 19-STOP-CAR Ts showed specific killing activity and IFNγ production in absence of Drug, comparable to 19-2G-CAR Ts. However, due to the high sensitivity of lymphoma and leukemia cell lines to Bcl-XL inhibitors, no long term cytotoxicity experiments where Drug was directly administered in the co-culture media were performed. Nevertheless to show the CDH off-switch in presence of CD19+ target, 19-STOP-CAR-Ts were preconditioned for 12 hours with 10 μM Drug and then set up the experimental co-culture in absence of the compounds. After 4 h co-culture, 19-STOP-CAR-Ts showed significant cytotoxic activity against BV173 and Bjab target cells, comparable to 19-2G-CAR Ts, while when pre-incubated with the Drug the killing activity is significantly decreased in both the experimental setting, thus showing the effectiveness of CDH Off-Switch in the context of a different scFv.

Figure 3:
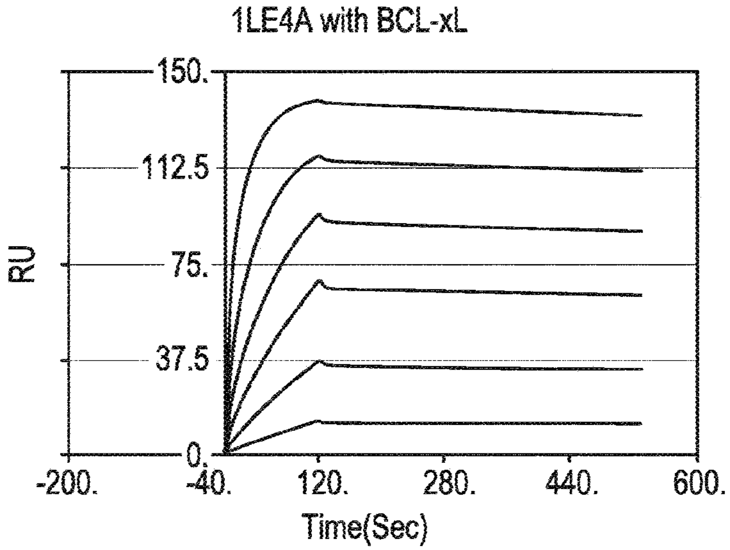
FIG. 3 shows the interaction of BCL-xL with 1LE4A.
Figure 22E:
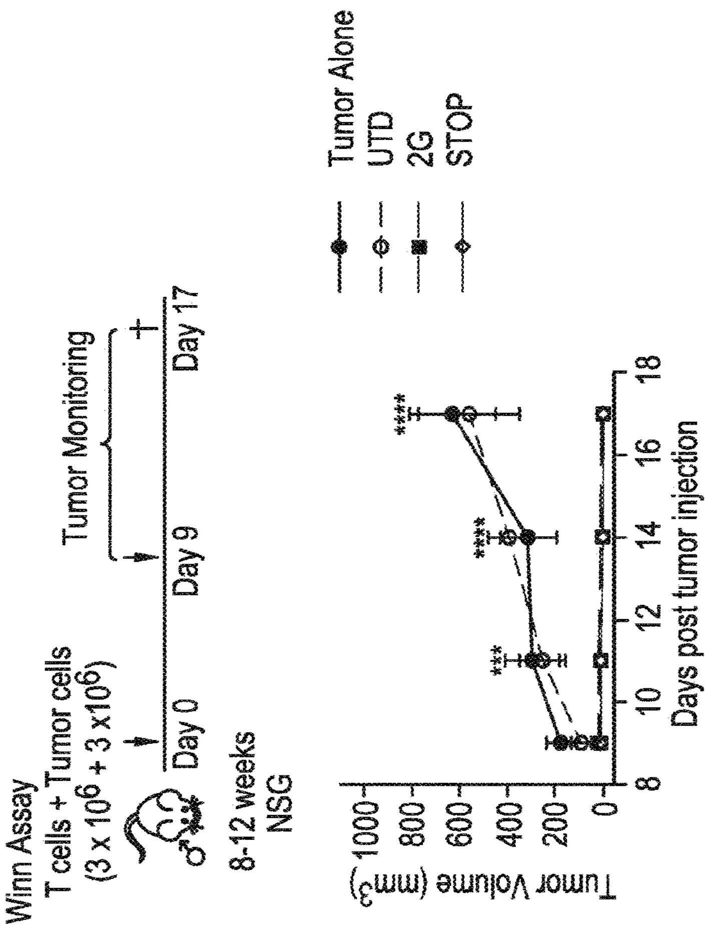
Figure 22F:
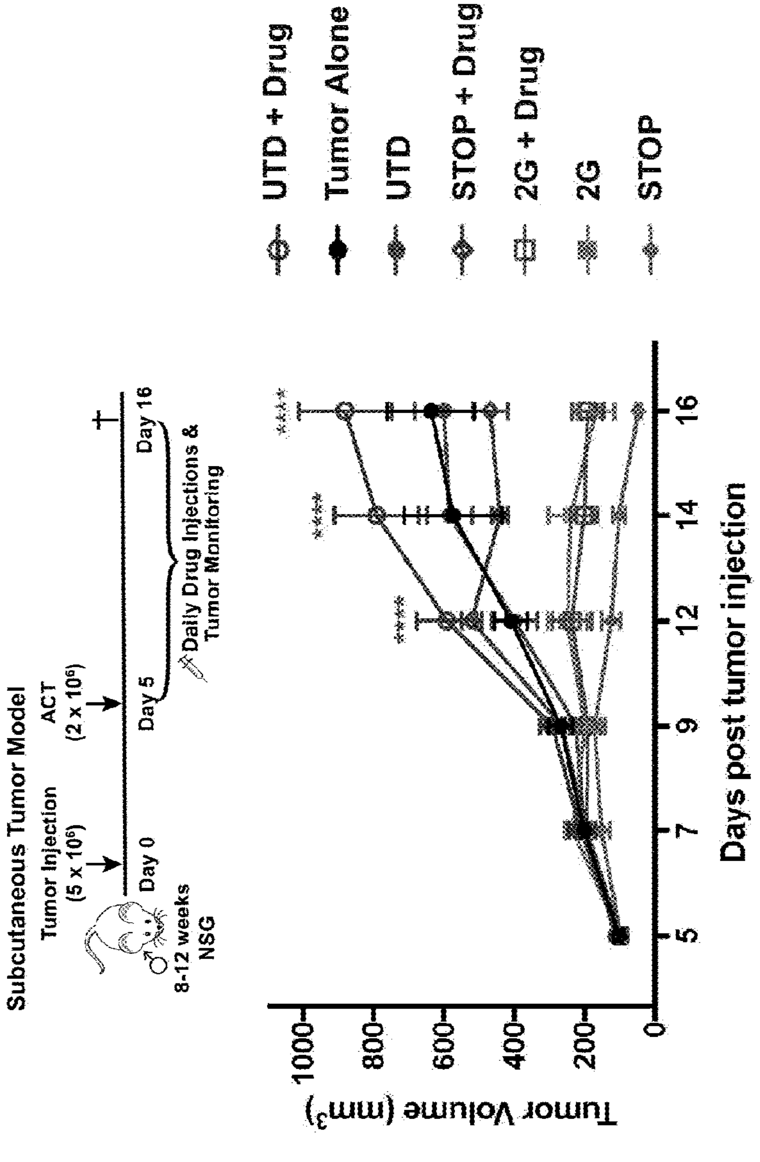
Figure 27B:
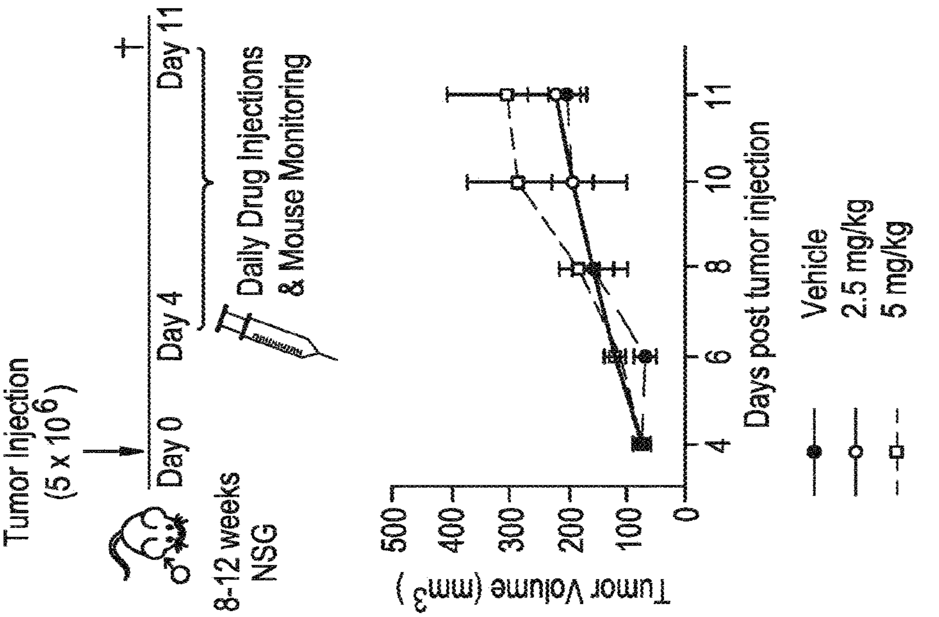
FIGS. 27A-27C show that Drug-2 is not toxic to mice nor does it impair tumor growth at doses of up to 5 mg/kg.
Figure 27A:
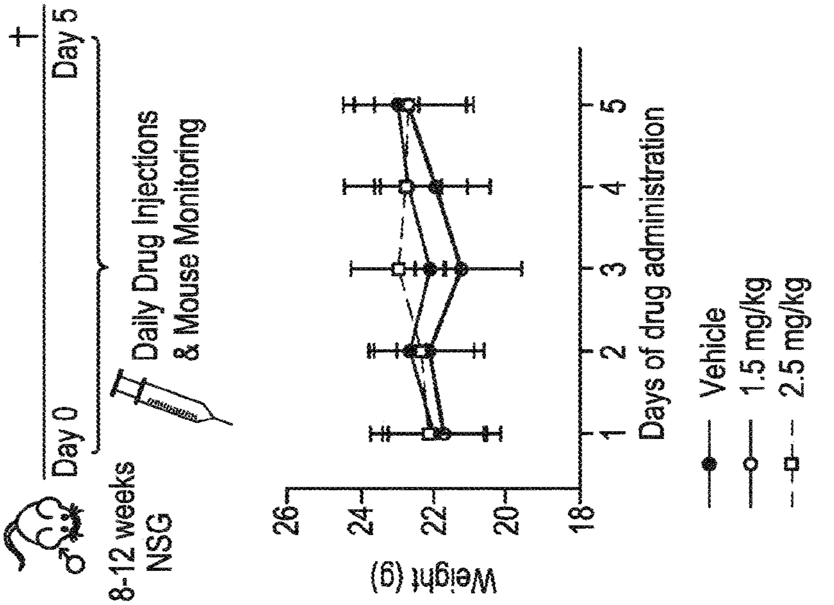
Figure 27C:
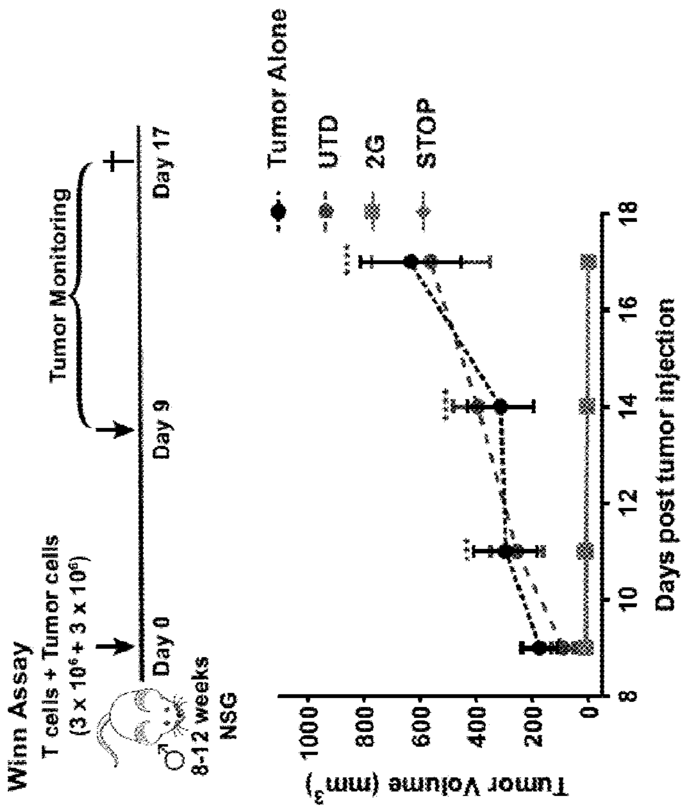

Lastly, the function of STOP-CAR-Ts was tested in vivo. In a Winn assay, where both STOP- and 2G-CAR-Ts were co-injected with tumor cells, both were able to fully control PC3-PIP tumor growth (FIG. 22E). As a proof-of-principle that STOP-CAR-T activity can be disrupted in vivo over an extended period of time by drug administration, CAR-Ts were further assayed against subcutaneous PC3-PIP tumors in two independent experiments, with or without Drug-2 as described below under the heading "Subcutaneous therapeutic prostate tumor model". Daily injections of up to 5 mg/kg of Drug-2 were not toxic to NSG mice and did not impair PC3-PIP tumor growth (FIG. 27). Mice inoculated with $5\times10^6$ tumor cells were treated (on day 5) with $2\times10^6$ CAR-Ts. Both 2G-CAR-Ts and STOP-CAR-Ts significantly controlled tumor growth in vivo, while the daily administration of Drug-2 disrupted STOP-CAR-T activity, resulting in uncontrolled tumor growth (FIG. 22F). Moreover, the dynamicity of the system was tested in vivo by adding Drug to STOP-CAR Ts after they showed significant tumor control (Day 11) or, on the opposite, by removing Drug after tumor escaped, proving the effective reversibility of STOP-CAR-Ts activity (FIG. 3F and FIG. 27). Thus, STOP-CAR-Ts controlled solid tumor growth with a similar efficacy as 2G-CAR-Ts, while their activity could be abrogated by a specific drug disruptor in vivo.

In summary, using a computational protein design approach, a high-affinity CDH comprising only 11 interface mutations relative to the initial human scaffold was developed. The CDH was incorporated into a heterodimeric STOP-CAR that can specifically activate primary human T-cells in the presence of target antigen. The efficacy of STOP-CAR-Ts was equivalent to conventional 2G CAR-Ts, but their in vitro and in vivo activities were specifically abrogated in the presence of a small-molecule drug disruptive to the CDH. In addition, STOP-CAR-T activity was restored following drug withdrawal. These results underscore that computational structure-based protein design holds enormous potential in the advancement of cellular therapies, both in terms of safety and function. The STOP-CAR-T data presented provide a proof-of-principle for a rationally designed safety mechanism with translational potential.

Materials and Methods

Computational Design

The design of the Bcl-XL binders was performed using a side-chain grafting approach[44]. Several crystal structures have revealed the drug binding pocket targeted by multiple drugs that inhibit the Bcl-XL:BIM-BH3 binding interaction[45]. Additionally, peptides derived from BIM-BH3 have also been crystallized in complex with Bcl-XL occupying the same binding pocket[46]. To design novel binders that could be competitively displaced by available small molecule drugs, the Bcl-XL:BIM-BH3 complex was used to search for proteins that could fulfill two criteria: I) backbone conformation that mimicked the BIM-BH3 peptide, which was fully helical; II) a three-dimensional topology that was compatible with the Bcl-XL structure to allow a productive binding interaction.

After candidate protein scaffolds were found, the hotspot side chains were transplanted to the scaffolds and additional design was performed in the interfacial positions of the putative scaffolds. Specifically, for the designs presented here, twelve residues were selected that form the binding motif of BIM-BH3 to Bcl-XL (residues 90 to 101). Residues 90, 91, 94, 97, 98, and 101 (BH3 numbering) were selected as 'hotspot' residues, and their identity maintained, while the remaining residues in the binding motif and interface were allowed to mutate. The scaffold search was performed in a subset of the PDB that fulfilled all the following criteria: I) monomeric proteins with one chain in the biological assembly; II) length between 80 and 160 residues; III) presence of helical motifs; IV) structures determined by x-ray crystallography. These filters resulted in a database of 11012 proteins to be searched as potential scaffolds.

The design protocol was encoded using the RosettaScripts interface[47] and consisted of the following steps: I) MotifGraft searched for structural matches of the helical segment of BIM-BH3 in the scaffold database that presented less than or equal to 1.0 Å backbone RMSD; II) if a backbone match was found, steric compatibility with the scaffold and Bcl-XL was assessed, scaffolds whose backbone clashed with the seed or with the target Bcl-XL were discarded. Scaffolds that fulfilled the matching criteria were carried to the design stage, hotspot residues and side chain conformations were transplanted to the scaffold and non-hotspot residues within 6 Å of Bcl-XL were allowed to mutate to any amino acid with a positive score according to the BLOSUM62 matrix[48]. This sequence constraint was utilized to minimize the changes from the original scaffold. The design procedure consisted of two rounds of sequence design[49] intercalated by two rounds of side chain continuous minimization[50], including small changes to the protein dihedral angles within their energy wells which allow them to escape steric clashes[51].

The final list of designs that was ranked by the Rosetta predicted ddG. Designs with a ddG superior to −10 were not considered. This resulted in a list of 85 designed scaffolds. After visual inspection of the resulting design, extra filters were applied to remove proteins that were not globular and showed extended conformations with designed binding motifs with very poor packing to the rest of the protein scaffold. As a first filter to select globular proteins a metric proposed by Miller et al. was used, which found that the solvent-accessible surface area A # of globular proteins correlates well with the mass M of the protein, under the power law:

$$A\# = 6.3M^{*.+}$$

The above power law was used to judge whether designed scaffolds were globular proteins or not. To filter for globularity, scaffolds whose ratio A #/6.3 $M^{*.+}$, was below a cutoff of 0.8 were removed from consideration. As a second filter the packing interactions of the binding motif with the remaining scaffold were quantified. Two structural features were measured: I) number of vdW contacts with binding segment and the scaffold, using the probe program[53]; II) buried surface area of the binding segment in the context of the scaffold. Scaffolds whose number of vdW contact dots between seed and scaffold was less than 900 or where the 'buried surface area' of the seed upon grafting was less than 4000, were discarded. These thresholds were determined empirically based on the metrics for well-packed seeds. Out of the 85 scaffolds selected by ddG, only 11 passed the packing and globularity filters.

After manual inspection and comparison to the original BIM-BH3 domains, two human and one rat protein (with a human homolog) scaffolds were selected from this list: rat Syntaxin6 (PDB ID: 1LVF, chain A)(LD1), Human Focal Adhesion Targeting (FAT) Domain (PDB ID: 3GM2, chain A)(LD2) and the human Apolipoprotein E4 mutant (PDB ID: 1LE4, chain A)(LD3). Three residues in LD1, and 4 residues in LD2 were manually reverted to their identity in the native scaffold as they were found to not interact with the target. In the case of LD3 an Ala residue in the interface was mutated to Gln in a second design run by Rosetta (Supp. FIG. 1).

Circular Dichroism

Folding of the designed scaffolds and Bcl-XL was measured using circular dichroism spectroscopy. Protein samples were dissolved in a phosphate saline buffer at a protein concentration of around 0.2 mg $mL^{-1}$ (20 μM). The sample was loaded into a 0.1 cm path-length quartz cuvette (Hellma). The far-UV CD spectrum between 190 nm and 250 nm was recorded by a J-815 spectrometer (Jasco) with a slit band-width of 2.0 nm, with a scanning speed at 20 nm/min. Response time was set to 0.125 sec and spectra were averaged from 2 individual scans.

Size Exclusion Chromatography Coupled with Multi-Angle Light Scattering

LD3 and Bcl-XL were characterized by size exclusion chromatography coupled to Light Scattering (SEC-MALS) to determine solution state, and to study dimerization and drug-induced monomerization properties. LD3 and Bcl-XL were injected at 50-100 μM in PBS or reducing elution buffer (5 mM Tris, 50 mM NaCl, 5 mM 2-mercaptoethanol), respectively, on a Superdex™ 75 300/10 GL column (GE Healthcare) using an HPLC system (Ultimate 3000, Thermo Scientific) with a flow rate of 0.5 ml/min. The UV spectrum at 280 nm was collected along with static light scatter signal by a multi-angle light scattering device (miniDAWN TREOS, Wyatt). For determining the drug-induced monomerization, 50 μM Bcl-XL was mixed with equimolar LD3. Either DMSO alone or Drug-2 (A1155463, ChemieTek) at 10 mM in DMSO were added to a final concentration of 100 μM (2-fold excess), and samples were directly analyzed by SEC-MALS in PBS to detect complex formation and forced dissociation. The light scatter signal of the sample was collected from three different angles, and the result was analyzed by the Wyatt evaluation software (ASTRA version 6).

Purification of Bcl-2 and LD3 for Crystallization

The Bcl-2 protein used in this study is a chimeric protein containing human Bcl-2 (residues 1-50 and 92-207) and human Bcl-XL (residues 35-50) that replaces along loop in Bcl-2 (residues 51-91)[54]. LD3 gene was cloned as described above. Both proteins were produced with an N-terminal 6×(His) tag in the *E. coli* BL21 (DE3) RIPL strain (Novagen) at 18° C. overnight. Cell lysate in a buffer solution containing 20 mM Tris-HCl (pH 7.5) and 100 mM NaCl was loaded onto Co-NTA resin (Thermo Scientific), and the proteins were eluted with the buffer solution containing 150 mM imidazole. While the 6×(His) tag on LD3 was uncleavable, that of Bcl-2 was cleaved with the TEV protease. The two proteins were further purified by using a HiTrap™ Q anion exchange column (GE Healthcare).

Preparation, Crystallization, and Structure Determination of the Bcl-2:LD3 Complex Purified Bcl-2 (0.9 mg/mL) was mixed with LD3 (4.9 mg/mL) in a 1:1 molar ratio, and the complex between the two proteins was isolated by gel filtration using a HiLoad® 26/60 Superdex® 75 (GE Healthcare). The crystals of the resulting complex were obtained by the hanging-drop vapor diffusion method at 22° C. by mixing and equilibrating 2 μl of each of the complex (24.3 mg/ml) and a precipitant solution containing 17% PEG2000, 0.1 M Sodium Succinate (pH 5.5) and 0.32 M Ammonium Sulfate. Before data collection, the crystals were immersed briefly in a cryoprotectant solution, which was the reservoir solution containing additional 12.5% glycerol. A diffraction data set at 2.5 Å was collected on the beam line 11C at the Pohang Accelerator Laboratory, Korea. The structure was determined by the molecular replacement method with the Phaser-MR[55] in the PHENIX suite[56] using the structures of BCL-2[54] and Apolipoprotein E (PDB ID: 1LE4[57]) as search models. Subsequently, model building and refinement were carried out using the programs COOT[58] and CNS[59]. The final model does not include residues 1-8, 32-48 (including the entire Bcl-XL substitution region) and 165-166 of BCL-2, and residues 1-9 and 151-156 of LD3, whose electron densities were not observed or very weak. Crystallographic data statistics are summarized in FIG. 18. The coordinates of the Bcl-2:LD3 structure will be deposited in the Protein Data Bank and released immediately upon publication.

Cell Lines

The prostate carcinoma cell lines, 22Rv1 ($PSMA^{lo}$), PC3-PIP ($PMSA^{hi}$), and PC3 ($PSMA^{-}$), as well as 293T human embryonic kidney (HEK-293T) and Jurkat cell lines, BV173 and Bjab were cultured in RPMI-1640 supplemented with 10% heat-inactivated fetal bovine serum (FBS), 2 mmol/L L-glutamine, 100 μg/mL penicillin, and 100 U/mL streptomycin, at 37° $CO^2$ in a 5% $CO^2$ atmosphere (Invitrogen, Lifetechnologies). HEK-293, 22Rv1, and Jurkat cell lines were purchased from the ATCC. PC3-PIP and PC3 cell lines were kindly provided by Dr. A. Rosato (University ofPadau, Padova)[17]. The HEK-293 cell line was used for lentiviral packaging and preparation. Jurkat reporter cells were developed by lentiviral transduction to stably express 6×NFAT-mCherry such that upon activation they turn red.

STOP-CAR Construction

The two STOP-CAR chains, R-chain (Recognition) and S-chain (Signaling), were synthesized as gene-strings (GeneArt™, Thermo Fischer Scientific) and cloned into a third-generation self-inactivating lentiviral expression vector, pELNS, with expression driven by the elongation factor-1α (EF-1α) promoter. The anti-PSMA scFv derived from monoclonal 29,30 antibody J591 was used as the tumor-targeting moiety[29,30]. J. Immunother., 2009 September; 32(7): 689-702. The R-chain comprises a CD8a leader sequence, anti-PSMA scFv, CD8a hinge, CD28 transmembrane (TM), CD28 endodomain (ED), a serine/glycine (SG) linker, LD3. The S-chain comprises CD8α leader sequence, cMyc, DAP10 ectodomain, CD8a hinge, CD28 TM, CD28 ED, SG linker, Bcl-XL, SG linker, CD3ζED.

Recombinant Lentivirus Production

High-titer replication-defective lentivirus (LV) were produced and concentrated by ultracentrifugation for primary T-cell transduction. Briefly, 24 h before transfection, HEK-293 cells were seeded at $10\times10^6$ in 30 mL medium in a T-150 tissue culture flask. All plasmid DNA was purified using the Endo-free Maxiprep kit (Invitrogen, Lifetechnologies). HEK-293 cells were transfected with 7 pg pVSV-G (VSV glycoprotein expression plasmid), 18 μg of R874 (Rev and Gag/Pol expression plasmid), and 15 μg of pELNS transgene plasmid, using a mix of Turbofect™ (Thermo Fisher Scientific AG) and Optimem™ media (Invitrogen, Life Technologies, 180 μL of Turbofect™ for 3 mL of Optimem™). The viral supernatant was harvested 48 h post-transfection. Viral particles were concentrated by ultracentrifugation for 2 h at 24,000 g and re-suspended in 400 μL complete RPMI-1640 media, followed by immediate snap freezing on dry ice.

Jurkat Cell Transduction

Jurkat cells were suspended at $1\times10^6$ cell/mL and seeded into 48-well plates at 500 μL/well. For each transduction, 50 μL of virus supernatant was used. After incubation for 24 h at 37° C. the cell media was refreshed, and the cells were incubated for an additional 72 h at 37° C. before use.

Primary Human T Cell Transduction

Primary human T cells were isolated from the peripheral blood mononuclear cells (PBMCs) of healthy donors (HDs; prepared as buffycoats or apheresis filters). All blood samples were collected with informed consent of the HDs, and genetically-engineered with Ethics Approval from the Canton of Vaud to the laboratory of Dr. Coukos. Total PBMCs were obtained via Lymphoprep™ (Axonlab) separation solution, using a standard protocol of centrifugation. $CD4^+$ and $CD8^+$ T cells were isolated using a magnetic bead-based negative selection kit following the manufacturer's recommendations (easySEP™, Stem Cell technology). Purified $CD4^+$ and $CD8^+$ T cells were cultured at a 1:1 ratio in RPMI-1640 with Glutamax, supplemented with 10% heat-inactivated FBS, 100 U/mL penicillin, 100 µg/mL streptomycin sulfate, and stimulated with anti-CD3 and anti-CD28 monoclonal antibody (mAb)-coated-beads (Lifetechnologies) in a ratio of 1:2, T cells: beads. T cells were transduced with lentivirus particles at multiplicity of infection (MOI) of ~5-10, at 18 to 22 h post-activation. Human recombinant interleukin-2 (h-IL2; Glaxo) was replenished every other day for a concentration of 50 IU/mL until 5d post-stimulation (day +5). At day +5, magnetic beads were removed, and h-IL7 and h-IL15 (Miltenyi Biotec GmbH) were added to the cultures in place of h-IL2 at 10 ng/mL. A cell density of $0.5\text{-}1\times10^6$ cells/mL was maintained for expansion. Rested engineered T cells were adjusted for equivalent transgene expression before all functional assays.

Cytokine Release Assays

Cytokine release assays were performed by co-culture of $5\times10^4$ T cells with $5\times10^4$ target cells per well in 96-well round bottom plates, in duplicate, in a final volume of 200 µL RPMI media. After 24 h the co-culture supernatants were harvested and tested for presence of IFNγ and IL2 by commercial ELISA Kits according to the manufacturer's protocol (Biolegend). Values were normalized to the maximum value (set to 1) for each donor to eliminate variability due to other factors such as age and sex among HDs. The reported values represent the mean of cytokine production by STOP-CAR engineered T cells derived from HDs +/−standard deviation.

Cytotoxicity Assays

Cytotoxicity assays were performed using the IncuCyte® Instrument (Essen Bioscience). Briefly, $1.25\times10^4$ target cells were seeded in flat bottom 96-well plates (Costar, Vitaris). Four hours later, rested T cells (no cytokine addition for 48 h) were washed and seeded at $2.5\times10^4$/well, at a 2:1 E:T ratio in complete media. No exogenous cytokines were added during the co-culture period of the assay. Cytotox™ Red reagent (Essen Bioscience) was added at a final concentration of 125 nM in a total volume of 200 µL. Internal experimental negative controls were included in all assays, including co-incubation of untransduced (UTD) T cells and tumor cells, as well as tumor cells alone, in the presence of CytotoxicRed reagent to monitor spontaneous cell death over time. As a positive control, tumor cells alone were treated with 1% Triton™ solution to evaluate maximal killing in the assay. Images of total red area/well were collected every 2 h of the co-culture. The total red area/well was obtained by using the same analysis protocol on the IncuCyte® ZOOM software provided by Essen Bioscience. Data are expressed as mean of different HDs +/−standard deviation.

Short term cytotoxicity was performed by quantitative FACS™ acquisition. Briefly, $1.25\times10^4$ target cells were seeded in U-bottom 96-well plates (Costar, Vitaris). Rested T cells (untreated or pre-conditioned with 10 µM Drug) were seeded at $1.25\times10^4$/well at 1:1 E:T Ratio and then incubated at 37° C. for 4 hours. Cells were collected, washed and stained for CD3, CD19 and Live dead marker. FACS™ acquisition was kept at constant speed, normalized for the same time of sample running (30 sec/tube). Residual live CD3-CD19+ target cells were quantified and used as a final readout.

Flow Cytometric Analysis

To evaluate cell-surface expression of the heterodimeric STOP-CAR, transduced cells were stained with fluorescenated anti-human F(ab)' mAb to detect the R-chain, and fluorescenated anti-human cMyc mAb to detect the S-chain. Aqua live Dye BV510 and near-IR fluorescent reactive dye (APC Cy-7) were used to assess viability (Invitrogen, Life Technologies). The following mAbs (BD, Bioscience) were used for phenotypic memory analysis: BV711 mouse-anti-human CD3; BV605 mouse-anti-human CD4; APC-Cy7-labeled anti-human CD8; PE-Texas red-labeled mouse-anti-human CD45RA; BV421 mouse-anti-human CCR7. For evaluating STOP-CAR chain expression, gating was performed to isolate live single-cells. To determine memory phenotype, the $CD3^+$ population was first gated, followed by the $CD4^+$ and $CD8^+$ subsets, which were then evaluated for CD45RA and CCR7 expression to determine the percentage of naïve ($T_N$), Central Memory ($T_{CM}$), Effector Memory ($T_{EM}$), and terminally differentiated ($T_{EMRA}$) T cells. Tumor cell surface expression of PSMA and CD19 were quantified by fluorescently labelled anti-human-PSMA and anti-human CD19 mAbs. Isotype control-staining was employed.

Acquisition and analysis was performed using a BD™ FACS LRSII and FACS DIVA™ software (BD Biosciences), respectively. AMNIS® imaging of transduced Jurkat cells stained with FITC-labelled anti-human F(ab)', and APC-labelled anti-human cMyc, was used to evaluate co-localization of the R- and S-chains of the STOP-CAR. IDEAs software was used to analyze the data and perform the co-localization analysis after gating on live (DAPI negative), single-cells that are double-positive for FITC and APC.

Mice and In Vivo Experiments

NOD SCID gamma knock-out (NSG) mice were bred and housed in a specific and opportunistic pathogen-free (SOPF) animal facility in the Oncology Department of the University of Lausanne. All experiments were conducted according to the Swiss Federal Veterinary Office guidelines and were approved by the Cantonal Veterinary Office. All cages housed 5 animals in an enriched environment providing free access to food and water. During experimentation, all animals were monitored at least every other day for signs of distress. Mice were euthanized at end-point by carbon dioxide overdose.

In Vivo Drug Toxicity Testing

NSG males, aged 8-12 weeks, were shaved in the right flank and treated daily with 50 µl subcutaneous (sc) injections of A-1155463 (Drug-2) dissolved at 1.25 mg/kg or 2.5 mg/kg in a solution of saline and 2% dimethyl sulfoxide (DMSO), or vehicle (2% DMSO in saline). The animals were monitored daily and weighed to asses any signs of drug toxicity. To determine the potential effect of drug-2 on in vivo tumor control, 5 mice per group were sc injected with $5\times10^6$ PC3-PIP tumor cells. At day 4 when the tumors were palpable, daily peritumoral injections of 2.5 mg/kg or 5 mg/kg of Drug-2, or vehicle were administered. The animals were monitored daily and the tumors were calipered every other day. Tumor volumes were calculated using the formula $V=\frac{1}{2}(\text{length}\times\text{width}^2)$, where length is the greatest longitudinal diameter and width is the greatest transverse diameter determined via caliper measurement.

Winn Assay

For a preliminary evaluation of tumor control by STOP-CAR-Ts in comparison to 2G-CAR-Ts, a Winn assay was performed in which 8-12 week-old NSG males were sc injected with $3\times10^6$ PC3-PIP tumor cells, mixed with either saline or $3\times10^6$ UTD-Ts, STOP-CAR-Ts, or 2G-CAR-Ts. The tumor volume was evaluated via caliper measurement every other day.

Subcutaneous Therapeutic Prostate Tumor Model

To evaluate the therapeutic potential of STOP-CAR-Ts, 8-12-week-old NSG males were sc injected with $5\times10^6$ PC3-PIP tumor cells. Once palpable (day 5), the mice treated by peritumoral injection of $2\times10^6$ T cells (UTD-Ts, 2G-CAR-Ts or STOP-CAR-Ts). At 2 h post-T cell transfer, a peritumoral injection of Drug-2 at 5 mg/kg was performed. Injections of the drug were then provided daily until end-point or switched at Day 11 for dynamic control evaluation. Tumor volume was assessed every other day by caliper measurement.

Statistical Analysis

The Student's unpaired Mann-Whitney U-test was used to evaluate differences in absolute numbers of T cells (expansion over 10 days), T cells in each memory category, transferred number of T cells analyzed ex vivo, and cytokine secretion. A two-way ANOVA with post-hoc Turkey test was used to evaluate significant differences in specific cytolysis in vitro and tumor growth in vivo. GraphPad Prism 4.0 (GraphPad Software, La Jolla, CA) was used for statistical calculations. $P\leq0.05$ was considered significant. $P\leq0.05$ is represented as *, $P\leq0.01$ is represented as , $P\leq0.001$ is represented as *, and $P<0.0001$ is represented as ****.

Example 3. STOP-CAR Validation: Anti-CD19-STOP-CAR Generation and Functional Characterization In this example, cell surface expression was monitored, an in vitro comparison to anti-CD19 2G-CAR T cells was performed, and functional blockade with drug was tested. The structure of the anti-CD19 2G-CAR is shown in FIG. 16A. An anti-human CD19-STOP-CAR, with the previously validated anti-CD19 scFv, FMC63 (J. Immunother. 2009, September; 32(7): 689-702) was engineered. The 19-STOP-CAR construct, as shown in FIG. 28A, has a similar design as that of the anti-PSMA STOP-CAR comprising the DAP1-dimerization domain.

Figure 28A:
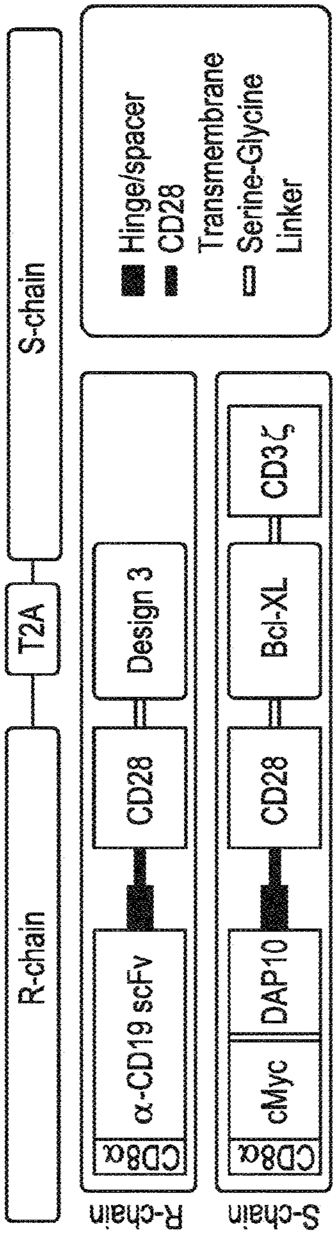
FIG. 28A is a schematic showing the architecture of the 19-STOP-CAR.
Figure 28B:
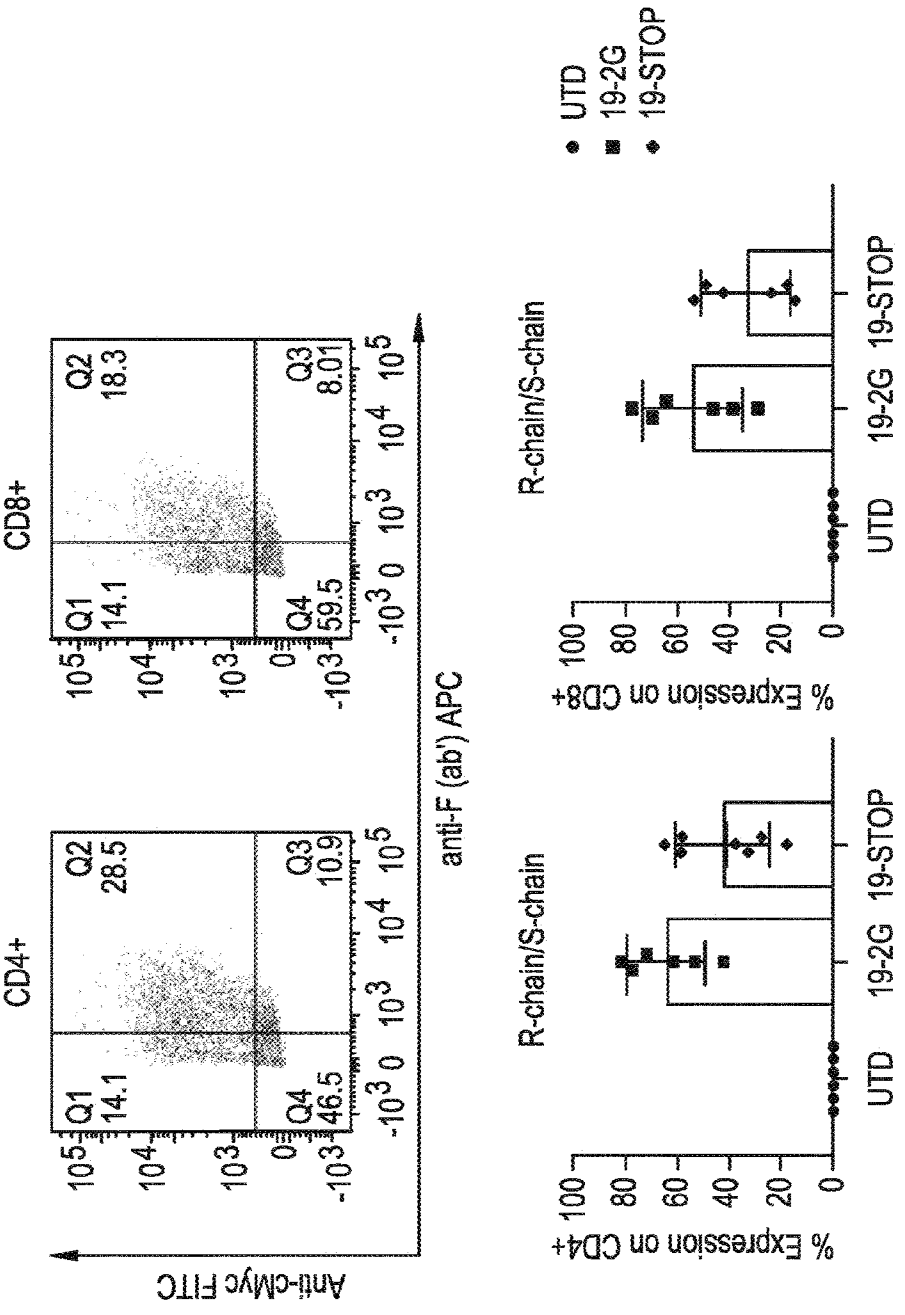
FIG. 28B is a graph showing the results of a flow cytometric evaluation of R- and S-chain level of co-expression on primary T cells, CD4 and CD8 respectively, stained by anti-human F(ab)-Ab-APC and anti-CMyc-Ab-FITC (left). The transduction efficiency of primary human CD4+ and CD8+ T cells with a second generation anti-CD19-CAR (19-2G) and CD19 STOP-CAR (19-STOP)(n=6) is shown.
Figure 28C:
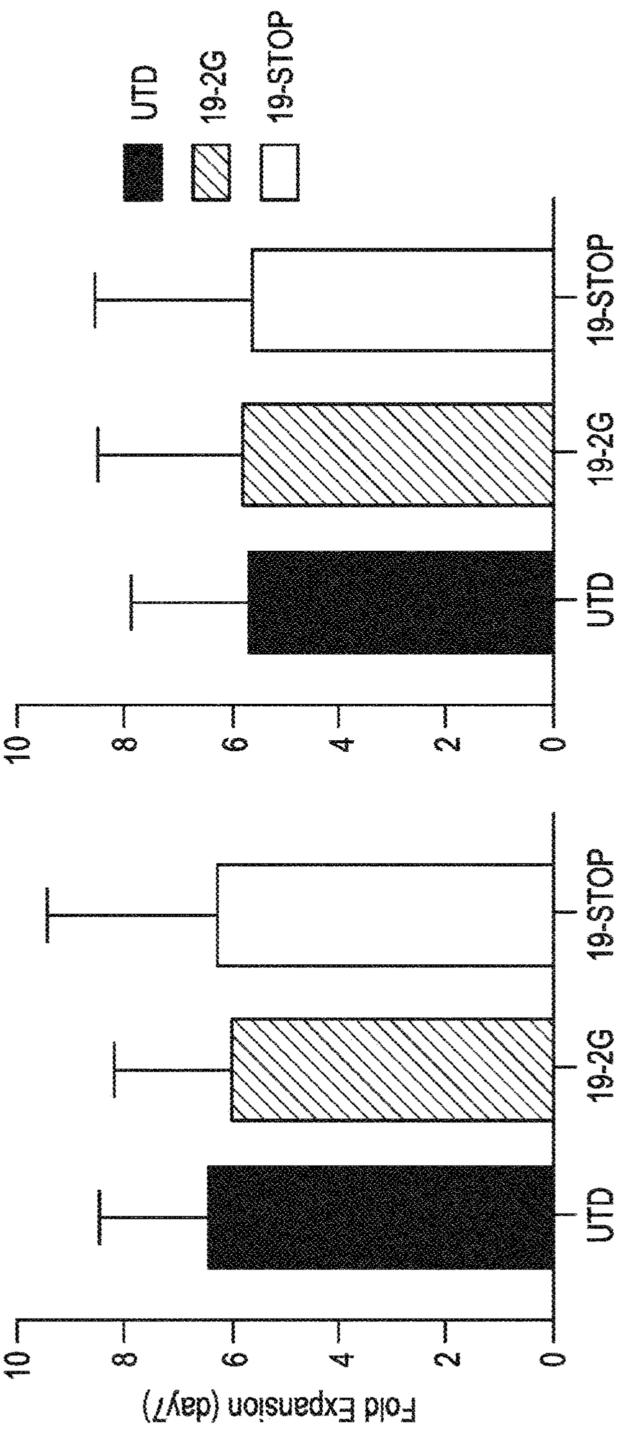
FIG. 28C is a graph showing the percentage fold expansion of UTD, 192G-Ts and 19-STOP-Ts (n=6). No difference in the fold expansion of any of UTD, 192G-Ts and 19-STOP-Ts was observed.
Figure 28D:
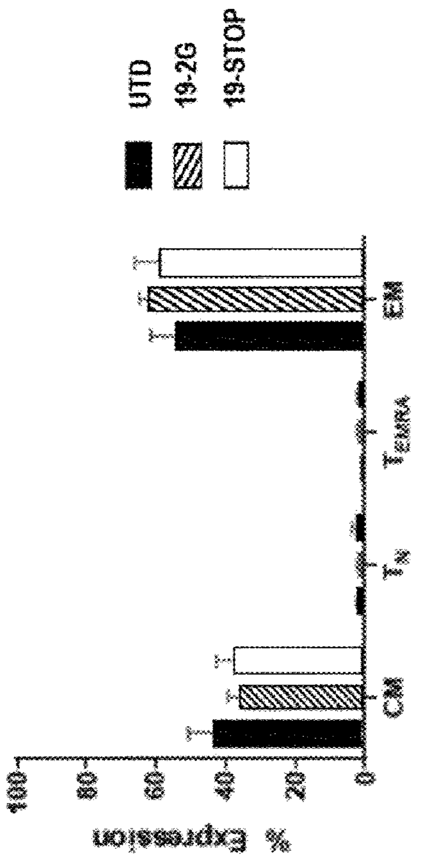
FIG. 28D is a graph showing that 19-STOP-CAR-Ts and 19-2G-CAR-Ts have a similar phenotype (n=3).
Figure 28E:
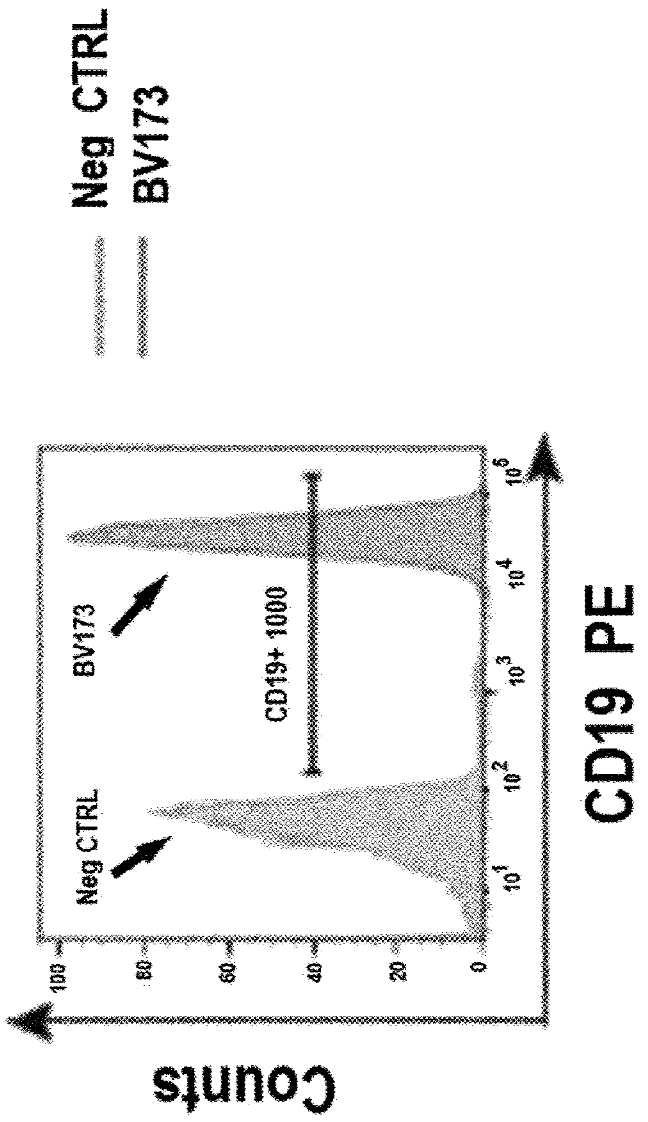
FIG. 28E is a graph showing the results of CD19 expression on negative control (left) and BV173 tumor cells (right) as assessed by flow cytometric analysis.
Figure 28G:
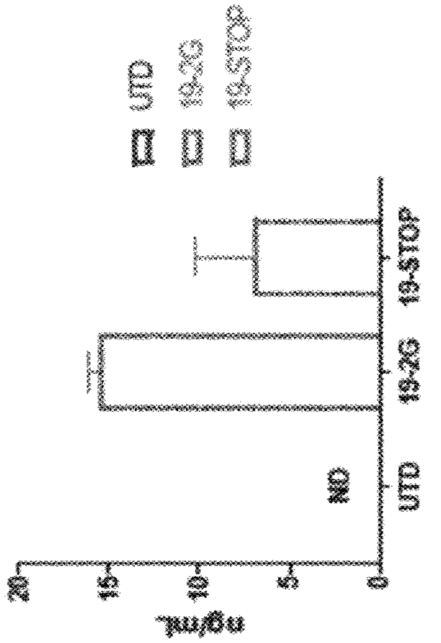
FIG. 28G is a graph showing the results of IFNγ production of 19-2G-CAR-Ts and 19-STOP-CAR-Ts upon BV173 stimulation for 24 h (n=3).
Figure 28F:
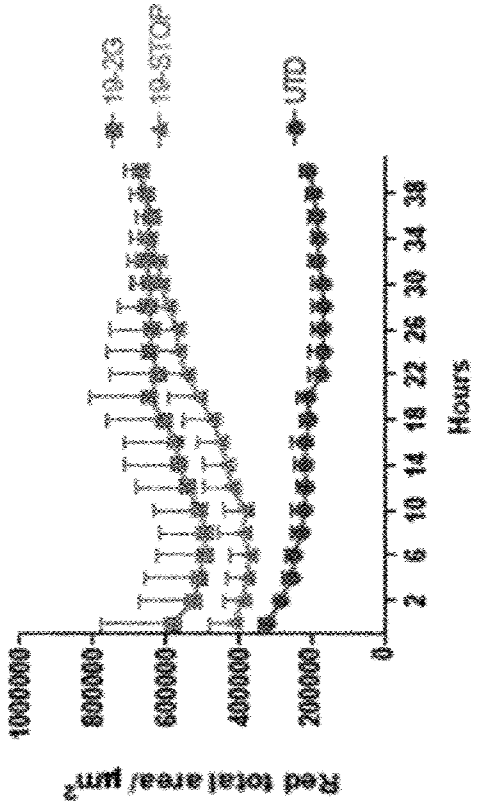
FIG. 28F is a graph showing IFNγ production of 19-2G-CAR-Ts and 19-STOP-CAR-Ts upon BV173 stimulation for 24 h (n=3).
Figure 28H:
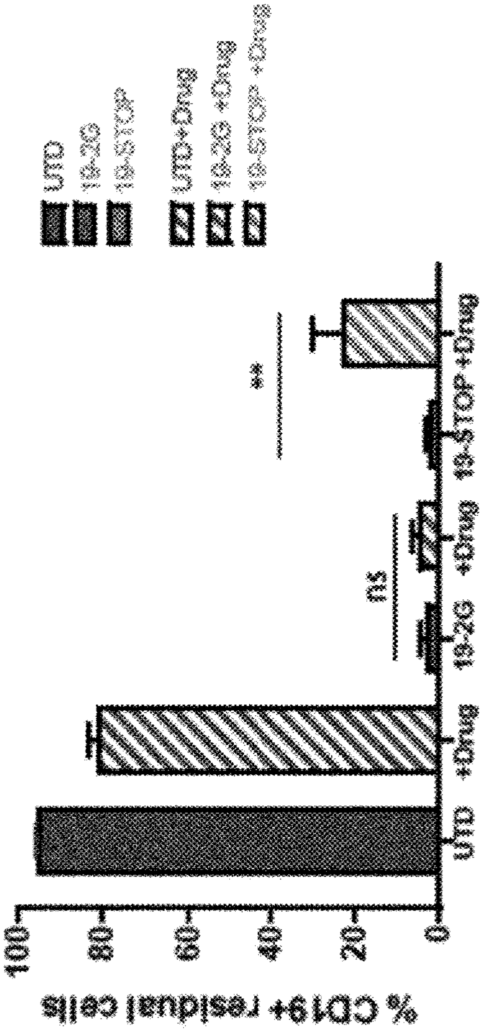
FIG. 28H is a graph showing the results of a short term cytotoxicity assay. FACS™ analysis of residual CD19+ target cells after 4 h co-culture with UTD, 19-2G-CAR-Ts and 19-STOP-CAR-Ts showed efficient killing when T cells were not preconditioned with 10 μM Drug, while 12 h pre-conditioning significantly impaired 10-STOP-CAR-Ts (p=0.0043, n=3 One-way ANOVA). On the contrary, no difference in 19-2G-CAR Ts was detected in presence of Drug preconditioning.
Figure 28I:
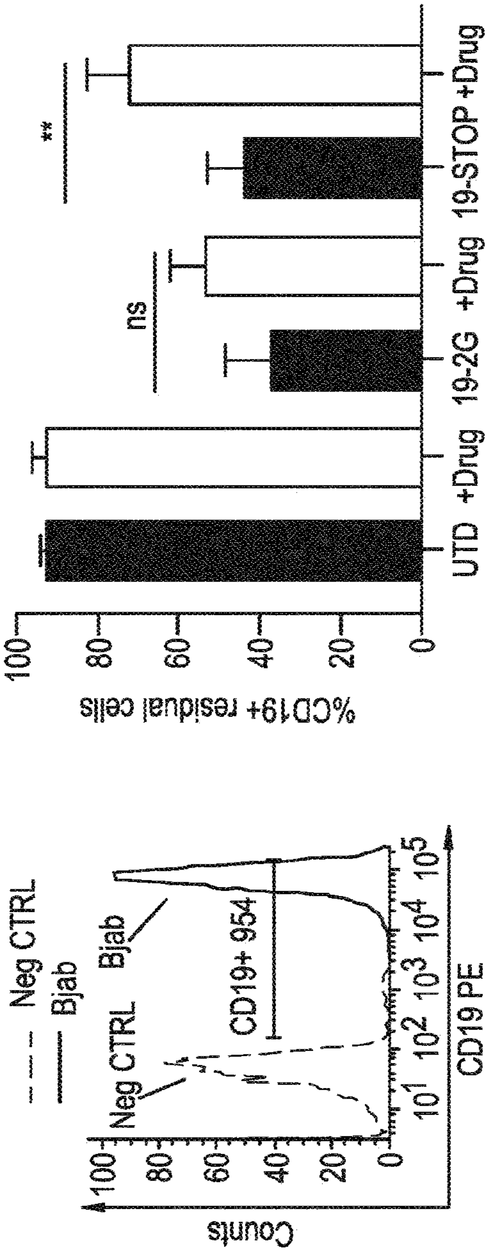
FIG. 28I depicts two graphs. On the left, CD19 expression on Bjab tumor cells was assessed by flow cytometric analysis. On the right, short term cytotoxicity assay showed 19-STOP-CAR-Ts can kill Bjab tumor cells in absence of Drug, while their activity can be significantly tuned down when preconditioned with 10 M Drug (p=0.0098, n=3 One-way ANOVA). 19-2G-STOP-Ts cytotoxic activity was not affected in presence of Drug.

The transduction of 19 STOP-CAR in primary human $CD4^{30}$ and $CD8^+$ provided an average R-chain/S-chain co-expression of 42% and 32% respectively, n=6 donors), as shown by the data in FIGS. 28A and 28B. The proliferative capacity of the 19-STOP-CAR-Ts was similar to UTD T-cells and phenotypic analysis revealed effector/memory differentiation similar to that of 19-2G-CAR-Ts (FIGS. 28C and 28D). When redirected against CD19+ target cells (FIG. 28E), 19-STOP-CAR Ts showed specific killing activity and IFNγ production in absence of Drug, comparable to 19-2G-CAR Ts (FIGS. 28F and 24G). [00398]19-STOP-CAR-Ts were preconditioned for 12 hours with 10 μM Drug, and then co-cultured with tumor cells in the absence of the Drug to avoid tumor cell death. After 4 hours of T cell:Tumor cell co-culture, 19-STOP-CAR-Ts showed significant cytotoxic activity against BV173 and Bjab target cells, comparable to 19-2G-CAR Ts. In contrast, when T cells were pre-incubated with the Drug, their killing activity was significantly decreased against both target cells, thus showing the effectiveness of Off-Switch in the context of a different scFv.

Example 4. STOP-CAR Dynamic Switch In Vivo

Figure 29A:
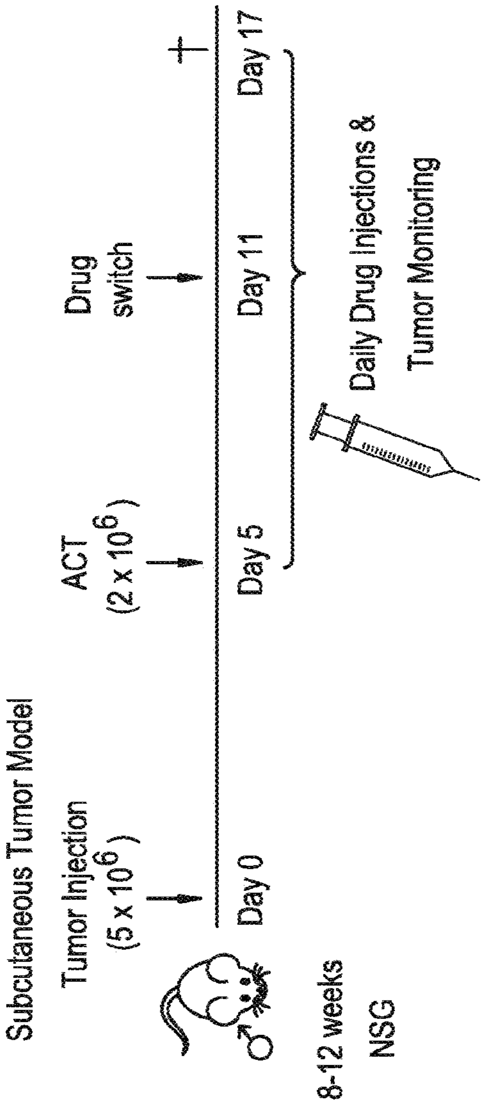
FIG. 29A is a schematic showing an experimental design in which NSG mice were inoculated subcutaneously with $5\times10^6$ PC3-PIP tumor cells, and on day 5 received 1 dose of $2\times10^6$ CAR-Ts or UTD-Ts. Dynamic addition of removal of 10 μM Drug-2 was tested starting from day 11.

In this example, the ability to activate STOP-CAR T cells was assessed in vivo by stopping drug application (uncontrolled tumors should start to be controlled), as well as by halting actively functioning STOP-CAR T cells (controlled tumors should start to escape). A schematic of the protocol is shown in FIG. 29A. Briefly, 8-12 weeks NSG mice were inoculated with $5\times10^6$ PC3PIP cells sub-cutaneous injection. After 5 days when the tumor was palpable, $2\times10^6$ UTD and STOP-CAR T were transferred peri-tumorally. Three different groups were set up for STOP-CAR-Ts: A. STOP-CAR-Ts without Drug-2; B. STOP-CAR-Ts with drug until Day 11, then No Drug; C. STOP-CAR-Ts No Drug until Day 11, then Drug addition every day. In another group "STOP+Drug", STOP-CAR-Ts were administered with the drug on all days of the study.

Figure 29B:
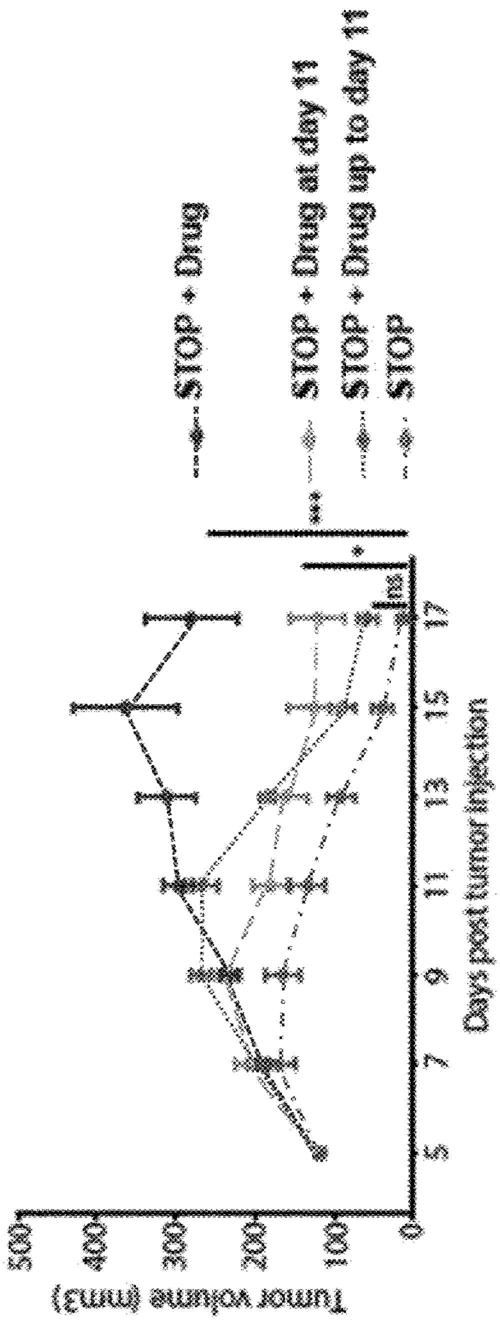
FIG. 29B is a graph showing the results. Drug-2 significantly impaired tumor control by STOP-CAR-Ts (p<0.0001) (n=7 mice/group). Day 11 Drug removal at day 11 significantly turned from uncontrolled growth to tumor control at Day 17 (Tumor control not significantly different from STOP-CAR-Ts) (n=7 mice/group), while the Day 11 Drug addition caused the switch from previous tumor control to tumor establishment (p<0.0130) (n=7 mice/group).

The results are shown in FIG. 29B. Group A ("STOP") was used to determine the tumor control therapeutic window. Group B ("STOP+Drug up to day 11") was used to show that until Drug was administered STOP-CAR-Ts cannot control tumor. Upon Drug removal STOP-CAR-Ts cells showed killing activity toward tumor arriving to Day 17 being as efficient as group A in tumor control. Group C ("STOP+Drug at day 11") was used to show STOP-CAR-Ts can be tuned after being activated and having efficiently controlled tumor growth. Tuning can involve titrating, or adjusting, the response based on the added drug concentration. The T cells of Group C were left without Drug up to Day 11 where they showed to control tumor as efficiently as Group A, then Drug was administered and the killing capability of STOP-CAR T cells was impaired.

Example 5. Generation of New CHDs Suitable for Clinical Application

The small drug used to disrupt the STOP-CAR iterations was the known BCL-XL inhibitor, A-1155463. This compound is well studied but not approved for the clinical use. For this reason, Prof Correia and collaborators proceeded with anew round of screening to identify protein-protein interactions that can be disrupted by clinical grade compound. Venetoclax, a compound used as second line treatment for chronic lymphocytic leukemia and small lymphocytic lymphoma, was selected as the Drug. Venetoclax blocks the anti-apoptotic B-cell lymphoma-2 (Bcl-2) protein, leading to programmed cell death in tumor cells, similarly to A-1155463 towards Bcl-XL.

In a first set of experiments, Bcl-2 was isolated and then tested with the previously identified Des3 (SEQ ID NO: 2) based variants for validating the affinity strength and the ability to disrupt the heterodimer interaction by using Venetoclax (Tables 2 and 3). In addition, the original sequence of Bcl-XL was mutated (E96D; Bclmut) in order to be susceptible to Venetoclax binding, thus augmenting the possible iterations of the new generation STOP-CARs.

TABLE 2

| | Affinity (nM) | | | |
|---|---|---|---|---|
| | Des3 | Des3a | Des3b | Des3c |
| Bcl-xL | 0.004 | 0.270 | 4.600 | 22.300 |
| Bcl-2 | 0.800 | 16.800 | 64.100 | 147.000 |
| Bclmut | 2.800 | 3.500 | 13.100 | 84.900 |

Affinity (nM) values were calculated by Surface plasmon resonance (SPR) data on a Biacore™ 8K device. Bcl-xL, Bcl-2 and Bclmut was immobilized while different concentrations of the Des3 variants (Des3, Des3a, Des3b, Des3c) was injected in serial dilutions. The affinity values (in nanomolar range) are shown.

TABLE 3

| | Drug $IC_{50}$ (nM) | | | | | | | | |
|---|---|---|---|---|---|---|---|---|---|
| | Bcl-xl:Des 3 | Bcl-xl:Des 3a | Bcl-xL:Des 3b | Bcl-xL:Des 3c | Bcl-2:Des 3 | Bcl-2:Des 3a | Bcl-2:Des 3b | Bcl-2:Des 3c | Bclmut: Des 4 |
| A-1155463 | 25 | 100 | 42 | 14 | 240 | 150 | 110 | 31 | 260 |
| Venetoclax | $10^4$ | $10^4$ | 1200 | 75 | 220 | 78 | 105 | 24 | 280 |
| A-1331852 | 115 | N/D | N/D | N/D | 220 | N/D | N/D | N/D | 150 |

Apparent IC50s for each of the three drugs were computed in SPR. 4 micro-molar of each protein binder (Des3, Des3a, Des3b, Des3c) were pre-incubated with different concentrations of A-1155463, A-1331852 or Venetoclax. The apparent IC50s for each drug towards a selected subset of (Bcl:Des) complexes is shown in nano-molar scale.

The sequences of the Bcl and Des3 variants tested include:

>Des3 sequence (highest affinity, shown to bind both Bcl-2 and Bcl-xL at 800 pM and 3.9 pM respectively)

(SEQ ID NO: 2)

QRWELALGRFLEYLSWVSTLSEQVQEELLSSQVTQELRALMDETMKELKA

YKSELEEQLTPVAEETRARLSKELQAAQARLGADMEDVRGRLVQYRGEVQ

AMLGQSTEELRVRLASHLIALQLRLIGDAFDLQKRLAVYQAGA

>'slightly' weaker affinity binder (Des3a): GLU124ALA (SEQ ID NO: 19)

QRWELALGRFLAYLSWVSTLSEQVQEELLSSQVTQELRALMDETMKELKA

YKSELEEQLTPVAEETRARLSKELQAAQARLGADMEDVRGRLVQYRGEVQ

AMLGQSTEELRVRLASHLIALQLRLIGDAFDLQKRLAVYQAGA

>'Medium' affinity binder: (Des3b) LEU235ALA (SEQ ID NO: 3)

QRAVELALGRFLEYLSWVSTLSEQVQEELLSSQVTQELRALMDETMKELK

AYKSELEEQLTPVAEETRARLSKELQAAQARLGADMEDVRGRINQYRGEV

QAMLGQSTEELRVRLASHLIALQARLIGDAFDLQKRLAVYQAGA

>'Weakest' affinity Des 3 binder (Des3c): mutation ASP240ALA:

(SEQ ID NO: 4)

QRWELALGRFLEYLSWVSTLSEQVQEELLSSQVTQELRALMDETMKELKA

YKSELEEQLTPVAEETRARLSKELQAAQARLGADMEDVRGRLVQYRGEVQ

AMLGQSTEELRVRLASHLIALQLRLIGAAFDLQKRLAVYQAGA

>Bcl-xL wildtype sequence (Bcl-xL) (the one tested):

(SEQ ID NO: 22)

MSQSNRELVVDFLSYKLSQKGYSWSQFSDVEENRTEAPEGTESEAVKQAL

REAGDEFELRYRRAFSDLTSQLHITPGTAYQSFEQVVNELFRDGVNWGRI

VAFFSFGGALCVESVDKEMQVLVSRIAAWMATYLNDHLEPWIQENGGWDT

FVELYGNNAAAESRKGQER

>Mutant of Bclxsl (BclMut) sensitive to Venetoclax. Contains mutation E96D wrt wildtype Bcl-xL (SEQ ID NO: 23)

MSQSNRELVVDFLSYKLSQKGYSWSQFSDVEENRTEAPEGTESEAVKQAL

REAGDDFELRYRRAFSDLTSQLHITPGTAYQSFEQVVNELFRDGVNWGRI

VAFFSFGGALCVESVDKEMQVLVSRIAAWMATYLNDHLEPWIQENGGWDT

-continued

FVELYGNNAAAESRKGQER

>BCL-2 sequence, inhibited by Venetoclax at <10 pM (Taken from Bcl-2 structure with PDB id 2XA0)

(SEQ ID NO: 24)

MAHAGRTGYDNREIVMKYIHYKLSQRGYEWDAGDVGAAPPGAAPAPGIFS

SQPGHTPHPAASRDPVARTSPLQTPAAPGAAAGPALSPVPPVVHLTLRQA

GDDFSRRYRRDFAEMSSQLHLTPFTARGRFATVVEELFRDGVNWGRIVAF

FEFGGVMCVESVNREMSPLVDNIALWMTEYLNRHLHTWIQDNGGWDAFVE

LYGPSMR

Example 6. Generation of New STOP-CARs Suitable for Clinical Application

Figure 30:
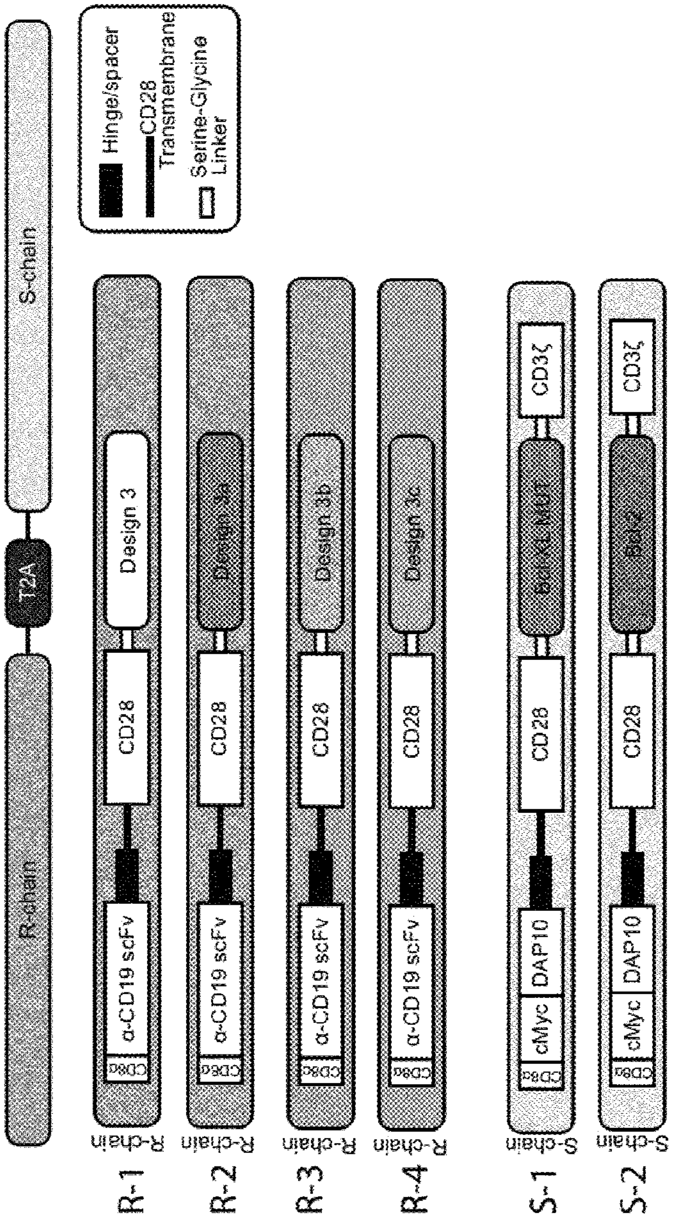
FIG. 30 shows a schematic of new R- and S-chains for 19-STOP-CAR responsive to Venetoclax, as described at least in Example 5. Primary human CD4+ and CD8+ T cells are transduced with the different iterations of STOP-CAR. The R chain will be detected with an anti-F(Ab)-APC antibody and the S-chain with an anti-c-Myc-FITC antibody to evaluate co-expression of the two chains. Second generation CAR will be always used as internal control. The cell growth rate and memory/effector phenotype will be monitored to assess any change due to transgene insertion.

Generated CDHs are incorporated into a STOP-CAR architecture as described in Examples 1 and 2. Four different R-chains (R1, R2, R3 and R4) and two S-chain (S1 and S2) are tested in the following combinations: R1:S1, R1:S2, R2:S1, R2:S2, R3 S1, R3 S2, R4: S, R4:S2, as shown in FIG. 30. Both α-PSMA and α-CD19 scFv are used for functional characterization.

In parallel, evaluation will be performed of the Venetoclax maximal dose concentration tolerated by target cell lines (CD19+ target BV173, Bjab and CD19KO-BV173 and PSMA+ target PC3PiP) and by T cells to be used in the functional tests. Briefly, IncuCyte® technology is used to seed target and T cells in presence of increasing concentration of Venetoclax ranging from 5 μM to 100 μM. Once the optimal range of concentration is found which does not kill or impair neither the tumor nor the T cells, functional tests are performed as follows.

Long-term cytotoxicity is evaluated by IncuCyte® technology, using 2:1 E:T Ratio, in the presence and in the absence of Venetoclax added daily to culture media. IFNγ, IL2 and TNFα secretion are also evaluated after 24 hours from antigen-specific stimulation. Dynamic in vitro studies are also performed. The sensitivity of the system described in this example is tested using different amounts of antigenic stimulation. PSMA+ or CD19+ tumor target cells are diluted with their negative counterpart (PC3PiP with PC3 and BV173 with CD19KO-BV173), and the responsiveness of STOP-CAR-Ts to Drug (Venetoclax) according to the amount of antigen stimulation is tested. The assay provides understanding as to whether the Drug concentration to STOP the CAR is strictly dependent on the level of antigen recognition. Secondly, the CDH off-switch in cells previously exposed to antigen is tested. The kinetics of activation shut down by cytokine secretion and killing activity is measured. This experiment allows for assessing the ability of the newly generated STOP-CARs to tune down in case of unexpected T cells activation and adverse reaction. Dynamic shut down is confirmed in vivo using the system described in FIG. 30.

Example 7

Figure 31A:
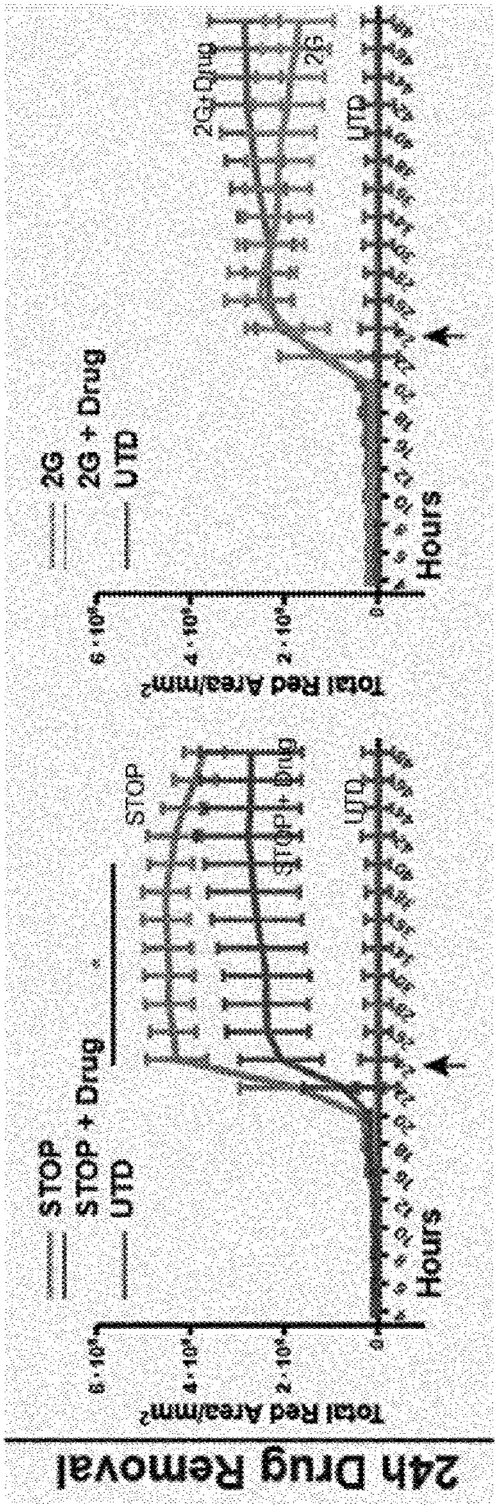
FIGS. 31A-31D show functional activity of STOP-CAR-Ts with 24 h of 10 μM Drug-2 inhibition continues to be impaired immediately after drug withdrawal, but with 5 μM Drug-2 there is no attenuation of activity upon 24 h drug withdrawal.

Functional activity of STOP-CAR was tested by IncuCyte® cytotoxicity assay after 24 h exposure of 10 μM Drug 2. PSMA+ target cells PC3PiP were plated at the concentration of 15000 cell/well (96 wells plate). UTD, 2G and STOP-CAR Ts were seeded at 30000 cell/well; the E:T Ratio was thus 2:1. STOP-CAR T cells were exposed to Drug 10 μM Drug 2 (Dark green line) in presence of antigen stimulation, or without drug (light green line). After 24 h of coculture incubation, the plate was removed from the IncuCyte® Instrument and centrifuged to spin down the cells. The supernatant was carefully aspirated to remove the Drug was removed (by careful aspiration) and fresh media was added. The plate was then re-inserted in the IncuCyte® Instrument and cytotoxic activity was monitored for the following 24 h. The results are shown in the left panel of FIG. 31A. As shown in the graph, STOP-CAR Ts that were never exposed to Drug (light green line) show efficient killing activity against the PSMA+ target cells while STOP-CAR Ts pre-exposed 10 μM Drug 2for 24 h do not fully recover their cytotoxic activity, even if Drug is not present anymore in the co-culture media (statistical difference between dark green line and light green line until hour 42, after which the Drug pre-exposed STOP-CAR Ts start to recover full cytotoxic activity.

Functional activity of STOP-CAR was tested by IncuCyte® cytotoxicity assay after 24 h exposure of 10 μM Drug 2. PSMA+ target cells PC3PiP were plated at the concentration of 15000 cell/well (96 wells plate). UTD, 2G and STOP-CAR Ts were seeded at 30000 cell/well; the E:T Ratio was thus 2:1. 2G T cells were exposed to Drug 10 μM Drug 2 (Dark orange line) in the presence of antigen stimulation, or without drug (light orange line). After 24 h of co-culture incubation, the plate was removed from IncuCyte® Instrument and centrifuged to spin down cells. The supernatant was carefully aspirated to remove the Drug and fresh media was added to the wells. Then the plate was re-inserted in the IncuCyte® instrument and cytotoxic activity was monitored for the following 24 h. The results are shown in the right panel of FIG. 31A. As shown in the graph, 2G-CAR Ts that were never exposed to Drug (light orange line) show efficient killing activity against the PSMA+ target cells. Similarly, 2G Ts pre-exposed to 10 μM Drug 2for 24 h do not present any decrease in their cytotoxic activity as compared to control 2G. (no statistical difference between dark orange line and light orange line), thus confirming the Drug activity only on STOP-CAR Ts.

Figure 31B:
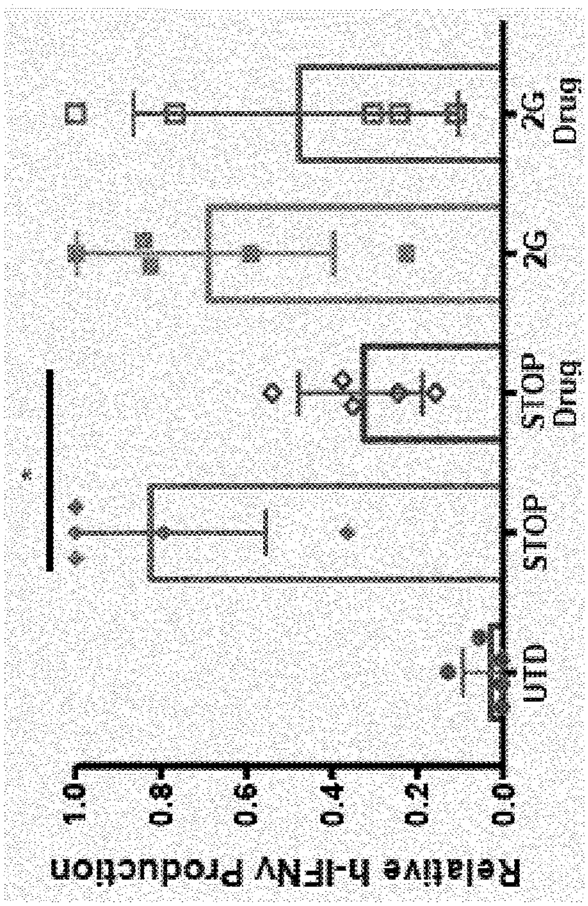

IFNg secretion by STOP-CAR and 2G Ts was tested after 24 h exposure of 10 μM Drug 2. PSMA+ target cells PC3PiP were plated at a concentration of 50000 cell/well (96 wells plate). UTD, 2G and STOP-CAR Ts were then seeded at 50000 cell/well for and E:T ratio of 1:1. STOP-CAR T cells and 2G Ts were exposed to Drug 10 μM Drug 2 (Dark green and orange bars) in presence of antigen stimulation, or without drug (light green and orange bars). After 24 h of coculture incubation, the plate was removed from the incubator and centrifuged to spin down cells. The supernatant was carefully aspirated to remove the drug and fresh media was added. The plate was then re-inserted in the incubator for another 24 h, after which the supernatant was finally collected to be tested by ELISA for the presence of IFNg. The results are shown in FIG. 31B. As shown in the graph, STOP-CAR Ts and 2G Ts that were never exposed to Drug produce reasonable amount of IFNg upon antigen stimulation. On the contrary, STOP-CAR Ts pre-exposed 10 μM Drug 2 for 24 h do not fully recover the ability to produce IFNg, even if Drug is no longer present in the co-culture media. 2G Ts pre-exposed to Drug are not statistically significant different to 2G control group, thus confirming the specificity of Drug 2 on STOP-CAR Ts.

Functional activity of STOP-CAR was tested by IncuCyte® assay after 24 h exposure of 5 μM Drug 2. PSMA+ target cells PC3PiP were plated at a concentration of 15000 cell/well (96 wells plate). UTD, 2G and STOP-CAR Ts were then seeded at 30000 cell/well for an E:T ratio of 2:1. STOP-CAR T cells were exposed to 5 μM Drug 2 (dark green line) in presence of antigen stimulation, with or without drug (light green line). After 24 h of co-culture incubation, the plate was removed from the IncuCyte® Instrument and centrifuged to spin down the cells. The supernatant was carefully aspirated to remove the drug and fresh media was added to the wells. The plate was then re-inserted in the IncuCyte® Instrument and cytotoxic activity was monitored for the following 24 h. The results are shown in the left panel of FIG. 31C. As shown in the graph, STOP-CAR Ts that were never exposed to Drug (light green line) show efficient killing activity against the PSMA+ target cells. Differently from 10 μM exposure, STOP-CAR Ts pre-exposed 5 μM Drug 2for 24 h do not present any tuning of their cytotoxic activity (no statistical difference between dark green line and light green line), thus confirming that Drug 2 activity of STOP-CAR Ts is dose-dependent.

Functional activity of STOP-CAR was tested by IncuCyte® assay after 24 h exposure of 5 μM Drug 2. PSMA+ target cells PC3PiP were plated at a concentration of 15000 cell/well (96 wells plate). UTD, 2G and STOP-CAR Ts were then seeded at 30000 cell/well for an E:T ratio of 2:1. 2G T cells were exposed to Drug 5 μM Drug 2 (dark orange line) in presence of antigen stimulation, with or without drug (light orange line). After 24 h of co-culture incubation, the plate was removed from IncuCyte® Instrument and centrifuged to spin down the cells. The supernatant was carefully aspirated to remove the drug and fresh media was added to the wells. The plate was then re-inserted in the IncuCyte® instrument and cytotoxic activity was monitored for the following 24 h. The results are shown in the right panel of FIG. 31C. As shown in the graph, 2G-CAR Ts that were never exposed to Drug (light orange line) show efficient killing activity against the PSMA+ target. Similarly 2G Ts pre-exposed 5 μM Drug 2for 24 h do not present any decrease in their cytotoxic activity as compared to control 2G.

Figure 31C:
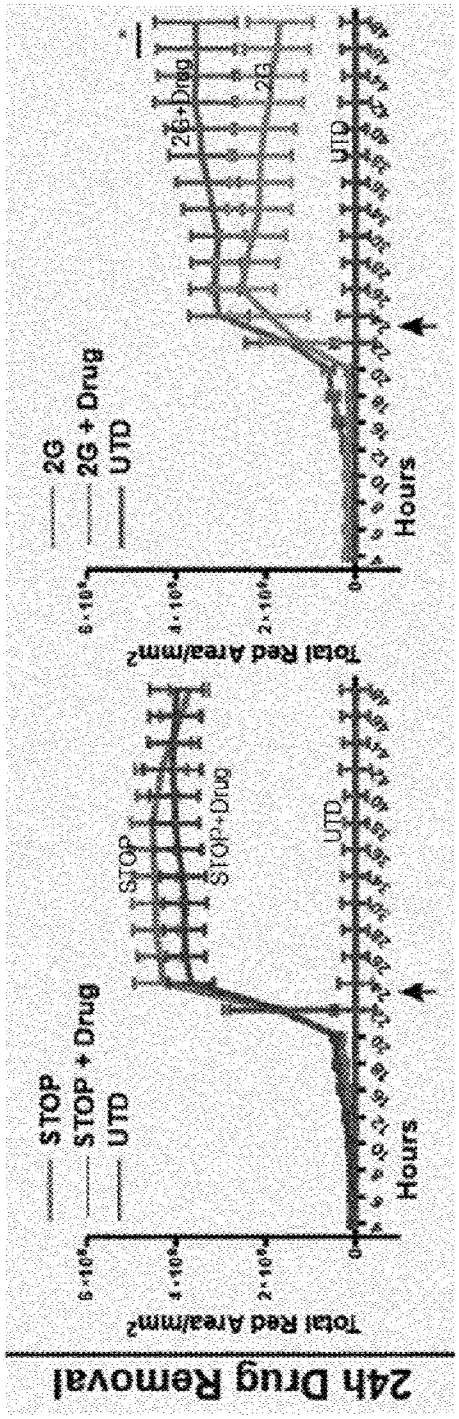
Figure 31D:
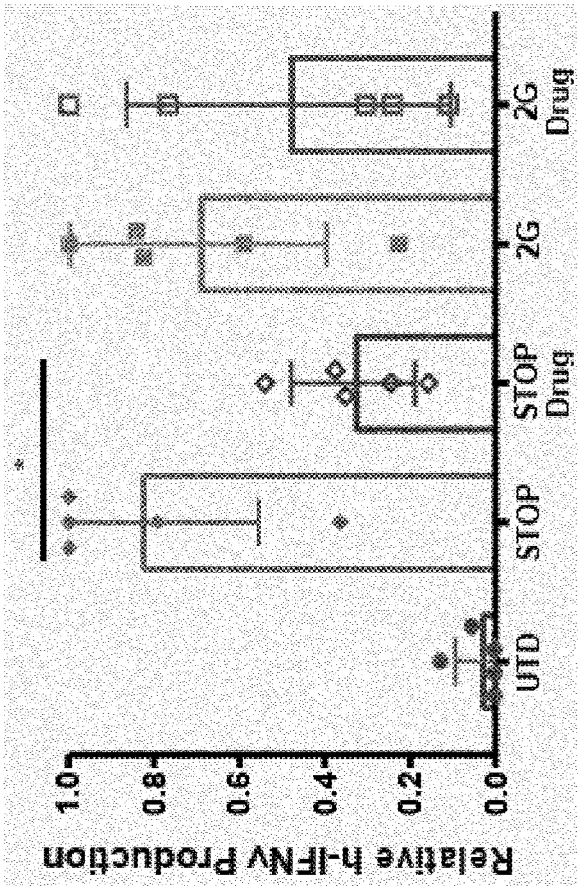

IFNg secretion by STOP-CAR and 2G Ts was tested after 24 h exposure of 5 μM Drug 2. PSMA+ target cells PC3PiP were plated at the concentration of 50000 cell/well (96 wells plate). UTD, 2G and STOP-CAR Ts were then seeded at 50000 cell/well, so E:T Ratio was 1:1. STOP-CAR T cells and 2G Ts were exposed to Drug 5 μM Drug 2 (Dark green and orange bars) in presence of antigen stimulation, with or without drug (light green and orange bars). After 24 h of co-culture incubation, the plate was removed from the incubator and centrifuged to spin down the cells. The supernatant was carefully aspirated to remove the Drug and fresh media was added to the wells. The plate was then re-inserted in the incubator for another 24 h, after which the supernatant was collected to be tested by ELISA for IFNg secretion. The results are shown in FIG. 31D. As shown in the graph, STOP-CAR Ts and 2G Ts that were never exposed to Drug produce reasonable amount of IFNg upon antigen stimulation. However, similarly to 10 μM Drug pre-incubation, STOP-CAR Ts pre-exposed 5 μM Drug 2 for 24 h do not recover the ability to produce IFNg upon antigen stimulation (while their cytotoxic activity is not impaired as shown in FIG. 31C). 2G Ts pre-exposed to Drug are not statistically significant different to 2G control group.

REFERENCES

1. Brentjens R J, Davila M L, Riviere I et al. CD19-targeted T cells rapidly induce molecular remissions in adults with chemotherapy-refractory acute lymphoblastic leukemia. Sci Transl Med 2013; 5: 177ra138.
2. Maude S L, Frey N, Shaw P A et al. Chimeric antigen receptor T cells for sustained remissions in leukemia. N Engl J Med 2014; 371: 1507-1517.
3. Maus M V, Grupp S A, Porter D L, June C H. Antibody-modified T cells: CARs take the front seat for hematologic malignancies. Blood 2014; 123: 2625-2635.
4. Morgan R A, Yang J C, Kitano M et al. Case report of a serious adverse event following the administration of T cells transduced with a chimeric antigen receptor recognizing ERBB2. Mol Ther 2010; 18: 843-851.
5. Gargett T, Brown M P. The inducible caspase-9 suicide gene system as a "safety switch" to limit on-target, off-tumor toxicities of chimeric antigen receptor T cells. Front Pharmacol 2014; 5: 235.
6. Jones B S, Lamb L S, Goldman F, Di Stasi A. Improving the safety of cell therapy products by suicide gene transfer. Front Pharmacol 2014; 5: 254.
7. Lanitis E, Poussin M, Klattenhoff A W et al. Chimeric antigen receptor T Cells with dissociated signaling domains exhibit focused antitumor activity with reduced potential for toxicity in vivo. Cancer Immunol Res 2013; 1: 43-53.
8. Wu C Y, Roybal K T, Puchner E M et al. Remote control of therapeutic T cells through a small molecule-gated chimeric receptor. Science 2015; 350: aab4077.
9. Gong M C, Latouche J B, Krause A et al. Cancer patient T cells genetically targeted to prostate-specific membrane antigen specifically lyse prostate cancer cells and release cytokines in response to prostate-specific membrane antigen. Neoplasia 1999; 1: 123-127.
10. Gong M C, Chang S S, Sadelain M et al. Prostate-specific membrane antigen (PSMA)-specific monoclonal antibodies in the treatment of prostate and other cancers. Cancer Metastasis Rev 1999; 18: 483-490.
11. Delgado-Soler L, Pinto M, Tanaka-Gil K, Rubio-Martinez J. Molecular determinants of Bim(BH3) peptide binding to pro-survival proteins. J Chem Inf Model 2012; 52: 2107-2118.
12. Kalos, M. et al. T cells with chimeric antigen receptors have potent antitumor effects and can establish memory in patients with advanced leukemia. Sci Transl Med 3, 95ra73 (2011).
13. Brentjens, R. J. et al. CD19-targeted T cells rapidly induce molecular remissions in adults with chemotherapy-refractory acute lymphoblastic leukemia. *Sci Transl Med* 5, 177ra138 (2013).
14. Maude, S. L. et al. Chimeric antigen receptor T cells for sustained remissions in leukemia. *N Engl J Med* 371, 1507-1517 (2014).
15. Turtle, C. J. et al. CD19 CAR-T cells of defined CD4+:CD8+ composition in adult B cell ALL patients. *J Clin Invest* 126, 2123-2138 (2016).
16. Lim, W. A. & June, C. H. The Principles of Engineering Immune Cells to Treat Cancer. Cell 168, 724-740 (2017).
17. Lanitis, E., Dangaj, D., Irving, M. & Coukos, G. Mechanisms regulating T-cell infiltration and activity in solid tumors. *Ann Oncol* 28, xii18-xii32(2017).
18. Adachi, K. et al. IL-7 and CCL19 expression in CAR-T cells improves immune cell infiltration and CAR-T cell survival in the tumor. *Nat Biotechnol* 36, 346-351 (2018).
19. Tang, L. et al. Enhancing T cell therapy through TCR-signaling-responsive nanoparticle drug delivery. *Nat Biotechnol* 36, 707-716(2018).
20. Morgan, R. A. et al. Case report of a serious adverse event following the administration of T cells transduced with a chimeric antigen receptor recognizing ERBB2. *Mol Ther* 18, 843-851 (2010).
21. Gargett, T. & Brown, M. P. The inducible caspase-9 suicide gene system as a "safety switch" to limit on-target, off-tumor toxicities of chimeric antigen receptor T cells. *Front Pharmacol* 5, 235 (2014).
22. Jones, B. S., Lamb, L. S., Goldman, F. & Di Stasi, A. Improving the safety of cell therapy products by suicide gene transfer. *Front Pharmacol* 5, 254 (2014).
23. Fedorov, V. D., Themeli, M. & Sadelain, M. PD-1- and CTLA-4-based inhibitory chimeric antigen receptors (iCARs) divert off-target immunotherapy responses. *Sci Transl Med* 5, 215ra172 (2013).
24. Lanitis, E. et al. Chimeric antigen receptor T Cells with dissociated signaling domains exhibit focused antitumor activity with reduced potential for toxicity in vivo. *Cancer Immunol Res* 1, 43-53 (2013).
25. Wu, C. Y., Roybal, K. T., Puchner, E. M., Onuffer, J. & Lim, W. A. Remote control of therapeutic T cells through a small molecule-gated chimeric receptor. *Science* 350, aab4077 (2015).
26. Cho, J. H., Collins, J. J. & Wong, W. W. Universal Chimeric Antigen Receptors for Multiplexed and Logical Control of T Cell Responses. *Cell* 173, 1426-1438 e1411 (2018).
27. Riddell, S. R. et al. T-cell mediated rejection of gene-modified HIV-specific cytotoxic T lymphocytes in HIV-infected patients. *Nat Med* 2, 216-223(1996).
28. Berger, C., Flowers, M. E., Warren, E. H. & Riddell, S. R. Analysis of transgene-specific immune responses that limit the in vivo persistence of adoptively transferred HSV-TK-modified donor T cells after allogeneic hematopoietic cell transplantation. Blood 107, 2294-2302 (2006).
29. Jensen, M. C. et al. Antitransgene rejection responses contribute to attenuated persistence of adoptively transferred CD20/CD19-specific chimeric antigen receptor redirected T cells in humans. *Biol BloodMarrow Transplant* 16, 1245-1256(2010).
30. Boncompain, G. et al. Synchronization of secretory protein traffic in populations of cells. *Nat Methods* 9, 493-498 (2012).
31. Rollins, C. T. et al. A ligand-reversible dimerization system for controlling protein-protein interactions. *Proc Natl Acad Sci USA* 97, 7096-7101(2000).
32. Bouillet, P. & Strasser, A. BH3-only proteins—evolutionarily conserved proapoptotic Bcl-2 family members essential for initiating programmed cell death. *J Cell Sci* 115, 1567-1574 (2002).
33. Leverson, J. D. et al. Exploiting selective BCL-2 family inhibitors to dissect cell survival dependencies and define improved strategies for cancer therapy. *Sci Transl Med* 7, 279ra240 (2015).
34. Hinds, M. G. et al. Bim, Bad and Bmf: intrinsically unstructured BH3-only proteins that undergo a localized conformational change upon binding to prosurvival Bcl-2 targets. *Cell Death Differ* 14, 128-136 (2007).
35. Procko, E. et al. A computationally designed inhibitor of an Epstein-Barr viral Bcl-2 protein induces apoptosis in infected cells. *Cell* 157, 1644-1656(2014).
36. Gemperli, A. C., Rutledge, S. E., Maranda, A. & Schepartz, A. Paralog-selective ligands for bcl-2 proteins. *J Am Chem Soc* 127, 1596-1597(2005).
37. Chin, J. W. & Schepartz, A. Design and Evolution of a Miniature Bcl-2 Binding Protein. *Angew Chem Int Ed Engl* 40, 3806-3809 (2001).
38. Silva, D. A., Correia, B. E. & Procko, E. Motif-Driven Design of Protein-Protein Interfaces. *Methods Mol Biol* 1414, 285-304 (2016).
39. Ku, B., Liang, C., Jung, J. U. & Oh, B. H. Evidence that inhibition of BAX activation by BCL-2 involves its tight and preferential interaction with the BH3 domain of BAX. *Cell Res* 21, 627-641 (2011).
40. Lanier, L. L. DAP10- and DAP12-associated receptors in innate immunity. *Immunol Rev* 227, 150-160 (2009).
41. Gong, M. C., Chang, S. S., Sadelain, M., Bander, N. H. & Heston, W. D. Prostate-specific membrane antigen (PSMA)-specific monoclonal antibodies in the treatment of prostate and other cancers. *Cancer Metastasis Rev* 18, 483-490 (1999).
42. Gong, M. C. et al. Cancer patient T cells genetically targeted to prostate-specific membrane antigen specifically lyse prostate cancer cells and release cytokines in response to prostate-specific membrane antigen. *Neoplasia* 1, 123-127(1999).
43. Ghosh, A., Wang, X., Klein, E. & Heston, W. D. Novel role of prostate-specific membrane antigen in suppressing prostate cancer invasiveness. *Cancer Res* 65,727-731 (2005).
44. Silva, D. A., Correia, B. E. & Procko, E. Motif-Driven Design of Protein-Protein Interfaces. *Methods Mol Biol* 1414, 285-304 (2016).
45. Leverson, J. D. et al. Exploiting selective BCL-2 family inhibitors to dissect cell survival dependencies and define improved strategies for cancer therapy. *Sci Transl Med* 7, 279ra240 (2015).
46. Lee, E. F. et al. High-resolution structural characterization of a helical alpha/beta-peptide foldamer bound to the anti-apoptotic protein Bcl-xL. *Angew Chem Int Ed Engl* 48, 4318-4322 (2009).
47. Fleishman, S. J. et al. RosettaScripts: a scripting language interface to the Rosetta macromolecular modeling suite. *PLoS One* 6, e20161 (2011).
48. Henikoff, S. & Henikoff, J. G. Amino acid substitution matrices from protein blocks. *Proc Natl Acad Sci USA* 89, 10915-10919(1992).
49. Kuhlman, B. & Baker, D. Native protein sequences are close to optimal for their structures. *Proc Natl Acad Sci USA* 97, 10383-10388(2000).
50. Wang, C., Schueler-Furman, O. & Baker, D. Improved side-chain modeling for protein-protein docking. *Protein Sci* 14, 1328-1339(2005).
51. Gainza, P., Roberts, K. E. & Donald, B. R. Protein design using continuous rotamers. *PLoS Comput Biol* 8, e1002335 (2012).
52. Miller, S., Janin, J., Lesk, A. M. & Chothia, C. Interior and surface of monomeric proteins. *J Mol Biol* 196, 641-656 (1987).
53. Word, J. M. et al. Visualizing and quantifying molecular goodness-of-fit: small-probe contact dots with explicit hydrogen atoms. *J Mol Biol* 285, 1711-1733 (1999).
54. Petros, A. M. et al. Solution structure of the antiapoptotic protein bcl-2. *Proc Natl Acad Sci USA* 98, 3012-3017 (2001).
55. McCoy, A. J. et al. Phaser crystallographic software. *J Appl Crystallogr* 40, 658-674 (2007).
56. Adams, P. D. et al. PHENIX: a comprehensive Python-based system for macromolecular structure solution. *Acta Crystallogr D Biol Crystallogr* 66, 213-221 (2010).
57. Dong, L. M. et al. Human apolipoprotein E. Role of arginine 61 in mediating the lipoprotein preferences of the E3 and E4 isoforms. *Journal of Biological Chemistry* 269, 22358-22365 (1994).
58. Emsley, P. & Cowtan, K. Coot: model-building tools for molecular graphics. *Acta Crystallographica* Section D 60, 2126-2132(2004).
59. Brunger, A. T. et al. Crystallography & NMR System: A New Software Suite for Macromolecular Structure Determination. *Acta Crystallographica Section D* 54, 905-921 (1998).
60. Ghosh, A., Wang, Y. N., Klein, E. & Heston, W. D. W. Novel role of prostate-specific membrane antigen in suppressing prostate cancer invasiveness. *Cancer Research*65, 727-731 (2005).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A heterodimeric inactivatable chimeric antigen receptor (CAR) comprising:

a) a first polypeptide chain comprising:
   i) an extracellular region;
   ii) a first transmembrane (TM) region;
   iii) a first co-stimulatory endodomain (ED); and
   iv) a first member of a dimerization pair; and b) a second polypeptide chain comprising:
   i) optionally, an extracellular region which does not comprise a target-binding region;
   ii) a second TM region;
   iii) optionally, a second co-stimulatory ED;
   iv) a second member of the dimerization pair; and
   v) an intracellular signaling ED, wherein the first and second member of the dimerization pair form a heterodimer, wherein the heterodimer formed by the first and second member of the dimerization pair is disrupted in the presence of an inhibitory molecule resulting in inhibition of CAR-mediated signaling, and wherein (1) the first member of the dimerization pair comprises a sequence selected from SEQ ID NO: 5, SEQ ID NO: 22, SEQ ID NO: 23, SEQ ID NO: 24, SEQ ID NO: 24 comprising residues 35-50 of SEQ ID NO: 22 in place of residues 51-91 of SEQ ID NO: 24, and SEQ ID NO: 30, and the second member of the dimerization pair comprises a sequence IAXXLXXIGXXF (SEQ ID NO: 179), wherein X is any natural amino acid and L is optionally substituted with A, or (2) the first member of the dimerization pair comprises a sequence IAXXLXXIGXXF (SEQ ID NO: 179), wherein X is any natural amino acid and L is optionally substituted with A, and the second member of the dimerization pair comprises a sequence selected from SEQ ID NO: 5, SEQ ID NO: 22, SEQ ID NO: 23, SEQ ID NO: 24, SEQ ID NO: 24 comprising residues 35-50 of SEQ ID NO: 22 in place of residues 51-91 of SEQ ID NO: 24, and SEQ ID NO: 30, and the inhibitory molecule is venetoclax, A-1331852, or A-1155463.

2. The CAR of claim 1, wherein the second polypeptide chain comprises an extracellular region which does not comprise a target-binding region.

3. The CAR of claim 1, wherein the first polypeptide chain does not comprise an intracellular signaling ED.

4. The CAR of claim 1, comprising:

a) a first polypeptide chain consisting essentially of in the direction from the N terminus to the C terminus:
   i) an extracellular target-binding region;
   ii) a first linker region;
   iii) a first transmembrane (TM) region;
   iv) a first co-stimulatory endodomain (ED); and
   v) a first member of a dimerization pair; and b) a second polypeptide chain consisting essentially of in the direction from the N terminus to the C terminus:
   i) an extracellular region which does not comprise a target-binding region;
   ii) a second linker region;
   iii) a second TM region;
   iv) a second co-stimulatory ED;
   v) a second member of the dimerization pair; and
   vi) an intracellular signaling ED, wherein the first polypeptide chain does not comprise an intracellular signaling ED.

5. The CAR of claim 1, wherein the extracellular region of the first polypeptide chain comprises an antigen-binding polypeptide, a receptor, or a natural ligand for a target cell antigen or receptor.

6. The CAR of claim 5, wherein the antigen recognized by the antigen-binding polypeptide is CD19, prostate-specific membrane antigen (PSMA), or mesothelin.

7. The CAR of claim 5, wherein the natural ligand for a target cell antigen or receptor is an NKG2D ectodomain.

8. The CAR of claim 1, wherein the extracellular region of the first polypeptide chain comprises a T-cell receptor (TCR)-based recognition domain.

9. The CAR of claim 1, wherein a) the first and/or second transmembrane (TM) region is derived from CD8, CD8α, CD4, CD3-zeta, CD3-epsilon, CD28, CD45, CD4, CD5, CD7, CD9, CD16, CD22, CD33, CD37, CD40, CD64, CD80, CD86, CD134 (OX-40), CD137, CD154, DAP10, or DAP12;

b) the first and/or second co-stimulatory ED is derived from 4-1BB (CD137), CD28, ICOS, CD134 (OX-40), BTLA, CD27, CD30, GITR, CD226, or HVEM;

c) the intracellular signaling ED of the second polypeptide chain is derived from DAP10, DAP12, Fc epsilon receptor I gamma chain (FCER1G), FcR beta CD3-delta, CD3-epsilon, CD3-gamma, CD3-zeta, CD226, CD66d, CD79A, or CD79B; and/or d) the first and/or second polypeptide chain further comprises one or more polypeptide sequences, wherein said one or more polypeptide sequences are selected from one or more additional co-stimulatory EDs, signal sequences, separation sequences, epitope tags, and polypeptides that produce a detectable signal.

10. The CAR of claim 1, wherein i) the first member of the dimerization pair comprises the sequence of SEQ ID NO: 2, SEQ ID NO: 3, SEQ ID NO: 4, or SEQ ID NO: 19;

ii) the second member of the dimerization pair comprises the sequence of SEQ ID NO: 5, SEQ ID NO: 22, SEQ ID NO: 23, SEQ ID NO: 24, or SEQ ID NO: 30;

iii) the extracellular region of the first polypeptide chain comprises the sequence of SEQ ID NO: 6, or SEQ ID NO: 49;

iv) the intracellular signaling ED of the second polypeptide chain comprises the sequence of SEQ ID NO: 7;

v) the first and/or second linker region comprises the sequence of SEQ ID NO: 9;

vi) the first and/or second TM region comprises the sequence of SEQ ID NO: 10; and/or vii) the first and/or second co-stimulatory ED comprises the sequence or SEQ ID NO: 11.

11. The CAR of claim 1, wherein:

a) the first polypeptide chain comprises the sequence of SEQ ID NO: 109, SEQ ID NO: 110, SEQ ID NO: 111, or SEQ ID NO: 112; and/or b) the second polypeptide chain comprises the sequence of SEQ ID NO: 113, SEQ ID NO: 114, SEQ ID NO: 115, SEQ ID NO: 116, or SEQ ID NO: 117.

12. The CAR of claim 1 comprising:

a) the first polypeptide chain comprising the sequence of SEQ ID NO: 109 and the second polypeptide chain comprising the sequence of SEQ ID NO: 113, SEQ ID NO: 114, SEQ ID NO: 115, SEQ ID NO: 116, or SEQ ID NO: 117;

b) the first polypeptide chain comprising the sequence of SEQ ID NO: 110 and the second polypeptide chain comprising the sequence of SEQ ID NO: 113, SEQ ID NO: 114, SEQ ID NO: 115, SEQ ID NO: 116, or SEQ ID NO: 117;

c) the first polypeptide chain comprising the sequence of SEQ ID NO: 111 and the second polypeptide chain comprising the sequence of SEQ ID NO: 113, SEQ ID NO: 114, SEQ ID NO: 115, SEQ ID NO: 116, or SEQ ID NO: 117; or d) the first polypeptide chain comprising the sequence of SEQ ID NO: 112 and the second polypeptide chain comprising the sequence of SEQ ID NO: 113, SEQ ID NO: 114, SEQ ID NO: 115, SEQ ID NO: 116, or SEQ ID NO: 117.

13. A nucleic acid molecule comprising a nucleotide sequence encoding the first polypeptide chain of the heterodimeric inactivatable CAR of claim 1, the second polypeptide chain of the heterodimeric inactivatable CAR of claim 1, or the first and second polypeptide chains of the heterodimeric inactivatable CAR of claim 1.

14. A recombinant vector comprising the nucleic acid molecule of claim 13.

15. An isolated, genetically modified host cell comprising the heterodimeric inactivatable CAR of claim 1.

16. The host cell of claim 15, which is selected from a cytotoxic cell, a T cell, a stem cell, a progenitor cell, a cell derived from a stem cell, and a cell derived from a progenitor cell.

17. A pharmaceutical composition comprising the host cell of claim 15 and a pharmaceutically acceptable carrier and/or excipient.

18. A method for producing a host cell comprising the heterodimeric inactivatable CAR of claim 1, said method comprising genetically modifying said cell with (i) a nucleic acid molecule comprising a nucleotide sequence encoding the first polypeptide chain of the heterodimeric inactivatable CAR of claim 1 and a nucleic acid molecule comprising a nucleotide sequence encoding the second polypeptide chain of the heterodimeric inactivatable CAR of claim 1 or (ii) a nucleic acid molecule comprising nucleotide sequence(s) encoding the first and second polypeptide chains of heterodimeric inactivatable CAR of claim 1.

19. A method for stimulating elimination of a prostate-specific membrane antigen (PSMA)-expressing cell or CD19-expressing cell, said method comprising contacting said cell with a T cells or natural killer (NK) cells comprising the heterodimeric inactivatable CAR of claim 1, wherein the extracellular region of the first polypeptide chain of said CAR binds to PSMA or CD19.

20. A method for treating a cancer in a subject having the cancer, said method comprising administering to the subject a therapeutically effective amount of T cells or natural killer (NK) cells comprising the heterodimeric inactivatable CAR of claim 1, wherein the cancer is prostate cancer, leukemia or lymphoma.

21. The method of claim 20, said method further comprising inhibiting the activity of the CAR by administering to the subject an effective amount of an inhibitory molecule, wherein the inhibitory molecule is venetoclax, A-1331852, or A-1155463.

22. A method for inhibiting the activity of the heterodimeric inactivatable CAR in the host cell of claim 15, comprising contacting the host cell with an inhibitory molecule, wherein the inhibitory molecule is venetoclax, A-1331852, or A-1155463.

23. The CAR of claim 1, wherein the extracellular region of the second polypeptide chain comprises a DAP10 ectodomain.

24. The CAR of claim 1, wherein the second member of the dimerization pair in (1) or the first member of the dimerization pair in (2) comprises Apolipoprotein E (ApoE) which comprises the sequence IAXXLXXIGXXF (SEQ ID NO: 179), wherein X is any natural amino acid and L is optionally substituted with A.

25. The CAR of claim 1, wherein the second member of the dimerization pair in (1) or the first member of the dimerization pair in (2) comprises the amino acid sequence SEQ ID NO: 1, 2, 3, 4, or 19.

* * * * *